US009127297B2

(12) United States Patent
Dühring et al.

(10) Patent No.: US 9,127,297 B2
(45) Date of Patent: *Sep. 8, 2015

(54) METABOLICALLY ENHANCED CYANOBACTERIAL CELL FOR THE PRODUCTION OF ETHANOL

(71) Applicant: Algenol Biofuels Inc., Fort Myers, FL (US)

(72) Inventors: Ulf Dühring, Fredersdorf (DE); Heike Enke, Berlin (DE); Karl Ziegler, Zeuthen (DE); Torsten Schwecke, Berlin (DE)

(73) Assignee: Algenol Biotech LLC, Fort Myers, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/305,781

(22) Filed: Jun. 16, 2014

(65) Prior Publication Data

US 2014/0370574 A1 Dec. 18, 2014

Related U.S. Application Data

(60) Provisional application No. 61/835,086, filed on Jun. 14, 2013.

(51) Int. Cl.

| | |
|---|---|
| ***C12N 1/12*** | (2006.01) |
| ***C12P 7/06*** | (2006.01) |
| ***C12N 15/00*** | (2006.01) |
| ***C12P 19/34*** | (2006.01) |
| ***C07H 21/04*** | (2006.01) |
| ***C07K 1/00*** | (2006.01) |

(52) U.S. Cl.

CPC .................................... *C12P 7/065* (2013.01)

(58) Field of Classification Search

CPC ...................................................... C12P 7/065

USPC .......... 435/257.2, 161, 320.1, 91.1; 536/23.1, 536/23.2; 530/350

See application file for complete search history.

(56) References Cited

U.S. PATENT DOCUMENTS

| | | | | |
|---|---|---|---|---|
| 5,750,380 | A | 5/1998 | Itakura et al. | |
| 6,306,639 | B1 | 10/2001 | Woods et al. | |
| 6,472,184 | B1 | 10/2002 | Hegemann | |
| 6,699,696 | B2 | 3/2004 | Woods et al. | |
| 7,785,861 | B2 * | 8/2010 | Devroe et al. | 435/252.3 |
| 7,794,969 | B1 * | 9/2010 | Reppas et al. | 435/41 |
| 7,968,321 | B1 | 6/2011 | Green et al. | |
| 7,981,647 | B2 | 7/2011 | Berry et al. | |
| 8,048,666 | B1 | 11/2011 | Green et al. | |
| 8,163,516 | B2 | 4/2012 | Dehring et al. | |
| 8,216,816 | B2 | 7/2012 | Green et al. | |
| 8,465,954 | B2 | 6/2013 | Green et al. | |
| 8,846,369 | B2 | 9/2014 | Piven et al. | |
| 2013/0252300 | A1 | 9/2013 | Green et al. | |
| 2014/0178958 | A1 * | 6/2014 | Piven et al. | 435/161 |
| 2015/0159178 | A1 | 6/2015 | Green et al. | |

FOREIGN PATENT DOCUMENTS

| | | |
|---|---|---|
| WO | WO2007084477 | 7/2007 |
| WO | WO2009078712 | 6/2009 |
| WO | WO2009098089 | 8/2009 |
| WO | WO/2009/111513 | 9/2009 |
| WO | WO/2010/044960 | 4/2010 |
| WO | WO2011018116 | 2/2011 |
| WO | WO2013098267 | 7/2013 |
| WO | WO2014100799 | 6/2014 |
| WO | WO2014198964 | 12/2014 |

OTHER PUBLICATIONS

Inokuma et al., (2007), "Characterization of enzymes involved in the ethanol production of *Moorella* sp. HUC22-1," Arch. Microbiol. 188:37-45.

Wang et al., (2012), "Application of synthetic biology in cyanobacteria and algae," Frontiers in Microbiology, 3(344): 1-15.

Desai et al., (2013), "Photosynthetic approaches to chemical biotechnology," Current Opinion in Biotechnology, 24:1031-1036.

Deng et al, (1999), "Ethanol synthesis by genetic engineering in cyanobacteria," Applied and Environmental Microbiology, 65:523-528.

Bowie et al., (1990), "Deciphering the Message in Protein Sequences: Tolerance to Amino Acid Substitution," Science 247:1306-1310.

Database EMBL, accession No. cz682401, *Arthrospira maxima* Fosmid Library, Jan. 1, 2006.

International Search Report for corresponding PCT application PCT/EP2014/062594 (Publication No. WO2014198964), Aug. 12, 2014.

Gao et al., (2012) "Photosynthetic production of ethanol from carbon dioxide in genetically engineered cyanobacteria," Energy & Environmental Science 5:9857-9865.

U.S. Appl. No. 61/184,757, filed Jun. 5, 2009.

U.S. Appl. No. 61/121,532, filed Dec. 12, 2008.

U.S. Appl. No. 61/106,543, filed Oct. 17, 2008.

Chinese Patent Application No. 200980114073.0. Document not available. (Chinese National Phase of PCT/US2009/035937, which is submitted herewith).

(Continued)

*Primary Examiner* — Ganapathirama Raghu

(74) *Attorney, Agent, or Firm* — Lawrence B. Ebert; Suzanne G. Jepson

(57) ABSTRACT

A metabolically enhanced cyanobacterial cell for the production of ethanol is provided. The metabolically enhanced cyanobacterial cell for the production of ethanol comprises at least one recombinant gene encoding a pyruvate decarboxylase enzyme (Pdc) converting pyruvate to acetaldehyde, and at least one recombinant gene encoding a first $Zn^{2+}$ dependent alcohol dehydrogenase enzyme (Adh) converting acetaldehyde to ethanol. The invention also provides a method for producing the metabolically enhanced cyanobacterium, a method for producing ethanol with the metabolically enhanced cyanobacterium, and a method for screening of alcohol dehydrogenase enzyme expressing cyanobacterial strains for the presence of NADPH-dependent native alcohol dehydrogenase enzymes.

24 Claims, 48 Drawing Sheets

(56) References Cited

OTHER PUBLICATIONS

Indian Patent Application No. 5951/CHENP/2010. Document not available. (Indian National Phase of PCT/US2009/035937, which is submitted herewith).
European Patent No. 2285948 (European National Phase of PCT/US2009/035937, which is submitted herewith).
U.S. Appl. No. 61/033,411, filed Mar. 3, 2008.
U.S. Appl. No. 61/033,402, filed Mar. 3, 2008.
U.S. Appl. No. 61/044,419, filed Apr. 11, 2008.
U.S. Appl. No. 61/056,999, filed May 29, 2008.
U.S. Appl. No. 61/058,182, filed Jun. 2, 2008.
U.S. Appl. No. 61/077,698, filed Jul. 2, 2008.
U.S. Appl. No. 61/,079,687 filed Jul. 10, 2008.
U.S. Appl. No. 61/079,688, filed Jul. 10, 2008.
U.S. Appl. No. 61/079,656, filed Jul. 10, 2008.
U.S. Appl. No. 61/079,665, filed Jul. 10, 2008.
U.S. Appl. No. 61/079,667, filed Jul. 10, 2008.
U.S. Appl. No. 61/079,673, filed Jul. 10, 2008.
U.S. Appl. No. 61/079,676, filed Jul. 10, 2008.
U.S. Appl. No. 61/079,707, filed Jul. 10, 2008.
U.S. Appl. No. 61/079,699, filed Jul. 10, 2008.
U.S. Appl. No. 61/079,692, filed Jul. 10, 2008.
U.S. Appl. No. 61/086,291, filed Aug. 5, 2008.
U.S. Appl. No. 61/086,288, filed Aug. 5, 2008.
U.S. Appl. No. 61/086,283, filed Aug. 5, 2008.
U.S. Appl. No. 61/086,285 filed Aug. 5, 2008.
U.S. Appl. No. 61/086,417, filed Aug. 5, 2008.
U.S. Appl. No. 61/086,418, filed Aug. 5, 2008.
U.S. Appl. No. 61/086,296, filed Aug. 5, 2008.
U.S. Appl. No. 61/086,300, filed Aug. 5, 2008.
U.S. Appl. No. 61/086,407, filed Aug. 5, 2008.
U.S. Appl. No. 61/086,410, filed Aug. 5, 2008.
U.S. Appl. No. 61/086,412, filed Aug. 5, 2008.
U.S. Appl. No. 61/086,414, filed Aug. 5, 2008.
U.S. Appl. No. 61/100,656, filed Sep. 26, 2008.
U.S. Appl. No. 61/100,665, filed Sep. 26, 2008.
U.S. Appl. No. 61/100,667, filed Sep. 26, 2008.
U.S. Appl. No. 61/100,660, filed Sep. 26, 2008.
U.S. Appl. No. 61/100,663, filed Sep. 26, 2008.
Canadian Patent Application No. 2740400. Document not available. (Canadian National Phase of PCT/US2009/055949, which is submitted herewith).
Chinese Patent Application No. 200980145256.9. Document not available. (Chinese National Phase of PCT/US2009/055949, which is submitted herewith).
European Patent Application No. 2009820965 (EP2344652A0). (Full document not available; EP2344652_A0 submitted herewith. (European National Phase of PCT/US2009/055949, which is submitted herewith).
Israel Patent Application No. 212362. Document not available. (Israel National Phase of PCT/US2009/055949, which is submitted herewith).
Indian Patent Application No. 2444/CHENP/2011. Document not available. (Indian National Phase of PCT/US2009/055949, which is submitted herewith).

* cited by examiner

Sequencing of smaller PCR products from PCR2 revealed:

| PCR product size [bp] | Cultivation N671 | Cultivation N672 |
|---|---|---|
| ~ 800 | Deletion from 2671 – 2923 ≙ ADH 170-422 | Deletion from 2671 – 2923 ≙ ADH 170-422 |
| ~ 400 | Deletion from 2725– 3371 ≙ ADH 244-870 | Deletion from 2725– 3371 ≙ ADH 244-870 |

SEQUENCE LISTING

```
<160> NUMBER OF SEQ ID NOS: 83

<210> SEQ ID NO 1
<211> LENGTH: 339
<212> TYPE: PRT
<213> ORGANISM: Lyngbya sp.

<400> SEQUENCE: 1

Met Ser Glu Thr Lys Phe Lys Ala Tyr Ala Val Met Asn Pro Gly Glu
1               5                   10                  15

Lys Leu Gln Pro Trp Glu Tyr Glu Pro Ala Pro Leu Gln Val Asp Glu
            20                  25                  30

Ile Glu Val Arg Val Thr His Asn Gly Leu Cys His Thr Asp Leu His
        35                  40                  45

Met Arg Asp Asn Asp Trp Asn Val Ser Glu Phe Pro Leu Val Ala Gly
    50                  55                  60

His Glu Val Val Gly Glu Val Thr Ala Val Gly Glu Lys Val Thr Ser
65                  70                  75                  80

Arg Lys Lys Gly Asp Arg Val Gly Val Gly Trp Ile Arg Asn Ser Cys
                85                  90                  95

Arg Ala Cys Asp His Cys Leu Gln Gly Glu Glu Asn Ile Cys Arg Glu
            100                 105                 110

Gly Tyr Thr Gly Leu Ile Val Gly His His Gly Gly Phe Ala Asp Arg
        115                 120                 125

Val Arg Val Pro Ala Asp Phe Thr Tyr Lys Ile Pro Asp Ala Leu Asp
    130                 135                 140

Ser Ala Ser Ala Ala Pro Leu Leu Cys Ala Gly Ile Thr Val Tyr Thr
145                 150                 155                 160
```

```
Pro Leu Arg Thr Tyr Ile Lys His Pro Gly Met Lys Val Gly Val Met
                165                 170                 175

Gly Ile Gly Gly Leu Gly His Leu Ala Ile Lys Phe Ala Arg Ala Met
            180                 185                 190

Gly Ala Glu Val Thr Ala Phe Ser Thr Ser Pro Asn Lys Glu Ala Gln
        195                 200                 205

Ala Lys Glu Phe Gly Ala His His Phe Gln Gln Trp Gly Thr Ala Glu
    210                 215                 220

Glu Met Lys Ala Val Ala Gly Asn Phe Asp Leu Val Leu Ser Thr Ile
225                 230                 235                 240

Ser Ala Glu Thr Asp Trp Asp Ala Ala Phe Ser Leu Leu Ala Asn Asn
                245                 250                 255

Gly Val Leu Cys Phe Val Gly Ile Pro Val Ser Ser Leu Asn Val Pro
            260                 265                 270

Leu Ile Pro Leu Ile Phe Gly Gln Lys Ser Val Val Gly Ser Val Val
        275                 280                 285

Gly Gly Arg Arg Phe Met Ala Glu Met Leu Glu Phe Ala Ala Val Asn
    290                 295                 300

Gln Ile Lys Pro Met Ile Glu Thr Met Pro Leu Ser Gln Val Asn Glu
305                 310                 315                 320

Ala Met Asp Lys Val Ala Ala Asn Lys Ala Arg Tyr Arg Ile Val Leu
                325                 330                 335

Leu Ser Glu


<210> SEQ ID NO 2
<211> LENGTH: 340
<212> TYPE: PRT
<213> ORGANISM: Arthrospira platensis

<400> SEQUENCE: 2

Met Thr Thr Ala Thr Lys Phe Lys Ala Tyr Ala Ala Leu Asn Ser Gly
1               5                   10                  15

Glu Lys Leu Gln Pro Trp Glu Tyr Glu Pro Glu Pro Leu Gln Val Asp
            20                  25                  30

Glu Val Glu Ile Arg Val Thr His Asn Gly Leu Cys His Thr Asp Leu
        35                  40                  45

His Met Arg Asp Asn Asp Trp Asn Val Ser Gln Tyr Pro Leu Val Pro
    50                  55                  60

Gly His Glu Val Val Gly Glu Val Thr Glu Val Gly Glu Lys Val Thr
65                  70                  75                  80

Ser Leu His Lys Gly Asp Arg Ile Gly Val Gly Trp Ile Arg Asn Ser
                85                  90                  95

Cys Arg Ser Cys Asp His Cys Leu Gln Gly Glu Glu Asn Ile Cys Arg
            100                 105                 110

Glu Gly Tyr Thr Gly Leu Ile Val Gly His His Gly Gly Phe Ala Asp
        115                 120                 125

Arg Leu Arg Val Pro Ala Asp Phe Thr Tyr Lys Ile Pro Asp Ala Leu
    130                 135                 140

Asp Ser Ala Ser Ala Ala Pro Leu Leu Cys Ala Gly Ile Thr Val Tyr
145                 150                 155                 160

Thr Pro Leu Arg Thr Tyr Ile Lys His Pro Gly Met Lys Val Gly Val
                165                 170                 175

Met Gly Ile Gly Gly Leu Gly His Leu Ala Ile Lys Phe Ala Arg Ala
            180                 185                 190
```

```
Met Gly Ala Glu Val Thr Ala Phe Ser Thr Ser Leu Asn Lys Gln Glu
        195                 200                 205

Gln Ala Lys Glu Phe Gly Ala His Asn Phe Gln Gln Trp Gly Thr Ala
    210                 215                 220

Glu Glu Met Lys Ala Ile Ala Gly Ser Phe Asp Leu Val Leu Ser Thr
225                 230                 235                 240

Ile Ser Ser Glu Thr Asp Trp Asp Ala Ala Phe Ser Leu Leu Ala Asn
                245                 250                 255

Asn Gly Val Leu Cys Phe Val Gly Ile Pro Val Ser Thr Leu Asn Ile
            260                 265                 270

Pro Leu Ile Pro Leu Ile Phe Gly Gln Lys Ala Val Val Gly Ser Ile
        275                 280                 285

Val Gly Gly Arg Arg Phe Met Ala Glu Met Leu Glu Phe Ala Ala Val
    290                 295                 300

Asn Gln Ile Lys Pro Met Ile Glu Thr Met Pro Leu Ser Gln Ile Asn
305                 310                 315                 320

Glu Ala Met Asp Lys Val Ala Ala Asn Gln Ala Arg Tyr Arg Ile Val
                325                 330                 335

Leu Leu Ala Asp
            340


<210> SEQ ID NO 3
<211> LENGTH: 328
<212> TYPE: PRT
<213> ORGANISM: Cyanothece sp.

<400> SEQUENCE: 3

Met Met Gln Ala Met Ile Leu Arg Ala Ala Lys Glu Lys Leu Arg Val
1               5                   10                  15

Glu Ser Val Pro Ile Pro Gln Pro Gln Ser His Gln Val Leu Val Lys
            20                  25                  30

Val Gln Ala Cys Gly Val Cys Arg Thr Asp Leu His Ile Val Asp Gly
        35                  40                  45

Asp Leu Thr Gln Pro Lys Phe Pro Leu Ile Leu Gly His Gln Ile Val
    50                  55                  60

Gly Ile Val Glu Lys Val Gly Lys Glu Val Arg Lys Phe Ser Pro Gly
65                  70                  75                  80

Met Arg Val Gly Val Pro Trp Leu Gly Lys Thr Cys Gln His Cys Leu
                85                  90                  95

Tyr Cys Gln Thr Gln Arg Glu Asn Leu Cys Asp Glu Ala Arg Phe Thr
            100                 105                 110

Gly Tyr Gln Leu Asp Gly Gly Tyr Ala Asp Tyr Ala Val Ala Asn Glu
        115                 120                 125

Gln Phe Cys Phe Ala Ile Pro Glu Ser Tyr Pro Ser Leu Gln Ala Ala
    130                 135                 140

Pro Leu Leu Cys Ala Gly Leu Ile Gly Tyr Arg Ser Tyr Arg Leu Val
145                 150                 155                 160

Gly Asp Ala Gln Lys Ile Gly Phe Tyr Gly Phe Gly Ala Ala Ala His
                165                 170                 175

Ile Leu Ile Gln Val Ala Arg Tyr Gln Gly Arg Glu Val Tyr Ala Phe
            180                 185                 190

Thr Arg Pro Gly Asp Ser Gln Ser Gln Ala Phe Ala Arg Ser Leu Gly
        195                 200                 205

Ala Val Trp Ala Gly Gly Ser Asp Glu Ser Pro Pro Asp Ile Leu Asp
    210                 215                 220
```

```
Gly Ala Ile Ile Phe Ala Pro Val Gly Ala Leu Val Pro Ala Ala Leu
225                 230                 235                 240

Lys Ala Ile Ala Lys Gly Gly Val Val Val Cys Ala Gly Ile His Met
                245                 250                 255

Ser Asp Ile Pro Ser Phe Pro Tyr Lys Ile Leu Trp Glu Glu Arg Val
            260                 265                 270

Leu Arg Ser Val Ala Asn Leu Thr Arg Gln Asp Gly Glu Glu Phe Leu
        275                 280                 285

Ala Leu Ala Pro Lys Ile Pro Ile Gln Thr Gln Val Ser Ser Phe Ala
    290                 295                 300

Leu Thr Gln Ala Asn Glu Ala Leu Glu Ala Leu Arg Gly Gly Lys Ile
305                 310                 315                 320

Glu Gly Ala Ala Val Leu Val Pro
                325


<210> SEQ ID NO 4
<211> LENGTH: 335
<212> TYPE: PRT
<213> ORGANISM: Synechococcus sp.

<400> SEQUENCE: 4

Met Pro Thr Ile Lys Ala Phe Ala Val His Glu Pro Ser Gly Asp Leu
1               5                   10                  15

Gln Pro Phe Glu Tyr Asp Pro Gly Glu Leu Leu Pro Asp Gln Val Glu
            20                  25                  30

Ile Glu Val Lys Tyr Cys Gly Ile Cys His Ser Asp Leu Ser Met Ile
        35                  40                  45

Gly Asn Glu Trp Gly Met Thr Gln Tyr Pro Leu Val Pro Gly His Glu
    50                  55                  60

Val Val Gly Ala Ile Ala Lys Val Gly Glu Asn Val Lys Asn Leu Ser
65                  70                  75                  80

Val Gly Gln Val Val Gly Leu Gly Trp His Ala Gly Tyr Cys Asn Glu
                85                  90                  95

Cys Pro Gln Cys Thr Thr Gly Asp Gln Asn Leu Cys Ala Thr Ala Gln
            100                 105                 110

Gly Thr Ile Val Gly His His Gly Gly Phe Ala Glu Lys Val Arg Ala
        115                 120                 125

Ala Ala Asn Ser Val Val Pro Ile Pro Asp Gly Ile Asp Leu Glu Ala
    130                 135                 140

Ala Gly Pro Leu Phe Cys Gly Gly Ile Thr Val Phe Asn Pro Leu Val
145                 150                 155                 160

Gln Tyr Gly Ile Gln Pro Thr Ser Lys Val Ala Val Leu Gly Ile Gly
                165                 170                 175

Gly Leu Gly His Met Ala Val Gln Phe Leu Asn Ala Trp Gly Cys Glu
            180                 185                 190

Val Thr Ala Phe Thr Ser Ser Glu Ala Lys Ile Thr Glu Ala Leu Glu
        195                 200                 205

Leu Gly Ala His His Thr Leu Asn Ser Arg Asp Pro Glu Ala Ile Ala
    210                 215                 220

Ala Ala Ala Gly Gln Phe Asp Leu Ile Ile Ser Thr Val Asn Val Lys
225                 230                 235                 240

Leu Asp Trp Asn Ala Tyr Leu Ser Thr Leu Lys Pro His Gly Arg Leu
                245                 250                 255

His Phe Val Gly Ala Thr Leu Asp Pro Leu Asp Ile Asn Val Phe Ala
```

```
            260                 265                 270

Leu Ile Met Gln Gln Arg Ser Ile Ser Gly Ser Pro Val Gly Ser Pro
        275                 280                 285

Ala Thr Ile Ala Lys Met Leu Glu Phe Ala Lys Leu His Asn Ile Gln
    290                 295                 300

Pro Lys Ile Glu Thr Phe Lys Phe Ala Asp Val Asn Lys Ala Ile Ala
305                 310                 315                 320

Arg Leu Lys Ser Gly Glu Ala His Tyr Arg Ile Val Leu Cys Arg
                325                 330                 335


<210> SEQ ID NO 5
<211> LENGTH: 335
<212> TYPE: PRT
<213> ORGANISM: Synechococcus sp.

<400> SEQUENCE: 5

Met Pro Thr Ile Lys Ala Phe Ala Ile His Glu Pro Ser Gly Asp Leu
1               5                   10                  15

Gln Pro Phe Glu Tyr Asp Pro Gly Glu Leu Leu Pro Asp Gln Val Glu
            20                  25                  30

Ile Glu Val Lys Tyr Cys Gly Ile Cys His Ser Asp Leu Ser Met Ile
        35                  40                  45

Gly Asn Glu Trp Gly Met Thr Gln Tyr Pro Leu Val Pro Gly His Glu
    50                  55                  60

Val Val Gly Ala Ile Ala Lys Val Gly Lys Asn Val Lys Asn Leu Ser
65                  70                  75                  80

Val Gly Gln Val Val Gly Leu Gly Trp His Ala Gly Tyr Cys Asn Glu
                85                  90                  95

Cys Ser Gln Cys Thr Thr Gly Asp Gln Asn Leu Cys Ala Thr Ala Gln
            100                 105                 110

Gly Thr Ile Val Gly His His Gly Gly Phe Ala Glu Lys Val Arg Ala
        115                 120                 125

Ala Ala Asn Ser Val Val Pro Ile Pro Asp Gly Ile Asp Leu Glu Ala
    130                 135                 140

Ala Gly Pro Leu Phe Cys Gly Gly Ile Thr Val Phe Asn Pro Leu Met
145                 150                 155                 160

Gln Tyr Gly Ile Gln Pro Thr Ser Lys Val Ala Val Leu Gly Ile Gly
                165                 170                 175

Gly Leu Gly His Met Ala Val Gln Phe Leu Asn Ala Trp Gly Cys Glu
            180                 185                 190

Val Thr Ala Phe Thr Ser Ser Glu Ala Lys Ile Thr Glu Ala Leu Glu
        195                 200                 205

Leu Gly Ala His His Thr Leu Asn Ser Arg Asp Pro Glu Ala Ile Ala
    210                 215                 220

Ala Ala Ala Gly Gln Phe Asp Leu Ile Ile Ser Thr Val Asn Val Lys
225                 230                 235                 240

Leu Asp Trp Asn Ala Tyr Leu Ser Thr Leu Lys Pro His Gly Arg Leu
                245                 250                 255

His Phe Val Gly Ala Thr Leu Asp Pro Leu Asp Ile Asn Val Phe Ala
            260                 265                 270

Leu Ile Met Gln Gln Arg Ser Ile Ser Gly Ser Pro Val Gly Ser Pro
        275                 280                 285

Ala Thr Ile Ala Lys Met Leu Glu Phe Ala Lys Leu His Asn Ile Gln
    290                 295                 300
```

```
Pro Lys Ile Glu Thr Phe Lys Phe Ala Asp Val Asn Lys Ala Ile Ala
305                 310                 315                 320

Arg Leu Lys Ser Gly Glu Ala His Tyr Arg Ile Val Leu Cys Arg
                325                 330                 335


<210> SEQ ID NO 6
<211> LENGTH: 335
<212> TYPE: PRT
<213> ORGANISM: Synechococcus sp.

<400> SEQUENCE: 6

Met Pro Met Ile Lys Ala Phe Ala Val His Glu Ser Asp Gly Asp Leu
1               5                   10                  15

Gln Pro Phe Glu Tyr Asp Pro Gly Ala Leu Leu Ser Asp Gln Val Glu
            20                  25                  30

Ile Glu Val Lys Tyr Cys Gly Ile Cys His Ser Asp Leu Ser Met Ile
        35                  40                  45

Ser Asn Glu Trp Gly Met Thr Gln Tyr Pro Leu Val Pro Gly His Glu
    50                  55                  60

Val Val Gly Ala Ile Ala Lys Val Gly Glu Asn Val Lys Asn Leu Ser
65                  70                  75                  80

Val Gly Gln Ile Val Gly Leu Gly Trp His Ala Gly Tyr Cys Asn Glu
                85                  90                  95

Cys Pro Gln Cys Thr Thr Gly Asp Gln Asn Leu Cys Ala Thr Ala Gln
            100                 105                 110

Gly Thr Ile Val Gly His His Gly Gly Phe Ala Glu Lys Val Arg Ala
        115                 120                 125

Ala Ala Asn Ser Val Val Pro Ile Pro Glu Gly Ile Asp Leu Glu Ala
    130                 135                 140

Ala Gly Pro Leu Phe Cys Gly Gly Ile Thr Val Phe Asn Pro Leu Val
145                 150                 155                 160

Gln Tyr Gly Ile Gln Pro Thr Ala Lys Val Ala Val Ile Gly Ile Gly
                165                 170                 175

Gly Leu Gly His Met Ala Val Gln Phe Leu Asn Ala Trp Gly Cys Glu
            180                 185                 190

Val Thr Ala Phe Thr Ser Ser Glu Ala Lys Ile Thr Glu Ala Leu Glu
        195                 200                 205

Leu Gly Ala His His Thr Leu Asn Ser Arg Asp Pro Glu Ala Ile Ala
    210                 215                 220

Ala Ala Ala Gly Gln Phe Asp Leu Ile Ile Ser Thr Val Asn Val Lys
225                 230                 235                 240

Leu Asp Trp Asn Ala Tyr Leu Ser Thr Leu Lys Pro His Gly Arg Leu
                245                 250                 255

His Phe Val Gly Ala Thr Leu Asp Pro Leu Asp Ile Asn Val Phe Ala
            260                 265                 270

Leu Ile Met Gln Gln Arg Ser Ile Ser Gly Ser Pro Val Gly Ser Pro
        275                 280                 285

Ala Thr Ile Ala Lys Met Leu Glu Phe Ala Lys Leu His Lys Ile Gln
    290                 295                 300

Pro Lys Ile Glu Thr Phe Lys Phe Glu Asp Val Asn Gln Ala Ile Ala
305                 310                 315                 320

Arg Leu Lys Ser Gly Glu Ala His Tyr Arg Ile Val Leu Cys Arg
                325                 330                 335


<210> SEQ ID NO 7
```

```
<211> LENGTH: 333
<212> TYPE: PRT
<213> ORGANISM: Chroococcidiopsis sp.

<400> SEQUENCE: 7

Met Ile Arg Ala Tyr Ala Ala Leu Glu Lys Gly Gly Glu Leu Lys Pro
1               5                   10                  15

Phe Glu Tyr Glu Pro Lys Pro Leu Gly Ser Glu Asp Val Glu Ile Asp
            20                  25                  30

Val Glu Tyr Cys Gly Ile Cys His Ser Asp Leu Ser Met Leu His Asn
        35                  40                  45

Asp Trp Gly Met Thr Gln Tyr Pro Phe Val Pro Gly His Glu Val Val
    50                  55                  60

Gly Lys Ile Ala Asp Val Gly Ser Ala Val Lys Lys Leu Gln Val Gly
65                  70                  75                  80

Gln Arg Val Gly Leu Gly Trp Tyr Ser Arg Ser Cys Met Thr Cys Glu
                85                  90                  95

Trp Cys Met Ser Gly Asn His Asn Leu Cys Ala Thr Ala Glu Gly Thr
            100                 105                 110

Ile Val Gly Arg Tyr Gly Gly Phe Ala Asp Lys Val Arg Ala His Glu
        115                 120                 125

Ala Trp Val Ala Pro Leu Pro Asp Ala Met Gln Pro Val Ser Ala Gly
    130                 135                 140

Pro Leu Phe Cys Gly Gly Ile Thr Val Phe Asn Pro Ile Val Gln Phe
145                 150                 155                 160

Asp Val Lys Pro Thr Asp Arg Val Gly Val Ile Gly Ile Gly Gly Leu
                165                 170                 175

Gly His Met Ala Leu Arg Phe Leu His Ala Trp Gly Cys Asp Val Ser
            180                 185                 190

Ala Phe Ser Ser Ser Ala Asp Lys Glu Pro Glu Ala Arg Glu Met Gly
        195                 200                 205

Ala Asn His Phe Ile Asn Ser Arg Asp Pro Asn Ala Leu Lys Ser Val
    210                 215                 220

Glu Gly Ser Phe Asp Leu Ile Leu Ser Thr Val Asn Ala Asp Leu Asp
225                 230                 235                 240

Trp Ser Thr Tyr Ile Ala Cys Leu Arg Pro Lys Gly Arg Leu His Phe
                245                 250                 255

Val Gly Val Val Pro Asn Pro Ile Ser Thr Glu Ile Phe Pro Leu Ile
            260                 265                 270

Met Ala Gln Arg Ser Ile Ser Gly Ser Pro Leu Gly Ser Pro Ala Thr
        275                 280                 285

Val Thr Gln Met Leu Asp Phe Ala Thr Arg His Gln Ile Glu Pro Ile
    290                 295                 300

Ile Glu Thr Phe Ser Phe Asp Gln Val Asn Glu Ala Leu Glu His Leu
305                 310                 315                 320

Arg Ser Gly Lys Ala Arg Tyr Arg Ile Val Leu Lys His
                325                 330


<210> SEQ ID NO 8
<211> LENGTH: 392
<212> TYPE: PRT
<213> ORGANISM: Arthronema africanum

<400> SEQUENCE: 8

Met Asp Thr Pro Val Pro Asn Glu Ser Ala Gly Ser Asp Glu Arg Gln
1               5                   10                  15
```

```
Leu Gln Pro Ala Gly Cys Asp Ile Thr Leu Gly Gln Gly Arg Ser Arg
            20                  25                  30

Pro Val Phe Ser His Arg Pro Ile Ser Pro Leu Gln Cys Lys Ala Asp
        35                  40                  45

Gln Ser His Ser Val Arg Gln Ala Phe Phe Pro Met Ile Lys Ala Tyr
    50                  55                  60

Ala Val His Glu Pro Gly Gly Gln Leu Glu His Phe Glu Tyr Asp Pro
65                  70                  75                  80

Gly Pro Leu Gly Lys Gln Glu Val Glu Ile Gln Val Glu Tyr Cys Gly
                85                  90                  95

Ile Cys His Ser Asp Leu Ser Met Val Asp Asn Glu Trp Gly Ile Ser
            100                 105                 110

Gln Tyr Pro Leu Val Pro Gly His Glu Val Ile Gly Ala Ile Ala Ala
        115                 120                 125

Val Gly Glu Glu Val Thr Thr Leu Ser Val Gly Gln Arg Val Gly Leu
    130                 135                 140

Gly Trp Phe Ser Gln Ser Cys Met His Cys Glu Trp Cys Met Ser Gly
145                 150                 155                 160

Asp His Asn Leu Cys Gln Thr Ala Glu Ser Thr Ile Val Gly Arg Tyr
                165                 170                 175

Gly Gly Phe Ala Asp Arg Val Arg Ala His Gln Glu Trp Ala Ile Pro
            180                 185                 190

Leu Pro Ala Asp Leu Asp Pro Ala Lys Val Gly Pro Leu Phe Cys Gly
        195                 200                 205

Gly Leu Thr Val Phe Asn Pro Ile Ile Gln Leu Asn Ile Gln Pro Thr
    210                 215                 220

Asp Lys Val Gly Val Leu Gly Ile Gly Gly Leu Gly His Met Ala Leu
225                 230                 235                 240

Arg Phe Leu His Ala Trp Gly Cys Asp Val Thr Ala Phe Ser Thr Ser
                245                 250                 255

Pro Asp Lys Glu Ala Glu Ala Arg Glu Leu Gly Ala Asn His Phe Ile
            260                 265                 270

Asn Ser Arg Asp Pro Ala Ala Leu Lys Ser Val Glu Asn Thr Phe Asp
        275                 280                 285

Val Ile Ile Ser Thr Ile Ala Ala Asp Leu Asp Trp Ser Thr Tyr Ile
    290                 295                 300

Ala Ala Leu Arg Pro Lys Gly Arg Leu His Leu Val Gly Val Ala Pro
305                 310                 315                 320

Ser Pro Ile Ala Thr His Ile Phe Pro Met Ile Ser Gly Gln Lys Ser
                325                 330                 335

Leu Ser Gly Ser Pro Leu Gly Ser Pro Ala Thr Ala Ala Arg Met Leu
            340                 345                 350

Asp Phe Ala Ala Arg His Gly Ile Glu Pro Ile Val Glu Val Phe Ser
        355                 360                 365

Phe Asp Gln Val Asn Glu Ala Ile Glu Lys Leu Arg Asn Gly Gln Pro
    370                 375                 380

Arg Tyr Arg Leu Val Leu Lys His
385                 390
```

<210> SEQ ID NO 9
<211> LENGTH: 333
<212> TYPE: PRT
<213> ORGANISM: Chroococcidiopsis sp.

<400> SEQUENCE: 9

```
Met Ile Arg Ala Tyr Ala Ala Leu Glu Lys Gly Gly Glu Leu Lys Pro
1               5                   10                  15

Phe Glu Tyr Asp Pro Lys Pro Leu Gly Ser Glu Asp Val Glu Ile Asp
            20                  25                  30

Val Glu Tyr Cys Gly Ile Cys His Ser Asp Leu Ser Met Leu His Asn
        35                  40                  45

Asp Trp Gly Met Thr Gln Tyr Pro Phe Val Pro Gly His Glu Val Val
    50                  55                  60

Gly Lys Ile Ala Asp Val Gly Ser Ala Val Lys Lys Leu Gln Val Gly
65                  70                  75                  80

Gln Arg Val Gly Leu Gly Trp Tyr Ser Arg Ser Cys Met Thr Cys Glu
                85                  90                  95

Trp Cys Met Ser Gly Asn His Asn Leu Cys Ala Thr Ala Glu Gly Thr
            100                 105                 110

Ile Val Gly Arg Tyr Gly Gly Phe Ala Asp Lys Val Arg Ala His Glu
        115                 120                 125

Ala Trp Val Val Pro Leu Pro Glu Ala Met Gln Pro Val Ser Ala Gly
    130                 135                 140

Pro Leu Phe Cys Gly Gly Ile Thr Val Phe Asn Pro Ile Val Gln Phe
145                 150                 155                 160

Asp Val Lys Pro Thr Asp Arg Val Gly Val Ile Gly Ile Gly Gly Leu
                165                 170                 175

Gly His Met Ala Leu Arg Phe Leu His Ala Trp Gly Cys Asp Val Ser
            180                 185                 190

Ala Phe Ser Ser Ser Ala Asp Lys Glu Ala Glu Ala Arg Glu Met Gly
        195                 200                 205

Ala Asn His Phe Ile Asn Ser Arg Asp Pro Asn Ala Leu Lys Ser Val
    210                 215                 220

Glu Gly Ser Phe Asp Leu Ile Leu Ser Thr Val Asn Val Asp Leu Asp
225                 230                 235                 240

Trp Asn Thr Tyr Ile Ala Cys Leu Arg Pro Lys Gly Arg Leu His Phe
                245                 250                 255

Val Gly Val Val Pro Asn Pro Val Ser Ser Gln Val Phe Pro Leu Ile
            260                 265                 270

Ser Gly Gln Lys Ser Leu Ser Gly Ser Pro Leu Gly Ser Pro Ala Thr
        275                 280                 285

Val Val Gln Met Leu Asp Phe Ala Thr Arg His Gln Ile Glu Pro Ile
    290                 295                 300

Ile Glu Thr Phe Ser Phe Asp Gln Val Asn Glu Ala Leu Glu His Leu
305                 310                 315                 320

His Ser Gly Lys Ala Arg Tyr Arg Ile Val Leu Lys His
                325                 330
```

<210> SEQ ID NO 10
<211> LENGTH: 336
<212> TYPE: PRT
<213> ORGANISM: Cyanobacterium sp.

<400> SEQUENCE: 10

```
Met Thr Ile Val Asn Ala Tyr Ala Ala His Glu Ile Gly Gly Ile Leu
1               5                   10                  15

Lys Pro Phe Gln Tyr Glu Leu Pro Pro Ile Gly Ala Tyr Glu Val Asp
            20                  25                  30
```

```
Ile Gln Val Gln His Cys Gly Ile Cys His Ser Asp Leu Ser Leu Leu
        35                  40                  45

Glu Asn Ala Trp Gly Val Thr Gln Tyr Pro Phe Val Pro Gly His Glu
    50                  55                  60

Ile Val Gly Thr Val Leu Ala Val Gly Gln Asp Val Val His Leu Lys
65                  70                  75                  80

Lys Gly Asp Arg Val Gly Leu Gly Trp His Ser Ala Tyr Cys Leu His
                85                  90                  95

Cys Asp Gln Cys Leu Thr Gly Asn His Asn Met Cys Tyr Ser Ala Gln
            100                 105                 110

Ala Thr Ile Val Gly Arg His Gly Gly Phe Ala Asp Ile Val Arg Ala
        115                 120                 125

Lys Val Pro Ser Val Val Lys Leu Pro Asp Ser Val Asp Met Arg Thr
    130                 135                 140

Ala Gly Pro Leu Leu Cys Gly Gly Ile Thr Val Phe Asn Pro Leu Ile
145                 150                 155                 160

Gln Phe Asn Ile Leu Pro Thr Ala Lys Val Gly Val Ile Gly Ile Gly
                165                 170                 175

Gly Leu Gly His Ile Ala Val Gln Ile Leu Arg Ala Trp Gly Cys Glu
            180                 185                 190

Val Thr Ala Phe Thr Ser Ser Glu Ser Lys Ile Glu Glu Ala Leu Lys
        195                 200                 205

Met Gly Ala Asn Lys Thr Leu Asn Ser Arg Asp Ser Glu Glu Leu Lys
    210                 215                 220

Ser Ala Glu Asn Ser Phe Asp Leu Ile Leu Ser Thr Val Asn Val Glu
225                 230                 235                 240

Leu Asp Trp Ser Thr Tyr Leu Ser Leu Leu Lys Pro Lys Gly Arg Leu
                245                 250                 255

His Leu Leu Gly Val Val Leu Glu Pro Leu Asn Leu Ser Val Ser Ser
            260                 265                 270

Leu Leu Ser Arg Gln Lys Ser Val Ser Ala Ser Pro Val Gly Ser Pro
        275                 280                 285

Asn Ala Ile Ala Gln Met Leu Glu Phe Cys Gln Arg His Asn Ile Lys
    290                 295                 300

Pro Ile Thr Gln His Phe Pro Leu Lys Glu Val Asn Glu Ala Met Glu
305                 310                 315                 320

His Leu Arg Ala Gly Lys Ala Arg Tyr Arg Val Val Leu Asp Met Asn
                325                 330                 335


<210> SEQ ID NO 11
<211> LENGTH: 334
<212> TYPE: PRT
<213> ORGANISM: Microcystis aeruginosa PCC7806

<400> SEQUENCE: 11

Met Ile Arg Ala Tyr Ala Ala Gln Glu Lys Gly Gly Lys Leu Glu Pro
1               5                   10                  15

Phe Asp Tyr Asp Pro Gly Ile Leu Ala Asp Glu Asp Val Glu Ile Ala
            20                  25                  30

Val Glu Tyr Cys Gly Ile Cys His Ser Asp Leu Ser Met Leu Asp Asn
        35                  40                  45

Asp Trp Gly Leu Thr Thr Tyr Pro Phe Val Pro Gly His Glu Val Val
    50                  55                  60

Gly Thr Ile Ala Ala Leu Gly Ala Lys Val Lys Glu Leu Lys Leu Gly
65                  70                  75                  80
```

```
Gln Arg Val Gly Leu Gly Trp Phe Ser Arg Ser Cys Ser Thr Cys Glu
                85                  90                  95

Thr Cys Met Ser Gly Asp Gln Asn Leu Cys Ala Thr Ala Glu Gly Thr
            100                 105                 110

Ile Val Gly Arg His Gly Gly Phe Ala Glu Arg Val Arg Ala His His
        115                 120                 125

Ser Trp Leu Val Pro Leu Pro Asp Gln Leu Asp Ala Ala Lys Ala Gly
    130                 135                 140

Pro Leu Phe Cys Gly Gly Ile Thr Val Phe Asn Pro Ile Val Gln Phe
145                 150                 155                 160

Asn Ile Lys Pro Thr Ala Arg Val Gly Val Ile Gly Ile Gly Gly Leu
                165                 170                 175

Gly His Ile Ala Leu Lys Phe Leu Lys Ala Trp Gly Cys Glu Val Thr
            180                 185                 190

Ala Phe Ser Ser Ser Pro Asp Lys Glu Thr Glu Ala Lys Glu Leu Gly
        195                 200                 205

Ala Thr His Phe Ile Asn Ser Arg Asp Pro Glu Ala Leu Gln Ser Val
    210                 215                 220

Gln Asn Tyr Phe Asp Phe Ile Ile Ser Thr Val Asn Val Asn Leu Asp
225                 230                 235                 240

Trp Gly Leu Tyr Ile Ala Cys Leu Arg Pro Lys Gly Arg Leu His Ile
                245                 250                 255

Val Gly Ala Val Leu Glu Pro Met Ala Thr Tyr Ala Phe Pro Leu Ile
            260                 265                 270

Met Gly Gln Lys Ser Ile Ser Gly Ser Pro Leu Gly Ser Pro Ser Thr
        275                 280                 285

Val Ser Lys Met Ile Glu Phe Ala Ser Arg His Gly Ile Glu Pro Val
    290                 295                 300

Thr Glu Thr Tyr Pro Ile Ser Arg Val Asn Glu Ala Met Glu Lys Leu
305                 310                 315                 320

Arg Thr Gly Gln Pro Lys Tyr Arg Leu Val Leu Gln Ile Lys
                325                 330
```

<210> SEQ ID NO 12
<211> LENGTH: 34
<212> TYPE: DNA
<213> ORGANISM: Cyanobacterium sp.

<400> SEQUENCE: 12

```
gagttcggaa aagagaaaag gataaaagta gatg                                34
```

<210> SEQ ID NO 13
<211> LENGTH: 3186
<212> TYPE: DNA
<213> ORGANISM: Cyanobacterium sp.

<400> SEQUENCE: 13

```
atgatactcg gaaaacctag caattctcaa cccctaaaca aaagaaactt ccaaaaccct     60

gaccatataa aggagtggca acaatcagca atcagtcaag atttgatagc agaaaatctt    120

gtatcggttg ctaatggttt tgatgtacta tttatcggca ataaataccg aactaacacg    180

ggtgttctgt cacggcacat attaaactcc tattctcatt tagaagatgg tggttcgtat    240

ggtagaacat ttgacccatt taccaataaa gaaatgcagt gggttcaatt taaaccgaat    300

agaccaagaa aaggttctac tggtaaggta atcaaatatg aatcgccaaa aggtgaacct    360
```

```
acaagagttc taatgccgtt tgtgcctatg aaaatatggc aacggattag cgataagttc    420
ggagtaccga ttaatccgaa aaaagatact cacttttggg aatgggtaaa gaataatcca    480
tcgataccga ttgccattac agaaggaaat aaaaaagcta attgcctatt atcctatggc    540
tatcctgcta ttgcctttgt aggcatttgg aacggattag agaaaataaa tgatttctcg    600
aaggaaaagc agttaaaaga ggatttgaaa tggttgttat ccaacggcaa ccgaaatatt    660
aatatcatct ttgaccaaga ccagaaacaa aaaactgtaa ttaatgtaaa caaagctatt    720
ttcgctttat cttctctaat aagtagaaat ggtcataaag ttaatattgt gcaatggttg    780
ccgtcaaaag gtaaaggaat agatgattat ttggtagctt tacctttga gaaaagagaa    840
aatcatttag acaacttaat taaaattgca ccatcattta atttttggtc aactaaatac    900
ttattcaagt gtcgtaaacc agatttaacc gtaaattgcc gttatttgag cgatgcagta    960
aaagaattac ctcaagagga tatagcatta atagcacctc acggcacggg taaaacttca   1020
ttagtagcta ctcacgttaa gaatcggagt tatcacggaa ggaaaactat ttcattggtg   1080
catcttgaaa gtttagccaa agctaatggc aacgcacttg gattatatta ccgaaccgaa   1140
aataatattg aaaagcaata tcttggattt agcttatgtg tagatagttg ccgtgataag   1200
attaacggca ttacaactga tattatttca ggtcaagatt attgcctttt cattgatgaa   1260
attgaccaag taattccaca catccttaac agtgaaactg aagtaagtaa gtatagatgc   1320
accatcattg acactttttc tgaactggtg agaaatgctg aacaggtcat tattgctgat   1380
gctgatttat ccgatgtgac gattgaccta atagaaaaca tcagaggtaa aaaactatat   1440
gtaatcaaga atgaatatca gtatcaggga atgactttta acgccgttgg ttcaccatta   1500
gaaatgatgg caatgatggg aaaatcggtg tcagaaggca agaaattatt tattaacacc   1560
acatcccaaa aggcaaaaag taagtacggc acaatcgctc ttgagtctta tatttttggt   1620
ctaaataaag aagcaaagat attaagaata gactctgaaa ccactaaaaa ccctgaacat   1680
ccagcctata aaatcattga ccaagactta aataatatcc tcaaagatta tgattatgtc   1740
attgcctcac cttgccttca aacaggtgtc agtattacct taaaagggca ttttgaccag   1800
caatttaact tttccagtgg aaacattaca cctcattgct tttacagca aatgtggcgg   1860
ttgagggatg cagaaattga aagattctat tatgtgccga actcatctaa cctcaatctc   1920
attgggaata agtcaagttc accatcagac cttctaaaga gcaataacaa gatggcaacg   1980
gcaacggtta accttttggg tagaatcgac tccgaatatt ccctagagta tgaatcgcac   2040
ggcatttggc ttgagacgtg ggcaaaatta tcagcacggc ataacagttc aatgcgttgt   2100
tactctgaaa ttcttaccta tctaattacg tctcaagggc ataaattaaa tatcaacatt   2160
ccctcacctc ttgcagatat taagaagcta aatgatgagg taagtagtaa cagggaaaag   2220
gtaaaaaatg agagatactc tcagaggtta aactcaccag atattaacga tgcagaagct   2280
accatactcg aatctaaaga gcaaaaaatc ggattgactc tcaatgagag atgcacccta   2340
gaaaagcata aagttaagaa gcggtatggg aatgtaaaga tggatattct cacctttgat   2400
gatgatggac tataccccaa actcagacta ttttattacc tcaccatcgg taaacctcat   2460
ctcaaggcta atgacagaaa agctattgcc aaaatgggca atgacaataa aggcaagatt   2520
ctatcaaaag acttagttaa taaaacttac tccgctcgtg tgaaggtctt agagattctt   2580
aaactaactg actttatcga caatcttaga gatgaactct taataactcc caataatcca   2640
gctatcaccg attttaataa tcttctgcta agagctaaga aggatttaag agtattagga   2700
gtcaacatcg gaaaatatcc aatggccaac attaatgccg tacttactct cattggtcac   2760
```

```
aaactttctg taatgagaga tgagttcgga aaagagaaaa ggataaaagt agatggtaaa   2820

tcataccgat gttatcaact tgaaacatta ccagatttta ccaatgatac tcttgactac   2880

tggttagaaa atgatagcca aaaagaagta acagcaacag aaaattactc cgaaaatttt   2940

aacccttcaa atagctacaa tccagacagt aagacacttt cagagggtgc aaatttccta   3000

tatataaata aagaagaatt gcatccaaat aaattgcacc tagaaataaa agaaggtgct   3060

gaactttttt tattcggggt aaaggtgatt gtgaaaggaa tcttggacgg ggcagtaact   3120

atattctcta tgggtcaaga atacgattta tccctcaatg aactagaggg gatgttaaca   3180

tcatga                                                               3186
```

<210> SEQ ID NO 14
<211> LENGTH: 6828
<212> TYPE: DNA
<213> ORGANISM: Cyanobacterium sp.

<400> SEQUENCE: 14

```
aatatttttc gtcagatacg caaaccttac aaacataatt aacaactgaa actattgata     60

tgtctaggtt ttagctctat cacaggttgt tagacaccct gtcatgtatt ttatattatt    120

tatttcacca tacggattaa gtgaaaccta atgaaaatag tactttcgga gctttaactt    180

taatgaaggt atgttttttt atagacatcg atgtctggtt taacaatagg aaaaagtagc    240

taaaactccc atgaattaaa gaaataacaa ggtgtctaac aacctgttat taagaatgtt    300

agaaaagact taacatttgt gttgagtttt tatagacatt ggtgtctaga catacggtag    360

ataaggtttg ctcaaaaata aaataaaaaa agattggact aaaaaacatt taatttagta    420

caatttaatt agttattttt tcgtctcaaa ttttgctttg ttgagcagaa atttagataa    480

aaaaatcccc gtgatcagat tacaatgtcg ttcattgtac gatgtgtcga aaaatcttta    540

cgacactcta aactgaccac acgggggaaa aagaaaactg aactaataac atcatgatac    600

tcggaaaacc tagcaattct caacccctaa acaaaagaaa cttccaaaac cctgaccata    660

taaaggagtg gcaacaatca gcaatcagtc aagatttgat agcagaaaat cttgtatcgg    720

ttgctaatgg ttttgatgta ctatttatcg gcaataaata ccgaactaac acgggtgttc    780

tgtcacggca catattaaac tcctattctc atttagaaga tggtggttcg tatggtagaa    840

catttgaccc atttaccaat aaagaaatgc agtgggttca atttaaaccg aatagaccaa    900

gaaaaggttc tactggtaag gtaatcaaat atgaatcgcc aaaaggtgaa cctacaagag    960

ttctaatgcc gtttgtgcct atgaaaatat ggcaacggat tagcgataag ttcggagtac   1020

cgattaatcc gaaaaaagat actcactttt gggaatgggt aaagaataat ccatcgatac   1080

cgattgccat tacagaagga aataaaaaag ctaattgcct attatcctat ggctatcctg   1140

ctattgcctt tgtaggcatt tggaacggat tagagaaaat aaatgatttc tcgaaggaaa   1200

agcagttaaa agaggatttg aaatggttgt tatccaacgg caaccgaaat attaatatca   1260

tctttgacca agaccagaaa caaaaaactg taattaatgt aaacaaagct attttcgctt   1320

tatcttctct aataagtaga aatggtcata aagttaatat tgtgcaatgg ttgccgtcaa   1380

aaggtaaagg aatagatgat tatttggtag ctttaccttt tgagaaaaga gaaaatcatt   1440

tagacaactt aattaaaatt gcaccatcat ttaatttttg gtcaactaaa tacttattca   1500

agtgtcgtaa accagattta accgtaaatt gccgttattt gagcgatgca gtaaaagaat   1560

tacctcaaga ggatatagca ttaatagcac ctcacggcac gggtaaaact tcattagtag   1620
```

```
ctactcacgt taagaatcgg agttatcacg gaaggaaaac tatttcattg gtgcatcttg   1680
aaagtttagc caaagctaat ggcaacgcac ttggattata ttaccgaacc gaaaataata   1740
ttgaaaagca atatcttgga tttagcttat gtgtagatag ttgccgtgat aagattaacg   1800
gcattacaac tgatattatt tcaggtcaag attattgcct tttcattgat gaaattgacc   1860
aagtaattcc acacatcctt aacagtgaaa ctgaagtaag taagtataga tgcaccatca   1920
ttgacacttt ttctgaactg gtgagaaatg ctgaacaggt cattattgct gatgctgatt   1980
tatccgatgt gacgattgac ctaatagaaa acatcagagg taaaaaacta tatgtaatca   2040
agaatgaata tcagtatcag ggaatgactt ttaacgccgt tggttcacca ttagaaatga   2100
tggcaatgat gggaaaatcg gtgtcagaag gcaagaaatt atttattaac accacatccc   2160
aaaaggcaaa aagtaagtac ggcacaatcg ctcttgagtc ttatattttt ggtctaaata   2220
aagaagcaaa gatattaaga atagactctg aaaccactaa aaaccctgaa catccagcct   2280
ataaaatcat tgaccaagac ttaaataata tcctcaaaga ttatgattat gtcattgcct   2340
caccttgcct tcaaacaggt gtcagtatta ccttaaaagg gcattttgac cagcaattta   2400
acttttccag tggaaacatt acacctcatt gctttttaca gcaaatgtgg cggttgaggg   2460
atgcagaaat tgaaagattc tattatgtgc cgaactcatc taacctcaat ctcattggga   2520
ataagtcaag ttcaccatca gaccttctaa agagcaataa caagatggca acggcaacgg   2580
ttaacctttt gggtagaatc gactccgaat attccctaga gtatgaatcg cacggcattt   2640
ggcttgagac gtgggcaaaa ttatcagcac ggcataacag ttcaatgcgt tgttactctg   2700
aaattcttac ctatctaatt acgtctcaag ggcataaatt aaatatcaac attccctcac   2760
ctcttgcaga tattaagaag ctaaatgatg aggtaagtag taacagggaa aaggtaaaaa   2820
atgagagata ctctcagagg ttaaactcac cagatattaa cgatgcagaa gctaccatac   2880
tcgaatctaa agagcaaaaa atcggattga ctctcaatga gagatgcacc ctagaaaagc   2940
ataaagttaa gaagcggtat gggaatgtaa agatggatat tctcaccttt gatgatgatg   3000
gactataccc caaactcaga ctattttatt acctcaccat cggtaaacct catctcaagg   3060
ctaatgacag aaaagctatt gccaaaatgg gcaatgacaa taaaggcaag attctatcaa   3120
aagacttagt taataaaact tactccgctc gtgtgaaggt cttagagatt cttaaactaa   3180
ctgactttat cgacaatctt agagatgaac tcttaataac tcccaataat ccagctatca   3240
ccgattttaa taatcttctg ctaagagcta agaaggattt aagagtatta ggagtcaaca   3300
tcggaaaata tccaatggcc aacattaatg ccgtacttac tctcattggt cacaaacttt   3360
ctgtaatgag agatgagttc ggaaaagaga aaaggataaa agtagatggt aaatcatacc   3420
gatgttatca acttgaaaca ttaccagatt ttaccaatga tactcttgac tactggttag   3480
aaaatgatag ccaaaaagaa gtaacagcaa cagaaaatta ctccgaaaat tttaaccctt   3540
caaatagcta caatccagac agtaagacac tttcagaggg tgcaaatttc ctatatataa   3600
ataaagaaga attgcatcca aataaattgc acctagaaat aaaagaaggt gctgaacttt   3660
ttttattcgg ggtaaaggtg attgtgaaag gaatcttgga cggggcagta actatattct   3720
ctatgggtca agaatacgat ttatccctca atgaactaga ggggatgtta acatcatgaa   3780
ctttacaaga atctttttaa agggcgatcg caccatgtta aatgatggta catttgttca   3840
gatatttgat atttaccatg accacgcatt gggagtgacc cttgacctta agacagaaaa   3900
aattatttcc gatgatgtta gggtaattac tgtcaaagac ttattgttcg atggcactta   3960
taaaggggta aaatctttta tgcccgataa tgcccgataa tgcccgattg atgctacaaa   4020
```

```
atcccataat cataagcgat aatcccctaa tagcttgtaa ttcttgaacc gtagcgattt   4080
tagagtattc caaaaagaag aaataaacac cgcaaaatgt cgtatttcac atatataaac   4140
caaggttttt tgccctaaaa tctttatgtt tgtagtgtga tgttgggtca aaatggtcag   4200
aaaagttgca aggtttttat ggatgcttac gcgcgcgagg ggtaagcatc cccaaatagt   4260
tactttatcc tagtccatgc ccatttattg ccgtcccgtt cggctttaaa aaagtgccaa   4320
aactcacaag gtgcaataaa aagttctgta cctttcgcaa ccctagataa tctttcaaca   4380
gttacttttt ttcctattat ctcggtacaa agtttggcta gtttctcttt tccctctttt   4440
tcaatcaagc cttcttgtat gcccaactca ttgattaatc tctctatttt taccattatt   4500
tcccgttcag gtagtttatc ccctaaatct tcatcggggg gcaatgtagg gcattctgaa   4560
ggggcttttt cttctgtctg gacattatct aatattgaag taaccaaact atcttcagtt   4620
ttttctattc ctattaattc atattcggtt actgtatccg tatcaatatc cgaataacta   4680
tctttatccg tattagctat tcggttaagt ttatccgtta actcagaaac aagactatat   4740
agcggtttta gcttttcttc tatcctgtta tctaatacgg ataagtttat acggttatca   4800
ttatccgtat tagtatcatt gggctttttt ggtagttcta cccccctcata aaccgctttt   4860
attcccaatt ccaacagact gataacagta tcctttataa tgggtttttt gctgatatgg   4920
tgaacttttg ccccttccat cattgcgata ctttctatct cactcatcaa cttatcgctt   4980
aagtgaatct cgtatctgtt taatccctta ctggttttat tcatatccgt ttactttatt   5040
cggttaacaa ttctatttta tacgaataaa atattatacg gttaacttta tacgtttaac   5100
tattttatct atacggataa cagtaataag ttattcgtat tagttatacg tttactttta   5160
tccaaataaa attagtgcat ttaaactaaa agaatgattt tatcggagtt gatagcattg   5220
gattaaccta aagatgttta taagctatat ctgataagta tttaaggtta ttttgttatt   5280
ctgtttattg acattatcag aataaaagaa tagaatataa ttgttgagag ataagaggtt   5340
taagtgatta tggttaagaa gttagttggt tatgtcaggg tcagtagtga atcgcaagag   5400
gataacacta gcttacagaa tcagatagag agaattgaag catattgtat ggcttttggt   5460
tatgagttgg taaaaatatt caaagaggtt gccactggta caaaagcaga tattgaaacc   5520
cgtcctattt ttaatgaagc tatagaatac ttgaaacagg ataatgctaa tggaattatt   5580
gccttgaagc tagaccgaat cgcacggaat gctttagatg tattgcgttt ggttcgtgaa   5640
accttagaac cacaaaataa aatgttagtg ttactagata ttcaggtaga tacttcgaca   5700
ccttcaggaa aaatgatttt aactgtaatg agtgccgttg ctgaactcga aagagacatg   5760
atctatgatc gcactcaggg gggtagaaag actaaagccc aaaagggcgg gtatgcctac   5820
gggaaaccta aatttggcta taagactgaa gaaaaggaac taaaagaaga ttcagcacaa   5880
caggaaacta ttaaactaat taagagacac cgtaggtcag ggaaaagcta ccagaaaata   5940
gctgattatc tcaatgccca aagtattccc actaaacaag gtaagaaatg gagttctagc   6000
gtcgtctatc gaatctgtca ggaaaaagct ggttaagtct gtttatagat atttagaatt   6060
tattgaataa aaatagtatg aacaataaat atttatggac taaccacgct cggaaacgtt   6120
taactgaacg atgggaaata aaagaatcat gggttattga taccatcgaa aatcctgaac   6180
gttcagaatt tattgttgat gagtcagggg aaaaatatca ttactataaa agaatagcta   6240
agtttaagaa tagagtgtta gaagtgataa cttctgccaa ctcaacaccc acaagaataa   6300
taacctttta ctttaaccgt aacatgagga aaaatttatg attgttactt acgataatga   6360
```

```
agttgacgca atttatttta agttaacgga aaataaaatt gatagcaccg aacctcaaac   6420

agacaggatt atcattgatt acgatgaaag taataatatt gttggcattg aggtattaga   6480

ttttaattat cttgtcaaga aaggtttaac cgttgctgat ttaccttttt ctgaagatga   6540

aagattaaca gcttctcaat attttaattt tcctgttgct atctaatcca gaaggggcaa   6600

taatcccctt ctttcatcga gttagactta atatcacaaa agtcattttc attttaccgt   6660

ttcttttcca cagcgtccgt acgcccctcg ttaaatctca aaaccgacaa tttatgatgt   6720

ttataaaaag ttactcactt taataagtat ttatactcat taaagggtta ttcttttttt   6780

gtagcctgat aggttgggaa ggaatatttc agattatcag atttgttg                6828
```

<210> SEQ ID NO 15
<211> LENGTH: 1020
<212> TYPE: DNA
<213> ORGANISM: Lyngbya sp.

<400> SEQUENCE: 15

```
atgtctgaaa ctaaatttaa ggcctatgcc gttatgaatc ccggcgaaaa gctgcaaccc     60

tgggaatacg aaccggcgcc gctgcaagtg gatgaaattg aagtgcgggt gactcacaac    120

ggcctttgtc acaccgacct gcacatgagg gacaatgact ggaacgtgag cgaatttccc    180

ctcgttgccg gccacgaagt cgttggagaa gtgacggcag tcggggaaaa agtcacttca    240

cgaaagaaag gcgatcgcgt gggggtgggt tggatcagaa actcctgtcg ggcctgcgat    300

cattgtttgc aaggggaaga aaatatctgt cgcgaaggct atacaggtct gatcgtcggg    360

catcacggcg gatttgccga tcgcgttcgg gttccggccg atttcaccta caaaattccc    420

gacgccttgg actccgcgag tgccgcgccg ctgctgtgtg ccggcatcac cgtctacacc    480

cccctgcgga cttatatcaa acacccgggg atgaaagtcg gggtgatggg aatcggcgga    540

ctcggacatt tagcgatcaa atttgcccgg gcgatggggg cggaagtcac ggctttttcc    600

acatccccga ataaagaagc ccaagccaag gaatttggcg cccatcattt ccaacagtgg    660

ggaacagccg aagaaatgaa agcggtggcc ggaaatttcg atttggtgct ttccaccatc    720

tccgccgaaa ctgattggga tgcggcgttc agtttgctgg caaataacgg ggttttgtgt    780

ttcgtcggca ttccggtttc cagtttgaac gtgccgctga ttccgctgat tttcggtcaa    840

aaatccgtcg tcggcagcgt agtgggcggc cggcggttca tggcagaaat gttggaattt    900

gccgccgtga atcagatcaa accgatgatc gaaacgatgc cgttgagtca ggtgaacgag    960

gcgatggaca aggtagcggc gaataaagct cgctatcgga tcgtgttgct ttcggagtga   1020
```

<210> SEQ ID NO 16
<211> LENGTH: 1022
<212> TYPE: DNA
<213> ORGANISM: Arthrospira platensis

<400> SEQUENCE: 16

```
atgactacag caactaaatt taaggcttat gcggctttaa attccggtga aaaattgcaa     60

ccttgggaat atgaaccaga acctctacag gttgatgaag tagaaattcg agtcactcac    120

aacggcttgt gtcatacgga tcttcacatg agggataatg attggaatgt cagtcaatat    180

cccctggttc ccggtcatga agtggttgga gaagttacag aagttgggga aaaagtgact    240

tctctacata aaggcgatcg catagggggtt ggctggatta gaaattcctg taggtcttgc    300

gaccattgct tacaaggaga agaaaatatc tgtcgcgagg gctacacagg tctgattgta    360

ggtcatcatg gggatttgc tgaccgccta cgggttcccg cagattttac ctataaaata    420
```

```
cccgatgctt tagactccgc cagcgccgcc cccctattat gtgccggaat taccgtttat    480

accccccttgc ggacctatat aaaacacccc gggatgaaag ttggggtgat gggaattggc    540

ggactcggac acttagcgat taagtttgct agggctatgg gggctgaagt tacggcgttt    600

tctacttctt taaataaaca agaacaagct aaggaatttg gcgctcataa cttccaacaa    660

tgggggacgg ctgaagaaat gaaggcgatc gccggaagtt ttgatctagt gctttctact    720

atctcttcag aaactgattg ggatgcggct tttagcttgt tagctaataa cggggttttg    780

tgttttgtgg gtatcccagt ttcgacttta aatatacccc taattccttt gatttttggt    840

caaaaagctg tggtgggtag cattgtcggc ggtcggcggt ttatggcgga aatgctggag    900

tttgcagcgg tgaatcagat taaaccgatg attgaaacta tgccattaag tcaaatcaat    960

gaagctatgg ataaggtagc cgctaatcaa gcccgctatc ggattgtttt actagctgat   1020

ta                                                                  1022
```

<210> SEQ ID NO 17
<211> LENGTH: 1005
<212> TYPE: DNA
<213> ORGANISM: Cyanothece sp.

<400> SEQUENCE: 17

```
atggtgattc aagcatacgc ggcccatgaa aaggggggag aactaaaacc ttttgaatac     60

gatccagggg ttttaggtga agaagaagtg gaaattaatg tcgaatactg tggtatttgt    120

catagtgact taagtatgct cgacaacgag tggcaaatga gtgaatatcc tttggttcct    180

ggccatgaag tggtgggaac tgttggggca gttggcaatg gagtcgaaac cctctcagtg    240

ggacaaaaag tagggttagg ctggttttcc cgttcttgtt tcaattgtga atggtgtatt    300

ggcggtgatc agaacctttg tcgaacggct gaaggaacca ttgtgggtcg tcatgggggg    360

tttgccaata aagtacgggc ccatcatcgt tgggtgactc ctctcccctc tgaaattaac    420

ctagaaacag cagggccatt attttgcggt ggcataacgg tatttaaccc gattattcaa    480

tgtggcgtaa aaccaacgga acgggttggc gtgattggca ttgggggatt aggtcatctg    540

gcaattcaat ttcttcatgc ttggggatgt gaggttacag cattttctag tagtccagaa    600

aaagaagccg aagcacgaca gttgggggct gatcatttta ttaattcccg tgaaagcaat    660

gccttagaat cggtagaaaa ttcctttgat tttattattt caactgttaa tgtggatctt    720

gactggaatg gttatgtgaa tgctttacga ccgaaaggaa gattgcattt tgtgggagtg    780

atccctaatc cgttatccat tcaaattttt cctttactgg tgggccaaaa atcaatttcc    840

tctagtccct tgggtagtcc gataaccatt gcccaaatgt tggattttgc gacgcgccat    900

cacatagaac cgatgattga actcttttct ttggaaaagg tgaatgaggc cctgactaaa    960

ctaaaacagg gccagccgag atatcggtta gtgcttaaag tttaa                   1005
```

<210> SEQ ID NO 18
<211> LENGTH: 1008
<212> TYPE: DNA
<213> ORGANISM: Synechococcus sp.

<400> SEQUENCE: 18

```
atgcccacaa ttaaagcctt tgctgtccat gaaccttctg gtgatttaca accctttgaa     60

tatgaccccg gtgagctgct gccggatcag gtagagattg aggtgaaata ctgcggtatt    120

tgccatagtg acctcagcat gatcgggaat gagtggggca tgacccaata tcccccttgtc    180
```

```
cctggccacg aagtcgtggg ggcgatcgcc aaagttgggg aaaatgtcaa aaatctcagc    240
gttgggcaag ttgtcggcct cggttggcac gctggctatt gcaacgaatg cccccaatgc    300
accacaggcg atcagaacct ttgtgccacg gcccaaggca ccatcgtcgg ccaccatggc    360
ggttttgcag aaaaagtccg ggctgcggct aatagtgtgg tgccaattcc cgatggcatt    420
gacctcgaag ccgctggccc cctattttgt ggcggcatta ctgtttttaa ccccctcgtg    480
caatatggca tccaacccac ttctaaagtg gcggtgctcg gcattggtgg tttaggtcac    540
atggcggtgc agtttctcaa tgcctggggt tgtgaagtga cggcctttac ctccagcgaa    600
gcaaaaaatta cagaagccct ggaactcggt gctcaccata ccctcaattc ccgtgatcca    660
gaggcgatcg ccgctgctgc tggtcaattc gatctgatca tttcgactgt caatgtcaaa    720
ctcgattgga atgcctatct cagcaccctc aagccccatg gacgcttaca tttcgttggc    780
gcaaccctcg atcccctcga catcaacgtc tttgccctaa tcatgcaaca gcgttccatc    840
tccggttctc ctgtcggtag ccccgcaacc atcgccaaaa tgctggaatt tgccaaactg    900
cacaatattc agcccaaaat tgaaaccttc aaatttgcag acgtcaacaa ggcgatcgcc    960
cgcctaaaaa gtggcgaggc ccattaccgg atcgtgcttt gtcgctaa                1008
```

```
<210> SEQ ID NO 19
<211> LENGTH: 1008
<212> TYPE: DNA
<213> ORGANISM: Synechococcus sp.

<400> SEQUENCE: 19
```

```
atgcccacaa ttaaagcctt tgctatccat gaaccttctg gtgatttaca accctttgaa     60
tatgaccccg gtgagctgct gccggatcag gtagagattg aggtgaaata ctgcggtatt    120
tgccatagtg acctcagcat gatcgggaat gagtggggca tgacccaata tccccttgtc    180
cctggccacg aagtcgtggg ggcgatcgcc aaagttggga aaaatgtcaa aaatctcagc    240
gttgggcaag ttgtcggcct cggttggcac gctgggtatt gtaatgaatg ctcccaatgc    300
accacaggcg atcagaacct ttgtgccacg gcccaaggca ccatcgtcgg ccaccatggc    360
ggttttgcag aaaaagtccg ggctgcggcc aatagtgtgg tgccaattcc cgatggcatt    420
gacctcgaag ccgctggccc cctattttgt ggcggcatta ctgtttttaa ccccctcatg    480
caatatggca tccaacccac ttctaaggtg gcggtgctcg gcattggtgg tttaggtcac    540
atggcggtgc agtttcttaa tgcctggggt tgtgaagtga cggcctttac ctccagcgaa    600
gcaaaaaatta cagaagccct ggaactcggc gctcaccaca ccctcaattc ccgtgatcca    660
gaggcgatcg ccgctgctgc tggtcaattc gatctgatca tttcgactgt caatgtcaaa    720
ctcgattgga atgcctatct cagtaccctc aagccccatg gacgcttaca tttcgttggc    780
gcaaccctcg atcccctcga catcaacgtc tttgccctaa tcatgcaaca gcgttccatt    840
tctggttccc ccgtcggtag ccccgcaacc atcgccaaaa tgctggaatt tgccaaactg    900
cacaatattc agcccaaaat tgaaaccttc aaatttgcag atgtcaacaa ggcgatcgcc    960
cgtctaaaaa gtggcgaggc ccattaccgg atcgtgcttt gtcgctaa                1008
```

```
<210> SEQ ID NO 20
<211> LENGTH: 1008
<212> TYPE: DNA
<213> ORGANISM: Synechococcus sp.

<400> SEQUENCE: 20
```

```
atgccaatga ttaaagcctt tgctgtccat gaatctgacg gtgatttaca accctttgaa     60
```

```
tatgaccccg gtgcgctgct gtcggatcaa gtagaaattg aagtgaaata ttgcggcatt    120

tgtcacagtg acctcagcat gattagtaat gagtggggca tgacccaata tccccttgtc    180

cctggccatg aagtcgtcgg ggcgatcgcc aaggtcggag aaaacgtcaa aaatctcagc    240

gttgggcaaa tcgtcggcct cggttggcac gctggatatt gcaatgaatg tccccaatgc    300

accacaggcg atcaaaatct ttgtgccacg gcccaaggca ccatcgtcgg ccaccatggt    360

ggttttgcag aaaaagtccg agcggcggcc aatagtgtgg tgccaattcc cgaaggcatt    420

gacctagaag ctgctggccc cctcttttgt ggcggcatca ctgtttttaa ccccctcgtc    480

caatatggca tccaacccac tgccaaagtc gctgtgatcg gtatcggtgg cttgggtcac    540

atggcggtgc agtttctcaa tgcctggggt tgtgaagtga cggcctttac ctccagcgaa    600

gcaaaaatta cagaagccct tgagcttggt gcccaccaca ctctcaattc ccgtgatcca    660

gaggcgatcg ccgccgctgc gggtcaattt gatctgatta tttcgaccgt caatgtcaaa    720

ctcgattgga atgcctatct cagcaccctc aaaccccatg gacgtttgca tttcgttggc    780

gcaaccctcg atccccttga tatcaacgtc tttgccttaa tcatgcaaca acgatcaatc    840

tccggttccc ccgtcggtag ccccgcgacc atcgccaaaa tgctggaatt tgcaaaattg    900

cacaagattc agcccaaaat cgaaaccttt aaattcgaag acgtcaacca ggcgatcgcc    960

cgcctaaaaa gtggcgaagc ccattaccgg atcgtgcttt gtcgttaa                1008
```

<210> SEQ ID NO 21
<211> LENGTH: 1002
<212> TYPE: DNA
<213> ORGANISM: Chroococcidiopsis sp.

<400> SEQUENCE: 21

```
atgattcgtg cctacgcagc tttagaaaaa ggtggagaac tcaagccttt cgagtacgag     60

ccaaaaccgc tcggtagcga agatgtagag attgacgtag aatactgcgg gatttgccat    120

agcgacttga gtatgctcca taatgactgg ggcatgacac aatatccctt tgttccagga    180

cacgaagttg taggcaagat tgcggatgtt ggcagtgccg taaaaaaact ccaagtcgga    240

cagcgggtcg gattgggatg gtattcgcga tcgtgcatga cttgcgagtg gtgtatgtct    300

ggcaatcaca acctttgtgc caccgcagaa ggtacaattg tcggtcgcta tggtggtttt    360

gctgacaagg tgcgcgccca tgaagcttgg gttgctcccc tacccgatgc catgcagcca    420

gtgtcagccg gacccttatt ttgtggcgga attacggttt ttaacccaat cgtccaattt    480

gatgttaagc ctaccgatcg cgttggagtc attggtattg gcggcttggg acacatggca    540

ttgagatttc ttcatgcttg gggctgcgat gtcagtgcct tttccagcag cgccgataag    600

gaaccagaag caagggaaat gggtgctaac cacttcatca actcccgcga tccaaatgca    660

cttaaatcgg tagaaggctc ttttgacttg attctttcta ctgtgaatgc cgatctagac    720

tggagtacat acattgcctg tttgcgtcct aaaggacgat tgcattttgt aggtgtggtt    780

cctaacccta tttctacgga aatttttccc ttaattatgg ctcagcgatc gatctccggc    840

agtcccttgg gtagtccggc tactgtcacc caaatgcttg acttcgccac ccgccatcag    900

atcgaaccca taattgaaac cttcagtttt gaccaagtga acgaggcatt ggaacaccta    960

cgtagtggca aggcacgata tcggatcgtg ttgaaacatt aa                      1002
```

<210> SEQ ID NO 22
<211> LENGTH: 1179
<212> TYPE: DNA

<213> ORGANISM: Arthronema africanum

<400> SEQUENCE: 22

```
atggatacgc cagtcccaaa cgagtccgct ggctccgacg agaggcaact ccagccagcg     60
ggctgtgaca ttaccctggg ccaggggcga tcgcgccccg ttttttccca ccgcccaatt    120
tcccctttac aatgcaaagc agatcagtca cattctgtca ggcaagcatt ttttcctatg    180
attaaagcct acgcagtcca cgaacccggc ggccagttgg aacactttga gtacgatcca    240
gggccactgg gtaaacaaga agttgaaatt caagttgaat attgcggcat ctgccacagc    300
gatctcagca tggtggacaa cgaatggggg atttcccaat atccgctggt gccggggcac    360
gaagtcattg gggcgatcgc tgccgtcggt gaagaggtca ccaccttgag cgtgggccag    420
cgcgtggggt tggggtggtt ttcccagtcc tgtatgcatt gtgaatggtg catgtctggc    480
gatcacaatc tgtgccaaac cgccgaaagc actattgtcg ggcggtatgg tggctttgct    540
gatcgagtgc gagcccatca agagtgggca attcccctcc ccgcagacct cgaccccgca    600
aaagtcggcc ccctattttg tggtggcctg acggtgttca atccgatcat tcagttaaat    660
atccagccca ccgacaaagt tggtgtcctt ggcatcgggg gcttaggcca catggcgttg    720
cggtttctcc atgcgtgggg atgtgatgtc acggcatttt ccactagccc agacaaagaa    780
gccgaagccc gcgaactagg cgcaaaccat tttattaact cccgcgatcc cgcagcgttg    840
aaatccgttg agaatacgtt tgatgtgatt atttcaacga tcgccgctga tctcgattgg    900
agcacctata ttgccgccct gcgccccaaa ggtcggttgc atttagtcgg tgtcgcgccc    960
agcccgatcg ccacccacat tttcccatg atttctggcc aaaagtcgct ttctggcagt   1020
ccgctgggga gtccggccac cgccgcccga atgctagatt ttgcggcacg gcacggcatt   1080
gaacccatcg ttgaagtgtt ttcctttgac caggtgaacg aggcaataga gaagctccgg   1140
aatggacaac cccgctatcg actggtgctg aaacattag                          1179
```

<210> SEQ ID NO 23
<211> LENGTH: 1002
<212> TYPE: DNA
<213> ORGANISM: Chroococcidiopsis sp.

<400> SEQUENCE: 23

```
atgattcgtg cctacgcagc tttagaaaaa ggtggagaac tcaagccttt cgagtacgat     60
ccaaaaccgc tcggtagtga agatgtagag atcgacgtag aatactgcgg aatttgccat    120
agcgacttga gtatgcttca taatgactgg ggcatgacgc aataccccctt tgtcccagga   180
catgaagttg taggcaagat cgcggatgtt ggcagtgcgg tgaaaaaact tcaggtcggg    240
cagcgtgttg gactgggatg gtattcgcga tcgtgcatga cttgcgagtg gtgtatgtct    300
ggcaatcaca acctttgtgc caccgcagaa ggtacaattg tcggtcgcta cggtggcttt    360
gctgacaagg tacgcgccca tgaagcttgg gttgtcccct taccagaggc aatgcagcca    420
gtctcagctg gacccctatt ttgtggcgga attactgttt ttaacccaat cgtccaattt    480
gatgttaaac ctaccgatcg cgttggagtc attggtattg gtggcttagg acacatggca    540
ttgagatttc ttcatgcttg ggctgcgat gtcagtgcct tttccagcag cgctgataag     600
gaagcggaag caagagaaat gggtgctaac cacttcatta actctcgcga cccaaatgca    660
ctcaaatcgg tagaaggttc ttttgacttg attctttcta ctgtcaatgt agatctagac    720
tggaatacct acattgcctg cttgcgtcct aaagggcgat tgcatttcgt aggcgtggtt    780
cccaatcctg tctccagtca agtttttcct ttaatttcag gtcaaaaatc gctctctggt    840
```

```
agtcccttgg gtagtcctgc taccgtcgtc caaatgctcg attttgccac ccgacatcag    900
atcgaaccca taatcgaaac ctttagtttt gaccaagtca atgaggcatt ggaacactta    960
cacagcggta aggcacgata tcggatcgtg ttgaaacatt aa                      1002
```

<210> SEQ ID NO 24
<211> LENGTH: 1011
<212> TYPE: DNA
<213> ORGANISM: Cyanobacterium sp.

<400> SEQUENCE: 24

```
atgacgattg taaatgccta cgccgcccat gaaataggag ggatactcaa gccttttcaa     60
tatgaattac ctcccatcgg tgcttatgaa gttgatattc aagtacagca ttgcggtatt    120
tgtcatagtg acttaagttt gctggaaaat gcttggggtg ttactcaata tccttttgta    180
ccgggtcatg aaattgttgg tactgttttg gctgtcggac aagatgttgt tcacttaaaa    240
aaaggcgatc gcgtcggctt gggatggcac tcagcatatt gtttacactg tgatcaatgt    300
ttaactggta atcataatat gtgttactct gctcaagcta ctatcgtggg cagacatgga    360
ggattcgccg atatagttag ggcaaaagtt cctagtgtag ttaagttacc cgattctgtg    420
gatatgcgta ctgcaggacc tttactttgt ggtggtataa cggtttttaa tcctttaatt    480
caattcaata ttttgccaac ggctaaagtg ggagtgattg gcataggtgg tttaggtcat    540
attgcggtgc agattcttcg ggcttgggga tgtgaggtaa ctgcttttac ttctagtgag    600
tcaaaaatag aagaagcctt aaaaatgggg gcaaataaaa ctcttaactc tagggattca    660
gaggagttaa agtcagcaga aaatagtttt gatttgattc tctctactgt taatgttgag    720
cttgattgga gtacatattt aagtttactc aagccaaaag gtcgtcttca tcttttaggg    780
gtggttcttg aacccttaaa cctcagtgtt tcttctttgc tttcacgaca aaaatccgtt    840
tctgcttccc ctgtaggtag tccaaatgcg atcgcacaaa tgttggagtt ttgccaaaga    900
cataatataa agcccatcac acaacatttt cccctcaagg aagtgaatga agcaatggaa    960
catttgagag ctggaaaagc ccgttatcga gtggtgttag acatgaactg a            1011
```

<210> SEQ ID NO 25
<211> LENGTH: 1005
<212> TYPE: DNA
<213> ORGANISM: Microcystis aeruginosa PCC7806

<400> SEQUENCE: 25

```
atgattagag cctatgctgc ccaagaaaaa gggggaaaac tagagccttt tgactacgat     60
ccgggcatat tagcggatga agatgtagaa atcgcggtgg aatattgcgg catctgccac    120
agtgacctaa gtatgctcga taacgattgg ggactgacca cctatccctt tgtccctggc    180
catgaagtgg tcggcacgat cgccgctctt ggtgctaaag tcaaagagtt aaaattaggg    240
caaagagtcg gtctcggttg gttttcccgt tcctgttcca cctgtgaaac ctgtatgtca    300
ggggatcaaa acctttgtgc tactgccgaa ggaactatcg tcggtcgcca tggcggtttt    360
gccgaaagag tccgggccca tcatagttgg ttagttccct tgccggacca gttagatgct    420
gccaaagctg gcccgctttt ctgtggtggc attaccgtct ttaatccgat tgtccaattt    480
aatattaaac ccacggcccg agttggtgtc attggtattg gtggattggg ccatatagcc    540
ttaaaattcc tcaaagcttg gggctgcgaa gtaaccgctt tttccagtag tcccgacaaa    600
gaaacggaag caaaagaact aggagcgact cattttatca attccagaga ccccgaagct    660
```

```
ttgcaatcgg tacaaaatta ctttgatttt atcatctcta ccgttaacgt taatctcgat    720

tggggtcttt atatcgcctg tttacgaccc aaaggtcgcc tgcatattgt tggcgctgtt    780

cttgaaccca tggctaccta cgcttttccc ttgattatgg gtcaaaaatc gatttccggc    840

agtcctttgg gtagtcccag taccgtcagt aaaatgattg aatttgcctc tcgccatggc    900

attgaaccag tcacagaaac ctatcctatc tcccgggtga atgaagccat ggaaaaattg    960

cgaaccggac aacctaaata tcgcctcgtc ttgcaaataa aataa                   1005
```

```
<210> SEQ ID NO 26
<211> LENGTH: 336
<212> TYPE: PRT
<213> ORGANISM: Synechocystis sp. PCC6803

<400> SEQUENCE: 26

Met Ile Lys Ala Tyr Ala Ala Leu Glu Ala Asn Gly Lys Leu Gln Pro
1               5                   10                  15

Phe Glu Tyr Asp Pro Gly Ala Leu Gly Ala Asn Glu Val Glu Ile Glu
            20                  25                  30

Val Gln Tyr Cys Gly Val Cys His Ser Asp Leu Ser Met Ile Asn Asn
        35                  40                  45

Glu Trp Gly Ile Ser Asn Tyr Pro Leu Val Pro Gly His Glu Val Val
    50                  55                  60

Gly Thr Val Ala Ala Met Gly Glu Gly Val Asn His Val Glu Val Gly
65                  70                  75                  80

Asp Leu Val Gly Leu Gly Trp His Ser Gly Tyr Cys Met Thr Cys His
                85                  90                  95

Ser Cys Leu Ser Gly Tyr His Asn Leu Cys Ala Thr Ala Glu Ser Thr
            100                 105                 110

Ile Val Gly His Tyr Gly Gly Phe Gly Asp Arg Val Arg Ala Lys Gly
        115                 120                 125

Val Ser Val Val Lys Leu Pro Lys Gly Ile Asp Leu Ala Ser Ala Gly
    130                 135                 140

Pro Leu Phe Cys Gly Gly Ile Thr Val Phe Ser Pro Met Val Glu Leu
145                 150                 155                 160

Ser Leu Lys Pro Thr Ala Lys Val Ala Val Ile Gly Ile Gly Gly Leu
                165                 170                 175

Gly His Leu Ala Val Gln Phe Leu Arg Ala Trp Gly Cys Glu Val Thr
            180                 185                 190

Ala Phe Thr Ser Ser Ala Arg Lys Gln Thr Glu Val Leu Glu Leu Gly
        195                 200                 205

Ala His His Ile Leu Asp Ser Thr Asn Pro Glu Ala Ile Ala Ser Ala
    210                 215                 220

Glu Gly Lys Phe Asp Tyr Ile Ile Ser Thr Val Asn Leu Lys Leu Asp
225                 230                 235                 240

Trp Asn Leu Tyr Ile Ser Thr Leu Ala Pro Gln Gly His Phe His Phe
                245                 250                 255

Val Gly Val Val Leu Glu Pro Leu Asp Leu Asn Leu Phe Pro Leu Leu
            260                 265                 270

Met Gly Gln Arg Ser Val Ser Ala Ser Pro Val Gly Ser Pro Ala Thr
        275                 280                 285

Ile Ala Thr Met Leu Asp Phe Ala Val Arg His Asp Ile Lys Pro Val
    290                 295                 300

Val Glu Gln Phe Ser Phe Asp Gln Ile Asn Glu Ala Ile Ala His Leu
305                 310                 315                 320
```

```
Glu Ser Gly Lys Ala His Tyr Arg Val Val Leu Ser His Ser Lys Asn
                325                 330                 335


<210> SEQ ID NO 27
<211> LENGTH: 13449
<212> TYPE: DNA
<213> ORGANISM: Artificial
<220> FEATURE:
<223> OTHER INFORMATION: Synthetically produced plasmid construct TK293
      pABIcyano1::PnirA-zmPDC(opt1)-PrpsL-synADH(opt1)_ter

<400> SEQUENCE: 27

aatatttttc gtcagatacg caaaccttac aaacataatt aacaactgaa actattgata      60

tgtctaggtt ttagctctat cacaggttgg atctgtcgac aattaataac ttcttcctgt     120

acgggcgaat ggccatttgc tcctaactaa ctccgtactg ctttgcggaa cgagcgtagc     180

gaactctccg aattactaag ccttcatccc tgatagatgc aaaaaacgaa ttaaaattat     240

gtgtaaaaag aaaatgtgtc tttatttagt agtcaaagtt acaaaatatt aagaatcaaa     300

ttaataatgt attgggcagt taagtatata agtctttaaa tatttatttg tattcaatat     360

attaaccgag gacaaattat gaattcttat accgtgggta cttatttagc cgaacgctta     420

gtgcaaattg gtttaaaaca tcattttgcc gtggctgggg actataattt agtgttattg     480

gataacttat tattaaataa aaacatggaa caagtgtatt gttgtaatga attaaattgt     540

ggtttttctg ctgaaggtta tgctagagct aaaggtgcag ctgctgctgt tgttacttat     600

tctgtgggtg ctttatctgc ttttgatgct attggtggtg cttatgccga aaatttaccc     660

gtgattttaa tttctggtgc ccctaataat aatgatcatg ccgctggaca tgttttacat     720

catgccttag gtaaaaccga ttatcattat caattagaaa tggccaaaaa tattactgct     780

gctgccgaag ctatttatac tcctgaagaa gcccctgcca aaattgatca tgtgattaaa     840

accgccttac gcgaaaaaaa acccgtgtat ttagaaattg cctgtaatat tgcttctatg     900

ccttgtgctg ctcctgggcc tgcttctgct ttatttaatg atgaagcctc tgatgaagct     960

agtttaaatg ctgccgtgga agaaacctta aaatttattg ccaatcgcga taaagttgcc    1020

gtgttagttg gttctaaatt aagagctgct ggtgctgaag aagctgctgt taaatttgct    1080

gatgctttag gtggtgcagt tgctactatg gctgctgcca aatctttttt tcccgaagaa    1140

aatccccatt atattggaac tagttgggga gaagtttctt atcctggtgt ggaaaaaact    1200

atgaaagaag ccgacgctgt tattgcttta gcccctgtgt ttaatgatta ttctaccact    1260

ggttggactg atattcccga tcccaaaaaa ttagttttag ccgaacctcg ttctgttgtt    1320

gttaatggtg ttcgctttcc ctctgtgcat ttaaaagatt atttaacccg cttagcccaa    1380

aaagtttcta aaaaaactgg tgccttagat tttttaaat ctttaaatgc gggtgaatta    1440

aaaaaagctg ctcctgctga tccttctgct cctttagtta atgctgaaat tgcccgtcaa    1500

gttgaagcct tattaacccc taatactacc gttattgccg aaactggtga ttcttggttt    1560

aatgcccaac gcatgaaatt acctaatggt gcccgtgttg aatatgaaat gcaatggggt    1620

catattggtt ggtctgtacc tgctgctttt ggttatgctg ttggtgctcc tgaacgtcgt    1680

aatattttaa tggtgggtga tggttctttt caattaactg cccaagaagt tgcccaaatg    1740

gttcgcttaa aattacccgt tattattttt ttaataaata attatggtta taccattgaa    1800

gtgatgattc atgatgggcc atataataat attaaaaatt gggattatgc gggtttaatg    1860

gaagtgttta atggtaatgg tggttatgat tctggtgctg gtaaaggttt aaaagccaaa    1920
```

```
actggtggtg aattagctga agctattaaa gttgccttag ccaatactga tgggccaacc   1980
ttaattgaat gttttattgg tcgcgaagat tgtaccgaag aattagttaa atggggtaaa   2040
cgtgttgctg ctgctaattc tcgcaaaccc gtgaataaat tattgtaatt tttggggatc   2100
aattcgagct cctccgctta aaaaatttca tttttcgatc aaaaaagaca aattattact   2160
aattagctca tggcaataaa taatcagtag taatctgttt tcacatttta ttgttaattt   2220
ttattattgc taatatcaac cttttctact tctgcttaat attttattta tgctcaatgg   2280
gaaaatctga aataagattg agaacagtgt taccaataga agtatttaag gtttaaagca   2340
taccttaaag ataacatttt tttttgaaaa gagtcaaatt atttttgaaa ggctgatatt   2400
tttgatattt actaatattt tatttatttc tttttccctt aaaataagag ctaaatctgt   2460
ttttattatc atttatcaag ctctattaat acctcaactt tttcaagaaa aaataataat   2520
aatttttccc tctattctca tgacctttta ggaaaattaa ttttagaaaa actattgaca   2580
aacccataaa aaatgagata agattataga ttgtcactgg tattttatac tagaggcaaa   2640
ttatatttat atatacaaaa atgctgtata aaaaacatct catatgatta aagcctatgc   2700
tgccttagaa gccaatggta aattacaacc ctttgaatat gatcctggtg ctttaggtgc   2760
caatgaagtg gaaattgaag tgcaatattg tggtgtgtgt cattctgatt tatctatgat   2820
taataatgaa tggggtattt ctaattatcc cttagttcct ggtcatgaag ttgttggtac   2880
tgttgctgct atgggtgaag gtgttaatca tgtggaagtg ggtgatttag ttggtttagg   2940
ttggcattct ggttattgta tgacctgtca ttcttgttta tctggttatc ataatttatg   3000
tgccactgcc gaatctacta ttgtgggtca ttatggtggt tttggtgata gagttcgtgc   3060
taaaggtgtt tctgtggtga aattacccaa aggtattgat ttagcctctg ctgggccttt   3120
attttgtggt ggtattaccg tttttctcc catggtggaa ttatctttaa aacctaccgc   3180
caaagttgct gttattggta ttggtggttt aggtcattta gccgttcaat ttttaagagc   3240
ctggggttgt gaagttactg cttttacctc ttctgcccgt aaacaaaccg aagttttaga   3300
attaggtgcc catcatattt tagattctac caatcctgaa gctattgctt ctgccgaagg   3360
taaatttgat tatattattt ctaccgtgaa tttaaaatta gattggaatt tatatatcag   3420
taccttagcc cctcaaggtc attttcattt tgttggtgtg gtgttagaac ccttggactt   3480
aaacttattt cccttattaa tgggacaacg ttctgtttct gcttctcctg ttggttctcc   3540
tgctactatt gccactatgt tagattttgc cgtgcgtcat gatattaaac ccgtggtgga   3600
acaattttct tttgatcaaa ttaatgaagc cattgcccat ttagaatctg gtaaagccca   3660
ttatcgcgtg gtgttatctc attctaaaaa ttaataagat taacttctaa actgaaacaa   3720
atttgagggt aggcttcatt gtctgccctt attttttat ttaggaaaag tgaacagact   3780
aaagagtgtt ggctctattg ctttgagtat gtaaattagg cgttgctgaa ttaaggtatg   3840
atttttgacc ccttctctct tctgcagtta cctaggattt ctggcgaaag ggggatgtgc   3900
tgcaaggcga ttaagttggg taacgccagg gttttcccag tcacgacgtt gtaaaacgac   3960
ggccagtgag cgcgacgtaa tacgactcac tatagggcga attggcggaa ggccgtcaag   4020
gccgcatggc gcgcctacgt agacaattgt cgatgtaatt attaactatc ttattataga   4080
tgaggggaga gggagaaatt agttcggaga gaacgctcga gcgctcgttc cgcaaagcgg   4140
tacggagtta gttaggggct aatgggcatt ctcccgtaca ggaaagagtt agaagttatt   4200
aattatcaac aattctcctt tgcctagtgc atcgttacct tttaattaa aacataagga   4260
aaactaataa tcgtaataat ttaacctcaa agtgtaaaga aatgtgaaat tctgactttt   4320
```

```
ataacgttaa agagggaaaa attagcagtt taaaatacct agagaatagt ctggggtaag   4380
catagagaat tagattagtt aagttaatca aattcagaaa aaataataat cgtaaatagt   4440
taatctgggt gtatagaaaa tgatcccctt catgataaga tttaaactcg aaaagcaaaa   4500
gccaaaaaac taacttccat taaaagaagt tgttacatat aacgctataa agaaaattta   4560
tatatttgga ggataccaac catgtctcat attcaacgtg aaactagttg ttctcgtcct   4620
cgtttaaatt ctaatatgga tgccgattta tatggttata aatgggctcg tgataatgtt   4680
ggtcaatctg gtgctactat ttatcgttta tatggtaaac ctgatgctcc tgaattattc   4740
ttgaaacatg gtaaaggttc tgttgctaat gatgttactg atgaaatggt tcgtttaaac   4800
tggttgactg aatttatgcc tttacctact attaaacatt ttattcgtac tcccgatgat   4860
gcttggttat taactactgc tattcctggt aaaactgctt ttcaagtttt agaagaatat   4920
cctgattctg gtgaaaatat tgttgatgct ttagctgttt ttttacgtcg tttacattct   4980
attcccgttt gtaattgtcc ttttaattct gatcgtgttt ttcgtttagc tcaagctcaa   5040
tctcgtatga ataatggttt agttgatgct tctgattttg atgatgaacg taatggttgg   5100
cctgttgaac aagtttggaa agaaatgcac aaattgttac ctttttctcc tgattctgtt   5160
gttactcatg gtgatttttc tttagataat ttgatctttg atgaaggtaa attgattggt   5220
tgtattgatg ttggtcgtgt tggtattgct gatcgttatc aagatttagc tattttatgg   5280
aattgtttag gtgaattttc tccttcttta cagaaacgtt tatttcagaa atatggtatt   5340
gataatcctg atatgaacaa gttacaattt catttaatgt tggacgagtt cttttaagaa   5400
ttaattcatg accaaaatcc cttaacgtga gttttcgttc cactgagcgt cagaccccgt   5460
agaaaagatc aaaggatctt cttgagatcc tttttttctg cgcgtaatct gctgctattt   5520
aaattacgta cacgtgttat tactttgtta acgacaattg tcttaattaa ctgggcctca   5580
tgggccttcc gctcactgcc cgctttccag tcgggaaacc tgtcgtgcca gctctgcaga   5640
tgacggtgaa aacctctgac acatgcagct cccggagacg gtcacagctt gtctgtaagc   5700
ggatgccggg agcagacaag cccgtcaggg cgcgtcagcg ggtgttggcg ggtgtcgggg   5760
cgcagccatg acccagtcac gtagcgatag cggagtgtat actggcttaa ctatgcggca   5820
tcagagcaga ttgtactgag agtgcaccat atgcggtgtg aaataccgca cagatgcgta   5880
aggagaaaat accgcatcag gcgctcttcc gcttcctcgc tcactgactc gctgcgctcg   5940
gtcgttcggc tgcggcgagc ggtatcagct cactcaaagg cggtaatacg gttatccaca   6000
gaatcagggg ataacgcagg aaagaacatg tgagcaaaag gccagcaaaa ggccaggaac   6060
cgtaaaaagg ccgcgttgct ggcgtttttc cataggctcc gcccccctga cgagcatcac   6120
aaaaatcgac gctcaagtca gaggtggcga aacccgacag gactataaag ataccaggcg   6180
tttccccctg gaagctccct cgtgcgctct cctgttccga ccctgccgct taccggatac   6240
ctgtccgcct ttctcccttc gggaagcgtg gcgctttctc atagctcacg ctgtaggtat   6300
ctcagttcgg tgtaggtcgt tcgctccaag ctgggctgtg tgcacgaacc ccccgttcag   6360
cccgaccgct gcgccttatc cggtaactat cgtcttgagt ccaacccggt aagacacgac   6420
ttatcgccac tggcagcagc cactggtaac aggattagca gagcgaggta tgtaggcggt   6480
gctacagagt tcttgaagtg gtggcctaac tacggctaca ctagaaggac agtatttggt   6540
atctgcgctc tgctgaagcc agttaccttc ggaaaaagag ttggtagctc ttgatccggc   6600
aaacaaacca ccgctggtag cggtggtttt tttgtttgca agcagcagat tacgcgcaga   6660
```

-continued

```
aaaaaaggat ctcaagaaga tcctttgatc ttttctactg cagaagcttg ttagacaccc   6720
tgtcatgtat tttatattat ttatttcacc atacggatta agtgaaacct aatgaaaata   6780
gtactttcgg agctttaact ttaatgaagg tatgtttttt tatagacatc gatgtctggt   6840
ttaacaatag gaaaaagtag ctaaaactcc catgaattaa agaaataaca aggtgtctaa   6900
caacctgtta ttaagaatgt tagaaaagac ttaacatttg tgttgagttt ttatagacat   6960
tggtgtctag acatacggta gataaggttt gctcaaaaat aaaataaaaa aagattggac   7020
taaaaaacat ttaatttagt acaatttaat tagttatttt ttcgtctcaa attttgcttt   7080
gttgagcaga aatttagata aaaaaatccc cgtgatcaga ttacaatgtc gttcattgta   7140
cgatgtgtcg aaaaatcttt acgacactct aaactgacca cacgggggaa aaagaaaact   7200
gaactaataa catcatgata ctcggaaaac ctagcaattc tcaaccccta aacaaaagaa   7260
acttccaaaa ccctgaccat ataaaggagt ggcaacaatc agcaatcagt caagatttga   7320
tagcagaaaa tcttgtatcg gttgctaatg gttttgatgt actatttatc ggcaataaat   7380
accgaactaa cacgggtgtt ctgtcacggc acatattaaa ctcctattct catttagaag   7440
atggtggttc gtatggtaga acatttgacc catttaccaa taaagaaatg cagtgggttc   7500
aatttaaacc gaatagacca agaaaaggtt ctactggtaa ggtaatcaaa tatgaatcgc   7560
caaaaggtga acctacaaga gttctaatgc cgtttgtgcc tatgaaaata tggcaacgga   7620
ttagcgataa gttcggagta ccgattaatc cgaaaaaaga tactcacttt tgggaatggg   7680
taaagaataa tccatcgata ccgattgcca ttacagaagg aaataaaaaa gctaattgcc   7740
tattatccta tggctatcct gctattgcct ttgtaggcat ttggaacgga ttagagaaaa   7800
taaatgattt ctcgaaggaa aagcagttaa aagaggattt gaaatggttg ttatccaacg   7860
gcaaccgaaa tattaatatc atctttgacc aagaccagaa acaaaaaact gtaattaatg   7920
taaacaaagc tattttcgct ttatcttctc taataagtag aaatggtcat aaagttaata   7980
ttgtgcaatg gttgccgtca aaaggtaaag gaatagatga ttatttggta gctttacctt   8040
ttgagaaaag agaaaatcat ttagacaact taattaaaat tgcaccatca tttaattttt   8100
ggtcaactaa atacttattc aagtgtcgta aaccagattt aaccgtaaat tgccgttatt   8160
tgagcgatgc agtaaaagaa ttacctcaag aggatatagc attaatagca cctcacggca   8220
cgggtaaaac ttcattagta gctactcacg ttaagaatcg gagttatcac ggaaggaaaa   8280
ctatttcatt ggtgcatctt gaaagtttag ccaaagctaa tggcaacgca cttggattat   8340
attaccgaac cgaaaataat attgaaaagc aatatcttgg atttagctta tgtgtagata   8400
gttgccgtga taagattaac ggcattacaa ctgatattat ttcaggtcaa gattattgcc   8460
ttttcattga tgaaattgac caagtaattc cacacatcct taacagtgaa actgaagtaa   8520
gtaagtatag atgcaccatc attgacactt tttctgaact ggtgagaaat gctgaacagg   8580
tcattattgc tgatgctgat ttatccgatg tgacgattga cctaatagaa aacatcagag   8640
gtaaaaaact atatgtaatc aagaatgaat atcagtatca gggaatgact tttaacgccg   8700
ttggttcacc attagaaatg atggcaatga tgggaaaatc ggtgtcagaa ggcaagaaat   8760
tatttattaa caccacatcc caaaaggcaa aaagtaagta cggcacaatc gctcttgagt   8820
cttatatttt tggtctaaat aaagaagcaa agatattaag aatagactct gaaaccacta   8880
aaaaccctga acatccagcc tataaaatca ttgaccaaga cttaaataat atcctcaaag   8940
attatgatta tgtcattgcc tcaccttgcc ttcaaacagg tgtcagtatt accttaaaag   9000
ggcattttga ccagcaattt aacttttcca gtggaaacat tacacctcat tgcttttac    9060
```

```
agcaaatgtg gcggttgagg gatgcagaaa ttgaaagatt ctattatgtg ccgaactcat   9120
ctaacctcaa tctcattggg aataagtcaa gttcaccatc agaccttcta aagagcaata   9180
acaagatggc aacggcaacg gttaaccttt tgggtagaat cgactccgaa tattccctag   9240
agtatgaatc gcacggcatt tggcttgaga cgtgggcaaa attatcagca cggcataaca   9300
gttcaatgcg ttgttactct gaaattctta cctatctaat tacgtctcaa gggcataaat   9360
taaatatcaa cattccctca cctcttgcag atattaagaa gctaaatgat gaggtaagta   9420
gtaacaggga aaaggtaaaa aatgagagat actctcagag gttaaactca ccagatatta   9480
acgatgcaga agctaccata ctcgaatcta aagagcaaaa aatcggattg actctcaatg   9540
agagatgcac cctagaaaag cataaagtta agaagcggta tgggaatgta aagatggata   9600
ttctcacctt tgatgatgat ggactatacc ccaaactcag actattttat tacctcacca   9660
tcggtaaacc tcatctcaag gctaatgaca gaaaagctat tgccaaaatg ggcaatgaca   9720
ataaaggcaa gattctatca aaagacttag ttaataaaac ttactccgct cgtgtgaagg   9780
tcttagagat tcttaaacta actgacttta tcgacaatct tagagatgaa ctcttaataa   9840
ctcccaataa tccagctatc accgatttta ataatcttct gctaagagct aagaaggatt   9900
taagagtatt aggagtcaac atcggaaaat atccaatggc caacattaat gccgtactta   9960
ctctcattgg tcacaaactt tctgtaatga gagatgagtt cggaaaagag aaaaggataa  10020
aagtagatgg taaatcatac cgatgttatc aacttgaaac attaccagat tttaccaatg  10080
atactcttga ctactggtta gaaaatgata gccaaaaaga agtaacagca acagaaaatt  10140
actccgaaaa ttttaaccct tcaaatagct acaatccaga cagtaagaca ctttcagagg  10200
gtgcaaattt cctatatata aataaagaag aattgcatcc aaataaattg cacctagaaa  10260
taaaagaagg tgctgaactt tttttattcg gggtaaaggt gattgtgaaa ggaatcttgg  10320
acggggcagt aactatattc tctatgggtc aagaatacga tttatccctc aatgaactag  10380
aggggatgtt aacatcatga actttacaag aatcttttta aagggcgatc gcaccatgtt  10440
aaatgatggt acatttgttc agatatttga tatttaccat gaccacgcat tgggagtgac  10500
ccttgacctt aagacagaaa aaattatttc cgatgatgtt agggtaatta ctgtcaaaga  10560
cttattgttc gatggcactt ataaaggggt aaaatctttt atgcccgata atgcccgata  10620
atgcccgatt gatgctacaa aatcccataa tcataagcga taatccccta atagcttgta  10680
attcttgaac cgtagcgatt ttagagtatt ccaaaaagaa gaaataaaca ccgcaaaatg  10740
tcgtatttca catatataaa ccaaggtttt ttgccctaaa atctttatgt ttgtagtgtg  10800
atgttgggtc aaaatggtca gaaaagttgc aaggttttta tggatgctta cgcgcgcgag  10860
gggtaagcat ccccaaatag ttactttatc ctagtccatg cccatttatt gccgtcccgt  10920
tcggctttaa aaaagtgcca aaactcacaa ggtgcaataa aaagttctgt acctttcgca  10980
accctagata atctttcaac agttactttt tttcctatta tctcggtaca aagtttggct  11040
agtttctctt ttccctcttt ttcaatcaag ccttcttgta tgcccaactc attgattaat  11100
ctctctattt ttaccattat ttcccgttca ggtagtttat cccctaaatc ttcatcgggg  11160
ggcaatgtag ggcattctga aggggctttt tcttctgtct ggacattatc taatattgaa  11220
gtaaccaaac tatcttcagt tttttctatt cctattaatt catattcggt tactgtatcc  11280
gtatcaatat ccgaataact atctttatcc gtattagcta ttcggttaag tttatccgtt  11340
aactcagaaa caagactata tagcggtttt agcttttctt ctatcctgtt atctaatacg  11400
```

```
gataagttta tacggttatc attatccgta ttagtatcat tgggcttttt tggtagttct  11460

acccccctcat aaaccgcttt tattcccaat tccaacagac tgataacagt atcctttata  11520

atgggttttt tgctgatatg gtgaactttt gccccttcca tcattgcgat actttctatc  11580

tcactcatca acttatcgct taagtgaatc tcgtatctgt ttaatccctt actggtttta  11640

ttcatatccg tttactttat tcggttaaca attctatttt atacgaataa aatattatac  11700

ggttaacttt atacgtttaa ctattttatc tatacggata acagtaataa gttattcgta  11760

ttagttatac gtttactttt atccaaataa aattagtgca tttaaactaa aagaatgatt  11820

ttatcggagt tgatagcatt ggattaacct aaagatgttt ataagctata tctgataagt  11880

atttaaggtt attttgttat tctgtttatt gacattatca gaataaaaga atagaatata  11940

attgttgaga gataagaggt ttaagtgatt atggttaaga agttagttgg ttatgtcagg  12000

gtcagtagtg aatcgcaaga ggataacact agcttacaga atcagataga gagaattgaa  12060

gcatattgta tggcttttgg ttatgagttg gtaaaaatat tcaaagaggt tgccactggt  12120

acaaaagcag atattgaaac ccgtcctatt tttaatgaag ctatagaata cttgaaacag  12180

gataatgcta atggaattat tgccttgaag ctagaccgaa tcgcacggaa tgctttagat  12240

gtattgcgtt tggttcgtga aaccttagaa ccacaaaata aaatgttagt gttactagat  12300

attcaggtag atacttcgac accttcagga aaaatgattt taactgtaat gagtgccgtt  12360

gctgaactcg aaagagacat gatctatgat cgcactcagg ggggtagaaa gactaaagcc  12420

caaaagggcg ggtatgccta cgggaaacct aaatttggct ataagactga agaaaaggaa  12480

ctaaaagaag attcagcaca acaggaaact attaaactaa ttaagagaca ccgtaggtca  12540

gggaaaagct accagaaaat agctgattat ctcaatgccc aaagtattcc cactaaacaa  12600

ggtaagaaat ggagttctag cgtcgtctat cgaatctgtc aggaaaaagc tggttaagtc  12660

tgtttataga tatttagaat ttattgaata aaaatagtat gaacaataaa tatttatgga  12720

ctaaccacgc tcggaaacgt ttaactgaac gatgggaaat aaaagaatca tgggttattg  12780

ataccatcga aaatcctgaa cgttcagaat ttattgttga tgagtcaggg gaaaaatatc  12840

attactataa aagaatagct aagtttaaga atagagtgtt agaagtgata acttctgcca  12900

actcaacacc cacaagaata ataacctttt actttaaccg taacatgagg aaaaatttat  12960

gattgttact tacgataatg aagttgacgc aatttatttt aagttaacgg aaaataaaat  13020

tgatagcacc gaacctcaaa cagacaggat tatcattgat tacgatgaaa gtaataatat  13080

tgttggcatt gaggtattag attttaatta tcttgtcaag aaaggtttaa ccgttgctga  13140

tttacctttt tctgaagatg aaagattaac agcttctcaa tattttaatt ttcctgttgc  13200

tatctaatcc agaaggggca ataatcccct tctttcatcg agttagactt aatatcacaa  13260

aagtcatttt cattttaccg tttcttttcc acagcgtccg tacgcccctc gttaaatctc  13320

aaaaccgaca atttatgatg tttataaaaa gttactcact ttaataagta tttatactca  13380

ttaaagggtt attctttttt tgtagcctga taggttggga aggaatattt cagattatca  13440

gatttgttg                                                          13449
```

```
<210> SEQ ID NO 28
<211> LENGTH: 12680
<212> TYPE: DNA
<213> ORGANISM: Artificial
<220> FEATURE:
<223> OTHER INFORMATION: Synthetically produced plasmid construct #1646
      pABIcyano1::PnirA-zmPDC(opt1)dsrA-Prbc*(optRBS)-ADH111(opt)_ter
```

<400> SEQUENCE: 28

```
tcgacaatta ataacttctt cctgtacggg cgaatggcca tttgctccta actaactccg     60
tactgctttg cggaacgagc gtagcgaact ctccgaatta ctaagccttc atccctgata    120
gatgcaaaaa acgaattaaa attatgtgta aaaagaaaat gtgtctttat ttagtagtca    180
aagttacaaa atattaagaa tcaaattaat aatgtattgg gcagttaagt atataagtct    240
ttaaatattt atttgtattc aatatattaa ccgaggacaa attatgaatt cttataccgt    300
gggtacttat ttagccgaac gcttagtgca aattggttta aaacatcatt ttgccgtggc    360
tggggactat aatttagtgt tattggataa cttattatta aataaaaaca tggaacaagt    420
gtattgttgt aatgaattaa attgtggttt ttctgctgaa ggttatgcta gagctaaagg    480
tgcagctgct gctgttgtta cttattctgt gggtgcttta tctgcttttg atgctattgg    540
tggtgcttat gccgaaaatt tacccgtgat tttaatttct ggtgccccta ataataatga    600
tcatgccgct ggacatgttt tacatcatgc cttaggtaaa accgattatc attatcaatt    660
agaaatggcc aaaaatatta ctgctgctgc cgaagctatt tatactcctg aagaagcccc    720
tgccaaaatt gatcatgtga ttaaaaccgc cttacgcgaa aaaaaacccg tgtatttaga    780
aattgcctgt aatattgctt ctatgccttg tgctgctcct gggcctgctt ctgctttatt    840
taatgatgaa gcctctgatg aagctagttt aaatgctgcc gtggaagaaa ccttaaaatt    900
tattgccaat cgcgataaag ttgccgtgtt agttggttct aaattaagag ctgctggtgc    960
tgaagaagct gctgttaaat ttgctgatgc tttaggtggt gcagttgcta ctatggctgc   1020
tgccaaatct ttttttcccg aagaaaatcc ccattatatt ggaactagtt ggggagaagt   1080
ttcttatcct ggtgtggaaa aaactatgaa agaagccgac gctgttattg ctttagcccc   1140
tgtgtttaat gattattcta ccactggttg gactgatatt cccgatccca aaaaattagt   1200
tttagccgaa cctcgttctg ttgttgttaa tggtgttcgc tttccctctg tgcatttaaa   1260
agattattta acccgcttag cccaaaaagt ttctaaaaaa actggtgcct tagatttttt   1320
taaatcttta aatgcgggtg aattaaaaaa agctgctcct gctgatcctt ctgctccttt   1380
agttaatgct gaaattgccc gtcaagttga agccttatta acccctaata ctaccgttat   1440
tgccgaaact ggtgattctt ggtttaatgc ccaacgcatg aaattaccta atggtgcccg   1500
tgttgaatat gaaatgcaat ggggtcatat tggttggtct gtacctgctg cttttggtta   1560
tgctgttggt gctcctgaac gtcgtaatat tttaatggtg ggtgatggtt cttttcaatt   1620
aactgcccaa gaagttgccc aaatggttcg cttaaaatta cccgttatta ttttttttaat   1680
aaataattat ggttatacca ttgaagtgat gattcatgat gggccatata ataatattaa   1740
aaattgggat tatgcgggtt taatggaagt gtttaatggt aatggtggtt atgattctgg   1800
tgctggtaaa ggtttaaaag ccaaaactgg tggtgaatta gctgaagcta ttaaagttgc   1860
cttagccaat actgatgggc caaccttaat tgaatgtttt attggtcgcg aagattgtac   1920
cgaagaatta gttaaatggg gtaaacgtgt tgctgctgct aattctcgca aacccgtgaa   1980
taaattattg taatttttgg ggatcaattc gagctcagca agtttcatcc cgaccccctc   2040
agggtcggga ttttttttatt gtactagttg acataagtaa aggcatcccc tgcgtgatat   2100
aattaccttc agtttaagga ggtatacaca tatgagtgaa actaaattta aagcctatgc   2160
cgtaatgaat cctggtgaaa aattacaacc ctgggaatat gaacctgctc ctttacaggt   2220
agatgaaatt gaagtaagag ttactcacaa tggtttatgt cacactgact tacacatgag   2280
agataatgac tggaatgtta gtgagttccc cttagtagca ggtcatgaag ttgttggtga   2340
```

```
agtaaccgct gttggtgaaa aagtaaccag tcgtaaaaaa ggtgatagag ttggtgtagg   2400
ttggattcgt aattcttgtc gcgcttgtga ccattgttta caaggagaag agaacatttg   2460
tagagagggt tatactggtt taattgttgg tcatcacggt ggatttgctg atcgtgtacg   2520
tgtacctgct gacttcactt ataaaattcc tgatgcttta gatagtgcat ctgctgctcc   2580
tttattatgt gccggtatta ccgtttacac tcctttaaga acctacatta aacatcccgg   2640
tatgaaagta ggtgttatgg gtattggagg attaggacat ttagctatta aatttgctcg   2700
tgcaatggga gcagaagtta ctgcctttag taccagtcct aataaagaag cccaagccaa   2760
agaatttggt gctcatcatt tccaacaatg gggtactgct gaagaaatga aagctgttgc   2820
cggtaatttt gatttagttt tatctaccat ctctgctgaa actgactggg atgctgcctt   2880
ctctttatta gcaaataacg gtgtttttatg tttcgtaggt attcccgtta gttctttaaa   2940
tgttccttta attcctttaa ttttcggaca aaaatctgtt gtaggttctg tagttggagg   3000
aagaagattc atggcagaaa tgttagagtt cgccgctgta aatcagatta aacctatgat   3060
cgaaactatg cccttatctc aagtaaatga agctatggat aaagttgccg ccaataaagc   3120
cagatataga attgtattat tatctgaata actagatctc ctgcagagaa tataaaaagc   3180
cagattatta atccggcttt tttattattt aaatactgtg cacgatcctg caggatcatc   3240
ttgctgaaaa actcgagcgc tcgttccgca aagcggtacg gagttagtta ggggctaatg   3300
ggcattctcc cgtacaggaa agagttagaa gttattaatt atcaacaatt ctcctttgcc   3360
tagtgcatcg ttaccttttt aattaaaaca taaggaaaac taataatcgt aataatttaa   3420
cctcaaagtg taaagaaatg tgaaattctg acttttataa cgttaaagag ggaaaaatta   3480
gcagtttaaa atacctagag aatagtctgg ggtaagcata gagaattaga ttagttaagt   3540
taatcaaatt cagaaaaaat aataatcgta aatagttaat ctgggtgtat agaaaatgat   3600
ccccttcatg ataagattta aactcgaaaa gcaaaagcca aaaaactaac ttccattaaa   3660
agaagttgtt acatataacg ctataaagaa aatttatata tttggaggat accaaccatg   3720
tctcatattc aacgtgaaac tagttgttct cgccctcgtt taaattctaa tatggatgcc   3780
gatttatatg gttataaatg ggctcgtgat aatgttggtc aatctggtgc tactatttat   3840
cgtttatatg gtaaacctga tgctcctgaa ttattcttga aacatggtaa aggttctgtt   3900
gctaatgatg ttactgatga aatggttcgt ttaaactggt tgactgaatt tatgccttta   3960
cctactatta aacattttat tcgtactccc gatgatgctt ggttattaac tactgctatt   4020
cctggtaaaa ctgcttttca agttttagaa gaatatcctg attctggtga aaatattgtt   4080
gatgctttag ctgttttttt acgtcgttta cattctattc ccgtttgtaa ttgtcctttt   4140
aattctgatc gtgtttttcg tttagctcaa gctcaatctc gtatgaataa tggtttagtt   4200
gatgcttctg attttgatga tgaacgtaat ggttggcctg ttgaacaagt ttggaaagaa   4260
atgcacaaat tgttaccttt ttctcctgat tctgttgtta ctcatggtga tttttcttta   4320
gataatttga tctttgatga aggtaaattg attggttgta ttgatgttgg tcgtgttggt   4380
attgctgatc gttatcaaga tttagctatt ttatggaatt gtttaggtga attttctcct   4440
tctttacaga aacgtttatt tcagaaatat ggtattgata atcctgatat gaacaagtta   4500
caatttcatt taatgttgga cgagttcttt taagaattaa ttcatgacca aaatccctta   4560
acgtgagttt tcgttccact gagcgtcaga ccccgtagaa aagatcaaag gatcttcttg   4620
agatcctttt tttctgcgcg taatctgctg ctatttaaat tacgtacacg tgttattact   4680
```

```
ttgttaacga caattgtctt aattaactgg gcctcatggg ccttccgctc actgcccgct   4740
ttccagtcgg gaaacctgtc gtgccagctc tgcagatgac ggtgaaaacc tctgacacat   4800
gcagctcccg gagacggtca cagcttgtct gtaagcggat gccgggagca gacaagcccg   4860
tcagggcgcg tcagcgggtg ttggcgggtg tcggggcgca gccatgaccc agtcacgtag   4920
cgatagcgga gtgtatactg gcttaactat gcggcatcag agcagattgt actgagagtg   4980
caccatatgc ggtgtgaaat accgcacaga tgcgtaagga gaaaataccg catcaggcgc   5040
tcttccgctt cctcgctcac tgactcgctg cgctcggtcg ttcggctgcg gcgagcggta   5100
tcagctcact caaaggcggt aatacggtta tccacagaat caggggataa cgcaggaaag   5160
aacatgtgag caaaaggcca gcaaaaggcc aggaaccgta aaaaggccgc gttgctggcg   5220
tttttccata ggctccgccc ccctgacgag catcacaaaa atcgacgctc aagtcagagg   5280
tggcgaaacc cgacaggact ataaagatac caggcgtttc cccctggaag ctccctcgtg   5340
cgctctcctg ttccgaccct gccgcttacc ggatacctgt ccgcctttct cccttcggga   5400
agcgtggcgc tttctcatag ctcacgctgt aggtatctca gttcggtgta ggtcgttcgc   5460
tccaagctgg gctgtgtgca cgaacccccc gttcagcccg accgctgcgc cttatccggt   5520
aactatcgtc ttgagtccaa cccggtaaga cacgacttat cgccactggc agcagccact   5580
ggtaacagga ttagcagagc gaggtatgta ggcggtgcta cagagttctt gaagtggtgg   5640
cctaactacg gctacactag aaggacagta tttggtatct gcgctctgct gaagccagtt   5700
accttcggaa aaagagttgg tagctcttga tccggcaaac aaaccaccgc tggtagcggt   5760
ggtttttttg tttgcaagca gcagattacg cgcagaaaaa aaggatctca agaagatcct   5820
ttgatctttt ctactgcaga agcttgttag acaccctgtc atgtatttta tattatttat   5880
ttcaccatac ggattaagtg aaacctaatg aaaatagtac tttcggagct ttaactttaa   5940
tgaaggtatg ttttttttata gacatcgatg tctggtttaa caataggaaa aagtagctaa   6000
aactcccatg aattaaagaa ataacaaggt gtctaacaac ctgttattaa gaatgttaga   6060
aaagacttaa catttgtgtt gagtttttat agacattggt gtctagacat acggtagata   6120
aggtttgctc aaaaataaaa taaaaaaaga ttggactaaa aaacatttaa tttagtacaa   6180
tttaattagt tattttttcg tctcaaattt tgctttgttg agcagaaatt tagataaaaa   6240
aatccccgtg atcagattac aatgtcgttc attgtacgat gtgtcgaaaa atctttacga   6300
cactctaaac tgaccacacg gggaaaaag aaaactgaac taataacatc atgatactcg   6360
gaaaacctag caattctcaa cccctaaaca aaagaaactt ccaaaaccct gaccatataa   6420
aggagtggca acaatcagca atcagtcaag atttgatagc agaaaatctt gtatcggttg   6480
ctaatggttt tgatgtacta tttatcggca ataaataccg aactaacacg ggtgttctgt   6540
cacggcacat attaaactcc tattctcatt tagaagatgg tggttcgtat ggtagaacat   6600
ttgacccatt taccaataaa gaaatgcagt gggttcaatt taaaccgaat agaccaagaa   6660
aaggttctac tggtaaggta atcaaatatg aatcgccaaa aggtgaacct acaagagttc   6720
taatgccgtt tgtgcctatg aaaatatggc aacggattag cgataagttc ggagtaccga   6780
ttaatccgaa aaaagatact cacttttggg aatgggtaaa gaataatcca tcgataccga   6840
ttgccattac agaaggaaat aaaaaagcta attgcctatt atcctatggc tatcctgcta   6900
ttgcctttgt aggcatttgg aacggattag agaaaataaa tgatttctcg aaggaaaagc   6960
agttaaaaga ggatttgaaa tggttgttat ccaacggcaa ccgaaatatt aatatcatct   7020
ttgaccaaga ccagaaacaa aaaactgtaa ttaatgtaaa caaagctatt ttcgctttat   7080
```

```
cttctctaat aagtagaaat ggtcataaag ttaatattgt gcaatggttg ccgtcaaaag   7140

gtaaaggaat agatgattat ttggtagctt tacctttga gaaaagagaa aatcatttag   7200

acaacttaat taaaattgca ccatcattta atttttggtc aactaaatac ttattcaagt   7260

gtcgtaaacc agatttaacc gtaaattgcc gttatttgag cgatgcagta aaagaattac   7320

ctcaagagga tatagcatta atagcacctc acggcacggg taaaacttca ttagtagcta   7380

ctcacgttaa gaatcggagt tatcacggaa ggaaaactat ttcattggtg catcttgaaa   7440

gtttagccaa agctaatggc aacgcacttg gattatatta ccgaaccgaa aataatattg   7500

aaaagcaata tcttggattt agcttatgtg tagatagttg ccgtgataag attaacggca   7560

ttacaactga tattatttca ggtcaagatt attgcctttt cattgatgaa attgaccaag   7620

taattccaca catccttaac agtgaaactg aagtaagtaa gtatagatgc accatcattg   7680

acactttttc tgaactggtg agaaatgctg aacaggtcat tattgctgat gctgatttat   7740

ccgatgtgac gattgaccta atagaaaaca tcagaggtaa aaaactatat gtaatcaaga   7800

atgaatatca gtatcaggga atgactttta acgccgttgg ttcaccatta gaaatgatgg   7860

caatgatggg aaaatcggtg tcagaaggca agaaattatt tattaacacc acatcccaaa   7920

aggcaaaaag taagtacggc acaatcgctc ttgagtctta tatttttggt ctaaataaag   7980

aagcaaagat attaagaata gactctgaaa ccactaaaaa ccctgaacat ccagcctata   8040

aaatcattga ccaagactta aataatatcc tcaaagatta tgattatgtc attgcctcac   8100

cttgccttca aacaggtgtc agtattacct taaaagggca ttttgaccag caatttaact   8160

tttccagtgg aaacattaca cctcattgct tttacagca aatgtggcgg ttgagggatg   8220

cagaaattga aagattctat tatgtgccga actcatctaa cctcaatctc attgggaata   8280

agtcaagttc accatcagac cttctaaaga gcaataacaa gatggcaacg gcaacggtta   8340

accttttggg tagaatcgac tccgaatatt ccctagagta tgaatcgcac ggcatttggc   8400

ttgagacgtg ggcaaaatta tcagcacggc ataacagttc aatgcgttgt tactctgaaa   8460

ttcttaccta tctaattacg tctcaagggc ataaattaaa tatcaacatt ccctcacctc   8520

ttgcagatat taagaagcta aatgatgagg taagtagtaa cagggaaaag gtaaaaaatg   8580

agagatactc tcagaggtta aactcaccag atattaacga tgcagaagct accatactcg   8640

aatctaaaga gcaaaaaatc ggattgactc tcaatgagag atgcacccta gaaaagcata   8700

aagttaagaa gcggtatggg aatgtaaaga tggatattct cacctttgat gatgatggac   8760

tataccccaa actcagacta ttttattacc tcaccatcgg taaacctcat ctcaaggcta   8820

atgacagaaa agctattgcc aaaatgggca atgacaataa aggcaagatt ctatcaaaag   8880

acttagttaa taaaacttac tccgctcgtg tgaaggtctt agagattctt aaactaactg   8940

actttatcga caatcttaga gatgaactct taataactcc caataatcca gctatcaccg   9000

attttaataa tcttctgcta agagctaaga aggatttaag agtattagga gtcaacatcg   9060

gaaaatatcc aatggccaac attaatgccg tacttactct cattggtcac aaactttctg   9120

taatgagaga tgagttcgga aaagagaaaa ggataaaagt agatggtaaa tcataccgat   9180

gttatcaact tgaaacatta ccagatttta ccaatgatac tcttgactac tggttagaaa   9240

atgatagcca aaaagaagta acagcaacag aaaattactc cgaaaatttt aacccttcaa   9300

atagctacaa tccagacagt aagacacttt cagagggtgc aaatttccta tatataaata   9360

aagaagaatt gcatccaaat aaattgcacc tagaaataaa agaaggtgct gaactttttt   9420
```

-continued

```
tattcggggt aaaggtgatt gtgaaaggaa tcttggacgg ggcagtaact atattctcta   9480
tgggtcaaga atacgattta tccctcaatg aactagaggg gatgttaaca tcatgaactt   9540
tacaagaatc tttttaaagg gcgatcgcac catgttaaat gatggtacat ttgttcagat   9600
atttgatatt taccatgacc acgcattggg agtgaccctt gaccttaaga cagaaaaaat   9660
tatttccgat gatgttaggg taattactgt caaagactta ttgttcgatg gcacttataa   9720
aggggtaaaa tcttttatgc ccgataatgc ccgataatgc ccgattgatg ctacaaaatc   9780
ccataatcat aagcgataat cccctaatag cttgtaattc ttgaaccgta gcgattttag   9840
agtattccaa aaagaagaaa taaacaccgc aaaatgtcgt atttcacata tataaaccaa   9900
ggtttttgc cctaaaatct ttatgtttgt agtgtgatgt tgggtcaaaa tggtcagaaa   9960
agttgcaagg tttttatgga tgcttacgcg cgcgaggggt aagcatcccc aaatagttac  10020
tttatcctag tccatgccca tttattgccg tcccgttcgg ctttaaaaaa gtgccaaaac  10080
tcacaaggtg caataaaaag ttctgtacct ttcgcaaccc tagataatct ttcaacagtt  10140
acttttttc ctattatctc ggtacaaagt ttggctagtt tctcttttcc ctctttttca  10200
atcaagcctt cttgtatgcc caactcattg attaatctct ctatttttac cattatttcc  10260
cgttcaggta gtttatcccc taaatcttca tcggggggca atgtagggca ttctgaaggg  10320
gctttttctt ctgtctggac attatctaat attgaagtaa ccaaactatc ttcagttttt  10380
tctattccta ttaattcata ttcggttact gtatccgtat caatatccga ataactatct  10440
ttatccgtat tagctattcg gttaagttta tccgttaact cagaaacaag actatatagc  10500
ggttttagct tttcttctat cctgttatct aatacggata agtttatacg gttatcatta  10560
tccgtattag tatcattggg cttttttggt agttctaccc cctcataaac cgcttttatt  10620
cccaattcca acagactgat aacagtatcc tttataatgg gtttttttgct gatatggtga  10680
acttttgccc cttccatcat tgcgatactt tctatctcac tcatcaactt atcgcttaag  10740
tgaatctcgt atctgtttaa tcccttactg gttttattca tatccgttta ctttattcgg  10800
ttaacaattc tattttatac gaataaaata ttatacggtt aactttatac gtttaactat  10860
tttatctata cggataacag taataagtta ttcgtattag ttatacgttt acttttatcc  10920
aaataaaatt agtgcattta aactaaaaga atgattttat cggagttgat agcattggat  10980
taacctaaag atgtttataa gctatatctg ataagtattt aaggttattt tgttattctg  11040
tttattgaca ttatcagaat aaaagaatag aatataattg ttgagagata agaggtttaa  11100
gtgattatgg ttaagaagtt agttggttat gtcagggtca gtagtgaatc gcaagaggat  11160
aacactagct tacagaatca gatagagaga attgaagcat attgtatggc ttttggttat  11220
gagttggtaa aaatattcaa agaggttgcc actggtacaa aagcagatat tgaaacccgt  11280
cctattttta atgaagctat agaatacttg aaacaggata atgctaatgg aattattgcc  11340
ttgaagctag accgaatcgc acggaatgct ttagatgtat tgcgtttggt tcgtgaaacc  11400
ttagaaccac aaaataaaat gttagtgtta ctagatattc aggtagatac ttcgacacct  11460
tcaggaaaaa tgattttaac tgtaatgagt gccgttgctg aactcgaaag agacatgatc  11520
tatgatcgca ctcagggggg tagaaagact aaagcccaaa agggcgggta tgcctacggg  11580
aaacctaaat ttggctataa gactgaagaa aaggaactaa aagaagattc agcacaacag  11640
gaaactatta aactaattaa gagacaccgt aggtcaggga aaagctacca gaaaatagct  11700
gattatctca atgcccaaag tattcccact aaacaaggta agaaatggag ttctagcgtc  11760
gtctatcgaa tctgtcagga aaaagctggt taagtctgtt tatagatatt tagaatttat  11820
```

```
tgaataaaaa tagtatgaac aataaatatt tatggactaa ccacgctcgg aaacgtttaa  11880
ctgaacgatg ggaaataaaa gaatcatggg ttattgatac catcgaaaat cctgaacgtt  11940
cagaatttat tgttgatgag tcaggggaaa aatatcatta ctataaaaga atagctaagt  12000
ttaagaatag agtgttagaa gtgataactt ctgccaactc aacacccaca agaataataa  12060
ccttttactt taaccgtaac atgaggaaaa atttatgatt gttacttacg ataatgaagt  12120
tgacgcaatt tattttaagt taacggaaaa taaaattgat agcaccgaac ctcaaacaga  12180
caggattatc attgattacg atgaaagtaa taatattgtt ggcattgagg tattagattt  12240
taattatctt gtcaagaaag gtttaaccgt tgctgattta ccttttctg aagatgaaag  12300
attaacagct tctcaatatt ttaattttcc tgttgctatc taatccagaa ggggcaataa  12360
tccccttctt tcatcgagtt agacttaata tcacaaaagt cattttcatt ttaccgtttc  12420
ttttccacag cgtccgtacg cccctcgtta aatctcaaaa ccgacaattt atgatgttta  12480
taaaaagtta ctcactttaa taagtattta tactcattaa agggttattc tttttttgta  12540
gcctgatagg ttgggaagga atatttcaga ttatcagatt tgttgaatat ttttcgtcag  12600
atacgcaaac cttacaaaca taattaacaa ctgaaactat tgatatgtct aggttttagc  12660
tctatcacag gttggatctg                                              12680
```

```
<210> SEQ ID NO 29
<211> LENGTH: 12719
<212> TYPE: DNA
<213> ORGANISM: Artificial
<220> FEATURE:
<223> OTHER INFORMATION: Synthetically produced plasmid construct #1652
      pABIcyano1::PnirA-zmPDC(opt1)dsrA-PrpsL*4-ADH111(opt)_ter

<400> SEQUENCE: 29
```

```
tcgacaatta ataacttctt cctgtacggg cgaatggcca tttgctccta actaactccg     60
tactgctttg cggaacgagc gtagcgaact ctccgaatta ctaagccttc atccctgata    120
gatgcaaaaa acgaattaaa attatgtgta aaaagaaaat gtgtctttat ttagtagtca    180
aagttacaaa atattaagaa tcaaattaat aatgtattgg gcagttaagt atataagtct    240
ttaaatattt atttgtattc aatatattaa ccgaggacaa attatgaatt cttataccgt    300
gggtacttat ttagccgaac gcttagtgca aattggttta aaacatcatt ttgccgtggc    360
tggggactat aatttagtgt tattggataa cttattatta aataaaaaca tggaacaagt    420
gtattgttgt aatgaattaa attgtggttt ttctgctgaa ggttatgcta gagctaaagg    480
tgcagctgct gctgttgtta cttattctgt gggtgcttta tctgcttttg atgctattgg    540
tggtgcttat gccgaaaatt tacccgtgat tttaatttct ggtgccccta ataataatga    600
tcatgccgct ggacatgttt tacatcatgc cttaggtaaa accgattatc attatcaatt    660
agaaatggcc aaaaatatta ctgctgctgc cgaagctatt tatactcctg aagaagcccc    720
tgccaaaatt gatcatgtga ttaaaaccgc cttacgcgaa aaaaaacccg tgtatttaga    780
aattgcctgt aatattgctt ctatgccttg tgctgctcct gggcctgctt ctgctttatt    840
taatgatgaa gcctctgatg aagctagttt aaatgctgcc gtggaagaaa ccttaaaatt    900
tattgccaat cgcgataaag ttgccgtgtt agttggttct aaattaagag ctgctggtgc    960
tgaagaagct gctgttaaat ttgctgatgc tttaggtggt gcagttgcta ctatggctgc   1020
tgccaaatct ttttttcccg aagaaaatcc ccattatatt ggaactagtt ggggagaagt   1080
ttcttatcct ggtgtggaaa aaactatgaa agaagccgac gctgttattg ctttagcccc   1140
```

```
tgtgtttaat gattattcta ccactggttg gactgatatt cccgatccca aaaaattagt   1200
tttagccgaa cctcgttctg ttgttgttaa tggtgttcgc tttccctctg tgcatttaaa   1260
agattattta acccgcttag cccaaaaagt ttctaaaaaa actggtgcct tagatttttt   1320
taaatcttta aatgcgggtg aattaaaaaa agctgctcct gctgatcctt ctgctccttt   1380
agttaatgct gaaattgccc gtcaagttga agccttatta acccctaata ctaccgttat   1440
tgccgaaact ggtgattctt ggtttaatgc ccaacgcatg aaattaccta atggtgcccg   1500
tgttgaatat gaaatgcaat ggggtcatat tggttggtct gtacctgctg cttttggtta   1560
tgctgttggt gctcctgaac gtcgtaatat tttaatggtg ggtgatggtt cttttcaatt   1620
aactgcccaa gaagttgccc aaatggttcg cttaaaatta cccgttatta ttttttttaat   1680
aaataattat ggttatacca ttgaagtgat gattcatgat gggccatata ataatattaa   1740
aaattgggat tatgcgggtt taatggaagt gtttaatggt aatggtggtt atgattctgg   1800
tgctggtaaa ggtttaaaag ccaaaactgg tggtgaatta gctgaagcta ttaaagttgc   1860
cttagccaat actgatgggc caaccttaat tgaatgtttt attggtcgcg aagattgtac   1920
cgaagaatta gttaaatggg gtaaacgtgt tgctgctgct aattctcgca aacccgtgaa   1980
taaattattg taaggatcca gcaaggtttc atcccgaccc cctcagggtc gggatttttt   2040
tattgtgagc tcagaaaaac tattgacaaa cccataaaaa atgtgatata attatagatt   2100
gtcactggta ttttatacta gaggcaaatt atatttatat atacaaaaat gctgtaggag   2160
gatcagccat atgagtgaaa ctaaatttaa agcctatgcc gtaatgaatc ctggtgaaaa   2220
attacaaccc tgggaatatg aacctgctcc tttacaggta gatgaaattg aagtaagagt   2280
tactcacaat ggtttatgtc acactgactt acacatgaga gataatgact ggaatgttag   2340
tgagttcccc ttagtagcag gtcatgaagt tgttggtgaa gtaaccgctg ttggtgaaaa   2400
agtaaccagt cgtaaaaaag gtgatagagt tggtgtaggt tggattcgta attcttgtcg   2460
cgcttgtgac cattgtttac aaggagaaga gaacatttgt agagagggtt atactggttt   2520
aattgttggt catcacggtg gatttgctga tcgtgtacgt gtacctgctg acttcactta   2580
taaaattcct gatgctttag atagtgcatc tgctgctcct ttattatgtg ccggtattac   2640
cgtttacact cctttaagaa cctacattaa acatcccggt atgaaagtag gtgttatggg   2700
tattggagga ttaggacatt tagctattaa atttgctcgt gcaatgggag cagaagttac   2760
tgcctttagt accagtccta ataaagaagc ccaagccaaa gaatttggtg ctcatcattt   2820
ccaacaatgg ggtactgctg aagaaatgaa agctgttgcc ggtaattttg atttagtttt   2880
atctaccatc tctgctgaaa ctgactggga tgctgccttc tctttattag caaataacgg   2940
tgttttatgt ttcgtaggta ttcccgttag ttctttaaat gttcctttaa ttcctttaat   3000
tttcggacaa aaatctgttg taggttctgt agttggagga agaagattca tggcagaaat   3060
gttagagttc gccgctgtaa atcagattaa acctatgatc gaaactatgc ccttatctca   3120
agtaaatgaa gctatggata aagttgccgc caataaagcc agatatagaa ttgtattatt   3180
atctgaataa ctagatctcc tgcagagaat ataaaaagcc agattattaa tccggctttt   3240
ttattattta aatactgtgc acgatcctgc aggatcatct tgctgaaaaa ctcgagcgct   3300
cgttccgcaa agcggtacgg agttagttag gggctaatgg gcattctccc gtacaggaaa   3360
gagttagaag ttattaatta tcaacaattc tcctttgcct agtgcatcgt tacctttttta   3420
attaaaacat aaggaaaact aataatcgta ataatttaac ctcaaagtgt aaagaaatgt   3480
```

-continued

```
gaaattctga cttttataac gttaaagagg gaaaaattag cagtttaaaa tacctagaga   3540
atagtctggg gtaagcatag agaattagat tagttaagtt aatcaaattc agaaaaaata   3600
ataatcgtaa atagttaatc tgggtgtata gaaaatgatc cccttcatga taagatttaa   3660
actcgaaaag caaaagccaa aaaactaact tccattaaaa gaagttgtta catataacgc   3720
tataaagaaa atttatatat ttggaggata ccaaccatgt ctcatattca acgtgaaact   3780
agttgttctc gccctcgttt aaattctaat atggatgccg atttatatgg ttataaatgg   3840
gctcgtgata atgttggtca atctggtgct actatttatc gtttatatgg taaacctgat   3900
gctcctgaat tattcttgaa acatggtaaa ggttctgttg ctaatgatgt tactgatgaa   3960
atggttcgtt taaactggtt gactgaattt atgcctttac ctactattaa acattttatt   4020
cgtactcccg atgatgcttg gttattaact actgctattc ctggtaaaac tgcttttcaa   4080
gttttagaag aatatcctga ttctggtgaa aatattgttg atgctttagc tgttttttta   4140
cgtcgtttac attctattcc cgtttgtaat tgtcctttta attctgatcg tgtttttcgt   4200
ttagctcaag ctcaatctcg tatgaataat ggtttagttg atgcttctga ttttgatgat   4260
gaacgtaatg gttggcctgt tgaacaagtt tggaaagaaa tgcacaaatt gttacctttt   4320
tctcctgatt ctgttgttac tcatggtgat ttttctttag ataatttgat ctttgatgaa   4380
ggtaaattga ttggttgtat tgatgttggt cgtgttggta ttgctgatcg ttatcaagat   4440
ttagctattt tatggaattg tttaggtgaa ttttctcctt ctttacagaa acgtttattt   4500
cagaaatatg gtattgataa tcctgatatg aacaagttac aatttcattt aatgttggac   4560
gagttctttt aagaattaat tcatgaccaa aatcccttaa cgtgagtttt cgttccactg   4620
agcgtcagac cccgtagaaa agatcaaagg atcttcttga gatccttttt ttctgcgcgt   4680
aatctgctgc tatttaaatt acgtacacgt gttattactt tgttaacgac aattgtctta   4740
attaactggg cctcatgggc cttccgctca ctgcccgctt tccagtcggg aaacctgtcg   4800
tgccagctct gcagatgacg gtgaaaacct ctgacacatg cagctcccgg agacggtcac   4860
agcttgtctg taagcggatg ccgggagcag acaagcccgt cagggcgcgt cagcgggtgt   4920
tggcgggtgt cggggcgcag ccatgaccca gtcacgtagc gatagcggag tgtatactgg   4980
cttaactatg cggcatcaga gcagattgta ctgagagtgc accatatgcg gtgtgaaata   5040
ccgcacagat gcgtaaggag aaaataccgc atcaggcgct cttccgcttc ctcgctcact   5100
gactcgctgc gctcggtcgt tcggctgcgg cgagcggtat cagctcactc aaaggcggta   5160
atacggttat ccacagaatc aggggataac gcaggaaaga acatgtgagc aaaaggccag   5220
caaaaggcca ggaaccgtaa aaaggccgcg ttgctggcgt ttttccatag gctccgcccc   5280
cctgacgagc atcacaaaaa tcgacgctca agtcagaggt ggcgaaaccc gacaggacta   5340
taaagatacc aggcgtttcc ccctggaagc tccctcgtgc gctctcctgt tccgaccctg   5400
ccgcttaccg gatacctgtc cgcctttctc ccttcgggaa gcgtggcgct ttctcatagc   5460
tcacgctgta ggtatctcag ttcggtgtag gtcgttcgct ccaagctggg ctgtgtgcac   5520
gaaccccccg ttcagcccga ccgctgcgcc ttatccggta actatcgtct tgagtccaac   5580
ccggtaagac acgacttatc gccactggca gcagccactg gtaacaggat tagcagagcg   5640
aggtatgtag gcggtgctac agagttcttg aagtggtggc ctaactacgg ctacactaga   5700
aggacagtat ttggtatctg cgctctgctg aagccagtta ccttcggaaa aagagttggt   5760
agctcttgat ccggcaaaca aaccaccgct ggtagcggtg gtttttttgt ttgcaagcag   5820
cagattacgc gcagaaaaaa aggatctcaa gaagatcctt tgatcttttc tactgcagaa   5880
```

```
gcttgttaga caccctgtca tgtattttat attatttatt tcaccatacg gattaagtga   5940
aacctaatga aaatagtact ttcggagctt taactttaat gaaggtatgt ttttttatag   6000
acatcgatgt ctggtttaac aataggaaaa agtagctaaa actcccatga attaaagaaa   6060
taacaaggtg tctaacaacc tgttattaag aatgttagaa aagacttaac atttgtgttg   6120
agtttttata gacattggtg tctagacata cggtagataa ggtttgctca aaaataaaat   6180
aaaaaaagat tggactaaaa aacatttaat ttagtacaat ttaattagtt attttttcgt   6240
ctcaaatttt gctttgttga gcagaaattt agataaaaaa atccccgtga tcagattaca   6300
atgtcgttca ttgtacgatg tgtcgaaaaa tctttacgac actctaaact gaccacacgg   6360
gggaaaaaga aaactgaact aataacatca tgatactcgg aaaacctagc aattctcaac   6420
ccctaaacaa aagaaacttc caaaaccctg accatataaa ggagtggcaa caatcagcaa   6480
tcagtcaaga tttgatagca gaaaatcttg tatcggttgc taatggtttt gatgtactat   6540
ttatcggcaa taaataccga actaacacgg gtgttctgtc acggcacata ttaaactcct   6600
attctcattt agaagatggt ggttcgtatg gtagaacatt tgacccattt accaataaag   6660
aaatgcagtg ggttcaattt aaaccgaata gaccaagaaa aggttctact ggtaaggtaa   6720
tcaaatatga atcgccaaaa ggtgaaccta caagagttct aatgccgttt gtgcctatga   6780
aaatatggca acggattagc gataagttcg gagtaccgat taatccgaaa aaagatactc   6840
acttttggga atgggtaaag aataatccat cgataccgat tgccattaca gaaggaaata   6900
aaaaagctaa ttgcctatta tcctatggct atcctgctat tgcctttgta ggcatttgga   6960
acggattaga gaaaataaat gatttctcga aggaaaagca gttaaaagag gatttgaaat   7020
ggttgttatc caacggcaac cgaaatatta atatcatctt tgaccaagac cagaaacaaa   7080
aaactgtaat taatgtaaac aaagctattt tcgctttatc ttctctaata agtagaaatg   7140
gtcataaagt taatattgtg caatggttgc cgtcaaaagg taaaggaata gatgattatt   7200
tggtagcttt acctttttgag aaaagagaaa atcatttaga caacttaatt aaaattgcac   7260
catcatttaa tttttggtca actaaatact tattcaagtg tcgtaaacca gatttaaccg   7320
taaattgccg ttatttgagc gatgcagtaa aagaattacc tcaagaggat atagcattaa   7380
tagcacctca cggcacgggt aaaacttcat tagtagctac tcacgttaag aatcggagtt   7440
atcacggaag gaaaactatt tcattggtgc atcttgaaag tttagccaaa gctaatggca   7500
acgcacttgg attatattac cgaaccgaaa ataatattga aaagcaatat cttggattta   7560
gcttatgtgt agatagttgc cgtgataaga ttaacggcat tacaactgat attatttcag   7620
gtcaagatta ttgccttttc attgatgaaa ttgaccaagt aattccacac atccttaaca   7680
gtgaaactga agtaagtaag tatagatgca ccatcattga cacttttttct gaactggtga   7740
gaaatgctga acaggtcatt attgctgatg ctgatttatc cgatgtgacg attgacctaa   7800
tagaaaacat cagaggtaaa aaactatatg taatcaagaa tgaatatcag tatcagggaa   7860
tgacttttaa cgccgttggt tcaccattag aaatgatggc aatgatggga aaatcggtgt   7920
cagaaggcaa gaaattattt attaacacca catcccaaaa ggcaaaaagt aagtacggca   7980
caatcgctct tgagtcttat atttttggtc taaataaaga agcaaagata ttaagaatag   8040
actctgaaac cactaaaaac cctgaacatc cagcctataa aatcattgac caagacttaa   8100
ataatatcct caaagattat gattatgtca ttgcctcacc ttgccttcaa acaggtgtca   8160
gtattacctt aaaagggcat tttgaccagc aatttaactt ttccagtgga aacattacac   8220
```

```
ctcattgctt tttacagcaa atgtggcggt tgagggatgc agaaattgaa agattctatt   8280
atgtgccgaa ctcatctaac ctcaatctca ttgggaataa gtcaagttca ccatcagacc   8340
ttctaaagag caataacaag atggcaacgg caacggttaa ccttttgggt agaatcgact   8400
ccgaatattc cctagagtat gaatcgcacg gcatttggct tgagacgtgg gcaaaattat   8460
cagcacggca taacagttca atgcgttgtt actctgaaat tcttacctat ctaattacgt   8520
ctcaagggca taaattaaat atcaacattc cctcacctct tgcagatatt aagaagctaa   8580
atgatgaggt aagtagtaac agggaaaagg taaaaaatga gagatactct cagaggttaa   8640
actcaccaga tattaacgat gcagaagcta ccatactcga atctaaagag caaaaaatcg   8700
gattgactct caatgagaga tgcaccctag aaaagcataa agttaagaag cggtatggga   8760
atgtaaagat ggatattctc acctttgatg atgatggact ataccccaaa ctcagactat   8820
tttattacct caccatcggt aaacctcatc tcaaggctaa tgacagaaaa gctattgcca   8880
aaatgggcaa tgacaataaa ggcaagattc tatcaaaaga cttagttaat aaaacttact   8940
ccgctcgtgt gaaggtctta gagattctta aactaactga ctttatcgac aatcttagag   9000
atgaactctt aataactccc aataatccag ctatcaccga ttttaataat cttctgctaa   9060
gagctaagaa ggatttaaga gtattaggag tcaacatcgg aaaatatcca atggccaaca   9120
ttaatgccgt acttactctc attggtcaca aactttctgt aatgagagat gagttcggaa   9180
aagagaaaag gataaaagta gatggtaaat cataccgatg ttatcaactt gaaacattac   9240
cagattttac caatgatact cttgactact ggttagaaaa tgatagccaa aaagaagtaa   9300
cagcaacaga aaattactcc gaaaatttta acccttcaaa tagctacaat ccagacagta   9360
agacactttc agagggtgca aatttcctat atataaataa agaagaattg catccaaata   9420
aattgcacct agaaataaaa gaaggtgctg aacttttttt attcggggta aaggtgattg   9480
tgaaaggaat cttggacggg gcagtaacta tattctctat gggtcaagaa tacgatttat   9540
ccctcaatga actagagggg atgttaacat catgaacttt acaagaatct ttttaaaggg   9600
cgatcgcacc atgttaaatg atggtacatt tgttcagata tttgatattt accatgacca   9660
cgcattggga gtgacccttg accttaagac agaaaaaatt atttccgatg atgttagggt   9720
aattactgtc aaagacttat tgttcgatgg cacttataaa ggggtaaaat cttttatgcc   9780
cgataatgcc cgataatgcc cgattgatgc tacaaaatcc cataatcata agcgataatc   9840
ccctaatagc ttgtaattct tgaaccgtag cgattttaga gtattccaaa aagaagaaat   9900
aaacaccgca aaatgtcgta tttcacatat ataaaccaag gtttttgcc ctaaaatctt    9960
tatgtttgta gtgtgatgtt gggtcaaaat ggtcagaaaa gttgcaaggt ttttatggat  10020
gcttacgcgc gcgaggggta agcatcccca aatagttact ttatcctagt ccatgcccat  10080
ttattgccgt cccgttcggc tttaaaaaag tgccaaaact cacaaggtgc aataaaaagt  10140
tctgtacctt tcgcaaccct agataatctt tcaacagtta cttttttcc tattatctcg   10200
gtacaaagtt tggctagttt ctcttttccc tctttttcaa tcaagccttc ttgtatgccc  10260
aactcattga ttaatctctc tatttttacc attatttccc gttcaggtag tttatcccct  10320
aaatcttcat cgggggcaa tgtagggcat tctgaagggg ctttttcttc tgtctggaca   10380
ttatctaata ttgaagtaac caaactatct tcagtttttt ctattcctat taattcatat  10440
tcggttactg tatccgtatc aatatccgaa taactatctt tatccgtatt agctattcgg  10500
ttaagtttat ccgttaactc agaaacaaga ctatatagcg gttttagctt ttcttctatc  10560
ctgttatcta atacggataa gtttatacgg ttatcattat ccgtattagt atcattgggc  10620
```

```
tttttggta gttctacccc ctcataaacc gcttttattc ccaattccaa cagactgata  10680

acagtatcct ttataatggg ttttttgctg atatggtgaa cttttgcccc ttccatcatt  10740

gcgatacttt ctatctcact catcaactta tcgcttaagt gaatctcgta tctgtttaat  10800

cccttactgg ttttattcat atccgtttac tttattcggt taacaattct attttatacg  10860

aataaaatat tatacggtta actttatacg tttaactatt ttatctatac ggataacagt  10920

aataagttat tcgtattagt tatacgttta cttttatcca aataaaatta gtgcatttaa  10980

actaaaagaa tgattttatc ggagttgata gcattggatt aacctaaaga tgtttataag  11040

ctatatctga taagtattta aggttatttt gttattctgt ttattgacat tatcagaata  11100

aaagaataga atataattgt tgagagataa gaggtttaag tgattatggt taagaagtta  11160

gttggttatg tcagggtcag tagtgaatcg caagaggata acactagctt acagaatcag  11220

atagagagaa ttgaagcata ttgtatggct tttggttatg agttggtaaa aatattcaaa  11280

gaggttgcca ctggtacaaa agcagatatt gaaacccgtc ctatttttaa tgaagctata  11340

gaatacttga aacaggataa tgctaatgga attattgcct tgaagctaga ccgaatcgca  11400

cggaatgctt tagatgtatt gcgtttggtt cgtgaaacct tagaaccaca aaataaaatg  11460

ttagtgttac tagatattca ggtagatact tcgacacctt caggaaaaat gattttaact  11520

gtaatgagtg ccgttgctga actcgaaaga gacatgatct atgatcgcac tcagggggt   11580

agaaagacta aagcccaaaa gggcgggtat gcctacggga aacctaaatt tggctataag  11640

actgaagaaa aggaactaaa agaagattca gcacaacagg aaactattaa actaattaag  11700

agacaccgta ggtcagggaa aagctaccag aaaatagctg attatctcaa tgcccaaagt  11760

attcccacta aacaaggtaa gaaatggagt tctagcgtcg tctatcgaat ctgtcaggaa  11820

aaagctggtt aagtctgttt atagatattt agaatttatt gaataaaaat agtatgaaca  11880

ataaatattt atggactaac cacgctcgga aacgtttaac tgaacgatgg gaaataaaag  11940

aatcatgggt tattgatacc atcgaaaatc ctgaacgttc agaatttatt gttgatgagt  12000

caggggaaaa atatcattac tataaaagaa tagctaagtt taagaataga gtgttagaag  12060

tgataacttc tgccaactca acacccacaa gaataataac cttttacttt aaccgtaaca  12120

tgaggaaaaa tttatgattg ttacttacga taatgaagtt gacgcaattt attttaagtt  12180

aacggaaaat aaaattgata gcaccgaacc tcaaacagac aggattatca ttgattacga  12240

tgaaagtaat aatattgttg gcattgaggt attagatttt aattatcttg tcaagaaagg  12300

tttaaccgtt gctgatttac ctttttctga agatgaaaga ttaacagctt ctcaatattt  12360

taattttcct gttgctatct aatccagaag ggcaataat ccccttcttt catcgagtta  12420

gacttaatat cacaaaagtc attttcattt taccgtttct tttccacagc gtccgtacgc  12480

ccctcgttaa atctcaaaac cgacaattta tgatgtttat aaaaagttac tcactttaat  12540

aagtatttat actcattaaa gggttattct ttttttgtag cctgataggt tgggaaggaa  12600

tatttcagat tatcagattt gttgaatatt tttcgtcaga tacgcaaacc ttacaaacat  12660

aattaacaac tgaaactatt gatatgtcta ggttttagct ctatcacagg ttggatctg   12719
```

```
<210> SEQ ID NO 30
<211> LENGTH: 12649
<212> TYPE: DNA
<213> ORGANISM: Artificial
<220> FEATURE:
<223> OTHER INFORMATION: Synthetically produced plasmid construct #1658
      pABIcyano1::PnirA*2-zmPDC(opt3)dsrA-Prbc*(optRBS)-synADH_oop
```

<400> SEQUENCE: 30

```
tcgacaatta ataacttctt cctgtacggg cgaatggcca tttgctccta actaactccg     60
tactgctttg cggaacgagc gtagcgaact ctccgaatta ctaagccttc atccctgata    120
gatgcaaaaa acgaattaaa attatgtgta aaaagaaaat gtgtctttat ttagtagtca    180
aagttacaaa atattaagaa tcaaattaat aatgtattgg gcagttaagt atataagtct    240
ttaaatattt atttgtattc aatatattaa ggaggatcag ccttatgaat tcttacactg    300
ttggaaccta tttagcagaa cgtttagttc aaattggtct caaacaccat tttgcagtag    360
ctggtgatta taatttagtt ttattggata acttattgtt aaataagaat atggaacaag    420
tgtattgttg taatgaatta aactgtggtt tttctgctga gggatatgct cgtgcaaaag    480
gtgctgccgc agcagttgtt acttattctg ttggagcatt aagtgctttt gacgctattg    540
gaggtgctta tgcagaaaat ttacctgtaa tcttaatctc tggtgcaccc aataacaacg    600
atcacgctgc tggtcatgta ttgcatcatg ctttaggtaa aaccgattat cattaccaat    660
tagaaatggc aaaaaatatt accgctgccg cagaagctat ttatactccc gaagaagcac    720
ctgctaagat cgatcacgta attaaaaccg ctctccgtga gaaaaaaccc gtatatttag    780
aaatcgcttg caatatcgct tctatgcctt gtgcagctcc tggacctgct agtgctttat    840
ttaacgatga agcatctgat gaggctagtt taaatgccgc tgttgaagaa actttgaaat    900
ttattgctaa tcgtgataaa gtagctgttt tagttggttc taaactccgt gccgctggtg    960
cagaagaagc ggctgtaaaa ttcgcagatg ccttaggagg tgctgttgcc acaatggcag   1020
ccgctaaaag tttttttccc gaagaaaatc ctcattacat tggtacttct tggggtgagg   1080
tatcttaccc tggtgtagaa aaaaccatga aggaagctga tgcagtaatt gcattagctc   1140
ctgttttcaa tgattactct accactggtt ggactgatat tccagacccc aaaaaattag   1200
ttttagcaga acctcgctct gtagttgtga atggtgttag atttcccagt gtacatctca   1260
aagattattt aactcgttta gctcaaaaag tgagtaaaaa gactggcgca ctcgatttct   1320
ttaaatcttt aaatgctggt gaattaaaga aagcagctcc tgctgatccc agtgctcctt   1380
tagtgaatgc cgaaatcgca agacaagttg aagccttgtt aactcctaac actaccgtta   1440
ttgccgagac tggtgatagt tggttcaatg ctcaacgcat gaaattaccc aatggtgctc   1500
gtgttgagta tgaaatgcaa tggggtcaca ttggatggtc tgttcctgct gcatttggat   1560
atgcagttgg agcacctgag cgtagaaaca ttttaatggt aggtgatggt tctttccaac   1620
tcactgctca agaagttgca caaatggtac gtttaaaatt gcctgttatt atctttctca   1680
ttaacaacta tggttacacc attgaagtta tgattcatga tggtccttat aataacatta   1740
agaattggga ttacgcaggt ttaatggagg tatttaacgg taatggtgga tacgacagtg   1800
gagcaggtaa aggattaaaa gctaaaacag gaggtgagtt agctgaagca attaaagtag   1860
ctttagccaa tacagatggt cctaccttaa tcgaatgttt cattggacgt gaagattgta   1920
ctgaagagtt agttaaatgg ggaaagcgtg ttgccgctgc aaattctcgt aaacctgtaa   1980
acaaactctt gtagttagga tccgagctca gcaagtttca tcccgacccc ctcagggtcg   2040
ggattttttt attgtactag ttgacataag taaaggcatc ccctgcgtga tataattacc   2100
ttcagtttaa ggaggtatac acatatgatt aaagcctacg ctgccctgga agccaacgga   2160
aaactccaac cctttgaata cgaccccggt gccctgggtg ctaatgaggt ggagattgag   2220
gtgcagtatt gtggggtgtg ccacagtgat ttgtccatga ttaataacga atggggcatt   2280
```

```
tccaattacc ccctagtgcc gggtcatgag gtggtgggta ctgtggccgc catgggcgaa   2340
ggggtgaacc atgttgaggt gggggattta gtggggctgg gttggcattc gggctactgc   2400
atgacctgcc atagttgttt atctggctac cacaaccttt gtgccacggc ggaatcgacc   2460
attgtgggcc actacggtgg ctttggcgat cgggttcggg ccaagggagt cagcgtggtg   2520
aaattaccta aaggcattga cctagccagt gccgggcccc ttttctgtgg aggaattacc   2580
gttttcagtc ctatggtgga actgagttta aagcccactg caaaagtggc agtgatcggc   2640
attgggggct tgggccattt agcggtgcaa tttctccggg cctggggctg tgaagtgact   2700
gcctttacct ccagtgccag gaagcaaacg gaagtgttgg aattgggcgc tcaccacata   2760
ctagattcca ccaatccaga ggcgatcgcc agtgcggaag gcaaatttga ctatattatc   2820
tccactgtga acctgaagct tgactggaac ttatacatca gcaccctggc gccccaggga   2880
catttccact ttgttggggt ggtgttggag cctttggatc taaatctttt tccccttttg   2940
atgggacaac gctccgtttc tgcctcccca gtgggtagtc ccgccaccat tgccaccatg   3000
ttggactttg ctgtgcgcca tgacattaaa cccgtggtgg aacaatttag ctttgatcag   3060
atcaacgagg cgatcgccca tctagaaagc ggcaaagccc attatcgggt agtgctcagc   3120
catagtaaaa attagctctg caaaggttgc ttctgggtcc gtggaacgct cggttgccgc   3180
cgggcgtttt ttattcctgc aggatcatct tgctgaaaaa ctcgagcgct cgttccgcaa   3240
agcggtacgg agttagttag gggctaatgg gcattctccc gtacaggaaa gagttagaag   3300
ttattaatta tcaacaattc tcctttgcct agtgcatcgt taccttttta attaaaacat   3360
aaggaaaact aataatcgta ataatttaac ctcaaagtgt aaagaaatgt gaaattctga   3420
cttttataac gttaaagagg gaaaaattag cagtttaaaa tacctagaga atagtctggg   3480
gtaagcatag agaattagat tagttaagtt aatcaaattc agaaaaaata ataatcgtaa   3540
atagttaatc tgggtgtata gaaaatgatc cccttcatga taagatttaa actcgaaaag   3600
caaaagccaa aaaactaact tccattaaaa gaagttgtta catataacgc tataaagaaa   3660
atttatatat ttggaggata ccaaccatgt ctcatattca acgtgaaact agttgttctc   3720
gccctcgttt aaattctaat atggatgccg atttatatgg ttataaatgg gctcgtgata   3780
atgttggtca atctggtgct actatttatc gtttatatgg taaacctgat gctcctgaat   3840
tattcttgaa acatggtaaa ggttctgttg ctaatgatgt tactgatgaa atggttcgtt   3900
taaactggtt gactgaattt atgcctttac ctactattaa acattttatt cgtactcccg   3960
atgatgcttg gttattaact actgctattc ctggtaaaac tgcttttcaa gttttagaag   4020
aatatcctga ttctggtgaa aatattgttg atgctttagc tgttttttta cgtcgtttac   4080
attctattcc cgtttgtaat tgtcctttta attctgatcg tgtttttcgt ttagctcaag   4140
ctcaatctcg tatgaataat ggtttagttg atgcttctga ttttgatgat gaacgtaatg   4200
gttggcctgt tgaacaagtt tggaaagaaa tgcacaaatt gttacctttt tctcctgatt   4260
ctgttgttac tcatggtgat ttttctttag ataatttgat ctttgatgaa ggtaaattga   4320
ttggttgtat tgatgttggt cgtgttggta ttgctgatcg ttatcaagat ttagctattt   4380
tatggaattg tttaggtgaa ttttctcctt ctttacagaa acgtttattt cagaaatatg   4440
gtattgataa tcctgatatg aacaagttac aatttcattt aatgttggac gagttctttt   4500
aagaattaat tcatgaccaa aatcccttaa cgtgagtttt cgttccactg agcgtcagac   4560
cccgtagaaa agatcaaagg atcttcttga gatccttttt ttctgcgcgt aatctgctgc   4620
tatttaaatt acgtacacgt gttattactt tgttaacgac aattgtctta attaactggg   4680
```

```
cctcatgggc cttccgctca ctgcccgctt tccagtcggg aaacctgtcg tgccagctct   4740
gcagatgacg gtgaaaacct ctgacacatg cagctcccgg agacggtcac agcttgtctg   4800
taagcggatg ccgggagcag acaagcccgt cagggcgcgt cagcgggtgt tggcgggtgt   4860
cggggcgcag ccatgaccca gtcacgtagc gatagcggag tgtatactgg cttaactatg   4920
cggcatcaga gcagattgta ctgagagtgc accatatgcg gtgtgaaata ccgcacagat   4980
gcgtaaggag aaaataccgc atcaggcgct cttccgcttc ctcgctcact gactcgctgc   5040
gctcggtcgt tcggctgcgg cgagcggtat cagctcactc aaaggcggta atacggttat   5100
ccacagaatc aggggataac gcaggaaaga acatgtgagc aaaaggccag caaaaggcca   5160
ggaaccgtaa aaaggccgcg ttgctggcgt ttttccatag gctccgcccc cctgacgagc   5220
atcacaaaaa tcgacgctca agtcagaggt ggcgaaaccc gacaggacta taaagatacc   5280
aggcgtttcc ccctggaagc tccctcgtgc gctctcctgt tccgaccctg ccgcttaccg   5340
gatacctgtc cgcctttctc ccttcgggaa gcgtggcgct ttctcatagc tcacgctgta   5400
ggtatctcag ttcggtgtag gtcgttcgct ccaagctggg ctgtgtgcac gaaccccccg   5460
ttcagcccga ccgctgcgcc ttatccggta actatcgtct tgagtccaac ccggtaagac   5520
acgacttatc gccactggca gcagccactg gtaacaggat tagcagagcg aggtatgtag   5580
gcggtgctac agagttcttg aagtggtggc ctaactacgg ctacactaga aggacagtat   5640
ttggtatctg cgctctgctg aagccagtta ccttcggaaa aagagttggt agctcttgat   5700
ccggcaaaca aaccaccgct ggtagcggtg gtttttttgt ttgcaagcag cagattacgc   5760
gcagaaaaaa aggatctcaa gaagatcctt tgatcttttc tactgcagaa gcttgttaga   5820
caccctgtca tgtattttat attatttatt tcaccatacg gattaagtga aacctaatga   5880
aaatagtact ttcggagctt taactttaat gaaggtatgt ttttttatag acatcgatgt   5940
ctggtttaac aataggaaaa agtagctaaa actcccatga attaaagaaa taacaaggtg   6000
tctaacaacc tgttattaag aatgttagaa aagacttaac atttgtgttg agtttttata   6060
gacattggtg tctagacata cggtagataa ggtttgctca aaaataaaat aaaaaaagat   6120
tggactaaaa aacatttaat ttagtacaat ttaattagtt attttttcgt ctcaaatttt   6180
gctttgttga gcagaaattt agataaaaaa atccccgtga tcagattaca atgtcgttca   6240
ttgtacgatg tgtcgaaaaa tctttacgac actctaaact gaccacacgg gggaaaaaga   6300
aaactgaact aataacatca tgatactcgg aaaacctagc aattctcaac cctaaacaa    6360
aagaaacttc caaaaccctg accatataaa ggagtggcaa caatcagcaa tcagtcaaga   6420
tttgatagca gaaaatcttg tatcggttgc taatggtttt gatgtactat ttatcggcaa   6480
taaataccga actaacacgg gtgttctgtc acggcacata ttaaactcct attctcattt   6540
agaagatggt ggttcgtatg gtagaacatt tgacccattt accaataaag aaatgcagtg   6600
ggttcaattt aaaccgaata gaccaagaaa aggttctact ggtaaggtaa tcaaatatga   6660
atcgccaaaa ggtgaaccta caagagttct aatgccgttt gtgcctatga aaatatggca   6720
acggattagc gataagttcg gagtaccgat taatccgaaa aaagatactc acttttggga   6780
atgggtaaag aataatccat cgataccgat tgccattaca gaaggaaata aaaaagctaa   6840
ttgcctatta tcctatggct atcctgctat tgcctttgta ggcatttgga acggattaga   6900
gaaaataaat gatttctcga aggaaaagca gttaaaagag gatttgaaat ggttgttatc   6960
caacggcaac cgaaatatta atatcatctt tgaccaagac cagaaacaaa aaactgtaat   7020
```

```
taatgtaaac aaagctattt tcgctttatc ttctctaata agtagaaatg gtcataaagt   7080
taatattgtg caatggttgc cgtcaaaagg taaaggaata gatgattatt tggtagcttt   7140
acctttttgag aaaagagaaa atcatttaga caacttaatt aaaattgcac catcatttaa   7200
tttttggtca actaaatact tattcaagtg tcgtaaacca gatttaaccg taaattgccg   7260
ttatttgagc gatgcagtaa aagaattacc tcaagaggat atagcattaa tagcacctca   7320
cggcacgggt aaaacttcat tagtagctac tcacgttaag aatcggagtt atcacggaag   7380
gaaaactatt tcattggtgc atcttgaaag tttagccaaa gctaatggca acgcacttgg   7440
attatattac cgaaccgaaa ataatattga aaagcaatat cttggattta gcttatgtgt   7500
agatagttgc cgtgataaga ttaacggcat tacaactgat attatttcag gtcaagatta   7560
ttgccttttc attgatgaaa ttgaccaagt aattccacac atccttaaca gtgaaactga   7620
agtaagtaag tatagatgca ccatcattga cactttttct gaactggtga gaaatgctga   7680
acaggtcatt attgctgatg ctgatttatc cgatgtgacg attgacctaa tagaaaacat   7740
cagaggtaaa aaactatatg taatcaagaa tgaatatcag tatcagggaa tgacttttaa   7800
cgccgttggt tcaccattag aaatgatggc aatgatggga aaatcggtgt cagaaggcaa   7860
gaaattattt attaacacca catcccaaaa ggcaaaaagt aagtacggca caatcgctct   7920
tgagtcttat atttttggtc taaataaaga agcaaagata ttaagaatag actctgaaac   7980
cactaaaaac cctgaacatc cagcctataa aatcattgac caagacttaa ataatatcct   8040
caaagattat gattatgtca ttgcctcacc ttgccttcaa acaggtgtca gtattacctt   8100
aaaagggcat tttgaccagc aatttaactt ttccagtgga aacattacac ctcattgctt   8160
tttacagcaa atgtggcggt tgagggatgc agaaattgaa agattctatt atgtgccgaa   8220
ctcatctaac ctcaatctca ttgggaataa gtcaagttca ccatcagacc ttctaaagag   8280
caataacaag atggcaacgg caacggttaa ccttttgggt agaatcgact ccgaatattc   8340
cctagagtat gaatcgcacg gcatttggct tgagacgtgg gcaaaattat cagcacggca   8400
taacagttca atgcgttgtt actctgaaat tcttacctat ctaattacgt ctcaagggca   8460
taaattaaat atcaacattc cctcacctct tgcagatatt aagaagctaa atgatgaggt   8520
aagtagtaac agggaaaagg taaaaaatga gagatactct cagaggttaa actcaccaga   8580
tattaacgat gcagaagcta ccatactcga atctaaagag caaaaaatcg gattgactct   8640
caatgagaga tgcaccctag aaaagcataa agttaagaag cggtatggga atgtaaagat   8700
ggatattctc acctttgatg atgatggact ataccccaaa ctcagactat tttattacct   8760
caccatcggt aaacctcatc tcaaggctaa tgacagaaaa gctattgcca aaatgggcaa   8820
tgacaataaa ggcaagattc tatcaaaaga cttagttaat aaaacttact ccgctcgtgt   8880
gaaggtctta gagattctta aactaactga ctttatcgac aatcttagag atgaactctt   8940
aataactccc aataatccag ctatcaccga ttttaataat cttctgctaa gagctaagaa   9000
ggatttaaga gtattaggag tcaacatcgg aaaatatcca atggccaaca ttaatgccgt   9060
acttactctc attggtcaca aactttctgt aatgagagat gagttcggaa aagagaaaag   9120
gataaaagta gatggtaaat cataccgatg ttatcaactt gaaacattac cagattttac   9180
caatgatact cttgactact ggttagaaaa tgatagccaa aaagaagtaa cagcaacaga   9240
aaattactcc gaaaatttta acccttcaaa tagctacaat ccagacagta agacactttc   9300
agagggtgca aatttcctat atataaataa agaagaattg catccaaata aattgcacct   9360
agaaataaaa gaaggtgctg aactttttttt attcggggta aaggtgattg tgaaaggaat   9420
```

```
cttggacggg gcagtaacta tattctctat gggtcaagaa tacgatttat ccctcaatga   9480
actagagggg atgttaacat catgaacttt acaagaatct ttttaaaggg cgatcgcacc   9540
atgttaaatg atggtacatt tgttcagata tttgatattt accatgacca cgcattggga   9600
gtgacccttg accttaagac agaaaaaatt atttccgatg atgttagggt aattactgtc   9660
aaagacttat tgttcgatgg cacttataaa ggggtaaaat cttttatgcc cgataatgcc   9720
cgataatgcc cgattgatgc tacaaaatcc cataatcata agcgataatc ccctaatagc   9780
ttgtaattct tgaaccgtag cgattttaga gtattccaaa aagaagaaat aaacaccgca   9840
aaatgtcgta tttcacatat ataaaccaag gtttttttgcc ctaaaatctt tatgtttgta   9900
gtgtgatgtt gggtcaaaat ggtcagaaaa gttgcaaggt tttatggat gcttacgcgc   9960
gcgaggggta agcatcccca aatagttact ttatcctagt ccatgcccat ttattgccgt  10020
cccgttcggc tttaaaaaag tgccaaaact cacaaggtgc aataaaaagt tctgtacctt  10080
tcgcaaccct agataatctt tcaacagtta cttttttcc tattatctcg gtacaaagtt  10140
tggctagttt ctcttttccc tctttttcaa tcaagccttc ttgtatgccc aactcattga  10200
ttaatctctc tatttttacc attatttccc gttcaggtag tttatcccct aaatcttcat  10260
cggggggcaa tgtagggcat tctgaagggg ctttttcttc tgtctggaca ttatctaata  10320
ttgaagtaac caaactatct tcagtttttt ctattcctat taattcatat tcggttactg  10380
tatccgtatc aatatccgaa taactatctt tatccgtatt agctattcgg ttaagtttat  10440
ccgttaactc agaaacaaga ctatatagcg gttttagctt ttcttctatc ctgttatcta  10500
atacggataa gtttatacgg ttatcattat ccgtattagt atcattgggc ttttttggta  10560
gttctacccc ctcataaacc gcttttattc ccaattccaa cagactgata acagtatcct  10620
ttataatggg ttttttgctg atatggtgaa cttttgcccc ttccatcatt gcgatacttt  10680
ctatctcact catcaactta tcgcttaagt gaatctcgta tctgtttaat cccttactgg  10740
ttttattcat atccgtttac tttattcggt taacaattct attttatacg aataaaatat  10800
tatacggtta actttatacg tttaactatt ttatctatac ggataacagt aataagttat  10860
tcgtattagt tatacgttta cttttatcca aataaaatta gtgcatttaa actaaaagaa  10920
tgattttatc ggagttgata gcattggatt aacctaaaga tgtttataag ctatatctga  10980
taagtattta aggttatttt gttattctgt ttattgacat tatcagaata aaagaataga  11040
atataattgt tgagagataa gaggtttaag tgattatggt taagaagtta gttggttatg  11100
tcagggtcag tagtgaatcg caagaggata acactagctt acagaatcag atagagagaa  11160
ttgaagcata ttgtatggct tttggttatg agttggtaaa aatattcaaa gaggttgcca  11220
ctggtacaaa agcagatatt gaaacccgtc ctatttttaa tgaagctata gaatacttga  11280
aacaggataa tgctaatgga attattgcct tgaagctaga ccgaatcgca cggaatgctt  11340
tagatgtatt gcgtttggtt cgtgaaacct tagaaccaca aaataaaatg ttagtgttac  11400
tagatattca ggtagatact tcgacacctt caggaaaaat gattttaact gtaatgagtg  11460
ccgttgctga actcgaaaga gacatgatct atgatcgcac tcagggggt agaaagacta  11520
aagcccaaaa gggcgggtat gcctacggga aacctaaatt tggctataag actgaagaaa  11580
aggaactaaa agaagattca gcacaacagg aaactattaa actaattaag agacaccgta  11640
ggtcagggaa aagctaccag aaaatagctg attatctcaa tgcccaaagt attcccacta  11700
aacaaggtaa gaaatggagt tctagcgtcg tctatcgaat ctgtcaggaa aaagctggtt  11760
```

```
aagtctgttt atagatattt agaatttatt gaataaaaat agtatgaaca ataaatattt  11820

atggactaac cacgctcgga aacgtttaac tgaacgatgg gaaataaaag aatcatgggt  11880

tattgatacc atcgaaaatc ctgaacgttc agaatttatt gttgatgagt caggggaaaa  11940

atatcattac tataaaagaa tagctaagtt taagaataga gtgttagaag tgataacttc  12000

tgccaactca acacccacaa gaataataac cttttacttt aaccgtaaca tgaggaaaaa  12060

tttatgattg ttacttacga taatgaagtt gacgcaattt attttaagtt aacggaaaat  12120

aaaattgata gcaccgaacc tcaaacagac aggattatca ttgattacga tgaaagtaat  12180

aatattgttg gcattgaggt attagatttt aattatcttg tcaagaaagg tttaaccgtt  12240

gctgatttac ctttttctga agatgaaaga ttaacagctt ctcaatattt taattttcct  12300

gttgctatct aatccagaag ggcaataat cccccttcttt catcgagtta gacttaatat  12360

cacaaaagtc attttcattt taccgtttct tttccacagc gtccgtacgc ccctcgttaa  12420

atctcaaaac cgacaattta tgatgtttat aaaaagttac tcactttaat aagtatttat  12480

actcattaaa gggttattct tttttgtag cctgataggt tgggaaggaa tatttcagat  12540

tatcagattt gttgaatatt tttcgtcaga tacgcaaacc ttacaaacat aattaacaac  12600

tgaaactatt gatatgtcta ggttttagct ctatcacagg ttggatctg             12649
```

```
<210> SEQ ID NO 31
<211> LENGTH: 12673
<212> TYPE: DNA
<213> ORGANISM: Artificial
<220> FEATURE:
<223> OTHER INFORMATION: Synthetically produced plasmid construct #1684
      pABIcyano1::PnirA*2-zmPDC(opt3)dsrA-Prbc*(optRBS)-ADH111(opt)_ter

<400> SEQUENCE: 31

tcgacaatta ataacttctt cctgtacggg cgaatggcca tttgctccta actaactccg     60

tactgctttg cggaacgagc gtagcgaact ctccgaatta ctaagccttc atccctgata    120

gatgcaaaaa acgaattaaa attatgtgta aaaagaaaat gtgtctttat ttagtagtca    180

aagttacaaa atattaagaa tcaaattaat aatgtattgg gcagttaagt atataagtct    240

ttaaatattt atttgtattc aatatattaa ggaggatcag ccttatgaat tcttacactg    300

ttggaaccta tttagcagaa cgtttagttc aaattggtct caaacaccat tttgcagtag    360

ctggtgatta taatttagtt ttattggata acttattgtt aaataagaat atggaacaag    420

tgtattgttg taatgaatta aactgtggtt tttctgctga gggatatgct cgtgcaaaag    480

gtgctgccgc agcagttgtt acttattctg ttggagcatt aagtgctttt gacgctattg    540

gaggtgctta tgcagaaaat ttacctgtaa tcttaatctc tggtgcaccc aataacaacg    600

atcacgctgc tggtcatgta ttgcatcatg ctttaggtaa aaccgattat cattaccaat    660

tagaaatggc aaaaaatatt accgctgccg cagaagctat ttatactccc gaagaagcac    720

ctgctaagat cgatcacgta attaaaaccg ctctccgtga gaaaaaaccc gtatatttag    780

aaatcgcttg caatatcgct tctatgcctt gtgcagctcc tggacctgct agtgctttat    840

ttaacgatga agcatctgat gaggctagtt taaatgccgc tgttgaagaa actttgaaat    900

ttattgctaa tcgtgataaa gtagctgttt tagttggttc taaactccgt gccgctggtg    960

cagaagaagc ggctgtaaaa ttcgcagatg ccttaggagg tgctgttgcc acaatggcag   1020

ccgctaaaag ttttttcccc gaagaaaatc ctcattacat tggtacttct tggggtgagg   1080

tatcttaccc tggtgtagaa aaaaccatga aggaagctga tgcagtaatt gcattagctc   1140
```

```
ctgttttcaa tgattactct accactggtt ggactgatat tccagacccc aaaaaattag   1200
ttttagcaga acctcgctct gtagttgtga atggtgttag atttcccagt gtacatctca   1260
aagattattt aactcgttta gctcaaaaag tgagtaaaaa gactggcgca ctcgatttct   1320
ttaaatcttt aaatgctggt gaattaaaga aagcagctcc tgctgatccc agtgctcctt   1380
tagtgaatgc cgaaatcgca agacaagttg aagccttgtt aactcctaac actaccgtta   1440
ttgccgagac tggtgatagt tggttcaatg ctcaacgcat gaaattaccc aatggtgctc   1500
gtgttgagta tgaaatgcaa tggggtcaca ttggatggtc tgttcctgct gcatttggat   1560
atgcagttgg agcacctgag cgtagaaaca ttttaatggt aggtgatggt tctttccaac   1620
tcactgctca agaagttgca caaatggtac gtttaaaatt gcctgttatt atctttctca   1680
ttaacaacta tggttacacc attgaagtta tgattcatga tggtccttat aataacatta   1740
agaattggga ttacgcaggt ttaatggagg tatttaacgg taatggtgga tacgacagtg   1800
gagcaggtaa aggattaaaa gctaaaacag gaggtgagtt agctgaagca attaaagtag   1860
ctttagccaa tacagatggt cctaccttaa tcgaatgttt cattggacgt gaagattgta   1920
ctgaagagtt agttaaatgg ggaaagcgtg ttgccgctgc aaattctcgt aaacctgtaa   1980
acaaactctt gtagttagga tccgagctca gcaagtttca tcccgacccc ctcagggtcg   2040
ggattttttt attgtactag ttgacataag taaaggcatc ccctgcgtga tataattacc   2100
ttcagtttaa ggaggtatac acatatgagt gaaactaaat ttaaagccta tgccgtaatg   2160
aatcctggtg aaaaattaca accctgggaa tatgaacctg ctcctttaca ggtagatgaa   2220
attgaagtaa gagttactca caatggttta tgtcacactg acttacacat gagagataat   2280
gactggaatg ttagtgagtt cccccttagta gcaggtcatg aagttgttgg tgaagtaacc   2340
gctgttggtg aaaaagtaac cagtcgtaaa aaaggtgata gagttggtgt aggttggatt   2400
cgtaattctt gtcgcgcttg tgaccattgt ttacaaggag aagagaacat ttgtagagag   2460
ggttatactg gtttaattgt tggtcatcac ggtggatttg ctgatcgtgt acgtgtacct   2520
gctgacttca cttataaaat tcctgatgct ttagatagtg catctgctgc tcctttatta   2580
tgtgccggta ttaccgttta cactccttta agaacctaca ttaaacatcc cggtatgaaa   2640
gtaggtgtta tgggtattgg aggattagga catttagcta ttaaatttgc tcgtgcaatg   2700
ggagcagaag ttactgcctt tagtaccagt cctaataaag aagcccaagc caaagaattt   2760
ggtgctcatc atttccaaca atggggtact gctgaagaaa tgaaagctgt tgccggtaat   2820
tttgatttag ttttatctac catctctgct gaaactgact gggatgctgc cttctcttta   2880
ttagcaaata acggtgtttt atgtttcgta ggtattcccg ttagttcttt aaatgttcct   2940
ttaattcctt taattttcgg acaaaaatct gttgtaggtt ctgtagttgg aggaagaaga   3000
ttcatggcag aaatgttaga gttcgccgct gtaaatcaga ttaaacctat gatcgaaact   3060
atgcccttat ctcaagtaaa tgaagctatg gataaagttg ccgccaataa agccagatat   3120
agaattgtat tattatctga ataactagat ctcctgcaga gaatataaaa agccagatta   3180
ttaatccggc tttttttatta tttaaatact gtgcacgatc ctgcaggatc atcttgctga   3240
aaaactcgag cgctcgttcc gcaaagcggt acggagttag ttaggggcta atgggcattc   3300
tcccgtacag gaaagagtta gaagttatta attatcaaca attctccttt gcctagtgca   3360
tcgttacctt tttaattaaa acataaggaa aactaataat cgtaataatt taacctcaaa   3420
gtgtaaagaa atgtgaaatt ctgactttta taacgttaaa gagggaaaaa ttagcagttt   3480
aaaataccta gagaatagtc tggggtaagc atagagaatt agattagtta agttaatcaa   3540
```

```
attcagaaaa aataataatc gtaaatagtt aatctgggtg tatagaaaat gatccccttc   3600
atgataagat ttaaactcga aaagcaaaag ccaaaaaact aacttccatt aaaagaagtt   3660
gttacatata acgctataaa gaaaatttat atatttggag gataccaacc atgtctcata   3720
ttcaacgtga aactagttgt tctcgccctc gtttaaattc taatatggat gccgatttat   3780
atggttataa atgggctcgt gataatgttg gtcaatctgg tgctactatt tatcgtttat   3840
atggtaaacc tgatgctcct gaattattct tgaaacatgg taaaggttct gttgctaatg   3900
atgttactga tgaaatggtt cgtttaaact ggttgactga atttatgcct ttacctacta   3960
ttaaacattt tattcgtact cccgatgatg cttggttatt aactactgct attcctggta   4020
aaactgcttt tcaagtttta gaagaatatc ctgattctgg tgaaaatatt gttgatgctt   4080
tagctgtttt tttacgtcgt ttacattcta ttcccgtttg taattgtcct tttaattctg   4140
atcgtgtttt tcgtttagct caagctcaat ctcgtatgaa taatggttta gttgatgctt   4200
ctgattttga tgatgaacgt aatggttggc ctgttgaaca agtttggaaa gaaatgcaca   4260
aattgttacc tttttctcct gattctgttg ttactcatgg tgatttttct ttagataatt   4320
tgatctttga tgaaggtaaa ttgattggtt gtattgatgt tggtcgtgtt ggtattgctg   4380
atcgttatca agatttagct attttatgga attgtttagg tgaattttct ccttctttac   4440
agaaacgttt atttcagaaa tatggtattg ataatcctga tatgaacaag ttacaatttc   4500
atttaatgtt ggacgagttc ttttaagaat taattcatga ccaaaatccc ttaacgtgag   4560
ttttcgttcc actgagcgtc agaccccgta gaaaagatca aaggatcttc ttgagatcct   4620
tttttctgc gcgtaatctg ctgctattta aattacgtac acgtgttatt actttgttaa   4680
cgacaattgt cttaattaac tgggcctcat gggccttccg ctcactgccc gctttccagt   4740
cgggaaacct gtcgtgccag ctctgcagat gacggtgaaa acctctgaca catgcagctc   4800
ccggagacgg tcacagcttg tctgtaagcg gatgccggga gcagacaagc ccgtcagggc   4860
gcgtcagcgg gtgttggcgg gtgtcggggc gcagccatga cccagtcacg tagcgatagc   4920
ggagtgtata ctggcttaac tatgcggcat cagagcagat tgtactgaga gtgcaccata   4980
tgcggtgtga aataccgcac agatgcgtaa ggagaaaata ccgcatcagg cgctcttccg   5040
cttcctcgct cactgactcg ctgcgctcgg tcgttcggct gcggcgagcg gtatcagctc   5100
actcaaaggc ggtaatacgg ttatccacag aatcagggga taacgcagga aagaacatgt   5160
gagcaaaagg ccagcaaaag gccaggaacc gtaaaaaggc cgcgttgctg gcgtttttcc   5220
ataggctccg cccccctgac gagcatcaca aaaatcgacg ctcaagtcag aggtggcgaa   5280
acccgacagg actataaaga taccaggcgt ttccccctgg aagctccctc gtgcgctctc   5340
ctgttccgac cctgccgctt accggatacc tgtccgcctt tctcccttcg ggaagcgtgg   5400
cgctttctca tagctcacgc tgtaggtatc tcagttcggt gtaggtcgtt cgctccaagc   5460
tgggctgtgt gcacgaaccc cccgttcagc ccgaccgctg cgccttatcc ggtaactatc   5520
gtcttgagtc caacccggta agacacgact tatcgccact ggcagcagcc actggtaaca   5580
ggattagcag agcgaggtat gtaggcggtg ctacagagtt cttgaagtgg tggcctaact   5640
acggctacac tagaaggaca gtatttggta tctgcgctct gctgaagcca gttaccttcg   5700
gaaaaagagt tggtagctct tgatccggca aacaaaccac cgctggtagc ggtggttttt   5760
ttgtttgcaa gcagcagatt acgcgcagaa aaaaaggatc tcaagaagat cctttgatct   5820
tttctactgc agaagcttgt tagacaccct gtcatgtatt ttatattatt tatttcacca   5880
```

-continued

```
tacggattaa gtgaaaccta atgaaaatag tactttcgga gctttaactt taatgaaggt   5940
atgttttttt atagacatcg atgtctggtt taacaatagg aaaaagtagc taaaactccc   6000
atgaattaaa gaaataacaa ggtgtctaac aacctgttat taagaatgtt agaaaagact   6060
taacatttgt gttgagtttt tatagacatt ggtgtctaga catacggtag ataaggtttg   6120
ctcaaaaata aaataaaaaa agattggact aaaaaacatt taatttagta caatttaatt   6180
agttattttt tcgtctcaaa ttttgctttg ttgagcagaa atttagataa aaaaatcccc   6240
gtgatcagat tacaatgtcg ttcattgtac gatgtgtcga aaaatcttta cgacactcta   6300
aactgaccac acgggggaaa aagaaaactg aactaataac atcatgatac tcggaaaacc   6360
tagcaattct caacccctaa acaaaagaaa cttccaaaac cctgaccata taaaggagtg   6420
gcaacaatca gcaatcagtc aagatttgat agcagaaaat cttgtatcgg ttgctaatgg   6480
ttttgatgta ctatttatcg gcaataaata ccgaactaac acgggtgttc tgtcacggca   6540
catattaaac tcctattctc atttagaaga tggtggttcg tatggtagaa catttgaccc   6600
atttaccaat aaagaaatgc agtgggttca atttaaaccg aatagaccaa gaaaaggttc   6660
tactggtaag gtaatcaaat atgaatcgcc aaaaggtgaa cctacaagag ttctaatgcc   6720
gtttgtgcct atgaaaatat ggcaacggat tagcgataag ttcggagtac cgattaatcc   6780
gaaaaaagat actcactttt gggaatgggt aaagaataat ccatcgatac cgattgccat   6840
tacagaagga aataaaaaag ctaattgcct attatcctat ggctatcctg ctattgcctt   6900
tgtaggcatt tggaacggat tagagaaaat aaatgatttc tcgaaggaaa agcagttaaa   6960
agaggatttg aaatggttgt tatccaacgg caaccgaaat attaatatca tctttgacca   7020
agaccagaaa caaaaaactg taattaatgt aaacaaagct attttcgctt tatcttctct   7080
aataagtaga aatggtcata aagttaatat tgtgcaatgg ttgccgtcaa aaggtaaagg   7140
aatagatgat tatttggtag ctttaccttt tgagaaaaga gaaaatcatt tagacaactt   7200
aattaaaatt gcaccatcat ttaatttttg gtcaactaaa tacttattca agtgtcgtaa   7260
accagattta accgtaaatt gccgttattt gagcgatgca gtaaaagaat tacctcaaga   7320
ggatatagca ttaatagcac ctcacggcac gggtaaaact tcattagtag ctactcacgt   7380
taagaatcgg agttatcacg gaaggaaaac tatttcattg gtgcatcttg aaagtttagc   7440
caaagctaat ggcaacgcac ttggattata ttaccgaacc gaaaataata ttgaaaagca   7500
atatcttgga tttagcttat gtgtagatag ttgccgtgat aagattaacg gcattacaac   7560
tgatattatt tcaggtcaag attattgcct tttcattgat gaaattgacc aagtaattcc   7620
acacatcctt aacagtgaaa ctgaagtaag taagtataga tgcaccatca ttgacacttt   7680
ttctgaactg gtgagaaatg ctgaacaggt cattattgct gatgctgatt tatccgatgt   7740
gacgattgac ctaatagaaa acatcagagg taaaaaacta tatgtaatca agaatgaata   7800
tcagtatcag ggaatgactt ttaacgccgt tggttcacca ttagaaatga tggcaatgat   7860
gggaaaatcg gtgtcagaag gcaagaaatt atttattaac accacatccc aaaaggcaaa   7920
aagtaagtac ggcacaatcg ctcttgagtc ttatattttt ggtctaaata aagaagcaaa   7980
gatattaaga atagactctg aaaccactaa aaaccctgaa catccagcct ataaaatcat   8040
tgaccaagac ttaaataata tcctcaaaga ttatgattat gtcattgcct caccttgcct   8100
tcaaacaggt gtcagtatta ccttaaaagg gcattttgac cagcaattta acttttccag   8160
tggaaacatt acacctcatt gctttttaca gcaaatgtgg cggttgaggg atgcagaaat   8220
tgaaagattc tattatgtgc cgaactcatc taacctcaat ctcattggga ataagtcaag   8280
```

```
ttcaccatca gaccttctaa agagcaataa caagatggca acggcaacgg ttaacctttt   8340
gggtagaatc gactccgaat attccctaga gtatgaatcg cacggcattt ggcttgagac   8400
gtgggcaaaa ttatcagcac ggcataacag ttcaatgcgt tgttactctg aaattcttac   8460
ctatctaatt acgtctcaag ggcataaatt aaatatcaac attccctcac ctcttgcaga   8520
tattaagaag ctaaatgatg aggtaagtag taacagggaa aaggtaaaaa atgagagata   8580
ctctcagagg ttaaactcac cagatattaa cgatgcagaa gctaccatac tcgaatctaa   8640
agagcaaaaa atcggattga ctctcaatga gagatgcacc ctagaaaagc ataaagttaa   8700
gaagcggtat gggaatgtaa agatggatat tctcaccttt gatgatgatg gactataccc   8760
caaactcaga ctattttatt acctcaccat cggtaaacct catctcaagg ctaatgacag   8820
aaaagctatt gccaaaatgg gcaatgacaa taaaggcaag attctatcaa aagacttagt   8880
taataaaact tactccgctc gtgtgaaggt cttagagatt cttaaactaa ctgactttat   8940
cgacaatctt agagatgaac tcttaataac tcccaataat ccagctatca ccgattttaa   9000
taatcttctg ctaagagcta agaaggattt aagagtatta ggagtcaaca tcggaaaata   9060
tccaatggcc aacattaatg ccgtacttac tctcattggt cacaaacttt ctgtaatgag   9120
agatgagttc ggaaaagaga aaaggataaa agtagatggt aaatcatacc gatgttatca   9180
acttgaaaca ttaccagatt ttaccaatga tactcttgac tactggttag aaaatgatag   9240
ccaaaaagaa gtaacagcaa cagaaaatta ctccgaaaat tttaaccctt caaatagcta   9300
caatccagac agtaagacac tttcagaggg tgcaaatttc ctatatataa ataaagaaga   9360
attgcatcca aataaattgc acctagaaat aaaagaaggt gctgaacttt ttttattcgg   9420
ggtaaaggtg attgtgaaag gaatcttgga cggggcagta actatattct ctatgggtca   9480
agaatacgat ttatccctca atgaactaga ggggatgtta acatcatgaa ctttacaaga   9540
atctttttaa agggcgatcg caccatgtta aatgatggta catttgttca gatatttgat   9600
atttaccatg accacgcatt gggagtgacc cttgacctta agacagaaaa aattatttcc   9660
gatgatgtta gggtaattac tgtcaaagac ttattgttcg atggcactta taaaggggta   9720
aaatctttta tgcccgataa tgcccgataa tgcccgattg atgctacaaa atcccataat   9780
cataagcgat aatcccctaa tagcttgtaa ttcttgaacc gtagcgattt tagagtattc   9840
caaaaagaag aaataaacac cgcaaaatgt cgtatttcac atatataaac caaggttttt   9900
tgccctaaaa tctttatgtt tgtagtgtga tgttgggtca aatggtcag aaaagttgca   9960
aggtttttat ggatgcttac gcgcgcgagg ggtaagcatc cccaaatagt tactttatcc  10020
tagtccatgc ccatttattg ccgtcccgtt cggctttaaa aaagtgccaa aactcacaag  10080
gtgcaataaa aagttctgta cctttcgcaa ccctagataa tctttcaaca gttacttttt  10140
ttcctattat ctcggtacaa agtttggcta gtttctcttt tccctctttt tcaatcaagc  10200
cttcttgtat gcccaactca ttgattaatc tctctatttt taccattatt tcccgttcag  10260
gtagtttatc ccctaaatct tcatcggggg gcaatgtagg gcattctgaa ggggcttttt  10320
cttctgtctg gacattatct aatattgaag taaccaaact atcttcagtt ttttctattc  10380
ctattaattc atattcggtt actgtatccg tatcaatatc cgaataacta tctttatccg  10440
tattagctat tcggttaagt ttatccgtta actcagaaac aagactatat agcggtttta  10500
gcttttcttc tatcctgtta tctaatacgg ataagtttat acggttatca ttatccgtat  10560
tagtatcatt gggctttttt ggtagttcta ccccctcata aaccgctttt attcccaatt  10620
```

```
ccaacagact gataacagta tcctttataa tgggtttttt gctgatatgg tgaacttttg  10680
ccccttccat cattgcgata ctttctatct cactcatcaa cttatcgctt aagtgaatct  10740
cgtatctgtt taatccctta ctggttttat tcatatccgt ttactttatt cggttaacaa  10800
ttctatttta tacgaataaa atattatacg gttaacttta tacgtttaac tattttatct  10860
atacggataa cagtaataag ttattcgtat tagttatacg tttactttta tccaaataaa  10920
attagtgcat ttaaactaaa agaatgattt tatcggagtt gatagcattg gattaaccta  10980
aagatgttta taagctatat ctgataagta tttaaggtta ttttgttatt ctgtttattg  11040
acattatcag aataaaagaa tagaatataa ttgttgagag ataagaggtt taagtgatta  11100
tggttaagaa gttagttggt tatgtcaggg tcagtagtga atcgcaagag gataacacta  11160
gcttacagaa tcagatagag agaattgaag catattgtat ggcttttggt tatgagttgg  11220
taaaaatatt caaagaggtt gccactggta caaaagcaga tattgaaacc cgtcctattt  11280
ttaatgaagc tatagaatac ttgaaacagg ataatgctaa tggaattatt gccttgaagc  11340
tagaccgaat cgcacggaat gctttagatg tattgcgttt ggttcgtgaa accttagaac  11400
cacaaaataa aatgttagtg ttactagata ttcaggtaga tacttcgaca ccttcaggaa  11460
aaatgatttt aactgtaatg agtgccgttg ctgaactcga aagagacatg atctatgatc  11520
gcactcaggg gggtagaaag actaaagccc aaaagggcgg gtatgcctac gggaaaccta  11580
aatttggcta taagactgaa gaaaaggaac taaaagaaga ttcagcacaa caggaaacta  11640
ttaaactaat taagagacac cgtaggtcag ggaaaagcta ccagaaaata gctgattatc  11700
tcaatgccca aagtattccc actaaacaag gtaagaaatg gagttctagc gtcgtctatc  11760
gaatctgtca ggaaaaagct ggttaagtct gtttatagat atttagaatt tattgaataa  11820
aaatagtatg aacaataaat atttatggac taaccacgct cggaaacgtt taactgaacg  11880
atgggaaata aaagaatcat gggttattga taccatcgaa aatcctgaac gttcagaatt  11940
tattgttgat gagtcagggg aaaaatatca ttactataaa agaatagcta agtttaagaa  12000
tagagtgtta gaagtgataa cttctgccaa ctcaacaccc acaagaataa taacctttta  12060
ctttaaccgt aacatgagga aaaatttatg attgttactt acgataatga agttgacgca  12120
atttatttta agttaacgga aaataaaatt gatagcaccg aacctcaaac agacaggatt  12180
atcattgatt acgatgaaag taataatatt gttggcattg aggtattaga ttttaattat  12240
cttgtcaaga aaggtttaac cgttgctgat ttaccttttt ctgaagatga aagattaaca  12300
gcttctcaat attttaattt tcctgttgct atctaatcca gaaggggcaa taatcccctt  12360
ctttcatcga gttagactta atatcacaaa agtcattttc attttaccgt ttcttttcca  12420
cagcgtccgt acgcccctcg ttaaatctca aaaccgacaa tttatgatgt ttataaaaag  12480
ttactcactt taataagtat ttatactcat taaagggtta ttcttttttt gtagcctgat  12540
aggttgggaa ggaatatttc agattatcag atttgttgaa tatttttcgt cagatacgca  12600
aaccttacaa acataattaa caactgaaac tattgatatg tctaggtttt agctctatca  12660
caggttggat ctg                                                    12673
```

```
<210> SEQ ID NO 32
<211> LENGTH: 12683
<212> TYPE: DNA
<213> ORGANISM: Artificial
<220> FEATURE:
<223> OTHER INFORMATION: Synthetically produced plasmid construct #1754
      pABIcyano1::PnirA-zmPDC(opt1)dsrA-Prbc*(optRBS)-ADH1694(opt)_ter
```

<400> SEQUENCE: 32

```
tcgacaatta ataacttctt cctgtacggg cgaatggcca tttgctccta actaactccg     60
tactgctttg cggaacgagc gtagcgaact ctccgaatta ctaagccttc atccctgata    120
gatgcaaaaa acgaattaaa attatgtgta aaaagaaaat gtgtctttat ttagtagtca    180
aagttacaaa atattaagaa tcaaattaat aatgtattgg gcagttaagt atataagtct    240
ttaaatattt atttgtattc aatatattaa ccgaggacaa attatgaatt cttataccgt    300
gggtacttat ttagccgaac gcttagtgca aattggttta aaacatcatt ttgccgtggc    360
tggggactat aatttagtgt tattggataa cttattatta aataaaaaca tggaacaagt    420
gtattgttgt aatgaattaa attgtggttt ttctgctgaa ggttatgcta gagctaaagg    480
tgcagctgct gctgttgtta cttattctgt gggtgcttta tctgcttttg atgctattgg    540
tggtgcttat gccgaaaatt tacccgtgat tttaatttct ggtgccccta ataataatga    600
tcatgccgct ggacatgttt tacatcatgc cttaggtaaa accgattatc attatcaatt    660
agaaatggcc aaaaatatta ctgctgctgc cgaagctatt tatactcctg aagaagcccc    720
tgccaaaatt gatcatgtga ttaaaaccgc cttacgcgaa aaaaaacccg tgtatttaga    780
aattgcctgt aatattgctt ctatgccttg tgctgctcct gggcctgctt ctgctttatt    840
taatgatgaa gcctctgatg aagctagttt aaatgctgcc gtggaagaaa ccttaaaatt    900
tattgccaat cgcgataaag ttgccgtgtt agttggttct aaattaagag ctgctggtgc    960
tgaagaagct gctgttaaat ttgctgatgc tttaggtggt gcagttgcta ctatggctgc   1020
tgccaaatct ttttttcccg aagaaaatcc ccattatatt ggaactagtt ggggagaagt   1080
ttcttatcct ggtgtggaaa aaactatgaa agaagccgac gctgttattg ctttagcccc   1140
tgtgtttaat gattattcta ccactggttg gactgatatt cccgatccca aaaaattagt   1200
tttagccgaa cctcgttctg ttgttgttaa tggtgttcgc tttccctctg tgcatttaaa   1260
agattattta acccgcttag cccaaaaagt ttctaaaaaa actggtgcct tagatttttt   1320
taaatcttta aatgcgggtg aattaaaaaa agctgctcct gctgatcctt ctgctccttt   1380
agttaatgct gaaattgccc gtcaagttga agccttatta acccctaata ctaccgttat   1440
tgccgaaact ggtgattctt ggtttaatgc ccaacgcatg aaattaccta atggtgcccg   1500
tgttgaatat gaaatgcaat ggggtcatat tggttggtct gtacctgctg cttttggtta   1560
tgctgttggt gctcctgaac gtcgtaatat tttaatggtg ggtgatggtt cttttcaatt   1620
aactgcccaa gaagttgccc aaatggttcg cttaaaatta cccgttatta ttttttttaat   1680
aaataattat ggttatacca ttgaagtgat gattcatgat gggccatata ataatattaa   1740
aaattgggat tatgcgggtt taatggaagt gtttaatggt aatggtggtt atgattctgg   1800
tgctggtaaa ggtttaaaag ccaaaactgg tggtgaatta gctgaagcta ttaaagttgc   1860
cttagccaat actgatgggc caaccttaat tgaatgtttt attggtcgcg aagattgtac   1920
cgaagaatta gttaaatggg gtaaacgtgt tgctgctgct aattctcgca aacccgtgaa   1980
taaattattg taatttttgg ggatcaattc gagctcagca agtttcatcc cgaccccctc   2040
agggtcggga ttttttttatt gtactagttg acataagtaa aggcatcccc tgcgtgatat   2100
aattaccttc agtttaagga ggtatacaca tatgactacc gctactaaat ttaaagcata   2160
cgccgcatta aattctggtg aaaaattaca gccctgggaa tacgaacctg aacctttaca   2220
ggttgatgag gttgagatcc gtgtaaccca taacggttta tgtcatactg atttacacat   2280
gcgtgataat gattggaacg taagtcaata tcctttagta cccggtcacg aagtagttgg   2340
```

```
tgaggttacc gaggttggtg aaaaagtaac cagtttacac aaaggagaca gaattggtgt   2400
aggatggatt agaaattctt gtcgttcttg tgatcactgt ttacaaggag aggaaaacat   2460
ctgtcgtgaa ggatacactg gtttaattgt tggacaccac ggtggtttcg ctgatcgttt   2520
acgtgtacct gctgatttca cctacaaaat tcctgatgca ttagattctg cctctgccgc   2580
tcccttatta tgtgctggta ttactgttta tacccccttaa agaacttaca tcaaacaccc  2640
cggtatgaaa gttggtgtaa tgggaattgg tggtttaggt catttagcta ttaaatttgc   2700
tagagctatg ggagctgaag taactgcatt ttctacttct ttaaacaaac aagaacaggc   2760
aaaagagttt ggagcacaca attttcagca atggggaact gctgaagaga tgaaagctat   2820
tgctggttct ttcgatttag ttttatctac tatctctagt gaaactgatt gggatgctgc   2880
tttctcttta ttagctaaca atggtgtatt atgttttgtt ggtattcctg tttctacctt   2940
aaatattcct ttaatccctt taatctttgg tcaaaaagct gtagtaggaa gtattgttgg   3000
tggaagacgt tttatggctg agatgttaga atttgctgcc gttaatcaga tcaaacccat   3060
gattgagact atgcctttaa gtcaaatcaa cgaggctatg gataaagttg cagctaatca   3120
agcccgttat cgtattgtat tattagcaga ctaactagat ctcctgcaga gaatataaaa   3180
agccagatta ttaatccggc ttttttatta tttaaatact gtgcacgatc ctgcaggatc   3240
atcttgctga aaaactcgag cgctcgttcc gcaaagcggt acggagttag ttaggggcta   3300
atgggcattc tcccgtacag gaaagagtta gaagttatta attatcaaca attctccttt   3360
gcctagtgca tcgttacctt tttaattaaa acataaggaa aactaataat cgtaataatt   3420
taacctcaaa gtgtaaagaa atgtgaaatt ctgactttta taacgttaaa gagggaaaaa   3480
ttagcagttt aaaataccta gagaatagtc tggggtaagc atagagaatt agattagtta   3540
agttaatcaa attcagaaaa aataataatc gtaaatagtt aatctgggtg tatagaaaat   3600
gatccccttc atgataagat ttaaactcga aaagcaaaag ccaaaaaact aacttccatt   3660
aaaagaagtt gttacatata acgctataaa gaaaatttat atatttggag gataccaacc   3720
atgtctcata ttcaacgtga aactagttgt tctcgccctc gtttaaattc taatatggat   3780
gccgatttat atggttataa atgggctcgt gataatgttg gtcaatctgg tgctactatt   3840
tatcgtttat atggtaaacc tgatgctcct gaattattct tgaaacatgg taaaggttct   3900
gttgctaatg atgttactga tgaaatggtt cgtttaaact ggttgactga atttatgcct   3960
ttacctacta ttaaacattt tattcgtact cccgatgatg cttggttatt aactactgct   4020
attcctggta aaactgcttt tcaagtttta gaagaatatc ctgattctgg tgaaaatatt   4080
gttgatgctt tagctgtttt tttacgtcgt ttacattcta ttcccgtttg taattgtcct   4140
tttaattctg atcgtgtttt tcgtttagct caagctcaat ctcgtatgaa taatggttta   4200
gttgatgctt ctgattttga tgatgaacgt aatggttggc ctgttgaaca agtttggaaa   4260
gaaatgcaca aattgttacc tttttctcct gattctgttg ttactcatgg tgatttttct   4320
ttagataatt tgatctttga tgaaggtaaa ttgattggtt gtattgatgt tggtcgtgtt   4380
ggtattgctg atcgttatca agatttagct attttatgga attgtttagg tgaattttct   4440
ccttctttac agaaacgttt atttcagaaa tatggtattg ataatcctga tatgaacaag   4500
ttacaatttc atttaatgtt ggacgagttc ttttaagaat taattcatga ccaaaatccc   4560
ttaacgtgag ttttcgttcc actgagcgtc agaccccgta gaaaagatca aaggatcttc   4620
ttgagatcct ttttttctgc gcgtaatctg ctgctattta aattacgtac acgtgttatt   4680
```

-continued

```
actttgttaa cgacaattgt cttaattaac tgggcctcat gggccttccg ctcactgccc   4740
gctttccagt cgggaaacct gtcgtgccag ctctgcagat gacggtgaaa acctctgaca   4800
catgcagctc ccggagacgg tcacagcttg tctgtaagcg gatgccggga gcagacaagc   4860
ccgtcagggc gcgtcagcgg gtgttggcgg gtgtcggggc gcagccatga cccagtcacg   4920
tagcgatagc ggagtgtata ctggcttaac tatgcggcat cagagcagat tgtactgaga   4980
gtgcaccata tgcggtgtga aataccgcac agatgcgtaa ggagaaaata ccgcatcagg   5040
cgctcttccg cttcctcgct cactgactcg ctgcgctcgg tcgttcggct gcggcgagcg   5100
gtatcagctc actcaaaggc ggtaatacgg ttatccacag aatcagggga taacgcagga   5160
aagaacatgt gagcaaaagg ccagcaaaag gccaggaacc gtaaaaaggc cgcgttgctg   5220
gcgtttttcc ataggctccg cccccctgac gagcatcaca aaaatcgacg ctcaagtcag   5280
aggtggcgaa acccgacagg actataaaga taccaggcgt ttccccctgg aagctccctc   5340
gtgcgctctc ctgttccgac cctgccgctt accggatacc tgtccgcctt tctcccttcg   5400
ggaagcgtgg cgctttctca tagctcacgc tgtaggtatc tcagttcggt gtaggtcgtt   5460
cgctccaagc tgggctgtgt gcacgaaccc cccgttcagc ccgaccgctg cgccttatcc   5520
ggtaactatc gtcttgagtc caacccggta agacacgact tatcgccact ggcagcagcc   5580
actggtaaca ggattagcag agcgaggtat gtaggcggtg ctacagagtt cttgaagtgg   5640
tggcctaact acggctacac tagaaggaca gtatttggta tctgcgctct gctgaagcca   5700
gttaccttcg gaaaaagagt tggtagctct tgatccggca aacaaaccac cgctggtagc   5760
ggtggttttt ttgtttgcaa gcagcagatt acgcgcagaa aaaaaggatc tcaagaagat   5820
cctttgatct tttctactgc agaagcttgt tagacaccct gtcatgtatt ttatattatt   5880
tatttcacca tacggattaa gtgaaaccta atgaaaatag tactttcgga gctttaactt   5940
taatgaaggt atgttttttt atagacatcg atgtctggtt taacaatagg aaaaagtagc   6000
taaaactccc atgaattaaa gaaataacaa ggtgtctaac aacctgttat taagaatgtt   6060
agaaaagact taacatttgt gttgagtttt tatagacatt ggtgtctaga catacggtag   6120
ataaggtttg ctcaaaaata aaataaaaaa agattggact aaaaaacatt taatttagta   6180
caatttaatt agttattttt tcgtctcaaa ttttgctttg ttgagcagaa atttagataa   6240
aaaaatcccc gtgatcagat tacaatgtcg ttcattgtac gatgtgtcga aaaatcttta   6300
cgacactcta aactgaccac acgggggaaa aagaaaactg aactaataac atcatgatac   6360
tcggaaaacc tagcaattct caacccctaa acaaaagaaa cttccaaaac cctgaccata   6420
taaaggagtg gcaacaatca gcaatcagtc aagatttgat agcagaaaat cttgtatcgg   6480
ttgctaatgg ttttgatgta ctatttatcg gcaataaata ccgaactaac acgggtgttc   6540
tgtcacggca catattaaac tcctattctc atttagaaga tggtggttcg tatggtagaa   6600
catttgaccc atttaccaat aaagaaatgc agtgggttca atttaaaccg aatagaccaa   6660
gaaaaggttc tactggtaag gtaatcaaat atgaatcgcc aaaaggtgaa cctacaagag   6720
ttctaatgcc gtttgtgcct atgaaaatat ggcaacggat tagcgataag ttcggagtac   6780
cgattaatcc gaaaaaagat actcactttt gggaatgggt aaagaataat ccatcgatac   6840
cgattgccat tacagaagga aataaaaaag ctaattgcct attatcctat ggctatcctg   6900
ctattgcctt tgtaggcatt tggaacggat tagagaaaat aaatgatttc tcgaaggaaa   6960
agcagttaaa agaggatttg aaatggttgt tatccaacgg caaccgaaat attaatatca   7020
tctttgacca agaccagaaa caaaaaactg taattaatgt aaacaaagct attttcgctt   7080
```

```
tatcttctct aataagtaga aatggtcata aagttaatat tgtgcaatgg ttgccgtcaa   7140
aaggtaaagg aatagatgat tatttggtag ctttaccttt tgagaaaaga gaaaatcatt   7200
tagacaactt aattaaaatt gcaccatcat ttaatttttg gtcaactaaa tacttattca   7260
agtgtcgtaa accagattta accgtaaatt gccgttattt gagcgatgca gtaaaagaat   7320
tacctcaaga ggatatagca ttaatagcac ctcacggcac gggtaaaact tcattagtag   7380
ctactcacgt taagaatcgg agttatcacg gaaggaaaac tatttcattg gtgcatcttg   7440
aaagtttagc caaagctaat ggcaacgcac ttggattata ttaccgaacc gaaaataata   7500
ttgaaaagca atatcttgga tttagcttat gtgtagatag ttgccgtgat aagattaacg   7560
gcattacaac tgatattatt tcaggtcaag attattgcct tttcattgat gaaattgacc   7620
aagtaattcc acacatcctt aacagtgaaa ctgaagtaag taagtataga tgcaccatca   7680
ttgacacttt ttctgaactg gtgagaaatg ctgaacaggt cattattgct gatgctgatt   7740
tatccgatgt gacgattgac ctaatagaaa acatcagagg taaaaaacta tatgtaatca   7800
agaatgaata tcagtatcag ggaatgactt ttaacgccgt tggttcacca ttagaaatga   7860
tggcaatgat gggaaaatcg gtgtcagaag gcaagaaatt atttattaac accacatccc   7920
aaaaggcaaa aagtaagtac ggcacaatcg ctcttgagtc ttatattttt ggtctaaata   7980
aagaagcaaa gatattaaga atagactctg aaaccactaa aaaccctgaa catccagcct   8040
ataaaatcat tgaccaagac ttaaataata tcctcaaaga ttatgattat gtcattgcct   8100
caccttgcct tcaaacaggt gtcagtatta ccttaaaagg gcattttgac cagcaattta   8160
acttttccag tggaaacatt acacctcatt gctttttaca gcaaatgtgg cggttgaggg   8220
atgcagaaat tgaaagattc tattatgtgc cgaactcatc taacctcaat ctcattggga   8280
ataagtcaag ttcaccatca gaccttctaa agagcaataa caagatggca acggcaacgg   8340
ttaacctttt gggtagaatc gactccgaat attccctaga gtatgaatcg cacggcattt   8400
ggcttgagac gtgggcaaaa ttatcagcac ggcataacag ttcaatgcgt tgttactctg   8460
aaattcttac ctatctaatt acgtctcaag ggcataaatt aaatatcaac attccctcac   8520
ctcttgcaga tattaagaag ctaaatgatg aggtaagtag taacagggaa aaggtaaaaa   8580
atgagagata ctctcagagg ttaaactcac cagatattaa cgatgcagaa gctaccatac   8640
tcgaatctaa agagcaaaaa atcggattga ctctcaatga gagatgcacc ctagaaaagc   8700
ataaagttaa gaagcggtat gggaatgtaa agatggatat tctcaccttt gatgatgatg   8760
gactataccc caaactcaga ctattttatt acctcaccat cggtaaacct catctcaagg   8820
ctaatgacag aaaagctatt gccaaaatgg gcaatgacaa taaaggcaag attctatcaa   8880
aagacttagt taataaaact tactccgctc gtgtgaaggt cttagagatt cttaaactaa   8940
ctgactttat cgacaatctt agagatgaac tcttaataac tcccaataat ccagctatca   9000
ccgattttaa taatcttctg ctaagagcta agaaggattt aagagtatta ggagtcaaca   9060
tcggaaaata tccaatggcc aacattaatg ccgtacttac tctcattggt cacaaacttt   9120
ctgtaatgag agatgagttc ggaaaagaga aaaggataaa agtagatggt aaatcatacc   9180
gatgttatca acttgaaaca ttaccagatt ttaccaatga tactcttgac tactggttag   9240
aaaatgatag ccaaaaagaa gtaacagcaa cagaaaatta ctccgaaaat tttaaccctt   9300
caaatagcta caatccagac agtaagacac tttcagaggg tgcaaatttc ctatatataa   9360
ataaagaaga attgcatcca aataaattgc acctagaaat aaaagaaggt gctgaacttt   9420
```

```
ttttattcgg ggtaaaggtg attgtgaaag gaatcttgga cggggcagta actatattct   9480
ctatgggtca agaatacgat ttatccctca atgaactaga ggggatgtta acatcatgaa   9540
ctttacaaga atctttttaa agggcgatcg caccatgtta aatgatggta catttgttca   9600
gatatttgat atttaccatg accacgcatt gggagtgacc cttgacctta agacagaaaa   9660
aattatttcc gatgatgtta gggtaattac tgtcaaagac ttattgttcg atggcactta   9720
taaaggggta aaatctttta tgcccgataa tgcccgataa tgcccgattg atgctacaaa   9780
atcccataat cataagcgat aatcccctaa tagcttgtaa ttcttgaacc gtagcgattt   9840
tagagtattc caaaaagaag aaataaacac cgcaaaatgt cgtatttcac atatataaac   9900
caaggttttt tgccctaaaa tctttatgtt tgtagtgtga tgttgggtca aaatggtcag   9960
aaaagttgca aggtttttat ggatgcttac gcgcgcgagg ggtaagcatc cccaaatagt  10020
tactttatcc tagtccatgc ccatttattg ccgtcccgtt cggctttaaa aaagtgccaa  10080
aactcacaag gtgcaataaa aagttctgta cctttcgcaa ccctagataa tctttcaaca  10140
gttacttttt ttcctattat ctcggtacaa agtttggcta gtttctcttt tccctctttt  10200
tcaatcaagc cttcttgtat gcccaactca ttgattaatc tctctatttt taccattatt  10260
tcccgttcag gtagtttatc ccctaaatct tcatcggggg gcaatgtagg gcattctgaa  10320
ggggcttttt cttctgtctg gacattatct aatattgaag taaccaaact atcttcagtt  10380
ttttctattc ctattaattc atattcggtt actgtatccg tatcaatatc cgaataacta  10440
tctttatccg tattagctat tcggttaagt ttatccgtta actcagaaac aagactatat  10500
agcggtttta gcttttcttc tatcctgtta tctaatacgg ataagtttat acggttatca  10560
ttatccgtat tagtatcatt gggctttttt ggtagttcta ccccctcata aaccgctttt  10620
attcccaatt ccaacagact gataacagta tcctttataa tgggtttttt gctgatatgg  10680
tgaacttttg ccccttccat cattgcgata ctttctatct cactcatcaa cttatcgctt  10740
aagtgaatct cgtatctgtt taatccctta ctggttttat tcatatccgt ttactttatt  10800
cggttaacaa ttctatttta tacgaataaa atattatacg gttaacttta tacgtttaac  10860
tattttatct atacggataa cagtaataag ttattcgtat tagttatacg tttactttta  10920
tccaaataaa attagtgcat ttaaactaaa agaatgattt tatcggagtt gatagcattg  10980
gattaaccta aagatgttta taagctatat ctgataagta tttaaggtta ttttgttatt  11040
ctgtttattg acattatcag aataaaagaa tagaatataa ttgttgagag ataagaggtt  11100
taagtgatta tggttaagaa gttagttggt tatgtcaggg tcagtagtga atcgcaagag  11160
gataacacta gcttacagaa tcagatagag agaattgaag catattgtat ggcttttggt  11220
tatgagttgg taaaaatatt caaagaggtt gccactggta caaaagcaga tattgaaacc  11280
cgtcctattt ttaatgaagc tatagaatac ttgaaacagg ataatgctaa tggaattatt  11340
gccttgaagc tagaccgaat cgcacggaat gctttagatg tattgcgttt ggttcgtgaa  11400
accttagaac cacaaaataa aatgttagtg ttactagata ttcaggtaga tacttcgaca  11460
ccttcaggaa aaatgatttt aactgtaatg agtgccgttg ctgaactcga aagagacatg  11520
atctatgatc gcactcaggg gggtagaaag actaaagccc aaaagggcgg gtatgcctac  11580
gggaaaccta aatttggcta taagactgaa gaaaaggaac taaaagaaga ttcagcacaa  11640
caggaaacta ttaaactaat taagagacac cgtaggtcag ggaaaagcta ccagaaaata  11700
gctgattatc tcaatgccca aagtattccc actaaacaag gtaagaaatg gagttctagc  11760
gtcgtctatc gaatctgtca ggaaaaagct ggttaagtct gtttatagat atttagaatt  11820
```

```
tattgaataa aaatagtatg aacaataaat atttatggac taaccacgct cggaaacgtt  11880

taactgaacg atgggaaata aaagaatcat gggttattga taccatcgaa aatcctgaac  11940

gttcagaatt tattgttgat gagtcagggg aaaaatatca ttactataaa agaatagcta  12000

agtttaagaa tagagtgtta gaagtgataa cttctgccaa ctcaacaccc acaagaataa  12060

taacctttta ctttaaccgt aacatgagga aaaatttatg attgttactt acgataatga  12120

agttgacgca atttatttta agttaacgga aaataaaatt gatagcaccg aacctcaaac  12180

agacaggatt atcattgatt acgatgaaag taataatatt gttggcattg aggtattaga  12240

ttttaattat cttgtcaaga aaggtttaac cgttgctgat ttaccttttt ctgaagatga  12300

aagattaaca gcttctcaat attttaattt tcctgttgct atctaatcca gaaggggcaa  12360

taatcccctt ctttcatcga gttagactta atatcacaaa agtcattttc attttaccgt  12420

ttcttttcca cagcgtccgt acgcccctcg ttaaatctca aaaccgacaa tttatgatgt  12480

ttataaaaag ttactcactt taataagtat ttatactcat taaagggtta ttcttttttt  12540

gtagcctgat aggttgggaa ggaatatttc agattatcag atttgttgaa tatttttcgt  12600

cagatacgca aaccttacaa acataattaa caactgaaac tattgatatg tctaggtttt  12660

agctctatca caggttggat ctg                                          12683
```

```
<210> SEQ ID NO 33
<211> LENGTH: 12725
<212> TYPE: DNA
<213> ORGANISM: Artificial
<220> FEATURE:
<223> OTHER INFORMATION: Synthetically produced plasmid construct #1760
      pABIcyano1::PnirA-zmPDC(opt3)dsrA-PrpsL*4-ADH1694(opt)_ter

<400> SEQUENCE: 33
```

```
tcgacaatta ataacttctt cctgtacggg cgaatggcca tttgctccta actaactccg     60

tactgctttg cggaacgagc gtagcgaact ctccgaatta ctaagccttc atccctgata    120

gatgcaaaaa acgaattaaa attatgtgta aaaagaaaat gtgtctttat ttagtagtca    180

aagttacaaa atattaagaa tcaaattaat aatgtattgg gcagttaagt atataagtct    240

ttaaatattt atttgtattc aatatattaa ccgaggacaa attatgaatt cttacactgt    300

tggaacctat ttagcagaac gtttagttca aattggtctc aaacaccatt ttgcagtagc    360

tggtgattat aatttagttt tattggataa cttattgtta aataagaata tggaacaagt    420

gtattgttgt aatgaattaa actgtggttt ttctgctgag ggatatgctc gtgcaaaagg    480

tgctgccgca gcagttgtta cttattctgt tggagcatta agtgcttttg acgctattgg    540

aggtgcttat gcagaaaatt tacctgtaat cttaatctct ggtgcaccca ataacaacga    600

tcacgctgct ggtcatgtat tgcatcatgc tttaggtaaa accgattatc attaccaatt    660

agaaatggca aaaaatatta ccgctgccgc agaagctatt tatactcccg aagaagcacc    720

tgctaagatc gatcacgtaa ttaaaaccgc tctccgtgag aaaaaacccg tatatttaga    780

aatcgcttgc aatatcgctt ctatgccttg tgcagctcct ggacctgcta gtgctttatt    840

taacgatgaa gcatctgatg aggctagttt aaatgccgct gttgaagaaa ctttgaaatt    900

tattgctaat cgtgataaag tagctgtttt agttggttct aaactccgtg ccgctggtgc    960

agaagaagcg gctgtaaaat tcgcagatgc cttaggaggt gctgttgcca caatggcagc   1020

cgctaaaagt tttttccccg aagaaaatcc tcattacatt ggtacttctt ggggtgaggt   1080

atcttaccct ggtgtagaaa aaaccatgaa ggaagctgat gcagtaattg cattagctcc   1140
```

-continued

```
tgttttcaat gattactcta ccactggttg gactgatatt ccagacccca aaaaattagt   1200
tttagcagaa cctcgctctg tagttgtgaa tggtgttaga tttcccagtg tacatctcaa   1260
agattattta actcgtttag ctcaaaaagt gagtaaaaag actggcgcac tcgatttctt   1320
taaatcttta aatgctggtg aattaaagaa agcagctcct gctgatccca gtgctccttt   1380
agtgaatgcc gaaatcgcaa gacaagttga agccttgtta actcctaaca ctaccgttat   1440
tgccgagact ggtgatagtt ggttcaatgc tcaacgcatg aaattaccca atggtgctcg   1500
tgttgagtat gaaatgcaat ggggtcacat tggatggtct gttcctgctg catttggata   1560
tgcagttgga gcacctgagc gtagaaacat tttaatggta ggtgatggtt ctttccaact   1620
cactgctcaa gaagttgcac aaatggtacg tttaaaattg cctgttatta tctttctcat   1680
taacaactat ggttacacca ttgaagttat gattcatgat ggtccttata ataacattaa   1740
gaattgggat tacgcaggtt taatggaggt atttaacggt aatggtggat acgacagtgg   1800
agcaggtaaa ggattaaaag ctaaaacagg aggtgagtta gctgaagcaa ttaaagtagc   1860
tttagccaat acagatggtc ctaccttaat cgaatgtttc attggacgtg aagattgtac   1920
tgaagagtta gttaaatggg gaaagcgtgt tgccgctgca aattctcgta aacctgtaaa   1980
caaactcttg tagttaggat ccagcaaggt ttcatcccga ccccctcagg gtcgggattt   2040
ttttattgtg agctcagaaa aactattgac aaacccataa aaaatgtgat ataattatag   2100
attgtcactg gtattttata ctagaggcaa attatattta tatatacaaa aatgctgtag   2160
gaggatcagc catatgacta ccgctactaa atttaaagca tacgccgcat taaattctgg   2220
tgaaaaatta cagccctggg aatacgaacc tgaaccttta caggttgatg aggttgagat   2280
ccgtgtaacc cataacggtt tatgtcatac tgatttacac atgcgtgata atgattggaa   2340
cgtaagtcaa tatcctttag tacccggtca cgaagtagtt ggtgaggtta ccgaggttgg   2400
tgaaaaagta accagtttac acaaaggaga cagaattggt gtaggatgga ttagaaattc   2460
ttgtcgttct tgtgatcact gtttacaagg agaggaaaac atctgtcgtg aaggatacac   2520
tggtttaatt gttggacacc acggtggttt cgctgatcgt ttacgtgtac ctgctgattt   2580
cacctacaaa attcctgatg cattagattc tgcctctgcc gctcccttat tatgtgctgg   2640
tattactgtt tataccccct taagaactta catcaaacac cccggtatga aagttggtgt   2700
aatgggaatt ggtggtttag gtcatttagc tattaaattt gctagagcta tgggagctga   2760
agtaactgca ttttctactt ctttaaacaa acaagaacag gcaaaagagt ttggagcaca   2820
caattttcag caatggggaa ctgctgaaga gatgaaagct attgctggtt ctttcgattt   2880
agttttatct actatctcta gtgaaactga ttgggatgct gctttctctt tattagctaa   2940
caatggtgta ttatgttttg ttggtattcc tgtttctacc ttaaatattc ctttaatccc   3000
tttaatcttt ggtcaaaaag ctgtagtagg aagtattgtt ggtggaagac gttttatggc   3060
tgagatgtta gaatttgctg ccgttaatca gatcaaaccc atgattgaga ctatgccttt   3120
aagtcaaatc aacgaggcta tggataaagt tgcagctaat caagcccgtt atcgtattgt   3180
attattagca gactaactag atctcctgca gagaatataa aaagccagat tattaatccg   3240
gctttttat tatttaaata ctgtgcacga tcctgcagga tcatcttgct gaaaaactcg   3300
agcgctcgtt ccgcaaagcg gtacggagtt agttaggggc taatgggcat tctcccgtac   3360
aggaaagagt tagaagttat taattatcaa caattctcct ttgcctagtg catcgttacc   3420
tttttaatta aaacataagg aaaactaata atcgtaataa tttaacctca aagtgtaaag   3480
```

```
aaatgtgaaa ttctgacttt tataacgtta aagagggaaa aattagcagt ttaaaatacc   3540
tagagaatag tctggggtaa gcatagagaa ttagattagt taagttaatc aaattcagaa   3600
aaaataataa tcgtaaatag ttaatctggg tgtatagaaa atgatcccct tcatgataag   3660
atttaaactc gaaaagcaaa agccaaaaaa ctaacttcca ttaaaagaag ttgttacata   3720
taacgctata aagaaaattt atatatttgg aggataccaa ccatgtctca tattcaacgt   3780
gaaactagtt gttctcgccc tcgtttaaat tctaatatgg atgccgattt atatggttat   3840
aaatgggctc gtgataatgt tggtcaatct ggtgctacta tttatcgttt atatggtaaa   3900
cctgatgctc ctgaattatt cttgaaacat ggtaaaggtt ctgttgctaa tgatgttact   3960
gatgaaatgg ttcgtttaaa ctggttgact gaatttatgc ctttacctac tattaaacat   4020
tttattcgta ctcccgatga tgcttggtta ttaactactg ctattcctgg taaaactgct   4080
tttcaagttt tagaagaata tcctgattct ggtgaaaata ttgttgatgc tttagctgtt   4140
tttttacgtc gtttacattc tattcccgtt tgtaattgtc cttttaattc tgatcgtgtt   4200
tttcgtttag ctcaagctca atctcgtatg aataatggtt tagttgatgc ttctgatttt   4260
gatgatgaac gtaatggttg gcctgttgaa caagtttgga aagaaatgca caaattgtta   4320
ccttttctc ctgattctgt tgttactcat ggtgattttt ctttagataa tttgatcttt   4380
gatgaaggta aattgattgg ttgtattgat gttggtcgtg ttggtattgc tgatcgttat   4440
caagatttag ctattttatg gaattgttta ggtgaatttt ctccttcttt acagaaacgt   4500
ttatttcaga aatatggtat tgataatcct gatatgaaca agttacaatt tcatttaatg   4560
ttggacgagt tcttttaaga attaattcat gaccaaaatc ccttaacgtg agttttcgtt   4620
ccactgagcg tcagaccccg tagaaaagat caaaggatct tcttgagatc cttttttct   4680
gcgcgtaatc tgctgctatt taaattacgt acacgtgtta ttactttgtt aacgacaatt   4740
gtcttaatta actgggcctc atgggccttc cgctcactgc ccgctttcca gtcgggaaac   4800
ctgtcgtgcc agctctgcag atgacggtga aaacctctga cacatgcagc tcccggagac   4860
ggtcacagct tgtctgtaag cggatgccgg gagcagacaa gcccgtcagg gcgcgtcagc   4920
gggtgttggc gggtgtcggg gcgcagccat gacccagtca cgtagcgata gcggagtgta   4980
tactggctta actatgcggc atcagagcag attgtactga gagtgcacca tatgcggtgt   5040
gaaataccgc acagatgcgt aaggagaaaa taccgcatca ggcgctcttc cgcttcctcg   5100
ctcactgact cgctgcgctc ggtcgttcgg ctgcggcgag cggtatcagc tcactcaaag   5160
gcggtaatac ggttatccac agaatcaggg gataacgcag gaaagaacat gtgagcaaaa   5220
ggccagcaaa aggccaggaa ccgtaaaaag gccgcgttgc tggcgttttt ccataggctc   5280
cgcccccctg acgagcatca caaaaatcga cgctcaagtc agaggtggcg aaacccgaca   5340
ggactataaa gataccaggc gtttccccct ggaagctccc tcgtgcgctc tcctgttccg   5400
accctgccgc ttaccggata cctgtccgcc tttctccctt cgggaagcgt ggcgctttct   5460
catagctcac gctgtaggta tctcagttcg gtgtaggtcg ttcgctccaa gctgggctgt   5520
gtgcacgaac cccccgttca gcccgaccgc tgcgccttat ccggtaacta tcgtcttgag   5580
tccaacccgg taagacacga cttatcgcca ctggcagcag ccactggtaa caggattagc   5640
agagcgaggt atgtaggcgg tgctacagag ttcttgaagt ggtggcctaa ctacggctac   5700
actagaagga cagtatttgg tatctgcgct ctgctgaagc cagttacctt cggaaaaaga   5760
gttggtagct cttgatccgg caaacaaacc accgctggta gcggtggttt ttttgtttgc   5820
aagcagcaga ttacgcgcag aaaaaaagga tctcaagaag atcctttgat cttttctact   5880
```

```
gcagaagctt gttagacacc ctgtcatgta ttttatatta tttatttcac catacggatt   5940
aagtgaaacc taatgaaaat agtactttcg gagctttaac tttaatgaag gtatgttttt   6000
ttatagacat cgatgtctgg tttaacaata ggaaaaagta gctaaaactc ccatgaatta   6060
aagaaataac aaggtgtcta acaacctgtt attaagaatg ttagaaaaga cttaacattt   6120
gtgttgagtt tttatagaca ttggtgtcta gacatacggt agataaggtt tgctcaaaaa   6180
taaaataaaa aaagattgga ctaaaaaaca tttaatttag tacaatttaa ttagttattt   6240
tttcgtctca aattttgctt tgttgagcag aaatttagat aaaaaaatcc ccgtgatcag   6300
attacaatgt cgttcattgt acgatgtgtc gaaaaatctt tacgacactc taaactgacc   6360
acacgggga aaaagaaaac tgaactaata acatcatgat actcggaaaa cctagcaatt   6420
ctcaacccct aaacaaaaga aacttccaaa accctgacca tataaaggag tggcaacaat   6480
cagcaatcag tcaagatttg atagcagaaa atcttgtatc ggttgctaat ggttttgatg   6540
tactatttat cggcaataaa taccgaacta acacgggtgt tctgtcacgg cacatattaa   6600
actcctattc tcatttagaa gatggtggtt cgtatggtag aacatttgac ccatttacca   6660
ataaagaaat gcagtgggtt caatttaaac cgaatagacc aagaaaaggt tctactggta   6720
aggtaatcaa atatgaatcg ccaaaaggtg aacctacaag agttctaatg ccgtttgtgc   6780
ctatgaaaat atggcaacgg attagcgata agttcggagt accgattaat ccgaaaaaag   6840
atactcactt ttgggaatgg gtaaagaata atccatcgat accgattgcc attacagaag   6900
gaaataaaaa agctaattgc ctattatcct atggctatcc tgctattgcc tttgtaggca   6960
tttggaacgg attagagaaa ataaatgatt tctcgaagga aaagcagtta aaagaggatt   7020
tgaaatggtt gttatccaac ggcaaccgaa atattaatat catctttgac caagaccaga   7080
aacaaaaaac tgtaattaat gtaaacaaag ctattttcgc tttatcttct ctaataagta   7140
gaaatggtca taaagttaat attgtgcaat ggttgccgtc aaaaggtaaa ggaatagatg   7200
attatttggt agctttacct tttgagaaaa gagaaaatca tttagacaac ttaattaaaa   7260
ttgcaccatc atttaatttt tggtcaacta aatacttatt caagtgtcgt aaaccagatt   7320
taaccgtaaa ttgccgttat ttgagcgatg cagtaaaaga attacctcaa gaggatatag   7380
cattaatagc acctcacggc acgggtaaaa cttcattagt agctactcac gttaagaatc   7440
ggagttatca cggaaggaaa actatttcat tggtgcatct tgaaagttta gccaaagcta   7500
atggcaacgc acttggatta tattaccgaa ccgaaaataa tattgaaaag caatatcttg   7560
gatttagctt atgtgtagat agttgccgtg ataagattaa cggcattaca actgatatta   7620
tttcaggtca agattattgc cttttcattg atgaaattga ccaagtaatt ccacacatcc   7680
ttaacagtga aactgaagta agtaagtata gatgcaccat cattgacact ttttctgaac   7740
tggtgagaaa tgctgaacag gtcattattg ctgatgctga tttatccgat gtgacgattg   7800
acctaataga aaacatcaga ggtaaaaaac tatatgtaat caagaatgaa tatcagtatc   7860
agggaatgac ttttaacgcc gttggttcac cattagaaat gatggcaatg atgggaaaat   7920
cggtgtcaga aggcaagaaa ttatttatta acaccacatc ccaaaaggca aaaagtaagt   7980
acggcacaat cgctcttgag tcttatattt ttggtctaaa taaagaagca aagatattaa   8040
gaatagactc tgaaaccact aaaaaccctg aacatccagc ctataaaatc attgaccaag   8100
acttaaataa tatcctcaaa gattatgatt atgtcattgc ctcaccttgc cttcaaacag   8160
gtgtcagtat taccttaaaa gggcattttg accagcaatt taacttttcc agtggaaaca   8220
```

```
ttacacctca ttgcttttta cagcaaatgt ggcggttgag ggatgcagaa attgaaagat   8280
tctattatgt gccgaactca tctaacctca atctcattgg gaataagtca agttcaccat   8340
cagaccttct aaagagcaat aacaagatgg caacggcaac ggttaacctt ttgggtagaa   8400
tcgactccga atattcccta gagtatgaat cgcacggcat ttggcttgag acgtgggcaa   8460
aattatcagc acggcataac agttcaatgc gttgttactc tgaaattctt acctatctaa   8520
ttacgtctca agggcataaa ttaaatatca acattccctc acctcttgca gatattaaga   8580
agctaaatga tgaggtaagt agtaacaggg aaaaggtaaa aaatgagaga tactctcaga   8640
ggttaaactc accagatatt aacgatgcag aagctaccat actcgaatct aaagagcaaa   8700
aaatcggatt gactctcaat gagagatgca ccctagaaaa gcataaagtt aagaagcggt   8760
atgggaatgt aaagatggat attctcacct ttgatgatga tggactatac cccaaactca   8820
gactatttta ttacctcacc atcggtaaac ctcatctcaa ggctaatgac agaaaagcta   8880
ttgccaaaat gggcaatgac aataaaggca agattctatc aaaagactta gttaataaaa   8940
cttactccgc tcgtgtgaag gtcttagaga ttcttaaact aactgacttt atcgacaatc   9000
ttagagatga actcttaata actcccaata atccagctat caccgatttt aataatcttc   9060
tgctaagagc taagaaggat ttaagagtat taggagtcaa catcggaaaa tatccaatgg   9120
ccaacattaa tgccgtactt actctcattg gtcacaaact ttctgtaatg agagatgagt   9180
tcggaaaaga gaaaaggata aaagtagatg gtaaatcata ccgatgttat caacttgaaa   9240
cattaccaga ttttaccaat gatactcttg actactggtt agaaaatgat agccaaaaag   9300
aagtaacagc aacagaaaat tactccgaaa attttaaccc ttcaaatagc tacaatccag   9360
acagtaagac actttcagag ggtgcaaatt tcctatatat aaataaagaa gaattgcatc   9420
caaataaatt gcacctagaa ataaaagaag gtgctgaact ttttttattc ggggtaaagg   9480
tgattgtgaa aggaatcttg gacggggcag taactatatt ctctatgggt caagaatacg   9540
atttatccct caatgaacta gaggggatgt taacatcatg aactttacaa gaatcttttt   9600
aaagggcgat cgcaccatgt taaatgatgg tacatttgtt cagatatttg atatttacca   9660
tgaccacgca ttgggagtga cccttgacct taagacagaa aaaattattt ccgatgatgt   9720
tagggtaatt actgtcaaag acttattgtt cgatggcact tataaagggg taaaatcttt   9780
tatgcccgat aatgcccgat aatgcccgat tgatgctaca aaatcccata atcataagcg   9840
ataatcccct aatagcttgt aattcttgaa ccgtagcgat tttagagtat tccaaaaaga   9900
agaaataaac accgcaaaat gtcgtatttc acatatataa accaaggttt tttgccctaa   9960
aatctttatg tttgtagtgt gatgttgggt caaaatggtc agaaaagttg caaggttttt  10020
atggatgctt acgcgcgcga ggggtaagca tccccaaata gttactttat cctagtccat  10080
gcccatttat tgccgtcccg ttcggcttta aaaaagtgcc aaaactcaca aggtgcaata  10140
aaaagttctg tacctttcgc aaccctagat aatctttcaa cagttacttt ttttcctatt  10200
atctcggtac aaagtttggc tagtttctct tttccctctt tttcaatcaa gccttcttgt  10260
atgcccaact cattgattaa tctctctatt tttaccatta tttcccgttc aggtagttta  10320
tcccctaaat cttcatcggg gggcaatgta gggcattctg aaggggcttt ttcttctgtc  10380
tggacattat ctaatattga agtaaccaaa ctatcttcag ttttttctat tcctattaat  10440
tcatattcgg ttactgtatc cgtatcaata tccgaataac tatctttatc cgtattagct  10500
attcggttaa gtttatccgt taactcagaa acaagactat atagcggttt tagcttttct  10560
tctatcctgt tatctaatac ggataagttt atacggttat cattatccgt attagtatca  10620
```

```
ttgggctttt ttggtagttc taccccctca taaaccgctt ttattcccaa ttccaacaga  10680
ctgataacag tatcctttat aatgggtttt ttgctgatat ggtgaacttt tgccccttcc  10740
atcattgcga tactttctat ctcactcatc aacttatcgc ttaagtgaat ctcgtatctg  10800
tttaatccct tactggtttt attcatatcc gtttacttta ttcggttaac aattctattt  10860
tatacgaata aaatattata cggttaactt tatacgttta actattttat ctatacggat  10920
aacagtaata agttattcgt attagttata cgtttacttt tatccaaata aaattagtgc  10980
atttaaacta aaagaatgat tttatcggag ttgatagcat tggattaacc taaagatgtt  11040
tataagctat atctgataag tatttaaggt tattttgtta ttctgtttat tgacattatc  11100
agaataaaag aatagaatat aattgttgag agataagagg tttaagtgat tatggttaag  11160
aagttagttg gttatgtcag ggtcagtagt gaatcgcaag aggataacac tagcttacag  11220
aatcagatag agagaattga agcatattgt atggcttttg gttatgagtt ggtaaaaata  11280
ttcaaagagg ttgccactgg tacaaaagca gatattgaaa cccgtcctat ttttaatgaa  11340
gctatagaat acttgaaaca ggataatgct aatggaatta ttgccttgaa gctagaccga  11400
atcgcacgga atgctttaga tgtattgcgt ttggttcgtg aaaccttaga accacaaaat  11460
aaaatgttag tgttactaga tattcaggta gatacttcga caccttcagg aaaaatgatt  11520
ttaactgtaa tgagtgccgt tgctgaactc gaaagagaca tgatctatga tcgcactcag  11580
gggggtagaa agactaaagc ccaaaagggc gggtatgcct acgggaaacc taaatttggc  11640
tataagactg aagaaaagga actaaaagaa gattcagcac aacaggaaac tattaaacta  11700
attaagagac accgtaggtc agggaaaagc taccagaaaa tagctgatta tctcaatgcc  11760
caaagtattc ccactaaaca aggtaagaaa tggagttcta gcgtcgtcta tcgaatctgt  11820
caggaaaaag ctggttaagt ctgtttatag atatttagaa tttattgaat aaaaatagta  11880
tgaacaataa atatttatgg actaaccacg ctcggaaacg tttaactgaa cgatgggaaa  11940
taaaagaatc atgggttatt gataccatcg aaaatcctga acgttcagaa tttattgttg  12000
atgagtcagg ggaaaaatat cattactata aaagaatagc taagtttaag aatagagtgt  12060
tagaagtgat aacttctgcc aactcaacac ccacaagaat aataaccttt tactttaacc  12120
gtaacatgag gaaaaattta tgattgttac ttacgataat gaagttgacg caatttattt  12180
taagttaacg gaaaataaaa ttgatagcac cgaacctcaa acagacagga ttatcattga  12240
ttacgatgaa agtaataata ttgttggcat tgaggtatta gattttaatt atcttgtcaa  12300
gaaaggttta accgttgctg atttaccttt ttctgaagat gaaagattaa cagcttctca  12360
atattttaat tttcctgttg ctatctaatc cagaaggggc aataatcccc ttctttcatc  12420
gagttagact taatatcaca aaagtcattt tcattttacc gtttcttttc cacagcgtcc  12480
gtacgcccct cgttaaatct caaaaccgac aatttatgat gtttataaaa agttactcac  12540
tttaataagt atttatactc attaaagggt tattcttttt ttgtagcctg ataggttggg  12600
aaggaatatt tcagattatc agatttgttg aatatttttc gtcagatacg caaaccttac  12660
aaacataatt aacaactgaa actattgata tgtctaggtt ttagctctat cacaggttgg  12720
atctg                                                              12725
```

<210> SEQ ID NO 34
<211> LENGTH: 12648
<212> TYPE: DNA
<213> ORGANISM: Artificial
<220> FEATURE:

<223> OTHER INFORMATION: Synthetically produced plasmid construct #1578
pABIcyano1::PnirA-zmPDC(opt3)dsrA-Prbc*(optRBS)-synADH_oop

<400> SEQUENCE: 34

```
tcgacaatta ataacttctt cctgtacggg cgaatggcca tttgctccta actaactccg     60
tactgctttg cggaacgagc gtagcgaact ctccgaatta ctaagccttc atccctgata    120
gatgcaaaaa acgaattaaa attatgtgta aaaagaaaat gtgtctttat ttagtagtca    180
aagttacaaa atattaagaa tcaaattaat aatgtattgg gcagttaagt atataagtct    240
ttaaatattt atttgtattc aatatattaa ccgaggacaa attatgaatt cttacactgt    300
tggaacctat ttagcagaac gtttagttca aattggtctc aaacaccatt ttgcagtagc    360
tggtgattat aatttagttt tattggataa cttattgtta aataagaata tggaacaagt    420
gtattgttgt aatgaattaa actgtggttt ttctgctgag ggatatgctc gtgcaaaagg    480
tgctgccgca gcagttgtta cttattctgt tggagcatta agtgcttttg acgctattgg    540
aggtgcttat gcagaaaatt tacctgtaat cttaatctct ggtgcaccca ataacaacga    600
tcacgctgct ggtcatgtat tgcatcatgc tttaggtaaa accgattatc attaccaatt    660
agaaatggca aaaaatatta ccgctgccgc agaagctatt tatactcccg aagaagcacc    720
tgctaagatc gatcacgtaa ttaaaaccgc tctccgtgag aaaaaacccg tatatttaga    780
aatcgcttgc aatatcgctt ctatgccttg tgcagctcct ggacctgcta gtgctttatt    840
taacgatgaa gcatctgatg aggctagttt aaatgccgct gttgaagaaa ctttgaaatt    900
tattgctaat cgtgataaag tagctgtttt agttggttct aaactccgtg ccgctggtgc    960
agaagaagcg gctgtaaaat tcgcagatgc cttaggaggt gctgttgcca caatggcagc   1020
cgctaaaagt tttttccccg aagaaaatcc tcattacatt ggtacttctt ggggtgaggt   1080
atcttaccct ggtgtagaaa aaaccatgaa ggaagctgat gcagtaattg cattagctcc   1140
tgttttcaat gattactcta ccactggttg gactgatatt ccagacccca aaaaattagt   1200
tttagcagaa cctcgctctg tagttgtgaa tggtgttaga tttcccagtg tacatctcaa   1260
agattattta actcgtttag ctcaaaaagt gagtaaaaag actggcgcac tcgatttctt   1320
taaatcttta aatgctggtg aattaaagaa agcagctcct gctgatccca gtgctccttt   1380
agtgaatgcc gaaatcgcaa gacaagttga agccttgtta actcctaaca ctaccgttat   1440
tgccgagact ggtgatagtt ggttcaatgc tcaacgcatg aaattaccca atggtgctcg   1500
tgttgagtat gaaatgcaat ggggtcacat tggatggtct gttcctgctg catttggata   1560
tgcagttgga gcacctgagc gtagaaacat tttaatggta ggtgatggtt ctttccaact   1620
cactgctcaa gaagttgcac aaatggtacg tttaaaattg cctgttatta tctttctcat   1680
taacaactat ggttacacca ttgaagttat gattcatgat ggtccttata ataacattaa   1740
gaattgggat tacgcaggtt taatggaggt atttaacggt aatggtggat acgacagtgg   1800
agcaggtaaa ggattaaaag ctaaaacagg aggtgagtta gctgaagcaa ttaaagtagc   1860
tttagccaat acagatggtc ctaccttaat cgaatgtttc attggacgtg aagattgtac   1920
tgaagagtta gttaaatggg gaaagcgtgt tgccgctgca aattctcgta aacctgtaaa   1980
caaactcttg tagttaggat ccgagctcag caagtttcat cccgaccccc tcagggtcgg   2040
gattttttta ttgtactagt tgacataagt aaaggcatcc cctgcgtgat ataattacct   2100
tcagtttaag gaggtataca catatgatta aagcctacgc tgccctggaa gccaacggaa   2160
aactccaacc ctttgaatac gaccccggtg ccctgggtgc taatgaggtg gagattgagg   2220
```

-continued

```
tgcagtattg tggggtgtgc cacagtgatt tgtccatgat taataacgaa tggggcattt   2280
ccaattaccc cctagtgccg ggtcatgagg tggtgggtac tgtggccgcc atgggcgaag   2340
gggtgaacca tgttgaggtg ggggatttag tggggctggg ttggcattcg ggctactgca   2400
tgacctgcca tagttgttta tctggctacc acaacctttg tgccacggcg gaatcgacca   2460
ttgtgggcca ctacggtggc tttggcgatc gggttcgggc caagggagtc agcgtggtga   2520
aattacctaa aggcattgac ctagccagtg ccgggcccct tttctgtgga ggaattaccg   2580
ttttcagtcc tatggtggaa ctgagtttaa agcccactgc aaaagtggca gtgatcggca   2640
ttgggggctt gggccattta gcggtgcaat ttctccgggc ctggggctgt gaagtgactg   2700
cctttacctc cagtgccagg aagcaaacgg aagtgttgga attgggcgct caccacatac   2760
tagattccac caatccagag gcgatcgcca gtgcggaagg caaatttgac tatattatct   2820
ccactgtgaa cctgaagctt gactggaact tatacatcag caccctggcg ccccagggac   2880
atttccactt tgttggggtg gtgttggagc ctttggatct aaatcttttt ccccttttga   2940
tgggacaacg ctccgtttct gcctccccag tgggtagtcc cgccaccatt gccaccatgt   3000
tggactttgc tgtgcgccat gacattaaac ccgtggtgga acaatttagc tttgatcaga   3060
tcaacgaggc gatcgcccat ctagaaagcg gcaaagccca ttatcgggta gtgctcagcc   3120
atagtaaaaa ttagctctgc aaaggttgct tctgggtccg tggaacgctc ggttgccgcc   3180
gggcgttttt tattcctgca ggatcatctt gctgaaaaac tcgagcgctc gttccgcaaa   3240
gcggtacgga gttagttagg ggctaatggg cattctcccg tacaggaaag agttagaagt   3300
tattaattat caacaattct cctttgccta gtgcatcgtt accttttttaa ttaaaacata   3360
aggaaaacta ataatcgtaa taatttaacc tcaaagtgta aagaaatgtg aaattctgac   3420
ttttataacg ttaaagaggg aaaaattagc agtttaaaat acctagagaa tagtctgggg   3480
taagcataga gaattagatt agttaagtta atcaaattca gaaaaaataa taatcgtaaa   3540
tagttaatct gggtgtatag aaaatgatcc ccttcatgat aagatttaaa ctcgaaaagc   3600
aaaagccaaa aaactaactt ccattaaaag aagttgttac atataacgct ataaagaaaa   3660
tttatatatt tggaggatac caaccatgtc tcatattcaa cgtgaaacta gttgttctcg   3720
ccctcgttta aattctaata tggatgccga tttatatggt tataaatggg ctcgtgataa   3780
tgttggtcaa tctggtgcta ctatttatcg tttatatggt aaacctgatg ctcctgaatt   3840
attcttgaaa catggtaaag gttctgttgc taatgatgtt actgatgaaa tggttcgttt   3900
aaactggttg actgaattta tgcctttacc tactattaaa cattttattc gtactcccga   3960
tgatgcttgg ttattaacta ctgctattcc tggtaaaact gcttttcaag ttttagaaga   4020
atatcctgat tctggtgaaa atattgttga tgctttagct gttttttttac gtcgtttaca   4080
ttctattccc gtttgtaatt gtccttttaa ttctgatcgt gtttttcgtt tagctcaagc   4140
tcaatctcgt atgaataatg gtttagttga tgcttctgat tttgatgatg aacgtaatgg   4200
ttggcctgtt gaacaagttt ggaaagaaat gcacaaattg ttaccttttt ctcctgattc   4260
tgttgttact catggtgatt tttctttaga taatttgatc tttgatgaag gtaaattgat   4320
tggttgtatt gatgttggtc gtgttggtat tgctgatcgt tatcaagatt tagctatttt   4380
atggaattgt ttaggtgaat ttttctcctc tttacagaaa cgtttatttc agaaatatgg   4440
tattgataat cctgatatga acaagttaca atttcattta atgttggacg agttctttta   4500
agaattaatt catgaccaaa atcccttaac gtgagttttc gttccactga gcgtcagacc   4560
ccgtagaaaa gatcaaagga tcttcttgag atcctttttt tctgcgcgta atctgctgct   4620
```

```
atttaaatta cgtacacgtg ttattacttt gttaacgaca attgtcttaa ttaactgggc   4680
ctcatgggcc ttccgctcac tgcccgcttt ccagtcggga aacctgtcgt gccagctctg   4740
cagatgacgg tgaaaacctc tgacacatgc agctcccgga gacggtcaca gcttgtctgt   4800
aagcggatgc cgggagcaga caagcccgtc agggcgcgtc agcgggtgtt ggcgggtgtc   4860
ggggcgcagc catgacccag tcacgtagcg atagcggagt gtatactggc ttaactatgc   4920
ggcatcagag cagattgtac tgagagtgca ccatatgcgg tgtgaaatac cgcacagatg   4980
cgtaaggaga aaataccgca tcaggcgctc ttccgcttcc tcgctcactg actcgctgcg   5040
ctcggtcgtt cggctgcggc gagcggtatc agctcactca aaggcggtaa tacggttatc   5100
cacagaatca ggggataacg caggaaagaa catgtgagca aaaggccagc aaaaggccag   5160
gaaccgtaaa aaggccgcgt tgctggcgtt tttccatagg ctccgccccc ctgacgagca   5220
tcacaaaaat cgacgctcaa gtcagaggtg gcgaaacccg acaggactat aaagatacca   5280
ggcgtttccc cctggaagct ccctcgtgcg ctctcctgtt ccgaccctgc cgcttaccgg   5340
atacctgtcc gcctttctcc cttcgggaag cgtggcgctt tctcatagct cacgctgtag   5400
gtatctcagt tcggtgtagg tcgttcgctc caagctgggc tgtgtgcacg aaccccccgt   5460
tcagcccgac cgctgcgcct tatccggtaa ctatcgtctt gagtccaacc cggtaagaca   5520
cgacttatcg ccactggcag cagccactgg taacaggatt agcagagcga ggtatgtagg   5580
cggtgctaca gagttcttga agtggtggcc taactacggc tacactagaa ggacagtatt   5640
tggtatctgc gctctgctga agccagttac cttcggaaaa agagttggta gctcttgatc   5700
cggcaaacaa accaccgctg gtagcggtgg tttttttgtt tgcaagcagc agattacgcg   5760
cagaaaaaaa ggatctcaag aagatccttt gatcttttct actgcagaag cttgttagac   5820
accctgtcat gtattttata ttatttattt caccatacgg attaagtgaa acctaatgaa   5880
aatagtactt tcggagcttt aactttaatg aaggtatgtt tttttataga catcgatgtc   5940
tggtttaaca ataggaaaaa gtagctaaaa ctcccatgaa ttaaagaaat aacaaggtgt   6000
ctaacaacct gttattaaga atgttagaaa agacttaaca tttgtgttga gtttttatag   6060
acattggtgt ctagacatac ggtagataag gtttgctcaa aaataaaata aaaaaagatt   6120
ggactaaaaa acatttaatt tagtacaatt taattagtta ttttttcgtc tcaaattttg   6180
ctttgttgag cagaaattta gataaaaaaa tccccgtgat cagattacaa tgtcgttcat   6240
tgtacgatgt gtcgaaaaat ctttacgaca ctctaaactg accacacggg ggaaaaagaa   6300
aactgaacta ataacatcat gatactcgga aaacctagca attctcaacc cctaaacaaa   6360
agaaacttcc aaaaccctga ccatataaag gagtggcaac aatcagcaat cagtcaagat   6420
ttgatagcag aaaatcttgt atcggttgct aatggttttg atgtactatt tatcggcaat   6480
aaataccgaa ctaacacggg tgttctgtca cggcacatat taaactccta ttctcattta   6540
gaagatggtg gttcgtatgg tagaacattt gacccattta ccaataaaga aatgcagtgg   6600
gttcaattta aaccgaatag accaagaaaa ggttctactg gtaaggtaat caaatatgaa   6660
tcgccaaaag gtgaacctac aagagttcta atgccgtttg tgcctatgaa aatatggcaa   6720
cggattagcg ataagttcgg agtaccgatt aatccgaaaa aagatactca cttttgggaa   6780
tgggtaaaga ataatccatc gataccgatt gccattacag aaggaaataa aaaagctaat   6840
tgcctattat cctatggcta tcctgctatt gcctttgtag gcatttggaa cggattagag   6900
aaaataaatg atttctcgaa ggaaaagcag ttaaaagagg atttgaaatg gttgttatcc   6960
```

```
aacggcaacc gaaatattaa tatcatcttt gaccaagacc agaaacaaaa aactgtaatt   7020
aatgtaaaca aagctatttt cgctttatct tctctaataa gtagaaatgg tcataaagtt   7080
aatattgtgc aatggttgcc gtcaaaaggt aaaggaatag atgattattt ggtagcttta   7140
ccttttgaga aaagagaaaa tcatttagac aacttaatta aaattgcacc atcatttaat   7200
ttttggtcaa ctaaatactt attcaagtgt cgtaaaccag atttaaccgt aaattgccgt   7260
tatttgagcg atgcagtaaa agaattacct caagaggata tagcattaat agcacctcac   7320
ggcacgggta aaacttcatt agtagctact cacgttaaga atcggagtta tcacggaagg   7380
aaaactattt cattggtgca tcttgaaagt ttagccaaag ctaatggcaa cgcacttgga   7440
ttatattacc gaaccgaaaa taatattgaa aagcaatatc ttggatttag cttatgtgta   7500
gatagttgcc gtgataagat taacggcatt acaactgata ttatttcagg tcaagattat   7560
tgccttttca ttgatgaaat tgaccaagta attccacaca tccttaacag tgaaactgaa   7620
gtaagtaagt atagatgcac catcattgac actttttctg aactggtgag aaatgctgaa   7680
caggtcatta ttgctgatgc tgatttatcc gatgtgacga ttgacctaat agaaaacatc   7740
agaggtaaaa aactatatgt aatcaagaat gaatatcagt atcagggaat gacttttaac   7800
gccgttggtt caccattaga aatgatggca atgatgggaa aatcggtgtc agaaggcaag   7860
aaattattta ttaacaccac atcccaaaag gcaaaaagta agtacggcac aatcgctctt   7920
gagtcttata tttttggtct aaataaagaa gcaaagatat taagaataga ctctgaaacc   7980
actaaaaacc ctgaacatcc agcctataaa atcattgacc aagacttaaa taatatcctc   8040
aaagattatg attatgtcat tgcctcacct tgccttcaaa caggtgtcag tattacctta   8100
aaagggcatt ttgaccagca atttaacttt tccagtggaa acattacacc tcattgcttt   8160
ttacagcaaa tgtggcggtt gagggatgca gaaattgaaa gattctatta tgtgccgaac   8220
tcatctaacc tcaatctcat tgggaataag tcaagttcac catcagacct tctaaagagc   8280
aataacaaga tggcaacggc aacggttaac cttttgggta gaatcgactc cgaatattcc   8340
ctagagtatg aatcgcacgg catttggctt gagacgtggg caaaattatc agcacggcat   8400
aacagttcaa tgcgttgtta ctctgaaatt cttacctatc taattacgtc tcaagggcat   8460
aaattaaata tcaacattcc ctcacctctt gcagatatta agaagctaaa tgatgaggta   8520
agtagtaaca gggaaaaggt aaaaaatgag agatactctc agaggttaaa ctcaccagat   8580
attaacgatg cagaagctac catactcgaa tctaaagagc aaaaaatcgg attgactctc   8640
aatgagagat gcaccctaga aaagcataaa gttaagaagc ggtatgggaa tgtaaagatg   8700
gatattctca cctttgatga tgatggacta taccccaaac tcagactatt ttattacctc   8760
accatcggta aacctcatct caaggctaat gacagaaaag ctattgccaa aatgggcaat   8820
gacaataaag gcaagattct atcaaaagac ttagttaata aaacttactc cgctcgtgtg   8880
aaggtcttag agattcttaa actaactgac tttatcgaca atcttagaga tgaactctta   8940
ataactccca ataatccagc tatcaccgat tttaataatc ttctgctaag agctaagaag   9000
gatttaagag tattaggagt caacatcgga aaatatccaa tggccaacat taatgccgta   9060
cttactctca ttggtcacaa actttctgta atgagagatg agttcggaaa agagaaaagg   9120
ataaaagtag atggtaaatc ataccgatgt tatcaacttg aaacattacc agattttacc   9180
aatgatactc ttgactactg gttagaaaat gatagccaaa aagaagtaac agcaacagaa   9240
aattactccg aaaattttaa cccttcaaat agctacaatc cagacagtaa gacactttca   9300
gagggtgcaa atttcctata tataaataaa gaagaattgc atccaaataa attgcaccta   9360
```

```
gaaataaaag aaggtgctga actttttttta ttcggggtaa aggtgattgt gaaaggaatc   9420
ttggacgggg cagtaactat attctctatg ggtcaagaat acgatttatc cctcaatgaa   9480
ctagagggga tgttaacatc atgaacttta caagaatctt tttaaagggc gatcgcacca   9540
tgttaaatga tggtacattt gttcagatat ttgatattta ccatgaccac gcattgggag   9600
tgacccttga ccttaagaca gaaaaaatta tttccgatga tgttagggta attactgtca   9660
aagacttatt gttcgatggc acttataaag ggtaaaatc ttttatgccc gataatgccc   9720
gataatgccc gattgatgct acaaaatccc ataatcataa gcgataatcc cctaatagct   9780
tgtaattctt gaaccgtagc gattttagag tattccaaaa agaagaaata aacaccgcaa   9840
aatgtcgtat ttcacatata taaaccaagg ttttttgccc taaaatcttt atgtttgtag   9900
tgtgatgttg ggtcaaaatg gtcagaaaag ttgcaaggtt tttatggatg cttacgcgcg   9960
cgaggggtaa gcatccccaa atagttactt tatcctagtc catgcccatt tattgccgtc  10020
ccgttcggct ttaaaaaagt gccaaaactc acaaggtgca ataaaaagtt ctgtaccttt  10080
cgcaacccta gataatcttt caacagttac ttttttttcct attatctcgg tacaaagttt  10140
ggctagtttc tcttttccct ctttttcaat caagccttct tgtatgccca actcattgat  10200
taatctctct atttttacca ttatttcccg ttcaggtagt ttatccccta aatcttcatc  10260
ggggggcaat gtagggcatt ctgaaggggc tttttcttct gtctggacat tatctaatat  10320
tgaagtaacc aaactatctt cagtttttttc tattcctatt aattcatatt cggttactgt  10380
atccgtatca atatccgaat aactatcttt atccgtatta gctattcggt taagtttatc  10440
cgttaactca gaaacaagac tatatagcgg ttttagcttt tcttctatcc tgttatctaa  10500
tacggataag tttatacggt tatcattatc cgtattagta tcattgggct tttttggtag  10560
ttctaccccc tcataaaccg cttttattcc caattccaac agactgataa cagtatcctt  10620
tataatgggt tttttgctga tatggtgaac ttttgcccct tccatcattg cgatactttc  10680
tatctcactc atcaacttat cgcttaagtg aatctcgtat ctgtttaatc ccttactggt  10740
tttattcata tccgtttact ttattcggtt aacaattcta ttttatacga ataaaatatt  10800
atacggttaa ctttatacgt ttaactattt tatctatacg gataacagta ataagttatt  10860
cgtattagtt atacgtttac ttttatccaa ataaaattag tgcatttaaa ctaaaagaat  10920
gattttatcg gagttgatag cattggatta acctaaagat gtttataagc tatatctgat  10980
aagtatttaa ggttattttg ttattctgtt tattgacatt atcagaataa aagaatagaa  11040
tataattgtt gagagataag aggtttaagt gattatggtt aagaagttag ttggttatgt  11100
cagggtcagt agtgaatcgc aagaggataa cactagctta cagaatcaga tagagagaat  11160
tgaagcatat tgtatggctt ttggttatga gttggtaaaa atattcaaag aggttgccac  11220
tggtacaaaa gcagatattg aaacccgtcc tatttttaat gaagctatag aatacttgaa  11280
acaggataat gctaatggaa ttattgcctt gaagctagac cgaatcgcac ggaatgcttt  11340
agatgtattg cgtttggttc gtgaaacctt agaaccacaa aataaaatgt tagtgttact  11400
agatattcag gtagatactt cgacaccttc aggaaaaatg attttaactg taatgagtgc  11460
cgttgctgaa ctcgaaagag acatgatcta tgatcgcact caggggggta gaaagactaa  11520
agcccaaaag ggcgggtatg cctacgggaa acctaaattt ggctataaga ctgaagaaaa  11580
ggaactaaaa gaagattcag cacaacagga aactattaaa ctaattaaga gacaccgtag  11640
gtcagggaaa agctaccaga aaatagctga ttatctcaat gcccaaagta ttcccactaa  11700
```

```
acaaggtaag aaatggagtt ctagcgtcgt ctatcgaatc tgtcaggaaa aagctggtta  11760

agtctgttta tagatattta gaatttattg aataaaaata gtatgaacaa taaatattta  11820

tggactaacc acgctcggaa acgtttaact gaacgatggg aaataaaaga atcatgggtt  11880

attgatacca tcgaaaatcc tgaacgttca gaatttattg ttgatgagtc aggggaaaaa  11940

tatcattact ataaaagaat agctaagttt aagaatagag tgttagaagt gataacttct  12000

gccaactcaa cacccacaag aataataacc ttttacttta accgtaacat gaggaaaaat  12060

ttatgattgt tacttacgat aatgaagttg acgcaattta ttttaagtta acggaaaata  12120

aaattgatag caccgaacct caaacagaca ggattatcat tgattacgat gaaagtaata  12180

atattgttgg cattgaggta ttagatttta attatcttgt caagaaaggt ttaaccgttg  12240

ctgatttacc tttttctgaa gatgaaagat taacagcttc tcaatatttt aattttcctg  12300

ttgctatcta atccagaagg ggcaataatc cccttctttc atcgagttag acttaatatc  12360

acaaaagtca ttttcatttt accgtttctt ttccacagcg tccgtacgcc cctcgttaaa  12420

tctcaaaacc gacaatttat gatgtttata aaaagttact cactttaata agtatttata  12480

ctcattaaag ggttattctt tttttgtagc ctgataggtt gggaaggaat atttcagatt  12540

atcagatttg ttgaatattt ttcgtcagat acgcaaacct tacaaacata attaacaact  12600

gaaactattg atatgtctag gttttagctc tatcacaggt tggatctg              12648
```

```
<210> SEQ ID NO 35
<211> LENGTH: 12698
<212> TYPE: DNA
<213> ORGANISM: Artificial
<220> FEATURE:
<223> OTHER INFORMATION: Synthetically produced plasmid construct #1749
      pABIcyano1::PnirA-zmPDC(opt3)dsrA-PrpsL*4-synADH_oop

<400> SEQUENCE: 35
```

```
tcgacaatta ataacttctt cctgtacggg cgaatggcca tttgctccta actaactccg     60

tactgctttg cggaacgagc gtagcgaact ctccgaatta ctaagccttc atccctgata    120

gatgcaaaaa acgaattaaa attatgtgta aaaagaaaat gtgtctttat ttagtagtca    180

aagttacaaa atattaagaa tcaaattaat aatgtattgg gcagttaagt atataagtct    240

ttaaatattt atttgtattc aatatattaa ccgaggacaa attatgaatt cttacactgt    300

tggaacctat ttagcagaac gtttagttca aattggtctc aaacaccatt ttgcagtagc    360

tggtgattat aatttagttt tattggataa cttattgtta aataagaata tggaacaagt    420

gtattgttgt aatgaattaa actgtggttt ttctgctgag ggatatgctc gtgcaaaagg    480

tgctgccgca gcagttgtta cttattctgt tggagcatta agtgcttttg acgctattgg    540

aggtgcttat gcagaaaatt tacctgtaat cttaatctct ggtgcaccca ataacaacga    600

tcacgctgct ggtcatgtat tgcatcatgc tttaggtaaa accgattatc attaccaatt    660

agaaatggca aaaaatatta ccgctgccgc agaagctatt tatactcccg aagaagcacc    720

tgctaagatc gatcacgtaa ttaaaaccgc tctccgtgag aaaaaacccg tatatttaga    780

aatcgcttgc aatatcgctt ctatgccttg tgcagctcct ggacctgcta gtgctttatt    840

taacgatgaa gcatctgatg aggctagttt aaatgccgct gttgaagaaa ctttgaaatt    900

tattgctaat cgtgataaag tagctgtttt agttggttct aaactccgtg ccgctggtgc    960

agaagaagcg gctgtaaaat tcgcagatgc cttaggaggt gctgttgcca caatggcagc   1020

cgctaaaagt tttttccccg aagaaaatcc tcattacatt ggtacttctt ggggtgaggt   1080
```

```
atcttaccct ggtgtagaaa aaaccatgaa ggaagctgat gcagtaattg cattagctcc   1140
tgttttcaat gattactcta ccactggttg gactgatatt ccagacccca aaaaattagt   1200
tttagcagaa cctcgctctg tagttgtgaa tggtgttaga tttcccagtg tacatctcaa   1260
agattattta actcgtttag ctcaaaaagt gagtaaaaag actggcgcac tcgatttctt   1320
taaatcttta aatgctggtg aattaaagaa agcagctcct gctgatccca gtgctccttt   1380
agtgaatgcc gaaatcgcaa gacaagttga agccttgtta actcctaaca ctaccgttat   1440
tgccgagact ggtgatagtt ggttcaatgc tcaacgcatg aaattaccca atggtgctcg   1500
tgttgagtat gaaatgcaat ggggtcacat tggatggtct gttcctgctg catttggata   1560
tgcagttgga gcacctgagc gtagaaacat tttaatggta ggtgatggtt ctttccaact   1620
cactgctcaa gaagttgcac aaatggtacg tttaaaattg cctgttatta tctttctcat   1680
taacaactat ggttacacca ttgaagttat gattcatgat ggtccttata ataacattaa   1740
gaattgggat tacgcaggtt taatggaggt atttaacggt aatggtggat acgacagtgg   1800
agcaggtaaa ggattaaaag ctaaaacagg aggtgagtta gctgaagcaa ttaaagtagc   1860
tttagccaat acagatggtc ctaccttaat cgaatgtttc attggacgtg aagattgtac   1920
tgaagagtta gttaaatggg gaaagcgtgt tgccgctgca aattctcgta aacctgtaaa   1980
caaactcttg tagttaggat ccagcaaggt ttcatcccga ccccctcagg gtcgggattt   2040
ttttattgtg agctcagaaa aactattgac aaacccataa aaaatgtgat ataattatag   2100
attgtcactg gtattttata ctagaggcaa attatattta tatatacaaa aatgctgtag   2160
gaggatcagc catatgatta aagcctacgc tgccctggaa gccaacggaa aactccaacc   2220
ctttgaatac gaccccggtg ccctgggtgc taatgaggtg gagattgagg tgcagtattg   2280
tggggtgtgc cacagtgatt tgtccatgat taataacgaa tggggcattt ccaattaccc   2340
cctagtgccg ggtcatgagg tggtgggtac tgtggccgcc atgggcgaag ggggtgaacca   2400
tgttgaggtg ggggatttag tggggctggg ttggcattcg ggctactgca tgacctgcca   2460
tagttgttta tctggctacc acaacctttg tgccacggcg gaatcgacca ttgtgggcca   2520
ctacggtggc tttggcgatc gggttcgggc caagggagtc agcgtggtga aattacctaa   2580
aggcattgac ctagccagtg ccgggcccct tttctgtgga ggaattaccg ttttcagtcc   2640
tatggtggaa ctgagtttaa agcccactgc aaaagtggca gtgatcggca ttgggggctt   2700
gggccattta gcggtgcaat ttctccgggc ctggggctgt gaagtgactg cctttacctc   2760
cagtgccagg aagcaaacgg aagtgttgga attgggcgct caccacatac tagattccac   2820
caatccagag gcgatcgcca gtgcggaagg caaatttgac tatattatct ccactgtgaa   2880
cctgaagctt gactggaact tatacatcag caccctggcg ccccagggac atttccactt   2940
tgttggggtg gtgttggagc ctttggatct aaatcttttt cccctttgga tgggacaacg   3000
ctccgtttct gcctccccag tgggtagtcc cgccaccatt gccaccatgt tggactttgc   3060
tgtgcgccat gacattaaac ccgtggtgga acaatttagc tttgatcaga tcaacgaggc   3120
gatcgcccat ctagaaagcg gcaaagccca ttatcgggta gtgctcagcc atagtaaaaa   3180
ttagctctgc aaaggttgct tctagatctg tggaacgccc ggttgccacc gggcgttttt   3240
tattcctgca ggatcatctt gctgaaaaac tcgagcgctc gttccgcaaa gcggtacgga   3300
gttagttagg ggctaatggg cattctcccg tacaggaaag agttagaagt tattaattat   3360
caacaattct cctttgccta gtgcatcgtt accttttttaa ttaaaacata aggaaaacta   3420
ataatcgtaa taatttaacc tcaaagtgta aagaaatgtg aaattctgac ttttataacg   3480
```

```
ttaaagaggg aaaaattagc agtttaaaat acctagagaa tagtctgggg taagcataga   3540
gaattagatt agttaagtta atcaaattca gaaaaaataa taatcgtaaa tagttaatct   3600
gggtgtatag aaaatgatcc ccttcatgat aagatttaaa ctcgaaaagc aaaagccaaa   3660
aaactaactt ccattaaaag aagttgttac atataacgct ataaagaaaa tttatatatt   3720
tggaggatac caaccatgtc tcatattcaa cgtgaaacta gttgttctcg ccctcgttta   3780
aattctaata tggatgccga tttatatggt tataaatggg ctcgtgataa tgttggtcaa   3840
tctggtgcta ctatttatcg tttatatggt aaacctgatg ctcctgaatt attcttgaaa   3900
catggtaaag gttctgttgc taatgatgtt actgatgaaa tggttcgttt aaactggttg   3960
actgaattta tgcctttacc tactattaaa cattttattc gtactcccga tgatgcttgg   4020
ttattaacta ctgctattcc tggtaaaact gcttttcaag ttttagaaga atatcctgat   4080
tctggtgaaa atattgttga tgctttagct gtttttttac gtcgtttaca ttctattccc   4140
gtttgtaatt gtccttttaa ttctgatcgt gtttttcgtt tagctcaagc tcaatctcgt   4200
atgaataatg gtttagttga tgcttctgat tttgatgatg aacgtaatgg ttggcctgtt   4260
gaacaagttt ggaaagaaat gcacaaattg ttaccttttt ctcctgattc tgttgttact   4320
catggtgatt tttctttaga taatttgatc tttgatgaag gtaaattgat tggttgtatt   4380
gatgttggtc gtgttggtat tgctgatcgt tatcaagatt tagctatttt atggaattgt   4440
ttaggtgaat tttctccttc tttacagaaa cgtttatttc agaaatatgg tattgataat   4500
cctgatatga acaagttaca atttcattta atgttggacg agttctttta agaattaatt   4560
catgaccaaa atcccttaac gtgagttttc gttccactga gcgtcagacc ccgtagaaaa   4620
gatcaaagga tcttcttgag atcctttttt tctgcgcgta atctgctgct atttaaatta   4680
cgtacacgtg ttattacttt gttaacgaca attgtcttaa ttaactgggc ctcatgggcc   4740
ttccgctcac tgcccgcttt ccagtcggga aacctgtcgt gccagctctg cagatgacgg   4800
tgaaaacctc tgacacatgc agctcccgga gacggtcaca gcttgtctgt aagcggatgc   4860
cgggagcaga caagcccgtc agggcgcgtc agcgggtgtt ggcgggtgtc ggggcgcagc   4920
catgacccag tcacgtagcg atagcggagt gtatactggc ttaactatgc ggcatcagag   4980
cagattgtac tgagagtgca ccatatgcgg tgtgaaatac cgcacagatg cgtaaggaga   5040
aaataccgca tcaggcgctc ttccgcttcc tcgctcactg actcgctgcg ctcggtcgtt   5100
cggctgcggc gagcggtatc agctcactca aaggcggtaa tacggttatc cacagaatca   5160
ggggataacg caggaaagaa catgtgagca aaaggccagc aaaaggccag gaaccgtaaa   5220
aaggccgcgt tgctggcgtt tttccatagg ctccgccccc ctgacgagca tcacaaaaat   5280
cgacgctcaa gtcagaggtg gcgaaacccg acaggactat aaagatacca ggcgtttccc   5340
cctggaagct ccctcgtgcg ctctcctgtt ccgaccctgc cgcttaccgg atacctgtcc   5400
gcctttctcc cttcgggaag cgtggcgctt tctcatagct cacgctgtag gtatctcagt   5460
tcggtgtagg tcgttcgctc caagctgggc tgtgtgcacg aaccccccgt tcagcccgac   5520
cgctgcgcct tatccggtaa ctatcgtctt gagtccaacc cggtaagaca cgacttatcg   5580
ccactggcag cagccactgg taacaggatt agcagagcga ggtatgtagg cggtgctaca   5640
gagttcttga agtggtggcc taactacggc tacactagaa ggacagtatt tggtatctgc   5700
gctctgctga agccagttac cttcggaaaa agagttggta gctcttgatc cggcaaacaa   5760
accaccgctg gtagcggtgg tttttttgtt tgcaagcagc agattacgcg cagaaaaaaa   5820
```

```
ggatctcaag aagatccttt gatcttttct actgcagaag cttgttagac accctgtcat   5880
gtattttata ttatttattt caccatacgg attaagtgaa acctaatgaa aatagtactt   5940
tcggagcttt aactttaatg aaggtatgtt tttttataga catcgatgtc tggtttaaca   6000
ataggaaaaa gtagctaaaa ctcccatgaa ttaaagaaat aacaaggtgt ctaacaacct   6060
gttattaaga atgttagaaa agacttaaca tttgtgttga gtttttatag acattggtgt   6120
ctagacatac ggtagataag gtttgctcaa aaataaaata aaaaaagatt ggactaaaaa   6180
acatttaatt tagtacaatt taattagtta ttttttcgtc tcaaattttg ctttgttgag   6240
cagaaattta gataaaaaaa tccccgtgat cagattacaa tgtcgttcat tgtacgatgt   6300
gtcgaaaaat ctttacgaca ctctaaactg accacacggg ggaaaaagaa aactgaacta   6360
ataacatcat gatactcgga aaacctagca attctcaacc cctaaacaaa agaaacttcc   6420
aaaaccctga ccatataaag gagtggcaac aatcagcaat cagtcaagat ttgatagcag   6480
aaaatcttgt atcggttgct aatggttttg atgtactatt tatcggcaat aaataccgaa   6540
ctaacacggg tgttctgtca cggcacatat taaactccta ttctcattta gaagatggtg   6600
gttcgtatgg tagaacattt gacccattta ccaataaaga aatgcagtgg gttcaattta   6660
aaccgaatag accaagaaaa ggttctactg gtaaggtaat caaatatgaa tcgccaaaag   6720
gtgaacctac aagagttcta atgccgtttg tgcctatgaa aatatggcaa cggattagcg   6780
ataagttcgg agtaccgatt aatccgaaaa aagatactca cttttgggaa tgggtaaaga   6840
ataatccatc gataccgatt gccattacag aaggaaataa aaaagctaat tgcctattat   6900
cctatggcta tcctgctatt gcctttgtag gcatttggaa cggattagag aaaataaatg   6960
atttctcgaa ggaaaagcag ttaaaagagg atttgaaatg gttgttatcc aacggcaacc   7020
gaaatattaa tatcatcttt gaccaagacc agaaacaaaa aactgtaatt aatgtaaaca   7080
aagctatttt cgctttatct tctctaataa gtagaaatgg tcataaagtt aatattgtgc   7140
aatggttgcc gtcaaaaggt aaaggaatag atgattattt ggtagcttta ccttttgaga   7200
aaagagaaaa tcatttagac aacttaatta aaattgcacc atcatttaat ttttggtcaa   7260
ctaaatactt attcaagtgt cgtaaaccag atttaaccgt aaattgccgt tatttgagcg   7320
atgcagtaaa agaattacct caagaggata tagcattaat agcacctcac ggcacgggta   7380
aaacttcatt agtagctact cacgttaaga atcggagtta tcacggaagg aaaactattt   7440
cattggtgca tcttgaaagt ttagccaaag ctaatggcaa cgcacttgga ttatattacc   7500
gaaccgaaaa taatattgaa aagcaatatc ttggatttag cttatgtgta gatagttgcc   7560
gtgataagat taacggcatt acaactgata ttatttcagg tcaagattat tgccttttca   7620
ttgatgaaat tgaccaagta attccacaca tccttaacag tgaaactgaa gtaagtaagt   7680
atagatgcac catcattgac actttttctg aactggtgag aaatgctgaa caggtcatta   7740
ttgctgatgc tgatttatcc gatgtgacga ttgacctaat agaaaacatc agaggtaaaa   7800
aactatatgt aatcaagaat gaatatcagt atcagggaat gacttttaac gccgttggtt   7860
caccattaga aatgatggca atgatgggaa aatcggtgtc agaaggcaag aaattattta   7920
ttaacaccac atcccaaaag gcaaaaagta agtacggcac aatcgctctt gagtcttata   7980
tttttggtct aaataaagaa gcaaagatat taagaataga ctctgaaacc actaaaaacc   8040
ctgaacatcc agcctataaa atcattgacc aagacttaaa taatatcctc aaagattatg   8100
attatgtcat tgcctcacct tgccttcaaa caggtgtcag tattacctta aaagggcatt   8160
ttgaccagca atttaacttt tccagtggaa acattacacc tcattgcttt ttacagcaaa   8220
```

```
tgtggcggtt gagggatgca gaaattgaaa gattctatta tgtgccgaac tcatctaacc   8280
tcaatctcat tgggaataag tcaagttcac catcagacct tctaaagagc aataacaaga   8340
tggcaacggc aacggttaac cttttgggta gaatcgactc cgaatattcc ctagagtatg   8400
aatcgcacgg catttggctt gagacgtggg caaaattatc agcacggcat aacagttcaa   8460
tgcgttgtta ctctgaaatt cttacctatc taattacgtc tcaagggcat aaattaaata   8520
tcaacattcc ctcacctctt gcagatatta agaagctaaa tgatgaggta agtagtaaca   8580
gggaaaaggt aaaaaatgag agatactctc agaggttaaa ctcaccagat attaacgatg   8640
cagaagctac catactcgaa tctaaagagc aaaaaatcgg attgactctc aatgagagat   8700
gcaccctaga aaagcataaa gttaagaagc ggtatgggaa tgtaaagatg gatattctca   8760
cctttgatga tgatggacta taccccaaac tcagactatt ttattacctc accatcggta   8820
aacctcatct caaggctaat gacagaaaag ctattgccaa aatgggcaat gacaataaag   8880
gcaagattct atcaaaagac ttagttaata aaacttactc cgctcgtgtg aaggtcttag   8940
agattcttaa actaactgac tttatcgaca atcttagaga tgaactctta ataactccca   9000
ataatccagc tatcaccgat tttaataatc ttctgctaag agctaagaag gatttaagag   9060
tattaggagt caacatcgga aaatatccaa tggccaacat taatgccgta cttactctca   9120
ttggtcacaa actttctgta atgagagatg agttcggaaa agagaaaagg ataaaagtag   9180
atggtaaatc ataccgatgt tatcaacttg aaacattacc agattttacc aatgatactc   9240
ttgactactg gttagaaaat gatagccaaa aagaagtaac agcaacagaa aattactccg   9300
aaaattttaa cccttcaaat agctacaatc cagacagtaa gacactttca gagggtgcaa   9360
atttcctata tataaataaa gaagaattgc atccaaataa attgcaccta gaaataaaag   9420
aaggtgctga actttttta ttcggggtaa aggtgattgt gaaaggaatc ttggacgggg   9480
cagtaactat attctctatg ggtcaagaat acgatttatc cctcaatgaa ctagagggga   9540
tgttaacatc atgaacttta caagaatctt tttaaagggc gatcgcacca tgttaaatga   9600
tggtacattt gttcagatat ttgatattta ccatgaccac gcattgggag tgacccttga   9660
ccttaagaca gaaaaaatta tttccgatga tgttagggta attactgtca aagacttatt   9720
gttcgatggc acttataaag gggtaaaatc ttttatgccc gataatgccc gataatgccc   9780
gattgatgct acaaaatccc ataatcataa gcgataatcc cctaatagct tgtaattctt   9840
gaaccgtagc gattttagag tattccaaaa agaagaaata aacaccgcaa aatgtcgtat   9900
ttcacatata taaaccaagg ttttttgccc taaaatcttt atgtttgtag tgtgatgttg   9960
ggtcaaaatg gtcagaaaag ttgcaaggtt tttatggatg cttacgcgcg cgaggggtaa  10020
gcatccccaa atagttactt tatcctagtc catgcccatt tattgccgtc ccgttcggct  10080
ttaaaaaagt gccaaaactc acaaggtgca ataaaaagtt ctgtaccttt cgcaacccta  10140
gataatcttt caacagttac ttttttcct attatctcgg tacaaagttt ggctagtttc  10200
tcttttccct ctttttcaat caagccttct tgtatgccca actcattgat taatctctct  10260
atttttacca ttatttcccg ttcaggtagt ttatccccta aatcttcatc ggggggcaat  10320
gtagggcatt ctgaaggggc tttttcttct gtctggacat tatctaatat tgaagtaacc  10380
aaactatctt cagttttttc tattcctatt aattcatatt cggttactgt atccgtatca  10440
atatccgaat aactatcttt atccgtatta gctattcggt taagtttatc cgttaactca  10500
gaaacaagac tatatagcgg ttttagcttt tcttctatcc tgttatctaa tacggataag  10560
```

```
tttatacggt tatcattatc cgtattagta tcattgggct tttttggtag ttctaccccc  10620
tcataaaccg cttttattcc caattccaac agactgataa cagtatcctt tataatgggt  10680
tttttgctga tatggtgaac ttttgcccct tccatcattg cgatactttc tatctcactc  10740
atcaacttat cgcttaagtg aatctcgtat ctgtttaatc ccttactggt tttattcata  10800
tccgtttact ttattcggtt aacaattcta ttttatacga ataaaatatt atacggttaa  10860
ctttatacgt ttaactattt tatctatacg gataacagta ataagttatt cgtattagtt  10920
atacgtttac ttttatccaa ataaaattag tgcatttaaa ctaaaagaat gattttatcg  10980
gagttgatag cattggatta acctaaagat gtttataagc tatatctgat aagtatttaa  11040
ggttattttg ttattctgtt tattgacatt atcagaataa aagaatagaa tataattgtt  11100
gagagataag aggtttaagt gattatggtt aagaagttag ttggttatgt cagggtcagt  11160
agtgaatcgc aagaggataa cactagctta cagaatcaga tagagagaat tgaagcatat  11220
tgtatggctt ttggttatga gttggtaaaa atattcaaag aggttgccac tggtacaaaa  11280
gcagatattg aaacccgtcc tatttttaat gaagctatag aatacttgaa acaggataat  11340
gctaatggaa ttattgcctt gaagctagac cgaatcgcac ggaatgcttt agatgtattg  11400
cgtttggttc gtgaaacctt agaaccacaa aataaaatgt tagtgttact agatattcag  11460
gtagatactt cgacaccttc aggaaaaatg attttaactg taatgagtgc cgttgctgaa  11520
ctcgaaagag acatgatcta tgatcgcact caggggggta gaaagactaa agcccaaaag  11580
ggcgggtatg cctacgggaa acctaaattt ggctataaga ctgaagaaaa ggaactaaaa  11640
gaagattcag cacaacagga aactattaaa ctaattaaga gacaccgtag gtcagggaaa  11700
agctaccaga aaatagctga ttatctcaat gcccaaagta ttcccactaa acaaggtaag  11760
aaatggagtt ctagcgtcgt ctatcgaatc tgtcaggaaa aagctggtta agtctgttta  11820
tagatattta gaatttattg aataaaaata gtatgaacaa taaatattta tggactaacc  11880
acgctcggaa acgtttaact gaacgatggg aaataaaaga atcatgggtt attgatacca  11940
tcgaaaatcc tgaacgttca gaatttattg ttgatgagtc aggggaaaaa tatcattact  12000
ataaaagaat agctaagttt aagaatagag tgttagaagt gataacttct gccaactcaa  12060
cacccacaag aataataacc ttttacttta accgtaacat gaggaaaaat ttatgattgt  12120
tacttacgat aatgaagttg acgcaattta ttttaagtta acggaaaata aaattgatag  12180
caccgaacct caaacagaca ggattatcat tgattacgat gaaagtaata atattgttgg  12240
cattgaggta ttagatttta attatcttgt caagaaaggt ttaaccgttg ctgatttacc  12300
tttttctgaa gatgaaagat taacagcttc tcaatatttt aattttcctg ttgctatcta  12360
atccagaagg ggcaataatc cccttctttc atcgagttag acttaatatc acaaaagtca  12420
ttttcatttt accgtttctt ttccacagcg tccgtacgcc cctcgttaaa tctcaaaacc  12480
gacaatttat gatgtttata aaaagttact cactttaata agtatttata ctcattaaag  12540
ggttattctt tttttgtagc ctgataggtt gggaaggaat atttcagatt atcagatttg  12600
ttgaatattt ttcgtcagat acgcaaacct tacaaacata attaacaact gaaactattg  12660
atatgtctag gttttagctc tatcacaggt tggatctg                         12698
```

<210> SEQ ID NO 36
<211> LENGTH: 327
<212> TYPE: DNA
<213> ORGANISM: Cyanobacterium sp.

<400> SEQUENCE: 36

```
tgagaaaaag tgtaaacaaa tattaagaaa aagatcagaa aaatttaaca acacgtaata     60

aaaaaatgcg tcactacggg ttataaattt acatgaaagg ttaaaacact tttctgagac    120

gattttgata aaaaagttgt caaaaaatta agtttcttta caaatgctta acaaaaactt    180

ggttttaagc acaaaataag agagactaat ttgcagaagt tttacaagga aatcttgaag    240

aaaaagatct aagtaaaacg actctgttta accaaaattt aacaaattta acaaaacaaa    300

ctaaatctat taggagatta actaagc                                        327
```

<210> SEQ ID NO 37
<211> LENGTH: 405
<212> TYPE: DNA
<213> ORGANISM: Cyanobacterium sp.

<400> SEQUENCE: 37

```
atctgtcgac gagaagggga acagggaaaa gtatttataa ttgatacaaa ctgtggttca     60

acttatttta aagacatttt tctccattta atgattattt cggggaaaat tttgaggatt    120

tttgattctt aaattgacga tattttgtca ctaacacaac gtgagcggta aatttatata    180

tagacctaaa acctttacta taagtgttat atatttaaat cgctaagtat atagttaaag    240

tgtagccaat aattaacttt taacaagtga ttaccgttaa gtcccttaat ttatcactac    300

aagctaaaac aaatttttca attagatatg acattaggtc aaagttcata gtatgatagt    360

aaaaaataaa atttgacgat ctgtaaaaat aaaaaaacac aatga                    405
```

<210> SEQ ID NO 38
<211> LENGTH: 568
<212> TYPE: DNA
<213> ORGANISM: Synechocystis PCC 6803

<400> SEQUENCE: 38

```
gtcgacctcc ttaatccgat tcctgcaaat ggtctgcaac ttcccgatac aaattcatca     60

catgattatc cgccaagctg tagtaaacat tacggccgac ccggcgatac tttaccaggc    120

gctgcgatcg taaaattcgt aattgatggg aaactgccga ttcactcact ttcatcgccg    180

ctgctaaatc acagacacag agttcttggc gggccaatgc cgacattaaa cgcaaccgac    240

tcggatcagc tagtgcactg aaaaactccg ccatttgctg ggcctggtcc aatgacatca    300

cctctggttg aacctgtcgt acctgctcaa gatgaacaag aggttgatca caaaggggca    360

tctcttcgtt ctggcaggat tgtgactttg acaacgagga cttactcata gaggttggcg    420

ttaggagcta gggaaaaatt taaactggat ttagaaaatg attttcatcc taacatcttt    480

aatatctgag catatcttca ggtgtttcaa gatttgtgct acggttcaag gaggtttttc    540

tttaaatcac gttggccgcc atgaattc                                       568
```

<210> SEQ ID NO 39
<211> LENGTH: 503
<212> TYPE: DNA
<213> ORGANISM: Synechococcus PCC 7002

<400> SEQUENCE: 39

```
gtcgacgggc aaactttatg aagcagatca agcctatatc cgccaagcaa ccggcagccg     60

cgttgattag tgggtgtgtc catcctctgg ttcgtctagg tgctccgaag cgtcacgata    120

gagattaaga atgtggtgat ccttgaggcg ataaatcaca ttccgccctt ccttgcgata    180

gctcactaaa cgtgctgtgc gcagggttct tagttggtga gagacagccg attcactcat    240
```

```
ttcaacggcg gcggcgagtt cccccacccg catctctcca gtggccaggg ccgaaagaat    300

acgccagcgg ttggcatccc ccaagacacc aaaaaattcg gccatccgtt gggccttggc    360

ttggttcaag attttgccac tgtggtctgt cattgttcgc tgatctaaac aatacctgaa    420

taattgttca tgtgttaatc taaaaatgtg aacaatcgtt caactattta agacaatacc    480

ttggaggttt aaaccatgaa ttc                                            503
```

```
<210> SEQ ID NO 40
<211> LENGTH: 649
<212> TYPE: DNA
<213> ORGANISM: Anabaena PCC 7120

<400> SEQUENCE: 40

gtcgactaaa tcgtaatacc taaatcagcc aacaaaattt agcacaattg cacaggggag     60

aagttcagat taatacattt atactattaa tttgcgatca ccctgtgcca gttgcgtaag    120

tattgttttc cactaaagag cgatataagt taatgacgtg actgtcagcc aaactataat    180

aaacattccg accttctcga cgatagctga ctaaacgcat agctttcaat aaccgcagct    240

gatgacaaac agctgattca ctcattttgg ttaatgcagc tagatcgcaa acacacaact    300

cactagaagc caaagctgat aggaggcgta tacggtttgt atctgctaac accccaaaaa    360

tttctgccat ttgttgtgct ttatctgtcg gtaagatttg agcctgagat gagcgtacat    420

tatctagatg caccagatga gtatcacagg taggggtatc agaactttga attaagtcta    480

agtcctgctt tttcttgtgc ttattcatag caagttttac ttagcaatag ttatcaatct    540

caataatacc taaaatgata accattgtac aattgaatag ttgttcaatt gttgtattag    600

aatattggca gttaactttt tgccttaatt ctaaagctgc tatgaattc                649
```

```
<210> SEQ ID NO 41
<211> LENGTH: 1256
<212> TYPE: DNA
<213> ORGANISM: Synechocystis PCC 6803

<400> SEQUENCE: 41

gtcgaccatg cgtccaaaac tttcaccatc ctttccctat caacctttac tgcactaaag     60

acaagtgaga tagcagtggc aatctggctt tgcaatcaat gtttccacta aagcgtttag    120

cgttactgcg gctagaagtc ctccaccgag gctcccctga atggtgatat ggggaatggg    180

actggtcatc agtcgtcgtt ttgcccccgg agcatgacta aaaccgatcg gcattccgat    240

cacaagagcc ggctgaatat gttgttgctc tatcagctta caggcagtga gtaaaacaga    300

aggggcatag ccgatcgcca gcacacatcc ttggggaatc tgttgtaacc gctgttgcca    360

atggtcatgg tgccaaaaag cttgctcggc ttccctaagc cctgtgatgt gagggtcgtc    420

aatcagcgtt ttaaccgtac atcctaaatg agctaaccga gtttgatcaa gagccgcagc    480

cacaaccgga acatcggtga cgactggaca ccctgctttc agtgcatctc gtgccgaggc    540

gatcgctccc tgactcaatc gaacggcgtt taccaagcta acatcaccac aggccagcac    600

taattgatgt agtaagtgaa tggtaatttc agagtaagcc gataaatccg gtagcaggtg    660

tttgagggat tcctgaaagg cttctggatg agttgttgtc tccgcatcta ggttcgtcca    720

caactgatcg agttttccta acccctcctg gacatccaca tcaagctgtt tcagttgggc    780

cagagcttcc gcttgggtaa tctggcaact ctggtcgcgt cccagtaatc cttctaaagc    840

agatgcggtt tggcggagtc gagtaatctg ctgaatcaca gcctgatatt gctgttgcaa    900

ctgcaccatt agggtgggat caaggctctc ttcagaatgg ctatccagca gttgccgaat    960
```

```
atgagacaac tgaaagccct gctgtttgag ggcaatgact cgttggagcc gttgtacgtc   1020

ctgctgagta taaaggcggt agttgccctc tgagcgttga acggggggaa gcaatcccag   1080

ggtgtggtaa tggcgcacca tgcgaggcgt aacgccacct cccactgcat ctgtgagttc   1140

tttaatcgtt aagtgattag tcttcatccc tttagtttac tcaaaacctt gacattgaca   1200

ctaatgttaa ggtttaggct gagaaggtaa aatccaagt taaaaagcat gaattc        1256
```

<210> SEQ ID NO 42
<211> LENGTH: 2280
<212> TYPE: DNA
<213> ORGANISM: Synechocystis PCC 6803

<400> SEQUENCE: 42

```
gtcgacccta tatcgggctt ttctcaataa aatctttatt ttttgaggtg ctttttagcc     60

ataaataatc actttagtat aaaattttga cggcgtaaag ttgataaaat agaattaaga    120

atggactatc ggtacagaaa aaatgggtaa ctggatggtg aataaacttc ccttacccaa    180

tgcactctcc accgttaaag acccccctatg cttaacggtg atcacctggg caatggcgag   240

tcccaaccct gtcccccccg ttttgcgcga acgatctcga ttaactcggt aaaaacgctc    300

aaaaatgtgt tcctgttggt cgggggcaat gccgatgccg gtatcttgca cggtgatgat    360

agccatctgt tcatgggatg tcagggtaat atcaacacgt cccccagcag ttgtgtattg    420

aatggcgttg gcaattaggt ttgagaccag tcgatagagt tgggattcat taccccaggc    480

gtaaacttcc cctgaactca gatcactgct gagatcaatg tgggcggcga tcgctaattc    540

taaaaactct tcggtgaggt cactgactaa atcatttaaa caacaaagcc gccaatcttc    600

ggcggtggtt tcctgctcta agcgacttag tagcaataaa tccgtaatca attggcttaa    660

tcgccttccc tgtcgttcaa cggtatgtag catggtgtta atttctgggg aatggcttga    720

gtcgatgcgt aataccgctt ccaccgtggc caacagacta gccaatggcg atcgtaattc    780

atgggctgca ttcgcggtga attgttgttg ttgttggtag gactggtaaa tgggacgcat    840

ggctaacccc gctaagcccc aactggagaa ggcgaccaaa cccagggcaa tgggaaaact    900

aagccctaaa atccaaagaa tacgtttatt ttcggcatca aaggctgcca ggctccggcc    960

aatttgtaga tagccccagg aagatttgtc tgtattaccg gcgctatgca aaatggtggt   1020

gaattgtcga taccgatcgc cggttggggg gtgaatagtc tgccaagttt cctggttaaa   1080

aatggaggat agggaagccg gttgattagg cgaaaaagcc agcaggttgc cttgataatc   1140

aaataaacga atgtaatata aactgcgatc actaatgccc aacgtgtgac gttcaatcag   1200

ggtggggttg acctggcagg gttggttgac caaacacaga tcgggcaaca ttttttgtaa   1260

tactccggtg ggactagcat tactcggcaa catcggctct aaactgtcat gcaacgtccc   1320

ggcgatcgac tccacttctc gctccaacgc catccagttg gcctgcacaa tggcacgata   1380

aacccccaac cccaacaggg taagaatacc ccccattact agggcatacc agaaagccaa   1440

ttgcagacga ctacgggcaa agaggcgacg ggtattcatg gcgatagggt gaaccgatag   1500

ccttgaccgg gaactgtttt aattgggcaa ggacaatttt gttgagctag cttgcgtcgt   1560

atcaaacgca tttgggccgc caccacatta ctcatgggct cctcatcaag atcccacagt   1620

tgttgccgga tcttgctacc ggaaatgatc cgctctgggt tttgcatcag atattgaaaa   1680

atttgaaatt ctcttacggt taaagcaatt tcctgtcttt ctaggtttag tggctccgag   1740

atagttaccg ataacagatt attactggga tcaaggctga agttgcccaa agttaaaatt   1800
```

tgcggttgga attgtggcga tcgccgttgt agtgcccgca gtcttgctaa tagctctgcc 1860
atcacaaacg gttttgttag atagtcatct gccccggcat ctagtccttc gacacggttt 1920
tccggttctc ctaacgctgt taacatcaac accggcaagg aattaccctg ggttctcagt 1980
ttttgacaga gttccaaacc cgataatccc ggcagtaacc aatccacaat ggcaagggtg 2040
tattccgtcc attgattttc caaataatcc caagcttggg agccatccgt cacccaatcc 2100
accacatact tttcactaac tagcactttc ttaatagcca ttcccaaatc cgtctcatct 2160
tccaccagca aaattcgcat cgcctctgcc ttttttataa cggtctgatc ttagcggggg 2220
aaggagattt tcacctgaat ttcatacccc ctttggcaga ctgggaaaat cttggacaaa 2280

<210> SEQ ID NO 43
<211> LENGTH: 411
<212> TYPE: DNA
<213> ORGANISM: Cyanobacterium sp.

<400> SEQUENCE: 43
tatttatata taaactcgaa taaaattatc aatataaagt caaactatat ctatcctatt 60
ttaactgcta ttggtaagtc ccttaattag tgttggggtg aatagatttt aaaagggcaa 120
accccccttt atcctccctc gagagggggg agggcaaaag gcaaggggca agggaaaaat 180
taagaattaa gaattaaaaa ctccgaacac ctgtaggggc gaatagccat tcgcttcccc 240
tcatcccccc atctccccaa caccctaagc ccctactcgt tactcattta tttacatcat 300
ttatttacat cattaagaaa agtaacaaat tttgacaagt agtcttttga caggaaaaag 360
caaattctcg aagatgaaaa caatagaaaa aaattcaatc ttacagtaac g 411

<210> SEQ ID NO 44
<211> LENGTH: 12762
<212> TYPE: DNA
<213> ORGANISM: Artificial
<220> FEATURE:
<223> OTHER INFORMATION: Synthetically produced plasmid construct #1606
pABIcyano1-PnirA-zmPDC(opt1)_dsrA-Prbc*(optRBS)-synADH(opt1)_ter

<400> SEQUENCE: 44
tcgacaatta ataacttctt cctgtacggg cgaatggcca tttgctccta actaactccg 60
tactgctttg cggaacgagc gtagcgaact ctccgaatta ctaagccttc atccctgata 120
gatgcaaaaa acgaattaaa attatgtgta aaaagaaaat gtgtctttat ttagtagtca 180
aagttacaaa atattaagaa tcaaattaat aatgtattgg gcagttaagt atataagtct 240
ttaaatattt atttgtattc aatatattaa ccgaggacaa attatgaatt cttataccgt 300
gggtacttat ttagccgaac gcttagtgca aattggttta aaacatcatt ttgccgtggc 360
tggggactat aatttagtgt tattggataa cttattatta aataaaaaca tggaacaagt 420
gtattgttgt aatgaattaa attgtggttt ttctgctgaa ggttatgcta gagctaaagg 480
tgcagctgct gctgttgtta cttattctgt gggtgcttta tctgcttttg atgctattgg 540
tggtgcttat gccgaaaatt tacccgtgat tttaatttct ggtgccccta ataataatga 600
tcatgccgct ggacatgttt tacatcatgc cttaggtaaa accgattatc attatcaatt 660
agaaatggcc aaaaatatta ctgctgctgc cgaagctatt tatactcctg aagaagcccc 720
tgccaaaatt gatcatgtga ttaaaaccgc cttacgcgaa aaaaaacccg tgtatttaga 780
aattgcctgt aatattgctt ctatgccttg tgctgctcct gggcctgctt ctgctttatt 840
taatgatgaa gcctctgatg aagctagttt aaatgctgcc gtggaagaaa ccttaaaatt 900

```
tattgccaat cgcgataaag ttgccgtgtt agttggttct aaattaagag ctgctggtgc    960
tgaagaagct gctgttaaat ttgctgatgc tttaggtggt gcagttgcta ctatggctgc   1020
tgccaaatct ttttttcccg aagaaaatcc ccattatatt ggaactagtt ggggagaagt   1080
ttcttatcct ggtgtggaaa aaactatgaa agaagccgac gctgttattg ctttagcccc   1140
tgtgtttaat gattattcta ccactggttg gactgatatt cccgatccca aaaaattagt   1200
tttagccgaa cctcgttctg ttgttgttaa tggtgttcgc tttccctctg tgcatttaaa   1260
agattattta acccgcttag cccaaaaagt ttctaaaaaa actggtgcct tagatttttt   1320
taaatcttta aatgcgggtg aattaaaaaa agctgctcct gctgatcctt ctgctccttt   1380
agttaatgct gaaattgccc gtcaagttga agccttatta acccctaata ctaccgttat   1440
tgccgaaact ggtgattctt ggtttaatgc ccaacgcatg aaattaccta atggtgcccg   1500
tgttgaatat gaaatgcaat ggggtcatat tggttggtct gtacctgctg cttttggtta   1560
tgctgttggt gctcctgaac gtcgtaatat tttaatggtg ggtgatggtt cttttcaatt   1620
aactgcccaa gaagttgccc aaatggttcg cttaaaatta cccgttatta ttttttttaat   1680
aaataattat ggttatacca ttgaagtgat gattcatgat gggccatata ataatattaa   1740
aaattgggat tatgcgggtt taatggaagt gtttaatggt aatggtggtt atgattctgg   1800
tgctggtaaa ggtttaaaag ccaaaactgg tggtgaatta gctgaagcta ttaaagttgc   1860
cttagccaat actgatgggc caaccttaat tgaatgtttt attggtcgcg aagattgtac   1920
cgaagaatta gttaaatggg gtaaacgtgt tgctgctgct aattctcgca aacccgtgaa   1980
taaattattg taatttttgg ggatcaattc gagctcagca agtttcatcc cgaccccctc   2040
agggtcggga ttttttttatt gtactagttg acataagtaa aggcatcccc tgcgtgatat   2100
aattaccttc agtttaagga ggtatacaca tatgattaaa gcctatgctg ccttagaagc   2160
caatggtaaa ttacaaccct ttgaatatga tcctggtgct ttaggtgcca atgaagtgga   2220
aattgaagtg caatattgtg gtgtgtgtca ttctgattta tctatgatta ataatgaatg   2280
gggtatttct aattatccct tagttcctgg tcatgaagtt gttggtactg ttgctgctat   2340
gggtgaaggt gttaatcatg tggaagtggg tgatttagtt ggtttaggtt ggcattctgg   2400
ttattgtatg acctgtcatt cttgtttatc tggttatcat aatttatgtg ccactgccga   2460
atctactatt gtgggtcatt atggtggttt tggtgataga gttcgtgcta aaggtgtttc   2520
tgtggtgaaa ttacccaaag gtattgattt agcctctgct gggcctttat tttgtggtgg   2580
tattaccgtt ttttctccca tggtggaatt atctttaaaa cctaccgcca aagttgctgt   2640
tattggtatt ggtggtttag gtcatttagc cgttcaattt ttaagagcct ggggttgtga   2700
agttactgct tttacctctt ctgcccgtaa acaaaccgaa gttttagaat taggtgccca   2760
tcatatttta gattctacca atcctgaagc tattgcttct gccgaaggta aatttgatta   2820
tattatttct accgtgaatt taaaattaga ttggaattta tatatcagta ccttagcccc   2880
tcaaggtcat tttcattttg ttggtgtggt gttagaaccc ttggacttaa acttatttcc   2940
cttattaatg ggacaacgtt ctgtttctgc ttctcctgtt ggttctcctg ctactattgc   3000
cactatgtta gattttgccg tgcgtcatga tattaaaccc gtggtggaac aattttcttt   3060
tgatcaaatt aatgaagcca ttgcccattt agaatctggt aaagcccatt atcgcgtggt   3120
gttatctcat tctaaaaatt aataagatta acttctaaac tgaaacaaat ttgagggtag   3180
gcttcattgt ctgcccttat tttttttattt aggaaaagtg aacagactaa agagtgttgg   3240
ctctattgct ttgagtatgt aaattaggcg ttgctgaatt aaggtatgat tttgacccc   3300
```

```
ttctctcttc tgcaggatca tcttgctgaa aaactcgagc gctcgttccg caaagcggta   3360
cggagttagt taggggctaa tgggcattct cccgtacagg aaagagttag aagttattaa   3420
ttatcaacaa ttctcctttg cctagtgcat cgttaccttt ttaattaaaa cataaggaaa   3480
actaataatc gtaataattt aacctcaaag tgtaaagaaa tgtgaaattc tgacttttat   3540
aacgttaaag agggaaaaat tagcagttta aaatacctag agaatagtct ggggtaagca   3600
tagagaatta gattagttaa gttaatcaaa ttcagaaaaa ataataatcg taaatagtta   3660
atctgggtgt atagaaaatg atccccttca tgataagatt taaactcgaa aagcaaaagc   3720
caaaaaacta acttccatta aaagaagttg ttacatataa cgctataaag aaaatttata   3780
tatttggagg ataccaacca tgtctcatat tcaacgtgaa actagttgtt ctcgccctcg   3840
tttaaattct aatatggatg ccgatttata tggttataaa tgggctcgtg ataatgttgg   3900
tcaatctggt gctactattt atcgtttata tggtaaacct gatgctcctg aattattctt   3960
gaaacatggt aaaggttctg ttgctaatga tgttactgat gaaatggttc gtttaaactg   4020
gttgactgaa tttatgcctt tacctactat taaacatttt attcgtactc ccgatgatgc   4080
ttggttatta actactgcta ttcctggtaa aactgctttt caagttttag aagaatatcc   4140
tgattctggt gaaaatattg ttgatgcttt agctgttttt ttacgtcgtt tacattctat   4200
tcccgtttgt aattgtcctt ttaattctga tcgtgttttt cgtttagctc aagctcaatc   4260
tcgtatgaat aatggtttag ttgatgcttc tgattttgat gatgaacgta atggttggcc   4320
tgttgaacaa gtttggaaag aaatgcacaa attgttacct ttttctcctg attctgttgt   4380
tactcatggt gatttttctt tagataattt gatctttgat gaaggtaaat tgattggttg   4440
tattgatgtt ggtcgtgttg gtattgctga tcgttatcaa gatttagcta ttttatggaa   4500
ttgtttaggt gaattttctc cttctttaca gaaacgttta tttcagaaat atggtattga   4560
taatcctgat atgaacaagt tacaatttca tttaatgttg gacgagttct tttaagaatt   4620
aattcatgac caaaatccct taacgtgagt tttcgttcca ctgagcgtca gaccccgtag   4680
aaaagatcaa aggatcttct tgagatcctt tttttctgcg cgtaatctgc tgctatttaa   4740
attacgtaca cgtgttatta ctttgttaac gacaattgtc ttaattaact gggcctcatg   4800
ggccttccgc tcactgcccg ctttccagtc gggaaacctg tcgtgccagc tctgcagatg   4860
acggtgaaaa cctctgacac atgcagctcc cggagacggt cacagcttgt ctgtaagcgg   4920
atgccgggag cagacaagcc cgtcagggcg cgtcagcggg tgttggcggg tgtcggggcg   4980
cagccatgac ccagtcacgt agcgatagcg gagtgtatac tggcttaact atgcggcatc   5040
agagcagatt gtactgagag tgcaccatat gcggtgtgaa ataccgcaca gatgcgtaag   5100
gagaaaatac cgcatcaggc gctcttccgc ttcctcgctc actgactcgc tgcgctcggt   5160
cgttcggctg cggcgagcgg tatcagctca ctcaaaggcg gtaatacggt tatccacaga   5220
atcaggggat aacgcaggaa agaacatgtg agcaaaaggc cagcaaaagg ccaggaaccg   5280
taaaaaggcc gcgttgctgg cgtttttcca taggctccgc ccccctgacg agcatcacaa   5340
aaatcgacgc tcaagtcaga ggtggcgaaa cccgacagga ctataaagat accaggcgtt   5400
tccccctgga agctccctcg tgcgctctcc tgttccgacc ctgccgctta ccggatacct   5460
gtccgccttt ctcccttcgg gaagcgtggc gctttctcat agctcacgct gtaggtatct   5520
cagttcggtg taggtcgttc gctccaagct gggctgtgtg cacgaacccc ccgttcagcc   5580
cgaccgctgc gccttatccg gtaactatcg tcttgagtcc aacccggtaa gacacgactt   5640
```

-continued

```
atcgccactg gcagcagcca ctggtaacag gattagcaga gcgaggtatg taggcggtgc   5700
tacagagttc ttgaagtggt ggcctaacta cggctacact agaaggacag tatttggtat   5760
ctgcgctctg ctgaagccag ttaccttcgg aaaaagagtt ggtagctctt gatccggcaa   5820
acaaaccacc gctggtagcg gtggtttttt tgtttgcaag cagcagatta cgcgcagaaa   5880
aaaaggatct caagaagatc ctttgatctt ttctactgca gaagcttgtt agacaccctg   5940
tcatgtattt tatattattt atttcaccat acggattaag tgaaacctaa tgaaaatagt   6000
actttcggag ctttaacttt aatgaaggta tgttttttta tagacatcga tgtctggttt   6060
aacaatagga aaaagtagct aaaactccca tgaattaaag aaataacaag gtgtctaaca   6120
acctgttatt aagaatgtta gaaaagactt aacatttgtg ttgagttttt atagacattg   6180
gtgtctagac atacggtaga taaggtttgc tcaaaaataa aataaaaaaa gattggacta   6240
aaaaacattt aatttagtac aatttaatta gttatttttt cgtctcaaat tttgctttgt   6300
tgagcagaaa tttagataaa aaaatccccg tgatcagatt acaatgtcgt tcattgtacg   6360
atgtgtcgaa aaatctttac gacactctaa actgaccaca cgggggaaaa agaaaactga   6420
actaataaca tcatgatact cggaaaacct agcaattctc aacccctaaa caaaagaaac   6480
ttccaaaacc ctgaccatat aaaggagtgg caacaatcag caatcagtca agatttgata   6540
gcagaaaatc ttgtatcggt tgctaatggt tttgatgtac tatttatcgg caataaatac   6600
cgaactaaca cgggtgttct gtcacggcac atattaaact cctattctca tttagaagat   6660
ggtggttcgt atggtagaac atttgaccca tttaccaata aagaaatgca gtgggttcaa   6720
tttaaaccga atagaccaag aaaaggttct actggtaagg taatcaaata tgaatcgcca   6780
aaaggtgaac ctacaagagt tctaatgccg tttgtgccta tgaaaatatg gcaacggatt   6840
agcgataagt tcggagtacc gattaatccg aaaaaagata ctcacttttg ggaatgggta   6900
aagaataatc catcgatacc gattgccatt acagaaggaa ataaaaaagc taattgccta   6960
ttatcctatg gctatcctgc tattgccttt gtaggcattt ggaacggatt agagaaaata   7020
aatgatttct cgaaggaaaa gcagttaaaa gaggatttga aatggttgtt atccaacggc   7080
aaccgaaata ttaatatcat ctttgaccaa gaccagaaac aaaaaactgt aattaatgta   7140
aacaaagcta ttttcgcttt atcttctcta ataagtagaa atggtcataa agttaatatt   7200
gtgcaatggt tgccgtcaaa aggtaaagga atagatgatt atttggtagc tttacctttt   7260
gagaaaagag aaaatcattt agacaactta attaaaattg caccatcatt taatttttgg   7320
tcaactaaat acttattcaa gtgtcgtaaa ccagatttaa ccgtaaattg ccgttatttg   7380
agcgatgcag taaaagaatt acctcaagag gatatagcat taatagcacc tcacggcacg   7440
ggtaaaactt cattagtagc tactcacgtt aagaatcgga gttatcacgg aaggaaaact   7500
atttcattgg tgcatcttga aagtttagcc aaagctaatg gcaacgcact tggattatat   7560
taccgaaccg aaaataatat tgaaaagcaa tatcttggat ttagcttatg tgtagatagt   7620
tgccgtgata agattaacgg cattacaact gatattattt caggtcaaga ttattgcctt   7680
ttcattgatg aaattgacca agtaattcca cacatcctta acagtgaaac tgaagtaagt   7740
aagtatagat gcaccatcat tgacactttt tctgaactgg tgagaaatgc tgaacaggtc   7800
attattgctg atgctgattt atccgatgtg acgattgacc taatagaaaa catcagaggt   7860
aaaaaactat atgtaatcaa gaatgaatat cagtatcagg gaatgacttt taacgccgtt   7920
ggttcaccat tagaaatgat ggcaatgatg ggaaaatcgg tgtcagaagg caagaaatta   7980
tttattaaca ccacatccca aaaggcaaaa agtaagtacg gcacaatcgc tcttgagtct   8040
```

```
tatatttttg gtctaaataa agaagcaaag atattaagaa tagactctga aaccactaaa   8100
aaccctgaac atccagccta taaaatcatt gaccaagact taaataatat cctcaaagat   8160
tatgattatg tcattgcctc accttgcctt caaacaggtg tcagtattac cttaaaaggg   8220
cattttgacc agcaatttaa cttttccagt ggaaacatta cacctcattg ctttttacag   8280
caaatgtggc ggttgaggga tgcagaaatt gaaagattct attatgtgcc gaactcatct   8340
aacctcaatc tcattgggaa taagtcaagt tcaccatcag accttctaaa gagcaataac   8400
aagatggcaa cggcaacggt taacctttttg ggtagaatcg actccgaata ttccctagag   8460
tatgaatcgc acggcatttg gcttgagacg tgggcaaaat tatcagcacg gcataacagt   8520
tcaatgcgtt gttactctga aattcttacc tatctaatta cgtctcaagg gcataaatta   8580
aatatcaaca ttccctcacc tcttgcagat attaagaagc taaatgatga ggtaagtagt   8640
aacagggaaa aggtaaaaaa tgagagatac tctcagaggt taaactcacc agatattaac   8700
gatgcagaag ctaccatact cgaatctaaa gagcaaaaaa tcggattgac tctcaatgag   8760
agatgcaccc tagaaaagca taaagttaag aagcggtatg ggaatgtaaa gatggatatt   8820
ctcacctttg atgatgatgg actatacccc aaactcagac tattttatta cctcaccatc   8880
ggtaaacctc atctcaaggc taatgacaga aaagctattg ccaaaatggg caatgacaat   8940
aaaggcaaga ttctatcaaa agacttagtt aataaaactt actccgctcg tgtgaaggtc   9000
ttagagattc ttaaactaac tgactttatc gacaatctta gagatgaact cttaataact   9060
cccaataatc cagctatcac cgattttaat aatcttctgc taagagctaa gaaggattta   9120
agagtattag gagtcaacat cggaaaatat ccaatggcca acattaatgc cgtacttact   9180
ctcattggtc acaaactttc tgtaatgaga gatgagttcg gaaaagagaa aaggataaaa   9240
gtagatggta aatcataccg atgttatcaa cttgaaacat taccagattt taccaatgat   9300
actcttgact actggttaga aaatgatagc caaaaaagaag taacagcaac agaaaattac   9360
tccgaaaatt ttaacccttc aaatagctac aatccagaca gtaagacact ttcagagggt   9420
gcaaatttcc tatatataaa taaagaagaa ttgcatccaa ataaattgca cctagaaata   9480
aaagaaggtg ctgaactttt tttattcggg gtaaaggtga ttgtgaaagg aatcttggac   9540
ggggcagtaa ctatattctc tatgggtcaa gaatacgatt tatccctcaa tgaactagag   9600
gggatgttaa catcatgaac tttacaagaa tctttttaaa gggcgatcgc accatgttaa   9660
atgatggtac atttgttcag atatttgata tttaccatga ccacgcattg ggagtgaccc   9720
ttgaccttaa gacagaaaaa attatttccg atgatgttag ggtaattact gtcaaagact   9780
tattgttcga tggcacttat aaaggggtaa aatcttttat gcccgataat gcccgataat   9840
gcccgattga tgctacaaaa tcccataatc ataagcgata atcccctaat agcttgtaat   9900
tcttgaaccg tagcgatttt agagtattcc aaaaagaaga aataaacacc gcaaaatgtc   9960
gtatttcaca tatataaacc aaggtttttt gccctaaaat ctttatgttt gtagtgtgat  10020
gttgggtcaa aatggtcaga aaagttgcaa ggtttttatg gatgcttacg cgcgcgaggg  10080
gtaagcatcc ccaaatagtt actttatcct agtccatgcc catttattgc cgtcccgttc  10140
ggctttaaaa aagtgccaaa actcacaagg tgcaataaaa agttctgtac ctttcgcaac  10200
cctagataat ctttcaacag ttactttttt tcctattatc tcggtacaaa gtttggctag  10260
tttctctttt ccctcttttt caatcaagcc ttcttgtatg cccaactcat tgattaatct  10320
ctctattttt accattattt cccgttcagg tagtttatcc cctaaatctt catcgggggg  10380
```

```
caatgtaggg cattctgaag gggctttttc ttctgtctgg acattatcta atattgaagt  10440
aaccaaacta tcttcagttt tttctattcc tattaattca tattcggtta ctgtatccgt  10500
atcaatatcc gaataactat ctttatccgt attagctatt cggttaagtt tatccgttaa  10560
ctcagaaaca agactatata gcggttttag cttttcttct atcctgttat ctaatacgga  10620
taagtttata cggttatcat tatccgtatt agtatcattg ggcttttttg gtagttctac  10680
cccctcataa accgctttta ttcccaattc caacagactg ataacagtat cctttataat  10740
gggtttttttg ctgatatggt gaacttttgc cccttccatc attgcgatac tttctatctc  10800
actcatcaac ttatcgctta agtgaatctc gtatctgttt aatcccttac tggttttatt  10860
catatccgtt tactttattc ggttaacaat tctattttat acgaataaaa tattatacgg  10920
ttaactttat acgtttaact attttatcta tacggataac agtaataagt tattcgtatt  10980
agttatacgt ttacttttat ccaaataaaa ttagtgcatt taaactaaaa gaatgatttt  11040
atcggagttg atagcattgg attaacctaa agatgtttat aagctatatc tgataagtat  11100
ttaaggttat tttgttattc tgtttattga cattatcaga ataaaagaat agaatataat  11160
tgttgagaga taagaggttt aagtgattat ggttaagaag ttagttggtt atgtcagggt  11220
cagtagtgaa tcgcaagagg ataacactag cttacagaat cagatagaga gaattgaagc  11280
atattgtatg gcttttggtt atgagttggt aaaaaatattc aaagaggttg ccactggtac  11340
aaaagcagat attgaaaccc gtcctatttt taatgaagct atagaatact tgaaacagga  11400
taatgctaat ggaattattg ccttgaagct agaccgaatc gcacggaatg ctttagatgt  11460
attgcgtttg gttcgtgaaa ccttagaacc acaaaataaa atgttagtgt tactagatat  11520
tcaggtagat acttcgacac cttcaggaaa aatgatttta actgtaatga gtgccgttgc  11580
tgaactcgaa agagacatga tctatgatcg cactcagggg ggtagaaaga ctaaagccca  11640
aaagggcggg tatgcctacg ggaaacctaa atttggctat aagactgaag aaaaggaact  11700
aaaagaagat tcagcacaac aggaaactat taaactaatt aagagacacc gtaggtcagg  11760
gaaaagctac cagaaaatag ctgattatct caatgcccaa agtattccca ctaaacaagg  11820
taagaaatgg agttctagcg tcgtctatcg aatctgtcag gaaaaagctg gttaagtctg  11880
tttatagata tttagaattt attgaataaa aatagtatga acaataaata tttatggact  11940
aaccacgctc ggaaacgttt aactgaacga tgggaaataa aagaatcatg ggttattgat  12000
accatcgaaa atcctgaacg ttcagaattt attgttgatg agtcagggga aaaatatcat  12060
tactataaaa gaatagctaa gtttaagaat agagtgttag aagtgataac ttctgccaac  12120
tcaacaccca caagaataat aaccttttac tttaaccgta acatgaggaa aaatttatga  12180
ttgttactta cgataatgaa gttgacgcaa tttattttaa gttaacggaa aataaaattg  12240
atagcaccga acctcaaaca gacaggatta tcattgatta cgatgaaagt aataatattg  12300
ttggcattga ggtattagat tttaattatc ttgtcaagaa aggtttaacc gttgctgatt  12360
taccttttc tgaagatgaa agattaacag cttctcaata ttttaatttt cctgttgcta  12420
tctaatccag aaggggcaat aatccccttc tttcatcgag ttagacttaa tatcacaaaa  12480
gtcattttca ttttaccgtt tcttttccac agcgtccgta cgcccctcgt taaatctcaa  12540
aaccgacaat ttatgatgtt tataaaaagt tactcacttt aataagtatt tatactcatt  12600
aaagggttat tctttttttg tagcctgata ggttgggaag gaatatttca gattatcaga  12660
tttgttgaat atttttcgtc agatacgcaa accttacaaa cataattaac aactgaaact  12720
attgatatgt ctaggtttta gctctatcac aggttggatc tg                    12762
```

<210> SEQ ID NO 45
<211> LENGTH: 12668
<212> TYPE: DNA
<213> ORGANISM: Artificial
<220> FEATURE:
<223> OTHER INFORMATION: Synthetically produced plasmid construct #1645
pABIcyano1-PnirA-zmPDC(opt1)_dsrA-Prbc*(optRBS)-ADH916(opt)_ter

<400> SEQUENCE: 45

```
tcgacaatta ataacttctt cctgtacggg cgaatggcca tttgctccta actaactccg     60

tactgctttg cggaacgagc gtagcgaact ctccgaatta ctaagccttc atccctgata    120

gatgcaaaaa acgaattaaa attatgtgta aaaagaaaat gtgtctttat ttagtagtca    180

aagttacaaa atattaagaa tcaaattaat aatgtattgg gcagttaagt atataagtct    240

ttaaatattt atttgtattc aatatattaa ccgaggacaa attatgaatt cttataccgt    300

gggtacttat ttagccgaac gcttagtgca aattggttta aaacatcatt ttgccgtggc    360

tggggactat aatttagtgt tattggataa cttattatta aataaaaaca tggaacaagt    420

gtattgttgt aatgaattaa attgtggttt ttctgctgaa ggttatgcta gagctaaagg    480

tgcagctgct gctgttgtta cttattctgt gggtgcttta tctgcttttg atgctattgg    540

tggtgcttat gccgaaaatt tacccgtgat tttaatttct ggtgccccta ataataatga    600

tcatgccgct ggacatgttt tacatcatgc cttaggtaaa accgattatc attatcaatt    660

agaaatggcc aaaaatatta ctgctgctgc cgaagctatt tatactcctg aagaagcccc    720

tgccaaaatt gatcatgtga ttaaaaccgc cttacgcgaa aaaaaacccg tgtatttaga    780

aattgcctgt aatattgctt ctatgccttg tgctgctcct gggcctgctt ctgctttatt    840

taatgatgaa gcctctgatg aagctagttt aaatgctgcc gtggaagaaa ccttaaaatt    900

tattgccaat cgcgataaag ttgccgtgtt agttggttct aaattaagag ctgctggtgc    960

tgaagaagct gctgttaaat ttgctgatgc tttaggtggt gcagttgcta ctatggctgc   1020

tgccaaatct ttttttcccg aagaaaatcc ccattatatt ggaactagtt ggggagaagt   1080

ttcttatcct ggtgtggaaa aaactatgaa agaagccgac gctgttattg ctttagcccc   1140

tgtgtttaat gattattcta ccactggttg gactgatatt cccgatccca aaaaattagt   1200

tttagccgaa cctcgttctg ttgttgttaa tggtgttcgc tttccctctg tgcatttaaa   1260

agattattta acccgcttag cccaaaaagt ttctaaaaaa actggtgcct tagatttttt   1320

taaatcttta aatgcgggtg aattaaaaaa agctgctcct gctgatcctt ctgctccttt   1380

agttaatgct gaaattgccc gtcaagttga agccttatta acccctaata ctaccgttat   1440

tgccgaaact ggtgattctt ggtttaatgc ccaacgcatg aaattaccta atggtgcccg   1500

tgttgaatat gaaatgcaat ggggtcatat tggttggtct gtacctgctg cttttggtta   1560

tgctgttggt gctcctgaac gtcgtaatat tttaatggtg ggtgatggtt cttttcaatt   1620

aactgcccaa gaagttgccc aaatggttcg cttaaaatta cccgttatta ttttttaat    1680

aaataattat ggttatacca ttgaagtgat gattcatgat gggccatata ataatattaa   1740

aaattgggat tatgcgggtt taatggaagt gtttaatggt aatggtggtt atgattctgg   1800

tgctggtaaa ggtttaaaag ccaaaactgg tggtgaatta gctgaagcta ttaaagttgc   1860

cttagccaat actgatgggc caaccttaat tgaatgtttt attggtcgcg aagattgtac   1920

cgaagaatta gttaaatggg gtaaacgtgt tgctgctgct aattctcgca aacccgtgaa   1980

taaattattg taatttttgg ggatcaattc gagctcagca agtttcatcc cgacccccctc   2040
```

```
agggtcggga ttttttttatt gtactagttg acataagtaa aggcatcccc tgcgtgatat   2100
aattaccttc agtttaagga ggtatacaca tatgcctatg atcaaagcct tcgcagttca   2160
tgagtctgat ggagatttac agccttttga atatgatcct ggtgcattat tatctgatca   2220
agttgagatc gaagttaaat attgtggaat ttgtcattct gatttatcta tgatctctaa   2280
tgaatggggt atgacccaat accctttagt acctggacat gaggtagtag gtgcaatcgc   2340
caaagtaggt gaaaatgtta aaaatttatc tgttggtcaa attgtaggat taggttggca   2400
cgcaggttat tgtaacgaat gtcctcaatg tactactggt gatcaaaatt tatgtgctac   2460
tgctcaagga actattgtag gacatcatgg aggtttcgct gaaaaagttc gcgctgctgc   2520
aaattctgta gttcccatcc ctgaaggaat cgatttagaa gctgctggac ctttattttg   2580
tggaggtatc accgttttta atcctttagt acaatatgga atccaaccca ctgcaaaagt   2640
tgctgtaatt ggaattggag gtttaggtca catggctgtt caattcttaa acgcttgggg   2700
ttgtgaagtt accgctttta ccagttctga agcaaaaatc actgaggctt tagaattagg   2760
tgctcatcac actttaaaca gtcgtgaccc tgaagccatc gcagccgctg ctggacagtt   2820
tgatttaatc atttctaccg ttaacgttaa attagattgg aatgcctatt taagtacttt   2880
aaaacctcac ggtcgtttac acttcgtagg tgctacttta gatcccttag acattaacgt   2940
ttttgcttta atcatgcagc aacgttctat ctctggtagt cctgttggat ctcctgcaac   3000
catcgcaaaa atgttagaat ttgcaaaatt acataaaatt caacctaaaa ttgaaacctt   3060
taaatttgaa gatgttaacc aggctattgc acgtttaaaa agtggtgaag cccactatcg   3120
tattgtatta tgtagataac tagatctcct gcagagaata taaaaagcca gattattaat   3180
ccggcttttt tattatttaa atactgtgca cgatcctgca ggatcatctt gctgaaaaac   3240
tcgagcgctc gttccgcaaa gcggtacgga gttagttagg ggctaatggg cattctcccg   3300
tacaggaaag agttagaagt tattaattat caacaattct cctttgccta gtgcatcgtt   3360
acctttttaa ttaaaacata aggaaaacta ataatcgtaa taatttaacc tcaaagtgta   3420
aagaaatgtg aaattctgac ttttataacg ttaaagaggg aaaaattagc agtttaaaat   3480
acctagagaa tagtctgggg taagcataga gaattagatt agttaagtta atcaaattca   3540
gaaaaaataa taatcgtaaa tagttaatct gggtgtatag aaaatgatcc ccttcatgat   3600
aagatttaaa ctcgaaaagc aaaagccaaa aaactaactt ccattaaaag aagttgttac   3660
atataacgct ataaagaaaa tttatatatt tggaggatac caaccatgtc tcatattcaa   3720
cgtgaaacta gttgttctcg ccctcgttta aattctaata tggatgccga tttatatggt   3780
tataaatggg ctcgtgataa tgttggtcaa tctggtgcta ctatttatcg tttatatggt   3840
aaacctgatg ctcctgaatt attcttgaaa catggtaaag gttctgttgc taatgatgtt   3900
actgatgaaa tggttcgttt aaactggttg actgaattta tgcctttacc tactattaaa   3960
cattttattc gtactcccga tgatgcttgg ttattaacta ctgctattcc tggtaaaact   4020
gcttttcaag ttttagaaga atatcctgat tctggtgaaa atattgttga tgctttagct   4080
gtttttttac gtcgtttaca ttctattccc gtttgtaatt gtccttttaa ttctgatcgt   4140
gtttttcgtt tagctcaagc tcaatctcgt atgaataatg gtttagttga tgcttctgat   4200
tttgatgatg aacgtaatgg ttggcctgtt gaacaagttt ggaaagaaat gcacaaattg   4260
ttaccttttt ctcctgattc tgttgttact catggtgatt tttctttaga taatttgatc   4320
tttgatgaag gtaaattgat tggttgtatt gatgttggtc gtgttggtat tgctgatcgt   4380
```

```
tatcaagatt tagctatttt atggaattgt ttaggtgaat tttctccttc tttacagaaa   4440
cgtttatttc agaaatatgg tattgataat cctgatatga acaagttaca atttcattta   4500
atgttggacg agttctttta agaattaatt catgaccaaa atcccttaac gtgagttttc   4560
gttccactga gcgtcagacc ccgtagaaaa gatcaaagga tcttcttgag atcctttttt   4620
tctgcgcgta atctgctgct atttaaatta cgtacacgtg ttattacttt gttaacgaca   4680
attgtcttaa ttaactgggc ctcatgggcc ttccgctcac tgcccgcttt ccagtcggga   4740
aacctgtcgt gccagctctg cagatgacgg tgaaaacctc tgacacatgc agctcccgga   4800
gacggtcaca gcttgtctgt aagcggatgc cgggagcaga caagcccgtc agggcgcgtc   4860
agcgggtgtt ggcgggtgtc ggggcgcagc catgacccag tcacgtagcg atagcggagt   4920
gtatactggc ttaactatgc ggcatcagag cagattgtac tgagagtgca ccatatgcgg   4980
tgtgaaatac cgcacagatg cgtaaggaga aaataccgca tcaggcgctc ttccgcttcc   5040
tcgctcactg actcgctgcg ctcggtcgtt cggctgcggc gagcggtatc agctcactca   5100
aaggcggtaa tacggttatc cacagaatca ggggataacg caggaaagaa catgtgagca   5160
aaaggccagc aaaaggccag gaaccgtaaa aaggccgcgt tgctggcgtt tttccatagg   5220
ctccgccccc ctgacgagca tcacaaaaat cgacgctcaa gtcagaggtg gcgaaacccg   5280
acaggactat aaagatacca ggcgtttccc cctggaagct ccctcgtgcg ctctcctgtt   5340
ccgaccctgc cgcttaccgg atacctgtcc gcctttctcc cttcgggaag cgtggcgctt   5400
tctcatagct cacgctgtag gtatctcagt tcggtgtagg tcgttcgctc caagctgggc   5460
tgtgtgcacg aaccccccgt tcagcccgac cgctgcgcct tatccggtaa ctatcgtctt   5520
gagtccaacc cggtaagaca cgacttatcg ccactggcag cagccactgg taacaggatt   5580
agcagagcga ggtatgtagg cggtgctaca gagttcttga agtggtggcc taactacggc   5640
tacactagaa ggacagtatt tggtatctgc gctctgctga agccagttac cttcggaaaa   5700
agagttggta gctcttgatc cggcaaacaa accaccgctg gtagcggtgg tttttttgtt   5760
tgcaagcagc agattacgcg cagaaaaaaa ggatctcaag aagatccttt gatcttttct   5820
actgcagaag cttgttagac accctgtcat gtattttata ttatttattt caccatacgg   5880
attaagtgaa acctaatgaa aatagtactt tcggagcttt aactttaatg aaggtatgtt   5940
tttttataga catcgatgtc tggtttaaca ataggaaaaa gtagctaaaa ctcccatgaa   6000
ttaaagaaat aacaaggtgt ctaacaacct gttattaaga atgttagaaa agacttaaca   6060
tttgtgttga gtttttatag acattggtgt ctagacatac ggtagataag gtttgctcaa   6120
aaataaaata aaaaaagatt ggactaaaaa acatttaatt tagtacaatt taattagtta   6180
ttttttcgtc tcaaattttg ctttgttgag cagaaattta gataaaaaaa tccccgtgat   6240
cagattacaa tgtcgttcat tgtacgatgt gtcgaaaaat ctttacgaca ctctaaactg   6300
accacacggg ggaaaaagaa aactgaacta ataacatcat gatactcgga aaacctagca   6360
attctcaacc cctaaacaaa agaaacttcc aaaaccctga ccatataaag gagtggcaac   6420
aatcagcaat cagtcaagat ttgatagcag aaaatcttgt atcggttgct aatggttttg   6480
atgtactatt tatcggcaat aaataccgaa ctaacacggg tgttctgtca cggcacatat   6540
taaactccta ttctcattta gaagatggtg gttcgtatgg tagaacattt gacccattta   6600
ccaataaaga aatgcagtgg gttcaattta aaccgaatag accaagaaaa ggttctactg   6660
gtaaggtaat caaatatgaa tcgccaaaag gtgaacctac aagagttcta atgccgtttg   6720
tgcctatgaa aatatggcaa cggattagcg ataagttcgg agtaccgatt aatccgaaaa   6780
```

```
aagatactca cttttgggaa tgggtaaaga ataatccatc gataccgatt gccattacag   6840
aaggaaataa aaaagctaat tgcctattat cctatggcta tcctgctatt gcctttgtag   6900
gcatttggaa cggattagag aaaataaatg atttctcgaa ggaaaagcag ttaaaagagg   6960
atttgaaatg gttgttatcc aacggcaacc gaaatattaa tatcatcttt gaccaagacc   7020
agaaacaaaa aactgtaatt aatgtaaaca aagctatttt cgctttatct tctctaataa   7080
gtagaaatgg tcataaagtt aatattgtgc aatggttgcc gtcaaaaggt aaaggaatag   7140
atgattattt ggtagcttta ccttttgaga aaagagaaaa tcatttagac aacttaatta   7200
aaattgcacc atcatttaat ttttggtcaa ctaaatactt attcaagtgt cgtaaaccag   7260
atttaaccgt aaattgccgt tatttgagcg atgcagtaaa agaattacct caagaggata   7320
tagcattaat agcacctcac ggcacgggta aaacttcatt agtagctact cacgttaaga   7380
atcggagtta tcacggaagg aaaactattt cattggtgca tcttgaaagt ttagccaaag   7440
ctaatggcaa cgcacttgga ttatattacc gaaccgaaaa taatattgaa aagcaatatc   7500
ttggatttag cttatgtgta gatagttgcc gtgataagat taacggcatt acaactgata   7560
ttatttcagg tcaagattat tgccttttca ttgatgaaat tgaccaagta attccacaca   7620
tccttaacag tgaaactgaa gtaagtaagt atagatgcac catcattgac actttttctg   7680
aactggtgag aaatgctgaa caggtcatta ttgctgatgc tgatttatcc gatgtgacga   7740
ttgacctaat agaaaacatc agaggtaaaa aactatatgt aatcaagaat gaatatcagt   7800
atcagggaat gacttttaac gccgttggtt caccattaga aatgatggca atgatgggaa   7860
aatcggtgtc agaaggcaag aaattattta ttaacaccac atcccaaaag gcaaaaagta   7920
agtacggcac aatcgctctt gagtcttata tttttggtct aaataaagaa gcaaagatat   7980
taagaataga ctctgaaacc actaaaaacc ctgaacatcc agcctataaa atcattgacc   8040
aagacttaaa taatatcctc aaagattatg attatgtcat tgcctcacct tgccttcaaa   8100
caggtgtcag tattacctta aaagggcatt ttgaccagca atttaacttt tccagtggaa   8160
acattacacc tcattgcttt ttacagcaaa tgtggcggtt gagggatgca gaaattgaaa   8220
gattctatta tgtgccgaac tcatctaacc tcaatctcat tgggaataag tcaagttcac   8280
catcagacct tctaaagagc aataacaaga tggcaacggc aacggttaac cttttgggta   8340
gaatcgactc cgaatattcc ctagagtatg aatcgcacgg catttggctt gagacgtggg   8400
caaaattatc agcacggcat aacagttcaa tgcgttgtta ctctgaaatt cttacctatc   8460
taattacgtc tcaagggcat aaattaaata tcaacattcc ctcacctctt gcagatatta   8520
agaagctaaa tgatgaggta agtagtaaca gggaaaaggt aaaaaatgag agatactctc   8580
agaggttaaa ctcaccagat attaacgatg cagaagctac catactcgaa tctaaagagc   8640
aaaaaatcgg attgactctc aatgagagat gcaccctaga aaagcataaa gttaagaagc   8700
ggtatgggaa tgtaaagatg gatattctca cctttgatga tgatggacta taccccaaac   8760
tcagactatt ttattacctc accatcggta aacctcatct caaggctaat gacagaaaag   8820
ctattgccaa aatgggcaat gacaataaag gcaagattct atcaaaagac ttagttaata   8880
aaacttactc cgctcgtgtg aaggtcttag agattcttaa actaactgac tttatcgaca   8940
atcttagaga tgaactctta ataactccca ataatccagc tatcaccgat tttaataatc   9000
ttctgctaag agctaagaag gatttaagag tattaggagt caacatcgga aaatatccaa   9060
tggccaacat taatgccgta cttactctca ttggtcacaa actttctgta atgagagatg   9120
```

agttcggaaa agagaaaagg ataaaagtag atggtaaatc ataccgatgt tatcaacttg 9180
aaacattacc agattttacc aatgatactc ttgactactg gttagaaaat gatagccaaa 9240
aagaagtaac agcaacagaa aattactccg aaaattttaa cccttcaaat agctacaatc 9300
cagacagtaa gacactttca gagggtgcaa atttcctata tataaataaa gaagaattgc 9360
atccaaataa attgcaccta gaaataaaag aaggtgctga actttttta ttcggggtaa 9420
aggtgattgt gaaaggaatc ttggacgggg cagtaactat attctctatg ggtcaagaat 9480
acgatttatc cctcaatgaa ctagagggga tgttaacatc atgaacttta caagaatctt 9540
tttaaagggc gatcgcacca tgttaaatga tggtacattt gttcagatat ttgatattta 9600
ccatgaccac gcattgggag tgacccttga ccttaagaca gaaaaaatta tttccgatga 9660
tgttagggta attactgtca aagacttatt gttcgatggc acttataaag ggtaaaatc 9720
ttttatgccc gataatgccc gataatgccc gattgatgct acaaaatccc ataatcataa 9780
gcgataatcc cctaatagct tgtaattctt gaaccgtagc gattttagag tattccaaaa 9840
agaagaaata aacaccgcaa aatgtcgtat ttcacatata taaaccaagg ttttttgccc 9900
taaaatcttt atgtttgtag tgtgatgttg ggtcaaaatg gtcagaaaag ttgcaaggtt 9960
tttatggatg cttacgcgcg cgaggggtaa gcatccccaa atagttactt tatcctagtc 10020
catgcccatt tattgccgtc ccgttcggct ttaaaaaagt gccaaaactc acaaggtgca 10080
ataaaaagtt ctgtaccttt cgcaacccta gataatcttt caacagttac ttttttcct 10140
attatctcgg tacaaagttt ggctagtttc tcttttccct ctttttcaat caagccttct 10200
tgtatgccca actcattgat taatctctct atttttacca ttatttcccg ttcaggtagt 10260
ttatccccta aatcttcatc ggggggcaat gtagggcatt ctgaaggggc tttttcttct 10320
gtctggacat tatctaatat tgaagtaacc aaactatctt cagtttttc tattcctatt 10380
aattcatatt cggttactgt atccgtatca atatccgaat aactatcttt atccgtatta 10440
gctattcggt taagtttatc cgttaactca gaaacaagac tatatagcgg ttttagcttt 10500
tcttctatcc tgttatctaa tacggataag tttatacggt tatcattatc cgtattagta 10560
tcattgggct tttttggtag ttctaccccc tcataaaccg cttttattcc caattccaac 10620
agactgataa cagtatcctt tataatgggt tttttgctga tatggtgaac ttttgcccct 10680
tccatcattg cgatactttc tatctcactc atcaacttat cgcttaagtg aatctcgtat 10740
ctgtttaatc ccttactggt tttattcata tccgtttact ttattcggtt aacaattcta 10800
ttttatacga ataaaatatt atacggttaa ctttatacgt ttaactattt tatctatacg 10860
gataacagta ataagttatt cgtattagtt atacgtttac ttttatccaa ataaaattag 10920
tgcatttaaa ctaaaagaat gattttatcg gagttgatag cattggatta acctaaagat 10980
gtttataagc tatatctgat aagtatttaa ggttattttg ttattctgtt tattgacatt 11040
atcagaataa aagaatagaa tataattgtt gagagataag aggtttaagt gattatggtt 11100
aagaagttag ttggttatgt cagggtcagt agtgaatcgc aagaggataa cactagctta 11160
cagaatcaga tagagagaat tgaagcatat tgtatggctt ttggttatga gttggtaaaa 11220
atattcaaag aggttgccac tggtacaaaa gcagatattg aaacccgtcc tatttttaat 11280
gaagctatag aatacttgaa acaggataat gctaatggaa ttattgcctt gaagctagac 11340
cgaatcgcac ggaatgcttt agatgtattg cgtttggttc gtgaaacctt agaaccacaa 11400
aataaaatgt tagtgttact agatattcag gtagatactt cgacaccttc aggaaaaatg 11460
attttaactg taatgagtgc cgttgctgaa ctcgaaagag acatgatcta tgatcgcact 11520

```
caggggggta gaaagactaa agcccaaaag ggcgggtatg cctacgggaa acctaaattt  11580

ggctataaga ctgaagaaaa ggaactaaaa gaagattcag cacaacagga aactattaaa  11640

ctaattaaga gacaccgtag gtcagggaaa agctaccaga aaatagctga ttatctcaat  11700

gcccaaagta ttcccactaa acaaggtaag aaatggagtt ctagcgtcgt ctatcgaatc  11760

tgtcaggaaa aagctggtta agtctgttta tagatattta gaatttattg aataaaaata  11820

gtatgaacaa taaatattta tggactaacc acgctcggaa acgtttaact gaacgatggg  11880

aaataaaaga atcatgggtt attgatacca tcgaaaatcc tgaacgttca gaatttattg  11940

ttgatgagtc aggggaaaaa tatcattact ataaaagaat agctaagttt aagaatagag  12000

tgttagaagt gataacttct gccaactcaa cacccacaag aataataacc ttttacttta  12060

accgtaacat gaggaaaaat ttatgattgt tacttacgat aatgaagttg acgcaattta  12120

ttttaagtta acggaaaata aaattgatag caccgaacct caaacagaca ggattatcat  12180

tgattacgat gaaagtaata atattgttgg cattgaggta ttagatttta attatcttgt  12240

caagaaaggt ttaaccgttg ctgatttacc tttttctgaa gatgaaagat taacagcttc  12300

tcaatatttt aattttcctg ttgctatcta atccagaagg ggcaataatc cccttctttc  12360

atcgagttag acttaatatc acaaaagtca ttttcatttt accgtttctt ttccacagcg  12420

tccgtacgcc cctcgttaaa tctcaaaacc gacaatttat gatgtttata aaaagttact  12480

cactttaata agtatttata ctcattaaag ggttattctt tttttgtagc ctgataggtt  12540

gggaaggaat atttcagatt atcagatttg ttgaatattt ttcgtcagat acgcaaacct  12600

tacaaacata attaacaact gaaactattg atatgtctag gttttagctc tatcacaggt  12660

tggatctg                                                           12668
```

<210> SEQ ID NO 46
<211> LENGTH: 12678
<212> TYPE: DNA
<213> ORGANISM: Artificial
<220> FEATURE:
<223> OTHER INFORMATION: Synthetically produced plasmid construct #1753 pABIcyano1-PnirA-zmPDC(opt1)_dsrA-Prbc*(optRBS)-Adh111_ter standard

<400> SEQUENCE: 46

```
tcgacaatta ataacttctt cctgtacggg cgaatggcca tttgctccta actaactccg     60

tactgctttg cggaacgagc gtagcgaact ctccgaatta ctaagccttc atccctgata    120

gatgcaaaaa acgaattaaa attatgtgta aaaagaaaat gtgtctttat ttagtagtca    180

aagttacaaa atattaagaa tcaaattaat aatgtattgg gcagttaagt atataagtct    240

ttaaatattt atttgtattc aatatattaa ccgaggacaa attatgaatt cttataccgt    300

gggtacttat ttagccgaac gcttagtgca aattggttta aaacatcatt ttgccgtggc    360

tggggactat aatttagtgt tattggataa cttattatta aataaaaaca tggaacaagt    420

gtattgttgt aatgaattaa attgtggttt ttctgctgaa ggttatgcta gagctaaagg    480

tgcagctgct gctgttgtta cttattctgt gggtgcttta tctgcttttg atgctattgg    540

tggtgcttat gccgaaaatt tacccgtgat tttaatttct ggtgccccta ataataatga    600

tcatgccgct ggacatgttt tacatcatgc cttaggtaaa accgattatc attatcaatt    660

agaaatggcc aaaaatatta ctgctgctgc cgaagctatt tatactcctg aagaagcccc    720

tgccaaaatt gatcatgtga ttaaaaccgc cttacgcgaa aaaaaacccg tgtatttaga    780
```

-continued

```
aattgcctgt aatattgctt ctatgccttg tgctgctcct gggcctgctt ctgctttatt    840
taatgatgaa gcctctgatg aagctagttt aaatgctgcc gtggaagaaa ccttaaaatt    900
tattgccaat cgcgataaag ttgccgtgtt agttggttct aaattaagag ctgctggtgc    960
tgaagaagct gctgttaaat ttgctgatgc tttaggtggt gcagttgcta ctatggctgc   1020
tgccaaatct ttttttcccg aagaaaatcc ccattatatt ggaactagtt ggggagaagt   1080
ttcttatcct ggtgtggaaa aaactatgaa agaagccgac gctgttattg ctttagcccc   1140
tgtgtttaat gattattcta ccactggttg gactgatatt cccgatccca aaaaattagt   1200
tttagccgaa cctcgttctg ttgttgttaa tggtgttcgc tttccctctg tgcatttaaa   1260
agattattta acccgcttag cccaaaaagt ttctaaaaaa actggtgcct tagatttttt   1320
taaatcttta aatgcgggtg aattaaaaaa agctgctcct gctgatcctt ctgctccttt   1380
agttaatgct gaaattgccc gtcaagttga agccttatta acccctaata ctaccgttat   1440
tgccgaaact ggtgattctt ggtttaatgc ccaacgcatg aaattaccta atggtgcccg   1500
tgttgaatat gaaatgcaat ggggtcatat tggttggtct gtacctgctg cttttggtta   1560
tgctgttggt gctcctgaac gtcgtaatat tttaatggtg ggtgatggtt cttttcaatt   1620
aactgcccaa gaagttgccc aaatggttcg cttaaaatta cccgttatta ttttttaat    1680
aaataattat ggttatacca ttgaagtgat gattcatgat gggccatata ataatattaa   1740
aaattgggat tatgcgggtt taatggaagt gtttaatggt aatggtggtt atgattctgg   1800
tgctggtaaa ggtttaaaag ccaaaactgg tggtgaatta gctgaagcta ttaaagttgc   1860
cttagccaat actgatgggc caaccttaat tgaatgtttt attggtcgcg aagattgtac   1920
cgaagaatta gttaaatggg gtaaacgtgt tgctgctgct aattctcgca aacccgtgaa   1980
taaattattg taatttttgg ggatcaattc gagctcagca agtttcatcc cgaccccctc   2040
agggtcggga ttttttttatt gtactagttg acataagtaa aggcatcccc tgcgtgatat   2100
aattaccttc agtttaagga ggtatacaca tatgtctgaa actaaattta aggcctatgc   2160
cgttatgaat cccggcgaaa agctgcaacc ctgggaatac gaaccggcgc cgctgcaagt   2220
ggatgaaatt gaagtgcggg tgactcacaa cggcctttgt cacaccgacc tgcacatgag   2280
ggacaatgac tggaacgtga gcgaatttcc cctcgttgcc ggccacgaag tcgttggaga   2340
agtgacggca gtcggggaaa aagtcacttc acgaaagaaa ggcgatcgcg tgggggtggg   2400
ttggatcaga aactcctgtc gggcctgcga tcattgtttg caaggggaag aaaatatctg   2460
tcgcgaaggc tatacaggtc tgatcgtcgg gcatcacggc ggatttgccg atcgcgttcg   2520
ggttccggcc gatttcacct acaaaattcc cgacgccttg gactccgcga gtgccgcgcc   2580
gctgctgtgt gccggcatca ccgtctacac ccccctgcgg acttatatca aacacccggg   2640
gatgaaagtc ggggtgatgg gaatcggcgg actcggacat ttagcgatca aatttgcccg   2700
ggcgatgggg gcggaagtca cggctttttc cacatccccg aataaagaag cccaagccaa   2760
ggaatttggc gcccatcatt tccaacagtg gggaacagcc gaagaaatga aagcggtggc   2820
cggaaatttc gatttggtgc tttccaccat ctccgccgaa actgattggg atgcggcgtt   2880
cagtttgctg gcaaataacg gggttttgtg tttcgtcggc attccggttt ccagtttgaa   2940
cgtgccgctg attccgctga ttttcggtca aaaatccgtc gtcggcagcg tagtgggcgg   3000
ccggcggttc atggcagaaa tgttggaatt tgccgccgtg aatcagatca aaccgatgat   3060
cgaaacgatg ccgttgagtc aggtgaacga ggcgatggac aaggtagcgg cgaataaagc   3120
tcgctatcgg atcgtgttgc tttcggagtg aagatctcct gcagagaata taaaaagcca   3180
```

```
gattattaat ccggcttttt tattatttaa atactgtgca cgatcctgca ggatcatctt   3240
gctgaaaaac tcgagcgctc gttccgcaaa gcggtacgga gttagttagg ggctaatggg   3300
cattctcccg tacaggaaag agttagaagt tattaattat caacaattct cctttgccta   3360
gtgcatcgtt accttttttaa ttaaaacata aggaaaacta ataatcgtaa taatttaacc   3420
tcaaagtgta aagaaatgtg aaattctgac ttttataacg ttaaagaggg aaaaattagc   3480
agtttaaaat acctagagaa tagtctgggg taagcataga gaattagatt agttaagtta   3540
atcaaattca gaaaaaataa taatcgtaaa tagttaatct gggtgtatag aaaatgatcc   3600
ccttcatgat aagatttaaa ctcgaaaagc aaaagccaaa aaactaactt ccattaaaag   3660
aagttgttac atataacgct ataaagaaaa tttatatatt tggaggatac caaccatgtc   3720
tcatattcaa cgtgaaacta gttgttctcg ccctcgttta aattctaata tggatgccga   3780
tttatatggt tataaatggg ctcgtgataa tgttggtcaa tctggtgcta ctatttatcg   3840
tttatatggt aaacctgatg ctcctgaatt attcttgaaa catggtaaag gttctgttgc   3900
taatgatgtt actgatgaaa tggttcgttt aaactggttg actgaattta tgcctttacc   3960
tactattaaa cattttattc gtactcccga tgatgcttgg ttattaacta ctgctattcc   4020
tggtaaaact gcttttcaag ttttagaaga atatcctgat tctggtgaaa atattgttga   4080
tgctttagct gttttttttac gtcgtttaca ttctattccc gtttgtaatt gtccttttaa   4140
ttctgatcgt gtttttcgtt tagctcaagc tcaatctcgt atgaataatg gtttagttga   4200
tgcttctgat tttgatgatg aacgtaatgg ttggcctgtt gaacaagttt ggaaagaaat   4260
gcacaaattg ttacctttt ctcctgattc tgttgttact catggtgatt tttctttaga   4320
taatttgatc tttgatgaag gtaaattgat tggttgtatt gatgttggtc gtgttggtat   4380
tgctgatcgt tatcaagatt tagctatttt atggaattgt ttaggtgaat tttctccttc   4440
tttacagaaa cgtttatttc agaaatatgg tattgataat cctgatatga acaagttaca   4500
atttcattta atgttggacg agttctttta agaattaatt catgaccaaa atcccttaac   4560
gtgagttttc gttccactga gcgtcagacc ccgtagaaaa gatcaaagga tcttcttgag   4620
atcctttttt tctgcgcgta atctgctgct atttaaatta cgtacacgtg ttattacttt   4680
gttaacgaca attgtcttaa ttaactgggc ctcatgggcc ttccgctcac tgcccgcttt   4740
ccagtcggga aacctgtcgt gccagctctg cagatgacgg tgaaaacctc tgacacatgc   4800
agctcccgga gacggtcaca gcttgtctgt aagcggatgc cgggagcaga caagcccgtc   4860
agggcgcgtc agcgggtgtt ggcgggtgtc ggggcgcagc catgacccag tcacgtagcg   4920
atagcggagt gtatactggc ttaactatgc ggcatcagag cagattgtac tgagagtgca   4980
ccatatgcgg tgtgaaatac cgcacagatg cgtaaggaga aaataccgca tcaggcgctc   5040
ttccgcttcc tcgctcactg actcgctgcg ctcggtcgtt cggctgcggc gagcggtatc   5100
agctcactca aaggcggtaa tacggttatc cacagaatca ggggataacg caggaaagaa   5160
catgtgagca aaaggccagc aaaaggccag gaaccgtaaa aaggccgcgt tgctggcgtt   5220
tttccatagg ctccgccccc ctgacgagca tcacaaaaat cgacgctcaa gtcagaggtg   5280
gcgaaacccg acaggactat aaagatacca ggcgtttccc cctggaagct ccctcgtgcg   5340
ctctcctgtt ccgaccctgc cgcttaccgg atacctgtcc gcctttctcc cttcgggaag   5400
cgtggcgctt tctcatagct cacgctgtag gtatctcagt tcggtgtagg tcgttcgctc   5460
caagctgggc tgtgtgcacg aacccccgt tcagcccgac cgctgcgcct tatccggtaa   5520
```

```
ctatcgtctt gagtccaacc cggtaagaca cgacttatcg ccactggcag cagccactgg   5580
taacaggatt agcagagcga ggtatgtagg cggtgctaca gagttcttga agtggtggcc   5640
taactacggc tacactagaa ggacagtatt tggtatctgc gctctgctga agccagttac   5700
cttcggaaaa agagttggta gctcttgatc cggcaaacaa accaccgctg gtagcggtgg   5760
tttttttgtt tgcaagcagc agattacgcg cagaaaaaaa ggatctcaag aagatccttt   5820
gatcttttct actgcagaag cttgttagac accctgtcat gtattttata ttatttattt   5880
caccatacgg attaagtgaa acctaatgaa aatagtactt tcggagcttt aactttaatg   5940
aaggtatgtt tttttataga catcgatgtc tggtttaaca ataggaaaaa gtagctaaaa   6000
ctcccatgaa ttaaagaaat aacaaggtgt ctaacaacct gttattaaga atgttagaaa   6060
agacttaaca tttgtgttga gtttttatag acattggtgt ctagacatac ggtagataag   6120
gtttgctcaa aaataaaata aaaaaagatt ggactaaaaa acatttaatt tagtacaatt   6180
taattagtta ttttttcgtc tcaaattttg ctttgttgag cagaaattta gataaaaaaa   6240
tccccgtgat cagattacaa tgtcgttcat tgtacgatgt gtcgaaaaat ctttacgaca   6300
ctctaaactg accacacggg ggaaaaagaa aactgaacta ataacatcat gatactcgga   6360
aaacctagca attctcaacc cctaaacaaa agaaacttcc aaaaccctga ccatataaag   6420
gagtggcaac aatcagcaat cagtcaagat ttgatagcag aaaatcttgt atcggttgct   6480
aatggttttg atgtactatt tatcggcaat aaataccgaa ctaacacggg tgttctgtca   6540
cggcacatat taaactccta ttctcattta gaagatggtg gttcgtatgg tagaacattt   6600
gacccattta ccaataaaga aatgcagtgg gttcaattta aaccgaatag accaagaaaa   6660
ggttctactg gtaaggtaat caaatatgaa tcgccaaaag gtgaacctac aagagttcta   6720
atgccgtttg tgcctatgaa aatatggcaa cggattagcg ataagttcgg agtaccgatt   6780
aatccgaaaa aagatactca cttttgggaa tgggtaaaga ataatccatc gataccgatt   6840
gccattacag aaggaaataa aaaagctaat tgcctattat cctatggcta tcctgctatt   6900
gcctttgtag gcatttggaa cggattagag aaaataaatg atttctcgaa ggaaaagcag   6960
ttaaaagagg atttgaaatg gttgttatcc aacggcaacc gaaatattaa tatcatcttt   7020
gaccaagacc agaaacaaaa aactgtaatt aatgtaaaca aagctatttt cgctttatct   7080
tctctaataa gtagaaatgg tcataaagtt aatattgtgc aatggttgcc gtcaaaaggt   7140
aaaggaatag atgattattt ggtagcttta ccttttgaga aaagagaaaa tcatttagac   7200
aacttaatta aaattgcacc atcatttaat ttttggtcaa ctaaatactt attcaagtgt   7260
cgtaaaccag atttaaccgt aaattgccgt tatttgagcg atgcagtaaa agaattacct   7320
caagaggata tagcattaat agcacctcac ggcacgggta aaacttcatt agtagctact   7380
cacgttaaga atcggagtta tcacggaagg aaaactattt cattggtgca tcttgaaagt   7440
ttagccaaag ctaatggcaa cgcacttgga ttatattacc gaaccgaaaa taatattgaa   7500
aagcaatatc ttggatttag cttatgtgta gatagttgcc gtgataagat taacggcatt   7560
acaactgata ttatttcagg tcaagattat tgccttttca ttgatgaaat tgaccaagta   7620
attccacaca tccttaacag tgaaactgaa gtaagtaagt atagatgcac catcattgac   7680
actttttctg aactggtgag aaatgctgaa caggtcatta ttgctgatgc tgatttatcc   7740
gatgtgacga ttgacctaat agaaaacatc agaggtaaaa aactatatgt aatcaagaat   7800
gaatatcagt atcagggaat gacttttaac gccgttggtt caccattaga aatgatggca   7860
atgatgggaa aatcggtgtc agaaggcaag aaattattta ttaacaccac atcccaaaag   7920
```

```
gcaaaaagta agtacggcac aatcgctctt gagtcttata tttttggtct aaataaagaa   7980
gcaaagatat taagaataga ctctgaaacc actaaaaacc ctgaacatcc agcctataaa   8040
atcattgacc aagacttaaa taatatcctc aaagattatg attatgtcat tgcctcacct   8100
tgccttcaaa caggtgtcag tattacctta aaagggcatt ttgaccagca atttaacttt   8160
tccagtggaa acattacacc tcattgcttt ttacagcaaa tgtggcggtt gagggatgca   8220
gaaattgaaa gattctatta tgtgccgaac tcatctaacc tcaatctcat tgggaataag   8280
tcaagttcac catcagacct tctaaagagc aataacaaga tggcaacggc aacggttaac   8340
cttttgggta gaatcgactc cgaatattcc ctagagtatg aatcgcacgg catttggctt   8400
gagacgtggg caaaattatc agcacggcat aacagttcaa tgcgttgtta ctctgaaatt   8460
cttacctatc taattacgtc tcaagggcat aaattaaata tcaacattcc ctcacctctt   8520
gcagatatta agaagctaaa tgatgaggta agtagtaaca gggaaaaggt aaaaaatgag   8580
agatactctc agaggttaaa ctcaccagat attaacgatg cagaagctac catactcgaa   8640
tctaaagagc aaaaaatcgg attgactctc aatgagagat gcaccctaga aaagcataaa   8700
gttaagaagc ggtatgggaa tgtaaagatg gatattctca cctttgatga tgatggacta   8760
taccccaaac tcagactatt ttattacctc accatcggta aacctcatct caaggctaat   8820
gacagaaaag ctattgccaa aatgggcaat gacaataaag gcaagattct atcaaaagac   8880
ttagttaata aaacttactc cgctcgtgtg aaggtcttag agattcttaa actaactgac   8940
tttatcgaca atcttagaga tgaactctta ataactccca ataatccagc tatcaccgat   9000
tttaataatc ttctgctaag agctaagaag gatttaagag tattaggagt caacatcgga   9060
aaatatccaa tggccaacat taatgccgta cttactctca ttggtcacaa actttctgta   9120
atgagagatg agttcggaaa agagaaaagg ataaaagtag atggtaaatc ataccgatgt   9180
tatcaacttg aaacattacc agattttacc aatgatactc ttgactactg gttagaaaat   9240
gatagccaaa aagaagtaac agcaacagaa aattactccg aaaattttaa cccttcaaat   9300
agctacaatc cagacagtaa gacactttca gagggtgcaa atttcctata tataaataaa   9360
gaagaattgc atccaaataa attgcaccta gaaataaaag aaggtgctga acttttttta   9420
ttcggggtaa aggtgattgt gaaaggaatc ttggacgggg cagtaactat attctctatg   9480
ggtcaagaat acgatttatc cctcaatgaa ctagagggga tgttaacatc atgaacttta   9540
caagaatctt tttaaagggc gatcgcacca tgttaaatga tggtacattt gttcagatat   9600
ttgatattta ccatgaccac gcattgggag tgaccccttga ccttaagaca gaaaaaatta   9660
tttccgatga tgttagggta attactgtca aagacttatt gttcgatggc acttataaag   9720
gggtaaaatc ttttatgccc gataatgccc gataatgccc gattgatgct acaaaatccc   9780
ataatcataa gcgataatcc cctaatagct tgtaattctt gaaccgtagc gattttagag   9840
tattccaaaa agaagaaata aacaccgcaa aatgtcgtat ttcacatata taaaccaagg   9900
tttttttgccc taaaatcttt atgtttgtag tgtgatgttg ggtcaaaatg gtcagaaaag   9960
ttgcaaggtt tttatggatg cttacgcgcg cgaggggtaa gcatccccaa atagttactt  10020
tatcctagtc catgcccatt tattgccgtc ccgttcggct ttaaaaaagt gccaaaactc  10080
acaaggtgca ataaaaagtt ctgtaccttt cgcaacccta gataatcttt caacagttac  10140
ttttttttcct attatctcgg tacaaagttt ggctagtttc tcttttccct ctttttcaat  10200
caagccttct tgtatgccca actcattgat taatctctct atttttacca ttatttcccg  10260
```

```
ttcaggtagt ttatccccta aatcttcatc ggggggcaat gtagggcatt ctgaaggggc  10320
tttttcttct gtctggacat tatctaatat tgaagtaacc aaactatctt cagtttttc  10380
tattcctatt aattcatatt cggttactgt atccgtatca atatccgaat aactatcttt  10440
atccgtatta gctattcggt taagtttatc cgttaactca gaaacaagac tatatagcgg  10500
ttttagcttt tcttctatcc tgttatctaa tacggataag tttatacggt tatcattatc  10560
cgtattagta tcattgggct tttttggtag ttctaccccc tcataaaccg cttttattcc  10620
caattccaac agactgataa cagtatcctt tataatgggt tttttgctga tatggtgaac  10680
ttttgcccct tccatcattg cgatactttc tatctcactc atcaacttat cgcttaagtg  10740
aatctcgtat ctgtttaatc ccttactggt tttattcata tccgtttact ttattcggtt  10800
aacaattcta ttttatacga ataaaatatt atacggttaa ctttatacgt ttaactattt  10860
tatctatacg gataacagta ataagttatt cgtattagtt atacgtttac ttttatccaa  10920
ataaaattag tgcatttaaa ctaaaagaat gattttatcg gagttgatag cattggatta  10980
acctaaagat gtttataagc tatatctgat aagtatttaa ggttattttg ttattctgtt  11040
tattgacatt atcagaataa aagaatagaa tataattgtt gagagataag aggtttaagt  11100
gattatggtt aagaagttag ttggttatgt cagggtcagt agtgaatcgc aagaggataa  11160
cactagctta cagaatcaga tagagagaat tgaagcatat tgtatggctt ttggttatga  11220
gttggtaaaa atattcaaag aggttgccac tggtacaaaa gcagatattg aaacccgtcc  11280
tatttttaat gaagctatag aatacttgaa acaggataat gctaatggaa ttattgcctt  11340
gaagctagac cgaatcgcac ggaatgcttt agatgtattg cgtttggttc gtgaaacctt  11400
agaaccacaa aataaaatgt tagtgttact agatattcag gtagatactt cgacaccttc  11460
aggaaaaatg attttaactg taatgagtgc cgttgctgaa ctcgaaagag acatgatcta  11520
tgatcgcact caggggggta gaaagactaa agcccaaaag ggcgggtatg cctacgggaa  11580
acctaaattt ggctataaga ctgaagaaaa ggaactaaaa gaagattcag cacaacagga  11640
aactattaaa ctaattaaga gacaccgtag gtcagggaaa agctaccaga aaatagctga  11700
ttatctcaat gcccaaagta ttcccactaa acaaggtaag aaatggagtt ctagcgtcgt  11760
ctatcgaatc tgtcaggaaa aagctggtta agtctgttta tagatattta gaatttattg  11820
aataaaaata gtatgaacaa taaatattta tggactaacc acgctcggaa acgtttaact  11880
gaacgatggg aaataaaaga atcatgggtt attgatacca tcgaaaatcc tgaacgttca  11940
gaatttattg ttgatgagtc aggggaaaaa tatcattact ataaaagaat agctaagttt  12000
aagaatagag tgttagaagt gataacttct gccaactcaa cacccacaag aataataacc  12060
ttttacttta accgtaacat gaggaaaaat ttatgattgt tacttacgat aatgaagttg  12120
acgcaattta ttttaagtta acggaaaata aaattgatag caccgaacct caaacagaca  12180
ggattatcat tgattacgat gaaagtaata atattgttgg cattgaggta ttagatttta  12240
attatcttgt caagaaaggt ttaaccgttg ctgatttacc tttttctgaa gatgaaagat  12300
taacagcttc tcaatatttt aattttcctg ttgctatcta atccagaagg ggcaataatc  12360
cccttctttc atcgagttag acttaatatc acaaaagtca ttttcatttt accgtttctt  12420
ttccacagcg tccgtacgcc cctcgttaaa tctcaaaacc gacaatttat gatgtttata  12480
aaaagttact cactttaata agtatttata ctcattaaag ggttattctt tttttgtagc  12540
ctgataggtt gggaaggaat atttcagatt atcagatttg ttgaatattt ttcgtcagat  12600
acgcaaacct tacaaacata attaacaact gaaactattg atatgtctag gttttagctc  12660
```

tatcacaggt tggatctg 12678

<210> SEQ ID NO 47
<211> LENGTH: 12683
<212> TYPE: DNA
<213> ORGANISM: Artificial
<220> FEATURE:
<223> OTHER INFORMATION: Synthetically produced plasmid construct #1735
pABIcyano1-PnirA-zmPDC(opt1)_dsrA-Prbc*(optRBS)-Adh1694_ter
standard

<400> SEQUENCE: 47

```
tcgacaatta ataacttctt cctgtacggg cgaatggcca tttgctccta actaactccg     60
tactgctttg cggaacgagc gtagcgaact ctccgaatta ctaagccttc atccctgata    120
gatgcaaaaa acgaattaaa attatgtgta aaaagaaaat gtgtctttat ttagtagtca    180
aagttacaaa atattaagaa tcaaattaat aatgtattgg gcagttaagt atataagtct    240
ttaaatattt atttgtattc aatatattaa ccgaggacaa attatgaatt cttataccgt    300
gggtacttat ttagccgaac gcttagtgca aattggttta aaacatcatt ttgccgtggc    360
tggggactat aatttagtgt tattggataa cttattatta aataaaaaca tggaacaagt    420
gtattgttgt aatgaattaa attgtggttt ttctgctgaa ggttatgcta gagctaaagg    480
tgcagctgct gctgttgtta cttattctgt gggtgcttta tctgcttttg atgctattgg    540
tggtgcttat gccgaaaatt tacccgtgat tttaatttct ggtgccccta ataataatga    600
tcatgccgct ggacatgttt tacatcatgc cttaggtaaa accgattatc attatcaatt    660
agaaatggcc aaaaatatta ctgctgctgc cgaagctatt tatactcctg aagaagcccc    720
tgccaaaatt gatcatgtga ttaaaaccgc cttacgcgaa aaaaaacccg tgtatttaga    780
aattgcctgt aatattgctt ctatgccttg tgctgctcct gggcctgctt ctgctttatt    840
taatgatgaa gcctctgatg aagctagttt aaatgctgcc gtggaagaaa ccttaaaatt    900
tattgccaat cgcgataaag ttgccgtgtt agttggttct aaattaagag ctgctggtgc    960
tgaagaagct gctgttaaat ttgctgatgc tttaggtggt gcagttgcta ctatggctgc   1020
tgccaaatct ttttttcccg aagaaaatcc ccattatatt ggaactagtt ggggagaagt   1080
ttcttatcct ggtgtggaaa aaactatgaa agaagccgac gctgttattg ctttagcccc   1140
tgtgtttaat gattattcta ccactggttg gactgatatt cccgatccca aaaaattagt   1200
tttagccgaa cctcgttctg ttgttgttaa tggtgttcgc tttccctctg tgcatttaaa   1260
agattattta acccgcttag cccaaaaagt ttctaaaaaa actggtgcct tagatttttt   1320
taaatcttta aatgcgggtg aattaaaaaa agctgctcct gctgatcctt ctgctccttt   1380
agttaatgct gaaattgccc gtcaagttga agccttatta acccctaata ctaccgttat   1440
tgccgaaact ggtgattctt ggtttaatgc ccaacgcatg aaattaccta atggtgcccg   1500
tgttgaatat gaaatgcaat ggggtcatat tggttggtct gtacctgctg cttttggtta   1560
tgctgttggt gctcctgaac gtcgtaatat tttaatggtg ggtgatggtt cttttcaatt   1620
aactgcccaa gaagttgccc aaatggttcg cttaaaatta cccgttatta ttttttttaat   1680
aaataattat ggttatacca ttgaagtgat gattcatgat gggccatata ataatattaa   1740
aaattgggat tatgcgggtt taatggaagt gtttaatggt aatggtggtt atgattctgg   1800
tgctggtaaa ggtttaaaag ccaaaactgg tggtgaatta gctgaagcta ttaaagttgc   1860
cttagccaat actgatgggc caaccttaat tgaatgtttt attggtcgcg aagattgtac   1920
```

```
cgaagaatta gttaaatggg gtaaacgtgt tgctgctgct aattctcgca aacccgtgaa   1980
taaattattg taatttttgg ggatcaattc gagctcagca agtttcatcc cgaccccctc   2040
agggtcggga tttttttatt gtactagttg acataagtaa aggcatcccc tgcgtgatat   2100
aattaccttc agtttaagga ggtatacaca tatgactaca gcaactaaat ttaaggctta   2160
tgcggcttta aattccggtg aaaaattgca accttgggaa tatgaaccag aacctctaca   2220
ggttgatgaa gtagaaattc gagtcactca caacggcttg tgtcatacgg atcttcacat   2280
gagggataat gattggaatg tcagtcaata tcccctggtt cccggtcatg aagtggttgg   2340
agaagttaca gaagttgggg aaaaagtgac ttctctacat aaaggcgatc gcataggggt   2400
tggctggatt agaaattcct gtaggtcttg cgaccattgc ttacaaggag aagaaaatat   2460
ctgtcgcgag ggctacacag gtctgattgt aggtcatcat gggggatttg ctgaccgcct   2520
acgggttccc gcagatttta cctataaaat acccgatgct ttagactccg ccagcgccgc   2580
cccccctatta tgtgccggaa ttaccgttta taccccccttg cggacctata taaaacaccc   2640
cgggatgaaa gttggggtga tgggaattgg cggactcgga cacttagcga ttaagtttgc   2700
tagggctatg gggctgaag ttacggcgtt ttctacttct ttaaataaac aagaacaagc   2760
taaggaattt ggcgctcata acttccaaca atgggggacg gctgaagaaa tgaaggcgat   2820
cgccggaagt tttgatctag tgctttctac tatctcttca gaaactgatt gggatgcggc   2880
ttttagcttg ttagctaata acggggtttt gtgttttgtg ggtatcccag tttcgacttt   2940
aaatataccc ctaattcctt tgatttttgg tcaaaaagct gtggtgggta gcattgtcgg   3000
cggtcggcgg tttatggcgg aaatgctgga gtttgcagcg gtgaatcaga ttaaaccgat   3060
gattgaaact atgccattaa gtcaaatcaa tgaagctatg gataaggtag ccgctaatca   3120
agcccgctat cggattgttt tactagctga ttagccagat ctcctgcaga gaatataaaa   3180
agccagatta ttaatccggc ttttttatta tttaaatact gtgcacgatc ctgcaggatc   3240
atcttgctga aaaactcgag cgctcgttcc gcaaagcggt acggagttag ttaggggcta   3300
atgggcattc tcccgtacag gaaagagtta gaagttatta attatcaaca attctccttt   3360
gcctagtgca tcgttacctt tttaattaaa acataaggaa aactaataat cgtaataatt   3420
taacctcaaa gtgtaaagaa atgtgaaatt ctgactttta taacgttaaa gagggaaaaa   3480
ttagcagttt aaaataccta gagaatagtc tggggtaagc atagagaatt agattagtta   3540
agttaatcaa attcagaaaa aataataatc gtaaatagtt aatctgggtg tatagaaaat   3600
gatcccccttc atgataagat ttaaactcga aaagcaaaag ccaaaaaaact aacttccatt   3660
aaaagaagtt gttacatata acgctataaa gaaaatttat atatttggag gataccaacc   3720
atgtctcata ttcaacgtga aactagttgt tctcgccctc gtttaaattc taatatggat   3780
gccgatttat atggttataa atgggctcgt gataatgttg gtcaatctgg tgctactatt   3840
tatcgtttat atggtaaacc tgatgctcct gaattattct tgaaacatgg taaaggttct   3900
gttgctaatg atgttactga tgaaatggtt cgtttaaact ggttgactga atttatgcct   3960
ttacctacta ttaaacattt tattcgtact cccgatgatg cttggttatt aactactgct   4020
attcctggta aaactgcttt tcaagtttta gaagaatatc ctgattctgg tgaaaatatt   4080
gttgatgctt tagctgtttt tttacgtcgt ttacattcta ttcccgtttg taattgtcct   4140
tttaattctg atcgtgtttt tcgtttagct caagctcaat ctcgtatgaa taatggttta   4200
gttgatgctt ctgattttga tgatgaacgt aatggttggc ctgttgaaca agtttggaaa   4260
gaaatgcaca aattgttacc tttttctcct gattctgttg ttactcatgg tgatttttct   4320
```

```
ttagataatt tgatctttga tgaaggtaaa ttgattggtt gtattgatgt tggtcgtgtt   4380
ggtattgctg atcgttatca agatttagct attttatgga attgtttagg tgaattttct   4440
ccttctttac agaaacgttt atttcagaaa tatggtattg ataatcctga tatgaacaag   4500
ttacaatttc atttaatgtt ggacgagttc ttttaagaat taattcatga ccaaaatccc   4560
ttaacgtgag ttttcgttcc actgagcgtc agaccccgta gaaaagatca aaggatcttc   4620
ttgagatcct ttttttctgc gcgtaatctg ctgctattta aattacgtac acgtgttatt   4680
actttgttaa cgacaattgt cttaattaac tgggcctcat gggccttccg ctcactgccc   4740
gctttccagt cgggaaacct gtcgtgccag ctctgcagat gacggtgaaa acctctgaca   4800
catgcagctc ccggagacgg tcacagcttg tctgtaagcg gatgccggga gcagacaagc   4860
ccgtcagggc gcgtcagcgg gtgttggcgg gtgtcggggc gcagccatga cccagtcacg   4920
tagcgatagc ggagtgtata ctggcttaac tatgcggcat cagagcagat tgtactgaga   4980
gtgcaccata tgcggtgtga aataccgcac agatgcgtaa ggagaaaata ccgcatcagg   5040
cgctcttccg cttcctcgct cactgactcg ctgcgctcgg tcgttcggct gcggcgagcg   5100
gtatcagctc actcaaaggc ggtaatacgg ttatccacag aatcagggga taacgcagga   5160
aagaacatgt gagcaaaagg ccagcaaaag gccaggaacc gtaaaaaggc cgcgttgctg   5220
gcgtttttcc ataggctccg cccccctgac gagcatcaca aaaatcgacg ctcaagtcag   5280
aggtggcgaa acccgacagg actataaaga taccaggcgt ttccccctgg aagctccctc   5340
gtgcgctctc ctgttccgac cctgccgctt accggatacc tgtccgcctt tctcccttcg   5400
ggaagcgtgg cgctttctca tagctcacgc tgtaggtatc tcagttcggt gtaggtcgtt   5460
cgctccaagc tgggctgtgt gcacgaaccc cccgttcagc ccgaccgctg cgccttatcc   5520
ggtaactatc gtcttgagtc caacccggta agacacgact tatcgccact ggcagcagcc   5580
actggtaaca ggattagcag agcgaggtat gtaggcggtg ctacagagtt cttgaagtgg   5640
tggcctaact acggctacac tagaaggaca gtatttggta tctgcgctct gctgaagcca   5700
gttaccttcg gaaaaagagt tggtagctct tgatccggca aacaaaccac cgctggtagc   5760
ggtggttttt ttgtttgcaa gcagcagatt acgcgcagaa aaaaaggatc tcaagaagat   5820
cctttgatct tttctactgc agaagcttgt tagacaccct gtcatgtatt ttatattatt   5880
tatttcacca tacggattaa gtgaaaccta atgaaaatag tactttcgga gctttaactt   5940
taatgaaggt atgttttttt atagacatcg atgtctggtt taacaatagg aaaaagtagc   6000
taaaactccc atgaattaaa gaaataacaa ggtgtctaac aacctgttat taagaatgtt   6060
agaaaagact taacatttgt gttgagtttt tatagacatt ggtgtctaga catacggtag   6120
ataaggtttg ctcaaaaata aaataaaaaa agattggact aaaaaacatt taatttagta   6180
caatttaatt agttattttt tcgtctcaaa ttttgctttg ttgagcagaa atttagataa   6240
aaaaatcccc gtgatcagat tacaatgtcg ttcattgtac gatgtgtcga aaatctttta   6300
cgacactcta aactgaccac acgggggaaa aagaaaactg aactaataac atcatgatac   6360
tcggaaaacc tagcaattct caacccctaa acaaaagaaa cttccaaaac cctgaccata   6420
taaaggagtg gcaacaatca gcaatcagtc aagatttgat agcagaaaat cttgtatcgg   6480
ttgctaatgg ttttgatgta ctatttatcg gcaataaata ccgaactaac acgggtgttc   6540
tgtcacggca catattaaac tcctattctc atttagaaga tggtggttcg tatggtagaa   6600
catttgaccc atttaccaat aaagaaatgc agtgggttca atttaaaccg aatagaccaa   6660
```

```
gaaaaggttc tactggtaag gtaatcaaat atgaatcgcc aaaaggtgaa cctacaagag   6720
ttctaatgcc gtttgtgcct atgaaaatat ggcaacggat tagcgataag ttcggagtac   6780
cgattaatcc gaaaaaagat actcactttt gggaatgggt aaagaataat ccatcgatac   6840
cgattgccat tacagaagga aataaaaaag ctaattgcct attatcctat ggctatcctg   6900
ctattgcctt tgtaggcatt tggaacggat tagagaaaat aaatgatttc tcgaaggaaa   6960
agcagttaaa agaggatttg aaatggttgt tatccaacgg caaccgaaat attaatatca   7020
tctttgacca agaccagaaa caaaaaactg taattaatgt aaacaaagct attttcgctt   7080
tatcttctct aataagtaga aatggtcata aagttaatat tgtgcaatgg ttgccgtcaa   7140
aaggtaaagg aatagatgat tatttggtag ctttaccttt tgagaaaaga gaaaatcatt   7200
tagacaactt aattaaaatt gcaccatcat ttaatttttg gtcaactaaa tacttattca   7260
agtgtcgtaa accagattta accgtaaatt gccgttattt gagcgatgca gtaaaagaat   7320
tacctcaaga ggatatagca ttaatagcac ctcacggcac gggtaaaact tcattagtag   7380
ctactcacgt taagaatcgg agttatcacg gaaggaaaac tatttcattg gtgcatcttg   7440
aaagtttagc caaagctaat ggcaacgcac ttggattata ttaccgaacc gaaaataata   7500
ttgaaaagca atatcttgga tttagcttat gtgtagatag ttgccgtgat aagattaacg   7560
gcattacaac tgatattatt tcaggtcaag attattgcct tttcattgat gaaattgacc   7620
aagtaattcc acacatcctt aacagtgaaa ctgaagtaag taagtataga tgcaccatca   7680
ttgacacttt ttctgaactg gtgagaaatg ctgaacaggt cattattgct gatgctgatt   7740
tatccgatgt gacgattgac ctaatagaaa acatcagagg taaaaaacta tatgtaatca   7800
agaatgaata tcagtatcag ggaatgactt ttaacgccgt tggttcacca ttagaaatga   7860
tggcaatgat gggaaaatcg gtgtcagaag gcaagaaatt atttattaac accacatccc   7920
aaaaggcaaa aagtaagtac ggcacaatcg ctcttgagtc ttatattttt ggtctaaata   7980
aagaagcaaa gatattaaga atagactctg aaaccactaa aaaccctgaa catccagcct   8040
ataaaatcat tgaccaagac ttaaataata tcctcaaaga ttatgattat gtcattgcct   8100
caccttgcct tcaaacaggt gtcagtatta ccttaaaagg gcattttgac cagcaattta   8160
acttttccag tggaaacatt acacctcatt gctttttaca gcaaatgtgg cggttgaggg   8220
atgcagaaat tgaaagattc tattatgtgc cgaactcatc taacctcaat ctcattggga   8280
ataagtcaag ttcaccatca gaccttctaa agagcaataa caagatggca acggcaacgg   8340
ttaacctttt gggtagaatc gactccgaat attccctaga gtatgaatcg cacggcattt   8400
ggcttgagac gtgggcaaaa ttatcagcac ggcataacag ttcaatgcgt tgttactctg   8460
aaattcttac ctatctaatt acgtctcaag ggcataaatt aaatatcaac attccctcac   8520
ctcttgcaga tattaagaag ctaaatgatg aggtaagtag taacagggaa aaggtaaaaa   8580
atgagagata ctctcagagg ttaaactcac cagatattaa cgatgcagaa gctaccatac   8640
tcgaatctaa agagcaaaaa atcggattga ctctcaatga gagatgcacc ctagaaaagc   8700
ataaagttaa gaagcggtat gggaatgtaa agatggatat tctcaccttt gatgatgatg   8760
gactataccc caaactcaga ctattttatt acctcaccat cggtaaacct catctcaagg   8820
ctaatgacag aaaagctatt gccaaaatgg gcaatgacaa taaaggcaag attctatcaa   8880
aagacttagt taataaaact tactccgctc gtgtgaaggt cttagagatt cttaaactaa   8940
ctgactttat cgacaatctt agagatgaac tcttaataac tcccaataat ccagctatca   9000
ccgattttaa taatcttctg ctaagagcta agaaggattt aagagtatta ggagtcaaca   9060
```

```
tcggaaaata tccaatggcc aacattaatg ccgtacttac tctcattggt cacaaacttt   9120
ctgtaatgag agatgagttc ggaaaagaga aaaggataaa agtagatggt aaatcatacc   9180
gatgttatca acttgaaaca ttaccagatt ttaccaatga tactcttgac tactggttag   9240
aaaatgatag ccaaaaagaa gtaacagcaa cagaaaatta ctccgaaaat tttaaccctt   9300
caaatagcta caatccagac agtaagacac tttcagaggg tgcaaatttc ctatatataa   9360
ataaagaaga attgcatcca aataaattgc acctagaaat aaaagaaggt gctgaacttt   9420
ttttattcgg ggtaaaggtg attgtgaaag gaatcttgga cggggcagta actatattct   9480
ctatgggtca agaatacgat ttatccctca atgaactaga ggggatgtta acatcatgaa   9540
ctttacaaga atctttttaa agggcgatcg caccatgtta aatgatggta catttgttca   9600
gatatttgat atttaccatg accacgcatt gggagtgacc cttgacctta agacagaaaa   9660
aattatttcc gatgatgtta gggtaattac tgtcaaagac ttattgttcg atggcactta   9720
taaaggggta aaatctttta tgcccgataa tgcccgataa tgcccgattg atgctacaaa   9780
atcccataat cataagcgat aatcccctaa tagcttgtaa ttcttgaacc gtagcgattt   9840
tagagtattc caaaaagaag aaataaacac cgcaaaatgt cgtatttcac atatataaac   9900
caaggttttt tgccctaaaa tctttatgtt tgtagtgtga tgttgggtca aaatggtcag   9960
aaaagttgca aggtttttat ggatgcttac gcgcgcgagg ggtaagcatc cccaaatagt  10020
tactttatcc tagtccatgc ccatttattg ccgtcccgtt cggctttaaa aaagtgccaa  10080
aactcacaag gtgcaataaa aagttctgta cctttcgcaa ccctagataa tctttcaaca  10140
gttacttttt ttcctattat ctcggtacaa agtttggcta gtttctcttt tccctctttt  10200
tcaatcaagc cttcttgtat gcccaactca ttgattaatc tctctatttt taccattatt  10260
tcccgttcag gtagtttatc ccctaaatct tcatcggggg gcaatgtagg gcattctgaa  10320
ggggcttttt cttctgtctg gacattatct aatattgaag taaccaaact atcttcagtt  10380
ttttctattc ctattaattc atattcggtt actgtatccg tatcaatatc cgaataacta  10440
tctttatccg tattagctat tcggttaagt ttatccgtta actcagaaac aagactatat  10500
agcggtttta gcttttcttc tatcctgtta tctaatacgg ataagtttat acggttatca  10560
ttatccgtat tagtatcatt gggctttttt ggtagttcta ccccctcata aaccgctttt  10620
attcccaatt ccaacagact gataacagta tcctttataa tgggtttttt gctgatatgg  10680
tgaacttttg ccccttccat cattgcgata ctttctatct cactcatcaa cttatcgctt  10740
aagtgaatct cgtatctgtt taatccctta ctggttttat tcatatccgt ttactttatt  10800
cggttaacaa ttctatttta tacgaataaa atattatacg gttaacttta tacgtttaac  10860
tattttatct atacggataa cagtaataag ttattcgtat tagttatacg tttactttta  10920
tccaaataaa attagtgcat ttaaactaaa agaatgattt tatcggagtt gatagcattg  10980
gattaaccta aagatgttta taagctatat ctgataagta tttaaggtta ttttgttatt  11040
ctgtttattg acattatcag aataaaagaa tagaatataa ttgttgagag ataagaggtt  11100
taagtgatta tggttaagaa gttagttggt tatgtcaggg tcagtagtga atcgcaagag  11160
gataacacta gcttacagaa tcagatagag agaattgaag catattgtat ggcttttggt  11220
tatgagttgg taaaaatatt caaagaggtt gccactggta caaaagcaga tattgaaacc  11280
cgtcctattt ttaatgaagc tatagaatac ttgaaacagg ataatgctaa tggaattatt  11340
gccttgaagc tagaccgaat cgcacggaat gctttagatg tattgcgttt ggttcgtgaa  11400
```

```
accttagaac cacaaaataa aatgttagtg ttactagata ttcaggtaga tacttcgaca  11460
ccttcaggaa aaatgatttt aactgtaatg agtgccgttg ctgaactcga aagagacatg  11520
atctatgatc gcactcaggg gggtagaaag actaaagccc aaaagggcgg gtatgcctac  11580
gggaaaccta aatttggcta taagactgaa gaaaaggaac taaaagaaga ttcagcacaa  11640
caggaaacta ttaaactaat taagagacac cgtaggtcag ggaaaagcta ccagaaaata  11700
gctgattatc tcaatgccca aagtattccc actaaacaag gtaagaaatg gagttctagc  11760
gtcgtctatc gaatctgtca ggaaaaagct ggttaagtct gtttatagat atttagaatt  11820
tattgaataa aaatagtatg aacaataaat atttatggac taaccacgct cggaaacgtt  11880
taactgaacg atgggaaata aaagaatcat gggttattga taccatcgaa aatcctgaac  11940
gttcagaatt tattgttgat gagtcagggg aaaaatatca ttactataaa agaatagcta  12000
agtttaagaa tagagtgtta gaagtgataa cttctgccaa ctcaacaccc acaagaataa  12060
taacctttta ctttaaccgt aacatgagga aaaatttatg attgttactt acgataatga  12120
agttgacgca atttatttta agttaacgga aaataaaatt gatagcaccg aacctcaaac  12180
agacaggatt atcattgatt acgatgaaag taataatatt gttggcattg aggtattaga  12240
ttttaattat cttgtcaaga aaggtttaac cgttgctgat ttaccttttt ctgaagatga  12300
aagattaaca gcttctcaat attttaattt tcctgttgct atctaatcca gaaggggcaa  12360
taatcccctt ctttcatcga gttagactta atatcacaaa agtcattttc attttaccgt  12420
ttcttttcca cagcgtccgt acgcccctcg ttaaatctca aaaccgacaa tttatgatgt  12480
ttataaaaag ttactcactt taataagtat ttatactcat taaagggtta ttcttttttt  12540
gtagcctgat aggttgggaa ggaatatttc agattatcag atttgttgaa tatttttcgt  12600
cagatacgca aaccttacaa acataattaa caactgaaac tattgatatg tctaggtttt  12660
agctctatca caggttggat ctg                                         12683
```

```
<210> SEQ ID NO 48
<211> LENGTH: 359
<212> TYPE: DNA
<213> ORGANISM: Cyanobacterium sp. PTA-13311

<400> SEQUENCE: 48

cctcaactac aagttctttt atatattact ttaacctgag ttttggataa gctgaaagca     60
ttattttctc gtagtcagaa aaccttatag cttcttagaa ataacgataa aattacctta    120
atccgaactg acgttaaata tattcacccc tatcacccca aaaccctaag cccctacttc    180
cccctttccc ttcatcacct catcccccca tcccctaaca cttaacctta ttctttattc    240
ttaaaccgaa ctgaggtgaa gttgcagaat acccatgggg ggttacagca ttgtagaaaa    300
ataaatattc tttcattatt aaggttgttt ggtaaaaata tgtgaaaacc ctaataatt     359
```

```
<210> SEQ ID NO 49
<211> LENGTH: 239
<212> TYPE: DNA
<213> ORGANISM: Cyanobacterium sp. PTA-13311

<400> SEQUENCE: 49

ggggacagac atatttttat cataatggta aattcataat aattttagac tttttttgc      60
aaaaattaat ctcactctct tctttcccta tctcccattg tttcttatat cccaatgccc    120
caatacccaa agctcagaaa ataggtatta gcgaagaggt gttgatcccc tcccctagca    180
aaatatactc ctatatagta aagtgagaaa gtgaagaaat aagatcaagt tcgcaattt     239
```

<210> SEQ ID NO 50
<211> LENGTH: 496
<212> TYPE: DNA
<213> ORGANISM: Cyanobacterium sp. PTA-13311

<400> SEQUENCE: 50

```
caaatcacga gaatttatgt agggactatt ttgggttgac ggtggagagt atgtcgccct     60
tgaattatga cccgaagatg aagatgtcgg ggaggtggaa ggacggtctt taagaggttt    120
aacatcaaag ttggtcataa tctctgtccc tgtttgataa ctactattta attttgagtt    180
gttttaggta catcaaaata cccaaatcct tactctcccc tcaatataca acaaaaaaaa    240
ctttttgatt cactttagtc ataaaaatta gaatttatct accgaaatat tacataaatg    300
taatgtatat attttctgat ttattccgtg tgagccatga ttcataattt ataattcata    360
atttctaaat atgcccctac aatggatata gaatgtcatt ttaattatag gtatcataat    420
cgtggtagtt actccggaaa aaactattga atcaaattca gtctcacctg ctacagatag    480
agtagccgtt attctt                                                    496
```

<210> SEQ ID NO 51
<211> LENGTH: 290
<212> TYPE: DNA
<213> ORGANISM: Cyanobacterium sp. PTA-13311

<400> SEQUENCE: 51

```
ttgacgattg tattgactta cgccaaatgg cttaccctca tagtgaatag ttgataatta     60
agaattaaaa atcccgttca cgacagaagg gagtgtaaga gccttcggtg cgaactctca    120
tcttccctga aacctgacac ctgaaacctg acacctgaaa cctgacacct catctcccta    180
atcccctaat tttaatgaaa aaataccctg agtgggcatt gaaaaaaaag aaaagttgtt    240
cgactatgaa ataagaattc tgcacttcgt gagaaaaaag gaaatgaaat                290
```

<210> SEQ ID NO 52
<211> LENGTH: 355
<212> TYPE: DNA
<213> ORGANISM: Cyanobacterium sp. PTA-13311

<400> SEQUENCE: 52

```
ctatttaact aggaaaaggt aaagttaaaa ggacaagggt aaataattaa aaattaagaa     60
ttaagaactt ctaactctca ttactcatta cttatttcct cctctcaccc cttctcctga    120
tcacctcttc tcctcaatac tcggaactca tttccccatg gtgtgacact caaatcaaaa    180
gtctgttatt gactttcaga tgaaatatta ctatgataac aatatccccc ctatgggtat    240
ataaaaatat gagcgatatt agttaaaaat caaatttgga tttttttct gaaaatattt     300
taagattaag taaagataag taaagaaatt ataagcaatt ttgttaaatc atacc         355
```

<210> SEQ ID NO 53
<211> LENGTH: 619
<212> TYPE: DNA
<213> ORGANISM: Cyanobacterium sp. PTA-13311

<400> SEQUENCE: 53

```
ctcacactga aaatattgcc acaagaaata aagatcaagc aataatcctg actaaaaagg     60
aataaagtaa ttatcctttt cctgatatgt tatctgactt gttgtttctt agtcatgttc    120
cttccatttt tatttttgtt tttatcattt ttattacaaa aatttcttaa tagggctaaa    180
```

gcatttagtt agttttttag ctctcaacaa gttgactaat caatataatg ccctaagtta 240
atttgccctt ggtttgacgg aggatattgg aaaaaagaaa cttctcgttg tatttcacag 300
ggaaaagggg gaaattttat taataactaa acaatagaaa ataattattt atttatatta 360
ttttgtgaac aaatgttcaa gaattaaagt gtaataagaa aatttatttt tttatattta 420
tttaaaactt agatataagc ctaaaggtct gaaattatta ttagacaatc aattgattca 480
gaggtaatag ttttttactt aaaaatattt tttcaaaatt atcccctatt tgggtattga 540
aaaataaata aattcaagta ataatataca gaataaagga aaatctaatc ttaaaaattt 600
tgtgtgtgag gaattgaaa 619

<210> SEQ ID NO 54
<211> LENGTH: 190
<212> TYPE: DNA
<213> ORGANISM: Cyanobacterium sp. PTA-13311

<400> SEQUENCE: 54
tatcaccatt gtagaaaagc cagaaaatca attaacacaa atttcctgta aattattatg 60
tatgattttc cccttctccc cttaaaagga gaaataaaaa actatatccc ccaaccaccg 120
ataagcattg tgagagaaaa atcatttagg taggatcaat gctgtaaccg ataaagataa 180
ataaataatt 190

<210> SEQ ID NO 55
<211> LENGTH: 536
<212> TYPE: DNA
<213> ORGANISM: Cyanobacterium sp. PTA-13311

<400> SEQUENCE: 55
attctgtgaa ttgattagat ttgaggtttt ttaagaggtt gattaccttg cctccaaaaa 60
aatcataaca cactaatgct ctatatgaaa gggctttaga cccataggtt tttgagaaaa 120
aaacttgcta actctcggac aatgtcagca taactaaagt caattctttt cgtactttat 180
aattgtctat aatttaatat acaactgttc tgaaactagt ttttctctac attccttagt 240
tttatctgag taaggttgct tgtaacttaa cttcggttgg gcctaaaaat atccgattag 300
gagcaggtgt cagactttaa ttaattatta attattaatt gcttattgcc aaccctcggc 360
gacaccactt tttcatcagc cccagataaa gattgatgtt ttagttttgt ttctttttat 420
cccctaattc aactaataca agtaaaacta aggttgttta tcaaaaatga tggttgatgt 480
ttgggtaaat tttaagatat tatgaaaaga aaatgaataa aaaatgaaaa atcttt 536

<210> SEQ ID NO 56
<211> LENGTH: 283
<212> TYPE: DNA
<213> ORGANISM: Cyanobacterium sp. PTA-13311

<400> SEQUENCE: 56
ctacaggggc aagatttggc ggaaatctat atgtggattc tctttcaagt gaagaaggtg 60
cagtgccgac ttatctggac ttattagaat acgatattcg cactattact aatggtttgt 120
tagcaggagt gaacaattaa aaattttttc ctaattgacg aataaaaaat caatgtcaac 180
taatagttaa caatactctc tgaaaaccaa aaattgtcaa ccaaaacata acataatttt 240
tacccaaaaa cctcatttat aaactttaag gataaaatca atg 283

<210> SEQ ID NO 57
<211> LENGTH: 299

<212> TYPE: DNA
<213> ORGANISM: Cyanobacterium sp. PTA-13311

<400> SEQUENCE: 57
gggattagag agttcaaagt taggaatgag gtgtcaggtt ttaggtttca ggtttagggg 60
agcaatgaga aagaggtttc aggtttcagg tgtcaggttg caggtgtcac aggtgatgag 120
gggatggggg atgaggggga aacaagtaag taataagtgt tcggagtttt taattcttaa 180
ttcttaattt ttcctttgcc tcttgccttt tgccttgtct taattactaa tttctaatta 240
aaatgattgt gttttctagt ttagtctcat ggttacttga acccttacag catagtttt 299

<210> SEQ ID NO 58
<211> LENGTH: 414
<212> TYPE: DNA
<213> ORGANISM: Cyanobacterium sp. PTA-13311

<400> SEQUENCE: 58
ttacaaacgg cgggaattat tatggtagta gcgatgttag taaccccggg tgcgatcgca 60
tatttactta cagatcgttt tgatcaaatg ttaatcttat caatagttag tagtgttcta 120
tcttgtgttt taggcactta tttaagttat cattttgatg tttctacggg gggaagtatt 180
gtcgttttaa tgaccataat ttttatttta gcgatgattt ttgctcctaa atatggcatc 240
atcaatcaaa ataccaaaat atattctgct taacttgttt actgatactt caaataatca 300
tataacctat cttccgagtt aaaaataatg gatattatcc aactgaggtc gagaatagag 360
tttctttttt gatagaattt ttttacacca gttattcatt actatcatgg gata 414

<210> SEQ ID NO 59
<211> LENGTH: 412
<212> TYPE: DNA
<213> ORGANISM: Cyanobacterium sp. PTA-13311

<400> SEQUENCE: 59
taatatagtg attattataa atgcaatgtg aatcaaacct atattttacc gtacattgac 60
catggaactt aatttgaggt gattagtaga gggtgcgatc gccctatttg tcaaataata 120
aagataacat ttgacattgc tgattgaaga cataaaacac agaaaaaatc aggtaaaaat 180
ataaagctaa agtctaaata tggtttactt ttgccttcga cttacaacaa aaaatcatag 240
ctagaatcac caacgcctaa tattttattt agctgaaatt ttgggatgaa ctttttgtaa 300
aaatcggggg tctaaaaata tagcaaccac gatattaaat aactgagtga ttattttaat 360
ctattggggg cttattaact aaatacttgc atttttatgg agggttttaa tt 412

<210> SEQ ID NO 60
<211> LENGTH: 364
<212> TYPE: DNA
<213> ORGANISM: Cyanobacterium sp. PTA-13311

<400> SEQUENCE: 60
aaagattatt ttctacagaa gcaacccttt catcttccga attttcagga atttcctgct 60
tttgtttctg aatattagca taggcggctt ttgcccactc taaagaaggt tgagactgaa 120
tttctgaggt ttcagaagga gcattagatt gtttatcttc aacaacagga ggtttttgtt 180
caatattttc cttattctct tttttacggc gaaaccaatt aaacataatg attgtgcata 240
aatattcgtt aatatattgt aaccctagaa aggaatcggt ttcaggttta tccccagaga 300
atgtgaacct ttacagaaag taaaaagtct aaaatcgtag caacaataaa tcacagaaat 360

```
tgag                                                                 364

<210> SEQ ID NO 61
<211> LENGTH: 234
<212> TYPE: DNA
<213> ORGANISM: Cyanobacterium sp. PTA-13311

<400> SEQUENCE: 61

atctagtaat aatcatcaag agttgttaaa acttcactat caagaattgg tagcaagagg     60

attacaacat ctgagtttag atcatcgagc agttattgtt cttcatgatt tggaagattt    120

accacaacag gaaatagcgg aaatattatc tattcccctt ggtacggtca aatctcgttt    180

attcaaagcc agaaaaaatt tgcgtcaatt tttagaactt gaaggtatta gctt          234

<210> SEQ ID NO 62
<211> LENGTH: 246
<212> TYPE: DNA
<213> ORGANISM: Cyanobacterium sp. PTA-13311

<400> SEQUENCE: 62

ccaatatctt gtcatacata cttatttgcc tcactattag ccctatatgt ctctattgta     60

tttttctttt tctcctattc ctagatcttg taatgaatca ttactctctg aaatatagct    120

actaatttta tggttgtttg taaaatatat taacaaatga acaataaatc atattttgtg    180

ttaatctaat tattagacaa ctactgaatt tatattcaga tattcacaga taggagaatt    240

ttgatt                                                               246

<210> SEQ ID NO 63
<211> LENGTH: 346
<212> TYPE: DNA
<213> ORGANISM: Cyanobacterium sp. PTA-13311

<400> SEQUENCE: 63

attctattac cctccgaggg tggctatctc cttttatttg gtggctgata aaaccctatt     60

ctattaaagt agccaatgag ttagttaatg cggcggctaa atgtcactaa aatttcatct    120

taggttcaca tcaaagtcat atcggttgtt tatagtatta agtgtcaggg agaaagatag    180

gttttcctct ttagctcctt cgcaccttta atccctgact ttttttattt ttttgttcgt    240

gtgattaatc tatttgtgta gcaattattt ttatcttatt ttcttttcag tctagtaatt    300

aattattttt atattttgta ttatttttag agaggtttga gctgtt                   346

<210> SEQ ID NO 64
<211> LENGTH: 320
<212> TYPE: DNA
<213> ORGANISM: Cyanobacterium sp. PTA-13311

<400> SEQUENCE: 64

gaatatctca tccttagctt ctacttatac cttcagcata gttaaaaatc atccctttat     60

tgatggtaat aaaagaacag gttttattag tggagtaacc tttttaatgc tcaatggttc    120

tcactttact gcttctgaag tggaagtagt acatatcatc caaaccttag ctagtggcag    180

aattaccgag gaagaattac aacaatggtt cgtaaggaaa agtaagcaga tgaataatta    240

aagcatcatt tcatcctcat ttcatattct cctgtcacca tggtatggaa gattaggtaa    300

aaatgaggaa aaagtttatt                                                320

<210> SEQ ID NO 65
<211> LENGTH: 304
```

<212> TYPE: DNA
<213> ORGANISM: Cyanobacterium sp. PTA-13311

<400> SEQUENCE: 65
gcgattatca accacgaaaa catacaatta ttatcaaacc tgctgagaaa ttatccacag 60
aaatagatgt ttctgcgaag ggaaaatggg cttttcattg ccatttaatg tatcacatgg 120
atgtgggaat gtttcggact attaatgtta tttcctaaaa aataatagta ttaaagccta 180
aaatttttat aaaaaaattc atgtctttta ttagggtgag cattcttcct ttatgtctcc 240
ttattttacc tctttagagg taactacaaa cttaatcaaa aaatttagat aattaattat 300
atca 304

<210> SEQ ID NO 66
<211> LENGTH: 309
<212> TYPE: DNA
<213> ORGANISM: Cyanobacterium sp. PTA-13311

<400> SEQUENCE: 66
atacatggtt ggttcactga cttttacccc agttttctct ttgaacaatt ggcataactc 60
tgaaaaaatc agatcgggct tttgttgaat tatttgttca atcaaagcaa aaccgtgatt 120
gtctattttc ttttttttcc caccactcat agataaaaat ttatcccgaa ctcaggttat 180
attaagttcg gatgatcact taagataatt gatcagattg gttaagatag agaaaaattc 240
tttttcatag tgatttcata attgatagtt acaataacga ttattattta gtaaaaagat 300
tttcaaatc 309

<210> SEQ ID NO 67
<211> LENGTH: 330
<212> TYPE: DNA
<213> ORGANISM: Cyanobacterium sp. PTA-13311

<400> SEQUENCE: 67
tggtcaagtt actatatgtt tagaaacaac aaaaaaagaa gtcattataa aaataattga 60
tacaggaatt ggcattaata aagaagaaca aaaattaatt tttaatcgtt tttatcgaat 120
caataaagca agaaatagag agaaaggcag ttgcggatta ggtttagcta ttgcaaatgc 180
gatcgcgctt aatcatggtg gtagaataat tttagaaagt caagaaaatc aaggcagtat 240
ttttaccgtt tatttaccga aaatcatttc atcctaattt catattcttt tgacagaatc 300
aaaggtaaag ataaaaagag agaaacagtc 330

<210> SEQ ID NO 68
<211> LENGTH: 490
<212> TYPE: DNA
<213> ORGANISM: Cyanobacterium sp. PTA-13311

<400> SEQUENCE: 68
catctttact tttgactaac atttcatagg tatcatgacg aaaatttttt agtctgttat 60
atttgttcat gtagagagat tttaatttgt gattatttta ttttctctct atttttcttt 120
tttgtcttgt ccttcctcat ttttctctac atttagtcta aactacagct ctttaatctt 180
cagtttctct ttcctcctct tcctcatcaa ggtaatcatc ccaattaata tcttcttctt 240
gttctaattt gggttgagat tgttgtttat caatcatatt tcatactcct aaaactttct 300
tacttattta tcagttactt tttacccatt tatgcaatag tgtagaaatt tttttcgatc 360
gagttaatta atttttattt caaccatatc taaataattc ttgatggaca ttctagttaa 420

```
ctagaaggtt taagctaaaa ataattattg atattgcctt cggtataact aactatatcc    480

agagaaaaag                                                            490


<210> SEQ ID NO 69
<211> LENGTH: 433
<212> TYPE: DNA
<213> ORGANISM: Cyanobacterium sp. PTA-13311

<400> SEQUENCE: 69

tttatatata aactcgaata aaattatcaa tataaagtca aactatatct atcctatttt     60

aactgctatt ggtaagtccc ttaattagtg ttggggtgaa tagattttaa aagggcaaac    120

ccccctttat cctccctcga gaggggggag ggcaaaaggc aaggggcaag ggaaaaatta    180

agaattaaga attaaaaact ccgaacacct gtaggggcga atagccattc gcttcccctc    240

atccccccat ctccccaaca ccctaagccc ctactcgtta ctcatttatt tacatcattt    300

atttacatca ttaagaaaag taacaaattt tgacaagtag tcttttgaca ggaaaaagca    360

aattctcgaa gatgaaaaca atagaaaaaa attcaatctt acagtaacga tgaaaaaact    420

tttaggctta att                                                        433


<210> SEQ ID NO 70
<211> LENGTH: 306
<212> TYPE: DNA
<213> ORGANISM: Cyanobacterium sp. PTA-13311

<400> SEQUENCE: 70

ctcaagagat agttaaaaaa caaatagctt tagtctatca attaatcgaa ttatttttac     60

aaacaaattt tcataaaccc atagaactag aggaggaagt tatttatgtt taaaaatcta    120

aaagagtttt atattcccct aaaacccccct tagtaagagt gactttttttc atcatttgcc    180

tgtaaattct cctcttttaa taagagagct agggtgtttt aaaagaggat tttattgctt    240

tccaattcta actacttcaa aaacttattt tatactcaat aatttattaa tcaagaggaa    300

attacc                                                                306


<210> SEQ ID NO 71
<211> LENGTH: 13085
<212> TYPE: DNA
<213> ORGANISM: artificial
<220> FEATURE:
<223> OTHER INFORMATION: Synthetically produced plasmid construct #1790
      pABIcyano1-6.8::PnirA-zmPDC(opt3)-TdsrA-PcpcB-ADH242(opt)-TrbcS

<400> SEQUENCE: 71

tcgacaatta ataacttctt cctgtacggg cgaatggcca tttgctccta actaactccg     60

tactgctttg cggaacgagc gtagcgaact ctccgaatta ctaagccttc atccctgata    120

gatgcaaaaa acgaattaaa attatgtgta aaaagaaaat gtgtctttat ttagtagtca    180

aagttacaaa atattaagaa tcaaattaat aatgtattgg gcagttaagt atataagtct    240

ttaaatattt atttgtattc aatatattaa ccgaggacaa attatgaatt cttacactgt    300

tggaacctat ttagcagaac gtttagttca aattggtctc aaacaccatt ttgcagtagc    360

tggtgattat aatttagttt tattggataa cttattgtta aataagaata tggaacaagt    420

gtattgttgt aatgaattaa actgtggttt ttctgctgag ggatatgctc gtgcaaaagg    480

tgctgccgca gcagttgtta cttattctgt tggagcatta agtgcttttg acgctattgg    540

aggtgcttat gcagaaaatt tacctgtaat cttaatctct ggtgcaccca ataacaacga    600
```

```
tcacgctgct ggtcatgtat tgcatcatgc tttaggtaaa accgattatc attaccaatt    660
agaaatggca aaaaatatta ccgctgccgc agaagctatt tatactcccg aagaagcacc    720
tgctaagatc gatcacgtaa ttaaaaccgc tctccgtgag aaaaaacccg tatatttaga    780
aatcgcttgc aatatcgctt ctatgccttg tgcagctcct ggacctgcta gtgctttatt    840
taacgatgaa gcatctgatg aggctagttt aaatgccgct gttgaagaaa ctttgaaatt    900
tattgctaat cgtgataaag tagctgtttt agttggttct aaactccgtg ccgctggtgc    960
agaagaagcg gctgtaaaat tcgcagatgc cttaggaggt gctgttgcca caatggcagc   1020
cgctaaaagt tttttccccg aagaaaatcc tcattacatt ggtacttctt ggggtgaggt   1080
atcttaccct ggtgtagaaa aaaccatgaa ggaagctgat gcagtaattg cattagctcc   1140
tgttttcaat gattactcta ccactggttg gactgatatt ccagacccca aaaaattagt   1200
tttagcagaa cctcgctctg tagttgtgaa tggtgttaga tttcccagtg tacatctcaa   1260
agattattta actcgtttag ctcaaaaagt gagtaaaaag actggcgcac tcgatttctt   1320
taaatcttta aatgctggtg aattaaagaa agcagctcct gctgatccca gtgctccttt   1380
agtgaatgcc gaaatcgcaa gacaagttga agccttgtta actcctaaca ctaccgttat   1440
tgccgagact ggtgatagtt ggttcaatgc tcaacgcatg aaattaccca atggtgctcg   1500
tgttgagtat gaaatgcaat ggggtcacat tggatggtct gttcctgctg catttggata   1560
tgcagttgga gcacctgagc gtagaaacat tttaatggta ggtgatggtt ctttccaact   1620
cactgctcaa gaagttgcac aaatggtacg tttaaaattg cctgttatta tctttctcat   1680
taacaactat ggttacacca ttgaagttat gattcatgat ggtccttata ataacattaa   1740
gaattgggat tacgcaggtt taatggaggt atttaacggt aatggtggat acgacagtgg   1800
agcaggtaaa ggattaaaag ctaaaacagg aggtgagtta gctgaagcaa ttaaagtagc   1860
tttagccaat acagatggtc ctaccttaat cgaatgtttc attggacgtg aagattgtac   1920
tgaagagtta gttaaatggg gaaagcgtgt tgccgctgca aattctcgta aacctgtaaa   1980
caaactcttg tagttaggat ccagcaaggt ttcatcccga ccccctcagg gtcgggattt   2040
ttttattgtg agctcaactt tagatattcg tagttggcaa tgtcgtaaat gcggaacaat   2100
acatggaaaa catatagatt tgtaatgaga aaaagtgtaa acaaatatta agaaaaagat   2160
cagaaaaatt taacaacacg taataaaaaa atgcgtcact acgggttata aatttacatg   2220
aaaggttaaa acacttttct gagacgattt tgataaaaaa gttgtcaaaa aattaagttt   2280
ctttacaaat gcttaacaaa aacttggttt taagcacaaa ataagagaga ctaatttgca   2340
gaagttttac aaggaaatct tgaagaaaaa gatctaagta aaacgactct gtttaaccaa   2400
aatttaacaa atttaacaaa acaaactaaa tctattagga gattaactac atatgactac   2460
cgctactaaa tttaaagcat acgccgcatt aaattctggt gaaaaattac agccctggga   2520
atacgaacct gaacctttac aggttgatga ggttgagatc cgtgtaaccc ataacggttt   2580
atgtcatact gatttacaca tgcgtgataa tgattggaac gtaagtcaat atcctttagt   2640
acccggtcac gaagtagttg gtgaggttac cgaggttggt gaaaaagtaa ccagtttaca   2700
caaaggagac agaattggtg taggatggat tagaaattct tgtcgttctt gtgatcactg   2760
tttacaagga gaggaaaaca tctgtcgtga aggatacact ggtttaattg ttggacacca   2820
cggtggtttc gctgatcgtt tacgtgtacc tgctgatttc acctacaaaa ttcctgatgc   2880
attagattct gcctctgccg ctcccttatt atgtgctggt attactgttt atacccccctt   2940
aagaacttac atcaaacacc ccggtatgaa agttggtgta atgggaattg gtggtttagg   3000
```

tcatttagct attaaatttg ctagagctat gggagctgaa gtaactgcat tttctacttc 3060
tttaaacaaa caagaacagg caaaagagtt tggagcacac aattttcagc aatggggaac 3120
tgctgaagag atgaaagcta ttgctggttc tttcgattta gttttatcta ctatctctag 3180
tgaaactgat tgggatgctg ctttctcttt attagctaac aatggtgtat tatgttttgt 3240
tggtattcct gtttctacct taaatattcc tttaatccct ttaatctttg gtcaaaaagc 3300
tgtagtagga agtattgttg gtggaagacg ttttatggct gagatgttag aatttgctgc 3360
cgttaatcag atcaaaccca tgattgagac tatgccttta agtcaaatca acgaggctat 3420
ggataaagtt gcagctaatc aagcccgtta tcgtattgta ttattagcag actaactaga 3480
tctacttcta aactgaaaca aatttgaggg taggcttcat tgtctgccct tattttttta 3540
tttaggaaaa gtgaacagac taaagagtgt tggctctatt gctttgagta tgtaaattag 3600
gcgttgctga attaaggtat gatttttgac ccctgcagga tcatcttgct gaaaaactcg 3660
agcgctcgtt ccgcaaagcg gtacggagtt agttaggggc taatgggcat tctcccgtac 3720
aggaaagagt tagaagttat taattatcaa caattctcct ttgcctagtg catcgttacc 3780
tttttaatta aaacataagg aaaactaata atcgtaataa tttaacctca aagtgtaaag 3840
aaatgtgaaa ttctgacttt tataacgtta aagagggaaa aattagcagt ttaaaatacc 3900
tagagaatag tctggggtaa gcatagagaa ttagattagt taagttaatc aaattcagaa 3960
aaaataataa tcgtaaatag ttaatctggg tgtatagaaa atgatcccct tcatgataag 4020
atttaaactc gaaaagcaaa agccaaaaaa ctaacttcca ttaaaagaag ttgttacata 4080
taacgctata aagaaaattt atatatttgg aggataccaa ccatgtctca tattcaacgt 4140
gaaactagtt gttctcgccc tcgtttaaat tctaatatgg atgccgattt atatggttat 4200
aaatgggctc gtgataatgt tggtcaatct ggtgctacta tttatcgttt atatggtaaa 4260
cctgatgctc ctgaattatt cttgaaacat ggtaaaggtt ctgttgctaa tgatgttact 4320
gatgaaatgg ttcgtttaaa ctggttgact gaatttatgc ctttacctac tattaaacat 4380
tttattcgta ctcccgatga tgcttggtta ttaactactg ctattcctgg taaaactgct 4440
tttcaagttt tagaagaata tcctgattct ggtgaaaata ttgttgatgc tttagctgtt 4500
tttttacgtc gtttacattc tattcccgtt tgtaattgtc cttttaattc tgatcgtgtt 4560
tttcgtttag ctcaagctca atctcgtatg aataatggtt tagttgatgc ttctgatttt 4620
gatgatgaac gtaatggttg gcctgttgaa caagtttgga aagaaatgca caaattgtta 4680
cctttttctc ctgattctgt tgttactcat ggtgattttt ctttagataa tttgatcttt 4740
gatgaaggta aattgattgg ttgtattgat gttggtcgtg ttggtattgc tgatcgttat 4800
caagatttag ctattttatg gaattgttta ggtgaatttt ctccttcttt acagaaacgt 4860
ttatttcaga aatatggtat tgataatcct gatatgaaca agttacaatt tcatttaatg 4920
ttggacgagt tcttttaaga attaattcat gaccaaaatc ccttaacgtg agttttcgtt 4980
ccactgagcg tcagaccccg tagaaaagat caaaggatct tcttgagatc cttttttttct 5040
gcgcgtaatc tgctgctatt taaattacgt acacgtgtta ttactttgtt aacgacaatt 5100
gtcttaatta actgggcctc atgggccttc cgctcactgc ccgctttcca gtcgggaaac 5160
ctgtcgtgcc agctctgcag atgacggtga aaacctctga cacatgcagc tcccggagac 5220
ggtcacagct tgtctgtaag cggatgccgg gagcagacaa gcccgtcagg gcgcgtcagc 5280
gggtgttggc gggtgtcggg gcgcagccat gacccagtca cgtagcgata gcggagtgta 5340

```
tactggctta actatgcggc atcagagcag attgtactga gagtgcacca tatgcggtgt   5400
gaaataccgc acagatgcgt aaggagaaaa taccgcatca ggcgctcttc cgcttcctcg   5460
ctcactgact cgctgcgctc ggtcgttcgg ctgcggcgag cggtatcagc tcactcaaag   5520
gcggtaatac ggttatccac agaatcaggg gataacgcag gaaagaacat gtgagcaaaa   5580
ggccagcaaa aggccaggaa ccgtaaaaag gccgcgttgc tggcgttttt ccataggctc   5640
cgcccccctg acgagcatca caaaaatcga cgctcaagtc agaggtggcg aaacccgaca   5700
ggactataaa gataccaggc gtttccccct ggaagctccc tcgtgcgctc tcctgttccg   5760
accctgccgc ttaccggata cctgtccgcc tttctccctt cgggaagcgt ggcgctttct   5820
catagctcac gctgtaggta tctcagttcg gtgtaggtcg ttcgctccaa gctgggctgt   5880
gtgcacgaac cccccgttca gcccgaccgc tgcgccttat ccggtaacta tcgtcttgag   5940
tccaacccgg taagacacga cttatcgcca ctggcagcag ccactggtaa caggattagc   6000
agagcgaggt atgtaggcgg tgctacagag ttcttgaagt ggtggcctaa ctacggctac   6060
actagaagga cagtatttgg tatctgcgct ctgctgaagc cagttacctt cggaaaaaga   6120
gttggtagct cttgatccgg caaacaaacc accgctggta gcggtggttt ttttgtttgc   6180
aagcagcaga ttacgcgcag aaaaaaagga tctcaagaag atcctttgat cttttctact   6240
gcagaagctt gttagacacc ctgtcatgta ttttatatta tttatttcac catacggatt   6300
aagtgaaacc taatgaaaat agtactttcg gagctttaac tttaatgaag gtatgttttt   6360
ttatagacat cgatgtctgg tttaacaata ggaaaaagta gctaaaactc ccatgaatta   6420
aagaaataac aaggtgtcta acaacctgtt attaagaatg ttagaaaaga cttaacattt   6480
gtgttgagtt tttatagaca ttggtgtcta gacatacggt agataaggtt tgctcaaaaa   6540
taaaataaaa aaagattgga ctaaaaaaca tttaatttag tacaatttaa ttagttattt   6600
tttcgtctca aattttgctt tgttgagcag aaatttagat aaaaaaatcc ccgtgatcag   6660
attacaatgt cgttcattgt acgatgtgtc gaaaaatctt tacgacactc taaactgacc   6720
acacgggga aaaagaaaac tgaactaata acatcatgat actcggaaaa cctagcaatt   6780
ctcaacccct aaacaaaaga aacttccaaa accctgacca tataaaggag tggcaacaat   6840
cagcaatcag tcaagatttg atagcagaaa atcttgtatc ggttgctaat ggttttgatg   6900
tactatttat cggcaataaa taccgaacta acacgggtgt tctgtcacgg cacatattaa   6960
actcctattc tcatttagaa gatggtggtt cgtatggtag aacatttgac ccatttacca   7020
ataaagaaat gcagtgggtt caatttaaac cgaatagacc aagaaaaggt tctactggta   7080
aggtaatcaa atatgaatcg ccaaaaggtg aacctacaag agttctaatg ccgtttgtgc   7140
ctatgaaaat atggcaacgg attagcgata agttcggagt accgattaat ccgaaaaaag   7200
atactcactt ttgggaatgg gtaaagaata atccatcgat accgattgcc attacagaag   7260
gaaataaaaa agctaattgc ctattatcct atggctatcc tgctattgcc tttgtaggca   7320
tttggaacgg attagagaaa ataaatgatt tctcgaagga aaagcagtta aaagaggatt   7380
tgaaatggtt gttatccaac ggcaaccgaa atattaatat catctttgac caagaccaga   7440
aacaaaaaac tgtaattaat gtaaacaaag ctattttcgc tttatcttct ctaataagta   7500
gaaatggtca taaagttaat attgtgcaat ggttgccgtc aaaaggtaaa ggaatagatg   7560
attatttggt agctttacct tttgagaaaa gagaaaatca tttagacaac ttaattaaaa   7620
ttgcaccatc atttaatttt tggtcaacta aatacttatt caagtgtcgt aaaccagatt   7680
taaccgtaaa ttgccgttat ttgagcgatg cagtaaaaga attacctcaa gaggatatag   7740
```

```
cattaatagc acctcacggc acgggtaaaa cttcattagt agctactcac gttaagaatc   7800
ggagttatca cggaaggaaa actatttcat tggtgcatct tgaaagttta gccaaagcta   7860
atggcaacgc acttggatta tattaccgaa ccgaaaataa tattgaaaag caatatcttg   7920
gatttagctt atgtgtagat agttgccgtg ataagattaa cggcattaca actgatatta   7980
tttcaggtca agattattgc cttttcattg atgaaattga ccaagtaatt ccacacatcc   8040
ttaacagtga aactgaagta agtaagtata gatgcaccat cattgacact ttttctgaac   8100
tggtgagaaa tgctgaacag gtcattattg ctgatgctga tttatccgat gtgacgattg   8160
acctaataga aaacatcaga ggtaaaaaac tatatgtaat caagaatgaa tatcagtatc   8220
agggaatgac ttttaacgcc gttggttcac cattagaaat gatggcaatg atgggaaaat   8280
cggtgtcaga aggcaagaaa ttatttatta acaccacatc ccaaaaggca aaaagtaagt   8340
acggcacaat cgctcttgag tcttatattt ttggtctaaa taaagaagca aagatattaa   8400
gaatagactc tgaaaccact aaaaaccctg aacatccagc ctataaaatc attgaccaag   8460
acttaaataa tatcctcaaa gattatgatt atgtcattgc ctcaccttgc cttcaaacag   8520
gtgtcagtat taccttaaaa gggcattttg accagcaatt taacttttcc agtggaaaca   8580
ttacacctca ttgcttttta cagcaaatgt ggcggttgag ggatgcagaa attgaaagat   8640
tctattatgt gccgaactca tctaacctca atctcattgg gaataagtca agttcaccat   8700
cagaccttct aaagagcaat aacaagatgg caacggcaac ggttaacctt ttgggtagaa   8760
tcgactccga atattcccta gagtatgaat cgcacggcat ttggcttgag acgtgggcaa   8820
aattatcagc acggcataac agttcaatgc gttgttactc tgaaattctt acctatctaa   8880
ttacgtctca agggcataaa ttaaatatca acattccctc acctcttgca gatattaaga   8940
agctaaatga tgaggtaagt agtaacaggg aaaaggtaaa aaatgagaga tactctcaga   9000
ggttaaactc accagatatt aacgatgcag aagctaccat actcgaatct aaagagcaaa   9060
aaatcggatt gactctcaat gagagatgca ccctagaaaa gcataaagtt aagaagcggt   9120
atgggaatgt aaagatggat attctcacct ttgatgatga tggactatac cccaaactca   9180
gactatttta ttacctcacc atcggtaaac ctcatctcaa ggctaatgac agaaaagcta   9240
ttgccaaaat gggcaatgac aataaaggca agattctatc aaaagactta gttaataaaa   9300
cttactccgc tcgtgtgaag gtcttagaga ttcttaaact aactgacttt atcgacaatc   9360
ttagagatga actcttaata actcccaata atccagctat caccgatttt aataatcttc   9420
tgctaagagc taagaaggat ttaagagtat taggagtcaa catcggaaaa tatccaatgg   9480
ccaacattaa tgccgtactt actctcattg gtcacaaact ttctgtaatg agagatgagt   9540
tcggaaaaga gaaaaggata aaagtagatg gtaaatcata ccgatgttat caacttgaaa   9600
cattaccaga ttttaccaat gatactcttg actactggtt agaaaatgat agccaaaaag   9660
aagtaacagc aacagaaaat tactccgaaa attttaaccc ttcaaatagc tacaatccag   9720
acagtaagac actttcagag ggtgcaaatt tcctatatat aaataaagaa gaattgcatc   9780
caaataaatt gcacctagaa ataaaagaag gtgctgaact ttttttattc ggggtaaagg   9840
tgattgtgaa aggaatcttg gacggggcag taactatatt ctctatgggt caagaatacg   9900
atttatccct caatgaacta gaggggatgt taacatcatg aactttacaa gaatcttttt   9960
aaagggcgat cgcaccatgt taaatgatgg tacatttgtt cagatatttg atatttacca  10020
tgaccacgca ttgggagtga cccttgacct taagacagaa aaaattattt ccgatgatgt  10080
```

-continued

```
tagggtaatt actgtcaaag acttattgtt cgatggcact tataaagggg taaaatcttt  10140
tatgcccgat aatgcccgat aatgcccgat tgatgctaca aaatcccata atcataagcg  10200
ataatcccct aatagcttgt aattcttgaa ccgtagcgat tttagagtat tccaaaaaga  10260
agaaataaac accgcaaaat gtcgtatttc acatatataa accaaggttt tttgccctaa  10320
aatctttatg tttgtagtgt gatgttgggt caaaatggtc agaaaagttg caaggttttt  10380
atggatgctt acgcgcgcga ggggtaagca tccccaaata gttactttat cctagtccat  10440
gcccatttat tgccgtcccg ttcggcttta aaaaagtgcc aaaactcaca aggtgcaata  10500
aaaagttctg tacctttcgc aaccctagat aatctttcaa cagttacttt ttttcctatt  10560
atctcggtac aaagtttggc tagtttctct tttccctctt tttcaatcaa gccttcttgt  10620
atgcccaact cattgattaa tctctctatt tttaccatta tttcccgttc aggtagttta  10680
tcccctaaat cttcatcggg gggcaatgta gggcattctg aaggggcttt ttcttctgtc  10740
tggacattat ctaatattga agtaaccaaa ctatcttcag ttttttctat tcctattaat  10800
tcatattcgg ttactgtatc cgtatcaata tccgaataac tatctttatc cgtattagct  10860
attcggttaa gtttatccgt taactcagaa acaagactat atagcggttt tagcttttct  10920
tctatcctgt tatctaatac ggataagttt atacggttat cattatccgt attagtatca  10980
ttgggctttt ttggtagttc tacccccctca taaaccgctt ttattcccaa ttccaacaga  11040
ctgataacag tatcctttat aatgggtttt ttgctgatat ggtgaacttt tgccccttcc  11100
atcattgcga tactttctat ctcactcatc aacttatcgc ttaagtgaat ctcgtatctg  11160
tttaatccct tactggtttt attcatatcc gtttacttta ttcggttaac aattctattt  11220
tatacgaata aaatattata cggttaactt tatacgttta actattttat ctatacggat  11280
aacagtaata agttattcgt attagttata cgtttacttt tatccaaata aaattagtgc  11340
atttaaacta aaagaatgat tttatcggag ttgatagcat tggattaacc taaagatgtt  11400
tataagctat atctgataag tatttaaggt tattttgtta ttctgtttat tgacattatc  11460
agaataaaag aatagaatat aattgttgag agataagagg tttaagtgat tatggttaag  11520
aagttagttg gttatgtcag ggtcagtagt gaatcgcaag aggataacac tagcttacag  11580
aatcagatag agagaattga agcatattgt atggcttttg gttatgagtt ggtaaaaata  11640
ttcaaagagg ttgccactgg tacaaaagca gatattgaaa cccgtcctat ttttaatgaa  11700
gctatagaat acttgaaaca ggataatgct aatggaatta ttgccttgaa gctagaccga  11760
atcgcacgga atgctttaga tgtattgcgt ttggttcgtg aaaccttaga accacaaaat  11820
aaaatgttag tgttactaga tattcaggta gatacttcga caccttcagg aaaaatgatt  11880
ttaactgtaa tgagtgccgt tgctgaactc gaaagagaca tgatctatga tcgcactcag  11940
gggggtagaa agactaaagc ccaaaagggc gggtatgcct acgggaaacc taaatttggc  12000
tataagactg aagaaaagga actaaaagaa gattcagcac aacaggaaac tattaaacta  12060
attaagagac accgtaggtc agggaaaagc taccagaaaa tagctgatta tctcaatgcc  12120
caaagtattc ccactaaaca aggtaagaaa tggagttcta gcgtcgtcta tcgaatctgt  12180
caggaaaaag ctggttaagt ctgtttatag atatttagaa tttattgaat aaaaatagta  12240
tgaacaataa atatttatgg actaaccacg ctcggaaacg tttaactgaa cgatgggaaa  12300
taaaagaatc atgggttatt gataccatcg aaaatcctga acgttcagaa tttattgttg  12360
atgagtcagg ggaaaaatat cattactata aaagaatagc taagtttaag aatagagtgt  12420
tagaagtgat aacttctgcc aactcaacac ccacaagaat aataaccttt tactttaacc  12480
```

gtaacatgag gaaaaattta tgattgttac ttacgataat gaagttgacg caatttattt 12540
taagttaacg gaaaataaaa ttgatagcac cgaacctcaa acagacagga ttatcattga 12600
ttacgatgaa agtaataata ttgttggcat tgaggtatta gattttaatt atcttgtcaa 12660
gaaaggttta accgttgctg atttaccttt ttctgaagat gaaagattaa cagcttctca 12720
atattttaat tttcctgttg ctatctaatc cagaaggggc aataatcccc ttctttcatc 12780
gagttagact taatatcaca aaagtcattt tcattttacc gtttcttttc cacagcgtcc 12840
gtacgcccct cgttaaatct caaaaccgac aatttatgat gtttataaaa agttactcac 12900
tttaataagt atttatactc attaaagggt tattcttttt ttgtagcctg ataggttggg 12960
aaggaatatt tcagattatc agatttgttg aatatttttc gtcagatacg caaaccttac 13020
aaacataatt aacaactgaa actattgata tgtctaggtt ttagctctat cacaggttgg 13080
atctg 13085

<210> SEQ ID NO 72
<211> LENGTH: 13082
<212> TYPE: DNA
<213> ORGANISM: artificial
<220> FEATURE:
<223> OTHER INFORMATION: Synthetically produced plasmid construct #1791
pABIcyano1-6.8::PnirA-zmPDC(opt3)-TdsrA-PcpcB-ADH111(opt)-TrbcS

<400> SEQUENCE: 72
tcgacaatta ataacttctt cctgtacggg cgaatggcca tttgctccta actaactccg 60
tactgctttg cggaacgagc gtagcgaact ctccgaatta ctaagccttc atccctgata 120
gatgcaaaaa acgaattaaa attatgtgta aaaagaaaat gtgtctttat ttagtagtca 180
aagttacaaa atattaagaa tcaaattaat aatgtattgg gcagttaagt atataagtct 240
ttaaatattt atttgtattc aatatattaa ccgaggacaa attatgaatt cttacactgt 300
tggaacctat ttagcagaac gtttagttca aattggtctc aaacaccatt ttgcagtagc 360
tggtgattat aatttagttt tattggataa cttattgtta aataagaata tggaacaagt 420
gtattgttgt aatgaattaa actgtggttt ttctgctgag ggatatgctc gtgcaaaagg 480
tgctgccgca gcagttgtta cttattctgt tggagcatta agtgcttttg acgctattgg 540
aggtgcttat gcagaaaatt tacctgtaat cttaatctct ggtgcaccca ataacaacga 600
tcacgctgct ggtcatgtat tgcatcatgc tttaggtaaa accgattatc attaccaatt 660
agaaatggca aaaaatatta ccgctgccgc agaagctatt tatactcccg aagaagcacc 720
tgctaagatc gatcacgtaa ttaaaaccgc tctccgtgag aaaaaacccg tatatttaga 780
aatcgcttgc aatatcgctt ctatgccttg tgcagctcct ggacctgcta gtgctttatt 840
taacgatgaa gcatctgatg aggctagttt aaatgccgct gttgaagaaa ctttgaaatt 900
tattgctaat cgtgataaag tagctgtttt agttggttct aaactccgtg ccgctggtgc 960
agaagaagcg gctgtaaaat tcgcagatgc cttaggaggt gctgttgcca caatggcagc 1020
cgctaaaagt tttttccccg aagaaaatcc tcattacatt ggtacttctt ggggtgaggt 1080
atcttaccct ggtgtagaaa aaaccatgaa ggaagctgat gcagtaattg cattagctcc 1140
tgttttcaat gattactcta ccactggttg gactgatatt ccagacccca aaaaattagt 1200
tttagcagaa cctcgctctg tagttgtgaa tggtgttaga tttcccagtg tacatctcaa 1260
agattattta actcgtttag ctcaaaaagt gagtaaaaag actggcgcac tcgatttctt 1320
taaatcttta aatgctggtg aattaaagaa agcagctcct gctgatccca gtgctccttt 1380

```
agtgaatgcc gaaatcgcaa gacaagttga agccttgtta actcctaaca ctaccgttat   1440
tgccgagact ggtgatagtt ggttcaatgc tcaacgcatg aaattaccca atggtgctcg   1500
tgttgagtat gaaatgcaat ggggtcacat tggatggtct gttcctgctg catttggata   1560
tgcagttgga gcacctgagc gtagaaacat tttaatggta ggtgatggtt ctttccaact   1620
cactgctcaa gaagttgcac aaatggtacg tttaaaattg cctgttatta tctttctcat   1680
taacaactat ggttacacca ttgaagttat gattcatgat ggtccttata ataacattaa   1740
gaattgggat tacgcaggtt taatggaggt atttaacggt aatggtggat acgacagtgg   1800
agcaggtaaa ggattaaaag ctaaaacagg aggtgagtta gctgaagcaa ttaaagtagc   1860
tttagccaat acagatggtc ctaccttaat cgaatgtttc attggacgtg aagattgtac   1920
tgaagagtta gttaaatggg gaaagcgtgt tgccgctgca aattctcgta aacctgtaaa   1980
caaactcttg tagttaggat ccagcaaggt ttcatcccga ccccctcagg gtcgggattt   2040
ttttattgtg agctcaactt tagatattcg tagttggcaa tgtcgtaaat gcggaacaat   2100
acatggaaaa catatagatt tgtaatgaga aaaagtgtaa acaaatatta agaaaaagat   2160
cagaaaaatt taacaacacg taataaaaaa atgcgtcact acgggttata aatttacatg   2220
aaaggttaaa acacttttct gagacgattt tgataaaaaa gttgtcaaaa aattaagttt   2280
ctttacaaat gcttaacaaa aacttggttt taagcacaaa ataagagaga ctaatttgca   2340
gaagttttac aaggaaatct tgaagaaaaa gatctaagta aaacgactct gtttaaccaa   2400
aatttaacaa atttaacaaa acaaactaaa tctattagga gattaactac atatgagtga   2460
aactaaattt aaagcctatg ccgtaatgaa tcctggtgaa aaattacaac cctgggaata   2520
tgaacctgct cctttacagg tagatgaaat tgaagtaaga gttactcaca atggtttatg   2580
tcacactgac ttacacatga gagataatga ctggaatgtt agtgagttcc ccttagtagc   2640
aggtcatgaa gttgttggtg aagtaaccgc tgttggtgaa aaagtaacca gtcgtaaaaa   2700
aggtgataga gttggtgtag gttggattcg taattcttgt cgcgcttgtg accattgttt   2760
acaaggagaa gagaacattt gtagagaggg ttatactggt ttaattgttg gtcatcacgg   2820
tggatttgct gatcgtgtac gtgtacctgc tgacttcact tataaaattc ctgatgcttt   2880
agatagtgca tctgctgctc ctttattatg tgccggtatt accgtttaca ctcctttaag   2940
aacctacatt aaacatcccg gtatgaaagt aggtgttatg ggtattggag gattaggaca   3000
tttagctatt aaatttgctc gtgcaatggg agcagaagtt actgccttta gtaccagtcc   3060
taataaagaa gcccaagcca aagaatttgg tgctcatcat ttccaacaat ggggtactgc   3120
tgaagaaatg aaagctgttg ccggtaattt tgatttagtt ttatctacca tctctgctga   3180
aactgactgg gatgctgcct tctctttatt agcaaataac ggtgttttat gtttcgtagg   3240
tattcccgtt agttctttaa atgttccttt aattccttta attttcggac aaaaatctgt   3300
tgtaggttct gtagttggag gaagaagatt catggcagaa atgttagagt tcgccgctgt   3360
aaatcagatt aaacctatga tcgaaactat gcccttatct caagtaaatg aagctatgga   3420
taaagttgcc gccaataaag ccagatatag aattgtatta ttatctgaat aactagatct   3480
acttctaaac tgaaacaaat ttgagggtag gcttcattgt ctgcccttat ttttttattt   3540
aggaaaagtg aacagactaa agagtgttgg ctctattgct ttgagtatgt aaattaggcg   3600
ttgctgaatt aaggtatgat ttttgacccc tgcaggatca tcttgctgaa aaactcgagc   3660
gctcgttccg caaagcggta cggagttagt taggggctaa tgggcattct cccgtacagg   3720
```

```
aaagagttag aagttattaa ttatcaacaa ttctcctttg cctagtgcat cgttaccttt   3780
ttaattaaaa cataaggaaa actaataatc gtaataattt aacctcaaag tgtaaagaaa   3840
tgtgaaattc tgacttttat aacgttaaag agggaaaaat tagcagttta aaatacctag   3900
agaatagtct ggggtaagca tagagaatta gattagttaa gttaatcaaa ttcagaaaaa   3960
ataataatcg taaatagtta atctgggtgt atagaaaatg atccccttca tgataagatt   4020
taaactcgaa aagcaaaagc caaaaaacta acttccatta aaagaagttg ttacatataa   4080
cgctataaag aaaatttata tatttggagg ataccaacca tgtctcatat tcaacgtgaa   4140
actagttgtt ctcgccctcg tttaaattct aatatggatg ccgatttata tggttataaa   4200
tgggctcgtg ataatgttgg tcaatctggt gctactattt atcgtttata tggtaaacct   4260
gatgctcctg aattattctt gaaacatggt aaaggttctg ttgctaatga tgttactgat   4320
gaaatggttc gtttaaactg gttgactgaa tttatgcctt tacctactat taaacatttt   4380
attcgtactc ccgatgatgc ttggttatta actactgcta ttcctggtaa aactgctttt   4440
caagttttag aagaatatcc tgattctggt gaaaatattg ttgatgcttt agctgttttt   4500
ttacgtcgtt tacattctat tcccgtttgt aattgtcctt ttaattctga tcgtgttttt   4560
cgtttagctc aagctcaatc tcgtatgaat aatggtttag ttgatgcttc tgattttgat   4620
gatgaacgta atggttggcc tgttgaacaa gtttggaaag aaatgcacaa attgttacct   4680
ttttctcctg attctgttgt tactcatggt gatttttctt tagataattt gatctttgat   4740
gaaggtaaat tgattggttg tattgatgtt ggtcgtgttg gtattgctga tcgttatcaa   4800
gatttagcta ttttatggaa ttgtttaggt gaattttctc cttctttaca gaaacgttta   4860
tttcagaaat atggtattga taatcctgat atgaacaagt tacaatttca tttaatgttg   4920
gacgagttct tttaagaatt aattcatgac caaaatccct taacgtgagt tttcgttcca   4980
ctgagcgtca gaccccgtag aaaagatcaa aggatcttct tgagatcctt tttttctgcg   5040
cgtaatctgc tgctatttaa attacgtaca cgtgttatta ctttgttaac gacaattgtc   5100
ttaattaact gggcctcatg ggccttccgc tcactgcccg ctttccagtc gggaaacctg   5160
tcgtgccagc tctgcagatg acggtgaaaa cctctgacac atgcagctcc cggagacggt   5220
cacagcttgt ctgtaagcgg atgccgggag cagacaagcc cgtcagggcg cgtcagcggg   5280
tgttggcggg tgtcggggcg cagccatgac ccagtcacgt agcgatagcg gagtgtatac   5340
tggcttaact atgcggcatc agagcagatt gtactgagag tgcaccatat gcggtgtgaa   5400
ataccgcaca gatgcgtaag gagaaaatac cgcatcaggc gctcttccgc ttcctcgctc   5460
actgactcgc tgcgctcggt cgttcggctg cggcgagcgg tatcagctca ctcaaaggcg   5520
gtaatacggt tatccacaga atcaggggat aacgcaggaa agaacatgtg agcaaaaggc   5580
cagcaaaagg ccaggaaccg taaaaaggcc gcgttgctgg cgtttttcca taggctccgc   5640
ccccctgacg agcatcacaa aaatcgacgc tcaagtcaga ggtggcgaaa cccgacagga   5700
ctataaagat accaggcgtt tccccctgga agctccctcg tgcgctctcc tgttccgacc   5760
ctgccgctta ccggatacct gtccgccttt ctcccttcgg gaagcgtggc gctttctcat   5820
agctcacgct gtaggtatct cagttcggtg taggtcgttc gctccaagct gggctgtgtg   5880
cacgaacccc ccgttcagcc cgaccgctgc gccttatccg gtaactatcg tcttgagtcc   5940
aacccggtaa gacacgactt atcgccactg gcagcagcca ctggtaacag gattagcaga   6000
gcgaggtatg taggcggtgc tacagagttc ttgaagtggt ggcctaacta cggctacact   6060
agaaggacag tatttggtat ctgcgctctg ctgaagccag ttaccttcgg aaaaagagtt   6120
```

```
ggtagctctt gatccggcaa acaaaccacc gctggtagcg gtggtttttt tgtttgcaag   6180
cagcagatta cgcgcagaaa aaaaggatct caagaagatc ctttgatctt ttctactgca   6240
gaagcttgtt agacaccctg tcatgtattt tatattattt atttcaccat acggattaag   6300
tgaaacctaa tgaaaatagt actttcggag ctttaacttt aatgaaggta tgttttttta   6360
tagacatcga tgtctggttt aacaatagga aaaagtagct aaaactccca tgaattaaag   6420
aaataacaag gtgtctaaca acctgttatt aagaatgtta gaaaagactt aacatttgtg   6480
ttgagttttt atagacattg gtgtctagac atacggtaga taaggtttgc tcaaaaataa   6540
aataaaaaaa gattggacta aaaaacattt aatttagtac aatttaatta gttatttttt   6600
cgtctcaaat tttgctttgt tgagcagaaa tttagataaa aaaatccccg tgatcagatt   6660
acaatgtcgt tcattgtacg atgtgtcgaa aaatctttac gacactctaa actgaccaca   6720
cgggggaaaa agaaaactga actaataaca tcatgatact cggaaaacct agcaattctc   6780
aaccccctaaa caaaagaaac ttccaaaacc ctgaccatat aaaggagtgg caacaatcag   6840
caatcagtca agatttgata gcagaaaatc ttgtatcggt tgctaatggt tttgatgtac   6900
tatttatcgg caataaatac cgaactaaca cgggtgttct gtcacggcac atattaaact   6960
cctattctca tttagaagat ggtggttcgt atggtagaac atttgaccca tttaccaata   7020
aagaaatgca gtgggttcaa tttaaaccga atagaccaag aaaaggttct actggtaagg   7080
taatcaaata tgaatcgcca aaaggtgaac ctacaagagt tctaatgccg tttgtgccta   7140
tgaaaatatg gcaacggatt agcgataagt tcggagtacc gattaatccg aaaaaagata   7200
ctcacttttg ggaatgggta aagaataatc catcgatacc gattgccatt acagaaggaa   7260
ataaaaaagc taattgccta ttatcctatg gctatcctgc tattgccttt gtaggcattt   7320
ggaacggatt agagaaaata aatgatttct cgaaggaaaa gcagttaaaa gaggatttga   7380
aatggttgtt atccaacggc aaccgaaata ttaatatcat ctttgaccaa gaccagaaac   7440
aaaaaactgt aattaatgta aacaaagcta ttttcgcttt atcttctcta ataagtagaa   7500
atggtcataa agttaatatt gtgcaatggt tgccgtcaaa aggtaaagga atagatgatt   7560
atttggtagc tttacctttt gagaaaagag aaaatcattt agacaactta attaaaattg   7620
caccatcatt taatttttgg tcaactaaat acttattcaa gtgtcgtaaa ccagatttaa   7680
ccgtaaattg ccgttatttg agcgatgcag taaaagaatt acctcaagag gatatagcat   7740
taatagcacc tcacggcacg ggtaaaactt cattagtagc tactcacgtt aagaatcgga   7800
gttatcacgg aaggaaaact atttcattgg tgcatcttga aagtttagcc aaagctaatg   7860
gcaacgcact tggattatat taccgaaccg aaaataatat tgaaaagcaa tatcttggat   7920
ttagcttatg tgtagatagt tgccgtgata agattaacgg cattacaact gatattattt   7980
caggtcaaga ttattgcctt ttcattgatg aaattgacca agtaattcca cacatcctta   8040
acagtgaaac tgaagtaagt aagtatagat gcaccatcat tgacactttt tctgaactgg   8100
tgagaaatgc tgaacaggtc attattgctg atgctgattt atccgatgtg acgattgacc   8160
taatagaaaa catcagaggt aaaaaactat atgtaatcaa gaatgaatat cagtatcagg   8220
gaatgacttt taacgccgtt ggttcaccat tagaaatgat ggcaatgatg ggaaaatcgg   8280
tgtcagaagg caagaaatta tttattaaca ccacatccca aaaggcaaaa agtaagtacg   8340
gcacaatcgc tcttgagtct tatatttttg gtctaaataa agaagcaaag atattaagaa   8400
tagactctga aaccactaaa aaccctgaac atccagccta taaaatcatt gaccaagact   8460
```

```
taaataatat cctcaaagat tatgattatg tcattgcctc accttgcctt caaacaggtg   8520
tcagtattac cttaaaaggg cattttgacc agcaatttaa cttttccagt ggaaacatta   8580
cacctcattg ctttttacag caaatgtggc ggttgaggga tgcagaaatt gaaagattct   8640
attatgtgcc gaactcatct aacctcaatc tcattgggaa taagtcaagt tcaccatcag   8700
accttctaaa gagcaataac aagatggcaa cggcaacggt taaccttttg ggtagaatcg   8760
actccgaata ttccctagag tatgaatcgc acggcatttg gcttgagacg tgggcaaaat   8820
tatcagcacg gcataacagt tcaatgcgtt gttactctga aattcttacc tatctaatta   8880
cgtctcaagg gcataaatta aatatcaaca ttccctcacc tcttgcagat attaagaagc   8940
taaatgatga ggtaagtagt aacagggaaa aggtaaaaaa tgagagatac tctcagaggt   9000
taaactcacc agatattaac gatgcagaag ctaccatact cgaatctaaa gagcaaaaaa   9060
tcggattgac tctcaatgag agatgcaccc tagaaaagca taaagttaag aagcggtatg   9120
ggaatgtaaa gatggatatt ctcacctttg atgatgatgg actatacccc aaactcagac   9180
tattttatta cctcaccatc ggtaaacctc atctcaaggc taatgacaga aaagctattg   9240
ccaaaatggg caatgacaat aaaggcaaga ttctatcaaa agacttagtt aataaaactt   9300
actccgctcg tgtgaaggtc ttagagattc ttaaactaac tgactttatc gacaatctta   9360
gagatgaact cttaataact cccaataatc cagctatcac cgattttaat aatcttctgc   9420
taagagctaa gaaggattta agagtattag gagtcaacat cggaaaatat ccaatggcca   9480
acattaatgc cgtacttact ctcattggtc acaaactttc tgtaatgaga gatgagttcg   9540
gaaaagagaa aaggataaaa gtagatggta aatcataccg atgttatcaa cttgaaacat   9600
taccagattt taccaatgat actcttgact actggttaga aaatgatagc caaaaagaag   9660
taacagcaac agaaaattac tccgaaaatt ttaacccttc aaatagctac aatccagaca   9720
gtaagacact ttcagagggt gcaaatttcc tatatataaa taaagaagaa ttgcatccaa   9780
ataaattgca cctagaaata aaagaaggtg ctgaactttt tttattcggg gtaaaggtga   9840
ttgtgaaagg aatcttggac ggggcagtaa ctatattctc tatgggtcaa gaatacgatt   9900
tatccctcaa tgaactagag gggatgttaa catcatgaac tttacaagaa tctttttaaa   9960
gggcgatcgc accatgttaa atgatggtac atttgttcag atatttgata tttaccatga  10020
ccacgcattg ggagtgaccc ttgaccttaa gacagaaaaa attatttccg atgatgttag  10080
ggtaattact gtcaaagact tattgttcga tggcacttat aaaggggtaa aatcttttat  10140
gcccgataat gcccgataat gcccgattga tgctacaaaa tcccataatc ataagcgata  10200
atcccctaat agcttgtaat tcttgaaccg tagcgatttt agagtattcc aaaaagaaga  10260
aataaacacc gcaaaatgtc gtatttcaca tatataaacc aaggtttttt gccctaaaat  10320
ctttatgttt gtagtgtgat gttgggtcaa aatggtcaga aaagttgcaa ggtttttatg  10380
gatgcttacg cgcgcgaggg gtaagcatcc ccaaatagtt actttatcct agtccatgcc  10440
catttattgc cgtcccgttc ggctttaaaa aagtgccaaa actcacaagg tgcaataaaa  10500
agttctgtac ctttcgcaac cctagataat ctttcaacag ttactttttt tcctattatc  10560
tcggtacaaa gtttggctag tttctctttt ccctcttttt caatcaagcc ttcttgtatg  10620
cccaactcat tgattaatct ctctattttt accattattt cccgttcagg tagtttatcc  10680
cctaaatctt catcgggggg caatgtaggg cattctgaag ggctttttc ttctgtctgg  10740
acattatcta atattgaagt aaccaaacta tcttcagttt tttctattcc tattaattca  10800
tattcggtta ctgtatccgt atcaatatcc gaataactat ctttatccgt attagctatt  10860
```

```
cggttaagtt tatccgttaa ctcagaaaca agactatata gcggttttag cttttcttct  10920
atcctgttat ctaatacgga taagtttata cggttatcat tatccgtatt agtatcattg  10980
ggcttttttg gtagttctac cccctcataa accgctttta ttcccaattc caacagactg  11040
ataacagtat cctttataat gggtttttttg ctgatatggt gaacttttgc cccttccatc  11100
attgcgatac tttctatctc actcatcaac ttatcgctta agtgaatctc gtatctgttt  11160
aatcccttac tggttttatt catatccgtt tactttattc ggttaacaat tctattttat  11220
acgaataaaa tattatacgg ttaactttat acgtttaact attttatcta tacggataac  11280
agtaataagt tattcgtatt agttatacgt ttacttttat ccaaataaaa ttagtgcatt  11340
taaactaaaa gaatgatttt atcggagttg atagcattgg attaacctaa agatgtttat  11400
aagctatatc tgataagtat ttaaggttat tttgttattc tgtttattga cattatcaga  11460
ataaaagaat agaatataat tgttgagaga taagaggttt aagtgattat ggttaagaag  11520
ttagttggtt atgtcagggt cagtagtgaa tcgcaagagg ataacactag cttacagaat  11580
cagatagaga gaattgaagc atattgtatg gcttttggtt atgagttggt aaaaatattc  11640
aaagaggttg ccactggtac aaaagcagat attgaaaccc gtcctatttt taatgaagct  11700
atagaatact tgaaacagga taatgctaat ggaattattg ccttgaagct agaccgaatc  11760
gcacggaatg ctttagatgt attgcgtttg gttcgtgaaa ccttagaacc acaaaataaa  11820
atgttagtgt tactagatat tcaggtagat acttcgacac cttcaggaaa aatgatttta  11880
actgtaatga gtgccgttgc tgaactcgaa agagacatga tctatgatcg cactcagggg  11940
ggtagaaaga ctaaagccca aaagggcggg tatgcctacg ggaaacctaa atttggctat  12000
aagactgaag aaaaggaact aaaagaagat tcagcacaac aggaaactat taaactaatt  12060
aagagacacc gtaggtcagg gaaaagctac cagaaaatag ctgattatct caatgcccaa  12120
agtattccca ctaaacaagg taagaaatgg agttctagcg tcgtctatcg aatctgtcag  12180
gaaaaagctg gttaagtctg tttatagata tttagaattt attgaataaa aatagtatga  12240
acaataaata tttatggact aaccacgctc ggaaacgttt aactgaacga tgggaaataa  12300
aagaatcatg ggttattgat accatcgaaa atcctgaacg ttcagaattt attgttgatg  12360
agtcagggga aaaatatcat tactataaaa gaatagctaa gtttaagaat agagtgttag  12420
aagtgataac ttctgccaac tcaacaccca caagaataat aaccttttac tttaaccgta  12480
acatgaggaa aaatttatga ttgttactta cgataatgaa gttgacgcaa tttattttaa  12540
gttaacggaa aataaaattg atagcaccga acctcaaaca gacaggatta tcattgatta  12600
cgatgaaagt aataatattg ttggcattga ggtattagat tttaattatc ttgtcaagaa  12660
aggtttaacc gttgctgatt taccttttc tgaagatgaa agattaacag cttctcaata  12720
ttttaatttt cctgttgcta tctaatccag aaggggcaat aatccccttc tttcatcgag  12780
ttagacttaa tatcacaaaa gtcattttca ttttaccgtt tcttttccac agcgtccgta  12840
cgcccctcgt taaatctcaa aaccgacaat ttatgatgtt tataaaaagt tactcacttt  12900
aataagtatt tatactcatt aaagggttat tcttttttg tagcctgata ggttgggaag  12960
gaatatttca gattatcaga tttgttgaat atttttcgtc agatacgcaa accttacaaa  13020
cataattaac aactgaaact attgatatgt ctaggtttta gctctatcac aggttggatc  13080
tg                                                                 13082
```

<210> SEQ ID NO 73

```
<211> LENGTH: 13090
<212> TYPE: DNA
<213> ORGANISM: artificial
<220> FEATURE:
<223> OTHER INFORMATION: Synthetically produced plasmid construct #1792
      pABIcyano1-6.8::PnirA-zmPDC(opt3)-TdsrA-PcpcB-synADH-trbcS
      standard

<400> SEQUENCE: 73

tcgacaatta ataacttctt cctgtacggg cgaatggcca tttgctccta actaactccg     60

tactgctttg cggaacgagc gtagcgaact ctccgaatta ctaagccttc atccctgata    120

gatgcaaaaa acgaattaaa attatgtgta aaaagaaaat gtgtctttat ttagtagtca    180

aagttacaaa atattaagaa tcaaattaat aatgtattgg gcagttaagt atataagtct    240

ttaaatattt atttgtattc aatatattaa ccgaggacaa attatgaatt cttacactgt    300

tggaacctat ttagcagaac gtttagttca aattggtctc aaacaccatt ttgcagtagc    360

tggtgattat aatttagttt tattggataa cttattgtta aataagaata tggaacaagt    420

gtattgttgt aatgaattaa actgtggttt ttctgctgag ggatatgctc gtgcaaaagg    480

tgctgccgca gcagttgtta cttattctgt tggagcatta agtgcttttg acgctattgg    540

aggtgcttat gcagaaaatt tacctgtaat cttaatctct ggtgcaccca ataacaacga    600

tcacgctgct ggtcatgtat tgcatcatgc tttaggtaaa accgattatc attaccaatt    660

agaaatggca aaaaatatta ccgctgccgc agaagctatt tatactcccg aagaagcacc    720

tgctaagatc gatcacgtaa ttaaaaccgc tctccgtgag aaaaaacccg tatatttaga    780

aatcgcttgc aatatcgctt ctatgccttg tgcagctcct ggacctgcta gtgctttatt    840

taacgatgaa gcatctgatg aggctagttt aaatgccgct gttgaagaaa ctttgaaatt    900

tattgctaat cgtgataaag tagctgtttt agttggttct aaactccgtg ccgctggtgc    960

agaagaagcg gctgtaaaat tcgcagatgc cttaggaggt gctgttgcca caatggcagc   1020

cgctaaaagt tttttccccg aagaaaatcc tcattacatt ggtacttctt ggggtgaggt   1080

atcttaccct ggtgtagaaa aaaccatgaa ggaagctgat gcagtaattg cattagctcc   1140

tgttttcaat gattactcta ccactggttg gactgatatt ccagacccca aaaaattagt   1200

tttagcagaa cctcgctctg tagttgtgaa tggtgttaga tttcccagtg tacatctcaa   1260

agattattta actcgtttag ctcaaaaagt gagtaaaaag actggcgcac tcgatttctt   1320

taaatcttta aatgctggtg aattaaagaa agcagctcct gctgatccca gtgctccttt   1380

agtgaatgcc gaaatcgcaa gacaagttga agccttgtta actcctaaca ctaccgttat   1440

tgccgagact ggtgatagtt ggttcaatgc tcaacgcatg aaattaccca atggtgctcg   1500

tgttgagtat gaaatgcaat ggggtcacat tggatggtct gttcctgctg catttggata   1560

tgcagttgga gcacctgagc gtagaaacat tttaatggta ggtgatggtt ctttccaact   1620

cactgctcaa gaagttgcac aaatggtacg tttaaaattg cctgttatta tctttctcat   1680

taacaactat ggttacacca ttgaagttat gattcatgat ggtccttata ataacattaa   1740

gaattgggat tacgcaggtt taatggaggt atttaacggt aatggtggat acgacagtgg   1800

agcaggtaaa ggattaaaag ctaaaacagg aggtgagtta gctgaagcaa ttaaagtagc   1860

tttagccaat acagatggtc ctaccttaat cgaatgtttc attggacgtg aagattgtac   1920

tgaagagtta gttaaatggg gaaagcgtgt tgccgctgca aattctcgta aacctgtaaa   1980

caaactcttg tagttaggat ccagcaaggt ttcatcccga ccccctcagg gtcgggattt   2040

ttttattgtg agctcaactt tagatattcg tagttggcaa tgtcgtaaat gcggaacaat   2100
```

```
acatggaaaa catatagatt tgtaatgaga aaaagtgtaa acaaatatta agaaaaagat   2160
cagaaaaatt taacaacacg taataaaaaa atgcgtcact acgggttata aatttacatg   2220
aaaggttaaa acacttttct gagacgattt tgataaaaaa gttgtcaaaa aattaagttt   2280
ctttacaaat gcttaacaaa aacttggttt taagcacaaa ataagagaga ctaatttgca   2340
gaagttttac aaggaaatct tgaagaaaaa gatctaagta aaacgactct gtttaaccaa   2400
aatttaacaa atttaacaaa acaaactaaa tctattagga gattaactac atatgattaa   2460
agcctacgct gccctggaag ccaacggaaa actccaaccc tttgaatacg accccggtgc   2520
cctgggtgct aatgaggtgg agattgaggt gcagtattgt ggggtgtgcc acagtgattt   2580
gtccatgatt aataacgaat ggggcatttc caattacccc ctagtgccgg gtcatgaggt   2640
ggtgggtact gtggccgcca tgggcgaagg ggtgaaccat gttgaggtgg gggatttagt   2700
ggggctgggt tggcattcgg gctactgcat gacctgccat agttgtttat ctggctacca   2760
caacctttgt gccacggcgg aatcgaccat tgtgggccac tacggtggct ttggcgatcg   2820
ggttcgggcc aagggagtca gcgtggtgaa attacctaaa ggcattgacc tagccagtgc   2880
cgggcccctt ttctgtggag gaattaccgt tttcagtcct atggtggaac tgagtttaaa   2940
gcccactgca aaagtggcag tgatcggcat tgggggcttg ggccatttag cggtgcaatt   3000
tctccgggcc tggggctgtg aagtgactgc ctttacctcc agtgccagga agcaaacgga   3060
agtgttggaa ttgggcgctc accacatact agattccacc aatccagagg cgatcgccag   3120
tgcggaaggc aaatttgact atattatctc cactgtgaac ctgaagcttg actggaactt   3180
atacatcagc accctggcgc cccagggaca tttccacttt gttggggtgg tgttggagcc   3240
tttggatcta aatctttttc cccttttgat gggacaacgc tccgtttctg cctccccagt   3300
gggtagtccc gccaccattg ccaccatgtt ggactttgct gtgcgccatg acattaaacc   3360
cgtggtggaa caatttagct ttgatcagat caacgaggcg atcgcccatc tagaaagcgg   3420
caaagcccat tatcgggtag tgctcagcca tagtaaaaat tagctctgca aaggttgctt   3480
ctagatctac ttctaaactg aaacaaattt gagggtaggc ttcattgtct gcccttattt   3540
ttttatttag gaaaagtgaa cagactaaag agtgttggct ctattgcttt gagtatgtaa   3600
attaggcgtt gctgaattaa ggtatgattt ttgacccctg caggatcatc ttgctgaaaa   3660
actcgagcgc tcgttccgca aagcggtacg gagttagtta ggggctaatg ggcattctcc   3720
cgtacaggaa agagttagaa gttattaatt atcaacaatt ctcctttgcc tagtgcatcg   3780
ttaccttttt aattaaaaca taaggaaaac taataatcgt aataatttaa cctcaaagtg   3840
taaagaaatg tgaaattctg acttttataa cgttaaagag ggaaaaatta gcagtttaaa   3900
atacctagag aatagtctgg ggtaagcata gagaattaga ttagttaagt taatcaaatt   3960
cagaaaaaat aataatcgta aatagttaat ctgggtgtat agaaaatgat ccccttcatg   4020
ataagattta aactcgaaaa gcaaaagcca aaaaactaac ttccattaaa agaagttgtt   4080
acatataacg ctataaagaa aatttatata tttggaggat accaaccatg tctcatattc   4140
aacgtgaaac tagttgttct cgccctcgtt taaattctaa tatggatgcc gatttatatg   4200
gttataaatg ggctcgtgat aatgttggtc aatctggtgc tactatttat cgtttatatg   4260
gtaaacctga tgctcctgaa ttattcttga aacatggtaa aggttctgtt gctaatgatg   4320
ttactgatga aatggttcgt ttaaactggt tgactgaatt tatgccttta cctactatta   4380
aacattttat tcgtactccc gatgatgctt ggttattaac tactgctatt cctggtaaaa   4440
```

-continued

```
ctgcttttca agttttagaa gaatatcctg attctggtga aaatattgtt gatgctttag   4500
ctgttttttt acgtcgttta cattctattc ccgtttgtaa ttgtcctttt aattctgatc   4560
gtgtttttcg tttagctcaa gctcaatctc gtatgaataa tggtttagtt gatgcttctg   4620
attttgatga tgaacgtaat ggttggcctg ttgaacaagt ttggaaagaa atgcacaaat   4680
tgttaccttt ttctcctgat tctgttgtta ctcatggtga tttttcttta gataatttga   4740
tctttgatga aggtaaattg attggttgta ttgatgttgg tcgtgttggt attgctgatc   4800
gttatcaaga tttagctatt ttatggaatt gtttaggtga attttctcct tctttacaga   4860
aacgtttatt tcagaaatat ggtattgata atcctgatat gaacaagtta caatttcatt   4920
taatgttgga cgagttcttt taagaattaa ttcatgacca aaatccctta acgtgagttt   4980
tcgttccact gagcgtcaga ccccgtagaa aagatcaaag gatcttcttg agatcctttt   5040
tttctgcgcg taatctgctg ctatttaaat tacgtacacg tgttattact ttgttaacga   5100
caattgtctt aattaactgg gcctcatggg ccttccgctc actgcccgct ttccagtcgg   5160
gaaacctgtc gtgccagctc tgcagatgac ggtgaaaacc tctgacacat gcagctcccg   5220
gagacggtca cagcttgtct gtaagcggat gccgggagca gacaagcccg tcagggcgcg   5280
tcagcgggtg ttggcgggtg tcggggcgca gccatgaccc agtcacgtag cgatagcgga   5340
gtgtatactg gcttaactat gcggcatcag agcagattgt actgagagtg caccatatgc   5400
ggtgtgaaat accgcacaga tgcgtaagga gaaaataccg catcaggcgc tcttccgctt   5460
cctcgctcac tgactcgctg cgctcggtcg ttcggctgcg gcgagcggta tcagctcact   5520
caaaggcggt aatacggtta tccacagaat caggggataa cgcaggaaag aacatgtgag   5580
caaaaggcca gcaaaaggcc aggaaccgta aaaaggccgc gttgctggcg tttttccata   5640
ggctccgccc ccctgacgag catcacaaaa atcgacgctc aagtcagagg tggcgaaacc   5700
cgacaggact ataaagatac caggcgtttc cccctggaag ctccctcgtg cgctctcctg   5760
ttccgaccct gccgcttacc ggatacctgt ccgcctttct cccttcggga agcgtggcgc   5820
tttctcatag ctcacgctgt aggtatctca gttcggtgta ggtcgttcgc tccaagctgg   5880
gctgtgtgca cgaacccccc gttcagcccg accgctgcgc cttatccggt aactatcgtc   5940
ttgagtccaa cccggtaaga cacgacttat cgccactggc agcagccact ggtaacagga   6000
ttagcagagc gaggtatgta ggcggtgcta cagagttctt gaagtggtgg cctaactacg   6060
gctacactag aaggacagta tttggtatct gcgctctgct gaagccagtt accttcggaa   6120
aaagagttgg tagctcttga tccggcaaac aaaccaccgc tggtagcggt ggtttttttg   6180
tttgcaagca gcagattacg cgcagaaaaa aaggatctca agaagatcct ttgatctttt   6240
ctactgcaga agcttgttag acaccctgtc atgtatttta tattatttat ttcaccatac   6300
ggattaagtg aaacctaatg aaaatagtac tttcggagct ttaactttaa tgaaggtatg   6360
tttttttata gacatcgatg tctggtttaa caataggaaa aagtagctaa aactcccatg   6420
aattaaagaa ataacaaggt gtctaacaac ctgttattaa gaatgttaga aaagacttaa   6480
catttgtgtt gagtttttat agacattggt gtctagacat acggtagata aggtttgctc   6540
aaaaataaaa taaaaaaaga ttggactaaa aaacatttaa tttagtacaa tttaattagt   6600
tattttttcg tctcaaattt tgctttgttg agcagaaatt tagataaaaa aatccccgtg   6660
atcagattac aatgtcgttc attgtacgat gtgtcgaaaa atctttacga cactctaaac   6720
tgaccacacg gggaaaaaag aaaactgaac taataacatc atgatactcg gaaaacctag   6780
caattctcaa cccctaaaca aaagaaactt ccaaaaccct gaccatataa aggagtggca   6840
```

```
acaatcagca atcagtcaag atttgatagc agaaaatctt gtatcggttg ctaatggttt   6900
tgatgtacta tttatcggca ataaataccg aactaacacg ggtgttctgt cacggcacat   6960
attaaactcc tattctcatt tagaagatgg tggttcgtat ggtagaacat ttgacccatt   7020
taccaataaa gaaatgcagt gggttcaatt taaaccgaat agaccaagaa aaggttctac   7080
tggtaaggta atcaaatatg aatcgccaaa aggtgaacct acaagagttc taatgccgtt   7140
tgtgcctatg aaaatatggc aacggattag cgataagttc ggagtaccga ttaatccgaa   7200
aaaagatact cacttttggg aatgggtaaa gaataatcca tcgataccga ttgccattac   7260
agaaggaaat aaaaaagcta attgcctatt atcctatggc tatcctgcta ttgcctttgt   7320
aggcatttgg aacggattag agaaaataaa tgatttctcg aaggaaaagc agttaaaaga   7380
ggatttgaaa tggttgttat ccaacggcaa ccgaaatatt aatatcatct ttgaccaaga   7440
ccagaaacaa aaaactgtaa ttaatgtaaa caaagctatt ttcgctttat cttctctaat   7500
aagtagaaat ggtcataaag ttaatattgt gcaatggttg ccgtcaaaag gtaaaggaat   7560
agatgattat ttggtagctt taccttttga gaaaagagaa aatcatttag acaacttaat   7620
taaaattgca ccatcattta atttttggtc aactaaatac ttattcaagt gtcgtaaacc   7680
agatttaacc gtaaattgcc gttatttgag cgatgcagta aaagaattac ctcaagagga   7740
tatagcatta atagcacctc acggcacggg taaaacttca ttagtagcta ctcacgttaa   7800
gaatcggagt tatcacggaa ggaaaactat ttcattggtg catcttgaaa gtttagccaa   7860
agctaatggc aacgcacttg gattatatta ccgaaccgaa aataatattg aaaagcaata   7920
tcttggattt agcttatgtg tagatagttg ccgtgataag attaacggca ttacaactga   7980
tattatttca ggtcaagatt attgcctttt cattgatgaa attgaccaag taattccaca   8040
catccttaac agtgaaactg aagtaagtaa gtatagatgc accatcattg acactttttc   8100
tgaactggtg agaaatgctg aacaggtcat tattgctgat gctgatttat ccgatgtgac   8160
gattgaccta atagaaaaca tcagaggtaa aaaactatat gtaatcaaga atgaatatca   8220
gtatcaggga atgactttta acgccgttgg ttcaccatta gaaatgatgg caatgatggg   8280
aaaatcggtg tcagaaggca agaaattatt tattaacacc acatcccaaa aggcaaaaag   8340
taagtacggc acaatcgctc ttgagtctta tatttttggt ctaaataaag aagcaaagat   8400
attaagaata gactctgaaa ccactaaaaa ccctgaacat ccagcctata aaatcattga   8460
ccaagactta aataatatcc tcaaagatta tgattatgtc attgcctcac cttgccttca   8520
aacaggtgtc agtattacct taaaagggca ttttgaccag caatttaact tttccagtgg   8580
aaacattaca cctcattgct tttacagca aatgtggcgg ttgagggatg cagaaattga   8640
aagattctat tatgtgccga actcatctaa cctcaatctc attgggaata agtcaagttc   8700
accatcagac cttctaaaga gcaataacaa gatggcaacg gcaacggtta accttttggg   8760
tagaatcgac tccgaatatt ccctagagta tgaatcgcac ggcatttggc ttgagacgtg   8820
ggcaaaatta tcagcacggc ataacagttc aatgcgttgt tactctgaaa ttcttaccta   8880
tctaattacg tctcaagggc ataaattaaa tatcaacatt ccctcacctc ttgcagatat   8940
taagaagcta aatgatgagg taagtagtaa cagggaaaag gtaaaaaatg agagatactc   9000
tcagaggtta aactcaccag atattaacga tgcagaagct accatactcg aatctaaaga   9060
gcaaaaaatc ggattgactc tcaatgagag atgcacccta gaaaagcata aagttaagaa   9120
gcggtatggg aatgtaaaga tggatattct cacctttgat gatgatggac tataccccaa   9180
```

```
actcagacta ttttattacc tcaccatcgg taaacctcat ctcaaggcta atgacagaaa    9240
agctattgcc aaaatgggca atgacaataa aggcaagatt ctatcaaaag acttagttaa    9300
taaaacttac tccgctcgtg tgaaggtctt agagattctt aaactaactg actttatcga    9360
caatcttaga gatgaactct taataactcc caataatcca gctatcaccg attttaataa    9420
tcttctgcta agagctaaga aggatttaag agtattagga gtcaacatcg gaaaatatcc    9480
aatggccaac attaatgccg tacttactct cattggtcac aaactttctg taatgagaga    9540
tgagttcgga aaagagaaaa ggataaaagt agatggtaaa tcataccgat gttatcaact    9600
tgaaacatta ccagatttta ccaatgatac tcttgactac tggttagaaa atgatagcca    9660
aaaagaagta acagcaacag aaaattactc cgaaaatttt aacccttcaa atagctacaa    9720
tccagacagt aagacacttt cagagggtgc aaatttccta tatataaata aagaagaatt    9780
gcatccaaat aaattgcacc tagaaataaa agaaggtgct gaactttttt tattcggggt    9840
aaaggtgatt gtgaaaggaa tcttggacgg ggcagtaact atattctcta tgggtcaaga    9900
atacgattta tccctcaatg aactagaggg gatgttaaca tcatgaactt tacaagaatc    9960
tttttaaagg gcgatcgcac catgttaaat gatggtacat ttgttcagat atttgatatt   10020
taccatgacc acgcattggg agtgaccctt gaccttaaga cagaaaaaat tatttccgat   10080
gatgttaggg taattactgt caaagactta ttgttcgatg gcacttataa aggggtaaaa   10140
tcttttatgc ccgataatgc ccgataatgc ccgattgatg ctacaaaatc ccataatcat   10200
aagcgataat cccctaatag cttgtaattc ttgaaccgta gcgattttag agtattccaa   10260
aaagaagaaa taaacaccgc aaaatgtcgt atttcacata tataaaccaa ggtttttttgc   10320
cctaaaatct ttatgtttgt agtgtgatgt tgggtcaaaa tggtcagaaa agttgcaagg   10380
tttttatgga tgcttacgcg cgcgaggggt aagcatcccc aaatagttac tttatcctag   10440
tccatgccca tttattgccg tcccgttcgg ctttaaaaaa gtgccaaaac tcacaaggtg   10500
caataaaaag ttctgtacct ttcgcaaccc tagataatct ttcaacagtt actttttttc   10560
ctattatctc ggtacaaagt ttggctagtt tctcttttcc ctctttttca atcaagcctt   10620
cttgtatgcc caactcattg attaatctct ctatttttac cattatttcc cgttcaggta   10680
gtttatcccc taaatcttca tcggggggca atgtagggca ttctgaaggg gctttttctt   10740
ctgtctggac attatctaat attgaagtaa ccaaactatc ttcagttttt tctattccta   10800
ttaattcata ttcggttact gtatccgtat caatatccga ataactatct ttatccgtat   10860
tagctattcg gttaagttta tccgttaact cagaaacaag actatatagc ggttttagct   10920
tttcttctat cctgttatct aatacggata agtttatacg gttatcatta tccgtattag   10980
tatcattggg ctttttttggt agttctaccc cctcataaac cgcttttatt cccaattcca   11040
acagactgat aacagtatcc tttataatgg gtttttttgct gatatggtga acttttgccc   11100
cttccatcat tgcgatactt tctatctcac tcatcaactt atcgcttaag tgaatctcgt   11160
atctgtttaa tcccttactg gttttattca tatccgttta ctttattcgg ttaacaattc   11220
tattttatac gaataaaata ttatacggtt aactttatac gtttaactat tttatctata   11280
cggataacag taataagtta ttcgtattag ttatacgttt acttttatcc aaataaaatt   11340
agtgcattta aactaaaaga atgattttat cggagttgat agcattggat taacctaaag   11400
atgtttataa gctatatctg ataagtattt aaggttattt tgttattctg tttattgaca   11460
ttatcagaat aaaagaatag aatataattg ttgagagata agaggtttaa gtgattatgg   11520
ttaagaagtt agttggttat gtcagggtca gtagtgaatc gcaagaggat aacactagct   11580
```

```
tacagaatca gatagagaga attgaagcat attgtatggc ttttggttat gagttggtaa  11640
aaatattcaa agaggttgcc actggtacaa aagcagatat tgaaacccgt cctatttttta  11700
atgaagctat agaatacttg aaacaggata atgctaatgg aattattgcc ttgaagctag  11760
accgaatcgc acggaatgct ttagatgtat tgcgtttggt tcgtgaaacc ttagaaccac  11820
aaaataaaat gttagtgtta ctagatattc aggtagatac ttcgacacct tcaggaaaaa  11880
tgattttaac tgtaatgagt gccgttgctg aactcgaaag agacatgatc tatgatcgca  11940
ctcagggggg tagaaagact aaagcccaaa agggcgggta tgcctacggg aaacctaaat  12000
ttggctataa gactgaagaa aaggaactaa aagaagattc agcacaacag gaaactatta  12060
aactaattaa gagacaccgt aggtcaggga aaagctacca gaaaatagct gattatctca  12120
atgcccaaag tattcccact aaacaaggta agaaatggag ttctagcgtc gtctatcgaa  12180
tctgtcagga aaaagctggt taagtctgtt tatagatatt tagaatttat tgaataaaaa  12240
tagtatgaac aataaatatt tatggactaa ccacgctcgg aaacgtttaa ctgaacgatg  12300
ggaaataaaa gaatcatggg ttattgatac catcgaaaat cctgaacgtt cagaatttat  12360
tgttgatgag tcaggggaaa aatatcatta ctataaaaga atagctaagt ttaagaatag  12420
agtgttagaa gtgataactt ctgccaactc aacacccaca agaataataa cctttttactt  12480
taaccgtaac atgaggaaaa atttatgatt gttacttacg ataatgaagt tgacgcaatt  12540
tattttaagt taacggaaaa taaaattgat agcaccgaac ctcaaacaga caggattatc  12600
attgattacg atgaaagtaa taatattgtt ggcattgagg tattagattt taattatctt  12660
gtcaagaaag gtttaaccgt tgctgattta cctttttctg aagatgaaag attaacagct  12720
tctcaatatt ttaattttcc tgttgctatc taatccagaa ggggcaataa tccccttctt  12780
tcatcgagtt agacttaata tcacaaaagt cattttcatt ttaccgtttc ttttccacag  12840
cgtccgtacg cccctcgtta aatctcaaaa ccgacaattt atgatgttta taaaaagtta  12900
ctcactttaa taagtattta tactcattaa agggttattc tttttttgta gcctgatagg  12960
ttgggaagga atatttcaga ttatcagatt tgttgaatat ttttcgtcag atacgcaaac  13020
cttacaaaca taattaacaa ctgaaactat tgatatgtct aggttttagc tctatcacag  13080
gttggatctg                                                         13090
```

<210> SEQ ID NO 74
<211> LENGTH: 13070
<212> TYPE: DNA
<213> ORGANISM: artificial
<220> FEATURE:
<223> OTHER INFORMATION: Synthetically produced plasmid construct #1793 pABIcyano1-6.8::PnirA-zmPDC(opt3)-TdsrA-PcpcB-ADH916(opt)-TrbcS

<400> SEQUENCE: 74

```
tcgacaatta ataacttctt cctgtacggg cgaatggcca tttgctccta actaactccg     60
tactgctttg cggaacgagc gtagcgaact ctccgaatta ctaagccttc atccctgata    120
gatgcaaaaa acgaattaaa attatgtgta aaaagaaaat gtgtctttat ttagtagtca    180
aagttacaaa atattaagaa tcaaattaat aatgtattgg gcagttaagt atataagtct    240
ttaaatattt atttgtattc aatatattaa ccgaggacaa attatgaatt cttacactgt    300
tggaacctat ttagcagaac gtttagttca aattggtctc aaacaccatt ttgcagtagc    360
tggtgattat aatttagttt tattggataa cttattgtta aataagaata tggaacaagt    420
gtattgttgt aatgaattaa actgtggttt ttctgctgag ggatatgctc gtgcaaaagg    480
```

```
tgctgccgca gcagttgtta cttattctgt tggagcatta agtgcttttg acgctattgg    540
aggtgcttat gcagaaaatt tacctgtaat cttaatctct ggtgcaccca ataacaacga    600
tcacgctgct ggtcatgtat tgcatcatgc tttaggtaaa accgattatc attaccaatt    660
agaaatggca aaaaatatta ccgctgccgc agaagctatt tatactcccg aagaagcacc    720
tgctaagatc gatcacgtaa ttaaaaccgc tctccgtgag aaaaaacccg tatatttaga    780
aatcgcttgc aatatcgctt ctatgccttg tgcagctcct ggacctgcta gtgctttatt    840
taacgatgaa gcatctgatg aggctagttt aaatgccgct gttgaagaaa ctttgaaatt    900
tattgctaat cgtgataaag tagctgtttt agttggttct aaactccgtg ccgctggtgc    960
agaagaagcg gctgtaaaat tcgcagatgc cttaggaggt gctgttgcca caatggcagc   1020
cgctaaaagt tttttccccg aagaaaatcc tcattacatt ggtacttctt ggggtgaggt   1080
atcttaccct ggtgtagaaa aaaccatgaa ggaagctgat gcagtaattg cattagctcc   1140
tgttttcaat gattactcta ccactggttg gactgatatt ccagacccca aaaaattagt   1200
tttagcagaa cctcgctctg tagttgtgaa tggtgttaga tttcccagtg tacatctcaa   1260
agattattta actcgtttag ctcaaaaagt gagtaaaaag actggcgcac tcgatttctt   1320
taaatcttta aatgctggtg aattaaagaa agcagctcct gctgatccca gtgctccttt   1380
agtgaatgcc gaaatcgcaa gacaagttga agccttgtta actcctaaca ctaccgttat   1440
tgccgagact ggtgatagtt ggttcaatgc tcaacgcatg aaattaccca atggtgctcg   1500
tgttgagtat gaaatgcaat ggggtcacat tggatggtct gttcctgctg catttggata   1560
tgcagttgga gcacctgagc gtagaaacat tttaatggta ggtgatggtt ctttccaact   1620
cactgctcaa gaagttgcac aaatggtacg tttaaaattg cctgttatta tctttctcat   1680
taacaactat ggttacacca ttgaagttat gattcatgat ggtccttata ataacattaa   1740
gaattgggat tacgcaggtt taatggaggt atttaacggt aatggtggat acgacagtgg   1800
agcaggtaaa ggattaaaag ctaaaacagg aggtgagtta gctgaagcaa ttaaagtagc   1860
tttagccaat acagatggtc ctaccttaat cgaatgtttc attggacgtg aagattgtac   1920
tgaagagtta gttaaatggg gaaagcgtgt tgccgctgca aattctcgta aacctgtaaa   1980
caaactcttg tagttaggat ccagcaaggt ttcatcccga ccccctcagg gtcgggattt   2040
ttttattgtg agctcaactt tagatattcg tagttggcaa tgtcgtaaat gcggaacaat   2100
acatggaaaa catatagatt tgtaatgaga aaaagtgtaa acaaatatta agaaaaagat   2160
cagaaaaatt taacaacacg taataaaaaa atgcgtcact acgggttata aatttacatg   2220
aaaggttaaa acacttttct gagacgattt tgataaaaaa gttgtcaaaa aattaagttt   2280
ctttacaaat gcttaacaaa aacttggttt taagcacaaa ataagagaga ctaatttgca   2340
gaagttttac aaggaaatct tgaagaaaaa gatctaagta aaacgactct gtttaaccaa   2400
aatttaacaa atttaacaaa acaaactaaa tctattagga gattaactac atatgcctat   2460
gatcaaagcc ttcgcagttc atgagtctga tggagattta cagccttttg aatatgatcc   2520
tggtgcatta ttatctgatc aagttgagat cgaagttaaa tattgtggaa tttgtcattc   2580
tgatttatct atgatctcta atgaatgggg tatgacccaa taccctttag tacctggaca   2640
tgaggtagta ggtgcaatcg ccaaagtagg tgaaaatgtt aaaaatttat ctgttggtca   2700
aattgtagga ttaggttggc acgcaggtta ttgtaacgaa tgtcctcaat gtactactgg   2760
tgatcaaaat ttatgtgcta ctgctcaagg aactattgta ggacatcatg gaggtttcgc   2820
```

-continued

```
tgaaaaagtt cgcgctgctg caaattctgt agttcccatc cctgaaggaa tcgatttaga   2880
agctgctgga cctttatttt gtggaggtat caccgttttt aatcctttag tacaatatgg   2940
aatccaaccc actgcaaaag ttgctgtaat tggaattgga ggtttaggtc acatggctgt   3000
tcaattctta aacgcttggg gttgtgaagt taccgctttt accagttctg aagcaaaaat   3060
cactgaggct ttagaattag gtgctcatca cactttaaac agtcgtgacc ctgaagccat   3120
cgcagccgct gctggacagt ttgatttaat catttctacc gttaacgtta aattagattg   3180
gaatgcctat ttaagtactt taaaacctca cggtcgttta cacttcgtag gtgctacttt   3240
agatccctta gacattaacg tttttgcttt aatcatgcag caacgttcta tctctggtag   3300
tcctgttgga tctcctgcaa ccatcgcaaa aatgttagaa tttgcaaaat tacataaaat   3360
tcaacctaaa attgaaacct ttaaatttga agatgttaac caggctattg cacgtttaaa   3420
aagtggtgaa gcccactatc gtattgtatt atgtagataa ctagatctac ttctaaactg   3480
aaacaaattt gagggtaggc ttcattgtct gcccttattt ttttatttag gaaaagtgaa   3540
cagactaaag agtgttggct ctattgcttt gagtatgtaa attaggcgtt gctgaattaa   3600
ggtatgattt ttgacccctg caggatcatc ttgctgaaaa actcgagcgc tcgttccgca   3660
aagcggtacg gagttagtta ggggctaatg ggcattctcc cgtacaggaa agagttagaa   3720
gttattaatt atcaacaatt ctcctttgcc tagtgcatcg ttaccttttt aattaaaaca   3780
taaggaaaac taataatcgt aataatttaa cctcaaagtg taaagaaatg tgaaattctg   3840
acttttataa cgttaaagag ggaaaaatta gcagtttaaa atacctagag aatagtctgg   3900
ggtaagcata gagaattaga ttagttaagt taatcaaatt cagaaaaaat aataatcgta   3960
aatagttaat ctgggtgtat agaaaatgat ccccttcatg ataagattta aactcgaaaa   4020
gcaaaagcca aaaaactaac ttccattaaa agaagttgtt acatataacg ctataaagaa   4080
aatttatata tttggaggat accaaccatg tctcatattc aacgtgaaac tagttgttct   4140
cgccctcgtt taaattctaa tatggatgcc gatttatatg gttataaatg ggctcgtgat   4200
aatgttggtc aatctggtgc tactatttat cgtttatatg gtaaacctga tgctcctgaa   4260
ttattcttga aacatggtaa aggttctgtt gctaatgatg ttactgatga aatggttcgt   4320
ttaaactggt tgactgaatt tatgccttta cctactatta aacattttat tcgtactccc   4380
gatgatgctt ggttattaac tactgctatt cctggtaaaa ctgcttttca agttttagaa   4440
gaatatcctg attctggtga aaatattgtt gatgctttag ctgttttttt acgtcgttta   4500
cattctattc ccgtttgtaa ttgtcctttt aattctgatc gtgtttttcg tttagctcaa   4560
gctcaatctc gtatgaataa tggtttagtt gatgcttctg attttgatga tgaacgtaat   4620
ggttggcctg ttgaacaagt ttggaaagaa atgcacaaat tgttaccttt ttctcctgat   4680
tctgttgtta ctcatggtga tttttcttta gataatttga tctttgatga aggtaaattg   4740
attggttgta ttgatgttgg tcgtgttggt attgctgatc gttatcaaga tttagctatt   4800
ttatggaatt gtttaggtga attttctcct tctttacaga aacgtttatt tcagaaatat   4860
ggtattgata atcctgatat gaacaagtta caatttcatt taatgttgga cgagttcttt   4920
taagaattaa ttcatgacca aaatccctta acgtgagttt tcgttccact gagcgtcaga   4980
ccccgtagaa aagatcaaag gatcttcttg agatcctttt tttctgcgcg taatctgctg   5040
ctatttaaat tacgtacacg tgttattact ttgttaacga caattgtctt aattaactgg   5100
gcctcatggg ccttccgctc actgcccgct ttccagtcgg gaaacctgtc gtgccagctc   5160
tgcagatgac ggtgaaaacc tctgacacat gcagctcccg gagacggtca cagcttgtct   5220
```

```
gtaagcggat gccgggagca gacaagcccg tcagggcgcg tcagcgggtg ttggcgggtg   5280
tcggggcgca gccatgaccc agtcacgtag cgatagcgga gtgtatactg gcttaactat   5340
gcggcatcag agcagattgt actgagagtg caccatatgc ggtgtgaaat accgcacaga   5400
tgcgtaagga gaaaataccg catcaggcgc tcttccgctt cctcgctcac tgactcgctg   5460
cgctcggtcg ttcggctgcg gcgagcggta tcagctcact caaaggcggt aatacggtta   5520
tccacagaat caggggataa cgcaggaaag aacatgtgag caaaaggcca gcaaaaggcc   5580
aggaaccgta aaaaggccgc gttgctggcg tttttccata ggctccgccc ccctgacgag   5640
catcacaaaa atcgacgctc aagtcagagg tggcgaaacc cgacaggact ataaagatac   5700
caggcgtttc cccctggaag ctccctcgtg cgctctcctg ttccgaccct gccgcttacc   5760
ggatacctgt ccgcctttct cccttcggga agcgtggcgc tttctcatag ctcacgctgt   5820
aggtatctca gttcggtgta ggtcgttcgc tccaagctgg gctgtgtgca cgaacccccc   5880
gttcagcccg accgctgcgc cttatccggt aactatcgtc ttgagtccaa cccggtaaga   5940
cacgacttat cgccactggc agcagccact ggtaacagga ttagcagagc gaggtatgta   6000
ggcggtgcta cagagttctt gaagtggtgg cctaactacg gctacactag aaggacagta   6060
tttggtatct gcgctctgct gaagccagtt accttcggaa aaagagttgg tagctcttga   6120
tccggcaaac aaaccaccgc tggtagcggt ggtttttttg tttgcaagca gcagattacg   6180
cgcagaaaaa aaggatctca agaagatcct ttgatctttt ctactgcaga agcttgttag   6240
acaccctgtc atgtatttta tattatttat ttcaccatac ggattaagtg aaacctaatg   6300
aaaatagtac tttcggagct ttaactttaa tgaaggtatg tttttttata gacatcgatg   6360
tctggtttaa caataggaaa aagtagctaa aactcccatg aattaaagaa ataacaaggt   6420
gtctaacaac ctgttattaa gaatgttaga aaagacttaa catttgtgtt gagtttttat   6480
agacattggt gtctagacat acggtagata aggtttgctc aaaaataaaa taaaaaaaga   6540
ttggactaaa aaacatttaa tttagtacaa tttaattagt tattttttcg tctcaaattt   6600
tgctttgttg agcagaaatt tagataaaaa aatccccgtg atcagattac aatgtcgttc   6660
attgtacgat gtgtcgaaaa atctttacga cactctaaac tgaccacacg gggaaaaaag   6720
aaaactgaac taataacatc atgatactcg gaaaacctag caattctcaa cccctaaaca   6780
aaagaaactt ccaaaaccct gaccatataa aggagtggca acaatcagca atcagtcaag   6840
atttgatagc agaaaatctt gtatcggttg ctaatggttt tgatgtacta tttatcggca   6900
ataaataccg aactaacacg ggtgttctgt cacggcacat attaaactcc tattctcatt   6960
tagaagatgg tggttcgtat ggtagaacat ttgacccatt taccaataaa gaaatgcagt   7020
gggttcaatt taaaccgaat agaccaagaa aaggttctac tggtaaggta atcaaatatg   7080
aatcgccaaa aggtgaacct acaagagttc taatgccgtt tgtgcctatg aaaatatggc   7140
aacggattag cgataagttc ggagtaccga ttaatccgaa aaaagatact cacttttggg   7200
aatgggtaaa gaataatcca tcgataccga ttgccattac agaaggaaat aaaaaagcta   7260
attgcctatt atcctatggc tatcctgcta ttgcctttgt aggcatttgg aacggattag   7320
agaaaataaa tgatttctcg aaggaaaagc agttaaaaga ggatttgaaa tggttgttat   7380
ccaacggcaa ccgaaatatt aatatcatct ttgaccaaga ccagaaacaa aaaactgtaa   7440
ttaatgtaaa caaagctatt ttcgctttat cttctctaat aagtagaaat ggtcataaag   7500
ttaatattgt gcaatggttg ccgtcaaaag gtaaaggaat agatgattat ttggtagctt   7560
```

```
taccttttga gaaaagagaa aatcatttag acaacttaat taaaattgca ccatcattta   7620
atttttggtc aactaaatac ttattcaagt gtcgtaaacc agatttaacc gtaaattgcc   7680
gttatttgag cgatgcagta aaagaattac ctcaagagga tatagcatta atagcacctc   7740
acggcacggg taaaacttca ttagtagcta ctcacgttaa gaatcggagt tatcacggaa   7800
ggaaaactat ttcattggtg catcttgaaa gtttagccaa agctaatggc aacgcacttg   7860
gattatatta ccgaaccgaa aataatattg aaaagcaata tcttggattt agcttatgtg   7920
tagatagttg ccgtgataag attaacggca ttacaactga tattatttca ggtcaagatt   7980
attgcctttt cattgatgaa attgaccaag taattccaca catccttaac agtgaaactg   8040
aagtaagtaa gtatagatgc accatcattg acactttttc tgaactggtg agaaatgctg   8100
aacaggtcat tattgctgat gctgatttat ccgatgtgac gattgaccta atagaaaaca   8160
tcagaggtaa aaaactatat gtaatcaaga atgaatatca gtatcaggga atgactttta   8220
acgccgttgg ttcaccatta gaaatgatgg caatgatggg aaaatcggtg tcagaaggca   8280
agaaattatt tattaacacc acatcccaaa aggcaaaaag taagtacggc acaatcgctc   8340
ttgagtctta tatttttggt ctaaataaag aagcaaagat attaagaata gactctgaaa   8400
ccactaaaaa ccctgaacat ccagcctata aaatcattga ccaagactta aataatatcc   8460
tcaaagatta tgattatgtc attgcctcac cttgccttca aacaggtgtc agtattacct   8520
taaaagggca ttttgaccag caatttaact tttccagtgg aaacattaca cctcattgct   8580
ttttacagca aatgtggcgg ttgagggatg cagaaattga aagattctat tatgtgccga   8640
actcatctaa cctcaatctc attgggaata agtcaagttc accatcagac cttctaaaga   8700
gcaataacaa gatggcaacg gcaacggtta accttttggg tagaatcgac tccgaatatt   8760
ccctagagta tgaatcgcac ggcatttggc ttgagacgtg ggcaaaatta tcagcacggc   8820
ataacagttc aatgcgttgt tactctgaaa ttcttaccta tctaattacg tctcaagggc   8880
ataaattaaa tatcaacatt ccctcacctc ttgcagatat taagaagcta aatgatgagg   8940
taagtagtaa cagggaaaag gtaaaaaatg agagatactc tcagaggtta aactcaccag   9000
atattaacga tgcagaagct accatactcg aatctaaaga gcaaaaaatc ggattgactc   9060
tcaatgagag atgcacccta gaaaagcata aagttaagaa gcggtatggg aatgtaaaga   9120
tggatattct cacctttgat gatgatggac tataccccaa actcagacta ttttattacc   9180
tcaccatcgg taaacctcat ctcaaggcta atgacagaaa agctattgcc aaaatgggca   9240
atgacaataa aggcaagatt ctatcaaaag acttagttaa taaaacttac tccgctcgtg   9300
tgaaggtctt agagattctt aaactaactg actttatcga caatcttaga gatgaactct   9360
taataactcc caataatcca gctatcaccg attttaataa tcttctgcta agagctaaga   9420
aggatttaag agtattagga gtcaacatcg gaaaatatcc aatggccaac attaatgccg   9480
tacttactct cattggtcac aaactttctg taatgagaga tgagttcgga aaagagaaaa   9540
ggataaaagt agatggtaaa tcataccgat gttatcaact tgaaacatta ccagatttta   9600
ccaatgatac tcttgactac tggttagaaa atgatagcca aaaagaagta acagcaacag   9660
aaaattactc cgaaaatttt aacccttcaa atagctacaa tccagacagt aagacacttt   9720
cagagggtgc aaatttccta tatataaata aagaagaatt gcatccaaat aaattgcacc   9780
tagaaataaa agaaggtgct gaactttttt tattcggggt aaaggtgatt gtgaaaggaa   9840
tcttggacgg ggcagtaact atattctcta tgggtcaaga atacgattta tccctcaatg   9900
aactagaggg gatgttaaca tcatgaactt tacaagaatc tttttaaagg gcgatcgcac   9960
```

```
catgttaaat gatggtacat ttgttcagat atttgatatt taccatgacc acgcattggg  10020
agtgaccctt gaccttaaga cagaaaaaat tatttccgat gatgttaggg taattactgt  10080
caaagactta ttgttcgatg gcacttataa aggggtaaaa tcttttatgc ccgataatgc  10140
ccgataatgc ccgattgatg ctacaaaatc ccataatcat aagcgataat cccctaatag  10200
cttgtaattc ttgaaccgta gcgattttag agtattccaa aaagaagaaa taaacaccgc  10260
aaaatgtcgt atttcacata tataaaccaa ggtttttgc cctaaaatct ttatgtttgt  10320
agtgtgatgt tgggtcaaaa tggtcagaaa agttgcaagg tttttatgga tgcttacgcg  10380
cgcgaggggt aagcatcccc aaatagttac tttatcctag tccatgccca tttattgccg  10440
tcccgttcgg ctttaaaaaa gtgccaaaac tcacaaggtg caataaaaag ttctgtacct  10500
ttcgcaaccc tagataatct ttcaacagtt acttttttc ctattatctc ggtacaaagt  10560
ttggctagtt tctcttttcc ctctttttca atcaagcctt cttgtatgcc caactcattg  10620
attaatctct ctatttttac cattatttcc cgttcaggta gtttatcccc taaatcttca  10680
tcggggggca atgtagggca ttctgaaggg gctttttctt ctgtctggac attatctaat  10740
attgaagtaa ccaaactatc ttcagttttt tctattccta ttaattcata ttcggttact  10800
gtatccgtat caatatccga ataactatct ttatccgtat tagctattcg gttaagttta  10860
tccgttaact cagaaacaag actatatagc ggttttagct tttcttctat cctgttatct  10920
aatacggata agtttatacg gttatcatta tccgtattag tatcattggg ctttttggt  10980
agttctaccc cctcataaac cgcttttatt cccaattcca acagactgat aacagtatcc  11040
tttataatgg gtttttgct gatatggtga acttttgccc cttccatcat tgcgatactt  11100
tctatctcac tcatcaactt atcgcttaag tgaatctcgt atctgtttaa tcccttactg  11160
gttttattca tatccgttta ctttattcgg ttaacaattc tattttatac gaataaaata  11220
ttatacggtt aactttatac gtttaactat tttatctata cggataacag taataagtta  11280
ttcgtattag ttatacgttt acttttatcc aaataaaatt agtgcattta aactaaaaga  11340
atgattttat cggagttgat agcattggat taacctaaag atgtttataa gctatatctg  11400
ataagtattt aaggttattt tgttattctg tttattgaca ttatcagaat aaaagaatag  11460
aatataattg ttgagagata agaggtttaa gtgattatgg ttaagaagtt agttggttat  11520
gtcagggtca gtagtgaatc gcaagaggat aacactagct tacagaatca gatagagaga  11580
attgaagcat attgtatggc ttttggttat gagttggtaa aaatattcaa agaggttgcc  11640
actggtacaa aagcagatat tgaaacccgt cctattttta atgaagctat agaatacttg  11700
aaacaggata atgctaatgg aattattgcc ttgaagctag accgaatcgc acggaatgct  11760
ttagatgtat tgcgtttggt tcgtgaaacc ttagaaccac aaaataaaat gttagtgtta  11820
ctagatattc aggtagatac ttcgacacct tcaggaaaaa tgattttaac tgtaatgagt  11880
gccgttgctg aactcgaaag agacatgatc tatgatcgca ctcagggggg tagaaagact  11940
aaagcccaaa agggcgggta tgcctacggg aaacctaaat ttggctataa gactgaagaa  12000
aaggaactaa aagaagattc agcacaacag gaaactatta aactaattaa gagacaccgt  12060
aggtcaggga aaagctacca gaaaatagct gattatctca atgcccaaag tattcccact  12120
aaacaaggta agaaatggag ttctagcgtc gtctatcgaa tctgtcagga aaaagctggt  12180
taagtctgtt tatagatatt tagaatttat tgaataaaaa tagtatgaac aataaatatt  12240
tatggactaa ccacgctcgg aaacgtttaa ctgaacgatg ggaaataaaa gaatcatggg  12300
```

```
ttattgatac catcgaaaat cctgaacgtt cagaatttat tgttgatgag tcaggggaaa  12360

aatatcatta ctataaaaga atagctaagt ttaagaatag agtgttagaa gtgataactt  12420

ctgccaactc aacacccaca agaataataa ccttttactt taaccgtaac atgaggaaaa  12480

atttatgatt gttacttacg ataatgaagt tgacgcaatt tattttaagt taacggaaaa  12540

taaaattgat agcaccgaac ctcaaacaga caggattatc attgattacg atgaaagtaa  12600

taatattgtt ggcattgagg tattagattt taattatctt gtcaagaaag gtttaaccgt  12660

tgctgattta cctttttctg aagatgaaag attaacagct tctcaatatt ttaattttcc  12720

tgttgctatc taatccagaa ggggcaataa tccccttctt tcatcgagtt agacttaata  12780

tcacaaaagt cattttcatt ttaccgtttc ttttccacag cgtccgtacg cccctcgtta  12840

aatctcaaaa ccgacaattt atgatgttta taaaaagtta ctcactttaa taagtattta  12900

tactcattaa agggttattc tttttttgta gcctgatagg ttgggaagga atatttcaga  12960

ttatcagatt tgttgaatat ttttcgtcag atacgcaaac cttacaaaca taattaacaa  13020

ctgaaactat tgatatgtct aggttttagc tctatcacag gttggatctg             13070
```

<210> SEQ ID NO 75
<211> LENGTH: 13099
<212> TYPE: DNA
<213> ORGANISM: artificial
<220> FEATURE:
<223> OTHER INFORMATION: Synthetically produced plasmid construct #1795
pABIcyano1-6.8::PnirA-zmPDC(opt1)-TdsrA-PcpcB-ADH553(opt)-TrbcS

<400> SEQUENCE: 75

```
tcgacaatta ataacttctt cctgtacggg cgaatggcca tttgctccta actaactccg     60

tactgctttg cggaacgagc gtagcgaact ctccgaatta ctaagccttc atccctgata    120

gatgcaaaaa acgaattaaa attatgtgta aaaagaaaat gtgtctttat ttagtagtca    180

aagttacaaa atattaagaa tcaaattaat aatgtattgg gcagttaagt atataagtct    240

ttaaatattt atttgtattc aatatattaa ccgaggacaa attatgaatt cttataccgt    300

gggtacttat ttagccgaac gcttagtgca aattggttta aaacatcatt ttgccgtggc    360

tggggactat aatttagtgt tattggataa cttattatta aataaaaaca tggaacaagt    420

gtattgttgt aatgaattaa attgtggttt ttctgctgaa ggttatgcta gagctaaagg    480

tgcagctgct gctgttgtta cttattctgt gggtgcttta tctgcttttg atgctattgg    540

tggtgcttat gccgaaaatt tacccgtgat tttaatttct ggtgccccta ataataatga    600

tcatgccgct ggacatgttt tacatcatgc cttaggtaaa accgattatc attatcaatt    660

agaaatggcc aaaaatatta ctgctgctgc cgaagctatt tatactcctg aagaagcccc    720

tgccaaaatt gatcatgtga ttaaaaccgc cttacgcgaa aaaaaacccg tgtatttaga    780

aattgcctgt aatattgctt ctatgccttg tgctgctcct gggcctgctt ctgctttatt    840

taatgatgaa gcctctgatg aagctagttt aaatgctgcc gtggaagaaa ccttaaaatt    900

tattgccaat cgcgataaag ttgccgtgtt agttggttct aaattaagag ctgctggtgc    960

tgaagaagct gctgttaaat ttgctgatgc tttaggtggt gcagttgcta ctatggctgc   1020

tgccaaatct ttttttcccg aagaaaatcc ccattatatt ggaactagtt ggggagaagt   1080

ttcttatcct ggtgtggaaa aaactatgaa agaagccgac gctgttattg ctttagcccc   1140

tgtgtttaat gattattcta ccactggttg gactgatatt cccgatccca aaaaattagt   1200

tttagccgaa cctcgttctg ttgttgttaa tggtgttcgc tttccctctg tgcatttaaa   1260
```

```
agattattta acccgcttag cccaaaaagt ttctaaaaaa actggtgcct tagatttttt   1320
taaatcttta aatgcgggtg aattaaaaaa agctgctcct gctgatcctt ctgctccttt   1380
agttaatgct gaaattgccc gtcaagttga agccttatta acccctaata ctaccgttat   1440
tgccgaaact ggtgattctt ggtttaatgc ccaacgcatg aaattaccta atggtgcccg   1500
tgttgaatat gaaatgcaat ggggtcatat tggttggtct gtacctgctg cttttggtta   1560
tgctgttggt gctcctgaac gtcgtaatat tttaatggtg ggtgatggtt cttttcaatt   1620
aactgcccaa gaagttgccc aaatggttcg cttaaaatta cccgttatta tttttttaat   1680
aaataattat ggttatacca ttgaagtgat gattcatgat gggccatata ataatattaa   1740
aaattgggat tatgcgggtt taatggaagt gtttaatggt aatggtggtt atgattctgg   1800
tgctggtaaa ggtttaaaag ccaaaactgg tggtgaatta gctgaagcta ttaaagttgc   1860
cttagccaat actgatgggc caaccttaat tgaatgtttt attggtcgcg aagattgtac   1920
cgaagaatta gttaaatggg gtaaacgtgt tgctgctgct aattctcgca aacccgtgaa   1980
taaattattg taaggatcca gcaagtttca tcccgacccc ctcagggtcg ggattttttt   2040
attgtgagct caactttaga tattcgtagt tggcaatgtc gtaaatgcgg aacaatacat   2100
ggaaaacata tagatttgta atgagaaaaa gtgtaaacaa atattaagaa aaagatcaga   2160
aaaatttaac aacacgtaat aaaaaaatgc gtcactacgg gttataaatt tacatgaaag   2220
gttaaaacac ttttctgaga cgattttgat aaaaaagttg tcaaaaaatt aagtttcttt   2280
acaaatgctt aacaaaaact tggttttaag cacaaaataa gagagactaa tttgcagaag   2340
ttttacaagg aaatcttgaa gaaaaagatc taagtaaaac gactctgttt aaccaaaatt   2400
taacaaattt aacaaaacaa actaaatcta ttaggagatt aactacatat ggttatccag   2460
gcttacgctg ctcatgaaaa aggtggagag ttaaaacctt ttgagtatga tcccggtgta   2520
ttaggtgaag aagaagtaga aatcaatgta gaatactgtg gtatttgtca cagtgactta   2580
tctatgttag ataacgagtg gcagatgagt gaatatccct tagttcctgg acacgaggtt   2640
gtaggtactg ttggtgctgt aggtaacggt gtagaaacct tatctgtagg tcagaaagta   2700
ggtttaggtt ggtttagtcg tagttgtttt aactgtgaat ggtgtattgg tggagatcag   2760
aatttatgtc gtaccgctga aggaactatc gttggaagac atggaggttt tgctaacaaa   2820
gttcgtgctc atcatcgttg ggtaaccccc ttacccagtg aaatcaattt agagactgct   2880
ggtcccttat tctgtggtgg tatcactgtt tttaatccca tcattcaatg tggagtaaaa   2940
cctaccgagc gtgttggtgt tattggtatc ggtggattag gtcatttagc aatccaattt   3000
ttacatgctt ggggatgtga ggtaactgct tttcttctt ctcccgaaaa agaagcagaa   3060
gccagacaat taggagccga tcactttatc aattctcgtg aatctaatgc cttagaaagt   3120
gtagaaaatt ctttcgattt tatcattagt accgttaatg ttgatttaga ctggaacggt   3180
tatgttaatg ctttacgtcc caaaggaaga ttacattttg taggtgtaat ccctaatcct   3240
ttatctatcc aaattttccc tttattagta ggtcaaaaat ctattagtag ttctccctta   3300
ggatctccca ttactattgc ccaaatgtta gactttgcaa ctcgtcatca tattgaacct   3360
atgattgaat tatttcttt agaaaaagtt aacgaagcct taactaaatt aaaacaaggt   3420
caacctcgtt atcgtttagt attaaaagtt taactagatc ttccggatgg ctcgagtttt   3480
tcagcaagat aagatctact tctaaactga aacaaatttg agggtaggct tcattgtctg   3540
cccttatttt tttatttagg aaaagtgaac agactaaaga gtgttggctc tattgctttg   3600
agtatgtaaa ttaggcgttg ctgaattaag gtatgatttt tgacccctgc aggatcatct   3660
```

```
tgctgaaaaa ctcgagcgct cgttccgcaa agcggtacgg agttagttag gggctaatgg   3720
gcattctccc gtacaggaaa gagttagaag ttattaatta tcaacaattc tcctttgcct   3780
agtgcatcgt taccttttta attaaaacat aaggaaaact aataatcgta ataatttaac   3840
ctcaaagtgt aaagaaatgt gaaattctga cttttataac gttaaagagg gaaaaattag   3900
cagtttaaaa tacctagaga atagtctggg gtaagcatag agaattagat tagttaagtt   3960
aatcaaattc agaaaaaata ataatcgtaa atagttaatc tgggtgtata gaaaatgatc   4020
cccttcatga taagatttaa actcgaaaag caaaagccaa aaaactaact tccattaaaa   4080
gaagttgtta catataacgc tataaagaaa atttatatat ttggaggata ccaaccatgt   4140
ctcatattca acgtgaaact agttgttctc gccctcgttt aaattctaat atggatgccg   4200
atttatatgg ttataaatgg gctcgtgata atgttggtca atctggtgct actatttatc   4260
gtttatatgg taaacctgat gctcctgaat tattcttgaa acatggtaaa ggttctgttg   4320
ctaatgatgt tactgatgaa atggttcgtt taaactggtt gactgaattt atgcctttac   4380
ctactattaa acattttatt cgtactcccg atgatgcttg gttattaact actgctattc   4440
ctggtaaaac tgcttttcaa gttttagaag aatatcctga ttctggtgaa aatattgttg   4500
atgctttagc tgttttttta cgtcgtttac attctattcc cgtttgtaat tgtcctttta   4560
attctgatcg tgtttttcgt ttagctcaag ctcaatctcg tatgaataat ggtttagttg   4620
atgcttctga ttttgatgat gaacgtaatg gttggcctgt tgaacaagtt tggaaagaaa   4680
tgcacaaatt gttacctttt tctcctgatt ctgttgttac tcatggtgat ttttctttag   4740
ataatttgat ctttgatgaa ggtaaattga ttggttgtat tgatgttggt cgtgttggta   4800
ttgctgatcg ttatcaagat ttagctattt tatggaattg tttaggtgaa ttttctcctt   4860
ctttacagaa acgtttattt cagaaatatg gtattgataa tcctgatatg aacaagttac   4920
aatttcattt aatgttggac gagttctttt aagaattaat tcatgaccaa aatcccttaa   4980
cgtgagtttt cgttccactg agcgtcagac cccgtagaaa agatcaaagg atcttcttga   5040
gatccttttt ttctgcgcgt aatctgctgc tatttaaatt acgtacacgt gttattactt   5100
tgttaacgac aattgtctta attaactggg cctcatgggc cttccgctca ctgcccgctt   5160
tccagtcggg aaacctgtcg tgccagctct gcagatgacg gtgaaaacct ctgacacatg   5220
cagctcccgg agacggtcac agcttgtctg taagcggatg ccgggagcag acaagcccgt   5280
cagggcgcgt cagcgggtgt tggcgggtgt cggggcgcag ccatgaccca gtcacgtagc   5340
gatagcggag tgtatactgg cttaactatg cggcatcaga gcagattgta ctgagagtgc   5400
accatatgcg gtgtgaaata ccgcacagat gcgtaaggag aaaataccgc atcaggcgct   5460
cttccgcttc ctcgctcact gactcgctgc gctcggtcgt tcggctgcgg cgagcggtat   5520
cagctcactc aaaggcggta atacggttat ccacagaatc aggggataac gcaggaaaga   5580
acatgtgagc aaaaggccag caaaaggcca ggaaccgtaa aaaggccgcg ttgctggcgt   5640
ttttccatag gctccgcccc cctgacgagc atcacaaaaa tcgacgctca agtcagaggt   5700
ggcgaaaccc gacaggacta taaagatacc aggcgtttcc ccctggaagc tccctcgtgc   5760
gctctcctgt tccgaccctg ccgcttaccg gatacctgtc cgcctttctc ccttcgggaa   5820
gcgtggcgct ttctcatagc tcacgctgta ggtatctcag ttcggtgtag gtcgttcgct   5880
ccaagctggg ctgtgtgcac gaaccccccg ttcagcccga ccgctgcgcc ttatccggta   5940
actatcgtct tgagtccaac ccggtaagac acgacttatc gccactggca gcagccactg   6000
```

```
gtaacaggat tagcagagcg aggtatgtag gcggtgctac agagttcttg aagtggtggc   6060
ctaactacgg ctacactaga aggacagtat ttggtatctg cgctctgctg aagccagtta   6120
ccttcggaaa aagagttggt agctcttgat ccggcaaaca aaccaccgct ggtagcggtg   6180
gtttttttgt ttgcaagcag cagattacgc gcagaaaaaa aggatctcaa gaagatcctt   6240
tgatcttttc tactgcagaa gcttgttaga caccctgtca tgtattttat attatttatt   6300
tcaccatacg gattaagtga aacctaatga aaatagtact ttcggagctt taactttaat   6360
gaaggtatgt ttttttatag acatcgatgt ctggtttaac aataggaaaa agtagctaaa   6420
actcccatga attaaagaaa taacaaggtg tctaacaacc tgttattaag aatgttagaa   6480
aagacttaac atttgtgttg agtttttata gacattggtg tctagacata cggtagataa   6540
ggtttgctca aaaataaaat aaaaaaagat tggactaaaa aacatttaat ttagtacaat   6600
ttaattagtt attttttcgt ctcaaatttt gctttgttga gcagaaattt agataaaaaa   6660
atccccgtga tcagattaca atgtcgttca ttgtacgatg tgtcgaaaaa tctttacgac   6720
actctaaact gaccacacgg gggaaaaaga aaactgaact aataacatca tgatactcgg   6780
aaaacctagc aattctcaac ccctaaacaa aagaaacttc caaaaccctg accatataaa   6840
ggagtggcaa caatcagcaa tcagtcaaga tttgatagca gaaaatcttg tatcggttgc   6900
taatggtttt gatgtactat ttatcggcaa taaataccga actaacacgg gtgttctgtc   6960
acggcacata ttaaactcct attctcattt agaagatggt ggttcgtatg gtagaacatt   7020
tgacccattt accaataaag aaatgcagtg ggttcaattt aaaccgaata gaccaagaaa   7080
aggttctact ggtaaggtaa tcaaatatga atcgccaaaa ggtgaaccta caagagttct   7140
aatgccgttt gtgcctatga aaatatggca acggattagc gataagttcg gagtaccgat   7200
taatccgaaa aaagatactc acttttggga atgggtaaag aataatccat cgataccgat   7260
tgccattaca gaaggaaata aaaaagctaa ttgcctatta tcctatggct atcctgctat   7320
tgcctttgta ggcatttgga acggattaga gaaaataaat gatttctcga aggaaaagca   7380
gttaaaagag gatttgaaat ggttgttatc caacggcaac cgaaatatta atatcatctt   7440
tgaccaagac cagaaacaaa aaactgtaat taatgtaaac aaagctattt tcgctttatc   7500
ttctctaata agtagaaatg gtcataaagt taatattgtg caatggttgc cgtcaaaagg   7560
taaaggaata gatgattatt tggtagcttt accttttgag aaaagagaaa atcatttaga   7620
caacttaatt aaaattgcac catcatttaa tttttggtca actaaatact tattcaagtg   7680
tcgtaaacca gatttaaccg taaattgccg ttatttgagc gatgcagtaa aagaattacc   7740
tcaagaggat atagcattaa tagcacctca cggcacgggt aaaacttcat tagtagctac   7800
tcacgttaag aatcggagtt atcacggaag gaaaactatt tcattggtgc atcttgaaag   7860
tttagccaaa gctaatggca acgcacttgg attatattac cgaaccgaaa ataatattga   7920
aaagcaatat cttggattta gcttatgtgt agatagttgc cgtgataaga ttaacggcat   7980
tacaactgat attatttcag gtcaagatta ttgccttttc attgatgaaa ttgaccaagt   8040
aattccacac atccttaaca gtgaaactga agtaagtaag tatagatgca ccatcattga   8100
cactttttct gaactggtga gaaatgctga acaggtcatt attgctgatg ctgatttatc   8160
cgatgtgacg attgacctaa tagaaaacat cagaggtaaa aaactatatg taatcaagaa   8220
tgaatatcag tatcagggaa tgactttttaa cgccgttggt tcaccattag aaatgatggc   8280
aatgatggga aaatcggtgt cagaaggcaa gaaattattt attaacacca catcccaaaa   8340
ggcaaaaagt aagtacggca caatcgctct tgagtcttat atttttggtc taaataaaga   8400
```

```
agcaaagata ttaagaatag actctgaaac cactaaaaac cctgaacatc cagcctataa   8460
aatcattgac caagacttaa ataatatcct caaagattat gattatgtca ttgcctcacc   8520
ttgccttcaa acaggtgtca gtattacctt aaaagggcat tttgaccagc aatttaactt   8580
ttccagtgga aacattacac ctcattgctt tttacagcaa atgtggcggt tgagggatgc   8640
agaaattgaa agattctatt atgtgccgaa ctcatctaac ctcaatctca ttgggaataa   8700
gtcaagttca ccatcagacc ttctaaagag caataacaag atggcaacgg caacggttaa   8760
ccttttgggt agaatcgact ccgaatattc cctagagtat gaatcgcacg gcatttggct   8820
tgagacgtgg gcaaaattat cagcacggca taacagttca atgcgttgtt actctgaaat   8880
tcttacctat ctaattacgt ctcaagggca taaattaaat atcaacattc cctcacctct   8940
tgcagatatt aagaagctaa atgatgaggt aagtagtaac agggaaaagg taaaaaatga   9000
gagatactct cagaggttaa actcaccaga tattaacgat gcagaagcta ccatactcga   9060
atctaaagag caaaaaatcg gattgactct caatgagaga tgcaccctag aaaagcataa   9120
agttaagaag cggtatggga atgtaaagat ggatattctc acctttgatg atgatggact   9180
ataccccaaa ctcagactat tttattacct caccatcggt aaacctcatc tcaaggctaa   9240
tgacagaaaa gctattgcca aaatgggcaa tgacaataaa ggcaagattc tatcaaaaga   9300
cttagttaat aaaacttact ccgctcgtgt gaaggtctta gagattctta aactaactga   9360
ctttatcgac aatcttagag atgaactctt aataactccc aataatccag ctatcaccga   9420
ttttaataat cttctgctaa gagctaagaa ggatttaaga gtattaggag tcaacatcgg   9480
aaaatatcca atggccaaca ttaatgccgt acttactctc attggtcaca aactttctgt   9540
aatgagagat gagttcggaa aagagaaaag gataaaagta gatggtaaat cataccgatg   9600
ttatcaactt gaaacattac cagattttac caatgatact cttgactact ggttagaaaa   9660
tgatagccaa aaagaagtaa cagcaacaga aaattactcc gaaaatttta acccttcaaa   9720
tagctacaat ccagacagta agacactttc agagggtgca aatttcctat atataaataa   9780
agaagaattg catccaaata aattgcacct agaaataaaa gaaggtgctg aacttttttt   9840
attcggggta aaggtgattg tgaaaggaat cttggacggg gcagtaacta tattctctat   9900
gggtcaagaa tacgatttat ccctcaatga actagagggg atgttaacat catgaacttt   9960
acaagaatct ttttaaaggg cgatcgcacc atgttaaatg atggtacatt tgttcagata  10020
tttgatattt accatgacca cgcattggga gtgacccttg accttaagac agaaaaaatt  10080
atttccgatg atgttagggt aattactgtc aaagacttat tgttcgatgg cacttataaa  10140
ggggtaaaat cttttatgcc cgataatgcc cgataatgcc cgattgatgc tacaaaatcc  10200
cataatcata agcgataatc ccctaatagc ttgtaattct tgaaccgtag cgattttaga  10260
gtattccaaa aagaagaaat aaacaccgca aaatgtcgta tttcacatat ataaaccaag  10320
gtttttgcc ctaaaatctt tatgtttgta gtgtgatgtt gggtcaaaat ggtcagaaaa  10380
gttgcaaggt ttttatggat gcttacgcgc gcgaggggta agcatcccca aatagttact  10440
ttatcctagt ccatgcccat ttattgccgt cccgttcggc tttaaaaaag tgccaaaact  10500
cacaaggtgc aataaaaagt tctgtacctt tcgcaaccct agataatctt tcaacagtta  10560
cttttttcc tattatctcg gtacaaagtt tggctagttt ctcttttccc tctttttcaa  10620
tcaagccttc ttgtatgccc aactcattga ttaatctctc tatttttacc attatttccc  10680
gttcaggtag tttatcccct aaatcttcat cggggggcaa tgtagggcat tctgaagggg  10740
```

-continued

```
cttttcttc tgtctggaca ttatctaata ttgaagtaac caaactatct tcagtttttt 10800
ctattcctat taattcatat tcggttactg tatccgtatc aatatccgaa taactatctt 10860
tatccgtatt agctattcgg ttaagtttat ccgttaactc agaaacaaga ctatatagcg 10920
gttttagctt ttcttctatc ctgttatcta atacggataa gtttatacgg ttatcattat 10980
ccgtattagt atcattgggc ttttttggta gttctacccc ctcataaacc gcttttattc 11040
ccaattccaa cagactgata acagtatcct ttataatggg ttttttgctg atatggtgaa 11100
cttttgcccc ttccatcatt gcgatacttt ctatctcact catcaactta tcgcttaagt 11160
gaatctcgta tctgtttaat cccttactgg ttttattcat atccgtttac tttattcggt 11220
taacaattct attttatacg aataaaatat tatacggtta actttatacg tttaactatt 11280
ttatctatac ggataacagt aataagttat tcgtattagt tatacgttta cttttatcca 11340
aataaaatta gtgcatttaa actaaaagaa tgattttatc ggagttgata gcattggatt 11400
aacctaaaga tgtttataag ctatatctga taagtattta aggttatttt gttattctgt 11460
ttattgacat tatcagaata aaagaataga atataattgt tgagagataa gaggtttaag 11520
tgattatggt taagaagtta gttggttatg tcagggtcag tagtgaatcg caagaggata 11580
acactagctt acagaatcag atagagagaa ttgaagcata ttgtatggct tttggttatg 11640
agttggtaaa aatattcaaa gaggttgcca ctggtacaaa agcagatatt gaaacccgtc 11700
ctatttttaa tgaagctata gaatacttga aacaggataa tgctaatgga attattgcct 11760
tgaagctaga ccgaatcgca cggaatgctt tagatgtatt gcgtttggtt cgtgaaacct 11820
tagaaccaca aaataaaatg ttagtgttac tagatattca ggtagatact tcgacacctt 11880
caggaaaaat gattttaact gtaatgagtg ccgttgctga actcgaaaga gacatgatct 11940
atgatcgcac tcaggggggt agaaagacta aagcccaaaa gggcgggtat gcctacggga 12000
aacctaaatt tggctataag actgaagaaa aggaactaaa agaagattca gcacaacagg 12060
aaactattaa actaattaag agacaccgta ggtcagggaa aagctaccag aaaatagctg 12120
attatctcaa tgcccaaagt attcccacta aacaaggtaa gaaatggagt tctagcgtcg 12180
tctatcgaat ctgtcaggaa aaagctggtt aagtctgttt atagatattt agaatttatt 12240
gaataaaaat agtatgaaca ataaatattt atggactaac cacgctcgga aacgtttaac 12300
tgaacgatgg gaaataaaag aatcatgggt tattgatacc atcgaaaatc ctgaacgttc 12360
agaatttatt gttgatgagt caggggaaaa atatcattac tataaaagaa tagctaagtt 12420
taagaataga gtgttagaag tgataacttc tgccaactca acacccacaa gaataataac 12480
cttttacttt aaccgtaaca tgaggaaaaa tttatgattg ttacttacga taatgaagtt 12540
gacgcaattt attttaagtt aacggaaaat aaaattgata gcaccgaacc tcaaacagac 12600
aggattatca ttgattacga tgaaagtaat aatattgttg gcattgaggt attagatttt 12660
aattatcttg tcaagaaagg tttaaccgtt gctgatttac ctttttctga agatgaaaga 12720
ttaacagctt ctcaatattt taattttcct gttgctatct aatccagaag ggcaataat 12780
ccccttcttt catcgagtta gacttaatat cacaaaagtc attttcattt taccgtttct 12840
tttccacagc gtccgtacgc ccctcgttaa atctcaaaac cgacaattta tgatgtttat 12900
aaaaagttac tcactttaat aagtatttat actcattaaa gggttattct ttttttgtag 12960
cctgataggt tgggaaggaa tatttcagat tatcagattt gttgaatatt tttcgtcaga 13020
tacgcaaacc ttacaaacat aattaacaac tgaaactatt gatatgtcta ggttttagct 13080
ctatcacagg ttggatctg 13099
```

<210> SEQ ID NO 76
<211> LENGTH: 12905
<212> TYPE: DNA
<213> ORGANISM: artificial
<220> FEATURE:
<223> OTHER INFORMATION: Synthetically produced plasmid construct #1815
pABIcyano1-6.8::PnirA-zmPDC(opt1)TdsrA-PcpcB-ADH1102(nat) er

<400> SEQUENCE: 76

```
gtcgacaatt aataacttct tcctgtacgg gcgaatggcc atttgctcct aactaactcc     60

gtactgcttt gcggaacgag cgtagcgaac tctccgaatt actaagcctt catccctgat    120

agatgcaaaa aacgaattaa aattatgtgt aaaaagaaaa tgtgtcttta tttagtagtc    180

aaagttacaa aatattaaga atcaaattaa taatgtattg ggcagttaag tatataagtc    240

tttaaatatt tatttgtatt caatatatta accgaggaca aattatgaat tcttataccg    300

tgggtactta tttagccgaa cgcttagtgc aaattggttt aaaacatcat tttgccgtgg    360

ctggggacta taatttagtg ttattggata acttattatt aaataaaaac atggaacaag    420

tgtattgttg taatgaatta aattgtggtt tttctgctga aggttatgct agagctaaag    480

gtgcagctgc tgctgttgtt acttattctg tgggtgcttt atctgctttt gatgctattg    540

gtggtgctta tgccgaaaat ttacccgtga ttttaatttc tggtgcccct aataataatg    600

atcatgccgc tggacatgtt ttacatcatg ccttaggtaa aaccgattat cattatcaat    660

tagaaatggc caaaaatatt actgctgctg ccgaagctat ttatactcct gaagaagccc    720

ctgccaaaat tgatcatgtg attaaaaccg ccttacgcga aaaaaaaccc gtgtatttag    780

aaattgcctg taatattgct tctatgcctt gtgctgctcc tgggcctgct tctgctttat    840

ttaatgatga agcctctgat gaagctagtt taaatgctgc cgtggaagaa accttaaaat    900

ttattgccaa tcgcgataaa gttgccgtgt tagttggttc taaattaaga gctgctggtg    960

ctgaagaagc tgctgttaaa tttgctgatg ctttaggtgg tgcagttgct actatggctg   1020

ctgccaaatc tttttttccc gaagaaaatc cccattatat tggaactagt tggggagaag   1080

tttcttatcc tggtgtggaa aaaactatga aagaagccga cgctgttatt gctttagccc   1140

ctgtgtttaa tgattattct accactggtt ggactgatat tcccgatccc aaaaaattag   1200

ttttagccga acctcgttct gttgttgtta atggtgttcg ctttccctct gtgcatttaa   1260

aagattattt aacccgctta gcccaaaaag tttctaaaaa aactggtgcc ttagattttt   1320

ttaaatcttt aaatgcgggt gaattaaaaa aagctgctcc tgctgatcct tctgctcctt   1380

tagttaatgc tgaaattgcc cgtcaagttg aagccttatt aacccctaat actaccgtta   1440

ttgccgaaac tggtgattct tggtttaatg cccaacgcat gaaattacct aatggtgccc   1500

gtgttgaata tgaaatgcaa tggggtcata ttggttggtc tgtacctgct gcttttggtt   1560

atgctgttgg tgctcctgaa cgtcgtaata ttttaatggt gggtgatggt tcttttcaat   1620

taactgccca agaagttgcc caaatggttc gcttaaaatt acccgttatt atttttttaa   1680

taaataatta tggttatacc attgaagtga tgattcatga tgggccatat aataatatta   1740

aaaattggga ttatgcgggt ttaatggaag tgtttaatgg taatggtggt tatgattctg   1800

gtgctggtaa aggtttaaaa gccaaaactg gtggtgaatt agctgaagct attaaagttg   1860

ccttagccaa tactgatggg ccaaccttaa ttgaatgttt tattggtcgc gaagattgta   1920

ccgaagaatt agttaaatgg ggtaaacgtg ttgctgctgc taattctcgc aaacccgtga   1980

ataaattatt gtaaggatcc agcaaggttt catcccgacc ccctcagggt cgggattttt   2040
```

```
ttattgtgag ctcaacttta gatattcgta gttggcaatg tcgtaaatgc ggaacaatac   2100
atggaaaaca tatagatttg taatgagaaa aagtgtaaac aaatattaag aaaaagatca   2160
gaaaaattta acaacacgta ataaaaaaat gcgtcactac gggttataaa tttacatgaa   2220
aggttaaaac acttttctga gacgattttg ataaaaaagt tgtcaaaaaa ttaagtttct   2280
ttacaaatgc ttaacaaaaa cttggtttta agcacaaaat aagagagact aatttgcaga   2340
agttttacaa ggaaatcttg aagaaaaaga tctaagtaaa acgactctgt ttaaccaaaa   2400
tttaacaaat ttaacaaaac aaactaaatc tattaggaga ttaactacat atgattcgtg   2460
cctacgcagc tttagaaaaa ggtggagaac tcaagccttt cgagtacgat ccaaaaccgc   2520
tcggtagtga agatgtagag atcgacgtag aatactgcgg aatttgccat agcgacttga   2580
gtatgcttca taatgactgg ggcatgacgc aatacccctt tgtcccagga catgaagttg   2640
taggcaagat cgcggatgtt ggcagtgcgg tgaaaaaact tcaggtcggg cagcgtgttg   2700
gactgggatg gtattcgcga tcgtgcatga cttgcgagtg gtgtatgtct ggcaatcaca   2760
acctttgtgc caccgcagaa ggtacaattg tcggtcgcta cggtggcttt gctgacaagg   2820
tacgcgccca tgaagcttgg gttgtcccct taccagaggc aatgcagcca gtctcagctg   2880
gacccctatt ttgtggcgga attactgttt ttaacccaat cgtccaattt gatgttaaac   2940
ctaccgatcg cgttggagtc attggtattg gtggcttagg acacatggca ttgagatttc   3000
ttcatgcttg gggctgcgat gtcagtgcct tttccagcag cgctgataag gaagcggaag   3060
caagagaaat gggtgctaac cacttcatta actctcgcga cccaaatgca ctcaaatcgg   3120
tagaaggttc ttttgacttg attctttcta ctgtcaatgt agatctagac tggaatacct   3180
acattgcctg cttgcgtcct aaagggcgat tgcatttcgt aggcgtggtt cccaatcctg   3240
tctccagtca agtttttcct ttaatttcag gtcaaaaatc gctctctggt agtcccttgg   3300
gtagtcctgc taccgtcgtc caaatgctcg attttgccac ccgacatcag atcgaaccca   3360
taatcgaaac ctttagtttt gaccaagtca atgaggcatt ggaacactta cacagcggta   3420
aggcacgata tcggatcgtg ttgaaacatt aacctgcagg atcatcttgc tgaaaaactc   3480
gagcgctcgt tccgcaaagc ggtacggagt tagttagggg ctaatgggca ttctcccgta   3540
caggaaagag ttagaagtta ttaattatca acaattctcc tttgcctagt gcatcgttac   3600
ctttttaatt aaaacataag gaaaactaat aatcgtaata atttaacctc aaagtgtaaa   3660
gaaatgtgaa attctgactt ttataacgtt aaagagggaa aaattagcag tttaaaatac   3720
ctagagaata gtctggggta agcatagaga attagattag ttaagttaat caaattcaga   3780
aaaaataata atcgtaaata gttaatctgg gtgtatagaa aatgatcccc ttcatgataa   3840
gatttaaact cgaaaagcaa aagccaaaaa actaacttcc attaaaagaa gttgttacat   3900
ataacgctat aaagaaaatt tatatatttg gaggatacca accatgtctc atattcaacg   3960
tgaaactagt tgttctcgcc ctcgtttaaa ttctaatatg gatgccgatt tatatggtta   4020
taaatgggct cgtgataatg ttggtcaatc tggtgctact atttatcgtt tatatggtaa   4080
acctgatgct cctgaattat tcttgaaaca tggtaaaggt tctgttgcta atgatgttac   4140
tgatgaaatg gttcgtttaa actggttgac tgaatttatg cctttaccta ctattaaaca   4200
ttttattcgt actcccgatg atgcttggtt attaactact gctattcctg gtaaaactgc   4260
ttttcaagtt ttagaagaat atcctgattc tggtgaaaat attgttgatg ctttagctgt   4320
ttttttacgt cgtttacatt ctattcccgt ttgtaattgt ccttttaatt ctgatcgtgt   4380
```

```
ttttcgttta gctcaagctc aatctcgtat gaataatggt ttagttgatg cttctgattt   4440
tgatgatgaa cgtaatggtt ggcctgttga acaagtttgg aaagaaatgc acaaattgtt   4500
accttttct cctgattctg ttgttactca tggtgatttt tctttagata atttgatctt   4560
tgatgaaggt aaattgattg gttgtattga tgttggtcgt gttggtattg ctgatcgtta   4620
tcaagattta gctattttat ggaattgttt aggtgaattt tctccttctt tacagaaacg   4680
tttatttcag aaatatggta ttgataatcc tgatatgaac aagttacaat ttcatttaat   4740
gttggacgag ttcttttaag aattaattca tgaccaaaat cccttaacgt gagttttcgt   4800
tccactgagc gtcagacccc gtagaaaaga tcaaaggatc ttcttgagat ccttttttc   4860
tgcgcgtaat ctgctgctat ttaaattacg tacacgtgtt attactttgt taacgacaat   4920
tgtcttaatt aactgggcct catgggcctt ccgctcactg cccgctttcc agtcgggaaa   4980
cctgtcgtgc cagctctgca gatgacggtg aaaacctctg acacatgcag ctcccggaga   5040
cggtcacagc ttgtctgtaa gcggatgccg ggagcagaca agcccgtcag ggcgcgtcag   5100
cgggtgttgg cgggtgtcgg ggcgcagcca tgacccagtc acgtagcgat agcggagtgt   5160
atactggctt aactatgcgg catcagagca gattgtactg agagtgcacc atatgcggtg   5220
tgaaataccg cacagatgcg taaggagaaa ataccgcatc aggcgctctt ccgcttcctc   5280
gctcactgac tcgctgcgct cggtcgttcg gctgcggcga gcggtatcag ctcactcaaa   5340
ggcggtaata cggttatcca cagaatcagg ggataacgca ggaaagaaca tgtgagcaaa   5400
aggccagcaa aaggccagga accgtaaaaa ggccgcgttg ctggcgtttt tccataggct   5460
ccgcccccct gacgagcatc acaaaaatcg acgctcaagt cagaggtggc gaaacccgac   5520
aggactataa agataccagg cgtttccccc tggaagctcc ctcgtgcgct ctcctgttcc   5580
gaccctgccg cttaccggat acctgtccgc ctttctccct tcgggaagcg tggcgctttc   5640
tcatagctca cgctgtaggt atctcagttc ggtgtaggtc gttcgctcca agctgggctg   5700
tgtgcacgaa ccccccgttc agcccgaccg ctgcgcctta tccggtaact atcgtcttga   5760
gtccaacccg gtaagacacg acttatcgcc actggcagca gccactggta acaggattag   5820
cagagcgagg tatgtaggcg gtgctacaga gttcttgaag tggtggccta actacggcta   5880
cactagaagg acagtatttg gtatctgcgc tctgctgaag ccagttacct tcggaaaaag   5940
agttggtagc tcttgatccg gcaaacaaac caccgctggt agcggtggtt tttttgtttg   6000
caagcagcag attacgcgca gaaaaaaagg atctcaagaa gatcctttga tcttttctac   6060
tgcagaagct tgttagacac cctgtcatgt attttatatt atttatttca ccatacggat   6120
taagtgaaac ctaatgaaaa tagtactttc ggagctttaa ctttaatgaa ggtatgtttt   6180
tttatagaca tcgatgtctg gtttaacaat aggaaaaagt agctaaaact cccatgaatt   6240
aaagaaataa caaggtgtct aacaacctgt tattaagaat gttagaaaag acttaacatt   6300
tgtgttgagt ttttatagac attggtgtct agacatacgg tagataaggt ttgctcaaaa   6360
ataaaataaa aaaagattgg actaaaaaac atttaattta gtacaattta attagttatt   6420
ttttcgtctc aaattttgct ttgttgagca gaaatttaga taaaaaaatc cccgtgatca   6480
gattacaatg tcgttcattg tacgatgtgt cgaaaaatct ttacgacact ctaaactgac   6540
cacacggggg aaaaagaaaa ctgaactaat aacatcatga tactcggaaa acctagcaat   6600
tctcaacccc taaacaaaag aaacttccaa aaccctgacc atataaagga gtggcaacaa   6660
tcagcaatca gtcaagattt gatagcagaa aatcttgtat cggttgctaa tggttttgat   6720
gtactattta tcggcaataa ataccgaact aacacgggtg ttctgtcacg gcacatatta   6780
```

```
aactcctatt ctcatttaga agatggtggt tcgtatggta gaacatttga cccatttacc   6840
aataaagaaa tgcagtgggt tcaatttaaa ccgaatagac caagaaaagg ttctactggt   6900
aaggtaatca aatatgaatc gccaaaaggt gaacctacaa gagttctaat gccgtttgtg   6960
cctatgaaaa tatggcaacg gattagcgat aagttcggag taccgattaa tccgaaaaaa   7020
gatactcact tttgggaatg ggtaaagaat aatccatcga taccgattgc cattacagaa   7080
ggaaataaaa aagctaattg cctattatcc tatggctatc ctgctattgc ctttgtaggc   7140
atttggaacg gattagagaa aataaatgat ttctcgaagg aaaagcagtt aaaagaggat   7200
ttgaaatggt tgttatccaa cggcaaccga aatattaata tcatctttga ccaagaccag   7260
aaacaaaaaa ctgtaattaa tgtaaacaaa gctattttcg ctttatcttc tctaataagt   7320
agaaatggtc ataaagttaa tattgtgcaa tggttgccgt caaaaggtaa aggaatagat   7380
gattatttgg tagctttacc ttttgagaaa agagaaaatc atttagacaa cttaattaaa   7440
attgcaccat catttaattt ttggtcaact aaatacttat tcaagtgtcg taaaccagat   7500
ttaaccgtaa attgccgtta tttgagcgat gcagtaaaag aattacctca agaggatata   7560
gcattaatag cacctcacgg cacgggtaaa acttcattag tagctactca cgttaagaat   7620
cggagttatc acggaaggaa aactatttca ttggtgcatc ttgaaagttt agccaaagct   7680
aatggcaacg cacttggatt atattaccga accgaaaata atattgaaaa gcaatatctt   7740
ggatttagct tatgtgtaga tagttgccgt gataagatta acggcattac aactgatatt   7800
atttcaggtc aagattattg ccttttcatt gatgaaattg accaagtaat tccacacatc   7860
cttaacagtg aaactgaagt aagtaagtat agatgcacca tcattgacac tttttctgaa   7920
ctggtgagaa atgctgaaca ggtcattatt gctgatgctg atttatccga tgtgacgatt   7980
gacctaatag aaaacatcag aggtaaaaaa ctatatgtaa tcaagaatga atatcagtat   8040
cagggaatga cttttaacgc cgttggttca ccattagaaa tgatggcaat gatgggaaaa   8100
tcggtgtcag aaggcaagaa attatttatt aacaccacat cccaaaaggc aaaaagtaag   8160
tacggcacaa tcgctcttga gtcttatatt tttggtctaa ataaagaagc aaagatatta   8220
agaatagact ctgaaaccac taaaaaccct gaacatccag cctataaaat cattgaccaa   8280
gacttaaata atatcctcaa agattatgat tatgtcattg cctcaccttg ccttcaaaca   8340
ggtgtcagta ttaccttaaa agggcatttt gaccagcaat ttaacttttc cagtggaaac   8400
attacacctc attgcttttt acagcaaatg tggcggttga gggatgcaga aattgaaaga   8460
ttctattatg tgccgaactc atctaacctc aatctcattg ggaataagtc aagttcacca   8520
tcagaccttc taaagagcaa taacaagatg gcaacggcaa cggttaacct tttgggtaga   8580
atcgactccg aatattccct agagtatgaa tcgcacggca tttggcttga gacgtgggca   8640
aaattatcag cacggcataa cagttcaatg cgttgttact ctgaaattct tacctatcta   8700
attacgtctc aagggcataa attaaatatc aacattccct cacctcttgc agatattaag   8760
aagctaaatg atgaggtaag tagtaacagg gaaaaggtaa aaaatgagag atactctcag   8820
aggttaaact caccagatat taacgatgca gaagctacca tactcgaatc taaagagcaa   8880
aaaatcggat tgactctcaa tgagagatgc accctagaaa agcataaagt taagaagcgg   8940
tatgggaatg taaagatgga tattctcacc tttgatgatg atggactata ccccaaactc   9000
agactatttt attacctcac catcggtaaa cctcatctca aggctaatga cagaaaagct   9060
attgccaaaa tgggcaatga caataaaggc aagattctat caaaagactt agttaataaa   9120
```

```
acttactccg ctcgtgtgaa ggtcttagag attcttaaac taactgactt tatcgacaat   9180
cttagagatg aactcttaat aactcccaat aatccagcta tcaccgattt taataatctt   9240
ctgctaagag ctaagaagga tttaagagta ttaggagtca acatcggaaa atatccaatg   9300
gccaacatta atgccgtact tactctcatt ggtcacaaac tttctgtaat gagagatgag   9360
ttcggaaaag agaaaaggat aaaagtagat ggtaaatcat accgatgtta tcaacttgaa   9420
acattaccag attttaccaa tgatactctt gactactggt tagaaaatga tagccaaaaa   9480
gaagtaacag caacagaaaa ttactccgaa aattttaacc cttcaaatag ctacaatcca   9540
gacagtaaga cactttcaga gggtgcaaat ttcctatata taaataaaga agaattgcat   9600
ccaaataaat tgcacctaga aataaaagaa ggtgctgaac ttttttttatt cggggtaaag   9660
gtgattgtga aaggaatctt ggacggggca gtaactatat tctctatggg tcaagaatac   9720
gatttatccc tcaatgaact agaggggatg ttaacatcat gaactttaca agaatctttt   9780
taaagggcga tcgcaccatg ttaaatgatg gtacatttgt tcagatattt gatatttacc   9840
atgaccacgc attgggagtg acccttgacc ttaagacaga aaaaattatt tccgatgatg   9900
ttagggtaat tactgtcaaa gacttattgt tcgatggcac ttataaaggg gtaaaatctt   9960
ttatgcccga taatgcccga taatgcccga ttgatgctac aaaatcccat aatcataagc  10020
gataatcccc taatagcttg taattcttga accgtagcga ttttagagta ttccaaaaag  10080
aagaaataaa caccgcaaaa tgtcgtattt cacatatata aaccaaggtt ttttgcccta  10140
aaatctttat gtttgtagtg tgatgttggg tcaaaatggt cagaaaagtt gcaaggtttt  10200
tatggatgct tacgcgcgcg aggggtaagc atccccaaat agttacttta tcctagtcca  10260
tgcccattta ttgccgtccc gttcggcttt aaaaaagtgc caaaactcac aaggtgcaat  10320
aaaaagttct gtacctttcg caaccctaga taatctttca acagttactt tttttcctat  10380
tatctcggta caaagtttgg ctagtttctc ttttccctct ttttcaatca agccttcttg  10440
tatgcccaac tcattgatta atctctctat ttttaccatt atttcccgtt caggtagttt  10500
atcccctaaa tcttcatcgg ggggcaatgt agggcattct gaaggggctt tttcttctgt  10560
ctggacatta tctaatattg aagtaaccaa actatcttca gttttttcta ttcctattaa  10620
ttcatattcg gttactgtat ccgtatcaat atccgaataa ctatctttat ccgtattagc  10680
tattcggtta agtttatccg ttaactcaga aacaagacta tatagcggtt ttagcttttc  10740
ttctatcctg ttatctaata cggataagtt tatacggtta tcattatccg tattagtatc  10800
attgggcttt tttggtagtt ctaccccctc ataaaccgct tttattccca attccaacag  10860
actgataaca gtatccttta taatgggttt tttgctgata tggtgaactt ttgccccttc  10920
catcattgcg atactttcta tctcactcat caacttatcg cttaagtgaa tctcgtatct  10980
gtttaatccc ttactggttt tattcatatc cgtttacttt attcggttaa caattctatt  11040
ttatacgaat aaaatattat acggttaact ttatacgttt aactatttta tctatacgga  11100
taacagtaat aagttattcg tattagttat acgtttactt ttatccaaat aaaattagtg  11160
catttaaact aaaagaatga ttttatcgga gttgatagca ttggattaac ctaaagatgt  11220
ttataagcta tatctgataa gtatttaagg ttattttgtt attctgttta ttgacattat  11280
cagaataaaa gaatagaata taattgttga gagataagag gtttaagtga ttatggttaa  11340
gaagttagtt ggttatgtca gggtcagtag tgaatcgcaa gaggataaca ctagcttaca  11400
gaatcagata gagagaattg aagcatattg tatggctttt ggttatgagt tggtaaaaat  11460
attcaaagag gttgccactg gtacaaaagc agatattgaa acccgtccta tttttaatga  11520
```

```
agctatagaa tacttgaaac aggataatgc taatggaatt attgccttga agctagaccg  11580

aatcgcacgg aatgctttag atgtattgcg tttggttcgt gaaaccttag aaccacaaaa  11640

taaaatgtta gtgttactag atattcaggt agatacttcg acaccttcag gaaaaatgat  11700

tttaactgta atgagtgccg ttgctgaact cgaaagagac atgatctatg atcgcactca  11760

ggggggtaga aagactaaag cccaaaaggg cgggtatgcc tacgggaaac ctaaatttgg  11820

ctataagact gaagaaaagg aactaaaaga agattcagca caacaggaaa ctattaaact  11880

aattaagaga caccgtaggt cagggaaaag ctaccagaaa atagctgatt atctcaatgc  11940

ccaaagtatt cccactaaac aaggtaagaa atggagttct agcgtcgtct atcgaatctg  12000

tcaggaaaaa gctggttaag tctgtttata gatatttaga atttattgaa taaaaatagt  12060

atgaacaata aatatttatg gactaaccac gctcggaaac gtttaactga acgatgggaa  12120

ataaaagaat catgggttat tgataccatc gaaaatcctg aacgttcaga atttattgtt  12180

gatgagtcag ggaaaaaata tcattactat aaaagaatag ctaagtttaa gaatagagtg  12240

ttagaagtga taacttctgc caactcaaca cccacaagaa taataacctt ttactttaac  12300

cgtaacatga ggaaaaattt atgattgtta cttacgataa tgaagttgac gcaatttatt  12360

ttaagttaac ggaaaataaa attgatagca ccgaacctca aacagacagg attatcattg  12420

attacgatga aagtaataat attgttggca ttgaggtatt agattttaat tatcttgtca  12480

agaaaggttt aaccgttgct gatttacctt tttctgaaga tgaaagatta acagcttctc  12540

aatattttaa ttttcctgtt gctatctaat ccagaagggg caataatccc cttctttcat  12600

cgagttagac ttaatatcac aaaagtcatt ttcattttac cgtttctttt ccacagcgtc  12660

cgtacgcccc tcgttaaatc tcaaaaccga caatttatga tgtttataaa aagttactca  12720

ctttaataag tatttatact cattaaaggg ttattctttt tttgtagcct gataggttgg  12780

gaaggaatat ttcagattat cagatttgtt gaatattttt cgtcagatac gcaaacctta  12840

caaacataat taacaactga aactattgat atgtctaggt tttagctcta tcacaggttg  12900

gatct                                                              12905
```

<210> SEQ ID NO 77
<211> LENGTH: 12911
<212> TYPE: DNA
<213> ORGANISM: artificial
<220> FEATURE:
<223> OTHER INFORMATION: Synthetically produced plasmid construct #1831 pABIcyano1-6.8::PnirA-zmPDC(opt1)-TdsrA-PcpcB-ADH213(nat) er standard;

<400> SEQUENCE: 77

```
tcgacaatta ataacttctt cctgtacggg cgaatggcca tttgctccta actaactccg     60

tactgctttg cggaacgagc gtagcgaact ctccgaatta ctaagccttc atccctgata    120

gatgcaaaaa acgaattaaa attatgtgta aaaagaaaat gtgtctttat ttagtagtca    180

aagttacaaa atattaagaa tcaaattaat aatgtattgg gcagttaagt atataagtct    240

ttaaatattt atttgtattc aatatattaa ccgaggacaa attatgaatt cttataccgt    300

gggtacttat ttagccgaac gcttagtgca aattggttta aaacatcatt ttgccgtggc    360

tggggactat aatttagtgt tattggataa cttattatta aataaaaaca tggaacaagt    420

gtattgttgt aatgaattaa attgtggttt ttctgctgaa ggttatgcta gagctaaagg    480

tgcagctgct gctgttgtta cttattctgt gggtgcttta tctgcttttg atgctattgg    540
```

-continued

```
tggtgcttat gccgaaaatt tacccgtgat tttaatttct ggtgccccta ataataatga    600
tcatgccgct ggacatgttt tacatcatgc cttaggtaaa accgattatc attatcaatt    660
agaaatggcc aaaaatatta ctgctgctgc cgaagctatt tatactcctg aagaagcccc    720
tgccaaaatt gatcatgtga ttaaaaccgc cttacgcgaa aaaaaacccg tgtatttaga    780
aattgcctgt aatattgctt ctatgccttg tgctgctcct gggcctgctt ctgcttttatt    840
taatgatgaa gcctctgatg aagctagttt aaatgctgcc gtggaagaaa ccttaaaatt    900
tattgccaat cgcgataaag ttgccgtgtt agttggttct aaattaagag ctgctggtgc    960
tgaagaagct gctgttaaat ttgctgatgc tttaggtggt gcagttgcta ctatggctgc   1020
tgccaaatct ttttttcccg aagaaaatcc ccattatatt ggaactagtt ggggagaagt   1080
ttcttatcct ggtgtggaaa aaactatgaa agaagccgac gctgttattg ctttagcccc   1140
tgtgtttaat gattattcta ccactggttg gactgatatt cccgatccca aaaaattagt   1200
tttagccgaa cctcgttctg ttgttgttaa tggtgttcgc tttccctctg tgcatttaaa   1260
agattattta acccgcttag cccaaaaagt ttctaaaaaa actggtgcct tagatttttt   1320
taaatcttta aatgcgggtg aattaaaaaa agctgctcct gctgatcctt ctgctccttt   1380
agttaatgct gaaattgccc gtcaagttga agccttatta acccctaata ctaccgttat   1440
tgccgaaact ggtgattctt ggtttaatgc ccaacgcatg aaattaccta atggtgcccg   1500
tgttgaatat gaaatgcaat ggggtcatat tggttggtct gtacctgctg cttttggtta   1560
tgctgttggt gctcctgaac gtcgtaatat tttaatggtg ggtgatggtt cttttcaatt   1620
aactgcccaa gaagttgccc aaatggttcg cttaaaatta cccgttatta ttttttttaat   1680
aaataattat ggttatacca ttgaagtgat gattcatgat gggccatata ataatattaa   1740
aaattgggat tatgcgggtt taatggaagt gtttaatggt aatggtggtt atgattctgg   1800
tgctggtaaa ggtttaaaag ccaaaactgg tggtgaatta gctgaagcta ttaaagttgc   1860
cttagccaat actgatgggc caaccttaat tgaatgtttt attggtcgcg aagattgtac   1920
cgaagaatta gttaaatggg gtaaacgtgt tgctgctgct aattctcgca aacccgtgaa   1980
taaattattg taaggatcca gcaaggtttc atcccgaccc cctcagggtc gggatttttt   2040
tattgtgagc tcaactttag atattcgtag ttggcaatgt cgtaaatgcg gaacaataca   2100
tggaaaacat atagatttgt aatgagaaaa agtgtaaaca aatattaaga aaaagatcag   2160
aaaaatttaa caacacgtaa taaaaaaatg cgtcactacg ggttataaat ttacatgaaa   2220
ggttaaaaca cttttctgag acgattttga taaaaaagtt gtcaaaaaat taagtttctt   2280
tacaaatgct taacaaaaac ttggttttaa gcacaaaata agagagacta atttgcagaa   2340
gttttacaag gaaatcttga agaaaaagat ctaagtaaaa cgactctgtt taaccaaaat   2400
ttaacaaatt taacaaaaca aactaaatct attaggagat taactacata tgcccacaat   2460
taaagccttt gctatccatg aaccttctgg tgatttacaa ccctttgaat atgaccccgg   2520
tgagctgctg ccggatcagg tagagattga ggtgaaatac tgcggtattt gccatagtga   2580
cctcagcatg atcgggaatg agtggggcat gacccaatat ccccttgtcc ctggccacga   2640
agtcgtgggg gcgatcgcca aagttgggaa aaatgtcaaa aatctcagcg ttgggcaagt   2700
tgtcggcctc ggttggcacg ctgggtattg taatgaatgc tcccaatgca ccacaggcga   2760
tcagaacctt tgtgccacgg cccaaggcac catcgtcggc caccatggcg gttttgcaga   2820
aaaagtccgg gctgcggcca atagtgtggt gccaattccc gatggcattg acctcgaagc   2880
cgctggcccc ctattttgtg gcggcattac tgtttttaac cccctcatgc aatatggcat   2940
```

```
ccaacccact tctaaggtgg cggtgctcgg cattggtggt ttaggtcaca tggcggtgca   3000
gtttcttaat gcctggggtt gtgaagtgac ggcctttacc tccagcgaag caaaaattac   3060
agaagccctg gaactcggcg ctcaccacac cctcaattcc cgtgatccag aggcgatcgc   3120
cgctgctgct ggtcaattcg atctgatcat ttcgactgtc aatgtcaaac tcgattggaa   3180
tgcctatctc agtaccctca agccccatgg acgcttacat ttcgttggcg caaccctcga   3240
tcccctcgac atcaacgtct ttgccctaat catgcaacag cgttccattt ctggttcccc   3300
cgtcggtagc cccgcaacca tcgccaaaat gctggaattt gccaaactgc acaatattca   3360
gcccaaaatt gaaaccttca aatttgcaga tgtcaacaag gcgatcgccc gtctaaaaag   3420
tggcgaggcc cattaccgga tcgtgctttg tcgctaacct gcaggatcat cttgctgaaa   3480
aactcgagcg ctcgttccgc aaagcggtac ggagttagtt aggggctaat gggcattctc   3540
ccgtacagga aagagttaga agttattaat tatcaacaat tctcctttgc ctagtgcatc   3600
gttacctttt taattaaaac ataaggaaaa ctaataatcg taataattta acctcaaagt   3660
gtaaagaaat gtgaaattct gacttttata acgttaaaga gggaaaaatt agcagtttaa   3720
aatacctaga gaatagtctg ggtaagcat agagaattag attagttaag ttaatcaaat    3780
tcagaaaaaa taataatcgt aaatagttaa tctgggtgta tagaaaatga tccccttcat   3840
gataagattt aaactcgaaa agcaaaagcc aaaaaactaa cttccattaa aagaagttgt   3900
tacatataac gctataaaga aaatttatat atttggagga taccaaccat gtctcatatt   3960
caacgtgaaa ctagttgttc tcgccctcgt ttaaattcta atatggatgc cgatttatat   4020
ggttataaat gggctcgtga taatgttggt caatctggtg ctactattta tcgtttatat   4080
ggtaaacctg atgctcctga attattcttg aaacatggta aaggttctgt tgctaatgat   4140
gttactgatg aaatggttcg tttaaactgg ttgactgaat ttatgccttt acctactatt   4200
aaacatttta ttcgtactcc cgatgatgct tggttattaa ctactgctat tcctggtaaa   4260
actgcttttc aagttttaga agaatatcct gattctggtg aaaatattgt tgatgcttta   4320
gctgtttttt tacgtcgttt acattctatt cccgtttgta attgtccttt taattctgat   4380
cgtgtttttc gtttagctca agctcaatct cgtatgaata atggtttagt tgatgcttct   4440
gattttgatg atgaacgtaa tggttggcct gttgaacaag tttggaaaga aatgcacaaa   4500
ttgttacctt tttctcctga ttctgttgtt actcatggtg atttttcttt agataatttg   4560
atctttgatg aaggtaaatt gattggttgt attgatgttg gtcgtgttgg tattgctgat   4620
cgttatcaag atttagctat tttatggaat tgtttaggtg aattttctcc ttctttacag   4680
aaacgtttat ttcagaaata tggtattgat aatcctgata tgaacaagtt acaatttcat   4740
ttaatgttgg acgagttctt ttaagaatta attcatgacc aaaatccctt aacgtgagtt   4800
ttcgttccac tgagcgtcag accccgtaga aaagatcaaa ggatcttctt gagatccttt   4860
ttttctgcgc gtaatctgct gctatttaaa ttacgtacac gtgttattac tttgttaacg   4920
acaattgtct taattaactg ggcctcatgg gccttccgct cactgcccgc tttccagtcg   4980
ggaaacctgt cgtgccagct ctgcagatga cggtgaaaac ctctgacaca tgcagctccc   5040
ggagacggtc acagcttgtc tgtaagcgga tgccgggagc agacaagccc gtcagggcgc   5100
gtcagcgggt gttggcgggt gtcggggcgc agccatgacc cagtcacgta gcgatagcgg   5160
agtgtatact ggcttaacta tgcggcatca gagcagattg tactgagagt gcaccatatg   5220
cggtgtgaaa taccgcacag atgcgtaagg agaaaatacc gcatcaggcg ctcttccgct   5280
```

```
tcctcgctca ctgactcgct gcgctcggtc gttcggctgc ggcgagcggt atcagctcac   5340
tcaaaggcgg taatacggtt atccacagaa tcaggggata acgcaggaaa gaacatgtga   5400
gcaaaaggcc agcaaaaggc caggaaccgt aaaaaggccg cgttgctggc gtttttccat   5460
aggctccgcc cccctgacga gcatcacaaa aatcgacgct caagtcagag gtggcgaaac   5520
ccgacaggac tataaagata ccaggcgttt ccccctggaa gctccctcgt gcgctctcct   5580
gttccgaccc tgccgcttac cggatacctg tccgcctttc tcccttcggg aagcgtggcg   5640
ctttctcata gctcacgctg taggtatctc agttcggtgt aggtcgttcg ctccaagctg   5700
ggctgtgtgc acgaaccccc cgttcagccc gaccgctgcg ccttatccgg taactatcgt   5760
cttgagtcca acccggtaag acacgactta tcgccactgg cagcagccac tggtaacagg   5820
attagcagag cgaggtatgt aggcggtgct acagagttct tgaagtggtg gcctaactac   5880
ggctacacta gaaggacagt atttggtatc tgcgctctgc tgaagccagt taccttcgga   5940
aaaagagttg gtagctcttg atccggcaaa caaaccaccg ctggtagcgg tggttttttt   6000
gtttgcaagc agcagattac gcgcagaaaa aaaggatctc aagaagatcc tttgatcttt   6060
tctactgcag aagcttgtta gacaccctgt catgtatttt atattattta tttcaccata   6120
cggattaagt gaaacctaat gaaaatagta ctttcggagc tttaacttta atgaaggtat   6180
gtttttttat agacatcgat gtctggttta acaataggaa aaagtagcta aaactcccat   6240
gaattaaaga aataacaagg tgtctaacaa cctgttatta agaatgttag aaaagactta   6300
acatttgtgt tgagttttta tagacattgg tgtctagaca tacggtagat aaggtttgct   6360
caaaaataaa ataaaaaaag attggactaa aaaacattta atttagtaca atttaattag   6420
ttatttttc gtctcaaatt ttgctttgtt gagcagaaat ttagataaaa aaatccccgt   6480
gatcagatta caatgtcgtt cattgtacga tgtgtcgaaa aatctttacg acactctaaa   6540
ctgaccacac gggggaaaaa gaaaactgaa ctaataacat catgatactc ggaaaaccta   6600
gcaattctca accctaaac aaaagaaact tccaaaaccc tgaccatata aaggagtggc   6660
aacaatcagc aatcagtcaa gatttgatag cagaaaatct tgtatcggtt gctaatggtt   6720
ttgatgtact atttatcggc aataaatacc gaactaacac gggtgttctg tcacggcaca   6780
tattaaactc ctattctcat ttagaagatg gtggttcgta tggtagaaca tttgacccat   6840
ttaccaataa agaaatgcag tgggttcaat ttaaaccgaa tagaccaaga aaaggttcta   6900
ctggtaaggt aatcaaatat gaatcgccaa aaggtgaacc tacaagagtt ctaatgccgt   6960
ttgtgcctat gaaaatatgg caacggatta gcgataagtt cggagtaccg attaatccga   7020
aaaaagatac tcacttttgg gaatgggtaa agaataatcc atcgataccg attgccatta   7080
cagaaggaaa taaaaaagct aattgcctat tatcctatgg ctatcctgct attgcctttg   7140
taggcatttg gaacggatta gagaaaataa atgatttctc gaaggaaaag cagttaaaag   7200
aggatttgaa atggttgtta tccaacggca accgaaatat taatatcatc tttgaccaag   7260
accagaaaca aaaaactgta attaatgtaa acaaagctat tttcgcttta tcttctctaa   7320
taagtagaaa tggtcataaa gttaatattg tgcaatggtt gccgtcaaaa ggtaaaggaa   7380
tagatgatta tttggtagct ttaccttttg agaaaagaga aaatcattta gacaacttaa   7440
ttaaaattgc accatcattt aatttttggt caactaaata cttattcaag tgtcgtaaac   7500
cagatttaac cgtaaattgc cgttatttga gcgatgcagt aaaagaatta cctcaagagg   7560
atatagcatt aatagcacct cacggcacgg gtaaaacttc attagtagct actcacgtta   7620
agaatcggag ttatcacgga aggaaaacta tttcattggt gcatcttgaa agtttagcca   7680
```

```
aagctaatgg caacgcactt ggattatatt accgaaccga aaataatatt gaaaagcaat   7740
atcttggatt tagcttatgt gtagatagtt gccgtgataa gattaacggc attacaactg   7800
atattatttc aggtcaagat tattgccttt tcattgatga aattgaccaa gtaattccac   7860
acatccttaa cagtgaaact gaagtaagta agtatagatg caccatcatt gacacttttt   7920
ctgaactggt gagaaatgct gaacaggtca ttattgctga tgctgattta tccgatgtga   7980
cgattgacct aatagaaaac atcagaggta aaaaactata tgtaatcaag aatgaatatc   8040
agtatcaggg aatgactttt aacgccgttg gttcaccatt agaaatgatg gcaatgatgg   8100
gaaaatcggt gtcagaaggc aagaaattat ttattaacac cacatcccaa aaggcaaaaa   8160
gtaagtacgg cacaatcgct cttgagtctt atatttttgg tctaaataaa gaagcaaaga   8220
tattaagaat agactctgaa accactaaaa accctgaaca tccagcctat aaaatcattg   8280
accaagactt aaataatatc ctcaaagatt atgattatgt cattgcctca ccttgccttc   8340
aaacaggtgt cagtattacc ttaaaagggc attttgacca gcaatttaac ttttccagtg   8400
gaaacattac acctcattgc tttttacagc aaatgtggcg gttgagggat gcagaaattg   8460
aaagattcta ttatgtgccg aactcatcta acctcaatct cattgggaat aagtcaagtt   8520
caccatcaga ccttctaaag agcaataaca agatggcaac ggcaacggtt aacctttttgg   8580
gtagaatcga ctccgaatat tccctagagt atgaatcgca cggcatttgg cttgagacgt   8640
gggcaaaatt atcagcacgg cataacagtt caatgcgttg ttactctgaa attcttacct   8700
atctaattac gtctcaaggg cataaattaa atatcaacat tccctcacct cttgcagata   8760
ttaagaagct aaatgatgag gtaagtagta acagggaaaa ggtaaaaaat gagagatact   8820
ctcagaggtt aaactcacca gatattaacg atgcagaagc taccatactc gaatctaaag   8880
agcaaaaaat cggattgact ctcaatgaga gatgcaccct agaaaagcat aaagttaaga   8940
agcggtatgg gaatgtaaag atggatattc tcacctttga tgatgatgga ctatacccca   9000
aactcagact attttattac ctcaccatcg gtaaacctca tctcaaggct aatgacagaa   9060
aagctattgc caaaatgggc aatgacaata aaggcaagat tctatcaaaa gacttagtta   9120
ataaaactta ctccgctcgt gtgaaggtct tagagattct taaactaact gactttatcg   9180
acaatcttag agatgaactc ttaataactc ccaataatcc agctatcacc gattttaata   9240
atcttctgct aagagctaag aaggatttaa gagtattagg agtcaacatc ggaaaatatc   9300
caatggccaa cattaatgcc gtacttactc tcattggtca caaactttct gtaatgagag   9360
atgagttcgg aaaagagaaa aggataaaag tagatggtaa atcataccga tgttatcaac   9420
ttgaaacatt accagatttt accaatgata ctcttgacta ctggttagaa aatgatagcc   9480
aaaaagaagt aacagcaaca gaaaattact ccgaaaattt taacccttca aatagctaca   9540
atccagacag taagacactt tcagagggtg caaatttcct atatataaat aaagaagaat   9600
tgcatccaaa taaattgcac ctagaaataa aagaaggtgc tgaacttttt ttattcgggg   9660
taaaggtgat tgtgaaagga atcttggacg gggcagtaac tatattctct atgggtcaag   9720
aatacgattt atccctcaat gaactagagg ggatgttaac atcatgaact ttacaagaat   9780
ctttttaaag ggcgatcgca ccatgttaaa tgatggtaca tttgttcaga tatttgatat   9840
ttaccatgac cacgcattgg gagtgaccct tgaccttaag acagaaaaaa ttatttccga   9900
tgatgttagg gtaattactg tcaaagactt attgttcgat ggcacttata aaggggtaaa   9960
atcttttatg cccgataatg cccgataatg cccgattgat gctacaaaat cccataatca  10020
```

```
taagcgataa tcccctaata gcttgtaatt cttgaaccgt agcgatttta gagtattcca  10080

aaaagaagaa ataaacaccg caaaatgtcg tatttcacat atataaacca aggtttttttg  10140

ccctaaaatc tttatgtttg tagtgtgatg ttgggtcaaa atggtcagaa aagttgcaag  10200

gtttttatgg atgcttacgc gcgcgagggg taagcatccc caaatagtta ctttatccta  10260

gtccatgccc atttattgcc gtcccgttcg gctttaaaaa agtgccaaaa ctcacaaggt  10320

gcaataaaaa gttctgtacc tttcgcaacc ctagataatc tttcaacagt tactttttttt  10380

cctattatct cggtacaaag tttggctagt ttctcttttc cctctttttc aatcaagcct  10440

tcttgtatgc ccaactcatt gattaatctc tctattttta ccattatttc ccgttcaggt  10500

agtttatccc ctaaatcttc atcggggggc aatgtagggc attctgaagg ggcttttttct  10560

tctgtctgga cattatctaa tattgaagta accaaactat cttcagtttt ttctattcct  10620

attaattcat attcggttac tgtatccgta tcaatatccg aataactatc tttatccgta  10680

ttagctattc ggttaagttt atccgttaac tcagaaacaa gactatatag cggttttagc  10740

ttttcttcta tcctgttatc taatacggat aagtttatac ggttatcatt atccgtatta  10800

gtatcattgg gctttttttgg tagttctacc ccctcataaa ccgcttttat tcccaattcc  10860

aacagactga taacagtatc ctttataatg ggtttttttgc tgatatggtg aacttttgcc  10920

ccttccatca ttgcgatact ttctatctca ctcatcaact tatcgcttaa gtgaatctcg  10980

tatctgttta atcccttact ggttttattc atatccgttt actttattcg gttaacaatt  11040

ctattttata cgaataaaat attatacggt taactttata cgtttaacta ttttatctat  11100

acggataaca gtaataagtt attcgtatta gttatacgtt tacttttatc caaataaaat  11160

tagtgcattt aaactaaaag aatgatttta tcggagttga tagcattgga ttaacctaaa  11220

gatgtttata agctatatct gataagtatt taaggttatt ttgttattct gtttattgac  11280

attatcagaa taaaagaata gaatataatt gttgagagat aagaggttta agtgattatg  11340

gttaagaagt tagttggtta tgtcagggtc agtagtgaat cgcaagagga taacactagc  11400

ttacagaatc agatagagag aattgaagca tattgtatgg cttttggtta tgagttggta  11460

aaaatattca aagaggttgc cactggtaca aaagcagata ttgaaacccg tcctattttt  11520

aatgaagcta tagaatactt gaaacaggat aatgctaatg gaattattgc cttgaagcta  11580

gaccgaatcg cacggaatgc tttagatgta ttgcgtttgg ttcgtgaaac cttagaacca  11640

caaaataaaa tgttagtgtt actagatatt caggtagata cttcgacacc ttcaggaaaa  11700

atgattttaa ctgtaatgag tgccgttgct gaactcgaaa gagacatgat ctatgatcgc  11760

actcaggggg gtagaaagac taaagcccaa aagggcgggt atgcctacgg gaaacctaaa  11820

tttggctata agactgaaga aaaggaacta aaagaagatt cagcacaaca ggaaactatt  11880

aaactaatta agagacaccg taggtcaggg aaaagctacc agaaaatagc tgattatctc  11940

aatgcccaaa gtattcccac taaacaaggt aagaaatgga gttctagcgt cgtctatcga  12000

atctgtcagg aaaaagctgg ttaagtctgt ttatagatat ttagaattta ttgaataaaa  12060

atagtatgaa caataaatat ttatggacta accacgctcg gaaacgttta actgaacgat  12120

gggaaataaa agaatcatgg gttattgata ccatcgaaaa tcctgaacgt tcagaattta  12180

ttgttgatga gtcaggggaa aaatatcatt actataaaag aatagctaag tttaagaata  12240

gagtgttaga agtgataact tctgccaact caacacccac aagaataata accttttact  12300

ttaaccgtaa catgaggaaa aatttatgat tgttacttac gataatgaag ttgacgcaat  12360

ttattttaag ttaacggaaa ataaaattga tagcaccgaa cctcaaacag acaggattat  12420
```

```
cattgattac gatgaaagta ataatattgt tggcattgag gtattagatt ttaattatct  12480

tgtcaagaaa ggtttaaccg ttgctgattt accttttttct gaagatgaaa gattaacagc  12540

ttctcaatat tttaattttc ctgttgctat ctaatccaga aggggcaata atccccttct  12600

ttcatcgagt tagacttaat atcacaaaag tcattttcat tttaccgttt cttttccaca  12660

gcgtccgtac gcccctcgtt aaatctcaaa accgacaatt tatgatgttt ataaaaagtt  12720

actcacttta ataagtattt atactcatta aagggttatt cttttttttgt agcctgatag  12780

gttgggaagg aatatttcag attatcagat ttgttgaata tttttcgtca gatacgcaaa  12840

ccttacaaac ataattaaca actgaaacta ttgatatgtc taggttttag ctctatcaca  12900

ggttggatct g                                                        12911
```

<210> SEQ ID NO 78
<211> LENGTH: 12722
<212> TYPE: DNA
<213> ORGANISM: artificial
<220> FEATURE:
<223> OTHER INFORMATION: Synthetically produced plasmid construct #1750
pABIcyano1-6.8::PnirA-zmPDC(opt3)-TdsrA-PrpsL*4-ADH111(opt)-ter

<400> SEQUENCE: 78

```
tcgacaatta ataacttctt cctgtacggg cgaatggcca tttgctccta actaactccg     60

tactgctttg cggaacgagc gtagcgaact ctccgaatta ctaagccttc atccctgata    120

gatgcaaaaa acgaattaaa attatgtgta aaaagaaaat gtgtctttat ttagtagtca    180

aagttacaaa atattaagaa tcaaattaat aatgtattgg gcagttaagt atataagtct    240

ttaaatattt atttgtattc aatatattaa ccgaggacaa attatgaatt cttacactgt    300

tggaacctat ttagcagaac gtttagttca aattggtctc aaacaccatt ttgcagtagc    360

tggtgattat aatttagttt tattggataa cttattgtta aataagaata tggaacaagt    420

gtattgttgt aatgaattaa actgtggttt ttctgctgag ggatatgctc gtgcaaaagg    480

tgctgccgca gcagttgtta cttattctgt tggagcatta agtgcttttg acgctattgg    540

aggtgcttat gcagaaaatt tacctgtaat cttaatctct ggtgcaccca ataacaacga    600

tcacgctgct ggtcatgtat tgcatcatgc tttaggtaaa accgattatc attaccaatt    660

agaaatggca aaaaatatta ccgctgccgc agaagctatt tatactcccg aagaagcacc    720

tgctaagatc gatcacgtaa ttaaaaccgc tctccgtgag aaaaaacccg tatatttaga    780

aatcgcttgc aatatcgctt ctatgccttg tgcagctcct ggacctgcta gtgctttatt    840

taacgatgaa gcatctgatg aggctagttt aaatgccgct gttgaagaaa ctttgaaatt    900

tattgctaat cgtgataaag tagctgtttt agttggttct aaactccgtg ccgctggtgc    960

agaagaagcg gctgtaaaat tcgcagatgc cttaggaggt gctgttgcca caatggcagc   1020

cgctaaaagt ttttttccccg aagaaaatcc tcattacatt ggtacttctt ggggtgaggt   1080

atcttaccct ggtgtagaaa aaaccatgaa ggaagctgat gcagtaattg cattagctcc   1140

tgttttcaat gattactcta ccactggttg gactgatatt ccagacccca aaaaattagt   1200

tttagcagaa cctcgctctg tagttgtgaa tggtgttaga tttcccagtg tacatctcaa   1260

agattattta actcgtttag ctcaaaaagt gagtaaaaag actggcgcac tcgatttctt   1320

taaatcttta aatgctggtg aattaaagaa agcagctcct gctgatccca gtgctccttt   1380

agtgaatgcc gaaatcgcaa gacaagttga agccttgtta actcctaaca ctaccgttat   1440

tgccgagact ggtgatagtt ggttcaatgc tcaacgcatg aaattaccca atggtgctcg   1500
```

```
tgttgagtat gaaatgcaat ggggtcacat tggatggtct gttcctgctg catttggata   1560
tgcagttgga gcacctgagc gtagaaacat tttaatggta ggtgatggtt ctttccaact   1620
cactgctcaa gaagttgcac aaatggtacg tttaaaattg cctgttatta tctttctcat   1680
taacaactat ggttacacca ttgaagttat gattcatgat ggtccttata ataacattaa   1740
gaattgggat tacgcaggtt taatggaggt atttaacggt aatggtggat acgacagtgg   1800
agcaggtaaa ggattaaaag ctaaaacagg aggtgagtta gctgaagcaa ttaaagtagc   1860
tttagccaat acagatggtc ctaccttaat cgaatgtttc attggacgtg aagattgtac   1920
tgaagagtta gttaaatggg gaaagcgtgt tgccgctgca aattctcgta aacctgtaaa   1980
caaactcttg tagttaggat ccagcaaggt ttcatcccga ccccctcagg gtcgggattt   2040
ttttattgtg agctcagaaa aactattgac aaacccataa aaaatgtgat ataattatag   2100
attgtcactg gtattttata ctagaggcaa attatattta tatatacaaa aatgctgtag   2160
gaggatcagc catatgagtg aaactaaatt taaagcctat gccgtaatga atcctggtga   2220
aaaattacaa ccctgggaat atgaacctgc tcctttacag gtagatgaaa ttgaagtaag   2280
agttactcac aatggtttat gtcacactga cttacacatg agagataatg actggaatgt   2340
tagtgagttc cccttagtag caggtcatga agttgttggt gaagtaaccg ctgttggtga   2400
aaaagtaacc agtcgtaaaa aaggtgatag agttggtgta ggttggattc gtaattcttg   2460
tcgcgcttgt gaccattgtt tacaaggaga agagaacatt tgtagagagg gttatactgg   2520
tttaattgtt ggtcatcacg gtggatttgc tgatcgtgta cgtgtacctg ctgacttcac   2580
ttataaaatt cctgatgctt tagatagtgc atctgctgct cctttattat gtgccggtat   2640
taccgtttac actcctttaa gaacctacat taaacatccc ggtatgaaag taggtgttat   2700
gggtattgga ggattaggac atttagctat taaatttgct cgtgcaatgg gagcagaagt   2760
tactgccttt agtaccagtc ctaataaaga agcccaagcc aaagaatttg gtgctcatca   2820
tttccaacaa tggggtactg ctgaagaaat gaaagctgtt gccggtaatt ttgatttagt   2880
tttatctacc atctctgctg aaactgactg ggatgctgcc ttctctttat tagcaaataa   2940
cggtgtttta tgtttcgtag gtattcccgt tagttcttta aatgttcctt taattccttt   3000
aattttcgga caaaaatctg ttgtaggttc tgtagttgga ggaagaagat tcatggcaga   3060
aatgttagag ttcgccgctg taaatcagat taaacctatg atcgaaacta tgcccttatc   3120
tcaagtaaat gaagctatgg ataaagttgc cgccaataaa gccagatata gaattgtatt   3180
attatctgaa taactagatc tcctgcagag aatataaaaa gccagattat taatccggct   3240
tttttattat ttaaatactg tgcacgatcc tgcaggatca tcttgctgaa aaactcgagc   3300
gctcgttccg caaagcggta cggagttagt taggggctaa tgggcattct cccgtacagg   3360
aaagagttag aagttattaa ttatcaacaa ttctcctttg cctagtgcat cgttaccttt   3420
ttaattaaaa cataaggaaa actaataatc gtaataattt aacctcaaag tgtaaagaaa   3480
tgtgaaattc tgacttttat aacgttaaag agggaaaaat tagcagttta aaatacctag   3540
agaatagtct ggggtaagca tagagaatta gattagttaa gttaatcaaa ttcagaaaaa   3600
ataataatcg taaatagtta atctgggtgt atagaaaatg atccccttca tgataagatt   3660
taaactcgaa aagcaaaagc caaaaaacta acttccatta aaagaagttg ttacatataa   3720
cgctataaag aaaatttata tatttggagg ataccaacca tgtctcatat tcaacgtgaa   3780
actagttgtt ctcgccctcg tttaaattct aatatggatg ccgatttata tggttataaa   3840
```

```
tgggctcgtg ataatgttgg tcaatctggt gctactattt atcgtttata tggtaaacct   3900
gatgctcctg aattattctt gaaacatggt aaaggttctg ttgctaatga tgttactgat   3960
gaaatggttc gtttaaactg gttgactgaa tttatgcctt tacctactat taaacatttt   4020
attcgtactc ccgatgatgc ttggttatta actactgcta ttcctggtaa aactgctttt   4080
caagttttag aagaatatcc tgattctggt gaaaatattg ttgatgcttt agctgttttt   4140
ttacgtcgtt tacattctat tcccgtttgt aattgtcctt ttaattctga tcgtgttttt   4200
cgtttagctc aagctcaatc tcgtatgaat aatggtttag ttgatgcttc tgattttgat   4260
gatgaacgta atggttggcc tgttgaacaa gtttggaaag aaatgcacaa attgttacct   4320
ttttctcctg attctgttgt tactcatggt gatttttctt tagataattt gatctttgat   4380
gaaggtaaat tgattggttg tattgatgtt ggtcgtgttg gtattgctga tcgttatcaa   4440
gatttagcta ttttatggaa ttgtttaggt gaattttctc cttctttaca gaaacgttta   4500
tttcagaaat atggtattga taatcctgat atgaacaagt tacaatttca tttaatgttg   4560
gacgagttct tttaagaatt aattcatgac caaaatccct taacgtgagt tttcgttcca   4620
ctgagcgtca gaccccgtag aaaagatcaa aggatcttct tgagatcctt tttttctgcg   4680
cgtaatctgc tgctatttaa attacgtaca cgtgttatta ctttgttaac gacaattgtc   4740
ttaattaact gggcctcatg ggccttccgc tcactgcccg ctttccagtc gggaaacctg   4800
tcgtgccagc tctgcagatg acggtgaaaa cctctgacac atgcagctcc cggagacggt   4860
cacagcttgt ctgtaagcgg atgccgggag cagacaagcc cgtcagggcg cgtcagcggg   4920
tgttggcggg tgtcggggcg cagccatgac ccagtcacgt agcgatagcg gagtgtatac   4980
tggcttaact atgcggcatc agagcagatt gtactgagag tgcaccatat gcggtgtgaa   5040
ataccgcaca gatgcgtaag gagaaaatac cgcatcaggc gctcttccgc ttcctcgctc   5100
actgactcgc tgcgctcggt cgttcggctg cggcgagcgg tatcagctca ctcaaaggcg   5160
gtaatacggt tatccacaga atcaggggat aacgcaggaa agaacatgtg agcaaaaggc   5220
cagcaaaagg ccaggaaccg taaaaaggcc gcgttgctgg cgtttttcca taggctccgc   5280
cccccctgacg agcatcacaa aaatcgacgc tcaagtcaga ggtggcgaaa cccgacagga   5340
ctataaagat accaggcgtt tccccctgga agctccctcg tgcgctctcc tgttccgacc   5400
ctgccgctta ccggatacct gtccgccttt ctcccttcgg gaagcgtggc gctttctcat   5460
agctcacgct gtaggtatct cagttcggtg taggtcgttc gctccaagct gggctgtgtg   5520
cacgaacccc ccgttcagcc cgaccgctgc gccttatccg gtaactatcg tcttgagtcc   5580
aacccggtaa gacacgactt atcgccactg gcagcagcca ctggtaacag gattagcaga   5640
gcgaggtatg taggcggtgc tacagagttc ttgaagtggt ggcctaacta cggctacact   5700
agaaggacag tatttggtat ctgcgctctg ctgaagccag ttaccttcgg aaaaagagtt   5760
ggtagctctt gatccggcaa acaaaccacc gctggtagcg gtggtttttt tgtttgcaag   5820
cagcagatta cgcgcagaaa aaaaggatct caagaagatc ctttgatctt ttctactgca   5880
gaagcttgtt agacaccctg tcatgtattt tatattattt atttcaccat acggattaag   5940
tgaaacctaa tgaaaatagt actttcggag ctttaacttt aatgaaggta tgttttttta   6000
tagacatcga tgtctggttt aacaatagga aaaagtagct aaaactccca tgaattaaag   6060
aaataacaag gtgtctaaca acctgttatt aagaatgtta gaaaagactt aacatttgtg   6120
ttgagttttt atagacattg gtgtctagac atacggtaga taaggtttgc tcaaaaataa   6180
aataaaaaaa gattggacta aaaaacattt aatttagtac aatttaatta gttatttttt   6240
```

```
cgtctcaaat tttgctttgt tgagcagaaa tttagataaa aaaatccccg tgatcagatt   6300
acaatgtcgt tcattgtacg atgtgtcgaa aaatctttac gacactctaa actgaccaca   6360
cgggggaaaa agaaaactga actaataaca tcatgatact cggaaaacct agcaattctc   6420
aacccctaaa caaaagaaac ttccaaaacc ctgaccatat aaaggagtgg caacaatcag   6480
caatcagtca agatttgata gcagaaaatc ttgtatcggt tgctaatggt tttgatgtac   6540
tatttatcgg caataaatac cgaactaaca cgggtgttct gtcacggcac atattaaact   6600
cctattctca tttagaagat ggtggttcgt atggtagaac atttgaccca tttaccaata   6660
aagaaatgca gtgggttcaa tttaaaccga atagaccaag aaaaggttct actggtaagg   6720
taatcaaata tgaatcgcca aaaggtgaac ctacaagagt tctaatgccg tttgtgccta   6780
tgaaaatatg gcaacggatt agcgataagt tcggagtacc gattaatccg aaaaaagata   6840
ctcacttttg ggaatgggta aagaataatc catcgatacc gattgccatt acagaaggaa   6900
ataaaaaagc taattgccta ttatcctatg gctatcctgc tattgccttt gtaggcattt   6960
ggaacggatt agagaaaata aatgatttct cgaaggaaaa gcagttaaaa gaggatttga   7020
aatggttgtt atccaacggc aaccgaaata ttaatatcat ctttgaccaa gaccagaaac   7080
aaaaaactgt aattaatgta aacaaagcta ttttcgcttt atcttctcta ataagtagaa   7140
atggtcataa agttaatatt gtgcaatggt tgccgtcaaa aggtaaagga atagatgatt   7200
atttggtagc tttacctttt gagaaaagag aaaatcattt agacaactta attaaaattg   7260
caccatcatt taatttttgg tcaactaaat acttattcaa gtgtcgtaaa ccagatttaa   7320
ccgtaaattg ccgttatttg agcgatgcag taaaagaatt acctcaagag gatatagcat   7380
taatagcacc tcacggcacg ggtaaaactt cattagtagc tactcacgtt aagaatcgga   7440
gttatcacgg aaggaaaact atttcattgg tgcatcttga aagtttagcc aaagctaatg   7500
gcaacgcact tggattatat taccgaaccg aaaataatat tgaaaagcaa tatcttggat   7560
ttagcttatg tgtagatagt tgccgtgata agattaacgg cattacaact gatattattt   7620
caggtcaaga ttattgcctt ttcattgatg aaattgacca agtaattcca cacatcctta   7680
acagtgaaac tgaagtaagt aagtatagat gcaccatcat tgacactttt tctgaactgg   7740
tgagaaatgc tgaacaggtc attattgctg atgctgattt atccgatgtg acgattgacc   7800
taatagaaaa catcagaggt aaaaaactat atgtaatcaa gaatgaatat cagtatcagg   7860
gaatgacttt taacgccgtt ggttcaccat tagaaatgat ggcaatgatg ggaaaatcgg   7920
tgtcagaagg caagaaatta tttattaaca ccacatccca aaaggcaaaa agtaagtacg   7980
gcacaatcgc tcttgagtct tatattttg gtctaaataa agaagcaaag atattaagaa   8040
tagactctga aaccactaaa aaccctgaac atccagccta taaaatcatt gaccaagact   8100
taaataatat cctcaaagat tatgattatg tcattgcctc accttgcctt caaacaggtg   8160
tcagtattac cttaaaaggg cattttgacc agcaatttaa cttttccagt ggaaacatta   8220
cacctcattg ctttttacag caaatgtggc ggttgaggga tgcagaaatt gaaagattct   8280
attatgtgcc gaactcatct aacctcaatc tcattgggaa taagtcaagt tcaccatcag   8340
accttctaaa gagcaataac aagatggcaa cggcaacggt taacctttg ggtagaatcg   8400
actccgaata ttccctagag tatgaatcgc acggcatttg gcttgagacg tgggcaaaat   8460
tatcagcacg gcataacagt tcaatgcgtt gttactctga aattcttacc tatctaatta   8520
cgtctcaagg gcataaatta aatatcaaca ttccctcacc tcttgcagat attaagaagc   8580
```

```
taaatgatga ggtaagtagt aacagggaaa aggtaaaaaa tgagagatac tctcagaggt   8640
taaactcacc agatattaac gatgcagaag ctaccatact cgaatctaaa gagcaaaaaa   8700
tcggattgac tctcaatgag agatgcaccc tagaaaagca taaagttaag aagcggtatg   8760
ggaatgtaaa gatggatatt ctcacctttg atgatgatgg actataccccc aaactcagac   8820
tattttatta cctcaccatc ggtaaacctc atctcaaggc taatgacaga aaagctattg   8880
ccaaaatggg caatgacaat aaaggcaaga ttctatcaaa agacttagtt aataaaactt   8940
actccgctcg tgtgaaggtc ttagagattc ttaaactaac tgactttatc gacaatctta   9000
gagatgaact cttaataact cccaataatc cagctatcac cgattttaat aatcttctgc   9060
taagagctaa gaaggattta agagtattag gagtcaacat cggaaaatat ccaatggcca   9120
acattaatgc cgtacttact ctcattggtc acaaactttc tgtaatgaga gatgagttcg   9180
gaaaagagaa aaggataaaa gtagatggta aatcataccg atgttatcaa cttgaaacat   9240
taccagattt taccaatgat actcttgact actggttaga aaatgatagc caaaaagaag   9300
taacagcaac agaaaattac tccgaaaatt ttaacccttc aaatagctac aatccagaca   9360
gtaagacact ttcagagggt gcaaatttcc tatatataaa taaagaagaa ttgcatccaa   9420
ataaattgca cctagaaata aaagaaggtg ctgaactttt tttattcggg gtaaaggtga   9480
ttgtgaaagg aatcttggac ggggcagtaa ctatattctc tatgggtcaa gaatacgatt   9540
tatccctcaa tgaactagag ggatgttaa catcatgaac tttacaagaa tctttttaaa   9600
gggcgatcgc accatgttaa atgatggtac atttgttcag atatttgata tttaccatga   9660
ccacgcattg ggagtgaccc ttgaccttaa gacagaaaaa attatttccg atgatgttag   9720
ggtaattact gtcaaagact tattgttcga tggcacttat aaaggggtaa aatcttttat   9780
gcccgataat gcccgataat gcccgattga tgctacaaaa tcccataatc ataagcgata   9840
atcccctaat agcttgtaat tcttgaaccg tagcgatttt agagtattcc aaaaagaaga   9900
aataaacacc gcaaaatgtc gtatttcaca tatataaacc aaggtttttt gccctaaaat   9960
ctttatgttt gtagtgtgat gttgggtcaa aatggtcaga aaagttgcaa ggtttttatg  10020
gatgcttacg cgcgcgaggg gtaagcatcc ccaaatagtt actttatcct agtccatgcc  10080
catttattgc cgtcccgttc ggctttaaaa aagtgccaaa actcacaagg tgcaataaaa  10140
agttctgtac ctttcgcaac cctagataat ctttcaacag ttactttttt tcctattatc  10200
tcggtacaaa gtttggctag tttctctttt ccctcttttt caatcaagcc ttcttgtatg  10260
cccaactcat tgattaatct ctctattttt accattattt cccgttcagg tagtttatcc  10320
cctaaatctt catcgggggg caatgtaggg cattctgaag gggctttttc ttctgtctgg  10380
acattatcta atattgaagt aaccaaacta tcttcagttt tttctattcc tattaattca  10440
tattcggtta ctgtatccgt atcaatatcc gaataactat ctttatccgt attagctatt  10500
cggttaagtt tatccgttaa ctcagaaaca agactatata gcggttttag cttttcttct  10560
atcctgttat ctaatacgga taagtttata cggttatcat tatccgtatt agtatcattg  10620
ggcttttttg gtagttctac cccctcataa accgctttta ttcccaattc caacagactg  10680
ataacagtat cctttataat gggttttttg ctgatatggt gaacttttgc cccttccatc  10740
attgcgatac tttctatctc actcatcaac ttatcgctta agtgaatctc gtatctgttt  10800
aatcccttac tggttttatt catatccgtt tactttattc ggttaacaat tctattttat  10860
acgaataaaa tattatacgg ttaactttat acgtttaact attttatcta tacggataac  10920
agtaataagt tattcgtatt agttatacgt ttacttttat ccaaataaaa ttagtgcatt  10980
```

taaactaaaa gaatgatttt atcggagttg atagcattgg attaacctaa agatgtttat 11040
aagctatatc tgataagtat ttaaggttat tttgttattc tgtttattga cattatcaga 11100
ataaaagaat agaatataat tgttgagaga taagaggttt aagtgattat ggttaagaag 11160
ttagttggtt atgtcagggt cagtagtgaa tcgcaagagg ataacactag cttacagaat 11220
cagatagaga gaattgaagc atattgtatg gcttttggtt atgagttggt aaaaatattc 11280
aaagaggttg ccactggtac aaaagcagat attgaaaccc gtcctatttt taatgaagct 11340
atagaatact tgaaacagga taatgctaat ggaattattg ccttgaagct agaccgaatc 11400
gcacggaatg ctttagatgt attgcgtttg gttcgtgaaa ccttagaacc acaaaataaa 11460
atgttagtgt tactagatat tcaggtagat acttcgacac cttcaggaaa aatgatttta 11520
actgtaatga gtgccgttgc tgaactcgaa agagacatga tctatgatcg cactcagggg 11580
ggtagaaaga ctaaagccca aaagggcggg tatgcctacg ggaaacctaa atttggctat 11640
aagactgaag aaaaggaact aaaagaagat tcagcacaac aggaaactat taaactaatt 11700
aagagacacc gtaggtcagg gaaaagctac cagaaaatag ctgattatct caatgcccaa 11760
agtattccca ctaaacaagg taagaaatgg agttctagcg tcgtctatcg aatctgtcag 11820
gaaaaagctg gttaagtctg tttatagata tttagaattt attgaataaa aatagtatga 11880
acaataaata tttatggact aaccacgctc ggaaacgttt aactgaacga tgggaaataa 11940
aagaatcatg ggttattgat accatcgaaa atcctgaacg ttcagaattt attgttgatg 12000
agtcagggga aaaatatcat tactataaaa gaatagctaa gtttaagaat agagtgttag 12060
aagtgataac ttctgccaac tcaacaccca caagaataat aacctttac tttaaccgta 12120 acatgaggaa aaatttatga ttgttactta cgataatgaa gttgacgcaa tttattttaa 12180
gttaacggaa aataaaattg atagcaccga acctcaaaca gacaggatta tcattgatta 12240
cgatgaaagt aataatattg ttggcattga ggtattagat tttaattatc ttgtcaagaa 12300
aggtttaacc gttgctgatt taccttttc tgaagatgaa agattaacag cttctcaata 12360
ttttaatttt cctgttgcta tctaatccag aaggggcaat aatcccctc tttcatcgag 12420 ttagacttaa tatcacaaaa gtcattttca ttttaccgtt tcttttccac agcgtccgta 12480
cgcccctcgt taaatctcaa aaccgacaat ttatgatgtt tataaaaagt tactcacttt 12540
aataagtatt tatactcatt aaagggttat tcttttttg tagcctgata ggttgggaag 12600
gaatatttca gattatcaga tttgttgaat atttttcgtc agatacgcaa accttacaaa 12660
cataattaac aactgaaact attgatatgt ctaggtttta gctctatcac aggttggatc 12720
tg 12722

<210> SEQ ID NO 79
<211> LENGTH: 12978
<212> TYPE: DNA
<213> ORGANISM: artificial
<220> FEATURE:
<223> OTHER INFORMATION: Synthetically produced plasmid construct #1784 pABIcyano1-6.8::PnirA*2-zmPDC(opt3)-TdsrA-PcpcB-synADH-oop

<400> SEQUENCE: 79
gtcgacaatt aataacttct tcctgtacgg gcgaatggcc atttgctcct aactaactcc 60
gtactgcttt gcggaacgag cgtagcgaac tctccgaatt actaagcctt catccctgat 120
agatgcaaaa aacgaattaa aattatgtgt aaaaagaaaa tgtgtcttta tttagtagtc 180
aaagttacaa aatattaaga atcaaattaa taatgtattg ggcagttaag tatataagtc 240

```
tttaaatatt tatttgtatt caatatatta aggaggatca gccttatgaa ttcttacact    300
gttggaacct atttagcaga acgtttagtt caaattggtc tcaaacacca ttttgcagta    360
gctggtgatt ataatttagt tttattggat aacttattgt taaataagaa tatggaacaa    420
gtgtattgtt gtaatgaatt aaactgtggt ttttctgctg agggatatgc tcgtgcaaaa    480
ggtgctgccg cagcagttgt tacttattct gttggagcat taagtgcttt tgacgctatt    540
ggaggtgctt atgcagaaaa tttacctgta atcttaatct ctggtgcacc caataacaac    600
gatcacgctg ctggtcatgt attgcatcat gctttaggta aaaccgatta tcattaccaa    660
ttagaaatgg caaaaaatat taccgctgcc gcagaagcta tttatactcc cgaagaagca    720
cctgctaaga tcgatcacgt aattaaaacc gctctccgtg agaaaaaacc cgtatattta    780
gaaatcgctt gcaatatcgc ttctatgcct tgtgcagctc ctggacctgc tagtgcttta    840
tttaacgatg aagcatctga tgaggctagt ttaaatgccg ctgttgaaga aactttgaaa    900
tttattgcta atcgtgataa agtagctgtt ttagttggtt ctaaactccg tgccgctggt    960
gcagaagaag cggctgtaaa attcgcagat gccttaggag gtgctgttgc cacaatggca   1020
gccgctaaaa gtttttttccc cgaagaaaat cctcattaca ttggtacttc ttggggtgag   1080
gtatcttacc ctggtgtaga aaaaaccatg aaggaagctg atgcagtaat tgcattagct   1140
cctgttttca atgattactc taccactggt tggactgata ttccagaccc caaaaaatta   1200
gttttagcag aacctcgctc tgtagttgtg aatggtgtta gatttcccag tgtacatctc   1260
aaagattatt taactcgttt agctcaaaaa gtgagtaaaa agactggcgc actcgatttc   1320
tttaaatctt taaatgctgg tgaattaaag aaagcagctc ctgctgatcc cagtgctcct   1380
ttagtgaatg ccgaaatcgc aagacaagtt gaagccttgt taactcctaa cactaccgtt   1440
attgccgaga ctggtgatag ttggttcaat gctcaacgca tgaaattacc caatggtgct   1500
cgtgttgagt atgaaatgca atggggtcac attggatggt ctgttcctgc tgcatttgga   1560
tatgcagttg gagcacctga gcgtagaaac attttaatgg taggtgatgg ttctttccaa   1620
ctcactgctc aagaagttgc acaaatggta cgtttaaaat tgcctgttat tatctttctc   1680
attaacaact atggttacac cattgaagtt atgattcatg atggtcctta taataacatt   1740
aagaattggg attacgcagg tttaatggag gtatttaacg gtaatggtgg atacgacagt   1800
ggagcaggta aaggattaaa agctaaaaca ggaggtgagt tagctgaagc aattaaagta   1860
gctttagcca atacagatgg tcctacctta atcgaatgtt tcattggacg tgaagattgt   1920
actgaagagt tagttaaatg ggggaaagcgt gttgccgctg caaattctcg taaacctgta   1980
aacaaactct tgtagttagg atccagcaag gtttcatccc gaccccctca gggtcgggat   2040
ttttttattg tgagctcaac tttagatatt cgtagttggc aatgtcgtaa atgcggaaca   2100
atacatggaa aacatataga tttgtaatga gaaaaagtgt aaacaaatat taagaaaaag   2160
atcagaaaaa tttaacaaca cgtaataaaa aaatgcgtca ctacgggtta taaatttaca   2220
tgaaaggtta aaacactttt ctgagacgat tttgataaaa aagttgtcaa aaaattaagt   2280
ttctttacaa atgcttaaca aaaacttggt tttaagcaca aaataagaga gactaatttg   2340
cagaagtttt acaaggaaat cttgaagaaa aagatctaag taaaacgact ctgtttaacc   2400
aaaatttaac aaatttaaca aaacaaacta aatctattag gagattaact acatatgatt   2460
aaagcctacg ctgccctgga agccaacgga aaactccaac cctttgaata cgaccccggt   2520
gccctgggtg ctaatgaggt ggagattgag gtgcagtatt gtggggtgtg ccacagtgat   2580
```

```
ttgtccatga ttaataacga atggggcatt tccaattacc ccctagtgcc gggtcatgag   2640
gtggtgggta ctgtggccgc catgggcgaa ggggtgaacc atgttgaggt gggggattta   2700
gtggggctgg gttggcattc gggctactgc atgacctgcc atagttgttt atctggctac   2760
cacaaccttt gtgccacggc ggaatcgacc attgtgggcc actacggtgg ctttggcgat   2820
cgggttcggg ccaagggagt cagcgtggtg aaattaccta aaggcattga cctagccagt   2880
gccgggcccc ttttctgtgg aggaattacc gttttcagtc ctatggtgga actgagttta   2940
aagcccactg caaaagtggc agtgatcggc attgggggct tgggccattt agcggtgcaa   3000
tttctccggg cctggggctg tgaagtgact gcctttacct ccagtgccag gaagcaaacg   3060
gaagtgttgg aattgggcgc tcaccacata ctagattcca ccaatccaga ggcgatcgcc   3120
agtgcggaag gcaaatttga ctatattatc tccactgtga acctgaagct tgactggaac   3180
ttatacatca gcaccctggc gccccaggga catttccact ttgttggggt ggtgttggag   3240
cctttggatc taaatctttt tccccttttg atgggacaac gctccgtttc tgcctcccca   3300
gtgggtagtc ccgccaccat tgccaccatg ttggactttg ctgtgcgcca tgacattaaa   3360
cccgtggtgg aacaatttag ctttgatcag atcaacgagg cgatcgccca tctagaaagc   3420
ggcaaagccc attatcgggt agtgctcagc catagtaaaa attagctctg caaaggttgc   3480
ttctagatct gtggaacgcc cggttgccac cgggcgtttt ttattcctgc aggatcatct   3540
tgctgaaaaa ctcgagcgct cgttccgcaa agcggtacgg agttagttag ggctaatgg    3600
gcattctccc gtacaggaaa gagttagaag ttattaatta tcaacaattc tcctttgcct   3660
agtgcatcgt taccttttta attaaaacat aaggaaaact aataatcgta ataatttaac   3720
ctcaaagtgt aaagaaatgt gaaattctga cttttataac gttaaagagg gaaaaattag   3780
cagtttaaaa tacctagaga atagtctggg gtaagcatag agaattagat tagttaagtt   3840
aatcaaattc agaaaaaata ataatcgtaa atagttaatc tgggtgtata gaaaatgatc   3900
cccttcatga taagatttaa actcgaaaag caaaagccaa aaaactaact tccattaaaa   3960
gaagttgtta catataacgc tataaagaaa atttatatat ttggaggata ccaaccatgt   4020
ctcatattca acgtgaaact agttgttctc gccctcgttt aaattctaat atggatgccg   4080
atttatatgg ttataaatgg gctcgtgata atgttggtca atctggtgct actatttatc   4140
gtttatatgg taaacctgat gctcctgaat tattcttgaa acatggtaaa ggttctgttg   4200
ctaatgatgt tactgatgaa atggttcgtt taaactggtt gactgaattt atgcctttac   4260
ctactattaa acattttatt cgtactcccg atgatgcttg gttattaact actgctattc   4320
ctggtaaaac tgcttttcaa gttttagaag aatatcctga ttctggtgaa aatattgttg   4380
atgctttagc tgttttttta cgtcgtttac attctattcc cgtttgtaat tgtcctttta   4440
attctgatcg tgtttttcgt ttagctcaag ctcaatctcg tatgaataat ggtttagttg   4500
atgcttctga ttttgatgat gaacgtaatg gttggcctgt tgaacaagtt tggaaagaaa   4560
tgcacaaatt gttacctttt tctcctgatt ctgttgttac tcatggtgat ttttctttag   4620
ataatttgat ctttgatgaa ggtaaattga ttggttgtat tgatgttggt cgtgttggta   4680
ttgctgatcg ttatcaagat ttagctattt tatggaattg tttaggtgaa ttttctcctt   4740
ctttacagaa acgtttattt cagaaatatg gtattgataa tcctgatatg aacaagttac   4800
aatttcattt aatgttggac gagttctttt aagaattaat tcatgaccaa aatcccttaa   4860
cgtgagtttt cgttccactg agcgtcagac cccgtagaaa agatcaaagg atcttcttga   4920
gatccttttt ttctgcgcgt aatctgctgc tatttaaatt acgtacacgt gttattactt   4980
```

```
tgttaacgac aattgtctta attaactggg cctcatgggc cttccgctca ctgcccgctt   5040
tccagtcggg aaacctgtcg tgccagctct gcagatgacg gtgaaaacct ctgacacatg   5100
cagctcccgg agacggtcac agcttgtctg taagcggatg ccgggagcag acaagcccgt   5160
cagggcgcgt cagcgggtgt tggcgggtgt cggggcgcag ccatgaccca gtcacgtagc   5220
gatagcggag tgtatactgg cttaactatg cggcatcaga gcagattgta ctgagagtgc   5280
accatatgcg gtgtgaaata ccgcacagat gcgtaaggag aaaataccgc atcaggcgct   5340
cttccgcttc ctcgctcact gactcgctgc gctcggtcgt tcggctgcgg cgagcggtat   5400
cagctcactc aaaggcggta atacggttat ccacagaatc aggggataac gcaggaaaga   5460
acatgtgagc aaaaggccag caaaaggcca ggaaccgtaa aaaggccgcg ttgctggcgt   5520
ttttccatag gctccgcccc cctgacgagc atcacaaaaa tcgacgctca agtcagaggt   5580
ggcgaaaccc gacaggacta taaagatacc aggcgtttcc ccctggaagc tccctcgtgc   5640
gctctcctgt tccgaccctg ccgcttaccg gatacctgtc cgcctttctc ccttcgggaa   5700
gcgtggcgct ttctcatagc tcacgctgta ggtatctcag ttcggtgtag gtcgttcgct   5760
ccaagctggg ctgtgtgcac gaaccccccg ttcagcccga ccgctgcgcc ttatccggta   5820
actatcgtct tgagtccaac ccggtaagac acgacttatc gccactggca gcagccactg   5880
gtaacaggat tagcagagcg aggtatgtag gcggtgctac agagttcttg aagtggtggc   5940
ctaactacgg ctacactaga aggacagtat ttggtatctg cgctctgctg aagccagtta   6000
ccttcggaaa aagagttggt agctcttgat ccggcaaaca aaccaccgct ggtagcggtg   6060
gtttttttgt ttgcaagcag cagattacgc gcagaaaaaa aggatctcaa gaagatcctt   6120
tgatcttttc tactgcagaa gcttgttaga caccctgtca tgtattttat attatttatt   6180
tcaccatacg gattaagtga aacctaatga aaatagtact ttcggagctt taactttaat   6240
gaaggtatgt ttttttatag acatcgatgt ctggtttaac aataggaaaa agtagctaaa   6300
actcccatga attaaagaaa taacaaggtg tctaacaacc tgttattaag aatgttagaa   6360
aagacttaac atttgtgttg agtttttata gacattggtg tctagacata cggtagataa   6420
ggtttgctca aaaataaaat aaaaaaagat tggactaaaa aacatttaat ttagtacaat   6480
ttaattagtt attttttcgt ctcaaatttt gctttgttga gcagaaattt agataaaaaa   6540
atccccgtga tcagattaca atgtcgttca ttgtacgatg tgtcgaaaaa tctttacgac   6600
actctaaact gaccacacgg gggaaaaaga aaactgaact aataacatca tgatactcgg   6660
aaaacctagc aattctcaac ccctaaacaa aagaaacttc caaaaccctg accatataaa   6720
ggagtggcaa caatcagcaa tcagtcaaga tttgatagca gaaaatcttg tatcggttgc   6780
taatggtttt gatgtactat ttatcggcaa taaataccga actaacacgg gtgttctgtc   6840
acggcacata ttaaactcct attctcattt agaagatggt ggttcgtatg gtagaacatt   6900
tgacccattt accaataaag aaatgcagtg ggttcaattt aaaccgaata gaccaagaaa   6960
aggttctact ggtaaggtaa tcaaatatga atcgccaaaa ggtgaaccta caagagttct   7020
aatgccgttt gtgcctatga aaatatggca acggattagc gataagttcg gagtaccgat   7080
taatccgaaa aaagatactc acttttggga atgggtaaag aataatccat cgataccgat   7140
tgccattaca gaaggaaata aaaaagctaa ttgcctatta tcctatggct atcctgctat   7200
tgcctttgta ggcatttgga acggattaga gaaaataaat gatttctcga aggaaaagca   7260
gttaaaagag gatttgaaat ggttgttatc caacggcaac cgaaatatta atatcatctt   7320
```

```
tgaccaagac cagaaacaaa aaactgtaat taatgtaaac aaagctattt tcgctttatc   7380
ttctctaata agtagaaatg gtcataaagt taatattgtg caatggttgc cgtcaaaagg   7440
taaaggaata gatgattatt tggtagcttt accttttgag aaaagagaaa atcatttaga   7500
caacttaatt aaaattgcac catcatttaa tttttggtca actaaatact tattcaagtg   7560
tcgtaaacca gatttaaccg taaattgccg ttatttgagc gatgcagtaa aagaattacc   7620
tcaagaggat atagcattaa tagcacctca cggcacgggt aaaacttcat tagtagctac   7680
tcacgttaag aatcggagtt atcacggaag gaaaactatt tcattggtgc atcttgaaag   7740
tttagccaaa gctaatggca acgcacttgg attatattac cgaaccgaaa ataatattga   7800
aaagcaatat cttggattta gcttatgtgt agatagttgc cgtgataaga ttaacggcat   7860
tacaactgat attatttcag gtcaagatta ttgccttttc attgatgaaa ttgaccaagt   7920
aattccacac atccttaaca gtgaaactga agtaagtaag tatagatgca ccatcattga   7980
cactttttct gaactggtga gaaatgctga acaggtcatt attgctgatg ctgatttatc   8040
cgatgtgacg attgacctaa tagaaaacat cagaggtaaa aaactatatg taatcaagaa   8100
tgaatatcag tatcagggaa tgacttttaa cgccgttggt tcaccattag aaatgatggc   8160
aatgatggga aaatcggtgt cagaaggcaa gaaattattt attaacacca catcccaaaa   8220
ggcaaaaagt aagtacggca caatcgctct tgagtcttat atttttggtc taaataaaga   8280
agcaaagata ttaagaatag actctgaaac cactaaaaac cctgaacatc cagcctataa   8340
aatcattgac caagacttaa ataatatcct caaagattat gattatgtca ttgcctcacc   8400
ttgccttcaa acaggtgtca gtattacctt aaaagggcat tttgaccagc aatttaactt   8460
ttccagtgga aacattacac ctcattgctt tttacagcaa atgtggcggt tgagggatgc   8520
agaaattgaa agattctatt atgtgccgaa ctcatctaac ctcaatctca ttgggaataa   8580
gtcaagttca ccatcagacc ttctaaagag caataacaag atggcaacgg caacggttaa   8640
ccttttgggt agaatcgact ccgaatattc cctagagtat gaatcgcacg gcatttggct   8700
tgagacgtgg gcaaaattat cagcacggca taacagttca atgcgttgtt actctgaaat   8760
tcttacctat ctaattacgt ctcaagggca taaattaaat atcaacattc cctcacctct   8820
tgcagatatt aagaagctaa atgatgaggt aagtagtaac agggaaaagg taaaaaatga   8880
gagatactct cagaggttaa actcaccaga tattaacgat gcagaagcta ccatactcga   8940
atctaaagag caaaaaatcg gattgactct caatgagaga tgcaccctag aaaagcataa   9000
agttaagaag cggtatggga atgtaaagat ggatattctc acctttgatg atgatggact   9060
ataccccaaa ctcagactat tttattacct caccatcggt aaacctcatc tcaaggctaa   9120
tgacagaaaa gctattgcca aaatgggcaa tgacaataaa ggcaagattc tatcaaaaga   9180
cttagttaat aaaacttact ccgctcgtgt gaaggtctta gagattctta aactaactga   9240
ctttatcgac aatcttagag atgaactctt aataactccc aataatccag ctatcaccga   9300
ttttaataat cttctgctaa gagctaagaa ggatttaaga gtattaggag tcaacatcgg   9360
aaaatatcca atggccaaca ttaatgccgt acttactctc attggtcaca aactttctgt   9420
aatgagagat gagttcggaa aagagaaaag gataaaagta gatggtaaat cataccgatg   9480
ttatcaactt gaaacattac cagattttac caatgatact cttgactact ggttagaaaa   9540
tgatagccaa aaagaagtaa cagcaacaga aaattactcc gaaaatttta acccttcaaa   9600
tagctacaat ccagacagta agacactttc agagggtgca aatttcctat atataaataa   9660
agaagaattg catccaaata aattgcacct agaaataaaa gaaggtgctg aacttttttt   9720
```

```
attcggggta aaggtgattg tgaaaggaat cttggacggg gcagtaacta tattctctat   9780
gggtcaagaa tacgatttat ccctcaatga actagagggg atgttaacat catgaacttt   9840
acaagaatct ttttaaaggg cgatcgcacc atgttaaatg atggtacatt tgttcagata   9900
tttgatattt accatgacca cgcattggga gtgacccttg accttaagac agaaaaaatt   9960
atttccgatg atgttagggt aattactgtc aaagacttat tgttcgatgg cacttataaa  10020
ggggtaaaat cttttatgcc cgataatgcc cgataatgcc cgattgatgc tacaaaatcc  10080
cataatcata agcgataatc ccctaatagc ttgtaattct tgaaccgtag cgattttaga  10140
gtattccaaa aagaagaaat aaacaccgca aaatgtcgta tttcacatat ataaaccaag  10200
gtttttttgcc ctaaaatctt tatgtttgta gtgtgatgtt gggtcaaaat ggtcagaaaa  10260
gttgcaaggt ttttatggat gcttacgcgc gcgaggggta agcatcccca aatagttact  10320
ttatcctagt ccatgcccat ttattgccgt cccgttcggc tttaaaaaag tgccaaaact  10380
cacaaggtgc aataaaaagt tctgtacctt tcgcaaccct agataatctt tcaacagtta  10440
ctttttttcc tattatctcg gtacaaagtt tggctagttt ctcttttccc tctttttcaa  10500
tcaagccttc ttgtatgccc aactcattga ttaatctctc tatttttacc attatttccc  10560
gttcaggtag tttatcccct aaatcttcat cggggggcaa tgtagggcat tctgaagggg  10620
ctttttcttc tgtctggaca ttatctaata ttgaagtaac caaactatct tcagtttttt  10680
ctattcctat taattcatat tcggttactg tatccgtatc aatatccgaa taactatctt  10740
tatccgtatt agctattcgg ttaagtttat ccgttaactc agaaacaaga ctatatagcg  10800
gttttagctt ttcttctatc ctgttatcta atacggataa gtttatacgg ttatcattat  10860
ccgtattagt atcattgggc ttttttggta gttctacccc ctcataaacc gcttttattc  10920
ccaattccaa cagactgata acagtatcct ttataatggg ttttttgctg atatggtgaa  10980
cttttgcccc ttccatcatt gcgatacttt ctatctcact catcaactta tcgcttaagt  11040
gaatctcgta tctgtttaat cccttactgg ttttattcat atccgtttac tttattcggt  11100
taacaattct attttatacg aataaaatat tatacggtta actttatacg tttaactatt  11160
ttatctatac ggataacagt aataagttat tcgtattagt tatacgttta cttttatcca  11220
aataaaatta gtgcatttaa actaaaagaa tgattttatc ggagttgata gcattggatt  11280
aacctaaaga tgtttataag ctatatctga taagtattta aggttatttt gttattctgt  11340
ttattgacat tatcagaata aaagaataga atataattgt tgagagataa gaggtttaag  11400
tgattatggt taagaagtta gttggttatg tcagggtcag tagtgaatcg caagaggata  11460
acactagctt acagaatcag atagagagaa ttgaagcata ttgtatggct tttggttatg  11520
agttggtaaa aatattcaaa gaggttgcca ctggtacaaa agcagatatt gaaacccgtc  11580
ctatttttaa tgaagctata gaatacttga aacaggataa tgctaatgga attattgcct  11640
tgaagctaga ccgaatcgca cggaatgctt tagatgtatt gcgtttggtt cgtgaaacct  11700
tagaaccaca aaataaaatg ttagtgttac tagatattca ggtagatact tcgacacctt  11760
caggaaaaat gattttaact gtaatgagtg ccgttgctga actcgaaaga gacatgatct  11820
atgatcgcac tcagggggggt agaaagacta aagcccaaaa gggcgggtat gcctacggga  11880
aacctaaatt tggctataag actgaagaaa aggaactaaa agaagattca gcacaacagg  11940
aaactattaa actaattaag agacaccgta ggtcagggaa aagctaccag aaaatagctg  12000
attatctcaa tgcccaaagt attcccacta aacaaggtaa gaaatggagt tctagcgtcg  12060
```

```
tctatcgaat ctgtcaggaa aaagctggtt aagtctgttt atagatattt agaatttatt  12120

gaataaaaat agtatgaaca ataaatattt atggactaac cacgctcgga aacgtttaac  12180

tgaacgatgg gaaataaaag aatcatgggt tattgatacc atcgaaaatc ctgaacgttc  12240

agaatttatt gttgatgagt caggggaaaa atatcattac tataaaagaa tagctaagtt  12300

taagaataga gtgttagaag tgataacttc tgccaactca acacccacaa gaataataac  12360

cttttacttt aaccgtaaca tgaggaaaaa tttatgattg ttacttacga taatgaagtt  12420

gacgcaattt attttaagtt aacggaaaat aaaattgata gcaccgaacc tcaaacagac  12480

aggattatca ttgattacga tgaaagtaat aatattgttg gcattgaggt attagatttt  12540

aattatcttg tcaagaaagg tttaaccgtt gctgatttac ctttttctga agatgaaaga  12600

ttaacagctt ctcaatattt taattttcct gttgctatct aatccagaag ggcaataat   12660

ccccttcttt catcgagtta gacttaatat cacaaaagtc attttcattt taccgtttct  12720

tttccacagc gtccgtacgc ccctcgttaa atctcaaaac cgacaattta tgatgtttat  12780

aaaaagttac tcactttaat aagtatttat actcattaaa gggttattct ttttttgtag  12840

cctgataggt tgggaaggaa tatttcagat tatcagattt gttgaatatt tttcgtcaga  12900

tacgcaaacc ttacaaacat aattaacaac tgaaactatt gatatgtcta ggttttagct  12960

ctatcacagg ttggatct                                                12978
```

<210> SEQ ID NO 80
<211> LENGTH: 13139
<212> TYPE: DNA
<213> ORGANISM: artificial
<220> FEATURE:
<223> OTHER INFORMATION: Synthetically produced plasmid construct #1835
pABIcyano1-6.8::Porf0316-zmPDC(opt1)-TdsrA-PcpcB-synADH-TrbcS

<400> SEQUENCE: 80

```
tcgactggtc aagttactat atgtttagaa acaacaaaaa aagaagtcat tataaaaata    60

attgatacag gaattggcat taataaagaa gaacaaaaat taatttttaa tcgtttttat   120

cgaatcaata aagcaagaaa tagagagaaa ggcagttgcg gattaggttt agctattgca   180

aatgcgatcg cgcttaatca tggtggtaga ataattttag aaagtcaaga aaatcaaggc   240

agtattttta ccgtttattt accgaaaatc atttcatcct aatttcatat tcttttgaca   300

gaatcaaagg taaagataaa aagagagaaa cagtcatgaa ttcttatacc gtgggtactt   360

atttagccga acgcttagtg caaattggtt taaaacatca ttttgccgtg gctggggact   420

ataatttagt gttattggat aacttattat taaataaaaa catggaacaa gtgtattgtt   480

gtaatgaatt aaattgtggt ttttctgctg aaggttatgc tagagctaaa ggtgcagctg   540

ctgctgttgt tacttattct gtgggtgctt tatctgcttt tgatgctatt ggtggtgctt   600

atgccgaaaa tttacccgtg attttaattt ctggtgcccc taataataat gatcatgccg   660

ctggacatgt tttacatcat gccttaggta aaaccgatta tcattatcaa ttagaaatgg   720

ccaaaaatat tactgctgct gccgaagcta tttatactcc tgaagaagcc cctgccaaaa   780

ttgatcatgt gattaaaacc gccttacgcg aaaaaaaacc cgtgtattta gaaattgcct   840

gtaatattgc ttctatgcct tgtgctgctc ctgggcctgc ttctgcttta tttaatgatg   900

aagcctctga tgaagctagt ttaaatgctg ccgtggaaga aaccttaaaa tttattgcca   960

atcgcgataa agttgccgtg ttagttggtt ctaaattaag agctgctggt gctgaagaag  1020

ctgctgttaa atttgctgat gctttaggtg gtgcagttgc tactatggct gctgccaaat  1080
```

```
cttttttcc cgaagaaaat ccccattata ttggaactag ttggggagaa gtttcttatc   1140
ctggtgtgga aaaaactatg aaagaagccg acgctgttat tgctttagcc cctgtgttta   1200
atgattattc taccactggt tggactgata ttcccgatcc caaaaaatta gttttagccg   1260
aacctcgttc tgttgttgtt aatggtgttc gctttccctc tgtgcattta aaagattatt   1320
taacccgctt agcccaaaaa gtttctaaaa aaactggtgc cttagatttt tttaaatctt   1380
taaatgcggg tgaattaaaa aaagctgctc ctgctgatcc ttctgctcct ttagttaatg   1440
ctgaaattgc ccgtcaagtt gaagccttat taacccctaa tactaccgtt attgccgaaa   1500
ctggtgattc ttggtttaat gcccaacgca tgaaattacc taatggtgcc cgtgttgaat   1560
atgaaatgca atggggtcat attggttggt ctgtacctgc tgcttttggt tatgctgttg   1620
gtgctcctga acgtcgtaat attttaatgg tgggtgatgg ttcttttcaa ttaactgccc   1680
aagaagttgc ccaaatggtt cgcttaaaat tacccgttat tattttttta ataaataatt   1740
atggttatac cattgaagtg atgattcatg atgggccata taataatatt aaaaattggg   1800
attatgcggg tttaatggaa gtgtttaatg gtaatggtgg ttatgattct ggtgctggta   1860
aaggtttaaa agccaaaact ggtggtgaat tagctgaagc tattaaagtt gccttagcca   1920
atactgatgg gccaacctta attgaatgtt ttattggtcg cgaagattgt accgaagaat   1980
tagttaaatg gggtaaacgt gttgctgctg ctaattctcg caaacccgtg aataaattat   2040
tgtaaggatc cagcaaggtt tcatcccgac cccctcaggg tcgggatttt tttattgtga   2100
gctcaacttt agatattcgt agttggcaat gtcgtaaatg cggaacaata catggaaaac   2160
atatagattt gtaatgagaa aaagtgtaaa caaatattaa gaaaaagatc agaaaaattt   2220
aacaacacgt aataaaaaaa tgcgtcacta cgggttataa atttacatga aaggttaaaa   2280
cacttttctg agacgatttt gataaaaaag ttgtcaaaaa attaagtttc tttacaaatg   2340
cttaacaaaa acttggtttt aagcacaaaa taagagagac taatttgcag aagttttaca   2400
aggaaatctt gaagaaaaag atctaagtaa aacgactctg tttaaccaaa atttaacaaa   2460
tttaacaaaa caaactaaat ctattaggag attaactaca tatgattaaa gcctacgctg   2520
ccctggaagc caacggaaaa ctccaaccct ttgaatacga ccccggtgcc ctgggtgcta   2580
atgaggtgga gattgaggtg cagtattgtg gggtgtgcca cagtgatttg tccatgatta   2640
ataacgaatg gggcatttcc aattaccccc tagtgccggg tcatgaggtg gtgggtactg   2700
tggccgccat gggcgaaggg gtgaaccatg ttgaggtggg ggatttagtg gggctgggtt   2760
ggcattcggg ctactgcatg acctgccata gttgtttatc tggctaccac aacctttgtg   2820
ccacggcgga atcgaccatt gtgggccact acggtggctt tggcgatcgg gttcgggcca   2880
agggagtcag cgtggtgaaa ttacctaaag gcattgacct agccagtgcc gggcccctt   2940
tctgtggagg aattaccgtt ttcagtccta tggtggaact gagtttaaag cccactgcaa   3000
aagtggcagt gatcggcatt gggggcttgg gccatttagc ggtgcaattt ctccgggcct   3060
ggggctgtga agtgactgcc tttacctcca gtgccaggaa gcaaacggaa gtgttggaat   3120
tgggcgctca ccacatacta gattccacca atccagaggc gatcgccagt gcggaaggca   3180
aatttgacta tattatctcc actgtgaacc tgaagcttga ctggaactta tacatcagca   3240
ccctggcgcc ccagggacat ttccactttg ttggggtggt gttggagcct ttggatctaa   3300
atctttttcc ccttttgatg ggacaacgct ccgtttctgc ctccccagtg ggtagtcccg   3360
ccaccattgc caccatgttg gactttgctg tgcgccatga cattaaaccc gtggtggaac   3420
aatttagctt tgatcagatc aacgaggcga tcgcccatct agaaagcggc aaagcccatt   3480
```

```
atcgggtagt gctcagccat agtaaaaatt agctctgcaa aggttgcttc tagatctact   3540
tctaaactga aacaaatttg agggtaggct tcattgtctg ccttatttt tttatttagg    3600
aaaagtgaac agactaaaga gtgttggctc tattgctttg agtatgtaaa ttaggcgttg   3660
ctgaattaag gtatgatttt tgacccctgc aggatcatct tgctgaaaaa ctcgagcgct   3720
cgttccgcaa agcggtacgg agttagttag gggctaatgg gcattctccc gtacaggaaa   3780
gagttagaag ttattaatta tcaacaattc tcctttgcct agtgcatcgt tacctttta    3840
attaaaacat aaggaaaact aataatcgta ataatttaac ctcaaagtgt aaagaaatgt   3900
gaaattctga cttttataac gttaaagagg gaaaaattag cagtttaaaa tacctagaga   3960
atagtctggg gtaagcatag agaattagat tagttaagtt aatcaaattc agaaaaaata   4020
ataatcgtaa atagttaatc tgggtgtata gaaaatgatc cccttcatga taagatttaa   4080
actcgaaaag caaaagccaa aaaactaact tccattaaaa gaagttgtta catataacgc   4140
tataaagaaa atttatatat ttggaggata ccaaccatgt ctcatattca acgtgaaact   4200
agttgttctc gccctcgttt aaattctaat atggatgccg atttatatgg ttataaatgg   4260
gctcgtgata atgttggtca atctggtgct actatttatc gtttatatgg taaacctgat   4320
gctcctgaat tattcttgaa acatggtaaa ggttctgttg ctaatgatgt tactgatgaa   4380
atggttcgtt taaactggtt gactgaattt atgcctttac ctactattaa acattttatt   4440
cgtactcccg atgatgcttg gttattaact actgctattc ctggtaaaac tgcttttcaa   4500
gttttagaag aatatcctga ttctggtgaa aatattgttg atgctttagc tgtttttta    4560
cgtcgtttac attctattcc cgtttgtaat tgtcctttta attctgatcg tgtttttcgt   4620
ttagctcaag ctcaatctcg tatgaataat ggtttagttg atgcttctga ttttgatgat   4680
gaacgtaatg gttggcctgt tgaacaagtt tggaaagaaa tgcacaaatt gttacctttt   4740
tctcctgatt ctgttgttac tcatggtgat ttttctttag ataatttgat ctttgatgaa   4800
ggtaaattga ttggttgtat tgatgttggt cgtgttggta ttgctgatcg ttatcaagat   4860
ttagctattt tatggaattg tttaggtgaa ttttctcctt ctttacagaa acgtttattt   4920
cagaaatatg gtattgataa tcctgatatg aacaagttac aatttcattt aatgttggac   4980
gagttctttt aagaattaat tcatgaccaa aatcccttaa cgtgagtttt cgttccactg   5040
agcgtcagac cccgtagaaa agatcaaagg atcttcttga gatccttttt ttctgcgcgt   5100
aatctgctgc tatttaaatt acgtacacgt gttattactt tgttaacgac aattgtctta   5160
attaactggg cctcatgggc cttccgctca ctgcccgctt tccagtcggg aaacctgtcg   5220
tgccagctct gcagatgacg gtgaaaacct ctgacacatg cagctcccgg agacggtcac   5280
agcttgtctg taagcggatg ccgggagcag acaagcccgt cagggcgcgt cagcgggtgt   5340
tggcgggtgt cggggcgcag ccatgaccca gtcacgtagc gatagcggag tgtatactgg   5400
cttaactatg cggcatcaga gcagattgta ctgagagtgc accatatgcg gtgtgaaata   5460
ccgcacagat gcgtaaggag aaaataccgc atcaggcgct cttccgcttc ctcgctcact   5520
gactcgctgc gctcggtcgt tcggctgcgg cgagcggtat cagctcactc aaaggcggta   5580
atacggttat ccacagaatc aggggataac gcaggaaaga acatgtgagc aaaaggccag   5640
caaaaggcca ggaaccgtaa aaaggccgcg ttgctggcgt ttttccatag gctccgcccc   5700
cctgacgagc atcacaaaaa tcgacgctca agtcagaggt ggcgaaaccc gacaggacta   5760
taaagatacc aggcgtttcc ccctggaagc tccctcgtgc gctctcctgt tccgaccctg   5820
```

```
ccgcttaccg gatacctgtc cgcctttctc ccttcgggaa gcgtggcgct ttctcatagc   5880
tcacgctgta ggtatctcag ttcggtgtag gtcgttcgct ccaagctggg ctgtgtgcac   5940
gaaccccccg ttcagcccga ccgctgcgcc ttatccggta actatcgtct tgagtccaac   6000
ccggtaagac acgacttatc gccactggca gcagccactg gtaacaggat tagcagagcg   6060
aggtatgtag gcggtgctac agagttcttg aagtggtggc ctaactacgg ctacactaga   6120
aggacagtat ttggtatctg cgctctgctg aagccagtta ccttcggaaa aagagttggt   6180
agctcttgat ccggcaaaca aaccaccgct ggtagcggtg gtttttttgt ttgcaagcag   6240
cagattacgc gcagaaaaaa aggatctcaa gaagatcctt tgatcttttc tactgcagaa   6300
gcttgttaga caccctgtca tgtattttat attatttatt tcaccatacg gattaagtga   6360
aacctaatga aaatagtact ttcggagctt taactttaat gaaggtatgt ttttttatag   6420
acatcgatgt ctggtttaac aataggaaaa agtagctaaa actcccatga attaaagaaa   6480
taacaaggtg tctaacaacc tgttattaag aatgttagaa aagacttaac atttgtgttg   6540
agtttttata gacattggtg tctagacata cggtagataa ggtttgctca aaaataaaat   6600
aaaaaaagat tggactaaaa aacatttaat ttagtacaat ttaattagtt attttttcgt   6660
ctcaaatttt gctttgttga gcagaaattt agataaaaaa atccccgtga tcagattaca   6720
atgtcgttca ttgtacgatg tgtcgaaaaa tctttacgac actctaaact gaccacacgg   6780
gggaaaaaga aaactgaact aataacatca tgatactcgg aaaacctagc aattctcaac   6840
ccctaaacaa aagaaacttc caaaaccctg accatataaa ggagtggcaa caatcagcaa   6900
tcagtcaaga tttgatagca gaaaatcttg tatcggttgc taatggtttt gatgtactat   6960
ttatcggcaa taaataccga actaacacgg gtgttctgtc acggcacata ttaaactcct   7020
attctcattt agaagatggt ggttcgtatg gtagaacatt tgacccattt accaataaag   7080
aaatgcagtg ggttcaattt aaaccgaata gaccaagaaa aggttctact ggtaaggtaa   7140
tcaaatatga atcgccaaaa ggtgaaccta caagagttct aatgccgttt gtgcctatga   7200
aaatatggca acggattagc gataagttcg gagtaccgat taatccgaaa aaagatactc   7260
acttttggga atgggtaaag aataatccat cgataccgat tgccattaca gaaggaaata   7320
aaaaagctaa ttgcctatta tcctatggct atcctgctat tgcctttgta ggcatttgga   7380
acggattaga gaaaataaat gatttctcga aggaaaagca gttaaaagag gatttgaaat   7440
ggttgttatc caacggcaac cgaaatatta atatcatctt tgaccaagac cagaaacaaa   7500
aaactgtaat taatgtaaac aaagctattt tcgctttatc ttctctaata agtagaaatg   7560
gtcataaagt taatattgtg caatggttgc cgtcaaaagg taaaggaata gatgattatt   7620
tggtagcttt accttttgag aaaagagaaa atcatttaga caacttaatt aaaattgcac   7680
catcatttaa tttttggtca actaaatact tattcaagtg tcgtaaacca gatttaaccg   7740
taaattgccg ttatttgagc gatgcagtaa aagaattacc tcaagaggat atagcattaa   7800
tagcacctca cggcacgggt aaaacttcat tagtagctac tcacgttaag aatcggagtt   7860
atcacggaag gaaaactatt tcattggtgc atcttgaaag tttagccaaa gctaatggca   7920
acgcacttgg attatattac cgaaccgaaa ataatattga aaagcaatat cttggattta   7980
gcttatgtgt agatagttgc cgtgataaga ttaacggcat tacaactgat attatttcag   8040
gtcaagatta ttgccttttc attgatgaaa ttgaccaagt aattccacac atccttaaca   8100
gtgaaactga agtaagtaag tatagatgca ccatcattga cactttttct gaactggtga   8160
gaaatgctga acaggtcatt attgctgatg ctgatttatc cgatgtgacg attgacctaa   8220
```

```
tagaaaacat cagaggtaaa aaactatatg taatcaagaa tgaatatcag tatcagggaa   8280
tgacttttaa cgccgttggt tcaccattag aaatgatggc aatgatggga aaatcggtgt   8340
cagaaggcaa gaaattattt attaacacca catcccaaaa ggcaaaaagt aagtacggca   8400
caatcgctct tgagtcttat atttttggtc taaataaaga agcaaagata ttaagaatag   8460
actctgaaac cactaaaaac cctgaacatc cagcctataa aatcattgac caagacttaa   8520
ataatatcct caaagattat gattatgtca ttgcctcacc ttgccttcaa acaggtgtca   8580
gtattacctt aaaagggcat tttgaccagc aatttaactt ttccagtgga aacattacac   8640
ctcattgctt tttacagcaa atgtggcggt tgagggatgc agaaattgaa agattctatt   8700
atgtgccgaa ctcatctaac ctcaatctca ttgggaataa gtcaagttca ccatcagacc   8760
ttctaaagag caataacaag atggcaacgg caacggttaa ccttttgggt agaatcgact   8820
ccgaatattc cctagagtat gaatcgcacg gcatttggct tgagacgtgg gcaaaattat   8880
cagcacggca taacagttca atgcgttgtt actctgaaat tcttacctat ctaattacgt   8940
ctcaagggca taaattaaat atcaacattc cctcacctct tgcagatatt aagaagctaa   9000
atgatgaggt aagtagtaac agggaaaagg taaaaaatga gagatactct cagaggttaa   9060
actcaccaga tattaacgat gcagaagcta ccatactcga atctaaagag caaaaaatcg   9120
gattgactct caatgagaga tgcaccctag aaaagcataa agttaagaag cggtatggga   9180
atgtaaagat ggatattctc acctttgatg atgatggact ataccccaaa ctcagactat   9240
tttattacct caccatcggt aaacctcatc tcaaggctaa tgacagaaaa gctattgcca   9300
aaatgggcaa tgacaataaa ggcaagattc tatcaaaaga cttagttaat aaaacttact   9360
ccgctcgtgt gaaggtctta gagattctta aactaactga ctttatcgac aatcttagag   9420
atgaactctt aataactccc aataatccag ctatcaccga ttttaataat cttctgctaa   9480
gagctaagaa ggatttaaga gtattaggag tcaacatcgg aaaatatcca atggccaaca   9540
ttaatgccgt acttactctc attggtcaca aactttctgt aatgagagat gagttcggaa   9600
aagagaaaag gataaaagta gatggtaaat cataccgatg ttatcaactt gaaacattac   9660
cagattttac caatgatact cttgactact ggttagaaaa tgatagccaa aaagaagtaa   9720
cagcaacaga aaattactcc gaaaatttta acccttcaaa tagctacaat ccagacagta   9780
agacactttc agagggtgca aatttcctat atataaataa agaagaattg catccaaata   9840
aattgcacct agaaataaaa gaaggtgctg aactttttt attcggggta aaggtgattg    9900
tgaaaggaat cttggacggg gcagtaacta tattctctat gggtcaagaa tacgatttat   9960
ccctcaatga actagagggg atgttaacat catgaacttt acaagaatct ttttaaaggg  10020
cgatcgcacc atgttaaatg atggtacatt tgttcagata tttgatattt accatgacca  10080
cgcattggga gtgacccttg accttaagac agaaaaaatt atttccgatg atgttagggt  10140
aattactgtc aaagacttat tgttcgatgg cacttataaa ggggtaaaat cttttatgcc  10200
cgataatgcc cgataatgcc cgattgatgc tacaaaatcc cataatcata agcgataatc  10260
ccctaatagc ttgtaattct tgaaccgtag cgattttaga gtattccaaa aagaagaaat  10320
aaacaccgca aaatgtcgta tttcacatat ataaaccaag gttttttgcc ctaaaatctt  10380
tatgtttgta gtgtgatgtt gggtcaaaat ggtcagaaaa gttgcaaggt ttttatggat  10440
gcttacgcgc gcgaggggta agcatcccca aatagttact ttatcctagt ccatgcccat  10500
ttattgccgt cccgttcggc tttaaaaaag tgccaaaact cacaaggtgc aataaaaagt  10560
```

```
tctgtacctt tcgcaaccct agataatctt tcaacagtta ctttttttcc tattatctcg  10620
gtacaaagtt tggctagttt ctcttttccc tctttttcaa tcaagccttc ttgtatgccc  10680
aactcattga ttaatctctc tatttttacc attatttccc gttcaggtag tttatcccct  10740
aaatcttcat cggggggcaa tgtagggcat tctgaagggg ctttttcttc tgtctggaca  10800
ttatctaata ttgaagtaac caaactatct tcagtttttt ctattcctat taattcatat  10860
tcggttactg tatccgtatc aatatccgaa taactatctt tatccgtatt agctattcgg  10920
ttaagtttat ccgttaactc agaaacaaga ctatatagcg gttttagctt ttcttctatc  10980
ctgttatcta atacggataa gtttatacgg ttatcattat ccgtattagt atcattgggc  11040
tttttggta gttctacccc ctcataaacc gcttttattc ccaattccaa cagactgata  11100
acagtatcct ttataatggg ttttttgctg atatggtgaa cttttgcccc ttccatcatt  11160
gcgatacttt ctatctcact catcaactta tcgcttaagt gaatctcgta tctgtttaat  11220
cccttactgg ttttattcat atccgtttac tttattcggt taacaattct attttatacg  11280
aataaaatat tatacggtta actttatacg tttaactatt ttatctatac ggataacagt  11340
aataagttat tcgtattagt tatacgttta cttttatcca aataaaatta gtgcatttaa  11400
actaaaagaa tgattttatc ggagttgata gcattggatt aacctaaaga tgtttataag  11460
ctatatctga taagtattta aggttatttt gttattctgt ttattgacat tatcagaata  11520
aaagaataga atataattgt tgagagataa gaggtttaag tgattatggt taagaagtta  11580
gttggttatg tcagggtcag tagtgaatcg caagaggata acactagctt acagaatcag  11640
atagagagaa ttgaagcata ttgtatggct tttggttatg agttggtaaa aatattcaaa  11700
gaggttgcca ctggtacaaa agcagatatt gaaacccgtc ctatttttaa tgaagctata  11760
gaatacttga aacaggataa tgctaatgga attattgcct tgaagctaga ccgaatcgca  11820
cggaatgctt tagatgtatt gcgtttggtt cgtgaaacct tagaaccaca aaataaaatg  11880
ttagtgttac tagatattca ggtagatact tcgacacctt caggaaaaat gattttaact  11940
gtaatgagtg ccgttgctga actcgaaaga gacatgatct atgatcgcac tcaggggggt  12000
agaaagacta aagcccaaaa gggcgggtat gcctacggga aacctaaatt tggctataag  12060
actgaagaaa aggaactaaa agaagattca gcacaacagg aaactattaa actaattaag  12120
agacaccgta ggtcagggaa aagctaccag aaaatagctg attatctcaa tgcccaaagt  12180
attcccacta aacaaggtaa gaaatggagt tctagcgtcg tctatcgaat ctgtcaggaa  12240
aaagctggtt aagtctgttt atagatattt agaatttatt gaataaaaat agtatgaaca  12300
ataaatattt atggactaac cacgctcgga aacgtttaac tgaacgatgg gaaataaaag  12360
aatcatgggt tattgatacc atcgaaaatc ctgaacgttc agaatttatt gttgatgagt  12420
caggggaaaa atatcattac tataaaagaa tagctaagtt taagaataga gtgttagaag  12480
tgataacttc tgccaactca acacccacaa gaataataac cttttacttt aaccgtaaca  12540
tgaggaaaaa tttatgattg ttacttacga taatgaagtt gacgcaattt attttaagtt  12600
aacggaaaat aaaattgata gcaccgaacc tcaaacagac aggattatca ttgattacga  12660
tgaaagtaat aatattgttg gcattgaggt attagatttt aattatcttg tcaagaaagg  12720
tttaaccgtt gctgatttac ctttttctga agatgaaaga ttaacagctt ctcaatattt  12780
taattttcct gttgctatct aatccagaag gggcaataat ccccttcttt catcgagtta  12840
gacttaatat cacaaaagtc attttcattt taccgtttct tttccacagc gtccgtacgc  12900
ccctcgttaa atctcaaaac cgacaattta tgatgtttat aaaaagttac tcactttaat  12960
```

```
aagtatttat actcattaaa gggttattct ttttttgtag cctgataggt tgggaaggaa  13020

tatttcagat tatcagattt gttgaatatt tttcgtcaga tacgcaaacc ttacaaacat  13080

aattaacaac tgaaactatt gatatgtcta ggttttagct ctatcacagg ttggatctg   13139


<210> SEQ ID NO 81
<211> LENGTH: 13131
<212> TYPE: DNA
<213> ORGANISM: artificial
<220> FEATURE:
<223> OTHER INFORMATION: Synthetically produced plasmid construct #1938
      pABIcyano1-6.8::Porf0316-zmPDC(opt1)-TdsrA-PcpcB-ADH111(opt)-Trbc
      S

<400> SEQUENCE: 81

tcgactggtc aagttactat atgtttagaa acaacaaaaa aagaagtcat tataaaaata     60

attgatacag gaattggcat taataaagaa gaacaaaaat taatttttaa tcgtttttat    120

cgaatcaata aagcaagaaa tagagagaaa ggcagttgcg gattaggttt agctattgca    180

aatgcgatcg cgcttaatca tggtggtaga ataattttag aaagtcaaga aaatcaaggc    240

agtattttta ccgtttattt accgaaaatc atttcatcct aatttcatat tcttttgaca    300

gaatcaaagg taaagataaa aagagagaaa cagtcatgaa ttcttatacc gtgggtactt    360

atttagccga acgcttagtg caaattggtt taaaacatca ttttgccgtg gctggggact    420

ataatttagt gttattggat aacttattat taaataaaaa catggaacaa gtgtattgtt    480

gtaatgaatt aaattgtggt ttttctgctg aaggttatgc tagagctaaa ggtgcagctg    540

ctgctgttgt tacttattct gtgggtgctt tatctgcttt tgatgctatt ggtggtgctt    600

atgccgaaaa tttacccgtg attttaattt ctggtgcccc taataataat gatcatgccg    660

ctggacatgt tttacatcat gccttaggta aaaccgatta tcattatcaa ttagaaatgg    720

ccaaaaatat tactgctgct gccgaagcta tttatactcc tgaagaagcc cctgccaaaa    780

ttgatcatgt gattaaaacc gccttacgcg aaaaaaaacc cgtgtattta gaaattgcct    840

gtaatattgc ttctatgcct tgtgctgctc ctgggcctgc ttctgcttta tttaatgatg    900

aagcctctga tgaagctagt ttaaatgctg ccgtggaaga aaccttaaaa tttattgcca    960

atcgcgataa agttgccgtg ttagttggtt ctaaattaag agctgctggt gctgaagaag   1020

ctgctgttaa atttgctgat gctttaggtg gtgcagttgc tactatggct gctgccaaat   1080

cttttttttcc cgaagaaaat ccccattata ttggaactag ttggggagaa gtttcttatc   1140

ctggtgtgga aaaaactatg aaagaagccg acgctgttat tgctttagcc cctgtgttta   1200

atgattattc taccactggt tggactgata ttcccgatcc caaaaaatta gttttagccg   1260

aacctcgttc tgttgttgtt aatggtgttc gctttccctc tgtgcattta aaagattatt   1320

taacccgctt agcccaaaaa gtttctaaaa aaactggtgc cttagatttt tttaaatctt   1380

taaatgcggg tgaattaaaa aaagctgctc ctgctgatcc ttctgctcct ttagttaatg   1440

ctgaaattgc ccgtcaagtt gaagccttat taaccccctaa tactaccgtt attgccgaaa   1500

ctggtgattc ttggtttaat gcccaacgca tgaaattacc taatggtgcc cgtgttgaat   1560

atgaaatgca atggggtcat attggttggt ctgtacctgc tgcttttggt tatgctgttg   1620

gtgctcctga acgtcgtaat attttaatgg tgggtgatgg ttcttttcaa ttaactgccc   1680

aagaagttgc ccaaatggtt cgcttaaaat tacccgttat tatttttta ataaataatt   1740

atggttatac cattgaagtg atgattcatg atgggccata taataatatt aaaaattggg   1800
```

```
attatgcggg tttaatggaa gtgtttaatg gtaatggtgg ttatgattct ggtgctggta   1860
aaggtttaaa agccaaaact ggtggtgaat tagctgaagc tattaaagtt gccttagcca   1920
atactgatgg gccaacctta attgaatgtt ttattggtcg cgaagattgt accgaagaat   1980
tagttaaatg ggtaaacgt gttgctgctg ctaattctcg caaacccgtg aataaattat   2040
tgtaaggatc cagcaaggtt tcatcccgac cccctcaggg tcgggatttt tttattgtga   2100
gctcaacttt agatattcgt agttggcaat gtcgtaaatg cggaacaata catggaaaac   2160
atatagattt gtaatgagaa aaagtgtaaa caaatattaa gaaaaagatc agaaaaattt   2220
aacaacacgt aataaaaaaa tgcgtcacta cgggttataa atttacatga aaggttaaaa   2280
cacttttctg agacgatttt gataaaaaag ttgtcaaaaa attaagtttc tttacaaatg   2340
cttaacaaaa acttggtttt aagcacaaaa taagagagac taatttgcag aagttttaca   2400
aggaaatctt gaagaaaaag atctaagtaa aacgactctg tttaaccaaa atttaacaaa   2460
tttaacaaaa caaactaaat ctattaggag attaactaca tatgagtgaa actaaattta   2520
aagcctatgc cgtaatgaat cctggtgaaa aattacaacc ctgggaatat gaacctgctc   2580
ctttacaggt agatgaaatt gaagtaagag ttactcacaa tggtttatgt cacactgact   2640
tacacatgag agataatgac tggaatgtta gtgagttccc cttagtagca ggtcatgaag   2700
ttgttggtga agtaaccgct gttggtgaaa aagtaaccag tcgtaaaaaa ggtgatagag   2760
ttggtgtagg ttggattcgt aattcttgtc gcgcttgtga ccattgttta caaggagaag   2820
agaacatttg tagagagggt tatactggtt taattgttgg tcatcacggt ggatttgctg   2880
atcgtgtacg tgtacctgct gacttcactt ataaaattcc tgatgcttta gatagtgcat   2940
ctgctgctcc tttattatgt gccggtatta ccgtttacac tcctttaaga acctacatta   3000
aacatcccgg tatgaaagta ggtgttatgg gtattggagg attaggacat ttagctatta   3060
aatttgctcg tgcaatggga gcagaagtta ctgcctttag taccagtcct aataaagaag   3120
cccaagccaa agaatttggt gctcatcatt tccaacaatg gggtactgct gaagaaatga   3180
aagctgttgc cggtaatttt gatttagttt tatctaccat ctctgctgaa actgactggg   3240
atgctgcctt ctctttatta gcaaataacg gtgttttatg tttcgtaggt attcccgtta   3300
gttctttaaa tgttccttta attcctttaa ttttcggaca aaaatctgtt gtaggttctg   3360
tagttggagg aagaagattc atggcagaaa tgttagagtt cgccgctgta aatcagatta   3420
aacctatgat cgaaactatg cccttatctc aagtaaatga agctatggat aaagttgccg   3480
ccaataaagc cagatataga attgtattat tatctgaata actagatcta cttctaaact   3540
gaaacaaatt tgagggtagg cttcattgtc tgcccttatt tttttattta ggaaaagtga   3600
acagactaaa gagtgttggc tctattgctt tgagtatgta aattaggcgt tgctgaatta   3660
aggtatgatt tttgacccct gcaggatcat cttgctgaaa aactcgagcg ctcgttccgc   3720
aaagcggtac ggagttagtt aggggctaat gggcattctc ccgtacagga aagagttaga   3780
agttattaat tatcaacaat tctcctttgc ctagtgcatc gttacctttt taattaaaac   3840
ataaggaaaa ctaataatcg taataattta acctcaaagt gtaaagaaat gtgaaattct   3900
gacttttata acgttaaaga gggaaaaatt agcagtttaa aatacctaga gaatagtctg   3960
gggtaagcat agagaattag attagttaag ttaatcaaat tcagaaaaaa taataatcgt   4020
aaatagttaa tctgggtgta tagaaaatga tccccttcat gataagattt aaactcgaaa   4080
agcaaaagcc aaaaaactaa cttccattaa aagaagttgt tacatataac gctataaaga   4140
aaatttatat atttggagga taccaaccat gtctcatatt caacgtgaaa ctagttgttc   4200
```

```
tcgccctcgt ttaaattcta atatggatgc cgatttatat ggttataaat gggctcgtga   4260
taatgttggt caatctggtg ctactattta tcgtttatat ggtaaacctg atgctcctga   4320
attattcttg aaacatggta aaggttctgt tgctaatgat gttactgatg aaatggttcg   4380
tttaaactgg ttgactgaat ttatgccttt acctactatt aaacatttta ttcgtactcc   4440
cgatgatgct tggttattaa ctactgctat tcctggtaaa actgcttttc aagttttaga   4500
agaatatcct gattctggtg aaaatattgt tgatgcttta gctgtttttt tacgtcgttt   4560
acattctatt cccgtttgta attgtccttt taattctgat cgtgtttttc gtttagctca   4620
agctcaatct cgtatgaata atggtttagt tgatgcttct gattttgatg atgaacgtaa   4680
tggttggcct gttgaacaag tttggaaaga aatgcacaaa ttgttacctt tttctcctga   4740
ttctgttgtt actcatggtg atttttcttt agataatttg atctttgatg aaggtaaatt   4800
gattggttgt attgatgttg gtcgtgttgg tattgctgat cgttatcaag atttagctat   4860
tttatggaat tgtttaggtg aattttctcc ttctttacag aaacgtttat ttcagaaata   4920
tggtattgat aatcctgata tgaacaagtt acaatttcat ttaatgttgg acgagttctt   4980
ttaagaatta attcatgacc aaaatccctt aacgtgagtt ttcgttccac tgagcgtcag   5040
accccgtaga aaagatcaaa ggatcttctt gagatccttt ttttctgcgc gtaatctgct   5100
gctatttaaa ttacgtacac gtgttattac tttgttaacg acaattgtct taattaactg   5160
ggcctcatgg gccttccgct cactgcccgc tttccagtcg ggaaacctgt cgtgccagct   5220
ctgcagatga cggtgaaaac ctctgacaca tgcagctccc ggagacggtc acagcttgtc   5280
tgtaagcgga tgccgggagc agacaagccc gtcagggcgc gtcagcgggt gttggcgggt   5340
gtcggggcgc agccatgacc cagtcacgta gcgatagcgg agtgtatact ggcttaacta   5400
tgcggcatca gagcagattg tactgagagt gcaccatatg cggtgtgaaa taccgcacag   5460
atgcgtaagg agaaaatacc gcatcaggcg ctcttccgct tcctcgctca ctgactcgct   5520
gcgctcggtc gttcggctgc ggcgagcggt atcagctcac tcaaaggcgg taatacggtt   5580
atccacagaa tcaggggata acgcaggaaa gaacatgtga gcaaaaggcc agcaaaaggc   5640
caggaaccgt aaaaaggccg cgttgctggc gtttttccat aggctccgcc cccctgacga   5700
gcatcacaaa aatcgacgct caagtcagag gtggcgaaac ccgacaggac tataaagata   5760
ccaggcgttt ccccctggaa gctccctcgt gcgctctcct gttccgaccc tgccgcttac   5820
cggatacctg tccgcctttc tcccttcggg aagcgtggcg ctttctcata gctcacgctg   5880
taggtatctc agttcggtgt aggtcgttcg ctccaagctg ggctgtgtgc acgaaccccc   5940
cgttcagccc gaccgctgcg ccttatccgg taactatcgt cttgagtcca acccggtaag   6000
acacgactta tcgccactgg cagcagccac tggtaacagg attagcagag cgaggtatgt   6060
aggcggtgct acagagttct tgaagtggtg gcctaactac ggctacacta gaaggacagt   6120
atttggtatc tgcgctctgc tgaagccagt taccttcgga aaaagagttg gtagctcttg   6180
atccggcaaa caaaccaccg ctggtagcgg tggttttttt gtttgcaagc agcagattac   6240
gcgcagaaaa aaaggatctc aagaagatcc tttgatcttt tctactgcag aagcttgtta   6300
gacaccctgt catgtatttt atattattta tttcaccata cggattaagt gaaacctaat   6360
gaaaatagta ctttcggagc tttaacttta atgaaggtat gttttttttat agacatcgat   6420
gtctggttta acaataggaa aaagtagcta aaactcccat gaattaaaga aataacaagg   6480
tgtctaacaa cctgttatta agaatgttag aaaagactta acatttgtgt tgagtttta    6540
```

```
tagacattgg tgtctagaca tacggtagat aaggtttgct caaaaataaa ataaaaaaag   6600
attggactaa aaaacattta atttagtaca atttaattag ttattttttc gtctcaaatt   6660
ttgctttgtt gagcagaaat ttagataaaa aaatccccgt gatcagatta caatgtcgtt   6720
cattgtacga tgtgtcgaaa aatctttacg acactctaaa ctgaccacac gggggaaaaa   6780
gaaaactgaa ctaataacat catgatactc ggaaaaccta gcaattctca acccctaaac   6840
aaaagaaact tccaaaaccc tgaccatata aaggagtggc aacaatcagc aatcagtcaa   6900
gatttgatag cagaaaatct tgtatcggtt gctaatggtt ttgatgtact atttatcggc   6960
aataaatacc gaactaacac gggtgttctg tcacggcaca tattaaactc ctattctcat   7020
ttagaagatg gtggttcgta tggtagaaca tttgacccat ttaccaataa agaaatgcag   7080
tgggttcaat ttaaaccgaa tagaccaaga aaaggttcta ctggtaaggt aatcaaatat   7140
gaatcgccaa aaggtgaacc tacaagagtt ctaatgccgt ttgtgcctat gaaaatatgg   7200
caacggatta gcgataagtt cggagtaccg attaatccga aaaaagatac tcacttttgg   7260
gaatgggtaa agaataatcc atcgataccg attgccatta cagaaggaaa taaaaaagct   7320
aattgcctat tatcctatgg ctatcctgct attgcctttg taggcatttg gaacggatta   7380
gagaaaataa atgatttctc gaaggaaaag cagttaaaag aggatttgaa atggttgtta   7440
tccaacggca accgaaatat taatatcatc tttgaccaag accagaaaca aaaaactgta   7500
attaatgtaa acaaagctat tttcgcttta tcttctctaa taagtagaaa tggtcataaa   7560
gttaatattg tgcaatggtt gccgtcaaaa ggtaaaggaa tagatgatta tttggtagct   7620
ttacctttttg agaaaagaga aaatcattta gacaacttaa ttaaaattgc accatcattt   7680
aatttttggt caactaaata cttattcaag tgtcgtaaac cagatttaac cgtaaattgc   7740
cgttatttga gcgatgcagt aaaagaatta cctcaagagg atatagcatt aatagcacct   7800
cacggcacgg gtaaaacttc attagtagct actcacgtta agaatcggag ttatcacgga   7860
aggaaaacta tttcattggt gcatcttgaa agtttagcca aagctaatgg caacgcactt   7920
ggattatatt accgaaccga aaataatatt gaaaagcaat atcttggatt tagcttatgt   7980
gtagatagtt gccgtgataa gattaacggc attacaactg atattatttc aggtcaagat   8040
tattgccttt tcattgatga aattgaccaa gtaattccac acatccttaa cagtgaaact   8100
gaagtaagta agtatagatg caccatcatt gacacttttt ctgaactggt gagaaatgct   8160
gaacaggtca ttattgctga tgctgattta tccgatgtga cgattgacct aatagaaaac   8220
atcagaggta aaaaactata tgtaatcaag aatgaatatc agtatcaggg aatgactttt   8280
aacgccgttg gttcaccatt agaaatgatg gcaatgatgg gaaaatcggt gtcagaaggc   8340
aagaaattat ttattaacac cacatcccaa aaggcaaaaa gtaagtacgg cacaatcgct   8400
cttgagtctt atatttttgg tctaaataaa gaagcaaaga tattaagaat agactctgaa   8460
accactaaaa accctgaaca tccagcctat aaaatcattg accaagactt aaataatatc   8520
ctcaaagatt atgattatgt cattgcctca ccttgccttc aaacaggtgt cagtattacc   8580
ttaaaagggc attttgacca gcaatttaac ttttccagtg gaaacattac acctcattgc   8640
tttttacagc aaatgtggcg gttgagggat gcagaaattg aaagattcta ttatgtgccg   8700
aactcatcta acctcaatct cattgggaat aagtcaagtt caccatcaga ccttctaaag   8760
agcaataaca agatggcaac ggcaacggtt aaccttttgg gtagaatcga ctccgaatat   8820
tccctagagt atgaatcgca cggcatttgg cttgagacgt gggcaaaatt atcagcacgg   8880
cataacagtt caatgcgttg ttactctgaa attcttacct atctaattac gtctcaaggg   8940
```

```
cataaattaa atatcaacat tccctcacct cttgcagata ttaagaagct aaatgatgag    9000
gtaagtagta acagggaaaa ggtaaaaaat gagagatact ctcagaggtt aaactcacca    9060
gatattaacg atgcagaagc taccatactc gaatctaaag agcaaaaaat cggattgact    9120
ctcaatgaga gatgcaccct agaaaagcat aaagttaaga agcggtatgg gaatgtaaag    9180
atggatattc tcacctttga tgatgatgga ctataccca aactcagact attttattac    9240
ctcaccatcg gtaaacctca tctcaaggct aatgacagaa aagctattgc caaaatgggc    9300
aatgacaata aaggcaagat tctatcaaaa gacttagtta ataaaactta ctccgctcgt    9360
gtgaaggtct tagagattct taaactaact gactttatcg acaatcttag agatgaactc    9420
ttaataactc ccaataatcc agctatcacc gattttaata atcttctgct aagagctaag    9480
aaggatttaa gagtattagg agtcaacatc ggaaaatatc caatggccaa cattaatgcc    9540
gtacttactc tcattggtca caaactttct gtaatgagag atgagttcgg aaaagagaaa    9600
aggataaaag tagatggtaa atcataccga tgttatcaac ttgaaacatt accagatttt    9660
accaatgata ctcttgacta ctggttagaa aatgatagcc aaaaagaagt aacagcaaca    9720
gaaaattact ccgaaaattt taacccttca aatagctaca atccagacag taagacactt    9780
tcagagggtg caaatttcct atatataaat aaagaagaat tgcatccaaa taaattgcac    9840
ctagaaataa aagaaggtgc tgaacttttt ttattcgggg taaaggtgat tgtgaaagga    9900
atcttggacg gggcagtaac tatattctct atgggtcaag aatacgattt atccctcaat    9960
gaactagagg ggatgttaac atcatgaact ttacaagaat ctttttaaag ggcgatcgca   10020
ccatgttaaa tgatggtaca tttgttcaga tatttgatat ttaccatgac cacgcattgg   10080
gagtgaccct tgaccttaag acagaaaaaa ttatttccga tgatgttagg gtaattactg   10140
tcaaagactt attgttcgat ggcacttata aaggggtaaa atcttttatg cccgataatg   10200
cccgataatg cccgattgat gctacaaaat cccataatca taagcgataa tcccctaata   10260
gcttgtaatt cttgaaccgt agcgatttta gagtattcca aaaagaagaa ataaacaccg   10320
caaaatgtcg tatttcacat atataaacca aggtttttg ccctaaaatc tttatgtttg   10380
tagtgtgatg ttgggtcaaa atggtcagaa aagttgcaag gtttttatgg atgcttacgc   10440
gcgcgagggg taagcatccc caaatagtta ctttatccta gtccatgccc atttattgcc   10500
gtcccgttcg gctttaaaaa agtgccaaaa ctcacaaggt gcaataaaaa gttctgtacc   10560
tttcgcaacc ctagataatc tttcaacagt tacttttttt cctattatct cggtacaaag   10620
tttggctagt ttctctttc cctctttttc aatcaagcct tcttgtatgc ccaactcatt   10680
gattaatctc tctattttta ccattatttc ccgttcaggt agtttatccc ctaaatcttc   10740
atcgggggc aatgtagggc attctgaagg ggcttttct tctgtctgga cattatctaa   10800
tattgaagta accaaactat cttcagtttt ttctattcct attaattcat attcggttac   10860
tgtatccgta tcaatatccg aataactatc tttatccgta ttagctattc ggttaagttt   10920
atccgttaac tcagaaacaa gactatatag cggttttagc ttttcttcta tcctgttatc   10980
taatacggat aagtttatac ggttatcatt atccgtatta gtatcattgg gcttttttgg   11040
tagttctacc ccctcataaa ccgcttttat tcccaattcc aacagactga taacagtatc   11100
ctttataatg ggtttttgc tgatatggtg aacttttgcc ccttccatca ttgcgatact   11160
ttctatctca ctcatcaact tatcgcttaa gtgaatctcg tatctgttta atcccttact   11220
ggttttattc atatccgttt actttattcg gttaacaatt ctattttata cgaataaaat   11280
```

```
attatacggt taactttata cgtttaacta ttttatctat acggataaca gtaataagtt  11340
attcgtatta gttatacgtt tacttttatc caaataaaat tagtgcattt aaactaaaag  11400
aatgatttta tcggagttga tagcattgga ttaacctaaa gatgtttata agctatatct  11460
gataagtatt taaggttatt ttgttattct gtttattgac attatcagaa taaaagaata  11520
gaatataatt gttgagagat aagaggttta agtgattatg gttaagaagt tagttggtta  11580
tgtcagggtc agtagtgaat cgcaagagga taacactagc ttacagaatc agatagagag  11640
aattgaagca tattgtatgg cttttggtta tgagttggta aaaatattca aagaggttgc  11700
cactggtaca aaagcagata ttgaaacccg tcctattttt aatgaagcta tagaatactt  11760
gaaacaggat aatgctaatg gaattattgc cttgaagcta gaccgaatcg cacggaatgc  11820
tttagatgta ttgcgtttgg ttcgtgaaac cttagaacca caaaataaaa tgttagtgtt  11880
actagatatt caggtagata cttcgacacc ttcaggaaaa atgattttaa ctgtaatgag  11940
tgccgttgct gaactcgaaa gagacatgat ctatgatcgc actcaggggg gtagaaagac  12000
taaagcccaa aagggcgggt atgcctacgg gaaacctaaa tttggctata agactgaaga  12060
aaaggaacta aaagaagatt cagcacaaca ggaaactatt aaactaatta agagacaccg  12120
taggtcaggg aaaagctacc agaaaatagc tgattatctc aatgcccaaa gtattcccac  12180
taaacaaggt aagaaatgga gttctagcgt cgtctatcga atctgtcagg aaaaagctgg  12240
ttaagtctgt ttatagatat ttagaattta ttgaataaaa atagtatgaa caataaatat  12300
ttatggacta accacgctcg gaaacgttta actgaacgat gggaaataaa agaatcatgg  12360
gttattgata ccatcgaaaa tcctgaacgt tcagaattta ttgttgatga gtcaggggaa  12420
aaatatcatt actataaaag aatagctaag tttaagaata gagtgttaga agtgataact  12480
tctgccaact caacacccac aagaataata accttttact ttaaccgtaa catgaggaaa  12540
aatttatgat tgttacttac gataatgaag ttgacgcaat ttattttaag ttaacggaaa  12600
ataaaattga tagcaccgaa cctcaaacag acaggattat cattgattac gatgaaagta  12660
ataatattgt tggcattgag gtattagatt ttaattatct tgtcaagaaa ggtttaaccg  12720
ttgctgattt accttttttct gaagatgaaa gattaacagc ttctcaatat tttaattttc  12780
ctgttgctat ctaatccaga aggggcaata atccccttct ttcatcgagt tagacttaat  12840
atcacaaaag tcattttcat tttaccgttt cttttccaca gcgtccgtac gcccctcgtt  12900
aaatctcaaa accgacaatt tatgatgttt ataaaaagtt actcacttta ataagtattt  12960
atactcatta aagggtatt ctttttttgt agcctgatag gttgggaagg aatatttcag  13020
attatcagat ttgttgaata tttttcgtca gatacgcaaa ccttacaaac ataattaaca  13080
actgaaacta ttgatatgtc taggttttag ctctatcaca ggttggatct g           13131
```

```
<210> SEQ ID NO 82
<211> LENGTH: 400
<212> TYPE: DNA
<213> ORGANISM: Cyanobacterium sp.
<220> FEATURE:
<221> NAME/KEY: n
<222> LOCATION: (1)..(151)
<223> OTHER INFORMATION: A, T, C or G
<220> FEATURE:
<221> NAME/KEY: misc_feature
<222> LOCATION: (1)..(151)
<223> OTHER INFORMATION: n is a, c, g, or t
<220> FEATURE:
<221> NAME/KEY: n
<222> LOCATION: (158)..(164)
<223> OTHER INFORMATION: A, T, C or G
```

<220> FEATURE:
<221> NAME/KEY: misc_feature
<222> LOCATION: (158)..(164)
<223> OTHER INFORMATION: n is a, c, g, or t
<220> FEATURE:
<221> NAME/KEY: n
<222> LOCATION: (166)..(381)
<223> OTHER INFORMATION: A, T, C or G
<220> FEATURE:
<221> NAME/KEY: misc_feature
<222> LOCATION: (166)..(381)
<223> OTHER INFORMATION: n is a, c, g, or t
<220> FEATURE:
<221> NAME/KEY: n
<222> LOCATION: (388)..(397)
<223> OTHER INFORMATION: A, T, C or G
<220> FEATURE:
<221> NAME/KEY: misc_feature
<222> LOCATION: (388)..(397)
<223> OTHER INFORMATION: n is a, c, g, or t

<400> SEQUENCE: 82

```
nnnnnnnnnn nnnnnnnnnn nnnnnnnnnn nnnnnnnnnn nnnnnnnnnn nnnnnnnnnn     60

nnnnnnnnnn nnnnnnnnnn nnnnnnnnnn nnnnnnnnnn nnnnnnnnnn nnnnnnnnnn    120

nnnnnnnnnn nnnnnnnnnn nnnnnnnnnn ntataaannn nnnngnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnnnnn nnnnnnnnnn nnnnnnnnnn nnnnnnnnnn nnnnnnnnnn    360

nnnnnnnnnn nnnnnnnnnn naggagannn nnnnnnnatg                           400
```

<210> SEQ ID NO 83
<211> LENGTH: 400
<212> TYPE: DNA
<213> ORGANISM: Cyanobacterium sp.
<220> FEATURE:
<221> NAME/KEY: n
<222> LOCATION: (1)..(123)
<223> OTHER INFORMATION: A, T, C or G
<220> FEATURE:
<221> NAME/KEY: misc_feature
<222> LOCATION: (1)..(123)
<223> OTHER INFORMATION: n is a, c, g, or t
<220> FEATURE:
<221> NAME/KEY: n
<222> LOCATION: (131)..(151)
<223> OTHER INFORMATION: A, T, C or G
<220> FEATURE:
<221> NAME/KEY: misc_feature
<222> LOCATION: (131)..(151)
<223> OTHER INFORMATION: n is a, c, g, or t
<220> FEATURE:
<221> NAME/KEY: n
<222> LOCATION: (158)..(164)
<223> OTHER INFORMATION: A, T, C or G
<220> FEATURE:
<221> NAME/KEY: misc_feature
<222> LOCATION: (158)..(164)
<223> OTHER INFORMATION: n is a, c, g, or t
<220> FEATURE:
<221> NAME/KEY: n
<222> LOCATION: (166)..(263)
<223> OTHER INFORMATION: A, T, C or G
<220> FEATURE:
<221> NAME/KEY: misc_feature
<222> LOCATION: (166)..(263)
<223> OTHER INFORMATION: n is a, c, g, or t
<220> FEATURE:
<221> NAME/KEY: n
<222> LOCATION: (270)..(273)
<223> OTHER INFORMATION: A, T, C or G
<220> FEATURE:

```
<221> NAME/KEY: misc_feature
<222> LOCATION: (270)..(273)
<223> OTHER INFORMATION: n is a, c, g, or t
<220> FEATURE:
<221> NAME/KEY: n
<222> LOCATION: (281)..(284)
<223> OTHER INFORMATION: A, T, C or G
<220> FEATURE:
<221> NAME/KEY: misc_feature
<222> LOCATION: (281)..(284)
<223> OTHER INFORMATION: n is a, c, g, or t
<220> FEATURE:
<221> NAME/KEY: n
<222> LOCATION: (286)..(381)
<223> OTHER INFORMATION: A, T, C or G
<220> FEATURE:
<221> NAME/KEY: misc_feature
<222> LOCATION: (286)..(381)
<223> OTHER INFORMATION: n is a, c, g, or t
<220> FEATURE:
<221> NAME/KEY: n
<222> LOCATION: (388)..(397)
<223> OTHER INFORMATION: A, T, C or G
<220> FEATURE:
<221> NAME/KEY: misc_feature
<222> LOCATION: (388)..(397)
<223> OTHER INFORMATION: n is a, c, g, or t

<400> SEQUENCE: 83

nnnnnnnnnn nnnnnnnnnn nnnnnnnnnn nnnnnnnnnn nnnnnnnnnn nnnnnnnnnn      60

nnnnnnnnnn nnnnnnnnnn nnnnnnnnnn nnnnnnnnnn nnnnnnnnnn nnnnnnnnnn     120

nnncgtaata nnnnnnnnnn nnnnnnnnnn ntataaannn nnnngnnnnn nnnnnnnnnn     180

nnnnnnnnnn nnnnnnnnnn nnnnnnnnnn nnnnnnnnnn nnnnnnnnnn nnnnnnnnnn     240

nnnnnnnnnn nnnnnnnnnn nnnaaataan nnngactaat nnnnannnnn nnnnnnnnnn     300

nnnnnnnnnn nnnnnnnnnn nnnnnnnnnn nnnnnnnnnn nnnnnnnnnn nnnnnnnnnn     360

nnnnnnnnnn nnnnnnnnnn naggagannn nnnnnnnatg                           400
```

METABOLICALLY ENHANCED CYANOBACTERIAL CELL FOR THE PRODUCTION OF ETHANOL

CROSS-REFERENCE TO RELATED APPLICATIONS

This patent application claims the priority of the U.S. provisional application No. 61/835,086 filed on Jun. 14, 2013, the disclosure content of which is hereby incorporated by reference.

REFERENCE TO SEQUENCE LISTING

This application contains a sequence listing comprising 83 sequences, submitted by EFS-Web, thereby satisfying the requirements of 37 C.F.R. §§1.821-1.825. The sequence listing file, named "ADH_US_Seq_listing.txt", was created on Jun. 12, 2014, and is 487 kb in size.

FIELD OF THE INVENTION

The present invention relates to the metabolic enhancement of cyanobacteria to produce ethanol. In particular, the present invention relates to alcohol dehydrogenase enzymes that can be useful in metabolically enhancing cyanobacteria for ethanol production.

BACKGROUND OF THE INVENTION

Various chemical compounds of interest, such as biofuels, can be produced via metabolically enhanced cyanobacteria. One of these compounds is ethanol. In this context, the PCT patent application WO 2009/098089 A2 discloses the use of ethanologenic genes, for example pyruvate decarboxylase and alcohol dehydrogenase genes for the production of ethanol with cyanobacteria.

Despite a generally promising concept, the practical implementation of ethanol production with metabolically enhanced cyanobacteria still faces critical problems which have made it so far difficult to achieve economical production rates per production volume and area.

Therefore, there is a need for improved cyanobacterial cells which reduce or resolve at least some of these problems.

BRIEF SUMMARY OF THE INVENTION

This task is solved by providing a metabolically enhanced cyanobacterial cell for the production of ethanol, comprising at least one recombinant gene encoding a pyruvate decarboxylase enzyme (Pdc) converting pyruvate to acetaldehyde, and at least one recombinant gene encoding a first $Zn^{2+}$ dependent alcohol dehydrogenase enzyme (Adh) converting acetaldehyde to ethanol, wherein (i) the Michaelis constant $K_m$ for NADPH of the alcohol dehydrogenase enzyme is lower than the Michaelis constant $K_m$ for NADH of the alcohol dehydrogenase enzyme, and (ii) the Michaelis constant $K_m$ for acetaldehyde of the alcohol dehydrogenase enzyme is lower than $0.08 \cdot 10^{-3}$ M.

This task is also solved by providing a metabolically enhanced cyanobacterial cell for the production of ethanol, comprising at least one recombinant gene encoding a pyruvate decarboxylase enzyme (Pdc) converting pyruvate to acetaldehyde, and at least one recombinant gene encoding a first $Zn^{2+}$ dependent alcohol dehydrogenase enzyme (Adh) converting acetaldehyde to ethanol, wherein (i) the Michaelis constant $K_m$ for NADPH of the alcohol dehydrogenase enzyme is lower than the Michaelis constant $K_m$ for NADH of the alcohol dehydrogenase enzyme, and (ii) the Michaelis constant $K_m$ for acetaldehyde of the alcohol dehydrogenase enzyme is higher than $0.65 \cdot 10^{-3}$ M but lower than $10 \cdot 10^{-3}$ M, and (iii) the Michaelis constant $K_m$ for ethanol of the alcohol dehydrogenase enzyme is higher than $20 \cdot 10^{-3}$ M.

This task is further solved by providing a metabolically enhanced cyanobacterial cell for the production of ethanol, comprising at least one recombinant gene encoding a pyruvate decarboxylase enzyme (Pdc) converting pyruvate to acetaldehyde, and at least one recombinant gene encoding a first $Zn^{2+}$ dependent alcohol dehydrogenase enzyme (Adh) converting acetaldehyde to ethanol, wherein the alcohol dehydrogenase enzyme comprises an amino acid sequence having at least 80% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10.

This invention also provides method for producing the metabolically enhanced cyanobacterial cell for the production of ethanol, comprising the method steps of: A) providing a cyanobacterial cell, B) introducing the at least one recombinant gene encoding the pyruvate decarboxylase enzyme and the at least one recombinant gene encoding the $Zn^{2+}$ dependent alcohol dehydrogenase enzyme into the wild type host cell, wherein (i) the Michaelis constant $K_m$ for NADPH of the alcohol dehydrogenase enzyme is lower than the Michaelis constant $K_m$ for NADH of the alcohol dehydrogenase enzyme, and (ii) the Michaelis constant $K_m$ for acetaldehyde of the alcohol dehydrogenase enzyme is lower than $0.08 \cdot 10^{-3}$ M, or the Michaelis constant $K_m$ for acetaldehyde of the alcohol dehydrogenase enzyme is higher than $0.65 \cdot 10^{-3}$ M but lower than $10 \cdot 10^{-3}$ M, and the Michaelis constant Km for ethanol of the alcohol dehydrogenase enzyme is higher than $20 \cdot 10^{-3}$ M.

Further provided is a method for producing ethanol, comprising the method steps of: a) providing the metabolically enhanced cyanobacterial cell for the production of ethanol, b) culturing the metabolically enhanced cyanobacterial cell in a growth medium under the exposure of light, the cyanobacterial cell producing ethanol while being cultured, c) retrieving the ethanol from the cyanobacterial cell, the growth medium and/or a headspace above the growth medium.

This invention also provides an isolated nucleic acid sequence, comprising at least one recombinant gene encoding a $Zn^{2+}$ dependent alcohol dehydrogenase enzyme (Adh), wherein the recombinant gene comprises a nucleic acid sequence having at least 80% sequence identity to SEQ ID NO:15, SEQ ID NO:16 or SEQ ID NO:17, and wherein (i) the Michaelis constant $K_m$ for NADPH of the alcohol dehydrogenase enzyme is lower than the Michaelis constant $K_m$ for NADH of the alcohol dehydrogenase enzyme, and (ii) the Michaelis constant $K_m$ for acetaldehyde of the alcohol dehydrogenase enzyme is lower than $0.08 \cdot 10^{-3}$ M.

This invention further provides an isolated nucleic acid sequence, comprising at least one recombinant gene encoding a $Zn^{2+}$ dependent alcohol dehydrogenase enzyme (Adh), wherein the recombinant gene comprises a nucleic acid sequence having at least 80% sequence identity to SEQ ID NO:18, SEQ ID NO:19, SEQ ID NO:20 or SEQ ID NO:22, at least 92% sequence identity to SEQ ID NO:23, or at least 98% sequence identity to SEQ ID NO:24, and wherein (i) the Michaelis constant $K_m$ for NADPH of the alcohol dehydrogenase enzyme is lower than the Michaelis constant $K_m$ for NADH of the alcohol dehydrogenase enzyme, and (ii) the Michaelis constant $K_m$ for acetaldehyde of the alcohol dehydrogenase enzyme is higher than $0.65 \cdot 10^{-3}$ M but lower than $10 \cdot 10^{-3}$ M, and (iii) the Michaelis constant $K_m$ for ethanol of the alcohol dehydrogenase enzyme is higher than $20 \cdot 10^{-3}$ M, preferably higher than $25 \cdot 10^{-3}$ M, most preferred higher than $30 \cdot 10^{-3}$ M. Also provided is a use of a metabolically enhanced host cell for the production of a C3, C4, C5, C6, C7, C8, C9 and/or C10 alcohol, comprising at least one recombinant gene encoding a $Zn^{2+}$ dependent alcohol dehydrogenase enzyme (Adh) converting a C3, C4, C5, C6, C7, C8, C9 and/or C10 aldehyde into the corresponding alcohol, wherein the Michaelis constant $K_m$ for the C3, C4, C5, C6, C7, C8, C9 and/or C10 aldehyde of the alcohol dehydrogenase enzyme is lower than $0.2 \cdot 10^{-3}$ M.

This invention further provides a method for screening a plurality of alcohol dehydrogenase enzyme expressing cyanobacterial strains for the presence of NADPH-dependent native alcohol dehydrogenase enzymes, comprising the following steps: A1) preparing a first and a second sample from each of the plurality of alcohol dehydrogenase enzyme expressing cyanobacterial strains, A2) adding acetaldehyde to the first and second sample from each of the plurality of alcohol dehydrogenase enzyme expressing cyanobacterial strains, A3) keeping the first sample from each of the plurality of alcohol dehydrogenase enzyme expressing cyanobacterial strains under illumination and the second sample without illumination, A4) comparing the conversion of acetaldehyde into ethanol in the first and second sample from each of the plurality of alcohol dehydrogenase enzyme expressing cyanobacterial strains, A5) selecting cyanobacterial strains having a higher acetaldehyde conversion rate under illumination than without illumination for further characterization.

Additionally, this invention provides a metabolically enhanced cyanobacterial cell for the production of ethanol, comprising: at least one recombinant gene encoding a pyruvate decarboxylase enzyme (Pdc) converting pyruvate to acetaldehyde, and at least one recombinant gene encoding a first $Zn^{2+}$ dependent alcohol dehydrogenase enzyme (Adh) converting acetaldehyde to ethanol, wherein said $Zn^{2+}$ dependent alcohol dehydrogenase enzyme (Adh) is from an organism selected from the group consisting of *Arthrospira platensis, Arthronema africanum, Synechococcus* sp., *Chroococcidiopsis* sp., *Lyngbya* sp. and *Cyanothece* sp.

In another embodiment, a method of determining the $K_m$ of an alcohol dehydrogenase enzyme (forward reaction) in a microbial strain is provided, by culturing the strain and preparing a crude extract, clarifying the crude extract, mixing an aliquot of the clarified crude extract with the buffer: 30 mM HEPES/KOH pH 7.5, 150 mM KCl, and 1 mM DTT at 30° C., adding 0.15 mM NADPH, starting the reaction by adding acetaldehyde in an amount from about 1 μM to about 50 μM, measuring NADPH oxidation at a wavelength of 340 nm at 30° C., and correlating the NADPH oxidation measurement with a graph of known $K_m$ values to determine a $K_m$ value (forward) for the alcohol dehydrogenase.

In an embodiment, a method of determining the $K_m$ of an alcohol dehydrogenase enzyme (back reaction) in a microbial strain is provided, by culturing the microbial strain, preparing a crude extract from the culture, clarifying the crude extract, mixing an aliquot of the clarified crude extract with the buffer: 30 mM HEPES/KOH pH 7.5, 150 mM KCl, and 1 mM DTT at 30° C., adding 0.15 mM $NADP^+$, starting the reaction by adding ethanol in an amount from about 1 mM to about 2.5M, measuring the change in $NADP^+$ at a wavelength of 340 nm at 30° C., and correlating the change in $NADP^+$ with a graph of known Km values to determine a $K_m$ value (back reaction) for the alcohol dehydrogenase.

PTA-13311 harboring the different ethanologenic plasmids #1578, #1646 and #1753 over 40 hours cultivation under inducing conditions.

Figure 9A:
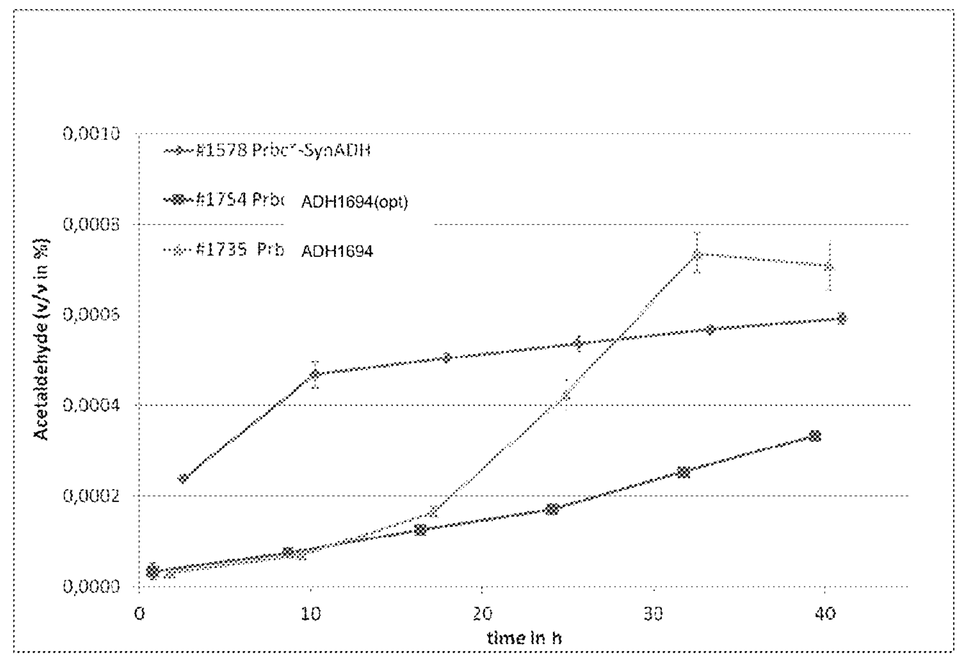
Figure 9B:
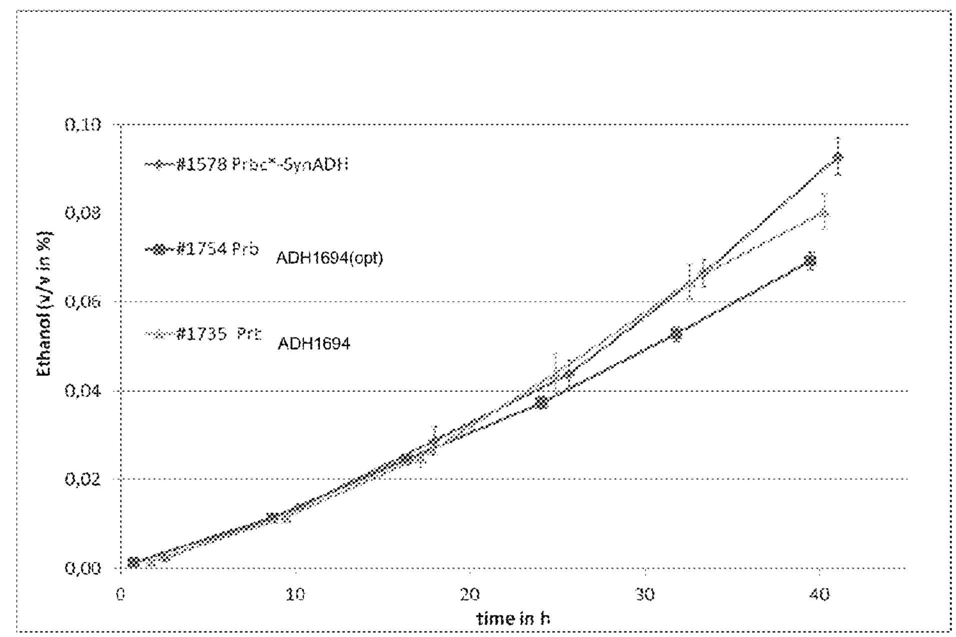
Figure 9C:
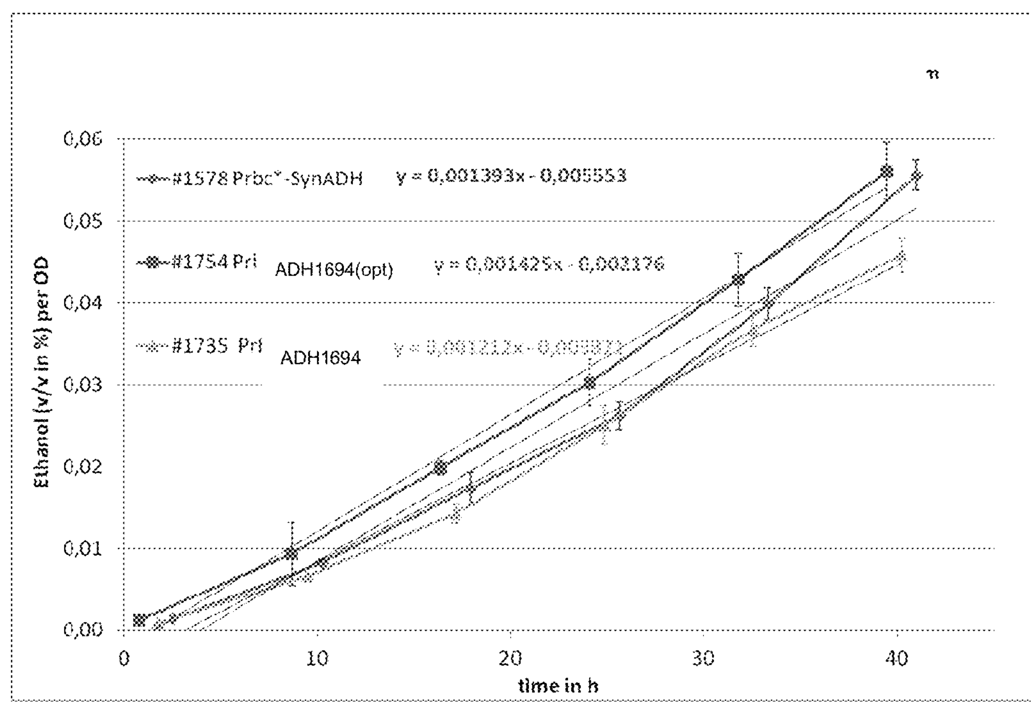

FIGS. 9A, 9B and 9C show a graphical evaluation of acetaldehyde accumulation (FIG. 9A) and absolute (FIG. 9B) as well as relative (FIG. 9C) ethanol production rates determined by the GC vial online method for Cyanobacterium sp. PTA-13311 harboring the different ethanologenic plasmids #1578, #1754 and #1735 over 40 hours cultivation under inducing conditions.

Figure 10A:
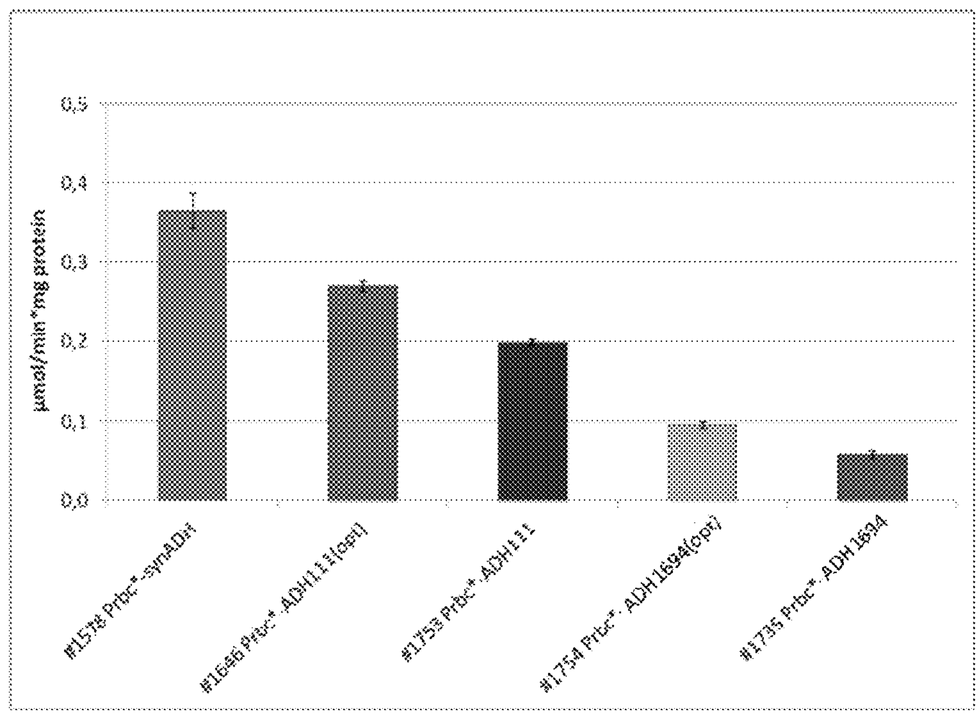
Figure 10B:
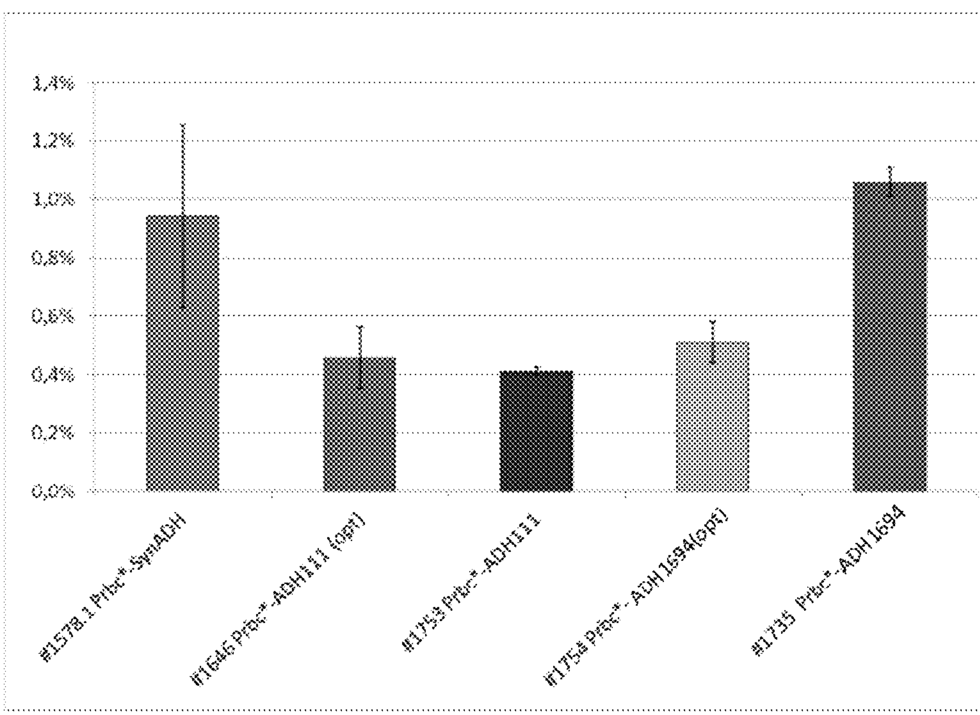

FIGS. 10A and 10B show a graphical evaluation of Adh activity levels (FIG. 10A) and acetaldehyde/ethanol ratios (FIG. 10B) determined by the GC vial online method for Cyanobacterium sp. PTA-13311 harboring the different ethanologenic plasmids #1578, #1646, #1753, #1754 and #1735 under inducing conditions.

Figure 11A:
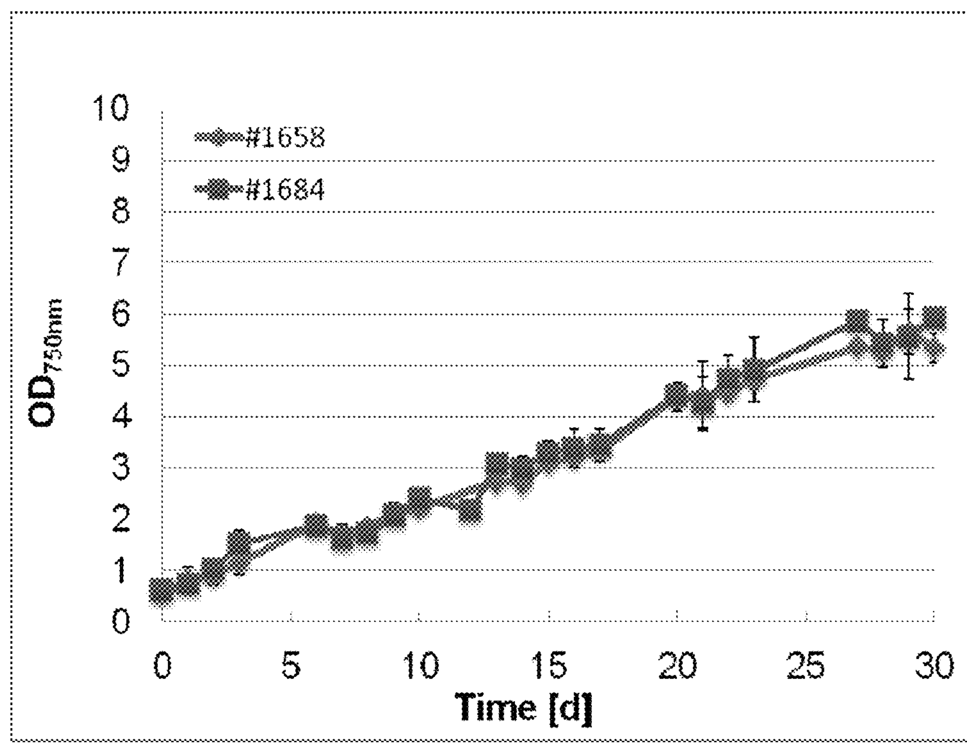
Figure 11B:
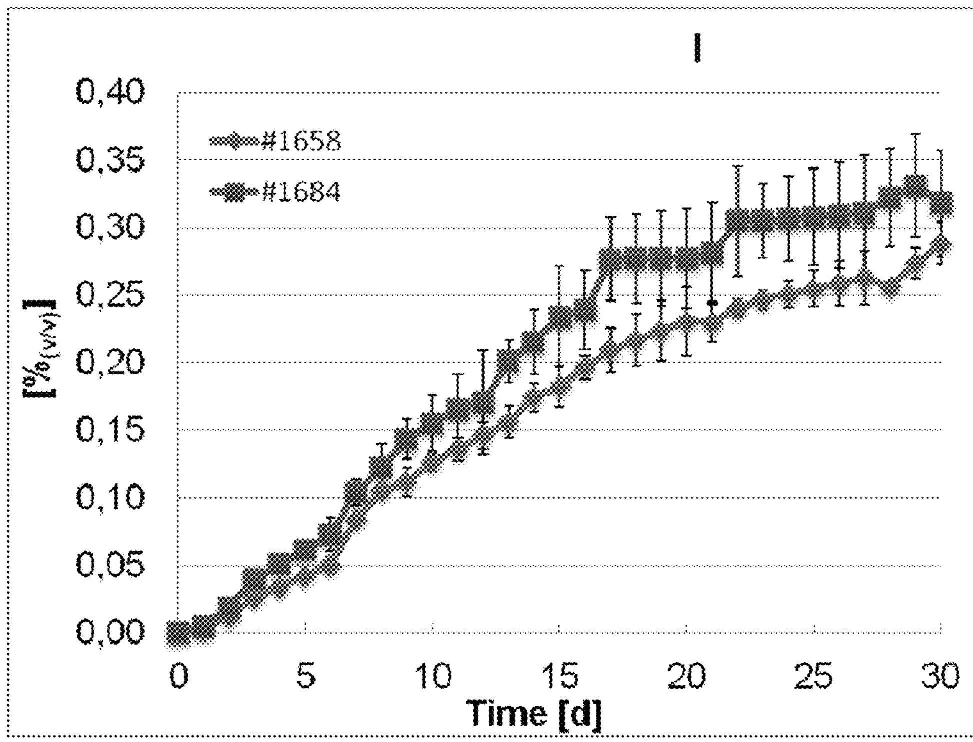

FIGS. 11A and 11B show a graphical evaluation of cell growth and (FIG. 11A) total ethanol accumulation (FIG. 11B) over 30 days cultivation for Cyanobacterium sp. PTA-13311 harboring the ethanologenic plasmids #1658 and #1684 under inducing conditions.

Figure 11C:
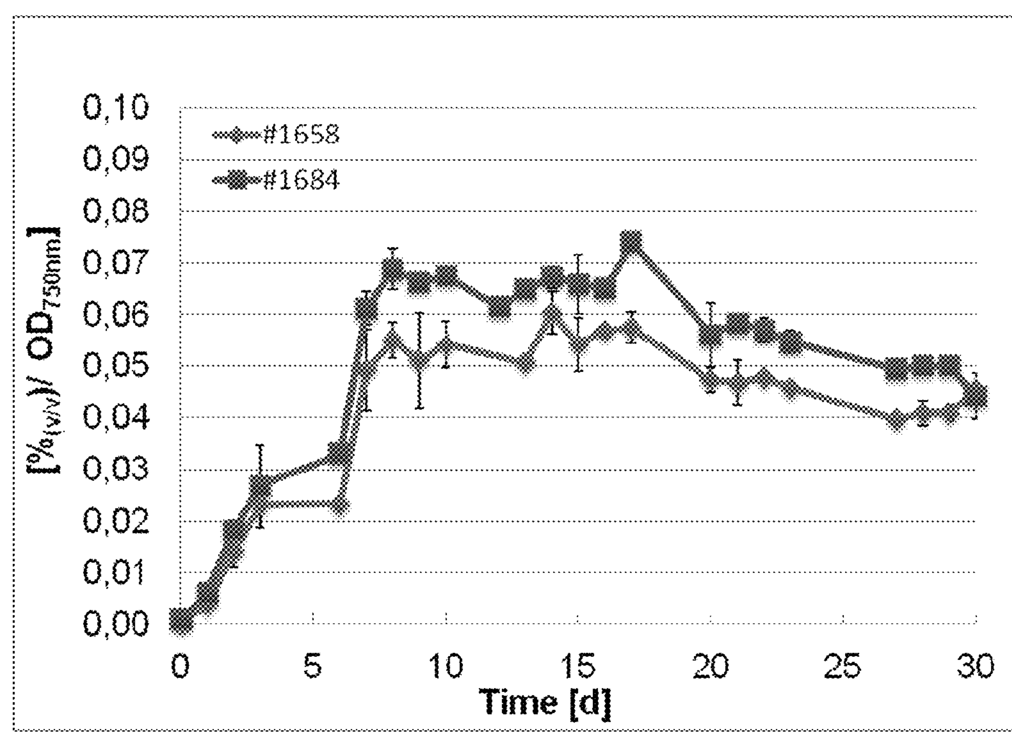

FIG. 11C shows a graphical evaluation of normalized ethanol accumulation per cell density over 30 days cultivation for Cyanobacterium sp. PTA-13311 harboring the ethanologenic plasmids #1658 and #1684 under inducing conditions.

Figure 12A:
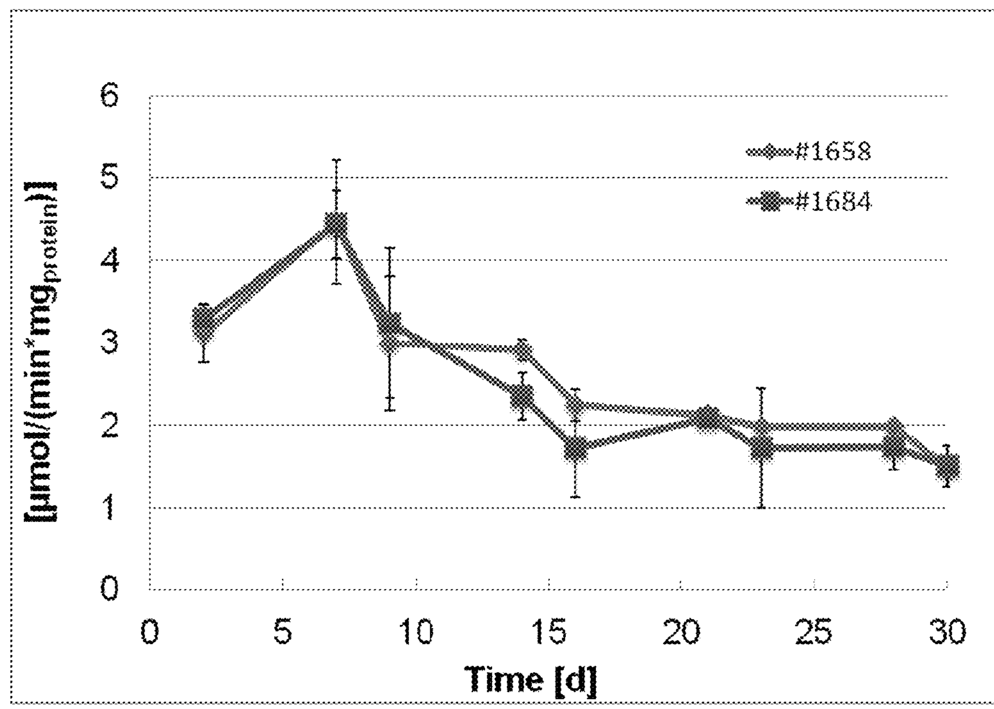
Figure 12B:
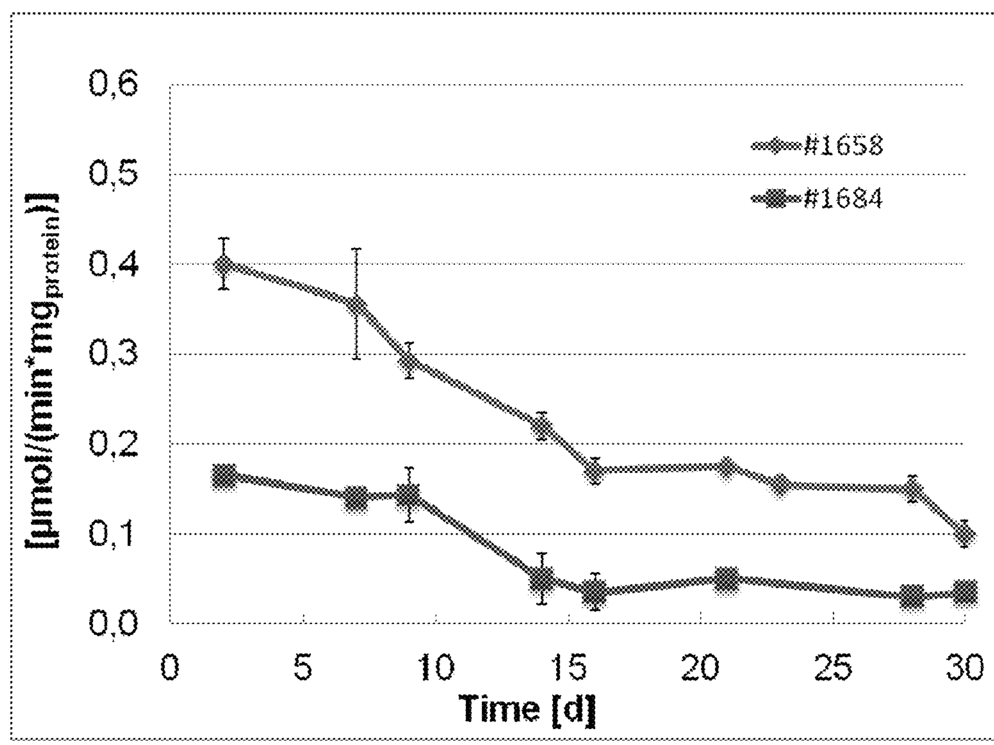

FIGS. 12A and 12B show a graphical evaluation of Pdc (FIG. 12A) and Adh (FIG. 12B) activity over 30 days cultivation for Cyanobacterium sp. PTA-13311 harboring the ethanologenic plasmids #1658 and #1684 under inducing conditions.

Figure 13A:
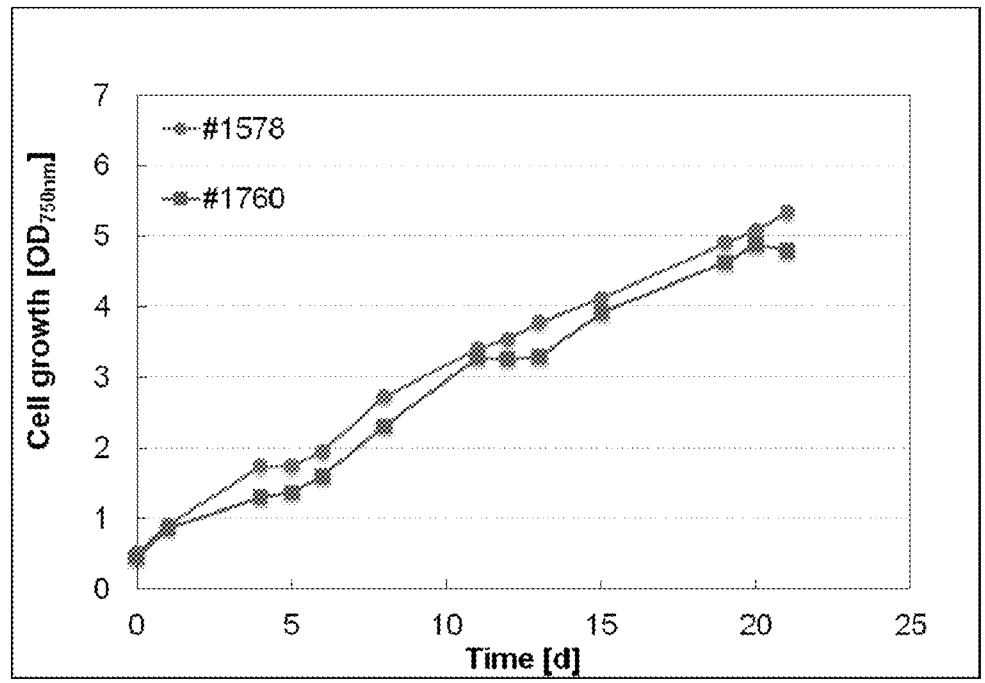
Figure 13B:
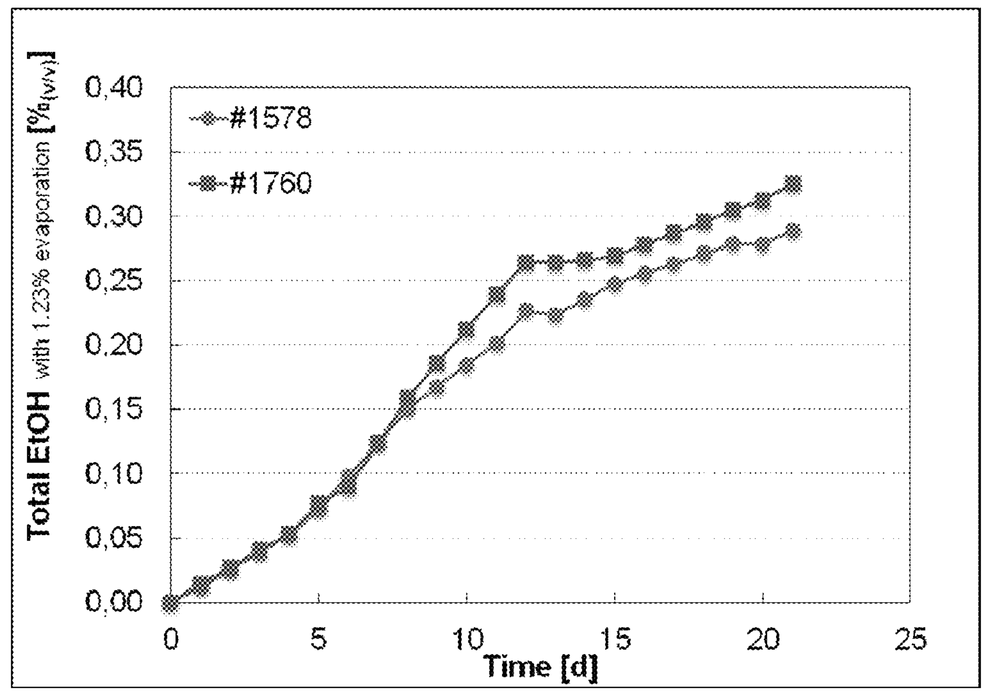

FIGS. 13A and 13B show a graphical evaluation of cell growth (FIG. 13A) and total ethanol accumulation (FIG. 13B) over 21 days cultivation for Cyanobacterium sp. PTA-13311 harboring the ethanologenic plasmids #1578 and #1760 under inducing conditions.

Figure 13C:
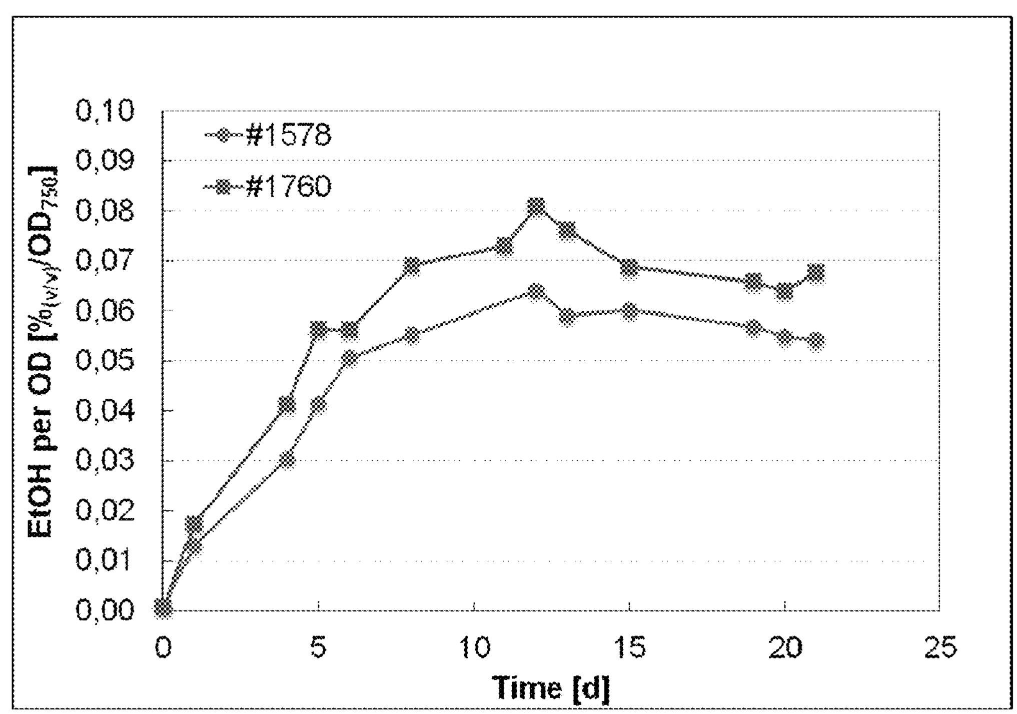

FIG. 13C shows a graphical evaluation of normalized ethanol accumulation per cell density over 21 days cultivation for Cyanobacterium sp. PTA-13311 harboring the ethanologenic plasmids #1578 and #1760 under inducing conditions.

Figure 14A:
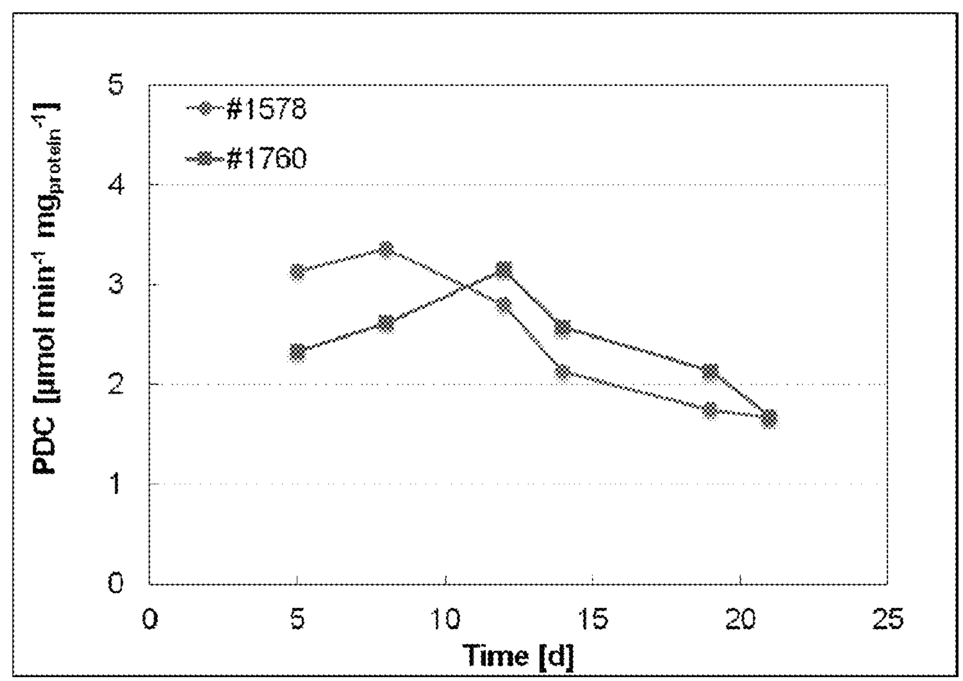
Figure 14B:
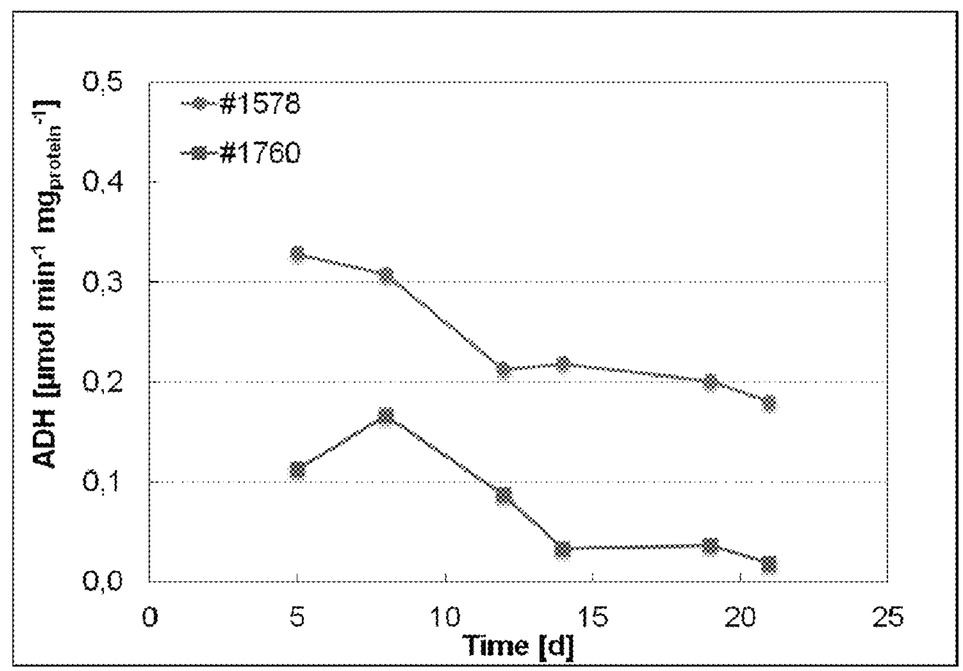

FIGS. 14A and 14B show a graphical evaluation of Pdc (FIG. 14A) and Adh (FIG. 14B) activity over 21 days cultivation for Cyanobacterium sp. PTA-13311 harboring the ethanologenic plasmids #1578 and #1760 under inducing conditions.

Figure 15A:
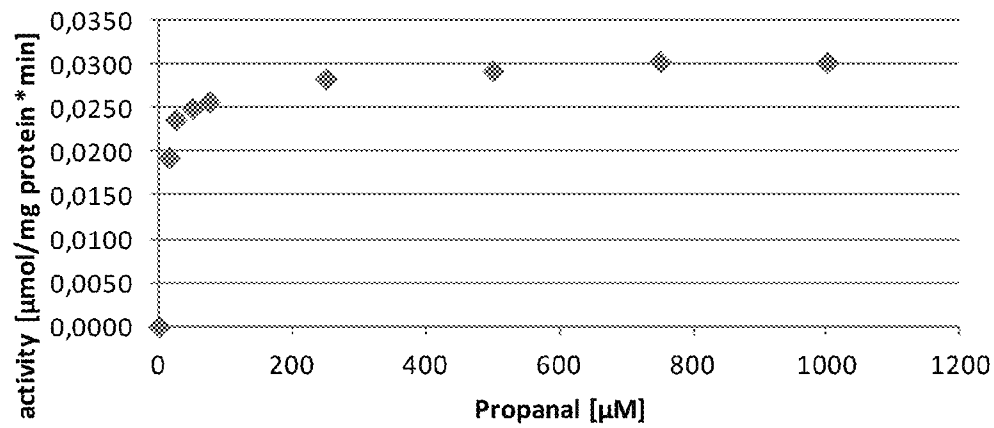

FIG. 15A shows an exemplary graphical plot of the kinetic analysis of the alcohol dehydrogenase enzyme with amino acid sequence SEQ ID NO:1 from which the Michaelis constant $K_m$ for propanal was computed using the GraphPad Prism software.

Figure 15B:
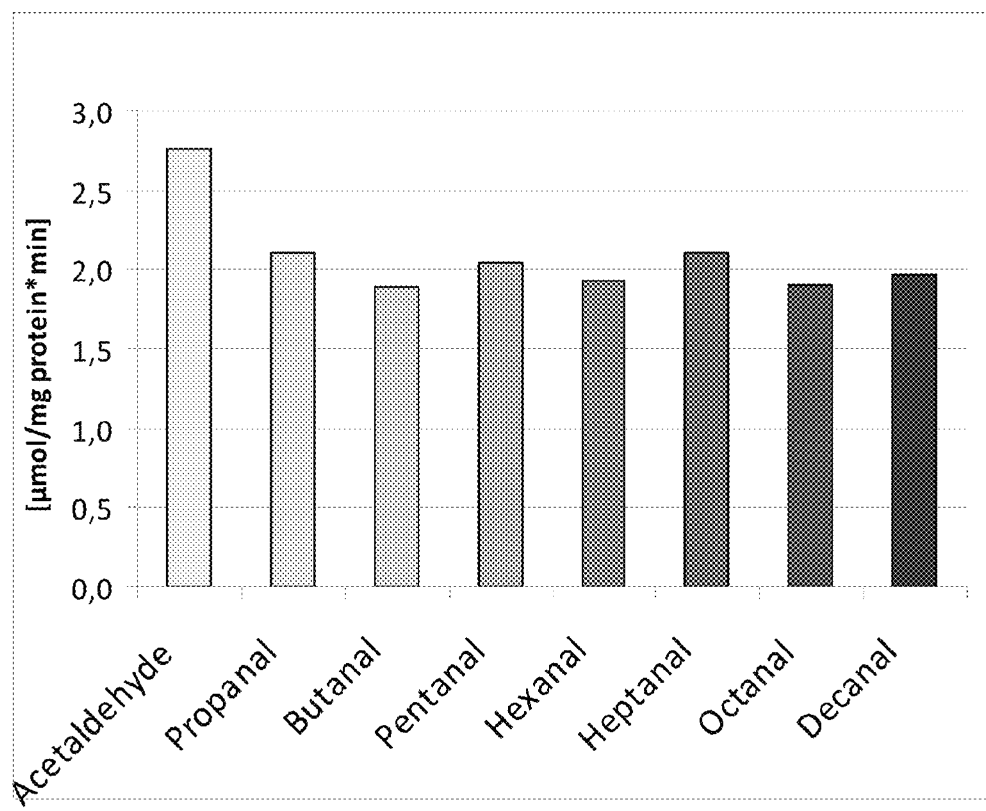

FIG. 15B shows the results of an Adh specific activity comparison in μmol per mg protein and min of the alcohol dehydrogenase with amino acid sequence SEQ ID NO:1 for a variety of different C2-C10 aldehyde substrates at 0.1 mM substrate concentration.

Figure 16A:
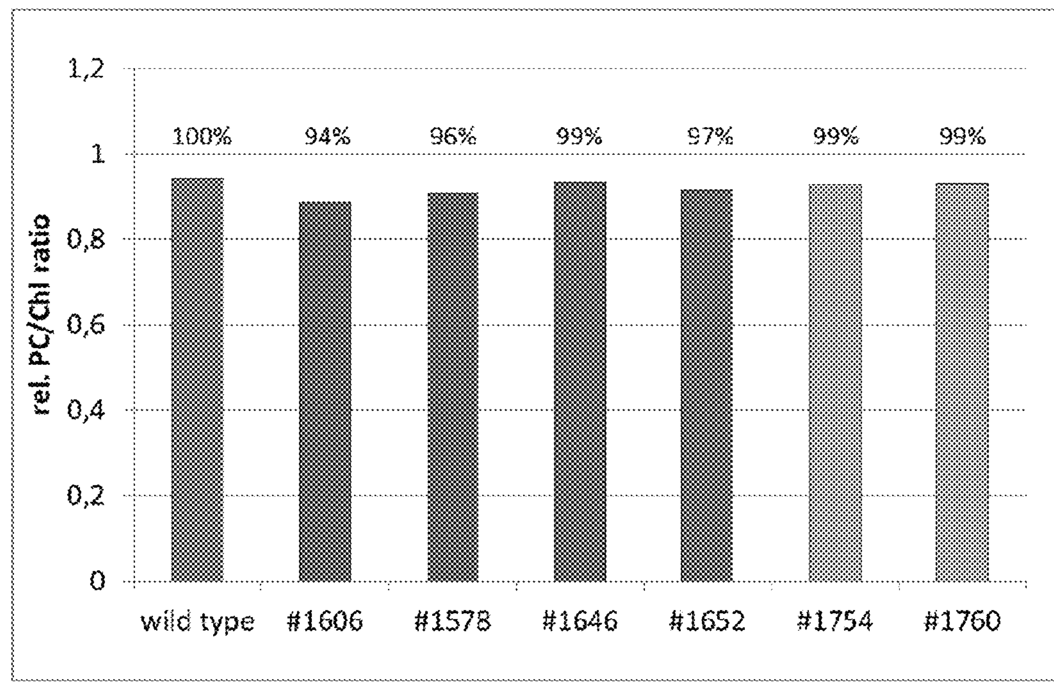
Figure 16B:
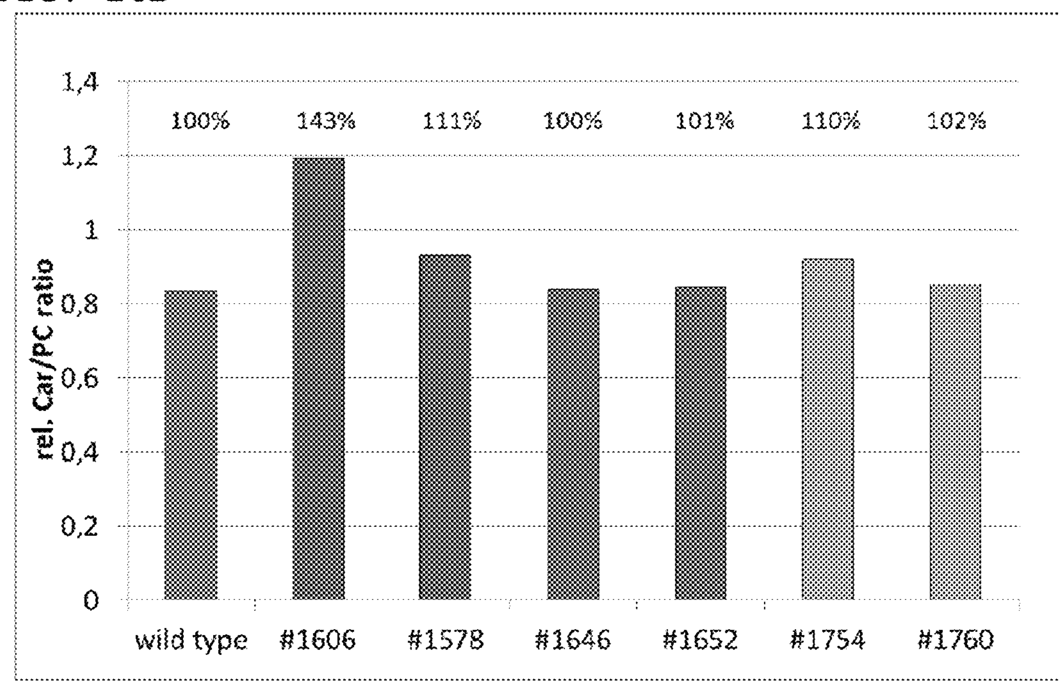

FIGS. 16A and 16B show the results of relative phycocyanin (PC)/chlorophyll (Chl) (FIG. 16A) and relative carotenoid (Car)/phycocyanin (PC) pigmentation (FIG. 16B) analysis of various metabolically enhanced Cyanobacterium sp. PTA-13311 harboring different ethanologenic plasmids under inducing conditions in comparison to the wild type Cyanobacterium sp. PTA-13311.

Figure 17A:
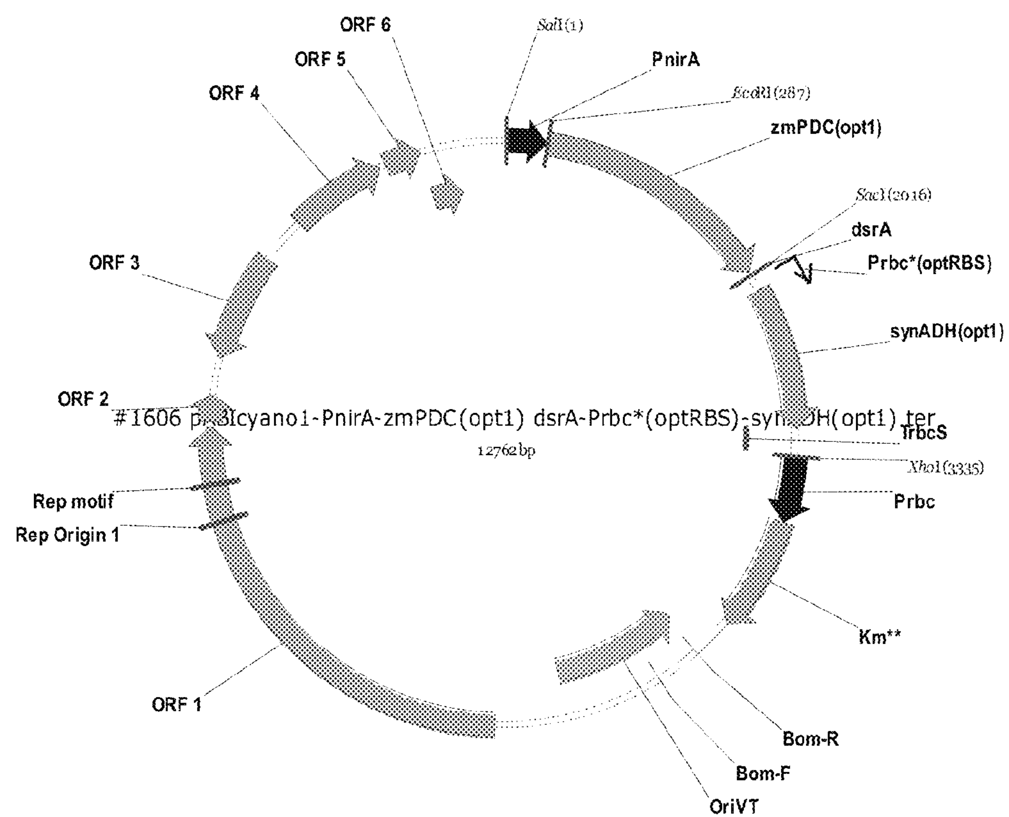

FIG. 17A is a map of plasmid construct #1606 with SEQ ID NO:44. #1606 is a derivative of TK293 containing the PnirA promoter upstream of a codon improved zmPDC gene and the Prbc promoter with optimized RBS upstream of a codon improved synAdh gene from *Synechocystis* sp. PCC6803 encoding the Adh enzyme with SEQ ID NO:26.

Figure 17B:
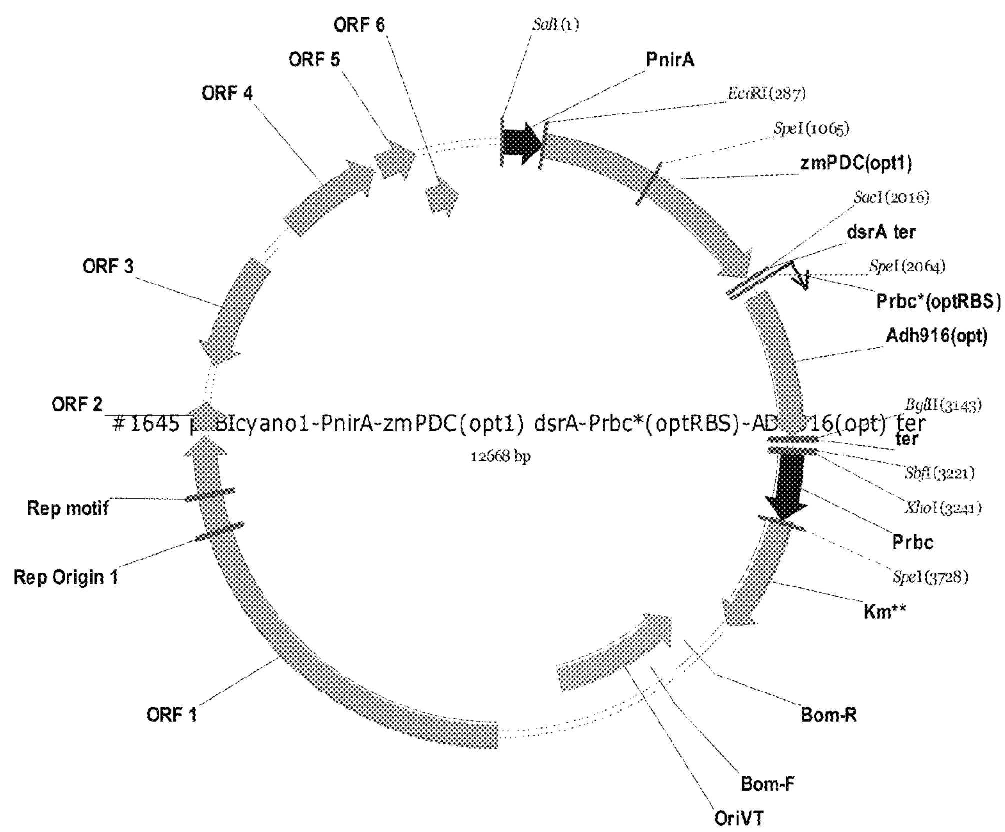

FIG. 17B is a map of plasmid construct #1645 with SEQ ID NO:45. #1645 is a derivative of TK293 containing the PnirA promoter upstream of a codon improved zmPDC gene and the Prbc promoter with optimized RBS upstream of a codon improved adh gene from *Synechococcus* sp. encoding the Adh enzyme with SEQ ID NO:6.

Figure 18A:
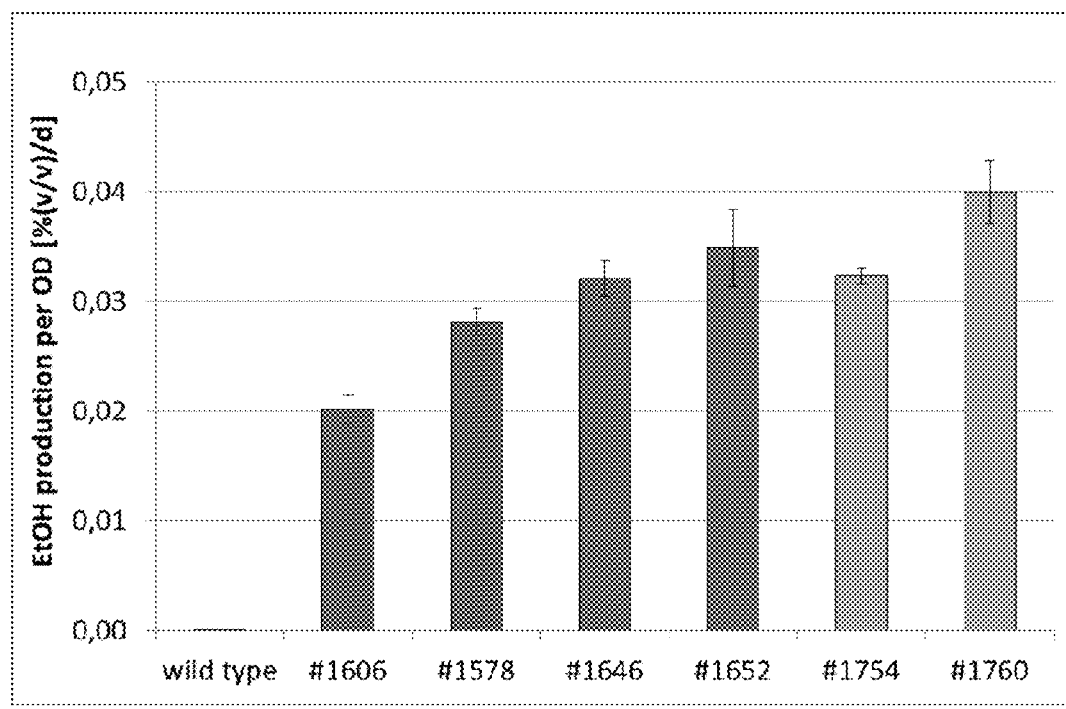
Figure 18B:
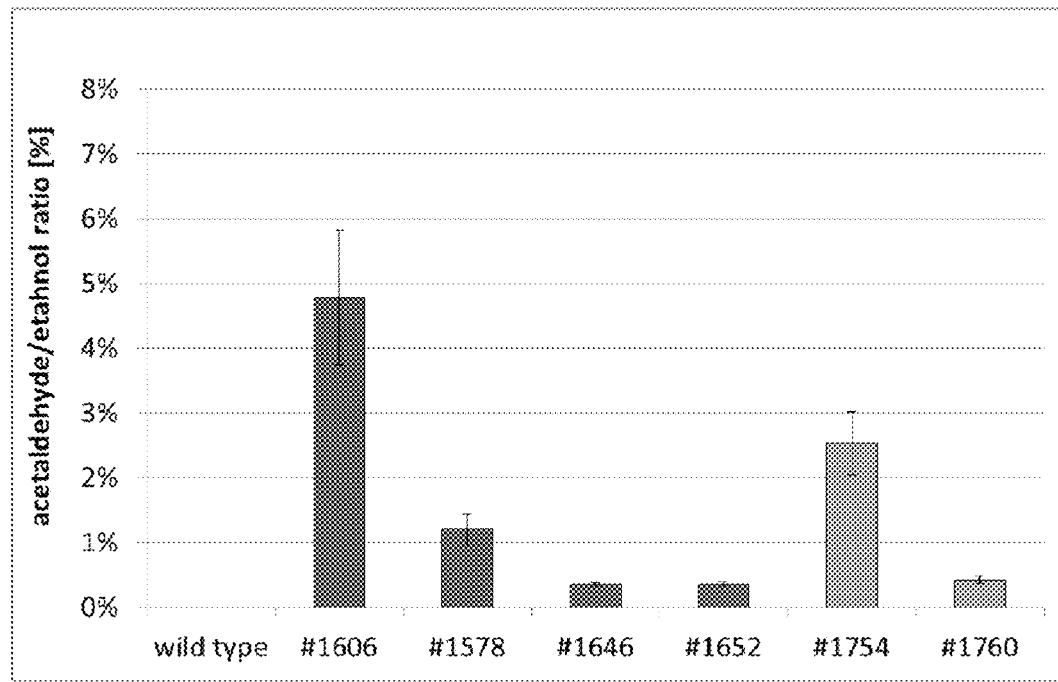

FIGS. 18A and 18B show the results of relative ethanol production rates per $OD_{750\ nm}$ (FIG. 18A) and acetaldehyde/ethanol ratios (FIG. 18B) of various metabolically enhanced Cyanobacterium sp. PTA-13311 hybrids harboring different ethanologenic plasmids under inducing conditions in comparison to the wild type Cyanobacterium sp. PTA-13311.

Figure 19A:
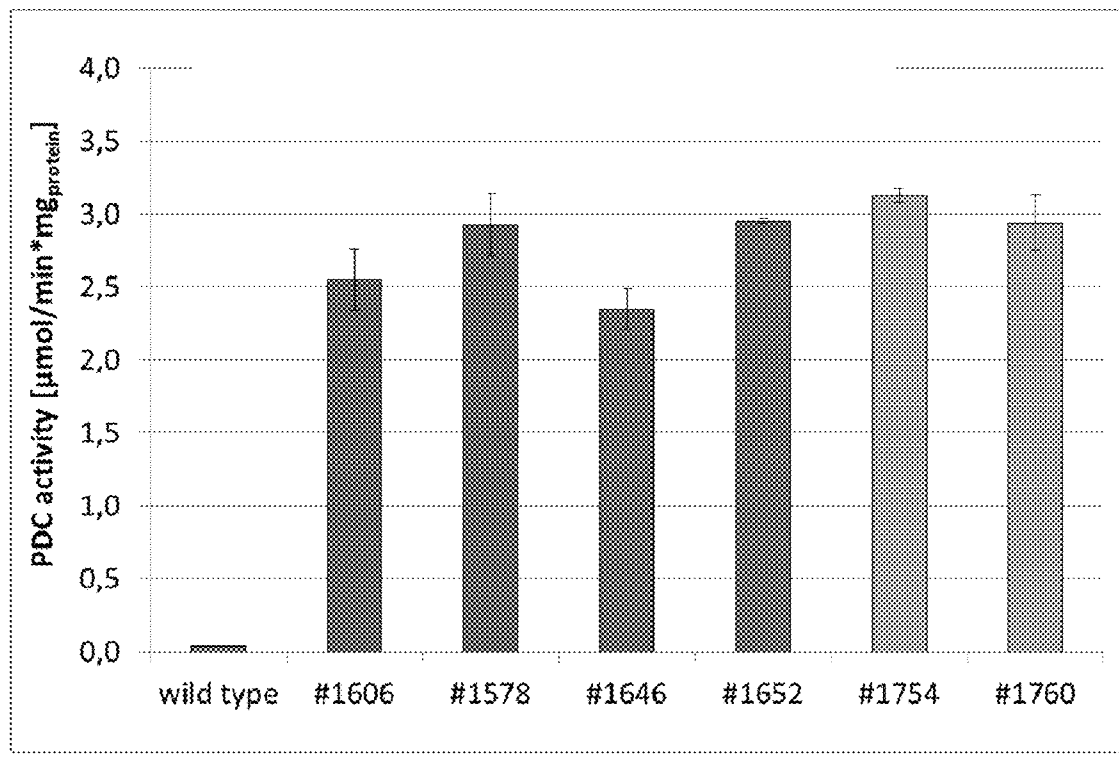
Figure 19B:
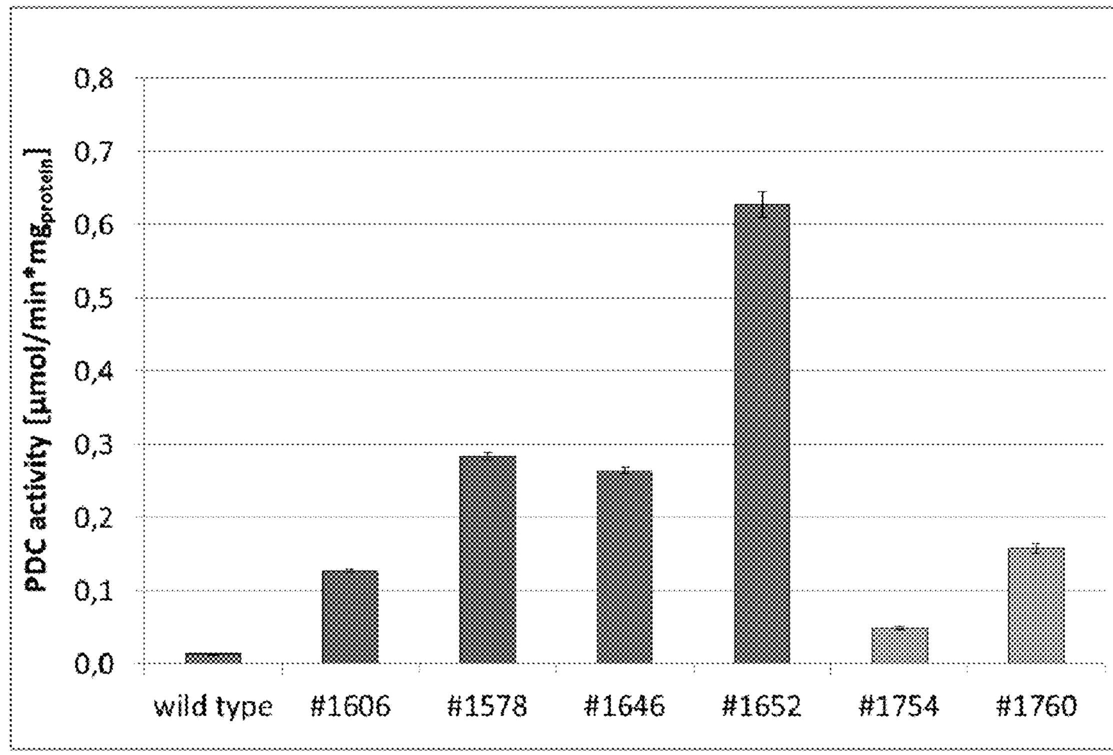

FIGS. 19A and 19B show the results of Pdc (FIG. 19A) and Adh (FIG. 19B) activity measurements of various metabolically enhanced Cyanobacterium sp. PTA-13311 hybrids harboring different ethanologenic plasmids under inducing conditions in comparison to the wild type Cyanobacterium sp. PTA-13311.

Figure 20A:
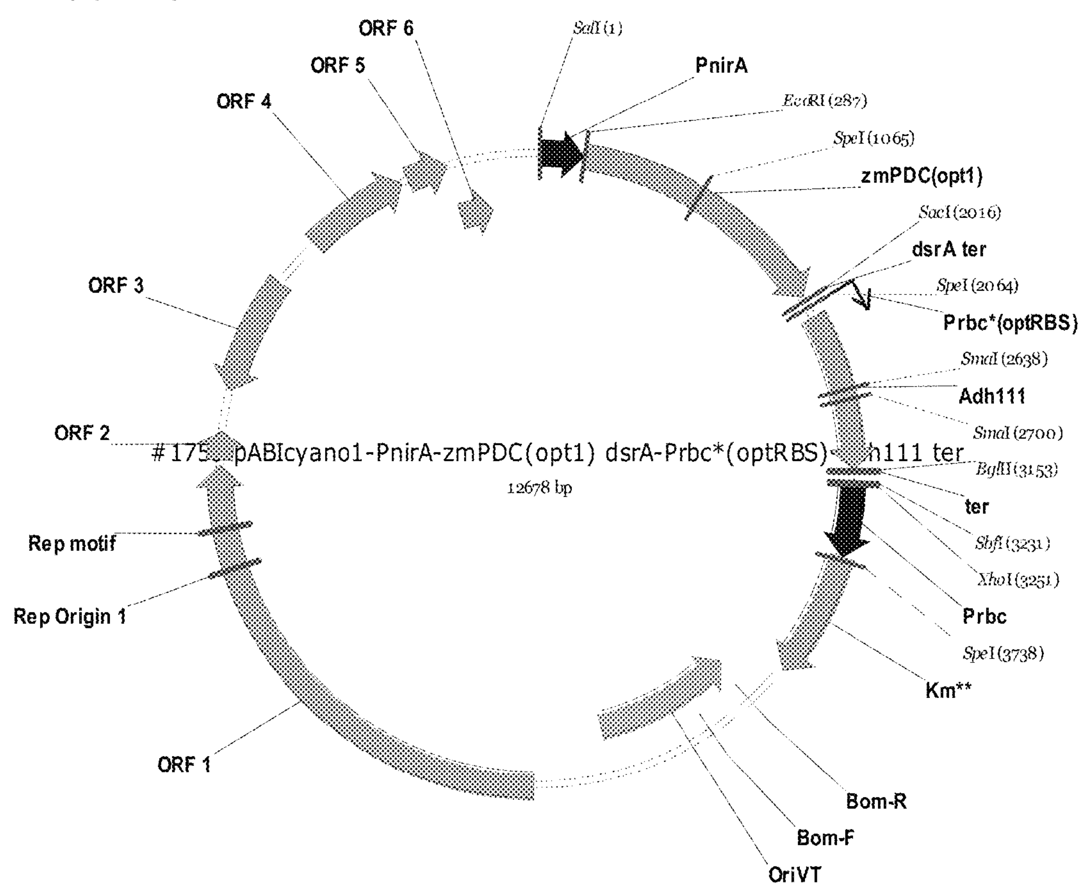

FIG. 20A is a map of plasmid construct #1753 with SEQ ID NO:46. #1753 is a derivative of TK293 containing the PnirA promoter upstream of a codon improved zmPDC gene and the Prbc promoter with optimized RBS upstream of an adh gene from *Lyngbya* sp. encoding the Adh enzyme with SEQ ID NO:1.

Figure 20B:
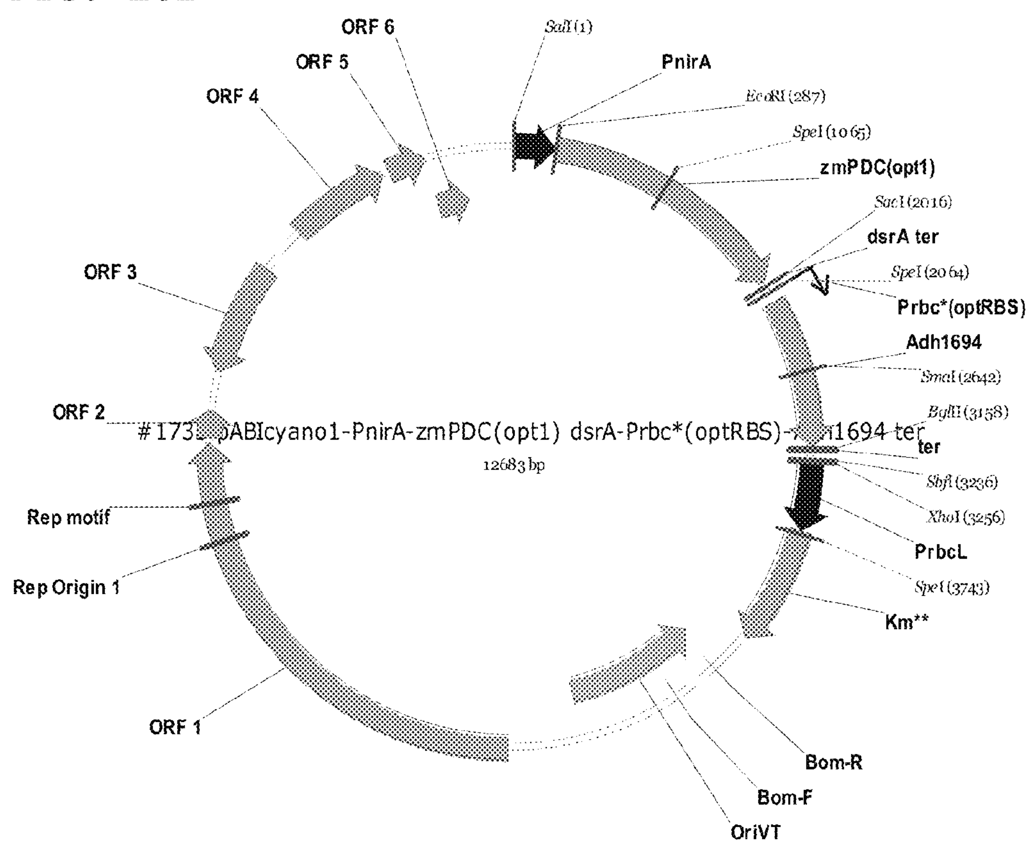

FIG. 20B is a map of plasmid construct #1735 with SEQ ID NO:47. #1735 is a derivative of TK293 containing the PnirA promoter upstream of a codon improved zmPDC gene and the Prbc promoter with optimized RBS upstream of an adh gene from *Arthrospira platensis* encoding the Adh enzyme with SEQ ID NO:2.

Figure 21A:
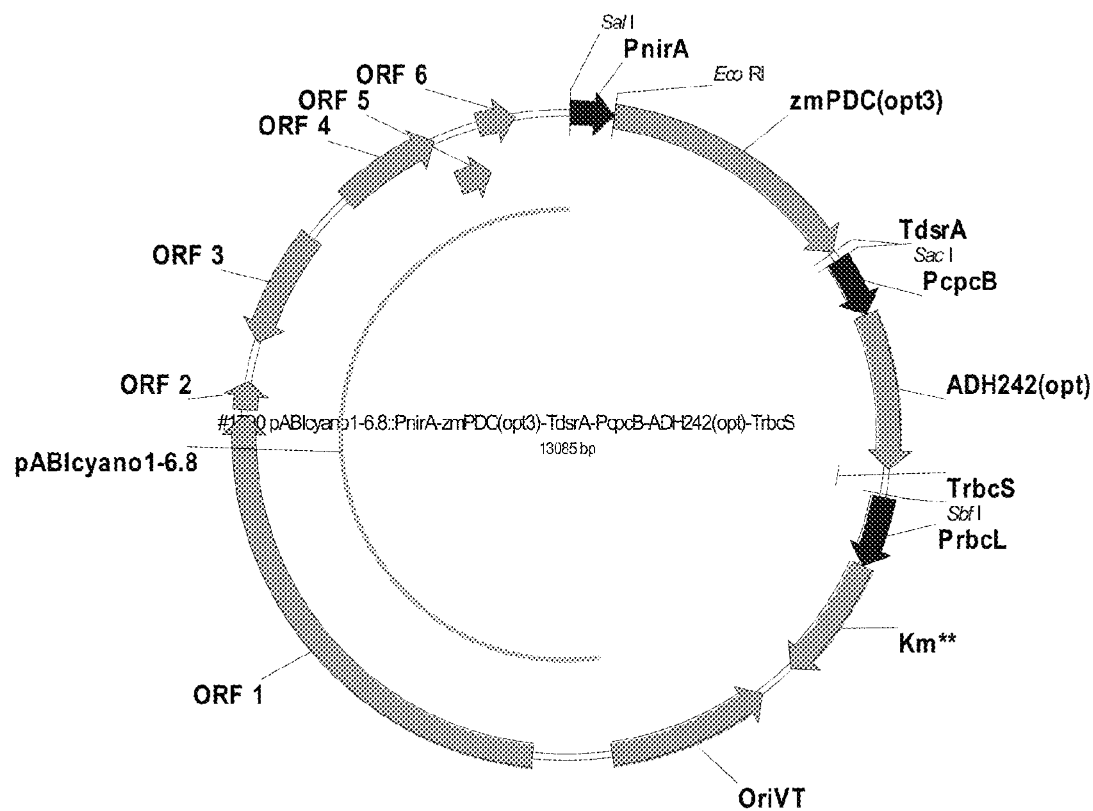

FIG. 21A is a map of plasmid construct #1790 with SEQ ID NO:71. #1790 is a derivative of TK293 containing the PnirA promoter upstream of a codon improved zmPDC gene and the PcpcB promoter upstream of an adh gene from *Arthrospira platensis* encoding the Adh enzyme with SEQ ID NO:2.

Figure 21B:
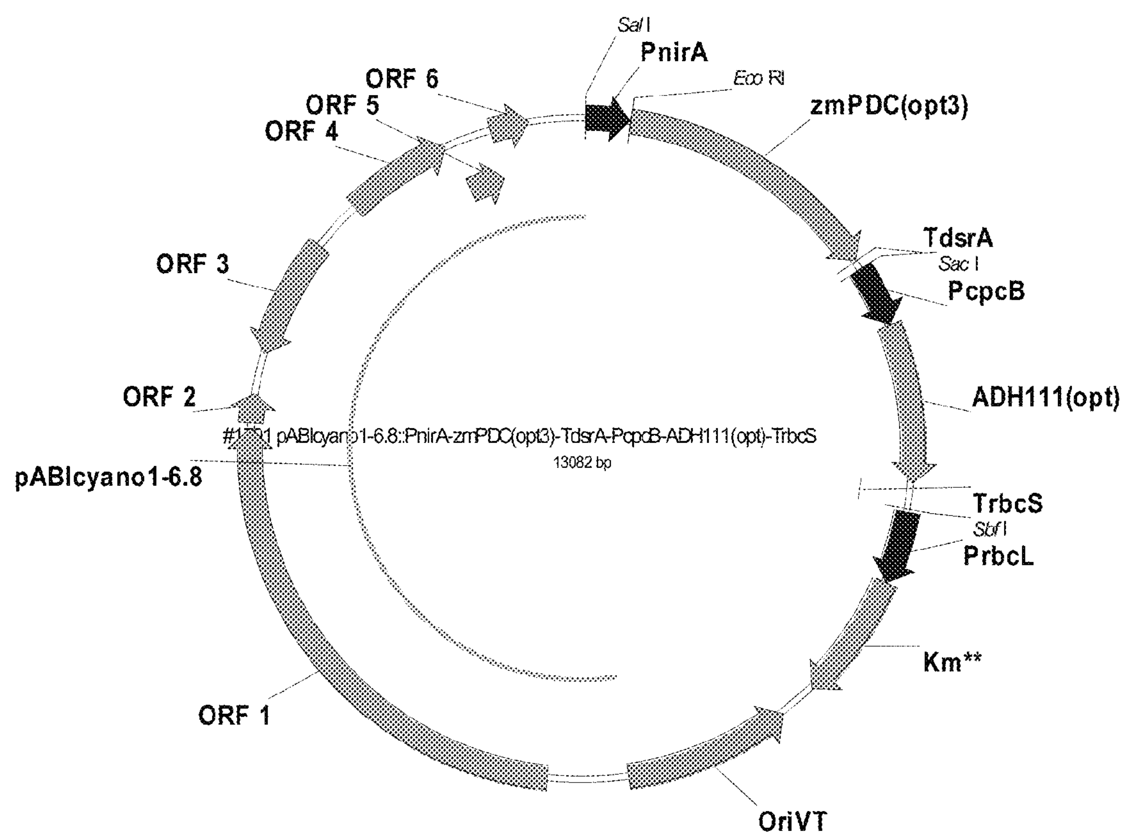

FIG. 21B is a map of plasmid construct #1791 with SEQ ID NO:72. #1791 is a derivative of TK293 containing the PnirA promoter upstream of a codon improved zmPDC gene and the PcpcB promoter upstream of an adh gene from *Lyngbya* sp. encoding the Adh enzyme with SEQ ID NO:1.

Figure 22A:
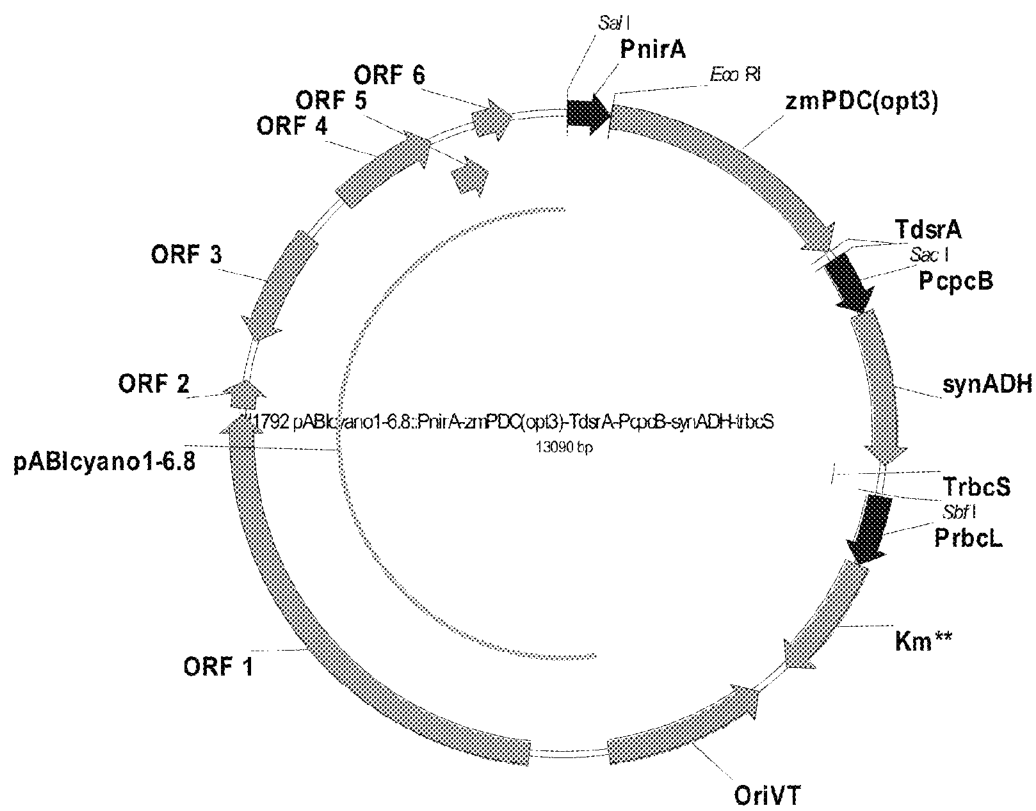

FIG. 22A is a map of plasmid construct #1792 with SEQ ID NO:73. #1792 is a derivative of TK293 containing the PnirA promoter upstream of a codon improved zmPDC gene and the PcpcB promoter upstream of a synADH gene from *Synechocystis* sp. encoding the Adh enzyme with SEQ ID NO:26.

Figure 22B:
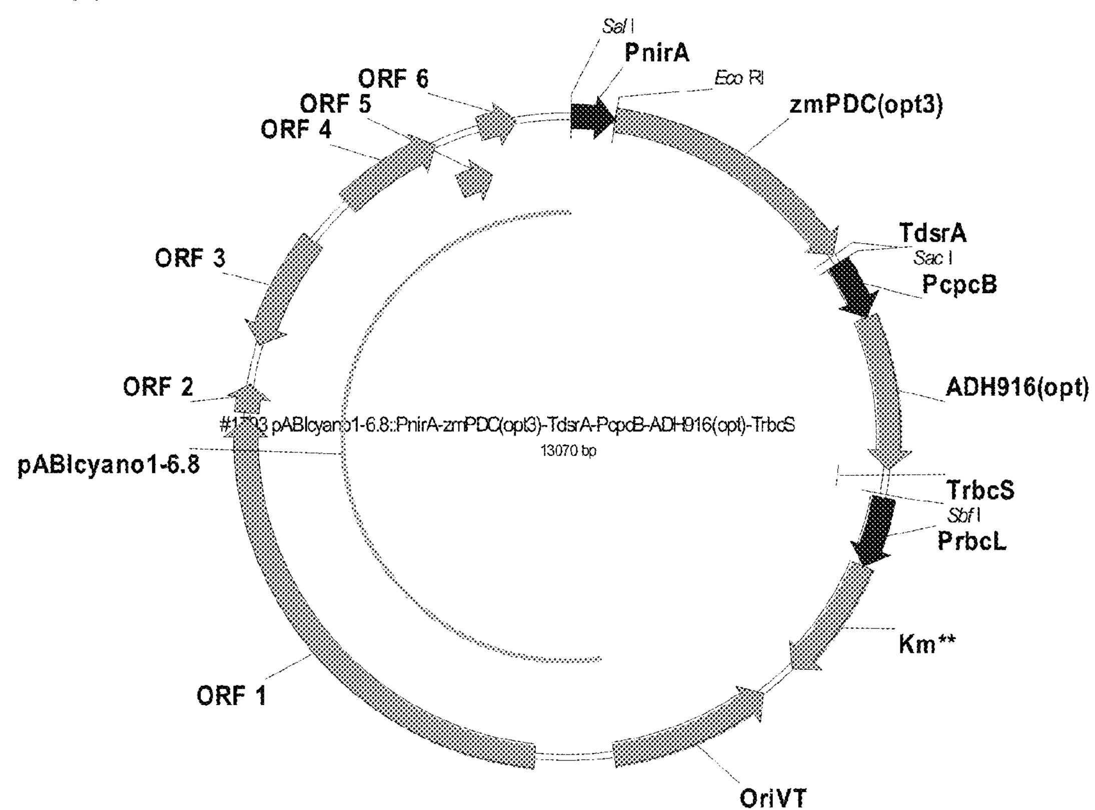

FIG. 22B is a map of plasmid construct #1793 with SEQ ID NO:74. #1793 is a derivative of TK293 containing the PnirA promoter upstream of a codon improved zmPDC gene and the PcpcB promoter upstream of an adh gene from *Synechococcus* sp. encoding the Adh enzyme with SEQ ID NO:6.

Figure 23A:
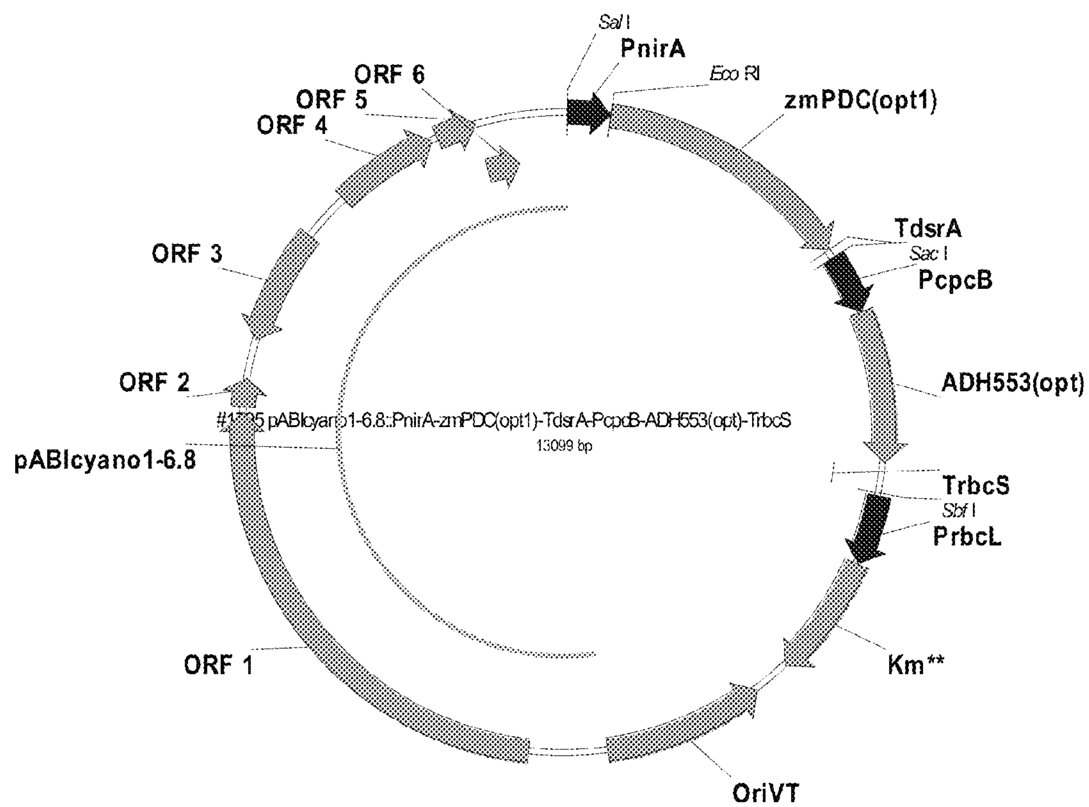

FIG. 23A is a map of plasmid construct #1795 with SEQ ID NO:75. #1795 is a derivative of TK293 containing the PnirA promoter upstream of a codon improved zmPDC gene and the PcpcB promoter upstream of an adh gene from *Cyanothece* sp. encoding the Adh enzyme with SEQ ID NO:3.

Figure 23B:
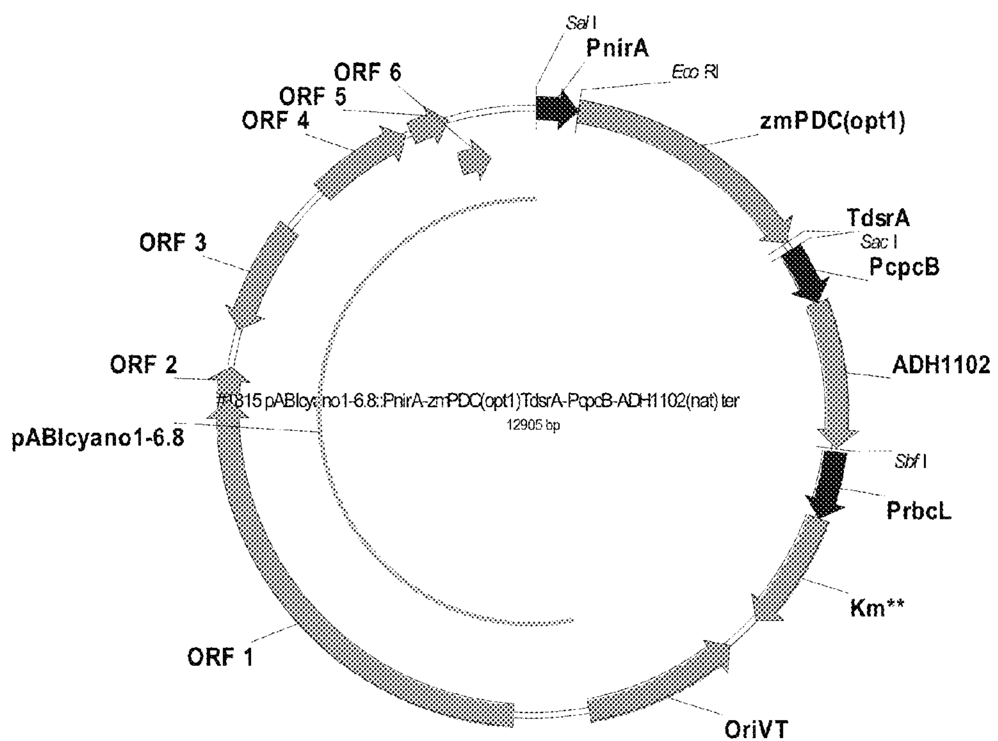

FIG. 23B is a map of plasmid construct #1815 with SEQ ID NO:76. #1815 is a derivative of TK293 containing the PnirA promoter upstream of a codon improved zmPDC gene and the PcpcB promoter upstream of an adh gene from *Chroococcidiopsis* sp. encoding the Adh enzyme with SEQ ID NO:9.

Figure 24A:
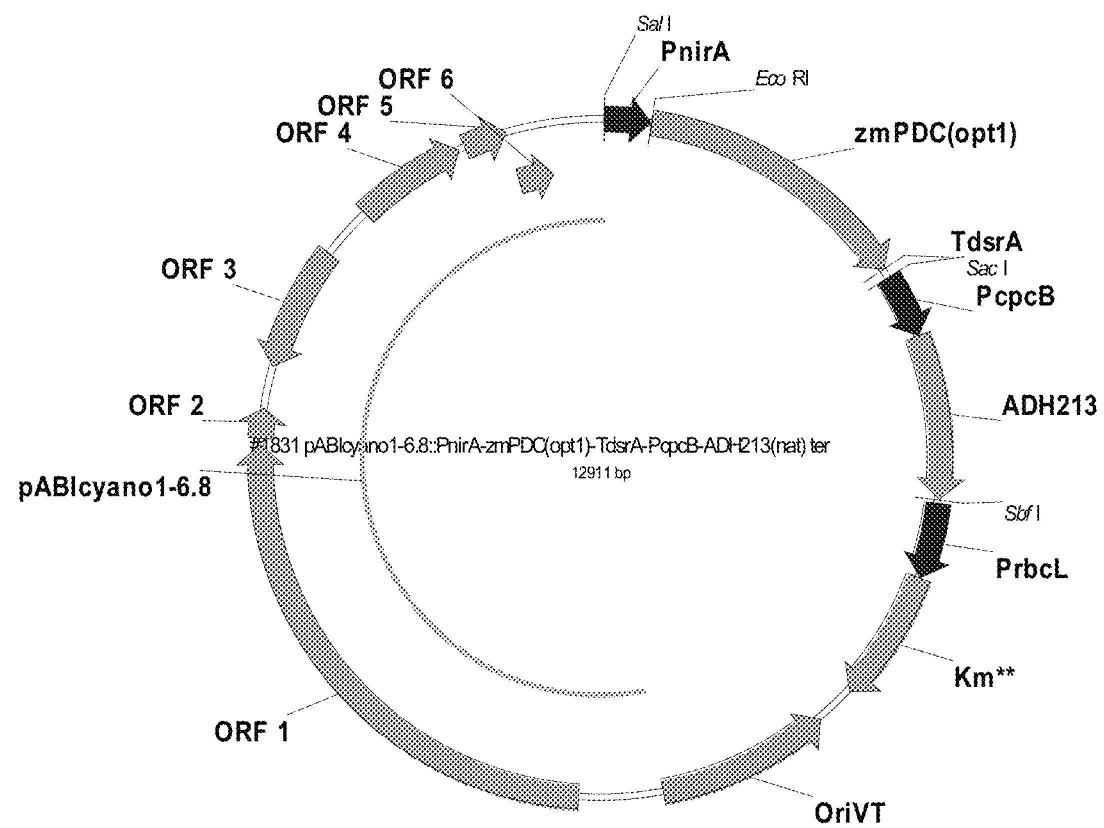

FIG. 24A is a map of plasmid construct #1831 with SEQ ID NO:77. #1831 is a derivative of TK293 containing the PnirA promoter upstream of a codon improved zmPDC gene and the PcpcB promoter upstream of an adh gene from *Synechococcus* sp. encoding the Adh enzyme with SEQ ID NO:5.

Figure 24B:
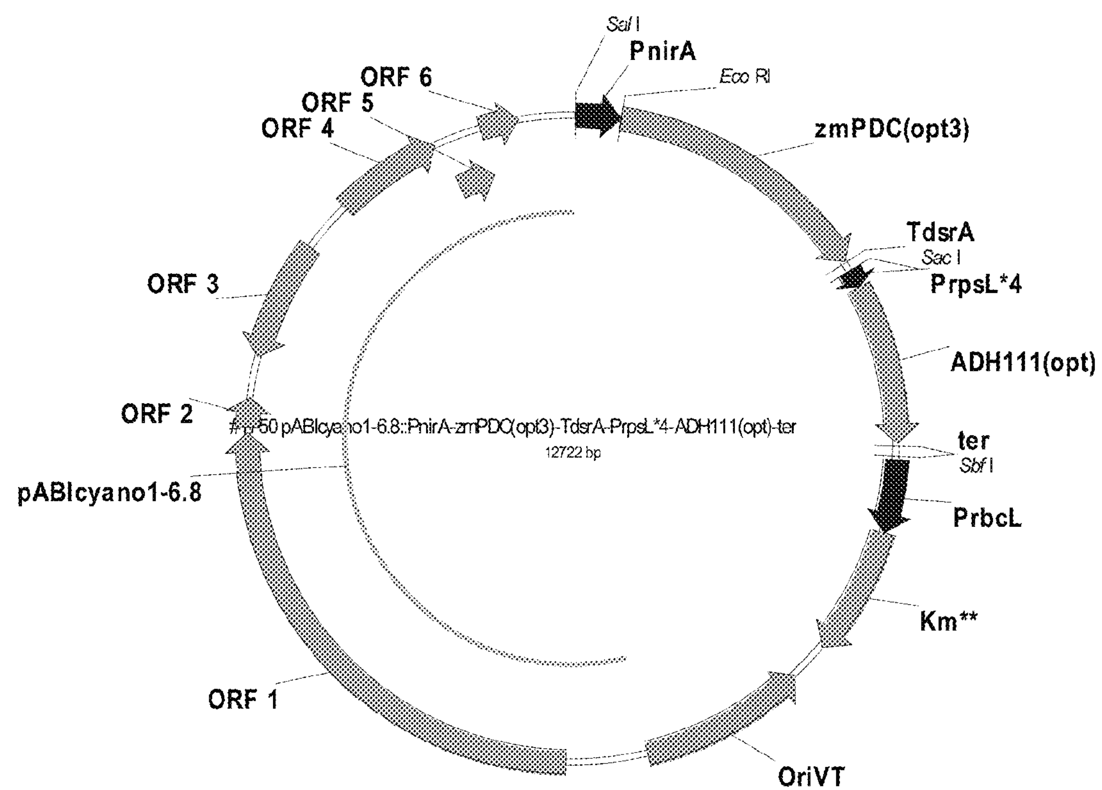

FIG. 24B is a map of plasmid construct #1750 with SEQ ID NO:78. #1750 is a derivative of TK293 containing the PnirA promoter upstream of a codon improved zmPDC gene and the PcpcB promoter upstream of an codon improved adh gene from *Lyngbya* sp. encoding the Adh enzyme with SEQ ID NO:1.

Figure 25A:
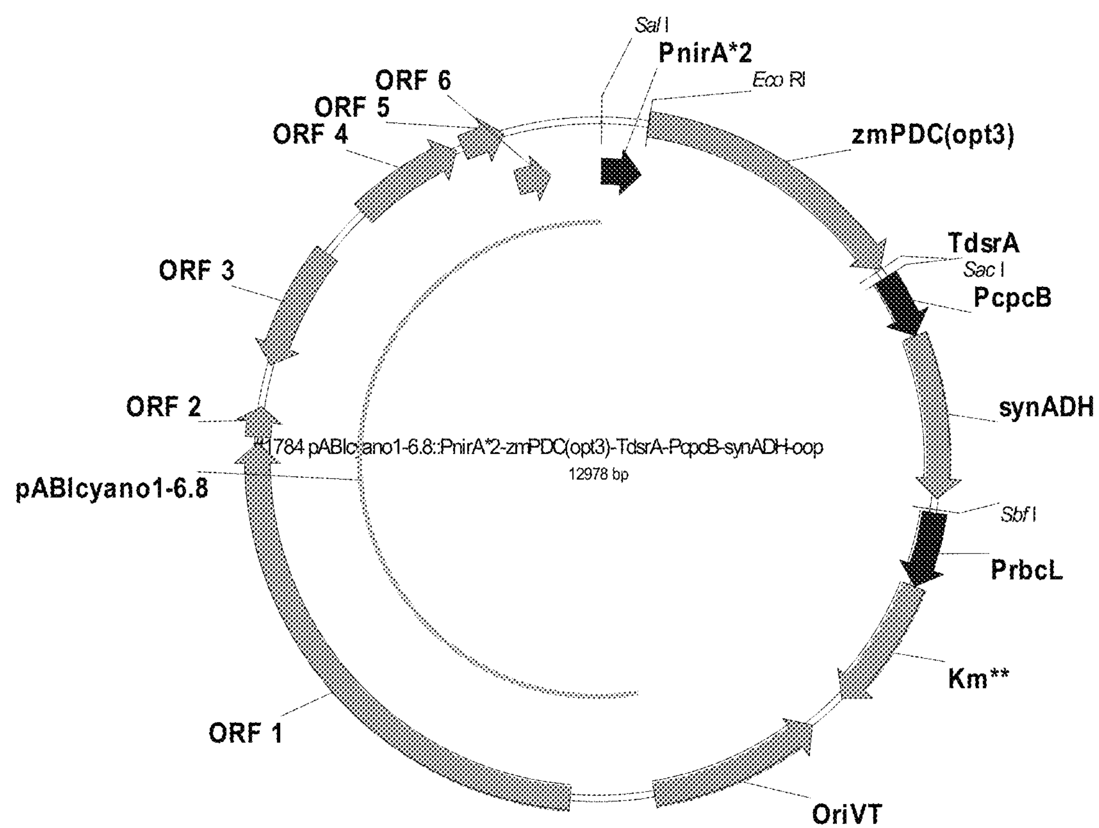

FIG. 25A is a map of plasmid construct #1784 with SEQ ID NO:79. #1784 is a derivative of TK293 containing the PnirA promoter with optimized RBS upstream of a codon improved zmPDC gene and the PcpcB promoter upstream of an adh gene from *Synechocystis* PCC6803 encoding the Adh enzyme with SEQ ID NO:26.

Figure 25B:
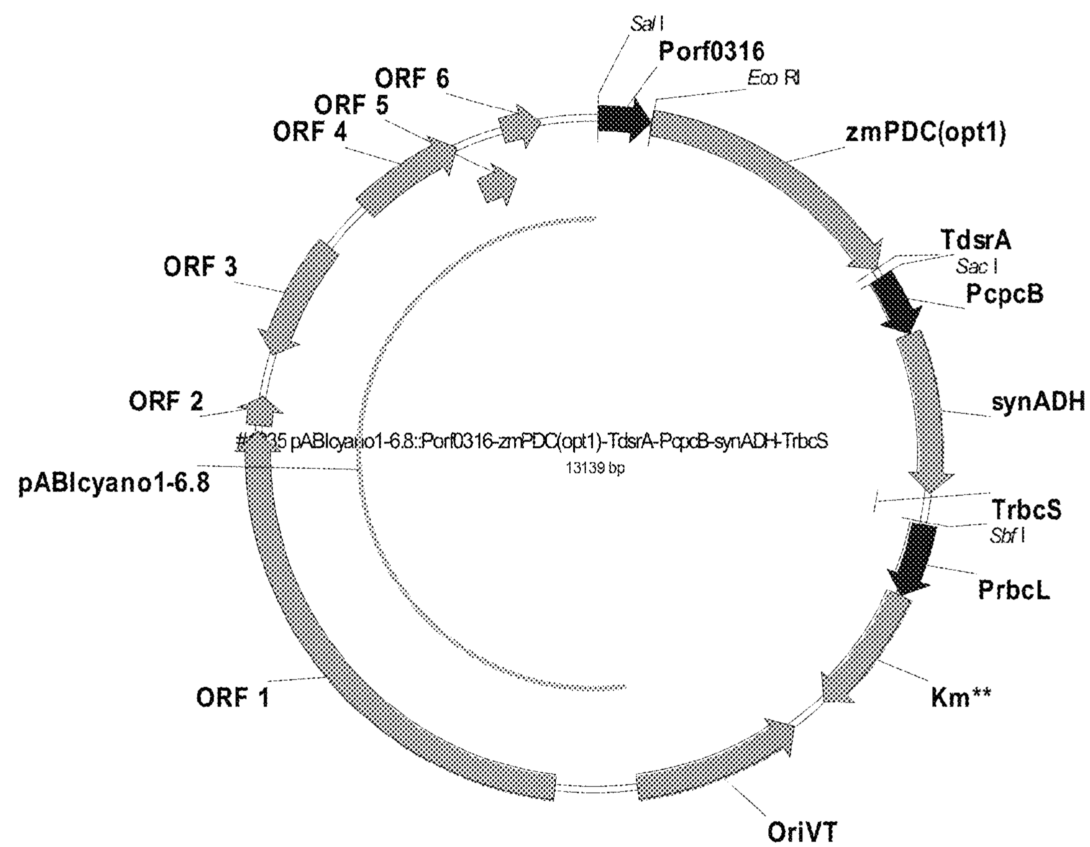

FIG. 25B is a map of plasmid construct #1835 with SEQ ID NO:80. #1835 is a derivative of TK293 containing the Porf0316 promoter upstream of a codon improved zmPDC gene and the PcpcB promoter upstream of an adh gene from *Synechocystis* PCC6803 encoding the Adh enzyme with SEQ ID NO:26.

Figure 26A:
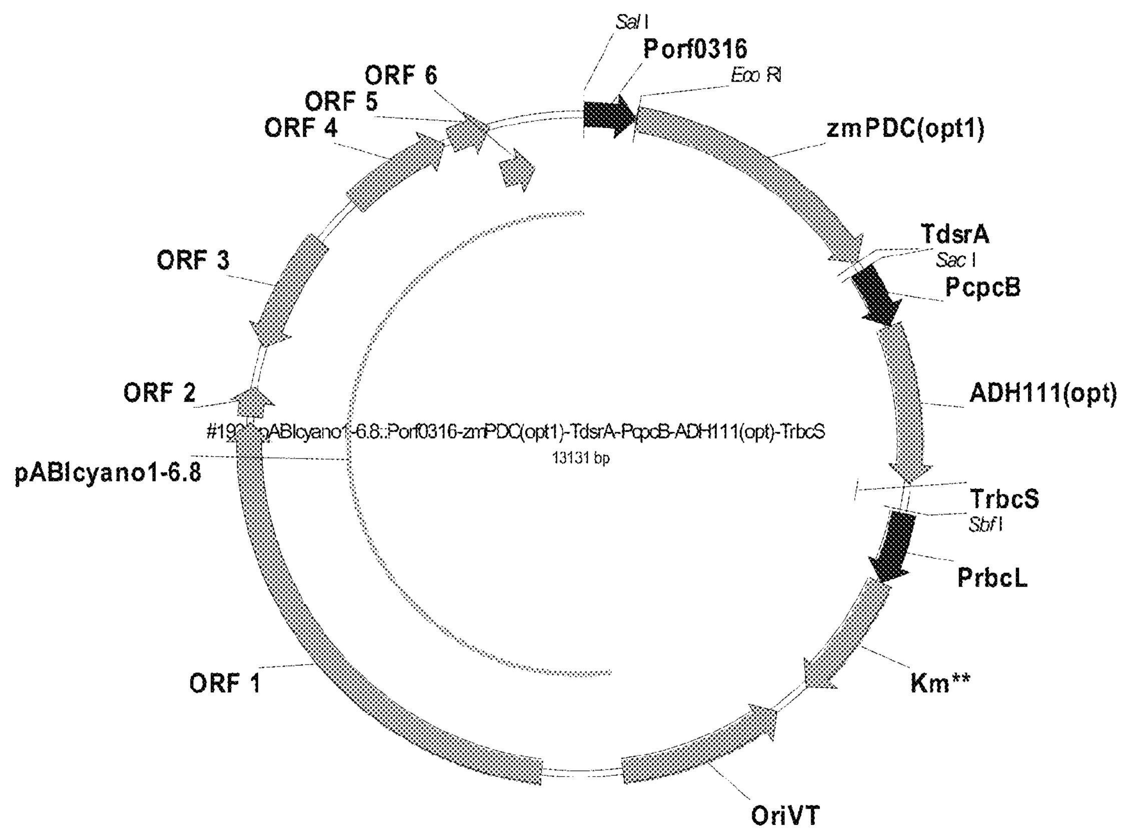

FIG. 26A is a map of plasmid construct #1938 with SEQ ID NO:81. #1938 is a derivative of TK293 containing the Porf0316 promoter upstream of a codon improved zmPDC gene and the PcpcB promoter upstream of an adh gene from *Lyngbya* sp. encoding a codon improved variant of the Adh enzyme with SEQ ID NO:1.

Figure 26B:
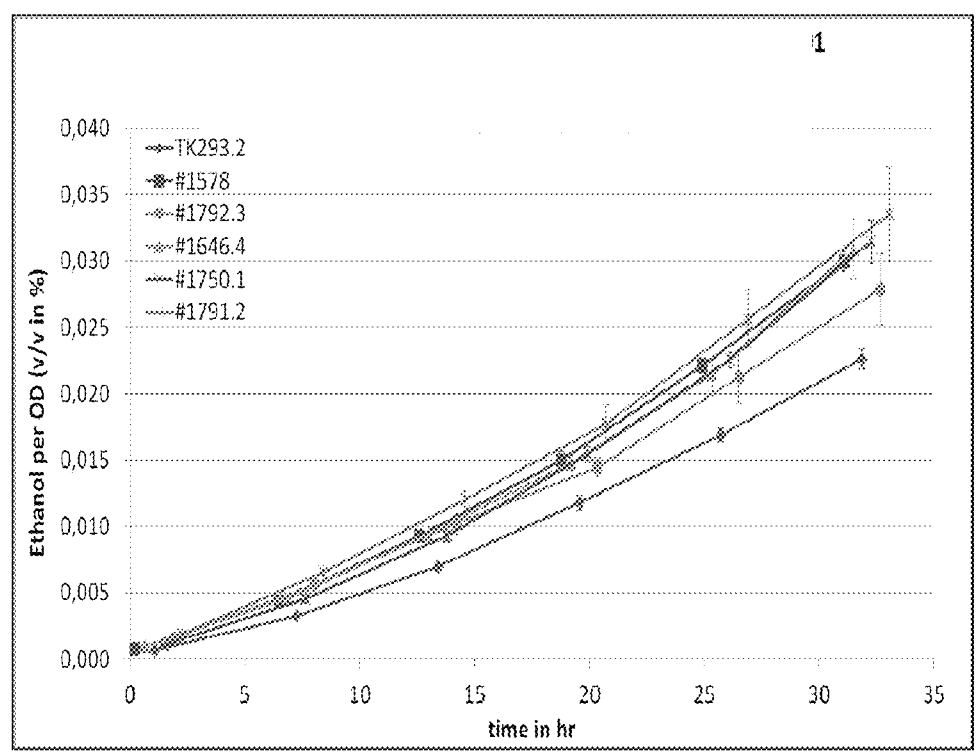

FIG. 26B shows a graphical evaluation of normalized ethanol accumulation (% v/v) per cell density over time for Cyanobacterium sp. PTA-13311 hybrids harboring the ethanologenic plasmids TK293, #1578, #1792, #1646, #1750 and #1791 under inducing conditions. Data represent mean values and standard deviations of four replicates.

Figure 27A:
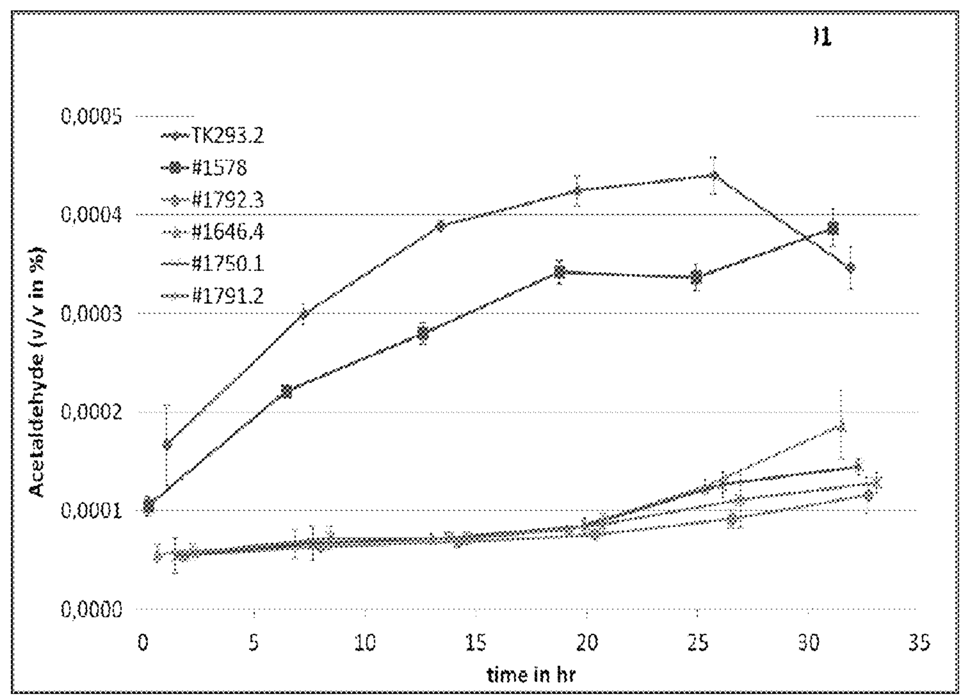

FIG. 27A shows a graphical evaluation of aldehyde accumulation (% v/v) over time for Cyanobacterium sp. PTA-13311 hybrids harboring the ethanologenic plasmids TK293, #1578, #1792, #1646, #1750 and #1791 under inducing. Data represent mean values and standard deviations of four replicates.

Figure 27B:
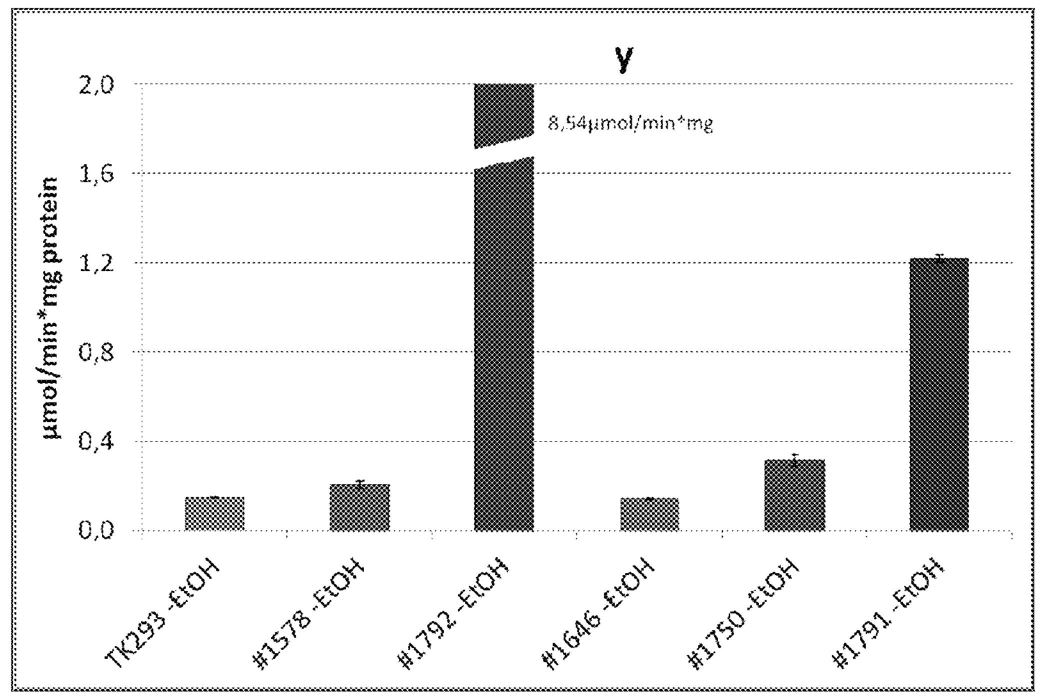

FIG. 27B shows a graphical evaluation of Adh activity in μmol per min and mg protein for Cyanobacterium sp. PTA-13311 hybrids harboring the ethanologenic plasmids TK293, #1578, #1792, #1646, #1750 and #1791 under inducing conditions. Data represent mean values and standard deviations of four replicates.

Figure 28A:
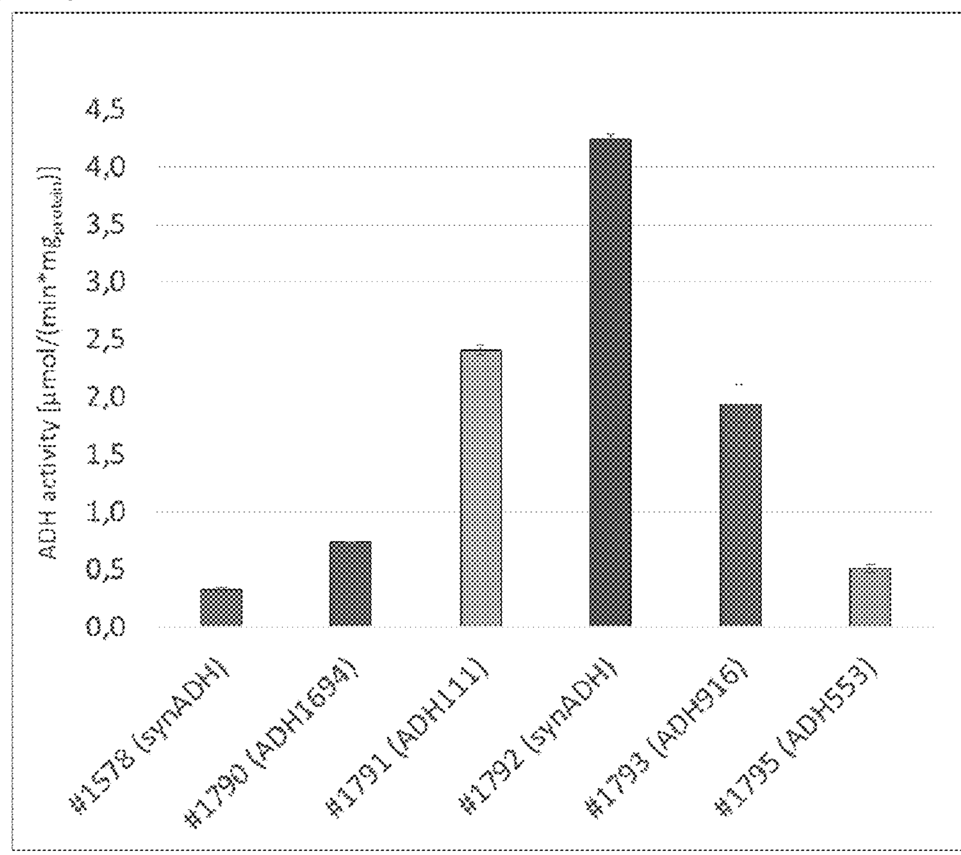

FIG. 28A shows a graphical evaluation of Adh activity in μmol per min and mg protein for Cyanobacterium sp. PTA-13311 hybrids harboring the ethanologenic plasmids #1578, #1790, #1791, #1792, #1793, and #1795 under inducing conditions. Data represent mean values and standard deviations of four replicates.

Figure 28B:
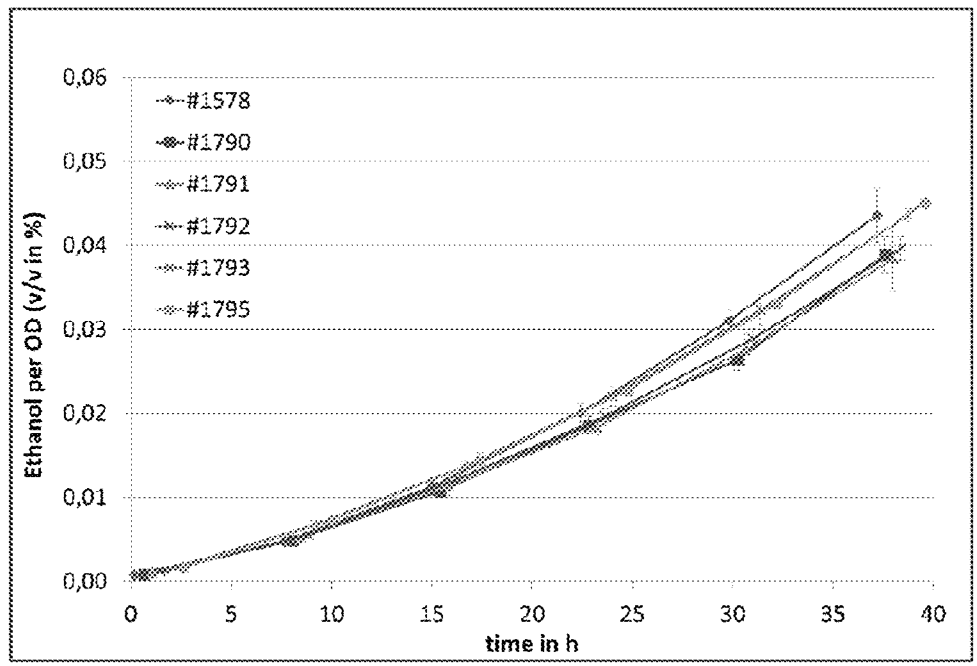

FIG. 28B shows a graphical evaluation of normalized ethanol accumulation (% v/v) per cell density over time for Cyanobacterium sp. PTA-13311 hybrids harboring the ethanologenic plasmids #1578, #1790, #1791, #1792, #1793, and #1795 under inducing conditions. Data represent mean values and standard deviations of four replicates.

Figure 29A:
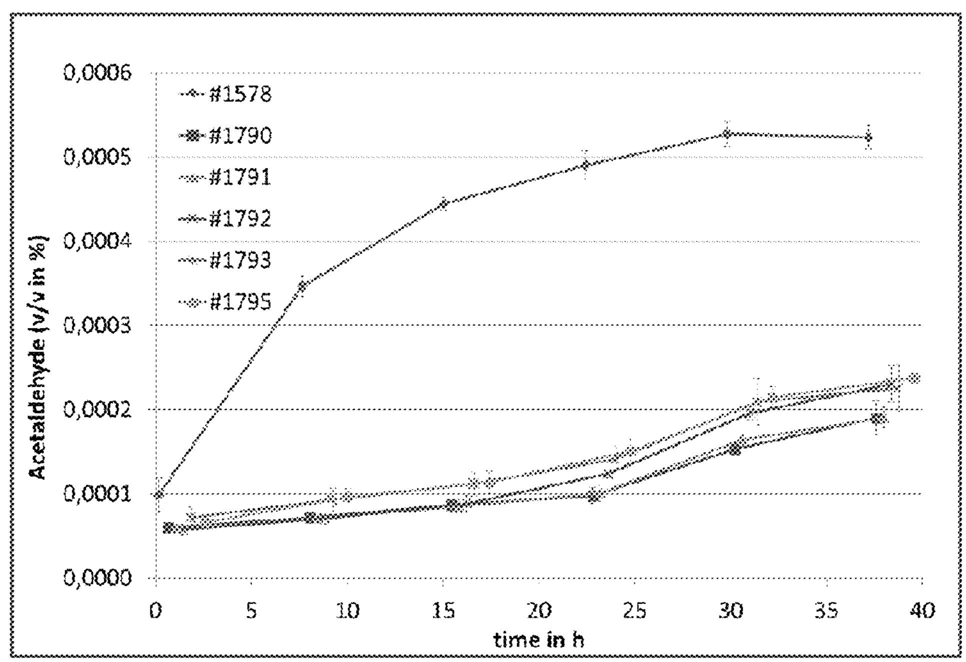

FIG. 29A shows a graphical evaluation of acetaldehyde accumulation (% v/v) over time for Cyanobacterium sp. PTA-13311 hybrids harboring the ethanologenic plasmids #1578, #1790, #1791, #1792, #1793, and #1795 under inducing conditions under inducing conditions. Data represent mean values and standard deviations of four replicates.

Figure 29B:
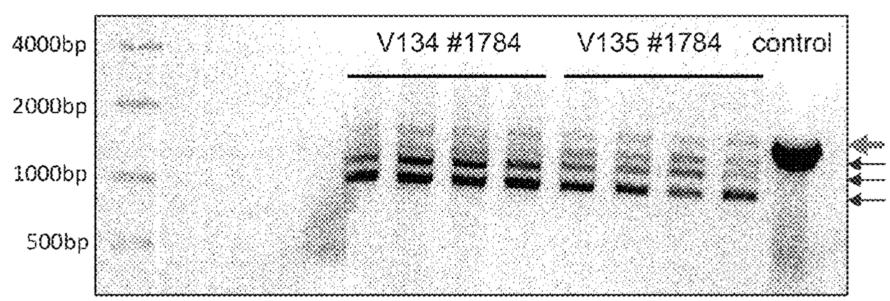

FIG. 29B shows a digital image of an agarose gel after electrophoretic analysis of PCR products from specific amplification of the synAdh gene in the plasmid #1784. Lanes V134 and V135: PCR products obtained after recovery of #1784 from different cultivations. Control: PCR products obtained from #1784 before cultivation. The top bold arrow shows the band of the full-length synAdh product. The thin arrows show different smaller sized synAdh amplificates.

Figure 30A:
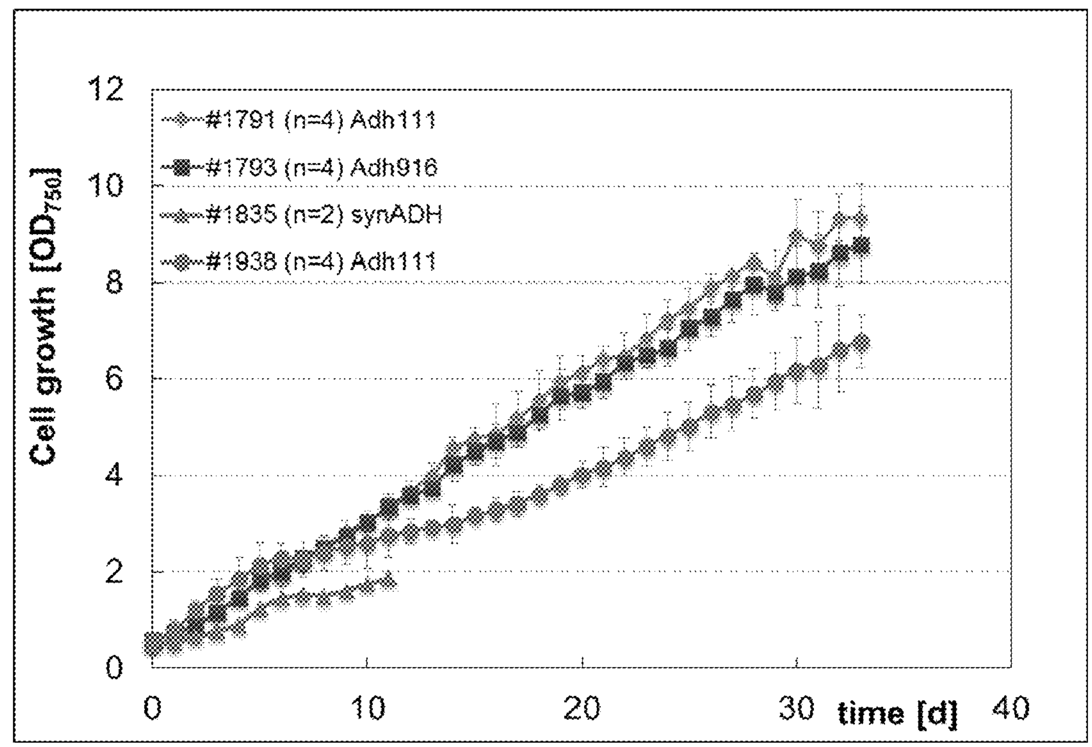

FIG. 30A shows a graphical evaluation of cell growth over time of cultures of Cyanobacterium sp. PTA-13311 hybrids harboring the ethanologenic plasmids #1791, #1793, #1835 and #1938 under inducing conditions. Data represent mean values and standard deviations of four replicates.

Figure 30B:
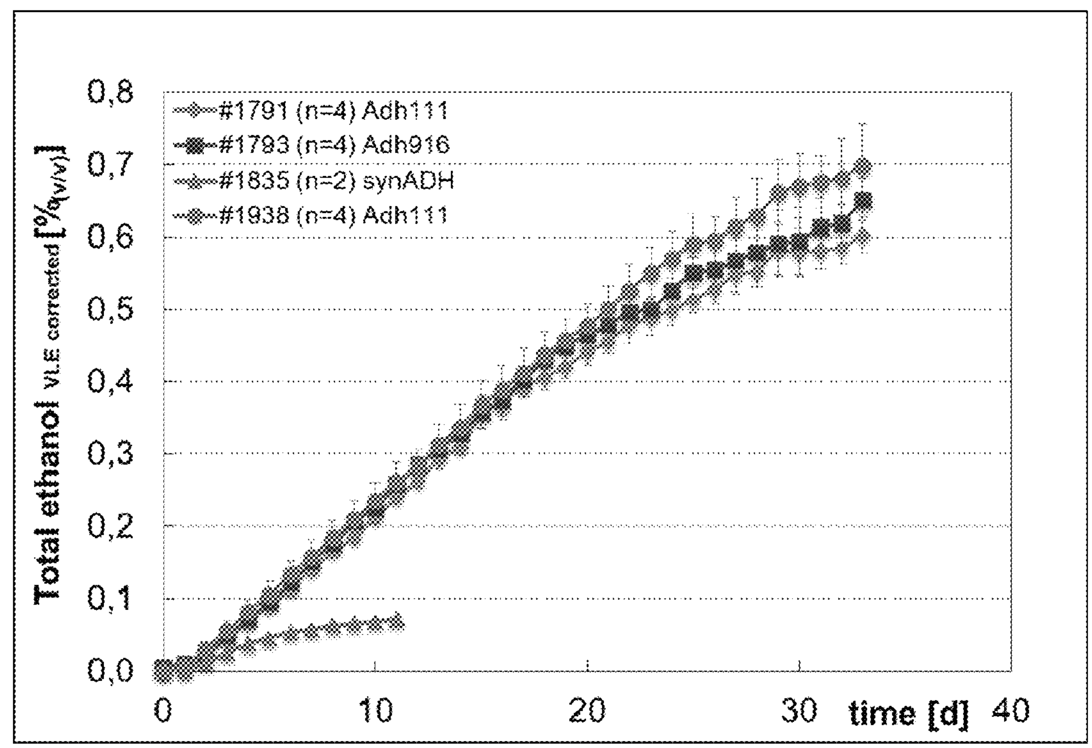

FIG. 30B shows a graphical evaluation of total ethanol production in % v/v (vapour loss-corrected) over cultivation time of Cyanobacterium sp. PTA-13311 hybrids harboring the ethanologenic plasmids #1791, #1793, #1835 and #1938 under inducing conditions. Data represent mean values and standard deviations of four replicates.

Figure 31A:
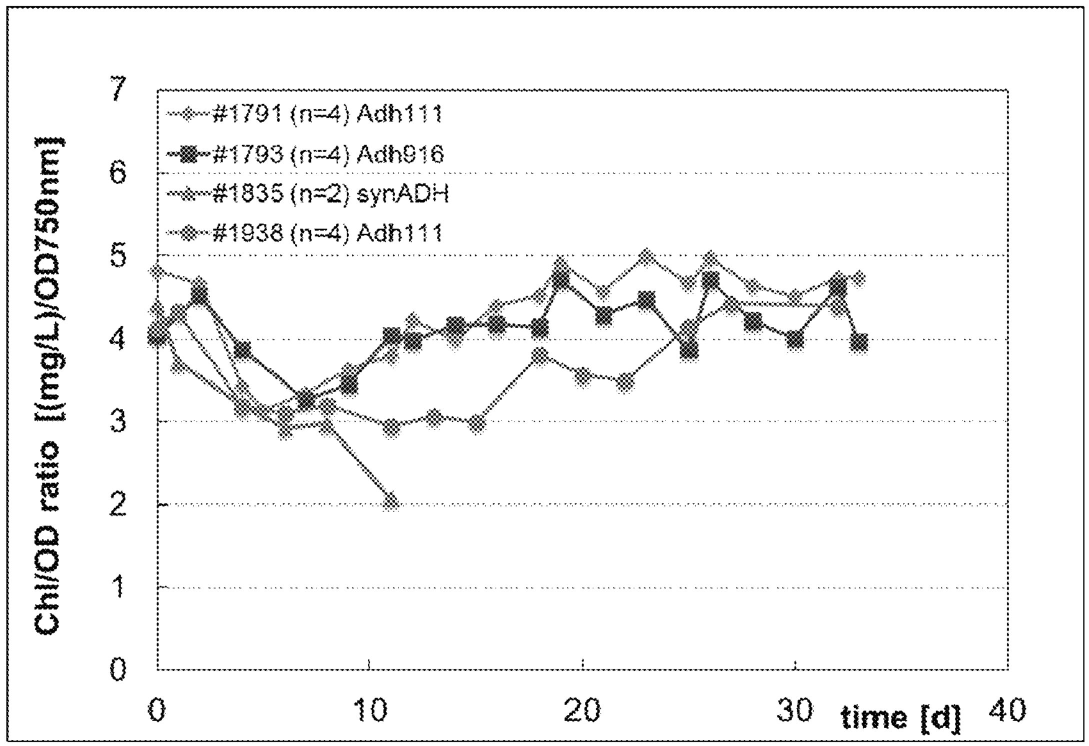

FIG. 31A shows a graphical evaluation of the chlorophyll/optical density ratio in (mg/L) per OD at 750 nm over cultivation time of Cyanobacterium sp. PTA-13311 hybrids harboring the ethanologenic plasmids #1791, #1793, #1835 and #1938 under inducing conditions. Data represent mean values and standard deviations of four replicates.

Figure 31B:
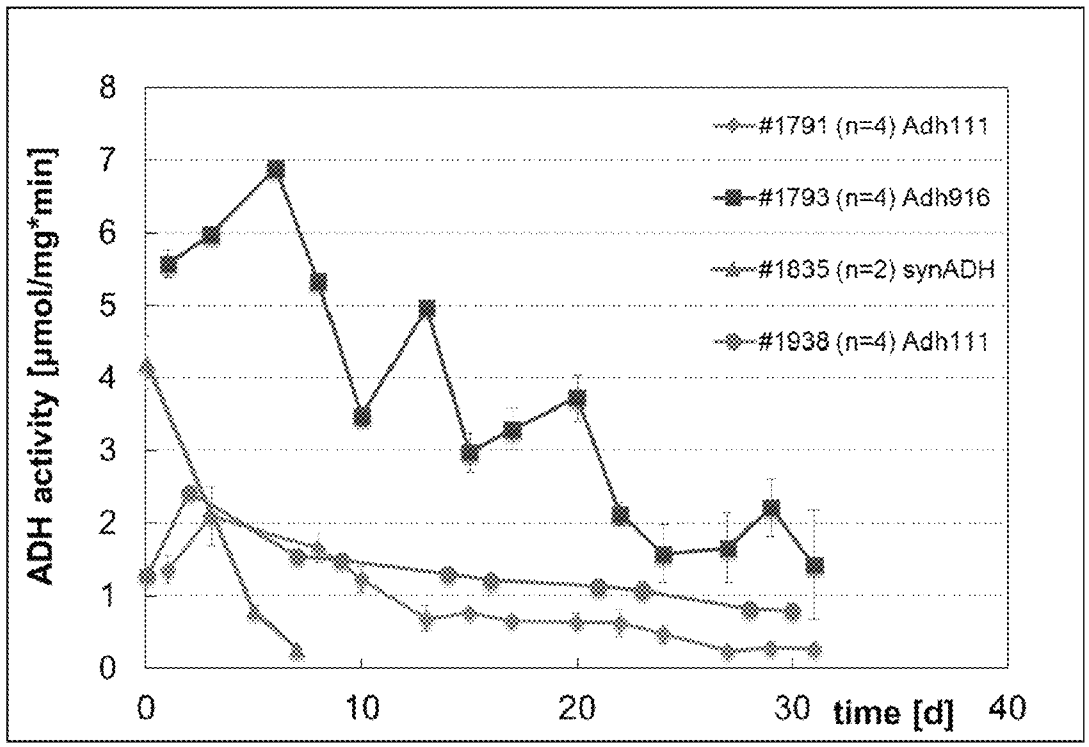

FIG. 31B shows a graphical evaluation of Adh activity in μmol per mg and min over cultivation time for Cyanobacterium sp. PTA-13311 hybrids harboring the ethanologenic plasmids #1791, #1793, #1835 and #1938 under inducing conditions. Data represent mean values and standard deviations of four replicates.

Figure 32A:
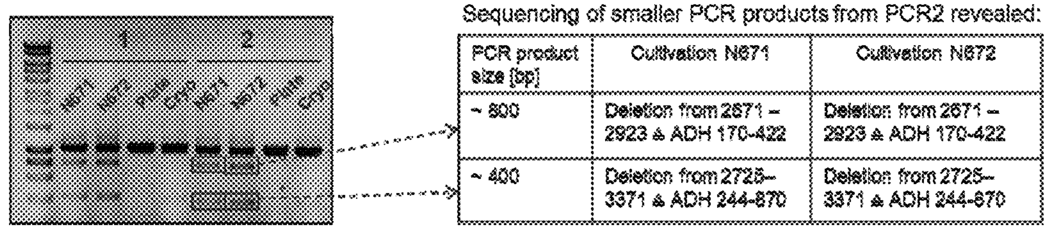

FIG. 32A shows a digital image of an agarose gel after electrophoretic analysis of PCR products from specific amplification of the synAdh gene in the plasmid #1835. Lanes N671 and N672: PCR products obtained after recovery of #1835 from two independent cultivations of the hybrid harboring #1835. Plate and Cryo: PCR products obtained from the strain harboring #1835 at different stages before cultivations N671 and N672 were inoculated with said strain. Dashed arrows representatively identify bands of specific synAdh amplificates with deletions of about 800 bp and about 400 bp.

Figure 32B:
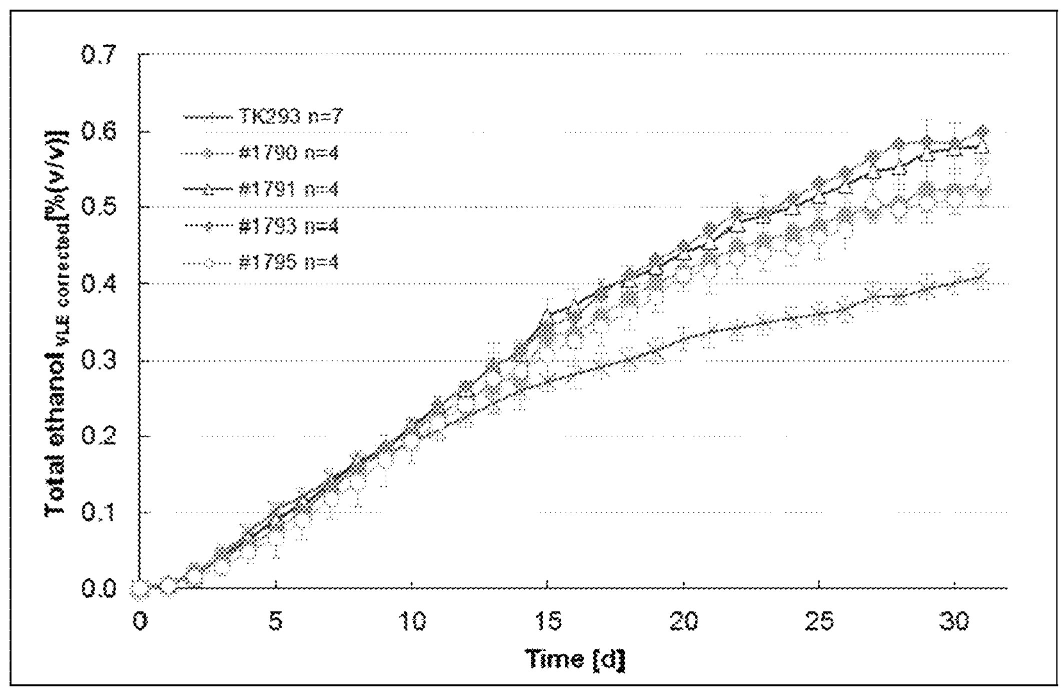

FIG. 32B shows a graphical evaluation of total ethanol production in % v/v (vapour loss-corrected) over cultivation time of Cyanobacterium sp. PTA-13311 hybrids harboring the ethanologenic plasmids TK293, #1790, #1791, #1793 and #1795 under inducing conditions. Data represent mean values and standard deviations of seven or four replicates, respectively.

BRIEF DESCRIPTION OF THE SEQUENCES

SEQ ID NO:1 is an amino acid sequence of an alcohol dehydrogenase enzyme from *Lyngbya* sp.

SEQ ID NO:2 is an amino acid sequence of an alcohol dehydrogenase enzyme from *Arthrospira platensis SEQ ID NO:*3 is an amino acid sequence of an alcohol dehydrogenase enzyme from *Cyanothece* sp.

SEQ ID NO:4 is an amino acid sequence of an alcohol dehydrogenase enzyme from *Synechococcus* sp.

SEQ ID NO:5 is an amino acid sequence of an alcohol dehydrogenase enzyme from *Synechococcus* sp.

SEQ ID NO:6 is an amino acid sequence of an alcohol dehydrogenase enzyme from *Synechococcus* sp.

SEQ ID NO:7 is an amino acid sequence of an alcohol dehydrogenase enzyme from *Chroococcidiopsis* sp.

SEQ ID NO:8 is an amino acid sequence of an alcohol dehydrogenase enzyme from *Arthronema africanum*

SEQ ID NO:9 is an amino acid sequence of an alcohol dehydrogenase enzyme from *Chroococcidiopsis* sp.

SEQ ID NO:10 is an amino acid sequence of an alcohol dehydrogenase enzyme from Cyanobacterium sp.

SEQ ID NO:11 is an amino acid sequence of an unnamed protein product of *Microcystis aeruginosa* PCC 7806 identified by Genbank Accession No. CAO90817.1

SEQ ID NO:12 is a nucleic acid sequence of a putative origin of replication from Cyanobacterium sp. accession no. PTA-13311

SEQ ID NO:13 is a nucleic acid sequence of a putative replication initiation factor from Cyanobacterium sp. accession no. PTA-13311

SEQ ID NO:14 is a nucleic acid sequence of an 6.8 kb endogenous plasmid isolated from Cyanobacterium sp. accession no. PTA-13311

SEQ ID NO:15 is a nucleic acid sequence of an alcohol dehydrogenase enzyme from *Lyngbya* sp.

SEQ ID NO:16 is a nucleic acid sequence of an alcohol dehydrogenase enzyme from *Arthrospira platensis*

SEQ ID NO:17 is a nucleic acid sequence of an alcohol dehydrogenase enzyme from *Cyanothece* sp.

SEQ ID NO:18 is a nucleic acid sequence of an alcohol dehydrogenase enzyme from *Synechococcus* sp.

SEQ ID NO:19 is a nucleic acid sequence of an alcohol dehydrogenase enzyme from *Synechococcus* sp.

SEQ ID NO:20 is a nucleic acid sequence of an alcohol dehydrogenase enzyme from *Synechococcus* sp.

SEQ ID NO:21 is a nucleic acid sequence of an alcohol dehydrogenase enzyme from *Chroococcidiopsis* sp.

SEQ ID NO:22 is a nucleic acid sequence of an alcohol dehydrogenase enzyme from *Arthronema africanum SEQ ID NO:*23 is a nucleic acid sequence of an alcohol dehydrogenase enzyme from *Chroococcidiopsis* sp.

SEQ ID NO:24 is a nucleic acid sequence of an alcohol dehydrogenase enzyme from Cyanobacterium sp.

SEQ ID NO:25 is a nucleic acid sequence of an unnamed protein product of *Microcystis aeruginosa* PCC 7806 identified by Genbank Accession No. CAO90817.1

SEQ ID NO:26 is an amino acid sequence of a state-of-the-art alcohol dehydrogenase enzyme from *Synechocystis* sp. PCC6803

SEQ ID NO:27 is a nucleotide sequence of plasmid TK293 pABIcyano1::PnirA-zmPDC(opt1)-PrpsL-synADH(opt1)_ter SEQ ID NO:28 is a nucleotide sequence of plasmid #1646 pABIcyano1::PnirA-zmPDC(opt1)dsrA-Prbc*(optRBS)-ADH111 (opt)_ter SEQ ID NO:29 is a nucleotide sequence of plasmid #1652 pABIcyano1::PnirA-zmPDC(opt1)dsrA-PrpsL*4-ADH111 (opt)_ter SEQ ID NO:30 is a nucleotide sequence of plasmid #1658 pABIcyano1::PnirA*2-zmPDC(opt3)dsrA-Prbc*(optRBS)-synADH_oop SEQ ID NO:31 is a nucleotide sequence of plasmid #1684 pABIcyano1::PnirA*2-zmPDC(opt3)dsrA-Prbc*(optRBS)-ADH111 (opt)_ter SEQ ID NO:32 is a nucleotide sequence of plasmid #1754 pABIcyano1::PnirA-zmPDC(opt1)dsrA-Prbc*(optRBS)-ADH1694(opt)_ter SEQ ID NO:33 is a nucleotide sequence of plasmid #1760 pABIcyano1::PnirA-zmPDC(opt3)dsrA-PrpsL*4-ADH1694(opt)_ter SEQ ID NO:34 is a nucleotide sequence of plasmid #1578 pABIcyano1::PnirA-zmPDC(opt3)dsrA-Prbc*(optRBS)-synADH_oop SEQ ID NO:35 is a nucleotide sequence of plasmid #1749 pABIcyano1::PnirA-zmPDC(opt3)dsrA-PrpsL*4-synADH_oop SEQ ID NO:36 is a nucleotide sequence of the PcpcB promoter endogenous to Cyanobacterium sp. accession no. PTA-13311

SEQ ID NO:37 is a nucleotide sequence of the PpetE promoter endogenous to Cyanobacterium sp. accession no. PTA-13311

SEQ ID NO:38 is a nucleotide sequence of the zinc inducible ziaR-PziaA promoter/regulator from *Synechocystis* PCC6803. The gene encoding the regulator ziaR runs in anti-sense direction to PziaA wherein the ziaR stop codon is tta of nucleotides 11 to 13 and the ziaR start codon is cat of the nucleotides 407 to 409.

SEQ ID NO:39 is a nucleotide sequence of the zinc-inducible smtA-PsmtA promoter/regulator from *Synechococcus* PCC 7002. The gene encoding the regulator smtB runs in anti-sense direction to PsmtA wherein the smtB stop codon is tta of nucleotides 67 to 69 and the smtB start codon is cat of the nucleotides 391 to 393.

SEQ ID NO:40 is a nucleotide sequence of the zinc-inducible aztA-PaztA promoter/regulator from *Anabaena* PCC 7120. The gene encoding the regulator aztR runs in anti-sense direction to PaztA wherein the aztR stop codon is tca of nucleotides 98 to 100 and the aztR start codon is cat of the nucleotides 506 to 508.

SEQ ID NO:41 is a nucleotide sequence of the cobalt-inducible corR-PcorT promoter/regulator from *Synechocystis* PCC6803. The gene encoding the regulator corR runs in anti-sense direction to PcorT wherein the corR stop codon is cta of nucleotides 55 to 57 and the corR start codon is cat of the nucleotides 1165 to 1167.

SEQ ID NO:42 is a nucleotide sequence of the nickel-responsive nrsS-nrsR-PnrsB promoter/regulator from *Synechocystis* PCC 6803. The gene encoding the regulator nrsS runs in anti-sense direction to PnrsB wherein the nrsS stop codon is tta of nucleotides 115 to 117 and the nrsS start codon is cat of the nucleotides 1477 to 1479. The gene encoding the regulator nrsR runs in anti-sense direction to PnrsB wherein the nrsR stop codon is tca of nucleotides 1476 to 1478 and the nrsR start codon is cat of the nucleotides 2178 to 2180.

SEQ ID NO:43 is a nucleotide sequence of the PpetJ promoter endogenous to Cyanobacterium sp. accession no. PTA-13311

SEQ ID NO:44 is a nucleotide sequence of plasmid #1606 pABIcyano1-PnirA-zmPDC(opt1)_dsrA-Prbc*(optRBS)-synADH(opt1)_ter SEQ ID NO:45 is a nucleotide sequence of plasmid #1645 pABIcyano1-PnirA-zmPDC(opt1)_dsrA-Prbc*(optRBS)-ADH916(opt)_ter SEQ ID NO:46 is a nucleotide sequence of plasmid #1753 pABIcyano1-PnirA-zmPDC(opt1)_dsrA-Prbc*(optRBS)-Adh111_ter SEQ ID NO:47 is a nucleotide sequence of plasmid #1735 pABIcyano1-PnirA-zmPDC(opt1)_dsrA-Prbc*(optRBS)-Adh1694_ter SEQ ID NO:48 is a nucleotide sequence of promoter Porf0128 of Cyanobacterium sp. PTA-13311

SEQ ID NO:49 is a nucleotide sequence of promoter Porf1486 of Cyanobacterium sp. PTA-13311

SEQ ID NO:50 is a nucleotide sequence of promoter Porf3164 of Cyanobacterium sp. PTA-13311

SEQ ID NO:51 is a nucleotide sequence of promoter Porf3293 of Cyanobacterium sp. PTA-13311

SEQ ID NO:52 is a nucleotide sequence of promoter Porf3621 of Cyanobacterium sp. PTA-13311

SEQ ID NO:53 is a nucleotide sequence of promoter Porf3635 of Cyanobacterium sp. PTA-13311

SEQ ID NO:54 is a nucleotide sequence of promoter Porf3858 of Cyanobacterium sp. PTA-13311

SEQ ID NO:55 is a nucleotide sequence of promoter Porf1071 of Cyanobacterium sp. PTA-13311

SEQ ID NO:56 is a nucleotide sequence of promoter Porf1072 of Cyanobacterium sp. PTA-13311

SEQ ID NO:57 is a nucleotide sequence of promoter Porf1074 of Cyanobacterium sp. PTA-13311

SEQ ID NO:58 is a nucleotide sequence of promoter Porf1075 of Cyanobacterium sp. PTA-13311

SEQ ID NO:59 is a nucleotide sequence of promoter Porf1542 of Cyanobacterium sp. PTA-13311

SEQ ID NO:60 is a nucleotide sequence of promoter Porf1823 of Cyanobacterium sp. PTA-13311

SEQ ID NO:61 is a nucleotide sequence of promoter Porf1824 of Cyanobacterium sp. PTA-13311

SEQ ID NO:62 is a nucleotide sequence of promoter Porf3126 of Cyanobacterium sp. PTA-13311

SEQ ID NO:63 is a nucleotide sequence of promoter Porf3389 of Cyanobacterium sp. PTA-13311

SEQ ID NO:64 is a nucleotide sequence of promoter Porf0221 of Cyanobacterium sp. PTA-13311

SEQ ID NO:65 is a nucleotide sequence of promoter Porf0222 of Cyanobacterium sp. PTA-13311

SEQ ID NO:66 is a nucleotide sequence of promoter Porf0223 of Cyanobacterium sp. PTA-13311

SEQ ID NO:67 is a nucleotide sequence of promoter Porf0316 of Cyanobacterium sp. PTA-13311

SEQ ID NO:68 is a nucleotide sequence of promoter Porf3232 of Cyanobacterium sp. PTA-13311

SEQ ID NO:69 is a nucleotide sequence of promoter Porf3461 (petJ) of Cyanobacterium sp. PTA-13311

SEQ ID NO:70 is a nucleotide sequence of promoter Porf3749 of Cyanobacterium sp. PTA-13311

SEQ ID NO:71 is a nucleotide sequence of plasmid #1790 pABIcyano1::PnirA-zmPDC(opt3)_TdsrA-PcpcB-ADH242 (opt)_TrbcS SEQ ID NO:72 is a nucleotide sequence of plasmid #1791 pABIcyano1::PnirA-zmPDC(opt3)_TdsrA-PcpcB-ADH111 (opt)_TrbcS SEQ ID NO:73 is a nucleotide sequence of plasmid #1792 pABIcyano1::PnirA-zmPDC(opt3)_TdsrA-PcpcB-synADH (nat)_TrbcS SEQ ID NO:74 is a nucleotide sequence of plasmid #1793 pABIcyano1::PnirA-zmPDC(opt3)_TdsrA-PcpcB-ADH916 (opt)_TrbcS SEQ ID NO:75 is a nucleotide sequence of plasmid #1795 pABIcyano1::PnirA-zmPDC(opt1)_TdsrA-PcpcB-ADH553 (opt)_TrbcS SEQ ID NO:76 is a nucleotide sequence of plasmid #1815 pABIcyano1::PnirA-zmPDC(opt1)_TdsrA-PcpcB-ADH1102(nat)_Ter SEQ ID NO:77 is a nucleotide sequence of plasmid #1831 pABIcyano1::PnirA-zmPDC(opt1)_TdsrA-PcpcB-ADH213 (nat)_Ter SEQ ID NO:78 is a nucleotide sequence of plasmid #1750 pABIcyano1-6.8::PnirA-zmPDC(opt3)-TdsrA-PrpsL*4-ADH111(opt)-ter SEQ ID NO:79 is a nucleotide sequence of plasmid #1784 pABIcyano1-6.8::PnirA*2-zmPDC(opt3)-TdsrA-PcpcB-synADH-oop SEQ ID NO:80 is a nucleotide sequence of plasmid #1835 pABIcyano1-6.8::Porf0316-zmPDC(opt1)-TdsrA-PcpcB-synADH-TrbcS SEQ ID NO:81 is a nucleotide sequence of plasmid #1938 pABIcyano1-6.8::Porf0316-zmPDC(opt1)-TdsrA-PcpcB-ADH111(opt)-TrbcS SEQ ID NO:82 is a nucleotide sequence of a generalized PcpcB promoter endogenous to Cyanobacterium sp. accession no. PTA-13311

SEQ ID NO:83 is a nucleotide sequence of a generalized PcpcB promoter with alternative transcriptional start points endogenous to Cyanobacterium sp. accession no. PTA-13311.

DETAILED DESCRIPTION OF THE INVENTION

All publications and patent applications mentioned in this specification are herein incorporated by reference to the same extent as if each individual publication or patent application was specifically and individually indicated to be incorporated by reference.

The following definitions and explanations are provided to better describe the present invention disclosure and to guide those of ordinary skill in the art in the understanding, interpretation and practice in the present invention. Unless explained otherwise, all technical and scientific terms used herein have the same meaning as commonly understood by one of ordinary skill in the art to which this disclosure belongs.

Cyanobacteria are small, prokaryotic, generally aquatic organisms that can be genetically manipulated to be capable of utilizing light and $CO_2$ to produce compounds of interest, such as biofuels. Cyanobacterial cells are capable of fixing carbon dioxide as a carbon source for autotrophic growth, and therefore do not require any costly input of organic carbon as a growth substrate. Furthermore, the $CO_2$ that is utilized by the cyanobacterial culture can be derived from any source, such as a waste byproduct of industrial production. In this way, cyanobacteria can be used to recycle $CO_2$ to desired products, such as biofuels.

The term "Cyanobacterium sp." means an unspecified cyanobacterial member of the genus Cyanobacterium, which was among other characterized by Rippka and Cohen-Bazire (Ann. Microbiol. (Inst. Pasteur), 1983, 134B:32).

As used herein the term "metabolically enhanced" refers to any change in the endogenous genome of a wild type host cell, or to the addition of endogenous and non-endogenous, exogenous genetic code to a wild type host cell, for example a wild type cyanobacterial cell. One example is the introduction of a heterologous gene. In particular, such changes are made by the hand of man through the use of recombinant DNA technology or mutagenesis. The changes can involve protein coding sequences and/or non-protein coding sequences in the genome such as regulatory sequences, non-coding RNA, antisense RNA, promoters or enhancers. Aspects of the invention utilize techniques and methods common to the fields of molecular biology, microbiology and cell culture. Useful laboratory references for these types of methodologies are readily available to those skilled in the art, see for example "Molecular Cloning: A laboratory Manual" (3rd edition), Sambrook, J. et al. (2001) Cold Spring Harbor Laboratory Press; "Current Protocols in Microbiology" (2007) edited by Coico, R. et al., John Wiley & Sons, Inc.; "The Molecular Biology of Cyanobacteria" (1994), Donald Bryant (Ed.), Springer Netherlands; "Handbook of Microalgal Culture: Biotechnology and Applied Phycology" (2003) Richmond, A. (Ed.), Blackwell Publishing; and "The Cyanobacteria, Molecular Biology, Genomics and Evolution", edited by Antonia Herrero and Enrique Flores, Caister Academic Press, Norfolk, UK, 2008.

Various cyanobacterial species have been metabolically enhanced to produce compounds of interest. The transformation of the cyanobacterial genus *Synechococcus* with genes that encode enzymes that can produce ethanol for biofuel production has been described (U.S. Pat. Nos. 6,699,696 and 6,306,639). The transformation of the cyanobacterial genus

*Synechocystis* has been described, for example, in WO 2009/098089 A2 and in WO 2011/018116 A1.

The Michaelis-Menten model is useful for determining kinetic parameters for enzymatically catalyzed reactions and is well known in the art (Michaelis and Menten, (1913), "Die Kinetik der Invertinwirkung," Biochem. Z. 49, 333-369). It is a model that describes the rate of enzymatic reactions by relating the reaction rate to the concentration of a substrate or substrates.

$K_m$ values of ADH enzymes were determined herein by varying concentrations of one substrate only while keeping all other substrates at saturated levels. The kinetic parameters of the ADH enzymes were determined herein on cellular extracts, and not on pure enzyme. $K_m$ was determined herein using a nonlinear regression algorithm for the single-substrate version of the Michaelis-Menten model by using GraphPad Prism Software (version 5). The detailed description of the algorithm is available on the world wide web at "graphpad.com/guides/prism/6/curve-fitting/index.htm-?reg_kcat.htm".

As used herein, the $K_m$ value was measured according to the method described in Example 4. The Km was measured using a crude cell extract, or a partially clarified extract, in 30 mM HEPES/KOH pH 7.5, 150 mM KCl, 1 mM DTT at a temperature of 30° C. For the forward reaction measurement, 0.15 mM NADPH was added, and acetaldehyde was added in differing amounts ranging from 1 μm to 50 mM. The NADPH oxidation was measured at a wavelength of 340 nm. For the back reaction, 0.15 mM $NADP^+$ was added, with ethanol in differing amounts ranging from 1 mM to 2.5 M.

Database entry numbers given in the following are from the NCBI database (National Center for Biotechnology Information; available on the world wide web at ncbi.nlm.nih.gov) or from the CyanoBase, the genome database for cyanobacteria (available on the world wide web at bacteria.kazusa.or.jp/cyanobase/index.html); Yazukazu et al. "CyanoBase, the genome database for *Synechocystis* sp. Strain PCC6803: status for the year 2000", Nucleic Acid Research, 2000, Vol. 18, page 72.

It is well known to a person of ordinary skill in the art that large plasmids can be produced using techniques such as the ones described in the U.S. Pat. No. 6,472,184 B1 titled "Method for producing nucleic acid polymers" and U.S. Pat. No. 5,750,380 titled "DNA polymerase mediated synthesis of double stranded nucleic acid molecules", which are hereby incorporated in their entirety.

Denominations of genes are in the following presented in a three letter lower case name followed by a capitalized letter if more than one related gene exists, for example ziaA for the gene encoding a zinc transporting ATPase. The respective protein encoded by that gene is denominated by the same name with the first letter capitalized, such as ZiaA.

Denominations for promoter sequences, which control the transcription of a certain gene in their natural environment are given by a capitalized letter "P" followed by the gene name according to the above described nomenclature, for example "PziaA" for the promoter controlling the transcription of the ziaA gene.

Denominations for enzyme names can be given in a two or three letter code indicating the origin of the enzyme, followed by the above mentioned three letter code for the enzyme itself, such as SynAdh ($Zn^{2+}$ dependent alcohol dehydrogenase from *Synechocystis* PCC6803), ZmPdc (pyruvate decarboxylase from *Zymomonas mobilis*).

The term "nucleic acid" is intended to include nucleic acid molecules, such as polynucleotides which include an open reading frame encoding a polypeptide, and can further include non-coding regulatory sequence of genes, such as promoters and enhancers as well as non-coding RNAs. In addition, the terms are intended to include one or more genes that are part of a functional operon. In addition, the terms are intended to include a specific gene for a selected purpose. The gene can be endogenous to the host cell or can be recombinantly introduced into the host cell. Likewise, the term "amino acid sequence" is intended to include polypeptides and proteins, such as enzymes. Such amino acid sequences can be endogenous to the host cell or can be recombinantly introduced into the host cell.

The percentage of identity of two nucleic acid sequences or two amino acid sequences, respectively, can be determined using the algorithm of Thompson et al. (ClustalW, 1994, Nucleic Acid Research, 22:4673-4680). A nucleotide sequence or an amino acid sequence can also be used as a so-called query sequence to perform a nucleic acid or amino acid sequence search against public nucleic acid or protein sequence databases in order to, for example, identify further homologous protein sequences and/or nucleic acid sequences which can also be used in embodiments of this invention. In addition, any nucleic acid sequence or protein sequence disclosed in this patent application can also be used as a query sequence in order to identify yet unknown sequences in public databases, which can encode for example new enzymes which could be useful in this invention. Such searches can be performed using the algorithm of Karlin and Altschul (Proceedings of the National Academy of Sciences, USA, 1990, 87:2264-2268), modified as in Karlin and Altschul (Proceedings of the National Academy of Sciences, USA, 1993, 90:5873-5877). Such an algorithm is incorporated in the nblast and xblast programs of Altschul et al. (Journal of Molecular Biology 1990, 215:403-410). Suitable parameters for these database searches with these programs are, for example, a score of 100 and a word length of 12 for BLAST nucleotide searches as performed with the NBLAST program. BLAST protein searches are performed with the XBLAST program with a score of 50 and a word length of 3. Where gaps exist between two sequences, the gapped BLAST is utilized as described in Altschul et al. (Nucleic Acid Research, 1997, 25:3389-3402).

The term "genome" refers to the chromosomal genome as well to extra chromosomal plasmids which are normally present in the wild type cyanobacterium without having performing recombinant DNA technology. For example, cyanobacteria can include at least up to six extrachromosomal plasmids in their wild type form.

The term "terminator" refers to a nucleic acid sequence, which is able to terminate the transcription of an mRNA. The terminators can exert their function in various ways including, but not limited to forming a hairpin structure in the mRNA transcript, which disrupts the mRNA-DNA RNA polymerase complex during transcription or via forming a recognition site for a transcription termination factor. Non-limiting examples are dsrA from *E. coli*, the oop terminator or the rho terminator.

The first aspect of the invention provides a metabolically enhanced cyanobacterial cell for the production of ethanol. The metabolically enhanced cyanobacterial cell comprises at least one recombinant gene encoding a pyruvate decarboxylase enzyme (Pdc) converting pyruvate to acetaldehyde, and at least one recombinant gene encoding a first $Zn^{2+}$ dependent alcohol dehydrogenase enzyme (Adh) converting acetaldehyde to ethanol. The alcohol dehydrogenase enzyme has (i) a Michaelis constant $K_m$ for NADPH which is lower than the Michaelis constant $K_m$ for NADH of the alcohol dehydrogenase enzyme, and (ii) a Michaelis constant $K_m$ for acetaldehyde which is lower than $0.08 \cdot 10^{-3}$ M, preferably lower than $0.07 \cdot 10^{-3}$ M, most preferred lower than $0.06 \cdot 10^{-3}$ M.

The second aspect of the invention provides a metabolically enhanced cyanobacterial cell for the production of ethanol. The metabolically enhanced cyanobacterial cell comprises at least one recombinant gene encoding a pyruvate decarboxylase enzyme (Pdc) converting pyruvate to acetaldehyde, and at least one recombinant gene encoding a first $Zn^{2+}$ dependent alcohol dehydrogenase enzyme (Adh) converting acetaldehyde to ethanol. The alcohol dehydrogenase enzyme has (i) a Michaelis constant $K_m$ for NADPH which is lower than the Michaelis constant $K_m$ for NADH of the alcohol dehydrogenase enzyme, (ii) a Michaelis constant $K_m$ for acetaldehyde which is higher than $0.65 \cdot 10^{-3}$ M, higher than $0.7 \cdot 10^{-3}$ M or higher than $0.73 \cdot 10^{-3}$ M, but lower than $10 \cdot 10^{-3}$ M, preferably lower than $9 \cdot 10^{-3}$ M, most preferred lower than $8 \cdot 10^{-3}$ M, and (iii) a Michaelis constant $K_m$ for ethanol which is higher than $20 \cdot 10^{-3}$ M, preferably higher than $25 \cdot 10^{-3}$ M, most preferred higher than $30 \cdot 10^{-3}$ M.

The third aspect of the invention provides a metabolically enhanced cyanobacterial cell for the production of ethanol. The metabolically enhanced cyanobacterial cell comprises at least one recombinant gene encoding a pyruvate decarboxylase enzyme (Pdc) converting pyruvate to acetaldehyde, and at least one recombinant gene encoding a first $Zn^{2+}$ dependent alcohol dehydrogenase enzyme (Adh) converting acetaldehyde to ethanol. The alcohol dehydrogenase enzyme comprises an amino acid sequence having at least 80% sequence identity, preferably at least 85% sequence identity, more preferably at least 90% sequence identity, more preferably at least 95% sequence identity, or 99% sequence identity, to SEQ ID NO:1,
SEQ ID NO:2,
SEQ ID NO:3,
SEQ ID NO:4,
SEQ ID NO:5,
SEQ ID NO:6,
SEQ ID NO:7,
SEQ ID NO:8,
SEQ ID NO:9, or
SEQ ID NO:10.

In the above aspects, the Km-values represent the Km-values of the native, i.e. non-recombinant, form of the alcohol dehydrogenase enzyme. A Km-value as used herein can be determined from the endogenously expressed alcohol dehydrogenase enzyme of a wild-type cyanobacterial cell. For example, a cell extract of the wild-type cyanobacterial cell which includes a minor portion of the alcohol dehydrogenase enzyme and a major portion which is larger than the minor portion of other proteins can be used for determination of the Km-value of the alcohol dehydrogenase enzyme. A suitable method for determining the Km-value of a native alcohol dehydrogenase enzyme within the meaning of the present invention is described further below in example 4. Accordingly, the Michaelis constant $K_m$ for acetaldehyde and the Michaelis constant $K_m$ for ethanol shall be understood with NADPH or NADP+, respectively, as co-factor of the alcohol dehydrogenase enzyme.

Further information with regard to the assignment of the SEQ ID NOs of the present invention to their corresponding strains of origin can be found in the section “BRIEF DESCRIPTION OF THE SEQUENCES” above.

The inventors of the present invention discovered that the type of Adh enzyme and its specific kinetic properties in terms of its forward reaction, i.e. the reduction of acetaldehyde to ethanol, and its back reaction, i.e. the conversion of acetaldehyde into ethanol, are of at least similar importance as its activity level for the ethanol production characteristic and performance of a metabolically enhanced cyanobacterial cell.

On the one hand, a relatively low affinity for acetaldehyde of a recombinant Adh enzyme can lead to a transient acetaldehyde accumulation in the initial phase of the cultivation of a metabolically enhanced cyanobacterial cell. First of all, this causes economically unfavorable production downtimes from the start of the cultivation. Secondly, the acetaldehyde accumulation can cause acetaldehyde-related toxic effects which harm the cyanobacterial cells, leading for example to reduced cell vitality and metabolic turnover, and shortening the total exploitable phase of ethanol production.

On the other hand, a low affinity for the product ethanol of the acetaldehyde dehydrogenase enzyme can be of particular importance. The inventors discovered that conventional alcohol dehydrogenase enzymes often exhibit Michaelis constants $K_m$ for ethanol, and in particular combinations of Michaelis constants $K_m$ for ethanol and Michaelis constants $K_m$ for acetaldehyde, which tend to favor the back reaction from ethanol to acetaldehyde at increasing ethanol concentrations. The observed effect resembles a product inhibition of the alcohol dehydrogenase enzyme at higher ethanol concentrations which significantly impairs achieving profitable ethanol concentrations with conventional metabolically enhanced cyanobacterial cells known in the art. As above, a concomitant effect is again the accumulation of acetaldehyde which harms the cyanobacterial cells.

In contrast, by incorporating an Adh enzyme having Michaelis constant $K_m$ for acetaldehyde which is lower than $0.08 \cdot 10^{-3}$ M, preferably lower than $0.07 \cdot 10^{-3}$ M, most preferred lower than $0.06 \cdot 10^{-3}$ M; or having a Michaelis constant $K_m$ for acetaldehyde which is higher than $0.65 \cdot 10^{-3}$ M, higher than $0.7 \cdot 10^{-3}$ M or higher than $0.73 \cdot 10^{-3}$ M but lower than $10 \cdot 10^{-3}$ M, preferably lower than $9 \cdot 10^{-3}$ M, most preferred lower than $8 \cdot 10^{-3}$ M in combination with a Michaelis constant $K_m$ for ethanol which is higher than $20 \cdot 10^{-3}$ M, preferably higher than $25 \cdot 10^{-3}$ M, most preferred higher than $30 \cdot 10^{-3}$ M, the inventors achieved a metabolic enhancement of a cyanobacterial cell that leads to an enhanced level of ethanol formation due to the fact that the recombinant alcohol dehydrogenase enzyme is capable of maintaining a low acetaldehyde level in the culture and/or tolerates high ethanol product concentrations with substantially reduced back-reaction. For at least the same reasons, the metabolically enhanced cyanobacterial cell of the present invention exhibits a higher vitality, maintains a high metabolic turnover during cultivation and achieves a timely extended phase of ethanol production in comparison to conventionally metabolically enhanced cyanobacterial cells.

The acetaldehyde and/or ethanol that is produced by a metabolically enhanced cyanobacterial cell can be quantified by several methods. In one method, gas chromatography is used, following methods similar to blood alcohol quantification methods, as described in example 7 of the present invention.

A useful indicator of the vitality of the metabolically enhanced cyanobacterial cell is, for example, the pigmentation of the cell during or after ethanol production. A reduction in the chlorophyll and/or phycocyanin pigmentation of the metabolically enhanced cyanobacterial cell in comparison to the wild type cyanobacterial cell can be an indicator of reduced cell vitality and stress. Another indicator for impaired cell vitality can be a reduction in the phycocyanin/chlorophyll ratio of the metabolically enhanced cyanobacterial cell in comparison to the wild type cyanobacterial cell. Reduced cell vitality can also be accompanied by an increased carotenoid/phycocyanin ratio of the metabolically enhanced cyanobacterial cell in comparison to the wild type cyanobacterial cell. The relative phycocyanin (PC) pigmentation can be photometrically measured at 620 nm wavelength. The relative chlorophyll (Chl) pigmentation can be photometrically measured at 680 nm wavelength. The relative carotenoid (Car) pigmentation can be photometrically measured in the range of 490 nm (+/−5 nm) wavelength. For example, the reduction in the relative phycocyanin/chlorophyll ratio of the metabolically enhanced cyanobacterial cell is less than 25%, preferably less than 20% in comparison to the wild type cyanobacterial cell. In another example, the increment in the relative carotenoid/phycocyanin ratio of the metabolically enhanced cyanobacterial cell is less than 100%, preferably less that 50%, most preferred less than 40% in comparison to the wild type cyanobacterial cell. Metabolically enhanced, ethanol-producing cyanobacterial cells exhibiting a relative phycocyanin/chlorophyll ratio and/or a carotenoid/phycocyanin ratio in these ranges are typically less affected by the ethanol production and have a vitality that is closer to that of a corresponding wild type cyanobacterium.

Furthermore, in many photoautotrophic cells, for example cyanobacterial cells, the level of total NAD+ and NADH to total NADP+ and NADPH is around 1:10. The inventors found that due to this pivotal imbalance of NADH to NADPH, an enhanced level of ethanol formation is achieved with metabolically enhanced cyanobacterial cells when the recombinant alcohol dehydrogenase enzyme has a Michaelis constant $K_m$ for NADPH which is lower than the Michaelis constant $K_m$ for NADH, thus having a higher affinity to the co-factor NADP+/NADPH than to the co-factor NAD+/NADH. An alcohol dehydrogenase enzyme having a higher affinity to the co-factor NADP+/NADPH than to the co-factor NAD+/NADH may in the following also be referred to as NADPH-dependent.

The inventors of the present invention developed a powerful forward-genetic screening method to analyze a plurality of wild-type strains, for example several cyanobacterial wild-type strains, for the presence of NADPH-dependent native Adh function of genes in the wild-type strains by analysing the wild-type strains in vivo for the phenotypic effect of acetaldehyde conversion into ethanol in dependence of light. The screening method proceeds in the opposite direction of so-called reverse genetic screens which start from a particular gene and seek to find what phenotype arises from this gene. In contrast, the present screening method does not require prior knowledge of the corresponding Adh-encoding genes and therefore allows particularly fast and cost-efficient discovery of native alcohol dehydrogenase enzymes from a large number of newly isolated and/or uncharacterised candidate strains. This method is also applicable without having any sequence information about the genomic DNA sequence of the candidate strain. The screening method comprises the following steps:

A1) preparing a first and a second sample from each of the plurality of alcohol dehydrogenase enzyme expressing cyanobacterial strains, A2) adding acetaldehyde to the first and second sample from each of the plurality of alcohol dehydrogenase enzyme expressing cyanobacterial strains, A3) keeping the first sample from each of the plurality of alcohol dehydrogenase enzyme expressing cyanobacterial strains under illumination and the second sample without illumination, A4) comparing the conversion of acetaldehyde into ethanol in the first and second sample of each of the plurality of alcohol dehydrogenase enzyme expressing cyanobacterial strains, A5) selecting cyanobacterial strains having a higher acetaldehyde conversion rate under illumination than without illumination for further characterization.

The illumination in method step A3) can be between 50 $\mu E\ m^{-2}\ s^{-1}$ and 180 $\mu E\ m^{-2}\ s^{-1}$, 80 $\mu E\ m^{-2}\ s^{-1}$ and 150 $\mu E\ m^{-2}\ s^{-1}$, preferably between 110 $\mu E\ m^{-2}\ s^{-1}$ and 130 $\mu E\ m^{-2}\ s^{-1}$.

The acetaldehyde conversion into ethanol may, for example, be determined by gas chromatography. For instance, the method described in example 6 of the present invention may be used.

The inventors of the present invention discovered that an enhanced in vivo acetaldehyde conversion into ethanol in the illuminated sample in comparison to the sample without illumination indicates a light-dependent acetaldehyde conversion which is a sign of NADPH-dependent ADH activity in the corresponding alcohol dehydrogenase enzyme expressing cyanobacterial strain. Accordingly, the method is particularly advantageous to efficiently and economically pre-select candidate cyanobacterial strains prior to performing more detailed ex vivo analyses of Adh activity.

Moreover, after identification and selection of candidate strains which have a higher acetaldehyde conversion rate under illumination than without illumination in step A5), the screening method can be further developed to easily determine important kinetic properties of a plurality of Adh enzymes, such as Km-values for acetaldehyde, NADPH and/or ethanol, by including the following additional steps:

A6) preparing cell extracts from the alcohol dehydrogenase enzyme expressing cyanobacterial selected in step A5), A7) contacting each of the cell extracts with a predetermined concentration of acetaldehyde and NADPH, or with a predetermined concentration of ethanol and $NADP^+$, A8) detecting conversion of acetaldehyde into ethanol or of ethanol into acetaldehyde in each of the cell extracts.

Typically, each of the cell extracts will contain a minor portion of alcohol dehydrogenase enzyme and a major portion of other cellular proteins being larger than the minor portion that are generally present in said alcohol dehydrogenase enzyme expressing cyanobacterial cell. For example, the portion of alcohol dehydrogenase enzyme is typically less than 1% of the cellular proteins. It is therefore a particular advantage of the screening method that a purification of the alcohol dehydrogenase enzyme from the cell extract is not necessary, resulting in considerable labor and cost savings in comparison to other methods. However, in certain variants, the method step A6) can also further comprise removal of molecules with a molecular size smaller than 1000 Da from the cell extracts, for instance by size exclusion chromatography.

In a further variant of the screening method, the method step A6) further comprises the substep A6') separating each of the cell extracts into a plurality of portions. In this way, a plurality of measurements can be made with each of the cell extracts. For example, method step A7) can further comprise the substep A7') contacting the plurality of portions of each of the cell extracts with a plurality of predetermined concentrations of acetaldehyde and NADPH, or with a plurality of predetermined concentrations of ethanol and NADP+. Typically, the plurality of predetermined concentrations comprises a plurality of different concentrations. For example, different concentrations of acetaldehyde can be used together with one concentration of NADPH. In another example, different concentrations of NADPH can be used together with one concentration of acetaldehyde. In a further example, different concentrations of ethanol can be used together with one concentration of NADP+. In this way, a concentration-dependent conversion of acetaldehyde into ethanol or of ethanol into acetaldehyde can be obtained. For example, the concentration-dependent conversion can be used in a further method step A9) for deriving the Km-value for acetaldehyde or the Km-value for ethanol of the alcohol dehydrogenase enzyme.

The conversion in method step A8) can, for example, be detected as a change in the absorption of the cell extracts over time at a wavelength between 300 nm and 380 nm wavelength, preferably between 320 nm and 360 nm wavelength, most preferred between 330 nm and 350 nm wavelength. At this wavelength range the oxidation of NADPH to NADP+ can be detected as a decrease in absorption, and the reduction of NADP+ to NADPH can be detected as an increase in absorption, respectively, which is proportional to the conversion of acetaldehyde into ethanol or of ethanol into acetaldehyde, respectively.

Preferably, the method comprises screening of a plurality of alcohol dehydrogenase enzyme expressing cyanobacterial strains for the presence of alcohol dehydrogenase enzymes with a Michaelis constant $K_m$ for acetaldehyde which is lower than $0.08 \cdot 10^{-3}$ M, preferably lower than $0.07 \cdot 10^{-3}$ M, most preferred lower than $0.06 \cdot 10^{-3}$ M; or higher than $0.65 \cdot 10^{-3}$ M, higher than $0.7 \cdot 10^{-3}$ M, or higher than $0.73 \cdot 10^{-3}$ M but lower than $10 \cdot 10^{-3}$ M, preferably lower than $9 \cdot 10^{-3}$ M, most preferred lower than $8 \cdot 10^{-3}$ M; and/or a Michaelis constant $K_m$ for ethanol which is higher than $20 \cdot 10^{-3}$ M, preferably higher than $25 \cdot 10^{-3}$ M, most preferred higher than $30 \cdot 10^{-3}$ M.

The inventors found that the screening method provides the consistency of results in terms of Adh activity and Km-values that are commensurate to comparison of the screening results from different strains. Accordingly, the inventors were able use the present method for screening of a large number of candidate strains expressing native Adh enzymes for suitable NADPH-dependent Adh enzymes.

The inventors discovered that particularly useful NADPH-dependent Adh enzymes for metabolically enhancing a cyanobacterial cell were typically of a cyanobacterial origin, or variants derived thereof. For example, the alcohol dehydrogenase enzyme can comprise an amino acid sequence having at least 80% sequence identity, preferably at least 85% sequence identity, more preferably at least 90% sequence identity and most preferred at least 95% sequence identity or at least 99% sequence identity to an alcohol dehydrogenase enzyme of cyanobacterial origin. These Adh enzymes possessed particularly favorable kinetic properties and allowed the inventors to achieve superior ethanol yields when these Adh enzymes were recombinantly expressed in the metabolically enhanced cyanobacterium.

After the initial screening for the alcohol dehydrogenase enzymes having the required Km-values for carrying out the present invention, the Adh-encoding genes and corresponding amino acid sequences were identified and sequenced.

Accordingly, the inventors already identified alcohol dehydrogenase enzymes which exemplarily possess the required features for carrying out the present invention. Specifically, the alcohol dehydrogenase enzyme comprises an amino acid sequence having at least 80% sequence identity, preferably at least 85% sequence identity, more preferably at least 90% sequence identity and most preferred at least 95% sequence identity or at least 99% sequence identity to SEQ ID NO:1,
SEQ ID NO:2,
SEQ ID NO:3,
SEQ ID NO:4,
SEQ ID NO:5,
SEQ ID NO:6,
SEQ ID NO:7,
SEQ ID NO:8,
SEQ ID NO:9, or
SEQ ID NO:10.

Phylogenetic analysis shows that the above-identified Adh enzymes represent a superior subgroup of the $Zn^{2+}$-binding GroES-like domain alcohol dehydrogenase phylogenetic family having the required $K_m$ values for carrying out the present invention. In a further embodiment of this invention, the $Zn^{2+}$ dependent alcohol dehydrogenase enzyme is therefore selected from a subgroup of the Zinc-binding GroES-like domain alcohol dehydrogenases having the required $K_m$ values. These enzymes result in a higher ethanol production rate and in addition in a higher growth rate of the metabolically enhanced cyanobacterial cells compared to cells containing Adh enzymes from other Adh families, such as AdhI or AdhII from *Zymomonas mobilis* or Adh enzymes from *Synechococcus elongatus* PCC7942 or *Anabaena* sp. 7120. A suitable tool for determining the alcohol dehydrogenase phylogenetic family is, for example, the MultiAlin Multiple sequence alignment program (Corpet, F.: Multiple sequence alignment with hierarchical clustering, Nucleic Acids Research 16 (1988), 10881-10890).

In one embodiment, the Adh comprises an amino acid sequence having at least 80% sequence identity, preferably at least 85% sequence identity, more preferably at least 90% sequence identity and most preferred at least 95% sequence identity to SEQ ID NO:1 which the inventors initially identified in *Lyngbya* sp. In another embodiment, the Adh comprises an amino acid sequence having at least 80% sequence identity, preferably at least 85% sequence identity, more preferably at least 90% sequence identity and most preferred at least 95% sequence identity to SEQ ID NO:2 which the inventors initially identified in *Arthrospira platensis*. In another embodiment, the Adh comprises an amino acid sequence having at least 80% sequence identity, preferably at least 85% sequence identity, more preferably at least 90% sequence identity and most preferred at least 95% sequence identity to SEQ ID NO:3 which the inventors initially identified in *Cyanothece* sp. In yet another embodiment the Adh enzyme comprises an amino acid sequence having at least 80% sequence identity, preferably at least 85% sequence identity, more preferably at least 90% sequence identity and most preferred at least 95% sequence identity to SEQ ID NO:4 which the inventors initially identified in *Synechococcus* sp. In yet another embodiment the Adh comprises an amino acid sequence having at least 80% sequence identity, preferably at least 85% sequence identity, more preferably at least 90% sequence identity and most preferred at least 95% sequence identity to SEQ ID NO:5 which the inventors initially identified in *Synechococcus* sp. In yet another embodiment the Adh enzyme comprises an amino acid sequence having at least 80% sequence identity, preferably at least 85% sequence identity, more preferably at least 90% sequence identity and most preferred at least 95% sequence identity to SEQ ID NO:6 which the inventors initially identified in *Synechococcus* sp. In yet another embodiment the Adh enzyme comprises an amino acid sequence having at least 80% sequence identity, preferably at least 85% sequence identity, more preferably at least 90% sequence identity and most preferred at least 95% sequence identity to SEQ ID NO:7 which the inventors initially identified in *Chroococcidiopsis* sp. In yet another embodiment the Adh enzyme comprises an amino acid sequence having at least 80% sequence identity, preferably at least 85% sequence identity, more preferably at least 90% sequence identity and most preferred at least 95% sequence identity to SEQ ID NO:8 which the inventors initially identified in *Arthronema africanum*. In yet another embodiment the Adh enzyme comprises an amino acid sequence having at least 80% sequence identity, preferably at least 85% sequence identity, more preferably at least 90% sequence identity and most preferred at least 95% sequence identity to SEQ ID NO:9 which the inventors initially identified in *Chroococcidiopsis* sp. In yet another embodiment the Adh enzyme comprises an amino acid sequence having at least 80% sequence identity, preferably at least 85% sequence identity, more preferably at least 90% sequence identity and most preferred at least 95% sequence identity to SEQ ID NO:10 which the inventors initially identified in Cyanobacterium sp.

In contrast, for example the state-of-the art alcohol dehydrogenase enzyme synAdh from *Synechocystis* sp. PCC6803 does not meet the requirements of the present invention, because, according to the inventors' screening, it has a $K_m$ for acetaldehyde of $0.35 \cdot 10^{-3}$ M and a $K_m$ for ethanol of $19 \cdot 10^{-3}$ M. Another example of a state-of-the art alcohol dehydrogenase enzyme which does not meet the requirements of the present invention is the alcohol dehydrogenases AdhA from *Moorella* sp. HUC22-1 which has a $K_m$ for acetaldehyde of $10 \cdot 10^{-3}$ M and a $K_m$ for ethanol of $40 \cdot 10^{-3}$ M (Inokuma et al.: Characterization of enzymes involved in the ethanol production of *Moorella* sp. HUC22-1, Arch Microbiol 188 (2007) 37-45). Another example of an alcohol dehydrogenase enzyme which the inventors initially identified in the screening but which did not meet the requirements of the present invention is the Adh from LPP having a $K_m$ for acetaldehyde of $0.12 \cdot 10^{-3}$ M and a $K_m$ for ethanol of $3.6 \cdot 10^{-3}$ M.

Regarding the alcohol dehydrogenase enzyme, the inventors of the present invention found that the ratio of the Michaelis constant $K_m$ for the product of the enzymatic reaction, for instance ethanol, and the Michaelis constant $K_m$ for the educt of the enzymatic reaction, for instance acetaldehyde, is a particularly valuable indicator for the enzyme's usefulness in the biogenic production of biofuels such as ethanol with metabolically enhanced cyanobacteria. For example, the inventors found that a high $K_m$ (ethanol)/$K_m$ (acetaldehyde) ratio allows to quickly achieve a low steady state ratio between acetaldehyde and ethanol which is essentially maintained throughout the cultivation. Therefore, in a further embodiment, the ratio of the Michaelis constant $K_m$ for ethanol and the Michaelis constant Km for acetaldehyde, $K_m$ (ethanol)/$K_m$ (acetaldehyde), of the alcohol dehydrogenase enzyme is higher than 55, preferably higher than 60, more preferred higher than 80, most preferred higher than 100. In certain embodiments, the ratio $K_m$ (ethanol)/$K_m$ (acetaldehyde) of the alcohol dehydrogenase enzyme is higher than 120, and more preferably higher than 140.

The recombinant gene encoding the alcohol dehydrogenase enzyme can be under the transcriptional control of a constitutive promoter. In this way, a certain level of transcription and, therefore, enzymatic activity of the corresponding Adh enzyme can be maintained during the whole period of cultivation. This is, for example, advantageous to maintain continuous conversion of acetaldehyde to ethanol by the cell and avoid harmful accumulation of acetaldehyde in higher amounts. In particular, this is important for the initial phase of ethanol production when the Pdc activity is induced and is strongly increasing.

For example, the constitutive promoter can be endogenous to the cyanobacterial cell. This has the advantage that no recombinant transcription factor has to be present in the host cell. The endogenous promoter is usually well-recognized by the metabolically enhanced cyanobacterial cell without the need to introduce further genetic modifications. Suitable constitutive promoters include, without limitation, the PrpsL promoter (Gene ID: ABICyano1_orf1758), PpsaA promoter (ABICyano1_orf3243), PpsbB (ABICyano1_orf2107), PcpcB promoter (ABICyano1_orf2472), PatpG (ABICyano1_orf1814), PrbcL promoter (ABICyano1_orf1369), PpetE promoter (ABICyano1_orf2417), and variations thereof. Further suitable endogenous constitutive promoters from genes with unknown function exhibiting appropriate transcriptional activity include, without limitation, the promoters of Gene IDs ABICyano_orf1924, ABICyano_orf1997, ABICyano_orf3446, ABICyano_orf0865, ABICyano_orf1919, ABICyano_orf3278, ABICyano_orf1181, ABICyano_orf1627, ABICyano_orf0265 and ABICyano_orf2536, and variants thereof.

In a particularly preferred variant, the recombinant gene encoding the alcohol dehydrogenase enzyme is under the transcriptional control of the PcpcB promoter or a variant thereof, having the general sequence:

```
                                          (SEQ ID NO: 82)
n151tataaan7Gn216aggagan10ATG
or

                                          (SEQ ID NO: 83)
n123cgtaatan21tataaan7Gn98aaataan4Gactaatn4An96agg

agan10ATG.
```

Herein, n stands for a, t, c or g, tataaa corresponds to the −10 region, the capital G represents a transcriptional start point, the second capital G and the capital A denote alternative transcriptional start points, aggaga corresponds to the ribosomal binding site and the capital ATG represents the start codon.

The inventors found that in this preferred variant the promoter guarantees a particularly strong and reliable expression of the adh gene in the cyanobacterial cells of the present invention. In this way, particularly low acetaldehyde accumulation and high ethanol production rates are achieved, whilst long ethanol production periods can be maintained. At the same time, it was surprisingly discovered that a combination of this preferred promoter with a conventional adh gene, such as the synAdh from *Synechocystis* sp. PCC 6803, does not lead to the beneficial effect of high ethanol production and long production periods, because in this combination the cyanobacterial cells tend to suppress the expression of the conventional adh gene by genetic alteration of the adh gene after a few days of cultivation.

In a preferred embodiment, the cyanobacterial cell is capable of producing ethanol for at least 20 days, preferably at least 30 days, most preferred at least 40 days.

In a further preferred embodiment, the cyanobacterial cell has an average ethanol production rate of at least 0.017% (v/v)/day, preferably at least 0.020% (v/v)/day, most preferred at least 0.022% (v/v)/day over a period of at least 30 days. The average ethanol production rate can for example be achieved with illumination at a photon flux density of 230 $\mu E/m^{-2} s^{-1}$. The illumination is preferably provided from one side to a culture of the cyanobacterial cell, for instance one side of a bioreactor in which the cyanobacterial cell is cultured. Furthermore, the illumination is preferably provided in 12 h/12 h day/night cycles.

According to another embodiment of the invention, the recombinant gene encoding the pyruvate decarboxylase enzyme is under the transcriptional control of an inducible promoter. In this way, the ethanol production can be decoupled from metabolic pathways of the cell which are essential for growth and proliferation, thereby allowing accumulation of high cell densities in the culture and large amounts of precursor substrates prior to induction of the Pdc and, thus, the ethanol formation. In this way, significantly increased amounts of ethanol can be produced.

In a further variant, the recombinant gene encoding the pyruvate decarboxylase enzyme and the recombinant gene encoding the first $Zn^{2+}$ dependent alcohol dehydrogenase enzyme are under the transcriptional control of different promoters. For example, the recombinant gene encoding the pyruvate decarboxylase enzyme can be under the transcriptional control of an inducible promoter and the recombinant gene encoding the first $Zn^{2+}$ dependent alcohol dehydrogenase enzyme can be under the transcriptional control of a constitutive promoter. Preferably, a transcription terminator is present between the recombinant gene encoding the pyruvate decarboxylase enzyme and the recombinant gene encoding the first $Zn^{2+}$ dependent alcohol dehydrogenase enzyme. The separate transcriptional control of both genes and the corresponding translation from separate mRNAs leads to significantly improved ethanol yields with the metabolically enhanced cyanobacterial cell.

In certain other embodiments, the transcription of both the recombinant gene encoding the pyruvate decarboxylase enzyme and the recombinant gene encoding the alcohol dehydrogenase enzymes are controlled by the same single promoter. For these embodiments, an inducible promoter is preferred. In this way, the conversion of pyruvate into acetaldehyde by action of the pyruvate decarboxylase and the subsequent conversion of acetaldehyde into ethanol by action of the alcohol dehydrogenase can be directly coupled. Hence, accumulation of harmful concentrations of the acetaldehyde intermediate is effectively prevented. In certain variants, the recombinant gene encoding the alcohol dehydrogenase is arranged upstream of the recombinant gene encoding the pyruvate decarboxylase enzyme, so that transcription of the alcohol dehydrogenase gene occurs before transcription of the pyruvate decarboxylase gene. In this way, a delay in Adh expression relative to Pdc expression can be avoided and a sufficiently high Adh expression level of Adh can be accomplished, so that transient acetaldehyde accumulation is effectively reduced.

In a further preferred embodiment, at least a first recombinant gene encoding a pyruvate decarboxylase enzyme under the transcriptional control of a first inducible promoter and a second recombinant gene encoding a pyruvate decarboxylase enzyme under the transcriptional control of a second inducible promoter are present, wherein the first and the second promoter are separately inducible under different conditions. For a more full description of this embodiment, the applicant's international application WO 2013/098262 is hereby incorporated by reference in its entirety. The inventors found that the separately inducible Pdc enzymes in combination with the Adh enzymes of the present invention allow maintaining a particularly long ethanol production phase of several weeks with at the same time high average ethanol production rates.

In a further embodiment, the inducible promoter is inducible by a change of a metal-ion concentration. Such a change of metal-ion concentration includes for instance the addition or depletion of certain metal ions. Suitable inducible promoters include, without limitation, the PziaA promoter, the PsmtA promoter, PaztA promoter, the PcorT promoter, the PnrsB promoter, the PpetJ promoter, the Porf0316 promoter, the Porf0221 promoter, the Porf0223 promoter, the Porf3126 promoter, the PmntC promoter, and variations thereof.

The inducible promoter can, for instance, also be a nitrate inducible promoter. Suitable nitrate inducible promoters include, without limitation, the PnirA promoter, the PnrtA promoter, the PnarB promoter, and variations thereof.

Preferably, the inducible promoter is endogenous to the cyanobacterial cell. An endogenous inducible promoter is usually well-recognized by the metabolically enhanced cyanobacterial cell without the need to introduce further genetic modifications.

In some embodiments, the constitutive and/or inducible promoter contains at least one activity-enhancing mutation increasing the expression of the gene encoding the alcohol dehydrogenase enzyme and/or the pyruvate decarboxylase enzyme in the cyanobacterial cell in comparison to the native promoter. Such an activity-enhancing mutation can, for example, improve promoter recognition by the metabolically enhanced cyanobacterial cell, tailor or improve the promoter strength and/or its induction conditions such as the required inductor concentration. Suitable genetic modifications of promoters include, for instance, truncated versions of promoters including only a small portion of the native promoter upstream of the transcription start point, such as the region ranging from −35 to the transcription start. Furthermore, nucleotide changes can be introduced into the promoter sequence, for example into the TATA box, the operator sequence and/or the ribosomal binding site (RBS).

In a further embodiment of the invention, at least one of said recombinant gene encoding the pyruvate decarboxylase enzyme and said recombinant gene encoding the alcohol dehydrogenase enzyme is integrated into an extrachromosomal plasmid. The extrachromosomal plasmid can, for example, replicate independently from the chromosome of the cyanobacterial cell. Moreover, the extrachromosomal plasmid can be present in a high copy number in the cyanobacterial cell. In this way, a high copy number of the gene encoding the pyruvate decarboxylase enzyme and/or the gene encoding the alcohol dehydrogenase enzyme can be present in the cell, in turn leading to high expression rates of the Pdc and/or Adh so that particularly high ethanol production rates can be achieved. The extrachromosomal plasmid preferably contains genes endogenous to the cyanobacterial host cell. For example, the plasmid can be derived from an endogenous plasmid of the cyanobacterial cell.

Alternatively or in addition, at least one of said recombinant gene encoding the pyruvate decarboxylase enzyme and said recombinant gene encoding the alcohol dehydrogenase enzyme is integrated into a chromosome. When the cyanobacterial cell is polyploid, the gene integrations can be present in all of the copies of the chromosome, or in some of the copies of the chromosome.

The cyanobacterial cell can be of a variety of suitable genera, including but not limited to genera of the group comprising *Synechocystis, Synechococcus, Anabaena, Chroococcidiopsis, Cyanothece, Lyngbya, Phormidium, Nostoc, Spirulina, Arthrospira, Trichodesmium, Leptolyngbya, Plectonema, Myxosarcina, Pleurocapsa, Oscillatoria, Pseudanabaena, Cyanobacterium, Geitlerinema, Euhalothece, Calothrix, Scytonema.*

In more preferred embodiments, the cyanobacterial cell is selected from the group consisting of Cyanobacterium sp., *Synechococcus* sp. and *Synechocystis* sp. Suitable strains include, without limitation, *Synechococcus* sp. PCC7002 and *Synechocystis* sp. PCC6803. In another embodiment, the cyanobacterial cell is a Cyanobacterium sp. cell.

Further preferred is a Cyanobacterium sp. which can, for instance, withstand about 1 vol % of ethanol in the culture medium for several weeks and is therefore particularly suitable for metabolic enhancement with the highly productive alcohol dehydrogenase enzymes of the present invention. Also preferred is a high temperature and pH tolerance, for example a strain that withstands at 48° C., preferably 50° C. most preferred at least 53° C. to 55° C. for at least 2 hours per day over a time period of at least 7 day. Furthermore, a strain which can also tolerate a wide range of pH values is preferred and can be cultured at a pH between 5.5 to 10, preferably at a pH between 6 to 7.5, most preferred at neutral or slightly alkaline pH of pH 7.5.

Therefore, in particularly preferred embodiments, the cyanobacterial cell is the Algenol Biofuels Inc. proprietary strain Cyanobacterium sp. with the ATCC accession number PTA-13311 that has been deposited with the American Type Culture Collection (ATCC), 10801 University Boulevard, Manassas, Va. 20110 on Nov. 9, 2012. In the following, this strain may also be referred to as ABIcyano1.

Cyanobacterium aponinum and Cyanobacterium sp. PTA-13311, i.e. ABICyano1, are two different organisms of the genus Cyanobacterium sp.

In certain preferred embodiments, the recombinant gene encoding the alcohol dehydrogenase enzyme and/or the recombinant gene encoding the pyruvate decarboxylase enzyme is adapted in the codon triplets coding for the amino acids for enhanced translation in the cyanobacterial cell. In particular, the adapted gene has a G+C content of ≤45%, preferably ≤40%, most preferred ≤35%. In addition, the adapted gene has a codon adaptation index (CAI) of ≥0.60, preferably ≥0.70, most preferred >0.80 based on the codon usage table of Cyanobacterium sp. with the accession no. PTA-13311 (Table 1).

TABLE 1

Codon usage table of *Cyanobacterium* sp. accession no. PTA-13311.

| AA | AmAcid | Codon | Fraction | Number | Frequency (/1000) |
|---|---|---|---|---|---|
| A | Ala | GCA | 0.293 | 20724 | 18.356 |
| A | Ala | GCC | 0.214 | 15144 | 13.414 |
| A | Ala | GCG | 0.14 | 9870 | 8.742 |
| A | Ala | GCT | 0.353 | 24915 | 22.068 |
| R | Arg | AGA | 0.347 | 16040 | 14.207 |
| R | Arg | AGG | 0.09 | 4158 | 3.683 |
| R | Arg | CGA | 0.106 | 4886 | 4.328 |
| R | Arg | CGC | 0.131 | 6043 | 5.353 |
| R | Arg | CGG | 0.039 | 1813 | 1.606 |
| R | Arg | CGT | 0.288 | 13329 | 11.806 |
| N | Asn | AAC | 0.22 | 14609 | 12.94 |
| N | Asn | AAT | 0.78 | 51712 | 45.804 |
| D | Asp | GAC | 0.193 | 11063 | 9.799 |
| D | Asp | GAT | 0.807 | 46399 | 41.098 |
| C | Cys | TGC | 0.218 | 2501 | 2.215 |
| C | Cys | TGT | 0.782 | 8976 | 7.95 |
| Q | Gln | CAA | 0.806 | 43747 | 38.749 |
| Q | Gln | CAG | 0.194 | 10554 | 9.348 |
| E | Glu | GAA | 0.787 | 60690 | 53.756 |
| E | Glu | GAG | 0.213 | 16451 | 14.571 |
| G | Gly | GGA | 0.324 | 22709 | 20.114 |
| G | Gly | GGC | 0.125 | 8720 | 7.724 |
| G | Gly | GGG | 0.151 | 10542 | 9.338 |
| G | Gly | GGT | 0.401 | 28065 | 24.859 |
| H | His | CAC | 0.251 | 4859 | 4.304 |

TABLE 1-continued

Codon usage table of *Cyanobacterium* sp. accession no. PTA-13311.

| AA | AmAcid | Codon | Fraction | Number | Frequency (/1000) |
|---|---|---|---|---|---|
| H | His | CAT | 0.749 | 14516 | 12.858 |
| I | Ile | ATA | 0.195 | 18334 | 16.239 |
| I | Ile | ATC | 0.19 | 17872 | 15.83 |
| I | Ile | ATT | 0.616 | 57964 | 51.342 |
| L | Leu | CTA | 0.088 | 10776 | 9.545 |
| L | Leu | CTC | 0.058 | 7129 | 6.314 |
| L | Leu | CTG | 0.033 | 4040 | 3.578 |
| L | Leu | CTT | 0.116 | 14162 | 12.544 |
| L | Leu | TTA | 0.571 | 69559 | 61.612 |
| L | Leu | TTG | 0.133 | 16235 | 14.38 |
| K | Lys | AAA | 0.836 | 59396 | 52.61 |
| K | Lys | AAG | 0.164 | 11694 | 10.358 |
| M | Met | ATG | 1 | 20093 | 17.797 |
| F | Phe | TTC | 0.172 | 8420 | 7.458 |
| F | Phe | TTT | 0.828 | 40450 | 35.829 |
| P | Pro | CCA | 0.169 | 7746 | 6.861 |
| P | Pro | CCC | 0.275 | 12613 | 11.172 |
| P | Pro | CCG | 0.066 | 3012 | 2.668 |
| P | Pro | CCT | 0.491 | 22560 | 19.982 |
| S | Ser | AGC | 0.088 | 6435 | 5.7 |
| S | Ser | AGT | 0.306 | 22393 | 19.835 |
| S | Ser | TCA | 0.14 | 10217 | 9.05 |
| S | Ser | TCC | 0.102 | 7465 | 6.612 |
| S | Ser | TCG | 0.044 | 3196 | 2.831 |
| S | Ser | TCT | 0.321 | 23473 | 20.791 |
| T | Thr | ACA | 0.26 | 15649 | 13.861 |
| T | Thr | ACC | 0.236 | 14251 | 12.623 |
| T | Thr | ACG | 0.083 | 5024 | 4.45 |
| T | Thr | ACT | 0.42 | 25340 | 22.445 |
| W | Trp | TGG | 1 | 14964 | 13.254 |
| Y | Tyr | TAC | 0.187 | 7364 | 6.523 |
| Y | Tyr | TAT | 0.813 | 31912 | 28.266 |
| V | Val | GTA | 0.28 | 18541 | 16.423 |
| V | Val | GTC | 0.117 | 7778 | 6.889 |
| V | Val | GTG | 0.184 | 12184 | 10.792 |
| V | Val | GTT | 0.419 | 27713 | 24.547 |
| * | End | TAA | 0.63 | 2495 | 2.23 |
| * | End | TAG | 0.22 | 848 | 0.76 |
| * | End | TGA | 0.15 | 591 | 0.53 |

In a further variant of the invention, the extrachromosomal plasmid comprises an origin of replication with a nucleotide sequence having at least 80%, 90%, preferably at least 95% identity to the sequence deposited under SEQ ID NO:12. This origin of replication is particularly suitable for replication in Cyanobacterium sp. with the accession number PTA-13311.

In a further variant the cyanobacterial cell further comprises a gene having at least 80%, 90%, preferably at least 95% sequence identity to the nucleotide sequence deposited under SEQ ID NO:13 which codes for a replication initiation factor binding to the above-mentioned origin of replication. The gene coding for the replication initiation factor binding to the origin of replication can, for instance, be present on the extrachromosomal plasmid itself which also harbors the origin of replication. Alternatively, the gene coding for the replication initiation factor can be present in the chromosomes or other extrachromosomal plasmids of the cyanobacterial cell. The origin of replication and the gene coding for the replication initiation protein binding to said origin of replication are particularly suitable for replication of the extrachromosomal plasmid in Cyanobacterium sp. with the accession number PTA-13311, and ensure stable replication of the plasmid in the metabolically enhanced cyanobacterial cell.

In a further variant of the invention, the extrachromosomal plasmid comprises a sequence having at least 90% identity, preferably at least 95% identity to the sequence deposited under SEQ ID NO:14. This plasmid is endogenous to the species Cyanobacterium sp. with the accession number PTA-13311 and is therefore more stable when transformed to the metabolically enhanced cyanobacterial cell than plasmids derived from completely different organisms. In some embodiments, the entire endogenous plasmid may be inserted in a vector.

The extrachromosomal plasmid can also be part of a shuttle vector which is characterized by being replicable in both *Escherichia coli* and cyanobacterial species. To this end, the shuttle vector can comprise a promoter functioning in cyanobacteria and *E. coli* and a DNA sequence encoding a protein functioning as a selective marker for both *Escherichia coli* and cyanobacteria. Alternatively, the shuttle vector can include two different promoter systems, one functioning in cyanobacteria and the other one functioning in *E. coli*. With such a shuttle vector the efficient transformation of cyanobacteria and the expression of recombinant genes of interest are enabled. The shuttle vector can further contain a replication unit that functions in a broad range of cyanobacterial genera. The shuttle vector can also contain a replication unit for propagation in *E. coli* for ease of cloning and genetic manipulation in *E. coli* prior to the transformation of the shuttle vector into cyanobacteria.

In a further embodiment, the metabolically enhanced cyanobacterial cell comprises at least one further recombinant gene encoding a second $Zn^{2+}$ dependent alcohol dehydrogenase enzyme. In some embodiments, the nucleic acid sequence of the recombinant gene encoding the first $Zn^{2+}$ dependent alcohol dehydrogenase enzyme differs from the nucleic acid sequence of the recombinant gene encoding the second $Zn^{2+}$ dependent alcohol dehydrogenase enzyme. Differences in the nucleic acid sequence of the adh gene can, for example, include degenerated gene sequences due to changes in the wobble bases in the triplet codon which do not change the amino acid encoded by this triplet. Another example of non-identical adh gene sequences comprises gene sequences comprising conservative mutations. In some further embodiments, the amino acid sequence of the first $Zn^{2+}$ dependent alcohol dehydrogenase enzyme differs from the amino acid sequence of the second $Zn^{2+}$ dependent alcohol dehydrogenase enzyme. Adh enzymes with different amino acid sequences can include, for example, neutral amino acid substitutions or enzyme isoforms. In this way, the gene copy number of alcohol dehydrogenase enzymes can be increased in the metabolically enhanced cyanobacterial cell to ensure an advantageously high expression level. At the same time, the risk of homologous recombination between the adh genes is avoided, which could otherwise lead to gene inactivation, for instance by an adh gene knock-out. As a result, the genetic stability of the metabolically enhanced cyanobacterium is improved so that a stable ethanol production can be maintained for a long cultivation time.

According to a further embodiment of the invention, the recombinant gene encoding the first $Zn^{2+}$ dependent alcohol dehydrogenase enzyme and the recombinant gene encoding the second $Zn^{2+}$ dependent alcohol dehydrogenase enzyme are both under the transcriptional control of an inducible promoter or are both under the transcriptional control of inducible promoters which are inducible under the same conditions. In this way, particularly high Adh activity levels can be achieved in the cyanobacterial cell and high ethanol production rates can be accomplished.

In particular, the inducible promoters of any of the above embodiments may be selected from the endogenous inducible promoters identified in Cyanobacterium sp. with the ATCC accession number PTA-13311 listed in Table 2, and variants thereof.

TABLE 2

Listing of promoters inducible by a change in the concentration of $Ni^{2+}$, $Cu^{2+}$ $Co^{2+}$ and $Zn^{2+}$ identified in ABICyano1:

| GENE ID | SEQ ID NO: | HOMOLOGY | INDUCIBLE BY |
|---|---|---|---|
| ABICyano1_orf0128 | 48 | hypothetical protein | $Ni^{2+}$ |
| ABICyano1_orf1486 | 49 | putative nickel-containing superoxide dismutase | $Ni^{2+}$ |
| ABICyano1_orf3164 | 50 | ferrochelatase | $Ni^{2+}$ |
| ABICyano1_orf3293 | 51 | hypothetical protein L8106_16134 | $Ni^{2+}$ |
| ABICyano1_orf3621 | 52 | hypothetical protein Cyan7822_1798 | $Ni^{2+}$ |
| ABICyano1_orf3635 | 53 | carbohydrate-selective porin | $Ni^{2+}$ |
| ABICyano1_orf3858 | 54 | manganese/iron superoxide dismutase-like protein | $Ni^{2+}$ |
| ABICyano1_orf1071 | 55 | Mn transporter | $Zn^{2+}$ |
| ABICyano1_orf1072 | 56 | ABC transporter family protein | $Zn^{2+}$ |
| ABICyano1_orf1074 | 57 | ABC 3 transport family | $Zn^{2+}$ |
| ABICyano1_orf1075 | 58 | No hits found –\|– KEGG: –\|– CyanoBase | $Zn^{2+}$ |
| ABICyano1_orf1542 | 59 | hypothetical protein PCC8801_4423 | $Zn^{2+}$ |
| ABICyano1_orf1823 | 60 | RNA polymerase sigma factor | $Zn^{2+}$ |
| ABICyano1_orf1824 | 61 | No hits found –\|– KEGG: –\|– CyanoBase | $Zn^{2+}$ |
| ABICyano1_orf3126 | 62 | Metallothionein | $Zn^{2+}$ |
| ABICyano1_orf3389 | 63 | HtrA2 peptidase | $Zn^{2+}$ |
| ABICyano1_orf0221 | 64 | CopA family copper-resistance protein | $Cu^{2+}$ |
| ABICyano1_orf0222 | 65 | copper resistance B | $Cu^{2+}$ |
| ABICyano1_orf0223 | 66 | No hits found –\|– KEGG: –\|– CyanoBase | $Cu^{2+}$ |
| ABICyano1_orf0316 | 67 | hypothetical protein CY0110_11047 | $Cu^{2+}$ |
| ABICyano1_orf3232 | 68 | cation-transporting ATPase | $Cu^{2+}$ |
| ABICyano1_orf3461 | 69 | petJ | $Cu^{2+}$ depletion |
| ABICyano1_orf3749 | 70 | conserved hypothetical protein | $Co^{2+}$ |

In a fourth aspect, this invention provides a method for producing the above-described metabolically enhanced cyanobacterial cell for the production of ethanol. The method comprises the steps of:

A) providing a cyanobacterial cell,

B) introducing the at least one recombinant gene encoding the pyruvate decarboxylase enzyme and the at least one recombinant gene encoding the first $Zn^{2+}$ dependent alcohol dehydrogenase enzyme into the wild type host cell, wherein (i) the Michaelis constant $K_m$ for NADPH of the alcohol dehydrogenase enzyme is lower than the Michaelis constant $K_m$ for NADH of the alcohol dehydrogenase enzyme, and (ii) the Michaelis constant $K_m$ for acetaldehyde of the alcohol dehydrogenase enzyme is lower than $0.08 \cdot 10^{-3}$ M, preferably lower than $0.07 \cdot 10^{-3}$ M, most preferred lower than $0.06 \cdot 10^{-3}$ M;

or the Michaelis constant $K_m$ for acetaldehyde of the alcohol dehydrogenase enzyme is higher than $0.65 \cdot 10^{-3}$ M, higher than $0.7 \cdot 10^{-3}$ M, or higher than $0.73 \cdot 10^{-3}$ M, but lower than $10 \cdot 10^{-3}$ M, preferably lower than $9 \cdot 10^{-3}$ M, most preferred lower than $8 \cdot 10^{-3}$ M, and the Michaelis constant $K_m$ for ethanol of the alcohol dehydrogenase enzyme is higher than $20 \cdot 10^{-3}$ M, preferably higher than $25 \cdot 10^{-3}$ M, most preferred higher than $30 \cdot 10^{-3}$ M, resulting in the metabolically enhanced cyanobacterial cell for the production of ethanol.

In further embodiments of the method, any one of the above-described variants of the metabolically enhanced cyanobacterial cell is produced.

In a fifth aspect, this invention provides a method for producing ethanol, comprising the method steps of:

a) providing the metabolically enhanced cyanobacterial cell for the production of ethanol or any of the variants thereof as described above,
b) culturing the metabolically enhanced cyanobacterial cell in a growth medium under the exposure of light, the cyanobacterial cell producing ethanol while being cultured,
c) retrieving the ethanol from the cyanobacterial cell, the growth medium and/or a headspace above the growth medium.

This method provides enhanced ethanol yields due to the principle features and associated advantageous properties of the above-described metabolically enhanced cyanobacterial host cell.

In one embodiment, the recombinant gene encoding the pyruvate decarboxylase enzyme is under the transcriptional control of an inducible promoter which can be induced by an exogenous stimulus. In this case, method step b) comprises providing or enhancing the exogenous stimulus, thereby inducing or enhancing ethanol production. In this way, the ethanol production can be decoupled from metabolic pathways of the cell which are essential for growth and proliferation, thereby allowing accumulation of high cell densities in the culture and large amounts of precursor substrates prior to induction of the Pdc and, thus, the ethanol formation. In this way, significantly increased amounts of ethanol can be produced.

In another embodiment, both the recombinant gene encoding the pyruvate decarboxylase enzyme and the recombinant gene encoding the $Zn^{2+}$ dependent alcohol dehydrogenase enzyme are under the transcriptional control of the same single inducible promoter which can be induced by an exogenous stimulus and method step b) comprises providing or enhancing the exogenous stimulus. In this way, particularly high ethanol production rates are achieved.

In a sixth aspect of the invention, an isolated nucleic acid sequence is provided which comprises at least one recombinant gene encoding a $Zn^{2+}$ dependent alcohol dehydrogenase enzyme (Adh). The recombinant gene comprises a nucleic acid sequence having at least 80% sequence identity, preferably at least 85% sequence identity, more preferably at least 90% sequence identity and most preferred at least 95% sequence identity to:

SEQ ID NO:15,
SEQ ID NO:16,
SEQ ID NO:17, subject to the condition that the requirements are fulfilled that (i) the Michaelis constant $K_m$ for NADPH of the alcohol dehydrogenase enzyme is lower than the Michaelis constant $K_m$ for NADH of the alcohol dehydrogenase enzyme, and (ii) the Michaelis constant $K_m$ for acetaldehyde of the alcohol dehydrogenase enzyme is lower than $0.08 \cdot 10^{-3}$ M, preferably lower than $0.07 \cdot 10^{-3}$ M, most preferred lower than $0.06 \cdot 10^{-3}$ M.

In a seventh aspect of the invention, an isolated nucleic acid sequence is provided which comprises at least one recombinant gene encoding a $Zn^{2+}$ dependent alcohol dehydrogenase enzyme (Adh). The recombinant gene comprises a nucleic acid sequence having at least 80% sequence identity, preferably at least 85% sequence identity, more preferably at least 90% sequence identity and most preferred at least 95% sequence identity to:

SEQ ID NO:18,
SEQ ID NO:19,
SEQ ID NO:20, or
SEQ ID NO:22, subject to the condition that the requirements are fulfilled that (i) the Michaelis constant $K_m$ for NADPH of the alcohol dehydrogenase enzyme is lower than the Michaelis constant $K_m$ for NADH of the alcohol dehydrogenase enzyme, and (ii) the Michaelis constant $K_m$ for acetaldehyde of the alcohol dehydrogenase enzyme is higher than $0.65 \cdot 10^{-3}$ M, higher than $0.7 \cdot 10^{-3}$ M or higher than $0.73 \cdot 10^{-3}$ M, but lower than $10 \cdot 10^{-3}$ M, preferably lower than $9 \cdot 10^{-3}$ M, most preferred lower than $8 \cdot 10^{-3}$ M, and at the same time (iii) the Michaelis constant $K_m$ for ethanol of the alcohol dehydrogenase enzyme is higher than $20 \cdot 10^{-3}$ M, preferably higher than $25 \cdot 10^{-3}$ M, most preferred higher than $30 \cdot 10^{-3}$ M.

In an eighth aspect of the invention, an isolated nucleic acid sequence is provided which comprises at least one recombinant gene encoding a $Zn^{2+}$ dependent alcohol dehydrogenase enzyme (Adh). The recombinant gene comprises a nucleic acid sequence having at least 92% sequence identity, preferably at least 95% sequence identity to:

SEQ ID NO:23, subject to the condition that the requirements are fulfilled that (i) the Michaelis constant $K_m$ for NADPH of the alcohol dehydrogenase enzyme is lower than the Michaelis constant $K_m$ for NADH of the alcohol dehydrogenase enzyme, and (ii) the Michaelis constant $K_m$ for acetaldehyde of the alcohol dehydrogenase enzyme is higher than $0.65 \cdot 10^{-3}$ M, higher than $0.7 \cdot 10^{-3}$ M or higher than $0.73 \cdot 10^{-3}$ M, but lower than $10 \cdot 10^{-3}$ M, preferably lower than $9 \cdot 10^{-3}$ M, most preferred lower than $8 \cdot 10^{-3}$ M, and at the same time (iii) the Michaelis constant $K_m$ for ethanol of the alcohol dehydrogenase enzyme is higher than $20 \cdot 10^{-3}$ M, preferably higher than $25 \cdot 10^{-3}$ M, most preferred higher than $30 \cdot 10^{-3}$ M.

In a ninth aspect of the invention, an isolated nucleic acid sequence is provided which comprises at least one recombinant gene encoding a $Zn^{2+}$ dependent alcohol dehydrogenase enzyme (Adh). The recombinant gene comprises a nucleic acid sequence having at least 98% sequence identity to:

SEQ ID NO:24, subject to the condition that the requirements are fulfilled that (i) the Michaelis constant $K_m$ for NADPH of the alcohol dehydrogenase enzyme is lower than the Michaelis constant $K_m$ for NADH of the alcohol dehydrogenase enzyme, and (ii) the Michaelis constant $K_m$ for acetaldehyde of the alcohol dehydrogenase enzyme is higher than $0.65 \cdot 10^{-3}$ M, higher than $0.7 \cdot 10^{-3}$ M or higher than $0.73 \cdot 10^{-3}$ M, but lower than $10 \cdot 10^{-3}$ M, preferably lower than $9 \cdot 10^{-3}$ M, most preferred lower than $8 \cdot 10^{-3}$ M, and at the same time (iii) the Michaelis constant $K_m$ for ethanol of the alcohol dehydrogenase enzyme is higher than $20 \cdot 10^{-3}$ M, preferably higher than $25 \cdot 10^{-3}$ M, most preferred higher than $30 \cdot 10^{-3}$ M.

The above-described recombinant genes encode $Zn^{2+}$ dependent alcohol dehydrogenase enzymes that were identified by the inventors in the screening procedure and exemplarily possess the $K_m$ values for NADPH, acetaldehyde and/or ethanol required for carrying out the present invention. Adh enzymes that were initially identified in the screening procedure but did not meet the required $K_m$ values were dismissed.

In some embodiments, the above-described isolated nucleic acid sequences further comprise at least one recombinant gene encoding a pyruvate decarboxylase enzyme (Pdc) converting pyruvate to acetaldehyde.

In further embodiments, a transcription terminator sequence is present between the recombinant gene encoding the pyruvate decarboxylase enzyme and the recombinant gene encoding the alcohol dehydrogenase enzyme. In this way, translation of the Pdc and Adh from separate mRNAs is achieved which has been found by the inventors to lead to significantly improved ethanol yields.

The recombinant gene encoding the alcohol dehydrogenase enzyme can be under the transcriptional control of a constitutive promoter. In this way, a certain level of transcription and, therefore, enzymatic activity of the corresponding Adh enzyme can be achieved when the isolated nucleic acid sequence is used for metabolically enhancing a host cell. This is, for example, advantageous to maintain continuous conversion of acetaldehyde to ethanol by the cell and avoid harmful accumulation of acetaldehyde in higher amounts. Suitable constitutive promoters include, without limitation, the PrpsL promoter (Gene ID: ABICyano1_orf1758), PpsaA promoter (ABICyano1_orf3243), PpsbB (ABICyano1_orf2107), PcpcB promoter (ABICyano1_orf2472), PatpG (ABICyano1_orf1814), PrbcL promoter (ABICyano1_orf1369), PpetE promoter (ABICyano1_orf2417), and variations thereof. Further suitable endogenous constitutive promoters from genes with unknown function exhibiting appropriate transcriptional activity include, without limitation, the promoters of Gene IDs ABICyano_orf1924, ABICyano_orf1997, ABICyano_orf3446, ABICyano_orf0865, ABICyano_orf1919, ABICyano_orf3278, ABICyano_orf1181, ABICyano_orf1627, ABICyano_orf0265 and ABICyano_orf2536, and variants thereof.

The recombinant gene encoding the pyruvate decarboxylase enzyme can be under the transcriptional control of an inducible promoter. The inducible promoter can, for example, be inducible by a change of a metal-ion concentration. Such a change of metal-ion concentration includes for instance the addition or depletion of certain metal ions. Suitable inducible promoters include, without limitation, the PziaA promoter, the PsmtA promoter, the PaztA promoter, the PcorT promoter, the PnrsB promoter, the PpetJ promoter, and variations thereof. The inducible promoter can, for instance, also be a nitrate inducible promoter. Suitable nitrate inducible promoters include, without limitation, the PnirA promoter, the PnrtA promoter, the PnarB promoter, the PmntC promoter, and variations thereof. Furthermore, the inducible promoter may be selected from the endogenous inducible promoters identified in Cyanobacterium sp. with the ATCC accession number PTA-13311 listed in Table 2 above, and variants thereof. Preferably, the promoter is copper-inducible, such as for instance the Porf0316 promoter or the Porf0221 promoter.

In preferred embodiments wherein the isolated nucleic acid sequence comprises both the recombinant gene encoding the pyruvate decarboxylase enzyme and the recombinant gene encoding the $Zn^{2+}$ dependent alcohol dehydrogenase enzyme, the recombinant gene encoding the pyruvate decarboxylase enzyme and the recombinant gene encoding the $Zn^{2+}$ dependent alcohol dehydrogenase enzyme are under the transcriptional control of different promoters. For example, the recombinant gene encoding the pyruvate decarboxylase enzyme can be under the transcriptional control of an inducible promoter and the recombinant gene encoding the $Zn^{2+}$ dependent alcohol dehydrogenase enzyme can be under the transcriptional control of a constitutive promoter. Preferably, a transcription terminator is present between the recombinant gene encoding the pyruvate decarboxylase enzyme and the recombinant gene encoding the $Zn^{2+}$ dependent alcohol dehydrogenase enzyme. The transcriptional control of the Pdc and Adh encoding genes by separate promoters and the corresponding translation from separate mRNAs is a combination that has been found to significantly improve ethanol production.

In a tenth aspect, use of a metabolically enhanced host cell for the production of a C3, C4, C5, C6, C7, C8, C9 and/or C10 alcohol is provided. The metabolically enhanced host cell comprises at least one recombinant gene encoding a $Zn^{2+}$ dependent alcohol dehydrogenase enzyme (Adh) converting a C3, C4, C5, C6, C7, C8, C9 and/or C10 aldehyde into the corresponding alcohol, wherein the Michaelis constant $K_m$ for the C3, C4, C5, C6, C7, C8, C9 and/or C10 aldehyde of the alcohol dehydrogenase enzyme is lower than $0.2 \cdot 10^{-3}$ M, preferably lower than $0.15 \cdot 10^{-3}$ M, most preferred lower than $0.12 \cdot 10^{-3}$ M.

Interestingly, such $Zn^{2+}$ dependent alcohol dehydrogenase enzymes exhibit a relatively broad substrate spectrum and efficiently convert C3, C4, C5, C6, C7, C8, C9 and/or C10 aldehydes into the corresponding alcohols. The activity and/or affinity for the C3, C4, C5, C6, C7, C8, C9 and/or C10 aldehyde substrate is often significantly higher than for acetaldehyde, so that these substrates are even more efficiently converted by the Adh enzymes.

In one embodiment, the Michaelis constant $K_m$ for NADPH of the alcohol dehydrogenase enzyme is lower than the Michaelis constant $K_m$ for NADH of the alcohol dehydrogenase enzyme.

In another embodiment, the alcohol dehydrogenase enzyme comprises an amino acid sequence having at least 80% sequence identity, preferably at least 85% sequence identity, more preferably at least 90% sequence identity and most preferred at least 95% sequence identity to SEQ ID NO:1,
SEQ ID NO:2,
SEQ ID NO:3, or
SEQ ID NO:11.

The C3, C4, C5, C6, C7, C8, C9 and/or C10 aldehyde can, for example, be provided as an aldehyde intermediate from a heterologous biosynthesis pathway, so that the aldehyde intermediate can be reduced by the alcohol dehydrogenase enzyme into the corresponding alcohol. Examples for suitable heterologous biosynthesis pathways include the expanded 1-butanol pathway, the engineered reversal of the β-oxidation pathway, and the 2-keto acid metabolic pathways. For a more detailed description of these and other suitable heterologous biosynthetic pathways for provision of the aldehyde intermediate, reference is made to Wang et al. (Wang, B., Wang, J., Zhang, W., Meldrum, D. R.: Application of synthetic biology in cyanobacteria and algae, Frontiers in Microbiology 2012, 3, 344) and Desai and Atsumi (Desai, S. H., Atsumi, S.: Photosynthetic approaches to chemical biotechnology, Current Opinion in Biotechnology 2013, 24, in press), as well as the references cited therein. Therefore, in another embodiment, the metabolically enhanced host cell comprises at least one metabolic enhancement resulting in an enhanced availability of a C3, C4, C5, C6, C7, C8, C9 and/or C10 aldehyde intermediate in the host cell in comparison to a wild type of the host cell. The last reduction step, from the aldehyde intermediate to the corresponding alcohol, of the heterologous biosynthetic pathway to produce longer chain alcohols can then be realized by the above-described recombinant genes encoding the $Zn^{2+}$ dependent alcohol dehydrogenase enzymes that were identified by the inventors in the screening procedure.

The alcohol can be a primary, secondary or tertiary alcohol. The alcohol can be an alkanol or a phenol. In particular, the alcohol is selected from the group comprising propan-1-ol (C3), butan-1-ol (C4), pentan-1-ol (C5), hexan-1-ol (C6), heptan-1-ol (C7), octan-1-ol (C8), nonan-1-ol (C9), decan-1-ol (C10), propan-2-ol (C3), butan-2-ol (C4), pentan-2-ol (C5), hexan-2-ol (C6), heptan-2-ol (C7), 2-methylbutan-1-ol (C5), cyclohexanol (C6), 2-methylpropan-2-ol (C4), 2-methylbutan-2-ol (C5), 2-methylpentan-2-ol (C6), 2-methylhexan-2-ol (C7), 2-methylheptan-2-ol (C8), 3-methylpentan-3-ol (C6), 3-methyloctan-3-ol (C9), benzyl alcohol (C7), phenylethyl alcohol (C8), and combinations thereof.

In yet further embodiments, the host cell may also comprise any of the features of the above-described metabolically enhanced cyanobacterial cells for ethanol production that are also commensurate to the production of the C3, C4, C5, C6, C7, C8, C9 and/or C10 alcohol from the C3, C4, C5, C6, C7, C8, C9 and/or C10 aldehyde.

FIGURES AND EMBODIMENTS

In the following, certain embodiments of the invention will be explained in more detail with reference to figures and experimental data. The figures and examples are not intended to be limiting with respect to specific details.

Example 1

Pre-Cultivation of Cyanobacterial Strains

Cyanobacterial cells were grown in 50 ml of BG11 or mBG11 medium in Erlenmeyer flasks.

The recipe for the cyanobacterial growth medium mBG11 was as follows:

$NaNO_3$: 1.5 g
$K_2HPO_4$: 0.04 g
$MgSO_4.7H_2O$: 0.075 g
$CaCl_2.2H_2O$: 0.036 g
Citric acid: 0.006 g
Ferric ammonium citrate: 0.006 g
EDTA (disodium salt): 0.001 g
$NaCO_3$: 0.02 g
Trace metal mix A5: 1.0 ml
Distilled water: 1.0 L
(pH 7.1 adjusted after sterilization)

Herein, the recipe for the trace metal mix A5 was:

$H_3BO_3$: 2.86 g
$MnCl_2.4H_2O$: 1.81 g
*$ZnSO_4.7H_2O$: 0.222 g
$NaMoO_4.2H_2O$: 0.39 g
$CuSO_4.5H_2O$: 0.079 g
*$Co(NO_3)_2.6H_2O$: 49.4 mg
Distilled water or seawater (35 practical salinity units=psu; see Unesco (1981a).
The Practical Salinity Scale 1978 and the International Equation of State of Seawater 1980. *Tech. Pap. Mar. Sci.,* 36: 25 pp.): 1.0 L The asterisk (*) denotes those metal supplements that can be either temporarily omitted or used in reduced amounts if these metals are also used as inductor for corresponding metal-inducible promoters in the metabolically enhanced cyanobacterial strain.

The cells were constantly illuminated at an illumination intensity of approximately 50 $\mu E \cdot s^{-1} \cdot m^{-2}$ at 28° C. on a rotary shaker.

Example 2

In Vivo Screening of NADPH-Dependent Native Adh Function of Genes in Wild-Type Strains For the in vivo screening of NADPH-dependent native Adh function of genes in wild-type strains, the cyanobacterial cells from the pre-culture of example 1 were pelleted by 15 minutes centrifugation at 4143 rcf at 20° C. on a Rotina 420R centrifuge from Hettich and then re-dissolved in 30 mM HEPES/KOH pH 7.5. 2 mL aliquots were transferred into 20 mL gas chromatography (GC) sampling vials and sealed with silicon septum caps. 5 mM acetaldehyde in water was added to the cells to obtain final concentrations of 125 μM and 250 μM acetaldehyde, respectively. At least two GC vials per wild-type strain were prepared. The GC vials were incubated at 37° C. on the GC's autosampler sample tray, wherein at least one GC vial per wild-type strain was incubated under constant illumination at a light intensity between 50 $\mu E\ m^{-2}\ s^{-1}$ and 180 $\mu E\ m^{-2}\ s^{-1}$. For example, a light intensity of 120 $\mu E\ m^2\ s^{-1}$ was used. At least one other GC vial per wild-type strain was incubated without illumination. Further on, the ethanol and acetaldehyde concentration in the GC vials was measured via headspace measurement as described further below in example 7. The measurements were repeated in intervals of 10 min and ethanol production rates and acetaldehyde consumption rates were calculated on the basis of total protein concentration in the sample. Total protein in the sample was determined as described further below in example 3. Afterwards, the ethanol production rates and acetaldehyde consumption rates for the illuminated sample and the non-illuminated sample of each wild-type strain were compared and the wild-type strains exhibiting higher ethanol production rates and acetaldehyde consumption rates under illumination were selected for further characterization.

Example 3

Preparation of Cell Extracts

Cyanobacterial cells from the liquid pre-culture from example 1 were pelleted by 15 minutes centrifugation at 4143 rcf at 20° C. on a Rotina 420R centrifuge from Hettich. The pellets were redissolved in 30 mM HEPES/KOH pH 7.5 with 150 mM KCl and 1 mM DTT, hereinafter referred to as lysis buffer. One milliliter of the cell slurry was transferred into a fresh 1.5 ml Eppendorf tube and 500 microliter of glass beads with 100 μm diameter were added. Cells were then disintegrated on a Retch mill bead mill at the highest frequency setting in two cycles of 10 minutes each with a break of 10 minutes between the cycles wherein the samples were kept on ice. Afterwards, cell debris and glass beads were removed by centrifugation at 22350 rcf for 10 minutes at 4° C. on a Micro 200R table top centrifuge from Hettich. Cell extract in the supernatant was transferred into a fresh Eppendorf tube. An aliquot of the cell extract was withdrawn for measuring the total protein concentration in the cell extract. For this purpose, a protein precipitation with DOC/TCA (Bensadoun, A. and Weinstein, D.: Assay of Proteins in the Presence of Interfering Materials, Analytical Biochemistry 1976, 70, 241-245) was performed in the aliquot. Afterwards, the protein precipitate was redissolved and the total protein concentration was measured with the method of Lowry (Lowry, O. H. et al.: Protein Measurement with the Folin Phenol Reagent, Journal of Biological Chemistry 1951, 193, 265-275). Typically, the proportion of adh enzyme amounts to less than 1% of the total protein content in the cell extract. The cell extracts were further purified by size exclusion chromatography on a PD-10 desalting column (GE Healthcare) which was equilibrated and eluted with lysis buffer according to the protocol provided by manufacturer. Accordingly, the first 3-6 ml of eluate contain the proteins including the alcohol dehydrogenase enzyme and were collected. Other fractions without proteins were discarded.

Example 4

Measurement of Adh Activity and Kinetic Constants

The optic enzymatic assay for determination of the alcohol dehydrogenase enzyme activity contained 30 mM HEPES/KOH pH 7.5, 150 mM KCl, 1 mM DTT and 0.15 mM NADPH, to which various amounts of the clarified cell extract of example 2 were added. The reaction was started by addition of acetaldehyde to a final concentration of 5 mM. The NADPH oxidation was followed at 340 nm wavelength on a Shimadzu UV2450 spectrophotometer. A constant temperature of 30° C. was maintained during the measurement (TCC controller, Shimadzu). The Adh activity was calculated in μmol/min·mg protein.

The optic enzymatic assay for determination of the $K_m$ values for acetaldehyde and NADPH of the alcohol dehydrogenase enzymes contained 30 mM HEPES/KOH pH 7.5, 150 mM KCl, 1 mM DTT and 0.15 mM NADPH. The reaction was started by addition of varying amounts of acetaldehyde in final concentrations between 1 μM and 50 mM. The NADPH oxidation was spectrophotometrically monitored at a wavelength of 340 nm on a Shimadzu UV2450 spectrophotometer. A constant temperature of 30° C. was maintained during the measurement (TCC controller, Shimadzu).

For measurement of the back reaction and the $K_m$ value for ethanol, the samples contained 0.15 mM NADP+ instead of 0.15 mM NADPH, and varying amounts of ethanol between 1 mM and about 2.5 M final concentration were added.

$K_m$ values were computed using the GraphPad Prism software, version 5 (GraphPad Software Inc., La Jolla, Calif., USA).

Figure 1A:
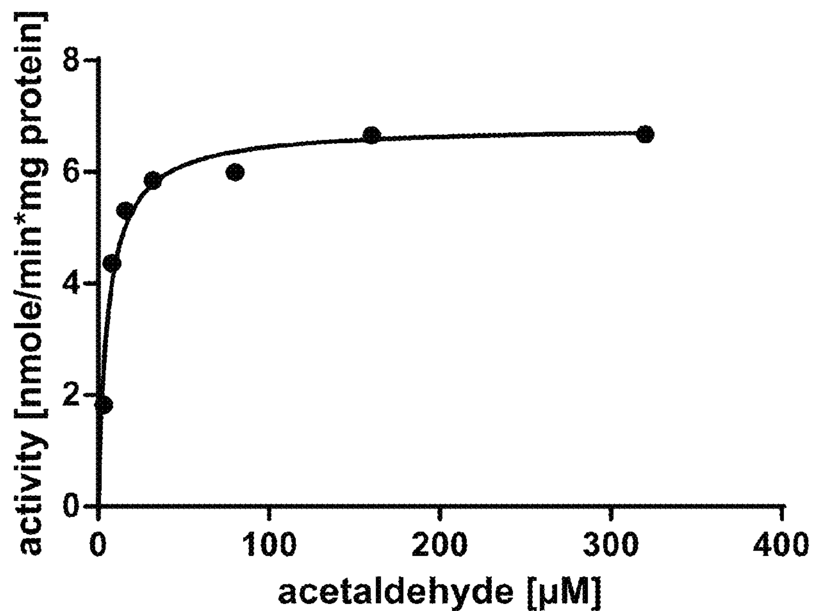
FIGS. 1A and 1B show exemplary graphical plots of the kinetic analysis of the alcohol dehydrogenase enzyme with amino acid sequence SEQ ID NO:1 from which the Michaelis constants $K_m$ for acetaldehyde (FIG. 1A) and ethanol (FIG. 1B) of the alcohol dehydrogenase enzyme were computed using the GraphPad Prism software.
Figure 1B:
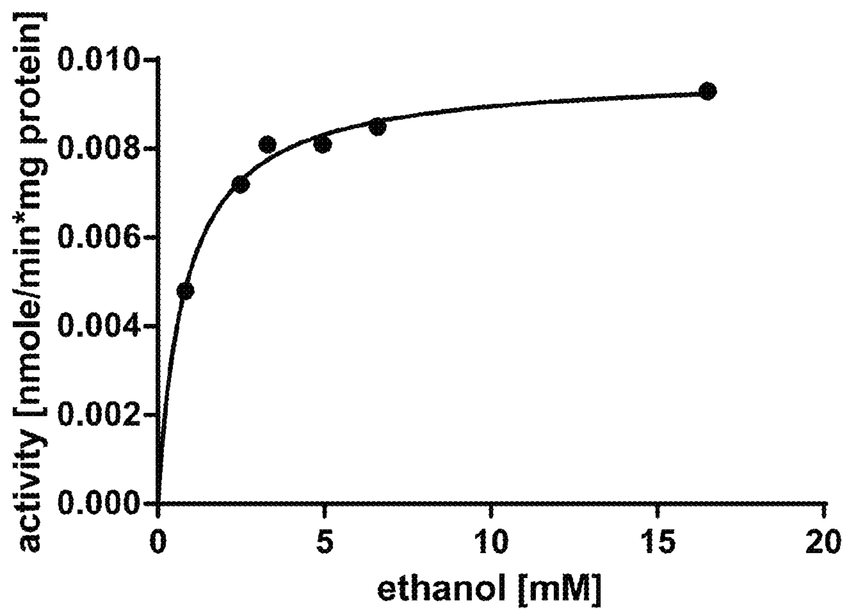
Figure 2A:
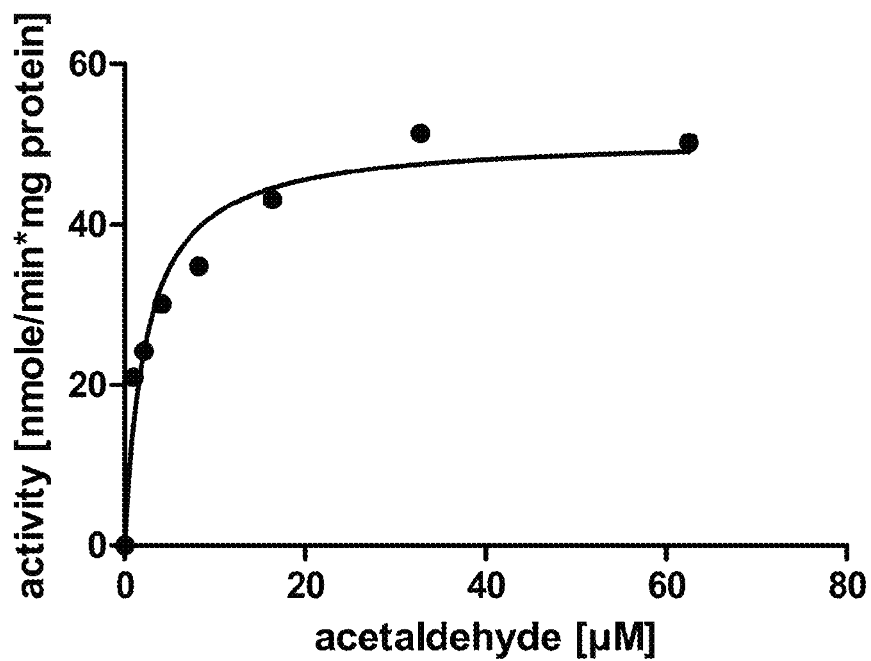
FIGS. 2A and 2B show exemplary graphical plots of the kinetic analysis of the alcohol dehydrogenase enzyme with amino acid sequence SEQ ID NO:2 from which the Michaelis constants $K_m$ for acetaldehyde (FIG. 2A) and ethanol (FIG. 2B) of the alcohol dehydrogenase enzyme were computed using the GraphPad Prism software.
Figure 2B:
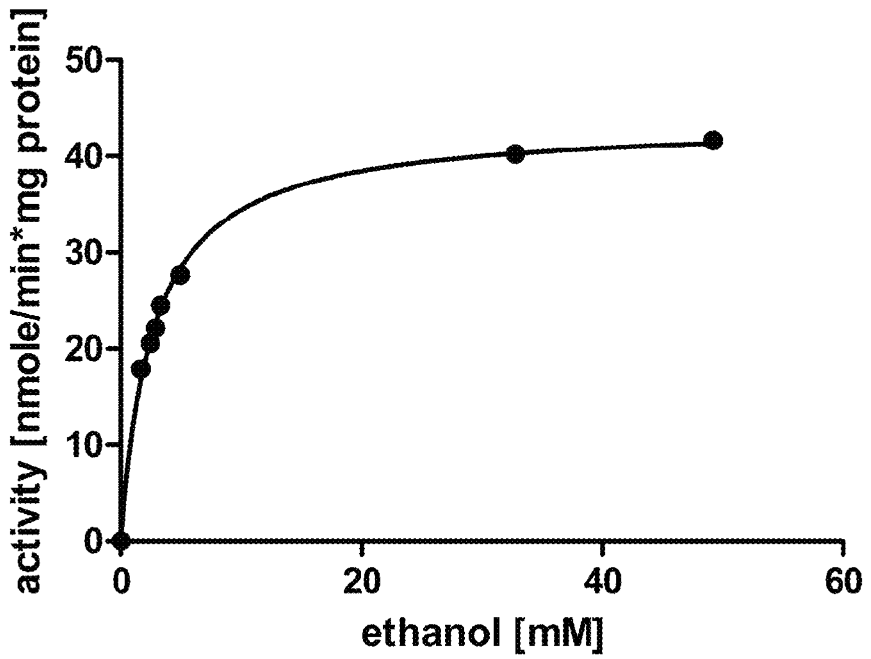

As an example, FIGS. 1A and 1B show the results from the graphical computation of the Michaelis constants $K_m$ for acetaldehyde and ethanol of the alcohol dehydrogenase from *Lyngbya* sp. with amino acid sequence SEQ ID NO:1. FIGS. 2A and 2B show the corresponding graphical computations of the Michaelis constants $K_m$ for acetaldehyde and ethanol of the alcohol dehydrogenase from *Arthrospira platensis* with amino acid sequence SEQ ID NO:2. A summary of the $K_m$ values for acetaldehyde and ethanol as well as the ratios of $K_m$ (ethanol)/$K_m$ (acetaldehyde) of the alcohol dehydrogenase enzymes of the present invention is provided in the following Table 3.

TABLE 3

Summary of the Michaelis constants for acetaldehyde (MeCHO) and ethanol (EtOH) and their corresponding ratio of the alcohol dehydrogenase enzymes of the present invention (values in brackets represent standard deviations). The alcohol dehydrogenase enzyme of *Synechocystis* sp. PCC6803 (SEQ ID NO: 26) is included as a comparative example.

| SEQ ID NO | Organism | $K_m(_{MeCHO})$ [mM] | $K_{m(EtOH)}$ [mM] | $K_{m(EtOH)}$/ $K_m(_{MeCHO})$ |
|---|---|---|---|---|
| 1 | *Lyngbya* sp. | 0.0058 (±0.0011) | 0.83 (±0.084) | 143 |
| 2 | *Arthrospira platensis* | 0.0023 (±0.0005) | 2.64 (±0.11) | 1056 |
| 3 | *Cyanothece* sp. | 0.0756 (±0.0056) | 9.33 (±1.39) | 123 |
| 4 | *Synechococcus* sp. | 0.731 (±0.070) | 32.4 (±12.4) | 44 |
| 5 | *Synechococcus* sp. | 0.783 (±0.086) | 67.0 (±16.3) | 86 |
| 6 | *Synechococcus* sp. | 1.13 (±0.076) | 29.3 (±8.5) | 26 |
| 7 | *Chroococcidiopsis* sp. | 1.79 (±0.119) | 107 (±18) | 60 |
| 8 | *Arthronema africanum* | 3.34 (±0.31) | 279 (±66) | 84 |
| 9 | *Chroococcidiopsis* sp. | 3.73 (±0.15) | 124 (±24) | 33 |
| 10 | *Cyanobacterium* sp. | 6.95 (±0.83) | 306 (±49) | 44 |
| 26 | *Synechocystis* sp. PCC6803 | 0.35 (±0.0385) | 19 (±3.61) | 54 |

Example 5

Construction of Ethanologenic Plasmid Vectors

Plasmid annotations were done with the program vector NTI. Abbreviations: CDS (coding DNA sequence); RBS (ribosome binding site); ORF (open reading frame); Km (kanamycin resistance gene). Asterisks (*) or (**), optionally followed by a number, denote recombinantly modified genes or promoters.

Figure 3A:
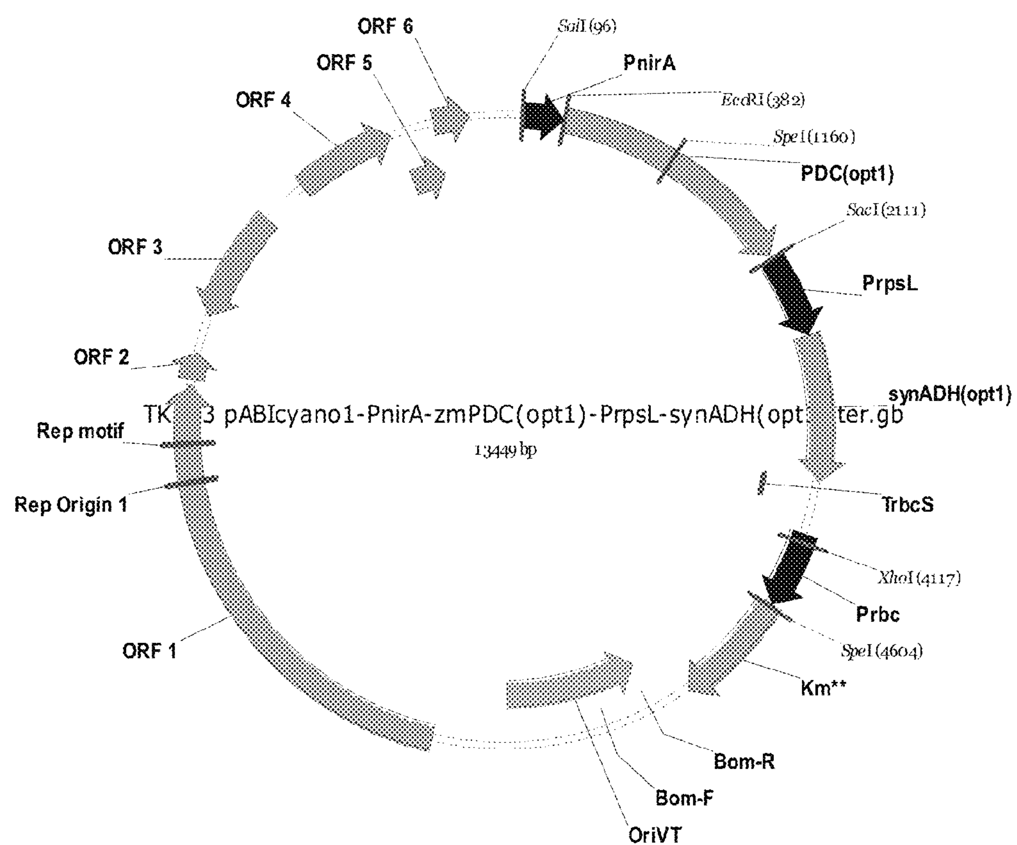
FIG. 3A is a map of plasmid construct TK293 with SEQ ID NO:27 containing the PrpsL promoter upstream of a codon improved synADH gene from *Synechocystis* sp. PCC6803 encoding the Adh enzyme with SEQ ID NO:26 and the PnirA promoter upstream of a codon improved zmPDC gene.

Plasmid construct TK293: The plasmid construct is a synthetic derivative of an endogenous 6.8 kB extrachromosomal plasmid of Cyanobacterium sp. PTA-13311. The map of TK293 is shown in FIG. 3A and its nucleotide sequence is deposited under SEQ ID NO:27. The plasmid harbors a codon improved variant of synAdh denoted synAdh(opt1) under the transcriptional control of the PrpsL promoter, and a codon improved variant from *Zymomonas mobilis* pyruvate decarboxylase denoted pdc(opt1) under the transcriptional control of the PnirA promoter. The plasmid annotations are as follows: 4055 . . . 4580 promoter Prbc; 4582 . . . 5397 CDS Km**; 12959 . . . 13207 CDS ORF6; 12699 . . . 12962 CDS ORF5; 11971 . . . 12657 CDS ORF4; 10881 . . . 11645 CDS ORF3; 10436 . . . 10621 CDS ORF2; 9736 . . . 9753 replication origin; 7215 . . . 10400 CDS replication origin binding protein; 5640 . . . 6698 replication origin OriVT; 2112 . . . 2680 PrpsL promoter; 379 . . . 2085 CDS PDC(opt1); 2684 . . . 3691 CDS synADH(opt1); 96 . . . 378 PnirA promoter; 3695 . . . 3850 TrbcS terminator.

Figure 3B:
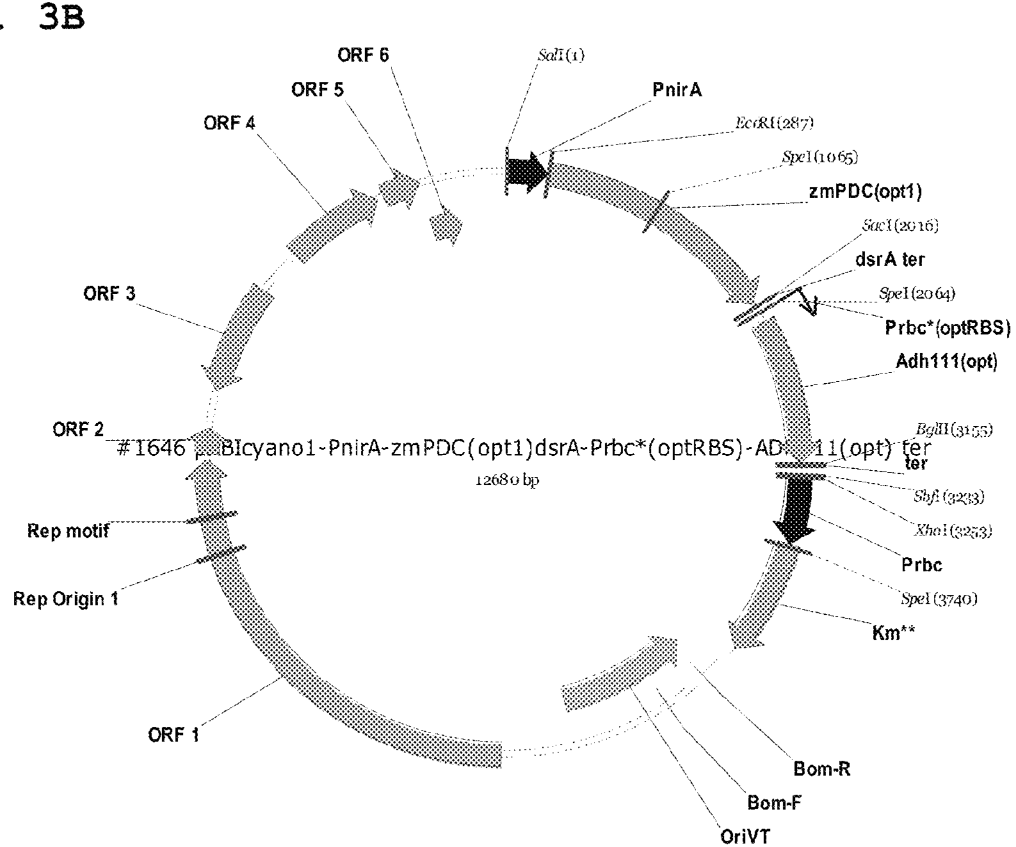
FIG. 3B is a map of plasmid construct #1646 with SEQ ID NO:28. #1646 is a derivative of TK293 containing the PnirA promoter upstream of a codon improved zmPDC gene and the Prbc promoter with optimized ribosome binding site (RBS) upstream of a codon improved adh gene from *Lyngbya* sp. encoding the Adh enzyme with SEQ ID NO:1.

Plasmid construct #1646: The plasmid construct is a derivative of TK293. The map of #1646 is shown in FIG. 3B and its nucleotide sequence is deposited under SEQ ID NO:28. The plasmid harbors a codon improved variant of an adh gene from *Lyngbya* sp., denoted Adh111(opt), encoding the Adh enzyme with SEQ ID NO:1 under the transcriptional control of the Prbc* promoter with optimized RBS, denoted Prbc*(optRBS). The plasmid further harbors a codon improved pyruvate decarboxylase gene from *Zymomonas mobilis* denoted zmPdc(opt1) under the transcriptional control of the PnirA promoter. The plasmid annotations are as follows: 284 . . . 1990 CDS zmPDC(opt1); 1 . . . 283 promoter PnirA; 4776 . . . 5834 replication origin OriVT; 6351 . . . 9536 CDS replication origin binding protein; 8872 . . . 8889 replication origin; 9572 . . . 9757 CDS ORF2; 10017 . . . 10781 CDS ORF3; 11107 . . . 11793 CDS ORF4; 11835 . . . 12098 CDS ORF5; 12095 . . . 12343 CDS ORF6; 3718.4533 Km**;

3253 . . . 3716 promoter Prbc; 2063 . . . 2131 promoter Prbc*(optRBS); 2017 . . . 2062 terminator dsrA\ter; 3167 . . . 3212 terminator ter; 2132 . . . 3148 CDS Adh111(opt).

Figure 4A:
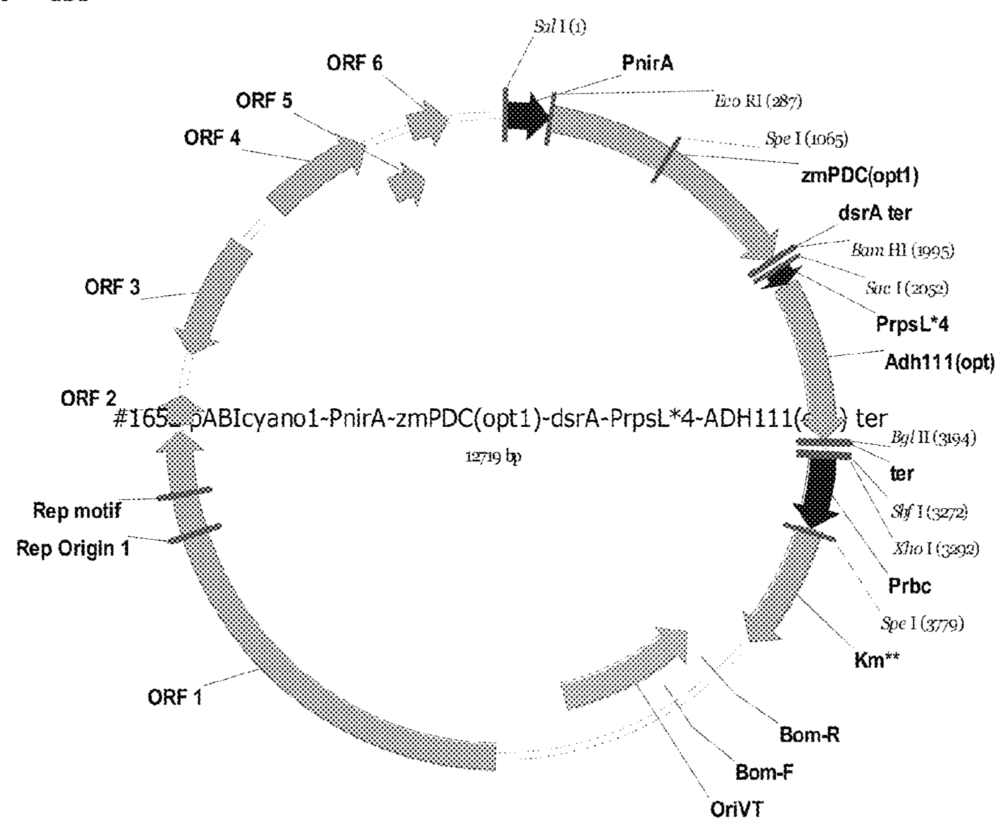
FIG. 4A is a map of plasmid construct #1652 with SEQ ID NO:29. #1652 is a derivative of TK293 containing the PnirA promoter upstream of a codon improved zmPDC gene and the PrpsL promoter with optimized RBS upstream of a codon improved adh gene from *Lyngbya* sp. encoding the Adh enzyme with SEQ ID NO:1.

Plasmid construct #1652: The plasmid construct is a derivative of TK293. The map of #1652 is shown in FIG. 4A and its nucleotide sequence is deposited under SEQ ID NO:29. The plasmid harbors a codon improved variant of an adh gene from *Lyngbya* sp., denoted Adh111(opt), encoding the Adh enzyme with SEQ ID NO:1 under the transcriptional control of the PrpsL promoter with optimized TATA box and RBS, denoted PrpsL*4. The plasmid further harbors a codon improved pyruvate decarboxylase gene from *Zymomonas mobilis* denoted zmPdc(opt1) under the transcriptional control of the PnirA promoter. The plasmid annotations are as follows: 2053 . . . 2170 promoter PrpsL*4; 3206 . . . 3251 terminator ter; 2171 . . . 3187 CDS Adh111(opt); 284 . . . 1990 CDS zmPDC(opt1); 3292 . . . 3755 promoter Prbc; 3757 . . . 4572 CDS Km**; 12134 . . . 12382 CDS ORF6; 11874 . . . 12137 CDS ORF5; 11146 . . . 11832 CDS ORF4; 10056 . . . 10820 CDS ORF3; 9611 . . . 9796 CDS ORF2; 8911 . . . 8928 replication origin; 6390 . . . 9575 replication origin binding protein; 4815 . . . 5873 origin OriVT; 1 . . . 283 promoter PnirA; 1995 . . . 2051 terminator dsrA\ter.

Figure 4B:
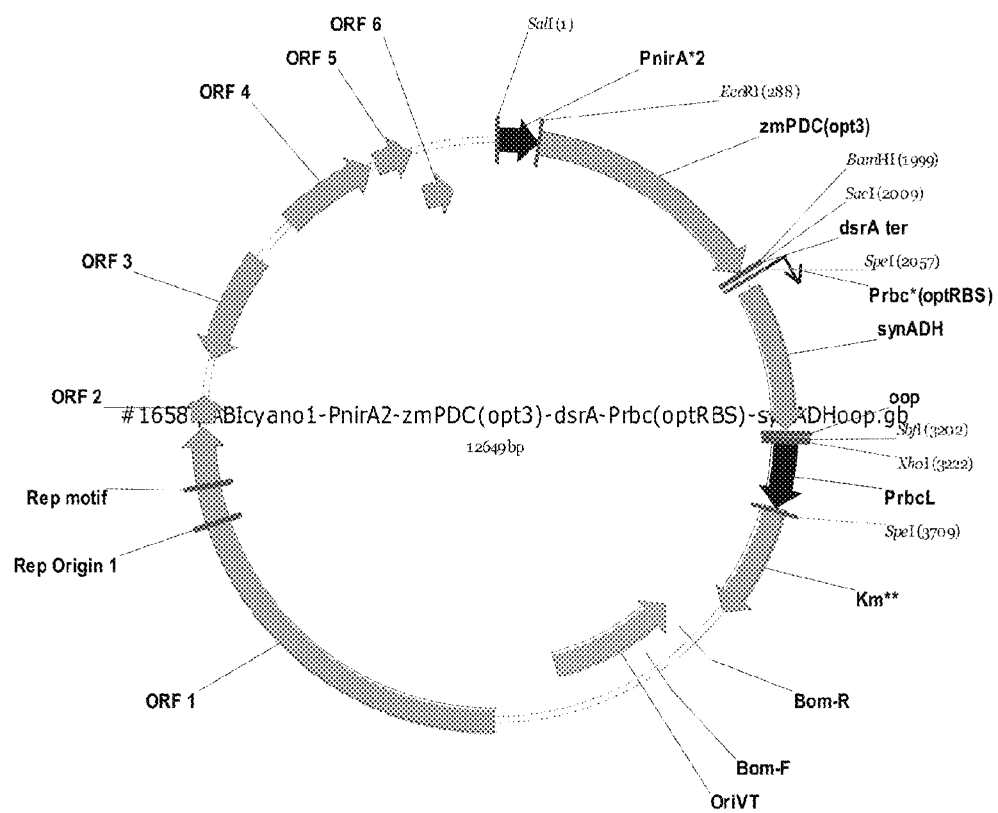
FIG. 4B is a map of plasmid construct #1658 with SEQ ID NO:30. #1658 is a derivative of TK293 containing the PnirA promoter with optimized RBS upstream of a codon improved zmPDC gene and the Prbc promoter with optimized RBS upstream of a synAdh gene from *Synechocystis* sp. PCC6803 encoding the Adh enzyme with SEQ ID NO:26.

Plasmid construct #1658: The plasmid construct is a derivative of TK293. The map of #1658 is shown in FIG. 4B and its nucleotide sequence is deposited under SEQ ID NO:30. The plasmid harbors the synAdh gene from *Synechocystis* sp. PCC6803 under the transcriptional control of the Prbc promoter with optimized RBS, denoted Prbc*(optRBS). The plasmid further harbors a codon improved pyruvate decarboxylase gene from *Zymomonas mobilis* denoted zmPdc(opt3) under the transcriptional control of an improved PnirA promoter, denoted PnirA*2. The plasmid annotations are as follows: 4745.5803 replication origin OriVT; 6320 . . . 9505 CDS replication origin binding protein; 8841 . . . 8858 replication origin; 9541 . . . 9726 CDS ORF2; 9986 . . . 10750 CDS ORF3; 11076 . . . 11762 CDS ORF4; 11804 . . . 12067 CDS ORF5; 12064 . . . 12312 CDS ORF6; 3687 . . . 4502 CDS Km**; 3222 . . . 3685 promoter PrbcL; 3165 . . . 3195 terminator oop; 2125 . . . 3135 CDS synADH; 2010 . . . 2055 terminator dsrA\ter; 2056 . . . 2124 promoter Prbc*(optRBS); 1 . . . 284 promoter PnirA*2; 285 . . . 1991 CDS zmPDC (opt3).

Figure 5A:
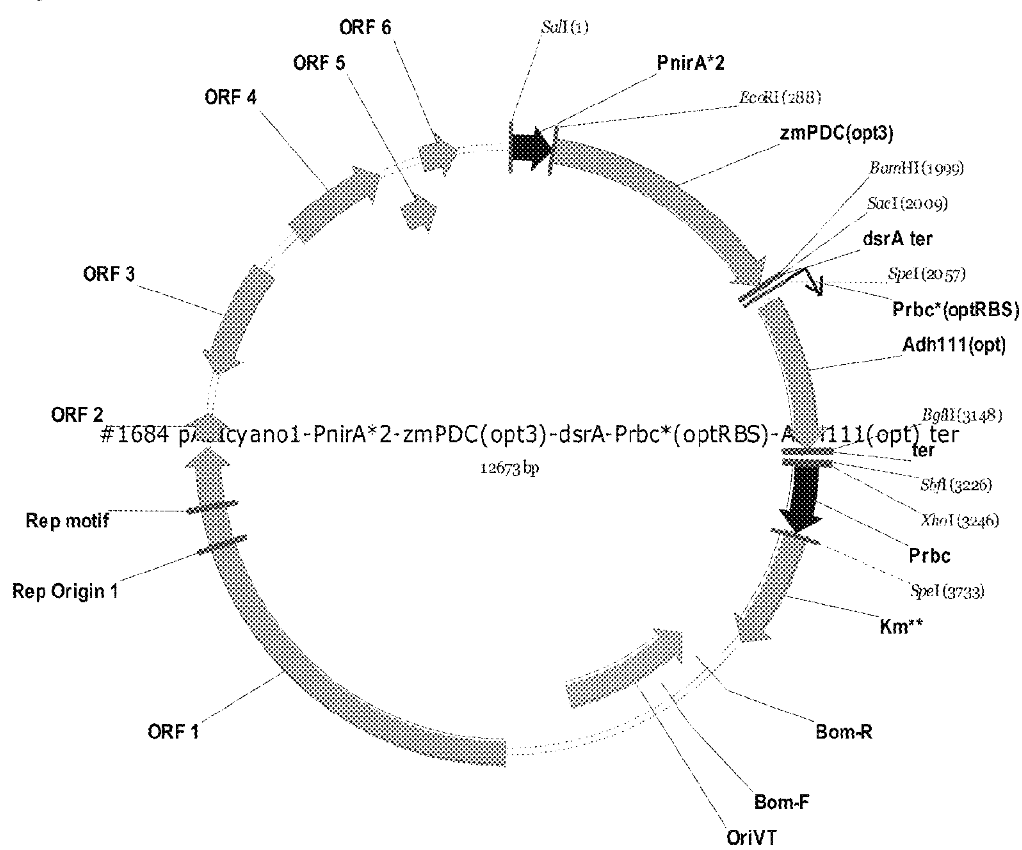
FIG. 5A is a map of plasmid construct #1684 with SEQ ID NO:31. #1684 is a derivative of TK293 containing the PnirA promoter with optimized RBS upstream of a codon improved zmPDC gene and the Prbc promoter with optimized RBS upstream of a codon improved adh gene from *Lyngbya* sp. encoding the Adh enzyme with SEQ ID NO:1.

Plasmid construct #1684: The plasmid construct is a derivative of TK293. The map of #1684 is shown in FIG. 5A and its nucleotide sequence is deposited under SEQ ID NO:31. The plasmid harbors a codon improved variant of the adh gene from *Lyngbya* sp., denoted Adh111(opt), encoding the Adh enzyme with SEQ ID NO:1 under the transcriptional control of the Prbc promoter with optimized RBS, denoted Prbc*(optRBS). The plasmid further harbors a codon improved pyruvate decarboxylase gene from *Zymomonas mobilis* denoted zmPdc(opt3) under the transcriptional control of the improved PnirA promoter, denoted PnirA*2. The plasmid annotations are as follows: 2125 . . . 3141 CDS Adh111(opt); 3160 . . . 3205 terminator ter; 2010 . . . 2055 terminator dsrA\ter; 2056 . . . 2124 promoter Prbc*(optRBS); 3246 . . . 3709 promoter Prbc; 3711 . . . 4526 CDS Km**; 12088 . . . 12336 CDS ORF6; 11828 . . . 12091 CDS ORF5; 11100 . . . 11786 CDS ORF4; 10010 . . . 10774 CDS ORF3; 9565 . . . 9750 CDS ORF2; 8865 . . . 8882 replication origin; CDS 6344 . . . 9529 replication origin binding protein; 4769 . . . 5827 origin OriVT; 4 . . . 287 promoter PnirA*2; 293 . . . 1991 CDS zmPDC(opt3).

Figure 5B:
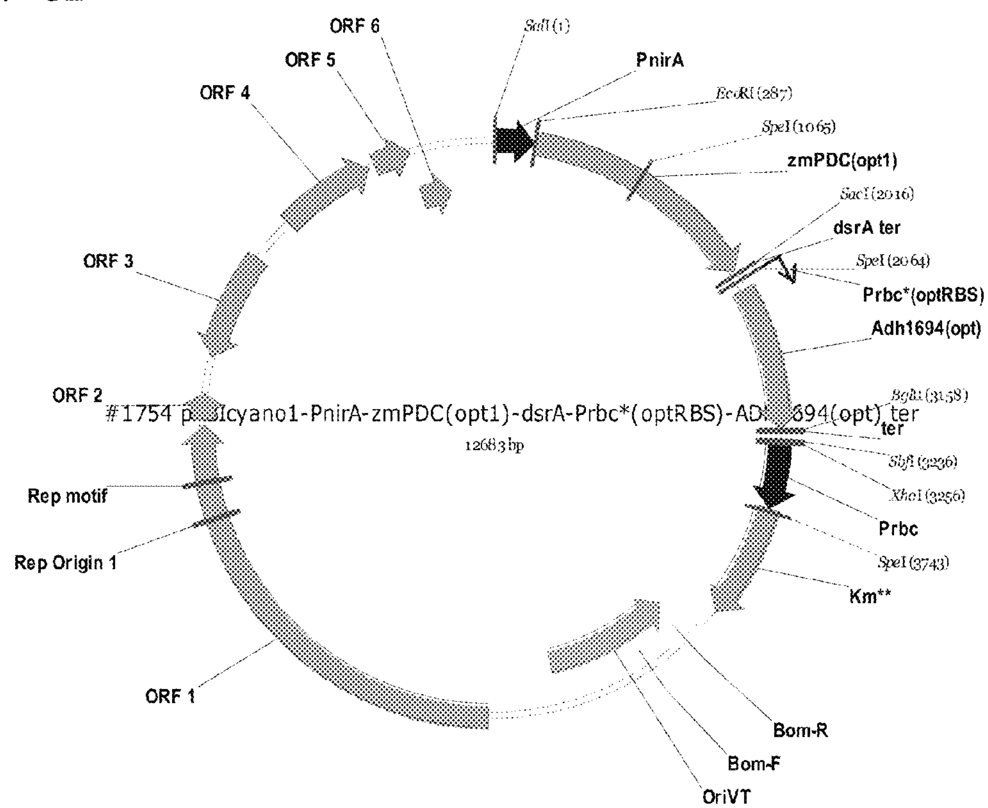
FIG. 5B is a map of plasmid construct #1754 with SEQ ID NO:32. #1754 is a derivative of TK293 containing the PnirA promoter upstream of a codon improved zmPDC gene and the Prbc promoter with optimized RBS upstream of a codon improved adh gene from *Arthrospira platensis* encoding the Adh enzyme with SEQ ID NO:2.

Plasmid construct #1754: The plasmid construct is a derivative of TK293. The map of #1754 is shown in FIG. 5B and its nucleotide sequence is deposited under SEQ ID NO:32. The plasmid harbors a codon improved variant of an adh gene from *Arthrospira platensis*, denoted Adh1694(opt), encoding the Adh enzyme with SEQ ID NO:2 under the transcriptional control of the Prbc promoter with optimized RBS, denoted Prbc*(optRBS). The plasmid further harbors a codon improved pyruvate decarboxylase gene from *Zymomonas* mobilis denoted zmPdc(opt1) under the transcriptional control of the PnirA promoter. The plasmid annotations are as follows: 2063 . . . 2131 promoter Prbc*(optRBS); 2017 . . . 2062 terminator dsrA\ter; 2132 . . . 3154 CDS Adh1694(opt); 3170 . . . 3215 terminator ter; 284 . . . 1990 CDS zmPDC (opt1); 1 . . . 283 promoter PnirA; 4779 . . . 5837 origin OriVT; 6354 . . . 9539 CDS replication origin binding protein; 8875 . . . 8892 replication origin; 9575 . . . 9760 CDS ORF2; 10020 . . . 10784 CDS ORF3; 11110 . . . 11796 CDS ORF4; 11838 . . . 12101 CDS ORF5; 12098 . . . 12346 CDS ORF6; 3721 . . . 4536 CDS Km**; 3256 . . . 3719 promoter Prbc.

Figure 6A:
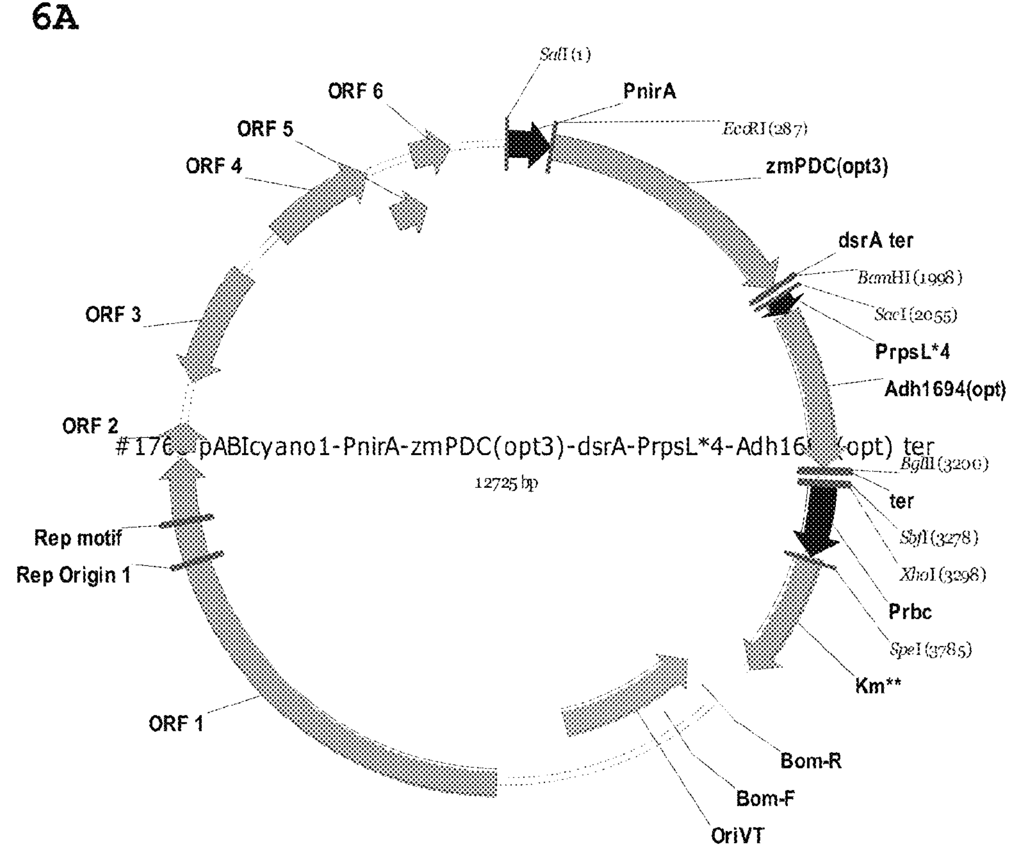
FIG. 6A is a map of plasmid construct #1760 with SEQ ID NO:33. #1760 is a derivative of TK293 containing the PnirA promoter upstream of a codon improved zmPDC gene and the PrpsL promoter with optimized RBS upstream of a codon improved adh gene from *Arthrospira platensis* encoding the Adh enzyme with SEQ ID NO:2.

Plasmid construct #1760: The plasmid construct is a derivative of TK293. The map of #1760 is shown in FIG. 6A and its nucleotide sequence is deposited under SEQ ID NO:33. The plasmid harbors a codon improved variant of an adh gene from *Arthrospira platensis*, denoted Adh1694(opt), encoding the Adh enzyme with SEQ ID NO:2 under the transcriptional control of the PrpsL promoter with optimized TATA box and RBS, denoted PrpsL*4. The plasmid further harbors a codon improved pyruvate decarboxylase gene from *Zymomonas mobilis* denoted zmPdc(opt3) under the transcriptional control of the PnirA promoter. The plasmid annotations are as follows: 3298 . . . 3761 promoter Prbc; 284 . . . 1990 CDS zmPDC(opt3); 3763 . . . 4578 CDS Km**, 12140 . . . 12388 CDS ORF6; 11880 . . . 12143 CDS ORF5; 11152 . . . 11838 CDS ORF4; 10062 . . . 10826 CDS ORF3; 9617 . . . 9802 CDS ORF2; 8917 . . . 8934 replication origin; 6396 . . . 9581 replication origin binding protein; 4821 . . . 5879 origin OriVT; 1 . . . 283 promoter PnirA; 1998 . . . 2054 terminator dsrA\ter; 2056.2173 promoter PrpsL*4; 2174 . . . 3196 CDS Adh1694(opt); 3212.3257 terminator ter.

Figure 6B:
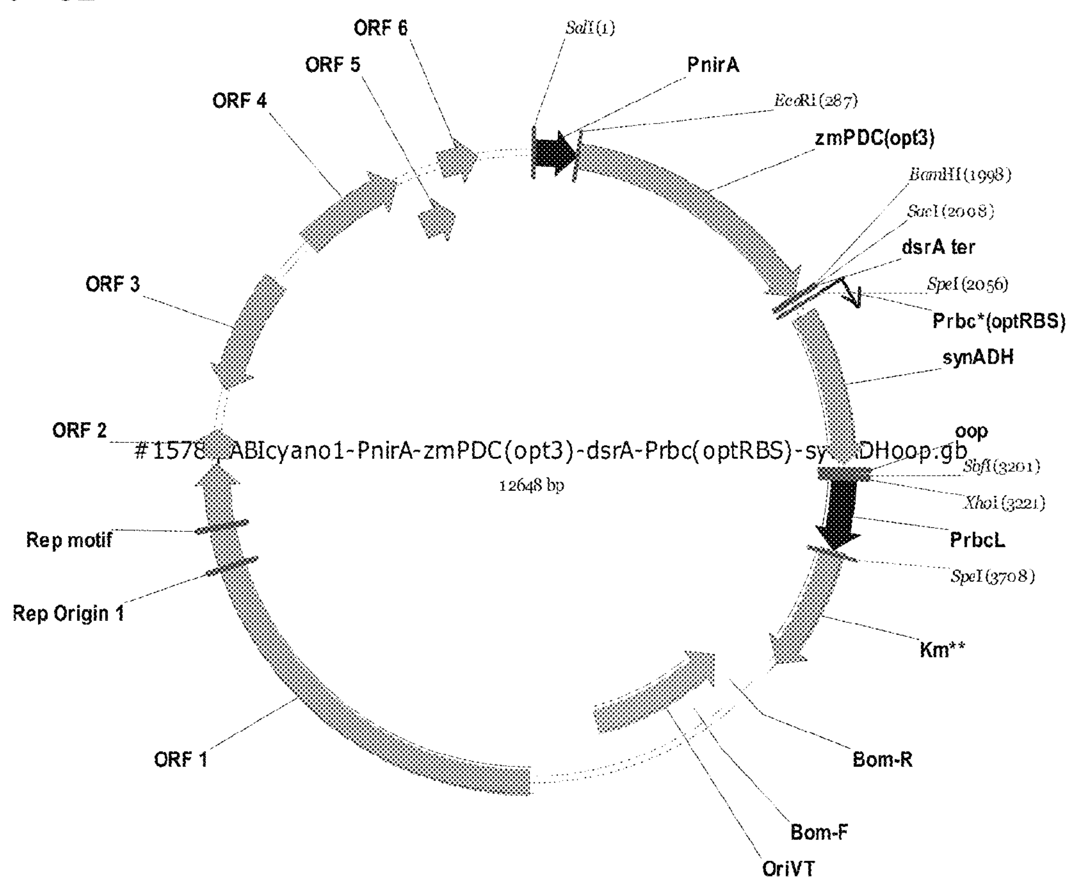
FIG. 6B is a map of plasmid construct #1578 with SEQ ID NO:34. #1578 is a derivative of TK293 containing the PnirA promoter upstream of a codon improved zmPDC gene and the Prbc promoter with optimized RBS upstream of the synAdh gene from *Synechocystis* sp. PCC6803 encoding the Adh enzyme with SEQ ID NO:26.

Plasmid construct #1578: The plasmid construct is a derivative of TK293. The map of #1578 is shown in FIG. 6B and its nucleotide sequence is deposited under SEQ ID NO:34. The plasmid harbors the synAdh gene from *Synechocystis* sp. PCC6803 under the transcriptional control of the Prbc promoter with optimized RBS, denoted Prbc*(optRBS). The plasmid further harbors a codon improved pyruvate decarboxylase gene from *Zymomonas* mobilis denoted zmPdc(opt3) under the transcriptional control of the PnirA promoter. The plasmid annotations are as follows: 2055.2123 promoter Prbc*(optRBS); 2009 . . . 2054 terminator dsrA\ter; 2124 . . . 3134 CDS synADH; 3164 . . . 3194 terminator oop; 3221 . . . 3684 promoter PrbcL; 284.1990 CDS zmPDC (opt3); 3686.4501 CDS Km**; 12063.12311 CDS ORF6; 11803 . . . 12066 CDS ORF5; 11075 . . . 11761 CDS ORF4; 9985.10749 CDS ORF3; 9540 . . . 9725 CDS ORF2; 8840 . . . 8857 replication origin; 6319 . . . 9504 CDS replication origin binding protein; 4744 . . . 5802 origin OriVT; 1 . . . 283 promoter PnirA.

Figure 7:
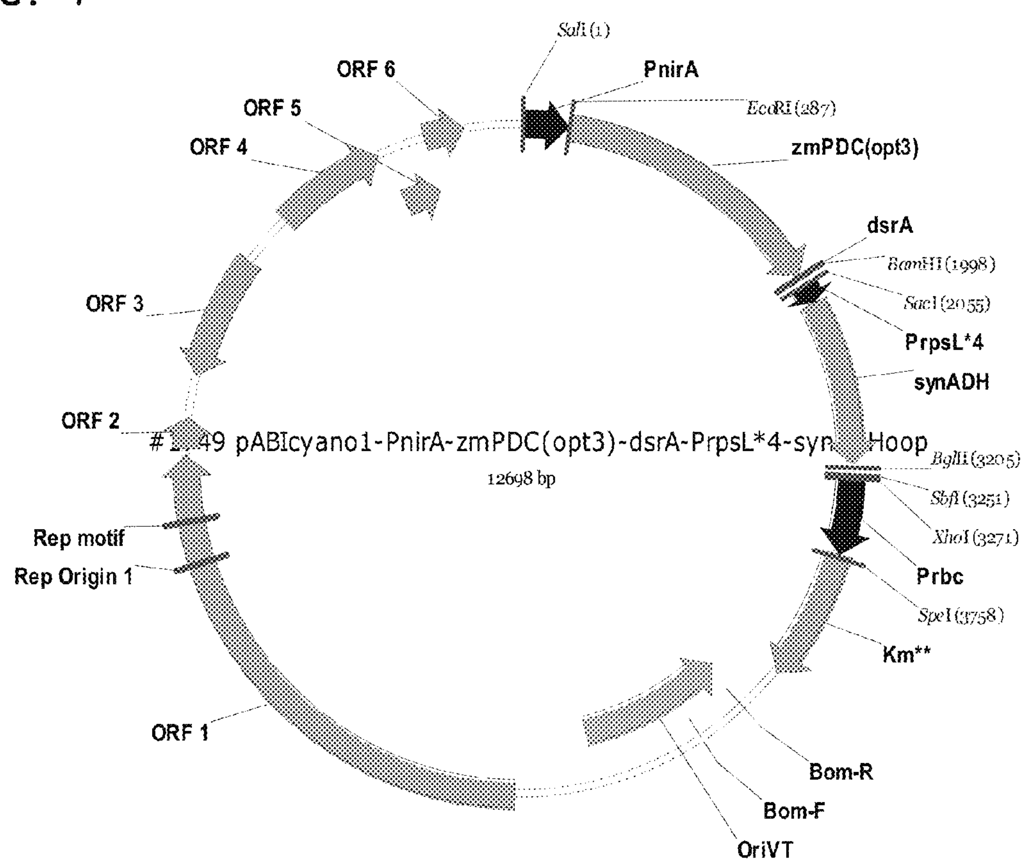
FIG. 7 is a map of plasmid construct #1749 with SEQ ID NO:35. #1749 is a derivative of TK293 containing the PnirA promoter upstream of a codon improved zmPDC gene and a modified PrpsL promoter upstream of the synAdh gene from *Synechocystis* sp. PCC6803 encoding the Adh enzyme with SEQ ID NO:26.

Plasmid construct #1749: The plasmid construct is a derivative of TK293. The map of #1749 is shown in FIG. 7A and its nucleotide sequence is deposited under SEQ ID NO:35. The plasmid harbors the synAdh gene from *Synechocystis* sp. PCC6803 under the transcriptional control of a modified PrpsL promoter, denoted PrpsL*4. The plasmid further harbors a codon improved pyruvate decarboxylase gene from *Zymomonas mobilis* denoted zmPdc(opt3) under the transcriptional control of the PnirA promoter. The plasmid annotations are as follows: 3271 . . . 3734 promoter PrbcL; 284 . . . 1990 CDS zmPDC(opt3); 3736 . . . 4551 CDS Km**; 12113 . . . 12361 CDS ORF6; 11853 . . . 12116 CDS ORF5; 11125 . . . 11811 CDS ORF4; 10035 . . . 10799 CDS ORF3; 9590 . . . 9775 CDS ORF2; 8890 . . . 8907 replication origin; 6369 . . . 9554 replication origin binding protein; 4794 . . . 5852 origin OriVT; 1.283 promoter PnirA; 1998 . . . 2054 terminator dsrA; 2056 . . . 2173 promoter PrpsL*4; 2174 . . . 3184 CDS synADH.

Plasmid construct #1606: The plasmid construct is a derivative of TK293. The map of #1606 is shown in FIG. 17A and its nucleotide sequence is deposited under SEQ ID NO:44. The plasmid harbors a codon improved synAdh gene from *Synechocystis* sp. PCC6803 under the transcriptional control of a Prbc promoter with optimized ribosome binding site, denoted Prbc*(optRBS). The plasmid further harbors a codon improved pyruvate decarboxylase gene from *Zymomonas mobilis* denoted zmPdc(opt1) under the transcriptional control of the PnirA promoter. The plasmid annotations are as follows: 2063 . . . 2131 promoter Prbc*(optRBS); 1 . . . 283 promoter PnirA; 4858 . . . 5916 OriVT; 6433 . . . 9618 CDS replication origin binding protein; 8954 . . . 8971 replication origin; 9654 . . . 9839 CDS ORF2; 10099 . . . 10863 CDS ORF3; 11189 . . . 11875 CDS ORF4; 11917 . . . 12180 CDS ORF5; 12177 . . . 12425 CDS ORF6; 3800 . . . 4615 CDS Km**; 3335 . . . 3798 promoter Prbc; 3143 . . . 3298 terminator TrbcS; 2132 . . . 3139 CDS synADH(opt1); 2017 . . . 2062 terminator dsrA; 284 . . . 1990 CDS zmPDC(opt1).

Plasmid construct #1645: The plasmid construct is a derivative of TK293. The map of #1645 is shown in FIG. 17B and its nucleotide sequence is deposited under SEQ ID NO:45. The plasmid harbors a codon improved Adh gene from *Synechoccocus* sp., denoted Adh916(opt), encoding the Adh enzyme with SEQ ID NO:6 under the transcriptional control of the Prbc promoter with optimized RBS, denoted Prbc*(optRBS). The plasmid further harbors a codon improved pyruvate decarboxylase gene from *Zymomonas mobilis* denoted zmPdc(opt1) under the transcriptional control of the PnirA promoter. The plasmid annotations are as follows: 2063 . . . 2131 promoter Prbc*(optRBS); 2017 . . . 2062 terminator dsrA\ter; 2132 . . . 3139 CDS Adh916(opt); 3155 . . . 3214 terminator ter; 284 . . . 1990 CDS zmPDC (opt1); 1 . . . 283 promoter PnirA; 4764 . . . 5822 OriVT; 6339 . . . 9524 CDS replication origin binding protein; 8860 . . . 8877 replication origin; 9560 . . . 9745 CDS ORF2; 10005 . . . 10769 CDS ORF3; 11095 . . . 11781 CDS ORF4; 11823 . . . 12086 CDS ORF5; 12083 . . . 12331 CDS ORF6; 3706 . . . 4521 CDS Km**; 3241 . . . 3704 promoter Prbc.

Plasmid construct #1753: The plasmid construct is a derivative of TK293. The map of #1753 is shown in FIG. 20A and its nucleotide sequence is deposited under SEQ ID NO:46. The plasmid harbors an Adh gene from *Lyngbya* sp., denoted Adh111, encoding the Adh enzyme with SEQ ID NO:1 under the transcriptional control of the Prbc promoter with optimized RBS, denoted Prbc*(optRBS). The plasmid further harbors a codon improved pyruvate decarboxylase gene from *Zymomonas mobilis* denoted zmPDC(opt1) under the transcriptional control of the PnirA promoter. The plasmid annotations are as follows: 2017 . . . 2062 dsrA\ter; 3165 . . . 3211 terminator ter; 2132 . . . 3151 CDS Adh111; 284 . . . 1990 CDS zmPDC(opt1); 1 . . . 283 promoter PnirA; 4774 . . . 5832 OriVT; 6349 . . . 9534 CDS replication origin binding protein; 8870 . . . 8887 replication origin; 9570 . . . 9755 CDS ORF2; 10015 . . . 10779 CDS ORF3; 11105 . . . 11791 CDS ORF4; 11833 . . . 12096 CDS ORF5; 12093 . . . 12341 CDS ORF6; 3716 . . . 4531 CDS Km**; 3251 . . . 3714 promoter Prbc; 2063 . . . 2131 promoter Prbc*(optRBS).

Plasmid construct #1735: The plasmid construct is a derivative of TK293. The map of #1735 is shown in FIG. 20B and its nucleotide sequence is deposited under SEQ ID NO:47. The plasmid harbors an Adh gene from *Arthrospira platensis*, denoted Adh1694, encoding the Adh enzyme with SEQ ID NO:2 under the transcriptional control of the Prbc promoter with optimized RBS, denoted Prbc*(optRBS). The plasmid further harbors a codon improved pyruvate decarboxylase gene from *Zymomonas mobilis* denoted zmPDC (opt1) under the transcriptional control of the PnirA promoter. The plasmid annotations are as follows: 2063 . . . 2131 promoter Prbc*(optRBS); 2017 . . . 2062 terminator dsrA\ter; 3170 . . . 3216 terminator ter; 2132 . . . 3151 CDS Adh1694; 284 . . . 1990 CDS zmPDC(opt1); 1 . . . 283 promoter PnirA; 4779 . . . 5837 OriVT; 6354 . . . 9539 CDS replication origin binding protein; 8875 . . . 8892 replication origin; 9575 . . . 9760 CDS ORF2; 10020 . . . 10784 CDS ORF3; 11110 . . . 11796 CDS ORF4; 11838 . . . 12101 CDS ORF5; 12098 . . . 12346 CDS ORF6; 3721 . . . 4536 CDS Km**; 3256 . . . 3719 promoter PrbcL.

Plasmid construct #1790: The plasmid construct is a derivative of TK293. The map of #1790 is shown in FIG. 21A and its nucleotide sequence is deposited under SEQ ID NO:71. The plasmid harbors an Adh gene from *Arthrospira platensis*, denoted Adh242(opt) (NB: for the purpose of the description of the present invention, the denotations Adh242 and Adh1694 are used synonymously for the same Adh enzyme from *Arthrospira platensis*), encoding a codon optimized variant of the Adh enzyme with SEQ ID NO:2 under the transcriptional control of the PcpcB promoter, denoted PcpcB. The plasmid further harbors a codon improved pyruvate decarboxylase gene from *Zymomonas mobilis* denoted zmPDC(opt3) under the transcriptional control of the PnirA promoter. The plasmid annotations are as follows: 2453 . . . 3475 ADH242(opt); 3479 . . . 3637 terminator TrbcS; 2055 . . . 2451 promoter PcpcB; 3658 . . . 4121 promoter PrbcL; 284 . . . 1990 CDS zmPDC(opt3); 4123 . . . 4938 CDS Km**; 12500 . . . 12748 CDS orf6; 12240 . . . 12503 CDS orf5; 11512 . . . 12198 CDS orf4; 10422 . . . 11186 CDS orf3; 9977 . . . 10162 CDS orf2; 6756.9941 CDS orf1 replication origin binding protein; 5181 . . . 6239 OriVT; 6246 . . . 13079 insert; 1 . . . 283 PnirA promoter; 1998 . . . 2054 TdsrA terminator.

Plasmid construct #1791: The plasmid construct is a derivative of TK293. The map of #1791 is shown in FIG. 21B and its nucleotide sequence is deposited under SEQ ID NO:72. The plasmid harbors an Adh gene from *Lyngbya* sp. denoted Adh111(opt), encoding a codon optimized variant of the Adh enzyme with SEQ ID NO:2 under the transcriptional control of the PcpcB promoter, denoted PcpcB. The plasmid further harbors a codon improved pyruvate decarboxylase gene from *Zymomonas mobilis* denoted zmPDC(opt3) under the transcriptional control of the PnirA promoter. The plasmid annotations are as follows: 2453 . . . 3469 CDS ADH111 (opt); 3476 . . . 3634 terminator TrbcS; 2055 . . . 2451 promoter PcpcB; 3655 . . . 4118 promoter PrbcL; 284 . . . 1990 CDS zmPDC(opt3); 4120 . . . 4935 CDS Km**; 12497 . . . 12745 CDS orf6; 12237 . . . 12500 CDS orf5; 11509 . . . 12195 CDS orf4; 10419 . . . 11183 CDS orf3; 9974 . . . 10159 CDS orf2; 6753 . . . 9938 CDS orf1 replication origin binding protein; 5178 . . . 6236 replication origin OriVT; 6243 . . . 13076 insertion sequence; 1 . . . 283 PnirA; 1998 . . . 2054 TdsrA.

Plasmid construct #1792: The plasmid construct is a derivative of TK293. The map of #1792 is shown in FIG. 22A and its nucleotide sequence is deposited under SEQ ID NO:73. The plasmid harbors an Adh gene from *Synechocystis* sp. denoted synADH, encoding the Adh enzyme with SEQ ID NO:26 under the transcriptional control of the PcpcB promoter, denoted PcpcB. The plasmid further harbors a codon improved pyruvate decarboxylase gene from *Zymomonas mobilis* denoted zmPDC(opt3) under the transcriptional control of the PnirA promoter. The plasmid annotations are as follows: 2453 . . . 3463 CDS synADH; 3484 . . . 3642 TrbcS; 2055 . . . 2451 PcpcB promoter; 3663 . . . 4126 PrbcL promoter; 284 . . . 1990 CDS zmPDC(opt3); 4128 . . . 4943 CDS Km**; 12505 . . . 12753 CDS orf6; 12245 . . . 12508 CDS orf5; 11517 . . . 12203 CDS orf4; 10427 . . . 11191 CDS orf3; 9982 . . . 10167 CDS orf2; 6761 . . . 9946 CDS orf1; 5186 . . . 6244 OriVT; 6251 . . . 13084 insert; 1 . . . 283 PnirA; 1998 . . . 2054 TdsrA.

Plasmid construct #1793: The plasmid construct is a derivative of TK293. The map of #1793 is shown in FIG. 22B and its nucleotide sequence is deposited under SEQ ID NO:74. The plasmid harbors an Adh gene from *Synechococcus* sp. denoted Adh916(opt), encoding a codon optimized variant of the Adh enzyme with SEQ ID NO:6 under the transcriptional control of the PcpcB promoter, denoted PcpcB. The plasmid further harbors a codon improved pyruvate decarboxylase gene from *Zymomonas mobilis* denoted zmPDC(opt3) under the transcriptional control of the PnirA promoter. The plasmid annotations are as follows: 2453 . . . 3460 CDS ADH916(opt); 3462 . . . 3616 TrbcS terminator; 2055 . . . 2451 PcpcB; 3643 . . . 4106 PrbcL; 284 . . . 1990 CDS zmPDC(opt3); 4108 . . . 4923 CDS Km**; 12485 . . . 12733 CDS orf6; 12225 . . . 12488 CDS orf5; 11497 . . . 12183 CDS orf4; 10407 . . . 11171 CDS orf3; 9962 . . . 10147 CDS orf2; 6741 . . . 9926 CDS orf1 replication origin binding protein; 5166 . . . 6224 OriVT; 6231 . . . 13064 insert; 1 . . . 283 PnirA; 1998 . . . 2054 TdsrA terminator.

Plasmid construct #1795: The plasmid construct is a derivative of TK293. The map of #1795 is shown in FIG. 23A and its nucleotide sequence is deposited under SEQ ID NO:75. The plasmid harbors an Adh gene from *Cyanothece* sp. denoted Adh553(opt), encoding a codon optimized variant of the Adh enzyme with SEQ ID NO:3 under the transcriptional control of the PcpcB promoter, denoted PcpcB. The plasmid further harbors a codon improved pyruvate decarboxylase gene from *Zymomonas mobilis* denoted zmPDC(opt1) under the transcriptional control of the PnirA promoter. The plasmid annotations are as follows: 2051 . . . 2447 PcpcB; 3491 . . . 3645 TrbcS terminator; 2449 . . . 3450 CDS ADH553(opt); 284 . . . 1990 CDS zmPDC(opt1); 1995 . . . 2050 TdsrA terminator; 1 . . . 283 PnirA; 6260 . . . 13093 insert; 5195 . . . 6253 OriVT; 6770 . . . 9955 CDS orf1; 9991 . . . 10176 CDS orf2; 10436 . . . 11200 CDS orf3; 11526 . . . 12212 CDS orf4; 12254 . . . 12517 CDS orf5; 12514 . . . 12762 CDS orf6; 4137 . . . 4952 CDS Km**; 3672 . . . 4135 PrbcL.

Plasmid construct #1815: The plasmid construct is a derivative of TK293. The map of #1815 is shown in FIG. 23B and its nucleotide sequence is deposited under SEQ ID NO:76. The plasmid harbors an Adh gene from *Chroococcidiopsis* sp. denoted Adh1102(nat), encoding the Adh enzyme with SEQ ID NO:9 under the transcriptional control of the PcpcB promoter, denoted PcpcB. The plasmid further harbors a codon improved pyruvate decarboxylase gene from *Zymomonas mobilis* denoted zmPDC(opt1) under the transcriptional control of the PnirA promoter. The plasmid annotations are as follows: 285 . . . 1994 CDS zmPDC(opt1); 1996 . . . 2052 terminator TdsrA; 2 . . . 284 PnirA; 6067 . . . 12900 insert; 5002 . . . 6060 OriVT; 6577 . . . 9762 CDS orf1; 9798 . . . 9983 CDS orf2; 10243 . . . 11007 CDS orf3; 11333 . . . 12019 CDS orf4; 12061 . . . 12324 CDS orf5; 12321 . . . 12569 CDS orf6; 3944 . . . 4759 CDS Km**; 3479 . . . 3942 PrbcL; 2451 . . . 3452 CDS ADH1102; 2053 . . . 2449 PcpcB.

Plasmid construct #1831: The plasmid construct is a derivative of TK293. The map of #1831 is shown in FIG. 24A and its nucleotide sequence is deposited under SEQ ID NO:77. The plasmid harbors an Adh gene from *Synechococcus* sp. denoted Adh213(nat), encoding the Adh enzyme with SEQ ID NO:5 under the transcriptional control of the PcpcB promoter, denoted PcpcB. The plasmid further harbors a codon improved pyruvate decarboxylase gene from *Zymomonas mobilis* denoted zmPDC(opt1) under the transcriptional control of the PnirA promoter. The plasmid annotations are as follows: 290 . . . 1993 CDS zmPDC(opt1); 1995 . . . 2051 terminator TdsrA; 1 . . . 283 PnirA; 6072 . . . 12905 insert; 5007 . . . 6065 OriVT; 6582 . . . 9767 CDS orf1; 9803 . . . 9988 CDS orf2; 10248 . . . 11012 CDS orf3; 11338 . . . 12024 CDS orf4; 12066 . . . 12329 CDS orf5; 12326 . . . 12574 CDS orf6; 3949 . . . 4764 CDS Km**; 3484 . . . 3947 PrbcL; 2450 . . . 3457 CDS ADH213; 2052 . . . 2448 PcpcB.

Plasmid construct #1750: The plasmid construct is a derivative of TK293. The map of #1750 is shown in FIG. 24B and its nucleotide sequence is deposited under SEQ ID NO:78. The plasmid harbors an Adh gene from *Lyngbya* sp. denoted Adh111(opt), encoding a variant of the Adh enzyme with SEQ ID NO:1 codon optimized for Cyanobacterium sp. PTA-13311 under the transcriptional control of the PrpsL promoter with optimized TATA box and RBS, denoted PrpsL*4. The plasmid further harbors a codon improved pyruvate decarboxylase gene from *Zymomonas mobilis* denoted zmPDC(opt3) under the transcriptional control of the PnirA promoter with optimized TATA box and RBS, denoted PnirA. The plasmid annotations are as follows: 3295 . . . 3758 PrbcL promoter; 284 . . . 1990 CDS zmPDC(opt3); 3760 . . . 4575 CDS Km**; 12137 . . . 12385 CDS orf6; 11877 . . . 12140 CDS orf5; 11149 . . . 11835 CDS orf4; 10059 . . . 10823 CDS orf3; 9614 . . . 9799 CDS orf2; 6393 . . . 9578 CDS orf1; 4818 . . . 5876 CDS OriVT; 5883 . . . 12716 insert; 1 . . . 283 PnirA; 1998 . . . 2054 TdsrA; 2056 . . . 2173 PrpsL*4; 2174 . . . 3190 CDS ADH111(opt); 3209 . . . 3254 ter.

Plasmid construct #1784: The plasmid construct is a derivative of TK293. The map of #1784 is shown in FIG. 25A and its nucleotide sequence is deposited under SEQ ID NO:79. The plasmid harbors an Adh gene from *Synechocystis* sp. denoted synADH, encoding the Adh enzyme with SEQ ID NO:26 under the transcriptional control of the PcpcB promoter, denoted PcpcB. The plasmid further harbors a codon improved pyruvate decarboxylase gene from *Zymomonas mobilis* denoted zmPDC(opt3) under the transcriptional control of an improved PnirA promoter, denoted PnirA*2. The plasmid annotations are as follows: 2455 . . . 3465 CDS synADH; 2057 . . . 2453 PcpcB; 2000 . . . 2056 TdsrA; 6140 . . . 12973 insert; 5075 . . . 6133 OriVT; 6650 . . . 9835 CDS orf1; 9871 . . . 10056 CDS orf2; 10316 . . . 11080 CDS orf3; 11406 . . . 12092 CDS orf4; 12134 . . . 12397 CDS orf5; 12394 . . . 12642 CDS orf6; 4017 . . . 4832 CDS Km**; 3552 . . . 4015 PrbcL; 286 . . . 1992 zmPDC(opt3); 2 . . . 288 PnirA*2.

Plasmid construct #1835: The plasmid construct is a derivative of TK293. The map of #1835 is shown in FIG. 25B and its nucleotide sequence is deposited under SEQ ID NO:80. The plasmid harbors an Adh gene from *Synechocystis* sp. denoted synADH, encoding the Adh enzyme with SEQ ID NO:26 under the transcriptional control of the PcpcB promoter, denoted PcpcB. The plasmid further harbors a codon improved pyruvate decarboxylase gene from *Zymomonas mobilis* denoted zmPDC(opt1) under the transcriptional control of the copper-inducible Porf0316 promoter, denoted Porf0316. The plasmid annotations are as follows: 336 . . . 2045 CDS zmPDC(opt1); 6 . . . 335 promoter Porf0316; 3712 . . . 4175 promoter PrbcL; 4177 . . . 4992 CDS Km**; 12554 . . . 12802 CDS orf6; 12294 . . . 12557 CDS orf5; 11566 . . . 12252 CDS orf4; 10476 . . . 11240 CDS orf3; 10031 . . . 10216 CDS orf2; 6810 . . . 9995 CDS orf1; 5235 . . . 6293 OriVT; 6300 . . . 13133 insert; 2047 . . . 2103 terminator TdsrA; 2502 . . . 3512 CDS synADH; 3533 . . . 3691 TrbcS; 2104 . . . 2500 PcpcB.

Plasmid construct #1938: The plasmid construct is a derivative of TK293. The map of #1938 is shown in FIG. 26A and its nucleotide sequence is deposited under SEQ ID NO:81. The plasmid harbors an Adh gene from *Lyngbya* sp. denoted ADH111(opt), encoding a codon optimized variant of the Adh enzyme with SEQ ID NO:1 under the transcriptional control of the PcpcB promoter, denoted PcpcB. The plasmid further harbors a codon improved pyruvate decarboxylase gene from *Zymomonas mobilis* denoted zmPDC (opt1) under the transcriptional control of the copper-inducible Porf0316 promoter, denoted Porf0316. The plasmid annotations are as follows: 2047 . . . 2103 terminator TdsrA; 6292 . . . 13125 insert; 5227 . . . 6285 OriVT; 6802 . . . 9987 CDS orf1; 10023 . . . 10208 CDS orf2; 10468 . . . 11232 CDS orf3; 11558 . . . 12244 CDS orf4; 12286 . . . 12549 CDS orf5; 12546 . . . 12794 CDS orf6; 4169 . . . 4984 CDS Km**; 3704.4167 promoter PrbcL; 2104 . . . 2500 PcpcB; 3525 . . . 3683 terminator TrbcS; 2502 . . . 3518 CDS ADH111(opt); 336 . . . 2045 CDS zmPDC(opt1); 6 . . . 335 promoter Porf0316.

Example 6

Transformation of Cyanobacterium sp. PTA-13311

The Cyanobacterium sp. PTA-13311 has a significant layer of extracellular polymeric substances (EPS) outside the cell. The following method was used to decrease the EPS layer prior to conjugation. The method involves several steps: treatment of cells with N-acetylcysteine (NAC); washing steps that utilize NaCl; a treatment with lysozyme and subsequent washing. Firstly, 200 ml of an exponentially growing culture ($0.5<OD_{750\ nm}<1$) was incubated with N-acetylcysteine (NAC) for 2 days at 16° C. at 0.1 mg/ml final concentration without shaking. Afterwards, the culture was pelleted at 4400 rpm and washed with 0.9% NaCl containing 8 mM EDTA. The cell pellet was resuspended in 0.5 M sucrose and incubated for 60 minutes at room temperature (RT) with slow shaking at 85 rpm. Then, cells were centrifuged and resuspended in 40 ml of a solution containing 50 mM Tris pH 8.0, mM EDTA pH 8.0, 4% sucrose, and 20-40 μg/ml lysozyme. After incubation at RT for 10-15 minutes, cells were centrifuged and washed three times using different washing solutions, namely i) with 30 mM Tris containing 4% sucrose and 1 mM EDTA, ii) with 100 mM Tris containing 2% sucrose and iii) with BG11 medium. All centrifugation steps before lysozyme treatment were performed at 4400 rpm for 10 min at 10° C., all centrifugations after the lysozyme treatment were performed at 2400 rpm for 5 minutes at 4° C.

Next, the cells were resuspended in 400 μl BG11 culture medium containing Tris/sucrose buffer and used for gene transfer via conjugation. Triparental mating was performed as follows. *E. coli* strain J53 bearing a conjugative RP4 plasmid and *E. coli* strain HB101 bearing the plasmid cargo to be introduced into Cyanobacterium sp. PTA-13311 and the pRL528 helper plasmid for in vivo methylation were used. *E. coli* strains were grown in LB broth supplemented with the appropriate antibiotics overnight at 37° C. with shaking at 100 rpm. An aliquot of 3-5 ml of each culture was centrifuged, washed twice with LB medium and resuspended in 200 μl LB medium. Subsequently, the *E. coli* strains were mixed, centrifuged and resuspended in 100 μl BG11 medium. A 100 μl aliquot of the resuspended cyanobacterial cells and the *E. coli* cultures was mixed and applied onto a membrane filter (Millipore GVWP, 0.22 μm pore size) placed on the surface of solid BG11 medium supplemented with 5% LB. Petri dishes were incubated under dim light of 5 μmol photons $m^{-2}$ $s^{-1}$ for two days. Cells were then resuspended in fresh BG11 medium and plated onto selective medium containing 10 and 15 μg/ml kanamycin, respectively. The following selection conditions were used: light intensity approximately 20-40 μmol photons $m^{-2}$ $s^{-1}$ at a temperature of approximately 28° C. Transformants were visible after approximately 10-14 days. The transformant colonies were then plated on BG11 medium containing 15 μg/ml kanamycin and then stepwise transferred to higher kanamycin concentrations up to kanamycin 60 μg/ml to aid in the selection process.

Example 7

Determination of Acetaldehyde and Ethanol Accumulation by Headspace Gas Chromatography (GC Vial Online Method)

GC headspace measurements were performed on a Shimadzu GC-2010 gas chromatograph with flame ionization detector. The instrument is connected in line with a Shimadzu PAL LHS2-SHIM/AOC-5000 autosampler, comprising a gas-tight syringe for transfer of headspace aliquots from the culture samples to the analytical unit. For illumination of the culture samples in the autosampler, each sample tray is exposed with a LED acrylic sheet (length: 230 mm, width: 120 mm, diameter: 8 mm, 24 Chip, S4, 5300K), equipped with a dimmer by company Stingl GmbH (Germany). Mixing of the samples in the autosampler was accomplished with the IKA RO5 power magnetic stirrer. A heating mat KM-SM3 of Mohr & Co. in combination with the JUMO dTRON 316 temperature regulator was used for thermostatization of the culture samples in the autosampler. The gas chromatograph was connected to helium carrier gas as well as hydrogen and artificial air as fuel gas and oxidizer gas, respectively, for the flame ionization detector. Oxidizer air was generated with the generator WGAZA50 from Science Support. The gas chromatograph was equipped with an FS-CS-624 medium bore capillary with a length of 30 m, internal diameter of 0.32 mm and film thickness of 1.8 μm from the GC supplier Chromatographie Service GmbH.

For sample preparation, the hybrid clones were grown on BG11 plates supplemented with 2 mM ammonia and 2 mM urea containing medium but without nitrate, since for nirA promoter constructs nitrate is the inducer. The sample was prepared by scratching an individual clone from the BG11 plate and resuspending the corresponding clone in marine BG11 liquid medium (mBG11) containing 50 mM TES pH 7.3 and 20 mM NaHCO3. Addition of inducing agent, e.g. nitrate or specific metal-salts, triggered acetaldehyde and ethanol production, respectively, in the sample by induction of the inducible promoter driving expression of the recombinant gene encoding the pyruvate decarboxylase enzyme and the recombinant gene encoding the alcohol dehydrogenase enzyme. The cell density in the sample was then adjusted to an optical density of approximately 0.7 at 750 nm wavelength. Two milliliters of sample were then filled into a gas-tight GC vial for headspace autosampling with a nominal volume of 20 ml. The sample headspace was supplemented with 5 ml $CO_2$. The vial was tightly closed with a cap with self-sealing silicon septum and placed into the autosampler which was temperature-controlled at 37° C. The illumination was set to 120 μE. The magnetic stirrer was configured for interval mixing of the samples, with cycles of two minutes mixing at 400 rpm, followed by 90 minutes without mixing. An automated process followed, wherein after given times aliquots of 500 μl of the headspace of the sample were automatically drawn with the gas-tight syringe and injected via the injection port into the gas chromatograph for analysis. Before each headspace autosampling, the mixing is changed for 10 minutes to continuous mixing with 750 rpm at 37° C. incubation temperature. The syringe temperature was set to 70° C. The fill speed was 250 μl per second, following an initial lag time of 1 second after the septum of the samples had been pierced by the syringe needle. The injection of the aliquot into the gas chromatograph happened with an injection speed of 500 μl per second. Afterwards, the syringe flushed for 3 minutes with air to prevent sample carryover between two injections. The gas chromatograph runtime was 4 minutes 30 seconds. The injection temperature on the gas chromatograph was 230° C. The column temperature was 60° C. Detection was accomplished with the flame ionization detector at 250° C. process temperature. The makeup gas was nitrogen at 30 ml per minute, the fuel gas was hydrogen at 35 ml per minute and the oxidizer gas was artificial air at 400 ml per minute.

After the final measurement, the final optical density of the samples was measured at 750 nm wavelength and an average cell density for each sample was determined by calculating the arithmetic mean of the optical density at the starting point and the optical density at the end point of the process, divided by two. Afterwards, the average ethanol production per cell density was calculated.

Example 8

Performance Comparison of Ethanologenic Cyanobacterium sp. PTA-13311 Hybrids #1646 and #1753 with #1578

Figure 8A:
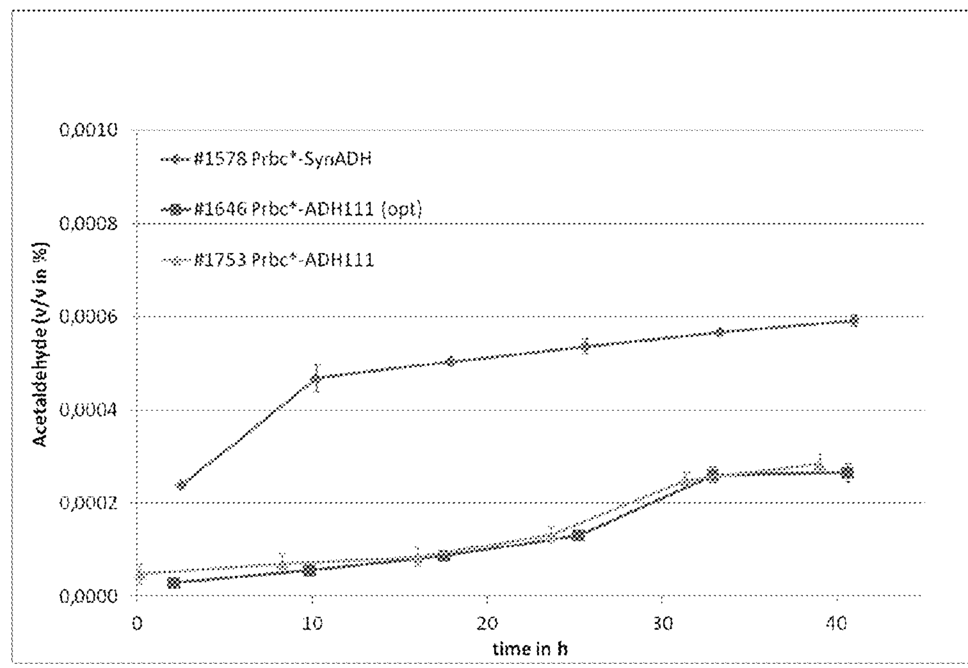
FIGS. 8A, 8B and 8C show a graphical evaluation of acetaldehyde accumulation (FIG. 8A) and absolute (FIG. 8B) as well as relative ethanol production rates (FIG. 8C) determined by the GC vial online method for Cyanobacterium sp.
Figure 8B:
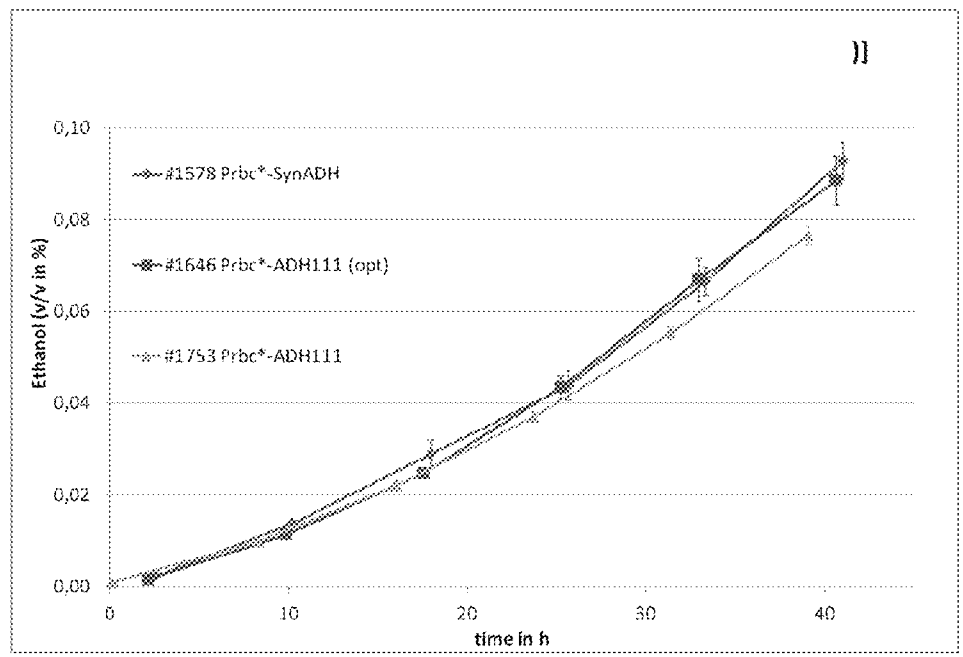
Figure 8C:
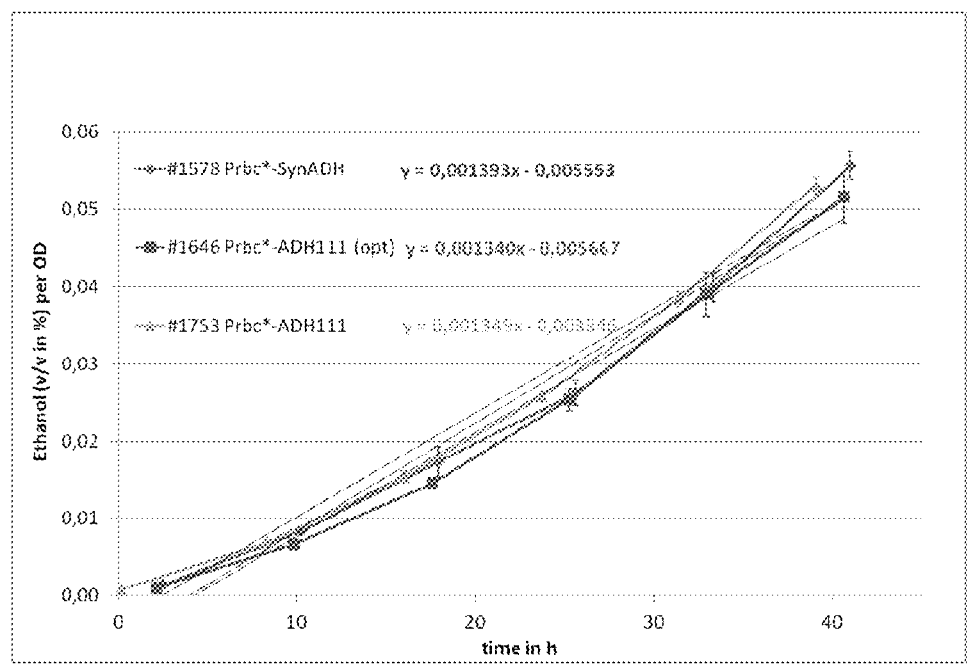

The metabolically enhanced Cyanobacterium sp. PTA-13311 hybrids #1646 and #1753 harboring the codon-optimized version of the alcohol dehydrogenase gene from *Lyngbya* sp. and, as a comparative example, the metabolically enhanced Cyanobacterium sp. PTA-13311 hybrid #1578 harboring the synADH gene from *Synechocystis* sp. PCC6803, were characterized by the GC vial online method with regard to their acetaldehyde accumulation and ethanol production. FIG. 8A shows the corresponding graphical evaluation of the acetaldehyde accumulation in vol % over the monitored cultivation time of 40 hours. Each data point represents the arithmetic mean and standard deviation of four independent samples. Both hybrid strains harboring the Adh gene from *Lyngbya* sp. were able to maintain a very low acetaldehyde level of less than about 0.0001 vol % from the start of the cultivation which only increases to about 0.00025 vol % towards the end of the cultivation. In contrast, the comparative example of the hybrid strain harboring the synADH gene from *Synechocystis* sp. PCC6803 rapidly accumulated acetaldehyde up to about 0.0005 vol % during the first 10 hours of cultivation. Thereafter, the acetaldehyde concentration continued to increase to about 0.0006 vol % towards the end of cultivation. FIG. 8B shows the corresponding graphical evaluation of the absolute ethanol production and FIG. 8C the corresponding relative ethanol production normalized to the cell density ($OD_{750\,nm}$) over the monitored cultivation time of 40 hours. Each data point again represents the arithmetic mean and standard deviation of four independent samples. A similar productivity was observed with all three hybrid strains during 40 hours of cultivation. This trend is also reflected in the fitted production rates which were 0.001340 and 0.001349 vol % per OD and hour, respectively, for the hybrid strains harboring the *Lyngbya* sp. Adh enzyme, whereas a production rate of 0.001393 vol % per OD and hour has been determined for the comparative example harboring the synADH enzyme.

In conclusion, lower acetaldehyde accumulation and high ethanol production rates were accomplished with a metabolically enhanced cyanobacterium harboring, for example, the Adh enzyme from *Lyngbya* sp. having a $K_m$ for acetaldehyde of 0.0058 mM, a $K_m$ for ethanol of 0.83 mM and a ratio $K_m$ (ethanol)/$K_m$ (acetaldehyde) of 143 in comparison to a metabolically enhanced cyanobacterium harboring the synADH enzyme from *Synechocystis* sp. PCC6803 having a $K_m$ for acetaldehyde of 0.35 mM, a $K_m$ for ethanol of 19 mM and a ratio $K_m$ ethanol/$K_m$ acetaldehyde) of 54.

Example 9

Performance Comparison of Ethanologenic Cyanobacterium sp. PTA-13311 Hybrids #1754 and #1735 with #1578

Essentially as described in Example 8, but wherein the metabolically enhanced Cyanobacterium sp. PTA-13311 hybrids #1754 and #1735 harboring the codon-optimized version of the alcohol dehydrogenase gene from *Arthrospira platensis* were compared with the hybrid #1578 harboring the synADH gene from *Synechocystis* sp. PCC6803. FIG. 9A shows the results from the acetaldehyde accumulation. Both hybrid strains harboring the Adh gene from *Arthrospira platensis* were able to maintain a significantly lower acetaldehyde level of less than about 0.0002 vol % during the first 18 hours of cultivation in comparison to the hybrid strain harboring the synADH gene from *Synechocystis* sp. PCC6803 which accumulated more than 0.0005 vol % acetaldehyde within the same period. The #1754 hybrid maintained a low acetaldehyde level of max. 0.00035 vol % until the end of cultivation, whereas the acetaldehyde level with #1735 amounted to approximately 0.0007 vol % after 40 hours. FIGS. 9B and 9C show the corresponding results from the ethanol production monitoring. Again, a similar productivity was observed with all three hybrid strains during the 40 hours cultivation. Accordingly, the observed production rates were 0.001425 and 0.001212 vol % per OD and hour, respectively, for the hybrid strains harboring the *Arthrospira platensis* Adh enzyme in comparison to the production rate of 0.001393 vol % per OD and hour of the comparative example harboring the synADH enzyme.

In conclusion, lower acetaldehyde accumulation and high ethanol production rates were accomplished with a metabolically enhanced cyanobacterium harboring, for example, the Adh enzyme from *Arthrospira platensis* having a $K_m$ for acetaldehyde of 0.0023 mM, a $K_m$ for ethanol of 2.64 mM and a ratio $K_m$ (ethanol)/$K_m$ (acetaldehyde) of 1056 in comparison to a metabolically enhanced cyanobacterium harboring the synADH enzyme from *Synechocystis* sp. PCC6803 having a $K_m$ for acetaldehyde of 0.35 mM, a $K_m$ for ethanol of 19 mM and a ratio $K_m$ ethanol/$K_m$ acetaldehyde) of 54.

Example 10

Correlation Between Adh Activity and Acetaldehyde/Ethanol Accumulation in Different Ethanologenic Cyanobacterium sp. PTA-13311 Hybrids The GC vial online method was used to compare the acetaldehyde to ethanol ratio during cultivation of Cyanobacterium sp. PTA-13311 hybrid strains harboring the ethanologenic plasmids #1646, #1753 with the Adh enzyme from *Lyngbya* sp. or the ethanologenic plasmids #1754, #1735 with the Adh enzyme from *Arthrospira platensis*, respectively, with that of comparative strain #1578 harboring the synADH gene from *Synechocystis* sp. PCC6803. In addition, the Adh activity of these hybrid strains was determined under acetaldehyde-saturating conditions after the GC vial experiments were completed. FIG. 10A is a column diagram showing the corresponding Adh activity in μmol/min·mg protein for the specified hybrid strains. Data represent mean values and standard deviations of two independent samples. A significantly higher Adh activity of approximately 0.37 μmol/min·mg protein was observed with the comparative hybrid expressing the synADH enzyme. The hybrids expressing the *Lyngbya* sp. or *Arthrospira platensis* Adh enzymes, respectively, exhibited significantly lower Adh activities between about 0.27 and 0.05 μmol/min·mg protein. FIG. 10B is a column diagram showing the acetaldehyde to ethanol ratio during cultivation of the corresponding hybrid strains averaged over at least three consecutive timepoints between cultivation hours 15-35. It was surprisingly found that, despite the significantly lower Adh activity levels of the hybrids expressing the *Lyngbya* sp. or *Arthrospira platensis* Adh enzymes in comparison to the synAdh activity of the comparative strain, a significantly lower acetaldehyde to ethanol ratio of about 0.4-0.5% was achieved with the hybrid strains #1646, #1753 and #1754 compared to the acetaldehyde to ethanol ratio of about 0.95% observed with the comparative strain. Remarkably, hybrid #1735 exhibiting an at least 7-fold lower Adh activity than the comparative strain still achieved an acetaldehyde to ethanol ratio that was with about 1.05% only marginally higher than that of the comparative strain. A low acetaldehyde to ethanol ratio is generally desirable because it indicates an efficient conversion of acetaldehyde into ethanol, translating into high ethanol production rates and at the same time avoiding acetaldehyde accumulation with toxic effects to the cyanobacterial cells.

These results clearly demonstrate that the type of Adh enzyme with respect to its $K_m$ values for acetaldehyde and ethanol provided in the metabolically enhanced cyanobacterial cell of the present invention can have an even higher positive impact on the ethanol production performance of the cyanobacterium than the gross Adh activity, i.e. the sum of expression level and turnover rate, of a conventionally enhanced cyanobacterial cell.

Example 11

Cell Growth and Total Ethanol Production in Ethanologenic Cyanobacterium sp. PTA-13311 Hybrids #1684 and #1658

The ethanologenic Cyanobacterium sp. PTA-13311 hybrid harboring the plasmid construct #1684 with the adh gene from *Lyngbya* sp. and, as a comparative example, the ethanologenic Cyanobacterium sp. PTA-13311 hybrid harboring the plasmid construct #1658 with the synADH gene from *Synechocystis* sp. PCC6803, were cultivated in parallel in 1.2 liter vertical photobioreactors in biological duplicates using artificial seawater (ASW) BG-11 medium pH 7.3 with 35 practical salinity units and 200 μg/L kanamycin supplementation. Over a cultivation period of 30 days, a continuous 12 h day/12 h night cycle was maintained, wherein the day phase included a cultivation temperature of 37° C. and an illumination density of 125 μmol $m^{-2}$ $s^{-1}$ provided by an array of fluorescence bulbs, whereas the night phase included a cultivation temperature of 25° C. and no illumination. The cultures were aerated and mixed by continuous bubbling of air enriched with 15% $CO_2$ at a gas flow rate of 38 ml/min including 15% $CO_2$. Ethanol production was induced on day 0 of the cultivation by addition of nitrate provided in standard ASW BG-11 medium in 17.5 mM NaNO3 final concentration. On a daily basis, samples were withdrawn from each culture for $OD_{750\ nm}$ cell density measurements and analysis of the total ethanol concentration by a standard GC headspace measurement, as well as Adh and Pdc activity measurements.

The PDC activity assay is a photometric kinetic reaction that can be monitored at 340 nm using a spectrophotometer. Pyruvate is enzymatically converted to acetaldehyde by pyruvate decarboxylase, which is reduced to ethanol by ethanol dehydrogenase under NADH oxidation. The determined PDC activity is related to the protein content.

For the Pdc activity assay, 5-15 mL fresh culture material were spun down in a 15 mL tube at 5,000 g for 10 min at 4° C. The culture volume was adapted to an optical density: $OD_{750}$<1: 20 ml, $OD_{750}$ 1-2: 15 ml, $OD_{750}$ 2-5: 5 ml, $OD_{750}$>5: 3 ml culture as approximation. The pellet is resuspended in 0.9 mL pre-chilled (4° C.) purification buffer containing 50 mM MES, 100 μM EDTA, 1 mM TPP, 2 mM DTT, 0.025 mg/mL Lysozyme. 0.9 mL supernatant were taken to which 750 μL pre-chilled glass beads were added in a 2.0 ml safe-lock Eppendorf tube. Cell disruption was done with the mixer mill (Retsch) for 15 min at 30 Hz. The resulting suspension was incubated at 35° C. for 30 min in a thermomixer. Afterwards, the samples were centrifuged at 10,000 g for 10 min and the supernatant was then used for the analysis.

The PDC activity measurement can be done in a photometer or in a plate reader. For the measurement in a cuvette 500 μL supernatant sample were mixed with 2 μL ADH in a concentration of 15 mg/mL and 463 μL of reaction buffer containing 43.2 mM MES buffer, 0.43 mM NADH, 10.8 mM $CaCl_2$ in the cuvette. For the measurement in a plate reader, 20 μL supernatant sample were mixed with 173 μL of reaction buffer containing 23.1 mM MES buffer, 0.231 mM NADH, 5.8 mM $CaCl_2$ and 0.031 mg/mL ADH in the microplate. The sample was incubated in the spectrophotometer or plate reader, respectively, until a stable baseline was observed, typically around 200 s.

The reaction was started by addition of 35 μL 300 mM pyruvate into the cuvette or 7 μl in each well of the 96 deep-well plate, respectively, and adsorption was recorded at a wavelength of 340 nm for 600 s. Oxidation of NADH was observed as a decrease of absorbance at 340 nm. Typical values from the bench top PBR were 100-300 nmol·$min^{-1}$·$mg^{-1}$ protein.

For calculating the specific PDC activity in the cell extract the protein amount in the supernatant based on the method Lowry et al. was determined, and for the sample preparation the DOC/TCA precipitation method was used (see above).

The graph shown in FIG. 11A illustrates the development of the cell culture density of the #1684 hybrid strain with the adh gene from *Lyngbya* sp. (square markers) and the comparative #1658 hybrid with the synADH gene from *Synechocystis* sp. PCC6803 (diamond markers) over the monitored cultivation time. Data represent mean values and standard deviations from biological duplicates cultivated in vertical photobioreactors illuminated with 125 μE $m^{-2}$ $s^{-1}$ from one side. The growth characteristics of both hybrids were essentially identical to one another, leading to a final $OD_{750\ nm}$ of about 6.0 for the #1684 hybrid and about 5.3 for the #1658 hybrid. The corresponding development of the total ethanol content in the culture over the cultivation time is shown in FIG. 11B. As of about the third day of cultivation, a significantly higher ethanol content was observed in the culture of the #1684 hybrid strain (square markers) in comparison to the comparative #1658 hybrid strain. The difference continued to increase essentially until the end of cultivation. For example, at cultivation day 29, about 0.33 vol % ethanol was present in the culture of the #1684 hybrid strain, whereas only about 0.27 vol % were measured in the culture of the comparative #1658 hybrid strain, corresponding to approximately 20% increased ethanol yield with the metabolically enhanced hybrid strain according to the present invention expressing the *Lyngbya* sp. Adh enzyme in comparison to the strain harboring the state-of-the art synAdh enzyme. FIG. 11C shows a complementary plot of the ethanol content normalized per cell density over the cultivation time. It can be derived that, on average, with this vPBR system illuminated from one side with 125 $\mu E\ m^{-2}\ s^{-1}$ a gain of approximately 0.01-0.015 vol % ethanol per $OD_{750\ nm}$ was achieved with the metabolically enhanced hybrid strain of the present invention (square markers) in comparison to the comparative hybrid strain (diamond markers).

FIGS. 12A and 12B show graphical evaluations of the concomitant Pdc and Adh activity measurements in μmol per min and mg protein over the 30 days of cultivation. Whilst no significant differences were observed in Pdc activity, a significantly lower Adh activity was observed throughout the cultivation in the metabolically enhanced #1684 hybrid strain expressing the *Lyngbya* sp. Adh enzyme in comparison to the comparative #1658 hybrid strain expressing the synADH enzyme.

In conclusion, the metabolically enhanced cyanobacterium of the present invention can outperform a conventionally enhanced cyanobacterium in terms of cell growth as well as relative and absolute ethanol production already at relatively low Adh activity levels.

Example 12

Cell Growth and Total Ethanol Production in Ethanologenic Cyanobacterium sp. PTA-13311 Hybrids #1760 and #1578

Essentially as described Example 11, but with the ethanologenic Cyanobacterium sp. PTA-13311 hybrid harboring the plasmid construct #1760 with the adh gene from *Arthrospira platensis* and, as a comparative example, the ethanologenic Cyanobacterium sp. PTA-13311 hybrid harboring the plasmid construct #1578 with the synADH gene from *Synechocystis* sp. PCC6803 cultivated over a period of 21 days.

The graph shown in FIG. 13A illustrates the development of the cell culture density of the #1760 hybrid strain with the adh gene from *Arthrospira platensis* (square markers) and the comparative #1578 hybrid with the synADH gene from *Synechocystis* sp. PCC6803 (circle markers) over the monitored cultivation time. The growth characteristics of both hybrids were similar to each other, leading to a $OD_{750\ nm}$ after 21 days of about 4.9 for the #1760 hybrid and about 5.1 for the #1578 hybrid. The corresponding development of the total ethanol content in the culture over the cultivation time is shown in FIG. 13B. As of about the eighth day of cultivation, a higher ethanol content was observed in the culture of the #1760 hybrid strain (square markers) in comparison to the comparative #1578 hybrid strain. The difference increased with further cultivation time and maintained constant until the end of cultivation. For example, at cultivation day 21, about 0.325 vol % ethanol was present in the culture of the #1760 hybrid strain, whereas only about 0.28 vol % were measured in the culture of the comparative #1578 hybrid strain, corresponding to approximately 14% increased ethanol yield with the metabolically enhanced hybrid strain according to the present invention expressing the *Arthrospira platensis* Adh enzyme in comparison to the strain harboring the state-of-the art synAdh enzyme. FIG. 13C shows a complementary plot of the ethanol content normalized per cell density over the cultivation time. It can be derived that, on average, with this vPBR system illuminated from one side with 125 $\mu E\ m^{-2}\ s^{-1}$ a gain of approximately 0.01-0.017 vol % ethanol per $OD_{750\ nm}$ was achieved with the metabolically enhanced hybrid strain of the present invention (square markers) in comparison to the comparative hybrid strain (circle markers).

FIGS. 14A and 14B show graphical evaluations of the concomitant Pdc and Adh activity measurements in μmol per min and mg protein over the 21 days of cultivation. Whilst no clear differences were observed in Pdc activity between both hybrids, a significantly lower Adh activity was observed throughout the cultivation in the metabolically enhanced #1760 hybrid strain expressing the *Arthrospira platensis* Adh enzyme in comparison to the comparative #1578 hybrid strain expressing the synADH enzyme.

These results further confirm that the metabolically enhanced cyanobacterium of the present invention can outperform a conventionally enhanced cyanobacterium in terms of relative and absolute ethanol production already at relatively low Adh activity levels.

Example 13

Measurement of Activity and Kinetic Constants of the Alcohol Dehydrogenase Enzyme from *Lyngbya* sp. for C3-C10 Aldehydes Essentially as described in Example 4, but wherein propanal (C3), butanal (C4), pentanal (C5), hexanal (C6), heptanal (C7) octanal (C8) and decanal (C10) were used as substrates instead of acetaldehyde. As an example, FIG. 15A show the result from the graphical computation of the Michaelis constants $K_m$ for propanal of the alcohol dehydrogenase from *Lyngbya* sp. with amino acid sequence SEQ ID NO:1. The $V_{max}$ corresponds to approximately 0.035 μmol per mg protein and min and the $K_m$ value corresponds to $0.0053 \cdot 10^{-3}$ M which is even slightly lower than the determined Km value for acetaldehyde of $0.006 \cdot 10^{-3}$ M of this enzyme. FIG. 15B is a column diagram showing the specific activity of the alcohol dehydrogenase from *Lyngbya* sp. for the conversion of the above-listed C3-C10 aldehydes in comparison to the conversion of acetaldehyde. It can be derived that all of the tested C3-C10 aldehydes were efficiently converted by the alcohol dehydrogenase enzyme with a specific activity of about 2 μmol/mg protein·min at a substrate concentration of 0.1 mM. This is only slightly lower than the specific activity of about 2.7 mmol/mg protein·min determined for the corresponding conversion of acetaldehyde.

In conclusion, the metabolically enhanced cyanobacterium of the present invention can be efficiently used for production of a C3, C4, C5, C6, C7, C8, C9 and/or C10 alcohols.

Example 14

Correlation Between Adh Activity and Cell Viability of Different Ethanologenic Cyanobacterium sp. PTA-13311 Hybrids A useful indicator of the vitality of the metabolically enhanced cyanobacterial cell is, for example, the pigmentation of the cell during or after ethanol production. Ethanologenic Cyanobacterium sp. PTA-13311 hybrids harboring the #1606, #1578, #1646, #1652, #1754 and #1760 plasmid constructs as well as a wild-type Cyanobacterium sp. PTA-13311 for comparative purposes were cultivated in GC vials as described before in example 7. After measurement of the optical density at 750 nm, needed for calculation of the cell normalized ethanol production (EtOH/OD) cell suspensions were adjusted to an $OD_{750\ nm}$ of 1.4 and the whole cell absorption spectra from 400 nm-750 nm was recorded using a UV-VIS spectrophotometer (Shimadzu UV-2450) and an integrating sphere (Shimadzu ISR-2200). From the recorded spectra, the relative phycocyanin pigmentation was determined at 620 nm wavelength, the relative chlorophyll pigmentation was determined at 680 nm wavelength and the relative carotenoid pigmentation was determined at 490 nm wavelength. From the relative pigment contents the corresponding PC/Chl and Car/PC ratios were calculated. A reduced relative PC/Chl ratio and a significantly increased relative Car/PC ratio in comparison to a corresponding wild-type cell are typical indicators of reduced cell viability and increased stress. The results are shown in FIGS. 16A and 16B. The hybrid strains #1646 and #1652 expressing the alcohol dehydrogenase gene from *Lyngbya* sp. and the hybrid strains #1754 and #1760 expressing the alcohol dehydrogenase gene from *Arthrospira platensis* exhibited a relative PC/Chl ratio which was essentially identical with that of the wild type strain and higher than that of the comparative hybrid strains #1606 and #1578 expressing the state-of-the-art synAdh enzyme (FIG. 16A). These results confirmed a superior viability of the metabolically enhanced cyanobacterial cells for the production of ethanol of the present invention in comparison to a conventionally enhanced cyanobacterial cell. The hybrid strain #1645 expressing the alcohol dehydrogenase gene from *Synechococcus* sp. exhibited a PC/Chl ratio which is about 13% lower than that of the wild-type strain and shows that the vitality of this hybrid was also little affected by the ethanol production. Likewise, the relative Car/PC ratio (FIG. 16B) that was determined for hybrid strains #1646 and #1652 expressing the alcohol dehydrogenase gene from *Lyngbya* sp. and the hybrid strain #1760 expressing the alcohol dehydrogenase gene from *Arthrospira platensis* was essentially identical to that of the wild-type strain, confirming the superior viability of these metabolically enhanced cyanobacterial cells of the present invention in comparison to the comparative hybrid strains expressing the synAdh enzyme which exhibited an increase in the relative Car/PC ratio between about 11% and 43% in comparison to the wild type strain. The relative Car/PC ratio of the hybrid strain #1754 was about 10% increased in comparison to the wild-type cell, demonstrating a vitality that was still close to that of the wild type cyanobacterium and little affected by the ethanol production.

The cell viability results correlated well with an enhanced relative ethanol production rate per cell density (FIG. 18A) and a reduced acetaldehyde/ethanol ratio (FIG. 18B) achieved with the hybrids #1646, #1652, #1754 and #1760 of the present invention expressing the alcohol dehydrogenase gene from *Lyngbya* sp. or *Arthrospira platensis*, respectively. With all of these strains a significantly higher relative ethanol production rate per cell density was achieved in comparison to the comparative strains expressing the synAdh enzyme. Whilst all of the tested hybrid strains exhibited essentially comparable Pdc activities (FIG. 19A), it is a remarkable and surprising result that the favorable effects achieved with the metabolically enhanced hybrids of the present invention were already achieved at relatively low Adh activity levels (FIG. 19B). In particular the lower Adh activity levels of constructs #1646, #1754 and #1760 in comparison to the comparative hybrids #1606 or #1578 demonstrated that the specific $K_m$ values for acetaldehyde and ethanol of the alcohol dehydrogenase enzyme of the metabolically enhanced cyanobacterial cell of the present invention can have an even higher positive impact on the cell viability and ethanol production performance of the cyanobacterium than the gross Adh activity, i.e. the sum of expression level and turnover rate, of a conventionally enhanced cyanobacterial cell. Therefore, it can be concluded that even further improved effects can be achieved when the gross activity of the alcohol dehydrogenase enzyme of the metabolically enhanced cyanobacterial cell of the present invention is further increased, for example by increasing the Adh expression level.

Example 15

Influence of the Promoter Type on Adh Activity and Acetaldehyde/Ethanol Accumulation in Different Ethanologenic Cyanobacterium sp. PTA-13311 Hybrids The GC vial online method was used to investigate the acetaldehyde accumulation and ethanol production during cultivation of Cyanobacterium sp. PTA-13311 hybrid strains harboring the ethanologenic plasmids #1646, #1750 and #1791 with the Adh enzyme from *Lyngbya* sp. under the control of the Prbc, PrpsL and PcpcB promoter, respectively. Hybrid strains harboring the ethanologenic plasmids TK293, #1578 and #1792 with the synADH gene from *Synechocystis* sp. PCC6803 under the control of the Prbc, PrpsL and PcpcB promoter, respectively, served as comparative examples. In addition, the Adh and Pdc activity of these hybrid strains was determined.

FIG. 26B shows the development of the ethanol content per OD in the cultures over the cultivation time. Data represent mean values and standard deviations of four independent samples. Over the monitored period of about 32 hours, similar ethanol productions rates were observed with strains harboring plasmids #1646, #1750 and #1791 as well as the reference strain harboring plasmid #1578, with slightly better rates of the former strains expressing the Adh enzyme from *Lyngbya* sp. The reference strain with plasmid #1792 and, in particular, the reference strain with plasmid TK293 expressing the synADH gene from *Synechocystis* sp. exhibited comparatively lower ethanol productivity.

FIG. 27A shows the corresponding acetaldehyde accumulation results. The comparative strains expressing the synADH enzyme under the control of the PrpsL or Prbc promoter accumulated between about 200-500% more acetaldehyde than the strains expressing the Adh enzyme from *Lyngbya* sp. or the reference strain expressing the synADH enzyme under the control of the PcpcB promoter. As noted above, a low acetaldehyde level is desirable because it indicates an efficient conversion of acetaldehyde into ethanol and, at the same time, avoids toxic effects of acetaldehyde to the cyanobacterial cells.

FIG. 27B is a column diagram showing the corresponding Adh activity in μmol/min·mg protein for the specified hybrid strains. Relatively low activity levels were observed when the strains expressed either the Adh from *Lyngbya* sp. or the synAdh under the control of the PrpsL or the Prbc promoter. Significantly increased Adh activity was observed when the hybrid strains expressed the Adh enzyme under the transcriptional control of the PcpcB promoter. Notably, the expression of synAdh under control of the PcpcB promoter in the reference strain harboring plasmid #1792 still resulted in about 700% higher Adh activity than the expression of the *Lyngbya* sp. Adh enzyme under control of the same PcpcB promoter in the strain harboring plasmid #1791, i.e. 8.54 μmol/min·mg versus 1.2 μmol/min·mg.

Thus, due to the low $K_m$ for acetaldehyde of the Adh enzymes of the present invention, a comparatively low gross Adh activity is already sufficient to maintain lower acetaldehyde accumulation in the culture, whilst at the same time a higher level of ethanol production is achieved. Conversely, conventional Adh enzymes such as the synAdh require much higher gross Adh activity in order to compensate for their lower substrate affinity to acetaldehyde. Thus, a very high expression of the conventional Adh enzymes is required to achieve similar low acetaldehyde accumulation and high ethanol production as with the Adh enzymes of the present invention. This may for instance be achieved by driving the expression of the conventional Adh enzyme with a strong promoter such as the PcpcB promoter.

However, a very high expression of a recombinant Adh enzyme imposes a tremendous metabolic burden on the ethanol-producing cyanobacterial host cell. For example, 3-5% of the total cell protein may be directed towards the overexpression of the Adh enzyme, to the expense and imbalance of other important anabolic and catabolic pathways. Moreover, the overabundance of the recombinant Adh enzyme can further undesirable side reactions in which the enzyme unspecifically reduces substrates other than acetaldehyde. All of these effects can be detrimental to the viability, longevity and productivity of the ethanol producing cyanobacterial host cell.

It is therefore a particular advantage that with the Adh enzymes of the present invention favorable acetaldehyde accumulation and ethanol production properties are achieved already at low Adh activity levels, because in this way the host cell's metabolic burden and the risk of undesirable side reactions can also be kept low without dispensing with ethanol yield.

Example 16

Adh Activity, Ethanol Production and Acetaldehyde Accumulation in Different Ethanologenic Cyanobacterium sp. PTA-13311 Hybrids with the Adh Gene Under Transcriptional Control of the PcpcB Promoter The GC vial online method was used to investigate the acetaldehyde accumulation and ethanol production during cultivation of Cyanobacterium sp. PTA-13311 hybrid strains harboring the ethanologenic plasmid #1790 with the Adh enzyme from *Arthrospira platensis,* #1791 with the Adh enzyme from *Lyngbya* sp., #1792 with the synAdh as a reference, #1793 with the Adh enzyme from *Synechococcus* sp. and #1795 with the Adh enzyme from *Cyanothece* sp., all of which have the respective adh gene under transcriptional control of the PcpcB promoter. A hybrid strain harboring the plasmid #1578 with the synadh gene under control of the Prbc promoter was used as an additional reference. In addition, the Adh activity of these hybrid strains was determined.

The Adh activity measurements (FIG. 28A) show that the highest Adh activity was again detected in the reference hybrid harboring the plasmid #1792 with the synAdh under control of the strong PcpcB promoter. Medium Adh activity levels were detected in the hybrids harboring the plasmid #1791 and #1793 with the Adh enzymes from *Lyngbya* sp. and *Synechococcus* sp., respectively. The Adh enzymes from *Arthrospira platensis* (#1790) and *Cyanothece* sp. (#1795) exhibited the lowest activity levels of the PcpcB controlled enzymes, which was comparable to that of the reference strain harboring the plasmid #1578 with the synadh gene under control of the Prbc promoter.

FIG. 28B shows the corresponding ethanol production per OD over the cultivation time. Despite the big differences in the Adh activity (see above), all strains exhibited essentially comparable ethanol production during the monitored 40 hours of cultivation.

The observed acetaldehyde accumulation with the hybrid strains is shown in FIG. 29A. The acetaldehyde accumulation is substantially lower for the strains expressing the Adh enzyme under the control of the PcpcB promoter than for the reference strain expressing the synAdh under control of the Prbc promoter. The lowest acetaldehyde levels were observed in the strains expressing the *Arthrospira platensis* and *Lyngbya* sp. Adh enzymes (#1790, #1791).

These results demonstrate that metabolic enhancement of cyanobacterial cells according to the present invention by incorporating an Adh enzyme having Michaelis constant $K_m$ for acetaldehyde which is lower than $0.08 \cdot 10^{-3}$ M (e.g. from *Arthrospira platensis, Lyngbya* sp. or *Cyanothece* sp.; #1790, #1791, #1795), or having a Michaelis constant $K_m$ for acetaldehyde which is higher than $0.65 \cdot 10^{-3}$ M but lower than $10 \cdot 10^{-3}$ M in combination with a Michaelis constant $K_m$ for ethanol which is higher than $20 \cdot 10^{-3}$ M (e.g. from *Synechococcus* sp.; #1793) leads to a high level of ethanol formation. This is due to the fact that the recombinant alcohol dehydrogenase enzymes of the present invention are capable of maintaining a low acetaldehyde level in the culture and/or tolerate high ethanol product concentrations with substantially reduced back-reaction already at comparatively low activity levels.

Example 17

Long-Term Cultivation in 0.5 L Photobioreactors (PBRs) and 1.2 L Vertical Photobioreactors (vPBRs)

1. Cultivation in 0.5 L PBRs

For scale up, the culture was maintained under repressed conditions, using mBG11 (35 psu) with ammonium and urea (2 mM of each) instead of nitrate as nitrogen source, 5 mM TES was used as buffer. For plasmid maintenance and contamination control, kanamycin (150 mg L-1) was used. For induction, cells were switched back to normal mBG11 with nitrate and no ammonium/urea. Cells were cultivated in 0.5 L round Schott bottles. Mixing was achieved using a magnetic stir bar at continuous 250 rpm. The gas flow rate was continuously 15 ml min-1 with $CO_2$ enriched air (5% $CO_2$). A light/dark period of 12 h:12 h was applied. Illumination of cultures was done with fluorescence lamps (Sylvana Grolux FHO 39W/T5/GRO). The cultures were illuminated from two sides with a photon flux density (PFD) of 230 μE $m^{-2}$ $s^{-1}$ each.

2. Cultivation in 1.2 L Vertical vPBRs

The strains were scaled up in 1 liter mBG11 with 0.5% continuous CO2 supply and continuous illumination with an intensity of 200-300 μmol photons $m^{-2}$ $s^{-1}$. The strains were cultivated under repressed conditions in media containing 2 mM ammonium and 2 mM urea as the nitrogen source. Furthermore 200 mg/L kanamycin was added and 5 mM TES buffer was used to keep the pH at 8.0.

1.2 L vPBRs were inoculated at a cell density of $OD_{750\ nm}$=0.5 in mBG-11 medium (35 psu) containing kanamycin (200 mg/L). The strains were cultivated at pH 7.3±0.01. $CO_2$ (15% $CO_2$ in air) was injected into the liquid phase in a pH controlled manner with continuous aeration (38 mL/min). The vPBRs were illuminated from one side using fluorescent bulbs with a photon flux density (PFD) of 230 μmol photons $m^{-2}$ $s^{-1}$ during the photoperiod of 12 hours. The temperature profile ranged from 25° C. at night and 37° C. during daytime. An average value of 2.5% ethanol vapor loss per day was assumed in order to compensate for the ethanol loss through vapor phase. The value 2.5% was calculated from several evaporation tests with ethanol spiked medium in vPBRs under these standardized conditions, where the decline of ethanol in the liquid phase had been determined experimentally. Nutrition was added several times during the cultivation. Ethanol production rates were calculated by subtracting ethanol values from the first day (due to lag phase) and the last day divided by the number of cultivation days.

Example 18

Genetic Integrity of Adh Enzyme Expression Cassettes in Ethanologenic Cyanobacterium sp. PTA-13311 Hybrids Long-term cultivation of Cyanobacterium sp. PTA-13311 hybrids harboring the reference plasmids #1792, #1784 and #1835, each containing an expression cassette with the synAdh gene under transcriptional control of the PcpcB promoter, unexpectedly showed a loss of Adh activity and ethanol production after a only few days of cultivation. For example, the recovery and subsequent PCR analysis of the plasmid #1784 from the cultures after loss of the Adh activity initially indicated that gene deletions of various lengths occurred in the synAdh gene (FIG. 29B). Whilst the full length PCR product of the synAdh has a size of about 1400 bp (bold arrow), specific synAdh PCR amplificates of smaller size due to deletions of about 490 bp and 680 bp (thin arrows) were obtained after the observed Adh activity loss.

Subsequently, the genetic integrity of the Adh enzymes from *Lyngbya* sp. and *Synechococcus* sp. of the present invention (plasmids #1791, #1793 and #1938) and, as a representative comparative example, of the synAdh enzyme (plasmid #1835) were studied in more detail during ethanologenic cultivation in 1.2 L vertical vPBRs.

The results are shown in FIGS. 30A through 32A. FIG. 30A depicts the cell density in the different cultures in relation to the cultivation time. The cyanobacteria expressing the Adh enzymes of the present invention (i.e. plasmids #1791, #1793 and #1938) exhibited an essentially constant growth over the monitored 35 days of cultivation. In contrast, the cell growth was significantly impaired in cyanobacteria harboring the plasmid #1835 with the synAdh enzyme under the control of the strong PcpcB promoter, presumably due to the high metabolic strain imposed on the cells by the overexpression of the synAdh. The cell viability of the cells was so defective that the cultivation of the cells harboring the plasmid #1835 had to be terminated on day 12. FIG. 30B shows the corresponding ethanol accumulation during the cultivation. After about 3-4 days of cultivation, the ethanol accumulation deteriorated in the cell culture harboring the plasmid #1835, whereas the cell cultures expressing the Adh enzymes of the present invention continued to accumulate ethanol at a constant rate until the end of the cultivation after 34 days. Determination of the chlorophyll/OD ratio of cyanobacterial cells during the cultivation (FIG. 31A) confirmed a strongly decreasing pigmentation of the cells expressing the synAdh under control of the PcpcB promoter, which is characteristic of a rapid loss of cell vitality. In contrast, relatively constant chlorophyll/OD ratios were present in the cells expressing the Adh enzymes of the present invention under the control of the PcpcB promoter, confirming that with these Adh enzymes the cells are less affected by the recombinant Adh expression and ethanol production and have a vitality that is closer to that of a corresponding wild type cyanobacterium. The measured Adh activity in the cultures is shown in FIG. 31B. The Adh activity in cells harboring the plasmid #1835 was almost completely lost after only about 8 days of cultivation, whereas only a comparatively moderate decrease in Adh activity was observed in the strains harboring the plasmids #1791, #1793 and #1938 with the Adh enzymes of the present invention.

PCR analysis of the recovered #1835 plasmids after cultivation confirmed genetic deletions in the synAdh gene of about 800 and 400 base pairs in length (FIG. 32A). Subsequent sequencing of the defective synAdh genes showed that the deletions comprised the region from bases 2671-2923 and 2725-3371 of the synAdh gene, respectively.

In conclusion, ethanol production with cyanobacterial cells harboring a recombinant PcpcB-synAdh expression cassette suffers from a rapid loss and/or inactivation of the synAdh gene due to partial gene deletions. The gene deletions are likely to occur due to the genetic pressure imposed on the cells as a result of the metabolic burden and harmful unspecific side reactions caused by the overexpression and overabundance of the synAdh enzyme. Accordingly, it is an unexpected and surprising effect that the metabolically enhanced cyanobacterial cells according to the present invention have improved genetic stability with respect to the recombinantly overexpressed adh gene in comparison to conventionally enhanced cyanobacterial cells overexpressing the state of the art synAdh enzyme. In particular, it is a favorable effect of the present invention that the expression of the Adh enzyme (e.g. from *Lyngbya* sp. or *Synechococcus* sp.) can be controlled by the PcpcB promoter, because this promoter is a particularly strong and reliable promoter in cyanobacteria such as the Cyanobacterium sp. PTA-13311.

Example 19

Ethanol Production Rates of Various PTA-13311 Hybrids in 0.5 L Photobioreactors and Ethanol Accumulation During Long-Term Cultivation in 1.2 L Vertical Photobioreactors The protocols described in Example 17 were used to investigate the ethanol production during cultivation of Cyanobacterium sp. PTA-13311 hybrid strains harboring the ethanologenic plasmids #1791 (Adh enzyme from *Lyngbya* sp.), #1793 (Adh enzyme from *Synechococcus* sp.), #1795 (Adh enzyme from *Cyanothece* sp.), #1815 (Adh enzyme from *Chroococcidiopsis* sp.) and #1831 (Adh enzyme from *Synechococcus* sp.). Hybrid strains harboring the ethanologenic plasmids #1578 and #1792 with the synAdh gene from *Synechocystis* sp. PCC6803 served as comparative examples.

Tables 4 and 5 provide a summary of the average ethanol production rates observed in the 0.5 L PBRs over 21 days of cultivation for the different hybrid strains with and without preliminary ethanol spiking

TABLE 4

Summary of average ethanol production rates over 21 days of strains with plasmids #1791 and #1795 in 0.5 L PBRs in comparison to the reference strain with plasmid #1792.

| Strain | unspiked | | 0.4% EtOH | |
|---|---|---|---|---|
| | % (v/v) EtOH/day | % of #1792 | % (v/v) EtOH/day | % of #1792 |
| #1792 (synADH) | 0.0325 | 100% | 0.0280 | 100% |
| #1791 (ADH111) | 0.0415 | 128% | 0.0310 | 111% |
| #1795 (ADH553) | 0.0350 | 108% | 0.0251 | 90% |

TABLE 5

Summary of ethanol production rates of strains with plasmids #1793, #1815 and #1831 in 0.5 L PBRs in comparison to the reference strain with plasmid #1792.

| Strain | unspiked | | 0.4% EtOH | |
|---|---|---|---|---|
| | % (v/v) EtOH/day | % of #1792 | % (v/v) EtOH/day | % of #1792 |
| #1792 (synADH) | 0.0370 | 100% | 0.0332 | 100% |
| #1793 (ADH916) | 0.0365 | 99% | 0.0299 | 90% |

TABLE 5-continued

Summary of ethanol production rates of strains with plasmids #1793, #1815 and #1831 in 0.5 L PBRs in comparison to the reference strain with plasmid #1792.

| Strain | unspiked | | 0.4% EtOH | |
|---|---|---|---|---|
| | % (v/v) EtOH/day | % of #1792 | % (v/v) EtOH/day | % of #1792 |
| #1815 (ADH1102) | 0.0409 | 111% | 0.0329 | 99% |
| #1831 (ADH213) | 0.0392 | 106% | 0.0340 | 102% |

The long term cultivation results of the total ethanol production in the 1.2 L vPBRs are summarized in FIG. 32B. Notably, the ethanol yield after 32 cultivation days is between about 25% and about 48% higher with the cyanobacterial strains of the present invention in comparison to the state-of-the-art reference strain.

The scope of protection of the invention is not limited to the examples given hereinabove. The invention is embodied in each novel characteristic and each combination of characteristics, which particularly includes every combination of any features which are stated in the claims, even if this feature or this combination of features is not explicitly stated in the claims or in the examples.

The invention claimed is:

1. A cyanobacterial cell for the production of ethanol, comprising:

a. a recombinant gene encoding a pyruvate decarboxylase enzyme (Pdc) converting pyruvate to acetaldehyde, and b. a recombinant gene encoding a $Zn^{2+}$ dependent alcohol dehydrogenase enzyme (Adh) converting acetaldehyde to ethanol, wherein the amino acid sequence of said $Zn^{2+}$ dependent alcohol dehydrogenase enzyme (Adh) is at least 95% identical to an Adh amino acid sequence selected from the group consisting of: SEQ ID NO: 1, SEQ ID NO: 3, SEQ ID NO: 4, SEQ ID NO: 5, SEQ ID NO: 6, and SEQ ID NO: 8.

2. The cyanobacterial cell of claim 1, wherein the Adh amino acid sequence is at least 95% identical to a sequence selected from the group consisting of SEQ ID NO: 1 and SEQ ID NO: 3.

3. The cyanobacterial cell of claim 2, wherein:

a. the Michaelis constant Km for NADPH of the alcohol dehydrogenase enzyme is lower than the Michaelis constant Km for NADH of the alcohol dehydrogenase enzyme; and b. the Michaelis constant Km for acetaldehyde of the alcohol dehydrogenase enzyme is lower than $0.08 \cdot 10^{-3}$ M.

4. The cyanobacterial cell of claim 3, wherein the Adh amino acid sequence is at least 95% identical to SEQ ID NO: 1.

5. The cyanobacterial cell of claim 1, wherein the Adh amino acid sequence is at least 95% identical to a sequence selected from the group consisting of SEQ ID NO: 4, SEQ ID NO: 5, SEQ ID NO: 6, and SEQ ID NO: 8.

6. The cyanobacterial cell of claim 5, wherein a. the Michaelis constant $K_m$ for NADPH of the alcohol dehydrogenase enzyme is lower than the Michaelis constant $K_m$ for NADH of the alcohol dehydrogenase enzyme;

b. the Michaelis constant $K_m$ for acetaldehyde of the alcohol dehydrogenase enzyme is higher than $0.65 \cdot 10^{-3}$ M, but lower than $10 \cdot 10^{-3}$ M; and c. the Michaelis constant $K_m$ for ethanol of the alcohol dehydrogenase enzyme is higher than $20 \cdot 10^{-3}$ M.

7. The cyanobacterial cell of claim 6, wherein the Adh amino acid sequence is at least 95% identical to SEQ ID NO: 8.

8. The cyanobacterial cell of claim 1, wherein the alcohol dehydrogenase enzyme comprises an amino acid sequence having at least 99% sequence identity to a sequence selected from the group consisting of: SEQ ID NO: 1, SEQ ID NO: 3, SEQ ID NO: 4, SEQ ID NO: 5, SEQ ID NO: 6, and SEQ ID NO: 8.

9. The cyanobacterial cell of claim 1, wherein the ratio of the Michaelis constant $K_m$ for ethanol and the Michaelis constant $K_m$ for acetaldehyde $K_m$(ethanol)/$K_m$(acetaldehyde) of the alcohol dehydrogenase enzyme is equal to or higher than 55.

10. The cyanobacterial cell of claim 9, wherein the amino acid sequence of the alcohol dehydrogenase enzyme is at least 95% identical to a sequence selected from the group consisting of SEQ ID NO: 1, SEQ ID NO: 3, SEQ ID NO: 5, and SEQ ID NO: 8.

11. The cyanobacterial cell of claim 1, wherein the recombinant gene encoding the alcohol dehydrogenase enzyme is under the transcriptional control of a constitutive promoter.

12. The cyanobacterial cell of claim 11, wherein the constitutive promoter is endogenous to said host cell.

13. The cyanobacterial cell of claim 12, wherein the constitutive promoter is selected from the group consisting of PrpsL, PcpcB, Prbc, PpetE, PpsaA, PpsbB, and PatpG.

14. The cyanobacterial cell of claim 1, wherein the recombinant gene encoding the pyruvate decarboxylase enzyme is under the transcriptional control of an inducible promoter.

15. The cyanobacterial cell of claim 14, wherein the inducible promoter is inducible by a change of a metal-ion concentration.

16. The cyanobacterial cell of claim 15, wherein the inducible promoter is selected from the group consisting of PziaA (SEQ ID NO: 38), PaztA (SEQ ID NO: 40), PsmtA (SEQ ID NO: 39), PcorT (SEQ ID NO: 41), PnrsB (SEQ ID NO: 42), Porf0316 (SEQ ID NO: 67), and PpetJ (SEQ ID NO: 43).

17. The cyanobacterial cell of claim 14, wherein the inducible promoter is a nitrate-inducible promoter.

18. The cyanobacterial cell of claim 17, wherein the nitrate-inducible promoter is selected from the group consisting of PnirA, PnrtA, and PnarB.

19. The cyanobacterial cell of claim 1, wherein at least one of said recombinant gene encoding the pyruvate decarboxylase enzyme and said recombinant gene encoding the alcohol dehydrogenase enzyme is integrated into an extrachromosomal plasmid.

20. The cyanobacterial cell of claim 1, wherein the cyanobacterial cell is Cyanobacterium sp.

21. The cyanobacterial cell of claim 20, wherein said recombinant gene encoding the alcohol dehydrogenase enzyme and/or said recombinant gene encoding the pyruvate decarboxylase enzyme gene is adapted in the codon triplets coding for the amino acids for enhanced translation in the cyanobacterial cell, the adapted gene comprising:

a. a G+C content of ≤45%; and b. a codon adaptation index (CAI) of ≥0.60, based on the reference codon usage table of Cyanobacterium sp. with the accession no. PTA-13311.

22. The cyanobacterial cell of claim 1, comprising alcohol dehydrogenase genes whose expressed proteins generate elevated ethanol productivity when compared to an enhanced cyanobacterial cell comprising only overexpressed alcohol dehydrogenase from *Synechocystis* sp. PCC 6803 (SEQ ID NO: 26).

23. The cyanobacterial cell of claim 22, comprising a plasmid having a nucleic acid sequence selected from the group consisting of SEQ ID NO: 72 and SEQ ID NO: 81.

24. A cyanobacterial cell for the production of ethanol, comprising a recombinant gene encoding a pyruvate decarboxylase enzyme (Pdc) converting pyruvate to acetaldehyde, and a recombinant gene encoding a $Zn^{2+}$ dependent alcohol dehydrogenase enzyme (Adh) converting acetaldehyde to ethanol, wherein said cell generates elevated ethanol productivity when compared to an enhanced cyanobacterial cell comprising only overexpressed alcohol dehydrogenase from *Synechocystis* sp. PCC 6803 (SEQ ID NO: 26), wherein the Pdc and Adh genes are present on a plasmid comprising a nucleic acid sequence selected from the group consisting of SEQ ID NO: 72 and SEQ ID NO: 81.

* * * * *